United States Patent
Gareau et al.

(10) Patent No.: US 11,760,754 B2
(45) Date of Patent: Sep. 19, 2023

(54) HETEROCYCLIC MITOCHONDRIAL ACTIVITY INHIBITORS AND USES THEREOF

(71) Applicant: UNIVERSITÉ DE MONTRÉAL, Montréal (CA)

(72) Inventors: Yves Gareau, Notre-Dame-de-l'Ile-Perrot (CA); Stéphane Gingras, Montreal (CA); Yves Chantigny, Pincourt (CA); Gaoqiang Yang, Montreal (CA); Guy Sauvageau, Montreal (CA); Irène Baccelli, Nantes (FR); Anne Marinier, Kirkland (CA)

(73) Assignee: UNIVERSITÉ DE MONTRÉAL, Montréal (CA)

( * ) Notice: Subject to any disclaimer, the term of this patent is extended or adjusted under 35 U.S.C. 154(b) by 0 days.

(21) Appl. No.: 16/761,210

(22) PCT Filed: Nov. 2, 2018

(86) PCT No.: PCT/CA2018/000206
§ 371 (c)(1),
(2) Date: May 1, 2020

(87) PCT Pub. No.: WO2019/084662
PCT Pub. Date: May 9, 2019

(65) Prior Publication Data
US 2021/0387980 A1 Dec. 16, 2021

Related U.S. Application Data

(60) Provisional application No. 62/581,239, filed on Nov. 3, 2017.

(30) Foreign Application Priority Data

Feb. 16, 2018 (CA) .................. CA 2995617

(51) Int. Cl.
| | | |
|---|---|---|
| *C07D 413/12* | (2006.01) | |
| *C07D 263/32* | (2006.01) | |
| *C07D 263/34* | (2006.01) | |
| *C07D 417/12* | (2006.01) | |
| *A61K 31/421* | (2006.01) | |
| *A61K 31/427* | (2006.01) | |
| *A61K 31/4439* | (2006.01) | |

(Continued)

(52) U.S. Cl.
CPC ......... *C07D 417/12* (2013.01); *C07D 249/04* (2013.01); *C07D 263/32* (2013.01); *C07D 263/34* (2013.01); *C07D 277/24* (2013.01); *C07D 413/12* (2013.01); *G01N 33/5011* (2013.01)

(58) Field of Classification Search
CPC .. C07D 413/12; C07D 263/32; C07D 263/34; C07D 417/12; A61K 31/421; A61K 31/427; A61K 31/4439; A61K 31/501; A61K 31/506; A61P 35/02
See application file for complete search history.

(56) References Cited

U.S. PATENT DOCUMENTS

| | | | |
|---|---|---|---|
| 6,984,653 B2 | 1/2006 | Tasaka et al. | |
| 7,247,649 B2 | 7/2007 | Bossenmaier et al. | |

(Continued)

FOREIGN PATENT DOCUMENTS

| | | |
|---|---|---|
| CA | 2481706 A1 | 10/2003 |
| DE | 945563 C | 7/1956 |

(Continued)

OTHER PUBLICATIONS

International Preliminary Report on Patentability received for PCT International Application No. PCT/CA2018/00206, dated May 14, 2020, 8 pages.
International Search Report and Written Opinion received for PCT Patent International Application No. PCTCA2018/00206, dated Feb. 14, 2019, 11 pages.
Stieber et al. (2003) "Multistep Solid-Phase Synthesis of an Antibiotic and Receptor Tyrosine Kinase Inhibitors Using the Traceless Phenylhydrazide Linker", Chemistry—A European Journal, 9(14):3282-91.

(Continued)

*Primary Examiner* — Bruck Kifle
(74) *Attorney, Agent, or Firm* — Seed IP Law Group LLP

(57) ABSTRACT

Heterocyclic compounds of Formula (I) and pharmaceutically acceptable salt thereof are disclosed. The use of such heterocyclic compounds and pharmaceutically acceptable salt thereof for the treatment of cancers, and more particularly cancers sensitive to mitochondrial activity inhibition and increased reactive oxygen species (ROS) levels, is also disclosed. Such cancers include acute myeloid leukemia (AML), preferably AML characterized by certain features, such as high level of expression of one or more Homeobox (HOX)-network genes, high and/or low expression of specific genes, the presence of one or more cytogenetic or molecular risk factors such as intermediate cytogenetic risk, Normal Karyotype (A/K), mutated NPM1, mutated CEBPA, mutated FLT3, mutated DNMT3A, mutated TET2, mutated IDH1, mutated IDH2, mutated RUNX1, mutated WT1, mutated SRSF2, intermediate cytogenetic risk with abnormal karyotype (intern(abnK)), trisomy 8 (+8) and/or abnormal chromosome (5/7), and/or a high leukemic stem cell (LSC) frequency.

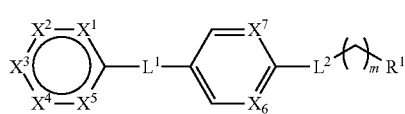

(I)

6 Claims, 24 Drawing Sheets

(51) Int. Cl.
*A61K 31/501* (2006.01)
*A61K 31/506* (2006.01)
*A61P 35/02* (2006.01)
*C07D 249/04* (2006.01)
*C07D 277/24* (2006.01)
*G01N 33/50* (2006.01)

(56) References Cited

U.S. PATENT DOCUMENTS

| | | | |
|---|---|---|---|
| 7,288,557 | B2 | 10/2007 | Friebe et al. |
| 7,429,605 | B2 | 9/2008 | Bossenmaier et al. |
| 7,432,291 | B2 | 10/2008 | Bossenmaier et al. |
| 2002/0173526 | A1* | 11/2002 | Tasaka ................ C07D 413/12 548/235 |
| 2003/0069275 | A1 | 4/2003 | Cheng et al. |
| 2004/0242659 | A1* | 12/2004 | Tasaka .................... A61P 31/12 548/235 |
| 2005/0267179 | A1* | 12/2005 | Bossenmaier ....... C07D 413/12 548/247 |
| 2006/0063812 | A1 | 3/2006 | Friess et al. |
| 2006/0116407 | A1 | 6/2006 | Bossenmaier et al. |
| 2009/0264485 | A1* | 10/2009 | Kreil ....................... A61P 43/00 548/235 |
| 2014/0128397 | A1 | 5/2014 | Irwin et al. |

FOREIGN PATENT DOCUMENTS

| | | |
|---|---|---|
| EP | 1445254 A1 | 8/2004 |
| JP | H11-60571 A | 3/1999 |
| JP | 2001-348385 A | 12/2001 |
| JP | 2003-48882 A | 2/2003 |
| JP | 2003-176287 A | 6/2003 |
| JP | 2003-277379 A | 10/2003 |
| WO | 9803505 A2 | 1/1998 |
| WO | 03/059907 | 7/2003 |
| WO | 2004052839 A1 | 6/2004 |
| WO | 2004085434 A1 | 10/2004 |
| WO | 2007/056366 | 7/2007 |
| WO | 2008103501 A1 | 8/2008 |

OTHER PUBLICATIONS

Baccelli et al., "A novel approach for the identification of efficient combination therapies in primary human acute myeloid leukemia specimens," *Blood Cancer Journal* 7(e529), Feb. 17, 2017. (8 pages).

* cited by examiner

HETEROCYCLIC MITOCHONDRIAL ACTIVITY INHIBITORS AND USES THEREOF

RELATED APPLICATION

This application claims priority under applicable laws and regulations to United Stated application No. 62/581,239 filed on Nov. 3, 2017 and to Canadian application No. 2,995,617 filed on Feb. 16, 2018, the contents of which are incorporated herein by reference in their entirety for all purposes.

TECHNICAL FIELD

The present disclosure generally relates to the inhibition of mitochondrial activity, for example for the treatment of cancers such as acute myeloid leukemia (AML), and more specifically of AML subtypes typically associated with poor prognosis.

BACKGROUND

Accumulating evidence suggests that mitochondrial bioenergetics, biosynthesis and signaling are involved in tumorigenesis. For example, the anti-diabetic drugs metformin and phenformin, which inhibit mitochondrial ETC complex I, have been shown to inhibit tumor growth in various cancers including lung, lymphoma, and breast cancers. In breast cancer cells, metformin and phenformin reduces tricarboxylic acid (TCA) cycle intermediate production through complex I inhibition (Janzer A, et al. *Proc Natl Acad Sci USA*. 2014; 111:10574-10579). Mitochondria produce reactive oxygen species (ROS) as a natural by-product of electron transport chain (ETC) activity. Some anticancer drugs are generators of ROS, inductors of oxidative stress and initiators of apoptosis in the cells. ROS, which include free radicals such as superoxide ($O_2^{*-}$), hydroxyl radical ($HO^-$) and hydrogen peroxide ($H_2O_2$) are often generated following inhibition of the mitochondrial ETC (Li et al., 2003. *J. Biol. Chem.* 278, 8516-8525; Muller et al., 2004. *J. Biol. Chem.* 279, 49064-49073), and leads to tumor cell death at least in part through autophagy-induced cell death (Chen et al., *Journal of Cell Science* 2007 120: 4155-4166). Thus, targeting mitochondrial activity/metabolism, notably to increase ROS levels in tumor cells, constitutes a promising approach for cancer therapy.

Acute Myeloid Leukemia (AML) is a particularly lethal form of cancer, with most patients dying within two years of diagnosis. It is one of the leading causes of death among young adults. AML is a collection of neoplasms with heterogeneous pathophysiology, genetics and prognosis. Mainly based on cytogenetics and molecular analysis, AML patients are presently classified into groups or subsets of AML with markedly contrasting prognosis. Approximately 45% of all AML patients are currently classified into distinct groups with variable prognosis based on the presence or absence of specific recurrent cytogenetic abnormalities.

Targeting FLT3 receptor tyrosine kinases with FLT3 tyrosine kinase inhibitors (TKIs) has shown encouraging results in the treatment of FLT3-mutated AML (generally associated with poor clinical outcome), but in most patients, responses are incomplete and not sustained. Also, the induction of acquired resistance to TKIs has emerged as a clinical problem. Also, inhibitors of other pathologically activated kinases in AML such as c-KIT and JAK2 have achieved only rare bone marrow responses.

There is a need for the identification of novel therapeutic strategies for the treatment of cancers, including AML such as AML associated with poor prognosis.

SUMMARY

According to one aspect, the present technology generally relates to compounds of Formula I or pharmaceutically acceptable salts thereof:

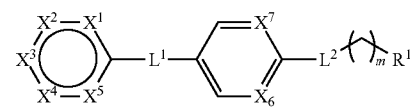

Formula I wherein:
$X^1$ represents —N=, —CH=, or —O—;
$X^2$ represents —CH=, —C($R^2$)=, or a covalent bond;
$X^3$ represents —CH=, —C($R^2$)=, or a covalent bond;
$X^4$ represents —O—, —C($R^3$)=, —N=, or —S—;
$X^5$ represents a covalent bond, —C($R^3$)=, or —O—;
provided that one of $X^2$ and $X^3$ is —C($R^2$)= and the other of $X^2$ and $X^3$ is —CH= or a covalent bond, and provided that at most only one of $X^2$, $X^3$, and $X^5$ represents a covalent bond;
$R^2$ represents ArylC($R^3$)=C(H)—, HeteroarylC($R^3$)=C(H)—, ArylN($R^3$)C(O)—, HeteroarylN($R^3$)C(O)—, Arylcyclopropyl-, Heteroarylcyclopropyl-, $R^3$OC(O)C(H)=C(H)—, $R^3$OC(O)—, Aryl-C≡C—, Heteroaryl-C≡C—, Aryl-, Heteroaryl-, Aryl-CH($R^3$)—CH($R^3$)—, or Heteroaryl-CH($R^3$)—CH($R^3$)—, wherein the Aryl group and the Heteroaryl group are optionally substituted with one to three $R^4$ groups, which are the same or different;
$R^3$ independently in each occurrence represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —$OR^6$, —N($R^6$)$_2$, —C(O)$OR^6$, —CN or —C(O)N($R^6$)$_2$;
$R^4$ independently in each occurrence represents —F, —Cl, —Br, —I, —$SR^3$, —$SOR^5$, —S(O)$_2R^5$, —S(O)$_2$N($R^3$)$_2$, -triazolyl, —CN, —C(O)$OR^3$, —C(O)$R^3$, —NO$_2$, —C(O)N($R^3$)$_2$, —$OR^3$, —C($R^3$)$_2$OH, —N($R^3$)$_2$, —N($R^3$)C(O)$R^3$, —N($R^3$)C(O)$OR^5$, —OC(O)N($R^3$)$_2$, —N$_3$, —$R^3$,

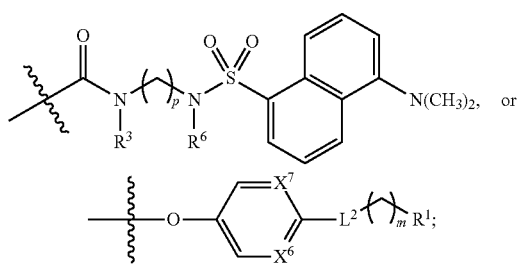

$R^5$ independently in each occurrence represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —$OR^6$, —N($R^6$)$_2$, —C(O)$OR^6$, —CN or —C(O)N($R^6$)$_2$;

$R^6$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl;

$L^1$ represents —CHR$^3$—O—, —CH$_2$—NH—, —C(O)NH—, —C(O)—CHR$^6$, —CR$^6$=CR$^6$—, —CH$_2$—S—, —CH$_2$—, or —CH$_2$—O—CH$_2$—;

$X^6$ and $X^7$ independently represent —CR$^3$=, or —N=;

$L^2$ represents a covalent bond, —C(O)—, —C(R$^3$)(OH)—, —O—, —S—, —CHR$^3$—, —CH(R$^3$)—S—, or —CH(R$^3$)—O—;

m independently in each occurrence represents an integer from 1 to 4;

p represents an integer from 1 to 6; and $R^1$ represents heteroaryl, aryl, —N$_3$, —OH, —OC(O)N(R$^7$)$_2$, —C(O)N(R$^7$)$_2$, —N(R$^7$)$_2$, —N(R$^7$)C(O)R$^7$, —N(R$^7$)C(O)OR$^8$, —N(R$^7$)C(O)-L$^3$-OR$^7$, or —N(R$^7$)C(O)-L$^3$-OC(O)N(R$^7$)$_2$, the heteroaryl and aryl being optionally substituted with one or more R$^9$, which are the same or different, wherein:

$L^3$ represents $C_1$-$C_5$alkylene, $C_2$-$C_5$alkenylene, $C_2$-$C_5$alkynylene, or $C_1$-$C_4$fluoroalkylene, the alkylene, alkenylene, and alkynylene being optionally substituted with one or more R$^9$, which are the same or different;

$R^7$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl; the alkyl, alkenyl, alkynyl, and cycloalkyl being optionally substituted with one or more R$^9$, which are the same or different, or when two R$^7$ groups are attached to a same nitrogen atom, the two R$^7$ groups together with the nitrogen atom to which they are attached optionally form a 5-7-membered heterocycloalkyl, the heterocycloalkyl optionally comprising one or more further heteroatom independently selected from —O—, —N(R$^3$)—, —S—, —S(O)— and —SO$_2$—, the heterocycloalkyl being optionally substituted with one or more R$^9$, which are the same or different;

$R^8$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl; the alkyl, alkenyl, alkynyl, and cycloalkyl being optionally substituted with one or more R$^9$, which are the same or different; and $R^9$ independently represents —$C_1$-$C_5$alkyl, —$C_0$-$C_6$alkyl-OR$^{11}$, —$C_3$-$C_5$cycloalkyl, —$C_3$-$C_5$cycloalkyl-OR$^{11}$, —$C_1$-$C_6$alkyl-OC(O)R$^{11}$, —$C_1$-$C_6$alkyl-OC(O)N(R$^1$)$_2$, —$C_1$-$C_6$alkyl-OC(O)N(R$^{11}$)-L$^4$-OR$^{11}$, —$C_0$-$C_6$alkyl-C(O)OR$^{11}$, —$C_0$-$C_6$alkyl-C(O)N(R$^{11}$)$_2$, —$C_1$-$C_6$alkyl-N(R$^{11}$)$_2$, —$C_1$-$C_5$alkyl-N(R$^{11}$)C(O)R$^{11}$, —$C_1$-$C_6$alkyl-N(R$^{11}$)C(O)-L$^4$-N(R$^{11}$)—C(O)R$^{11}$, —$C_1$-$C_6$alkyl-N(R$^{11}$)S(O)$_2$R$^{10}$, —$C_1$-$C_6$alkyl-N(R$^{11}$)S(O)$_2$-L$^4$-N(R$^{11}$)—C(O)OR$^{10}$, —Si($C_1$-$C_5$alkyl)$_3$, —C(O)—O—$C_1$-$C_5$alkyl, phenyl optionally substituted with R$^4$, benzyl optionally substituted with R$^4$, pyridinyl optionally substituted with R$^4$, or

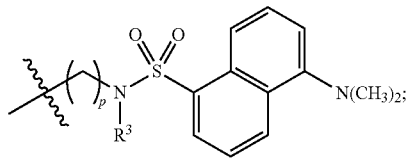

wherein:

$L^4$ represents $C_1$-$C_5$alkylene, $C_2$-$C_5$alkenylene, $C_2$-$C_5$alkynylene, or $C_1$-$C_4$fluoroalkylene; and $R^{10}$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —OR$^6$, —N(R$^6$)$_2$, —C(O)OR$^6$, —CN or —C(O)N(R$^6$)$_2$;

$R^{11}$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —OR$^6$, —N(R$^6$)$_2$, —C(O)OR$^6$, —CN or —C(O)N(R$^6$)$_2$, or when two R$^{11}$ groups are attached to a same nitrogen atom, the two R$^{11}$ groups together with the nitrogen atom to which they are attached optionally form a 5-7-membered heterocycloalkyl, the heterocycloalkyl optionally comprising one or more further heteroatom independently selected from —O—, —N(R$^3$)—, —S—, —S(O)— and —SO$_2$—.

According to one embodiment, in the compounds of Formula I, groups $R^5$, $R^8$ and $R^{10}$ are each other than —H. Other embodiments of the compounds, taken alone or in combination are as defined hereinbelow.

In another aspect, the present application relates to the use of a compound as herein defined, or a pharmaceutically acceptable salt thereof, for treating acute myeloid leukemia (AML) in a subject. Inversely, the application relates to a compound, or pharmaceutically acceptable salt thereof, as herein defined for use in the treatment of acute myeloid leukemia (AML). Alternatively, this application relates to the use of a compound as herein defined, or a pharmaceutically acceptable salt thereof, in the manufacture of a medicament for treating acute myeloid leukemia (AML) in a subject. In a further aspect, the application relates to a method for treating acute myeloid leukemia (AML), said method comprising administering to a subject in need thereof an effective amount of a compound as herein defined, or a pharmaceutically acceptable salt thereof. For instance, the subject is a pediatric subject. Alternatively, the subject is an adult subject.

In one embodiment, the AML is poor prognosis AML. In another embodiment, the AML comprises at least one of the following features: (a) high level of expression of one or more homeobox (HOX)-network genes; (b) high level of expression of one or more of the genes depicted in Table 1; (c) low level of expression of one or more of the genes depicted in Table 2; (d) one or more of the following cytogenetic or molecular risk factor: intermediate cytogenetic risk, Normal Karyotype (NK), mutated NPM1, mutated CEBPA, mutated FLT3, mutated DNA methylation genes, mutated RUNX1, mutated WT1, mutated SRSF2, intermediate cytogenetic risk with abnormal karyotype (intern(abnK)), trisomy 8 (+8) and abnormal chr(5/7); and (e) a leukemic stem cell (LSC) frequency of at least about 1 LSC per $1\times10^6$ total cells. For instance, the AML comprises high level of expression of one or more HOX-network genes, e.g. the one or more HOX-network genes being HOXB1, HOXB2, HOXB3, HOXB5, HOXB6, HOXB7, HOXB9, HOXB-AS3, HOXA1, HOXA2, HOXA3, HOXA4, HOXA5, HOXA6, HOXA7, HOXA9, HOXA10, HOXA10-AS, HOXA11, HOXA11-AS, MEIS1 and/or PBX3. For example, the one or more HOX-network genes are HOXA9 and/or HOXA10.

In another embodiment, the AML comprises high level of expression of one or more of the genes depicted in Table 1 hereinbelow. In further embodiment, the AML comprises low level of expression of one or more of the genes depicted in Table 2. In yet another embodiment, the AML comprises one or more of the cytogenetic or molecular risk factor defined in item (d) above, for instance, AML is intermediate cytogenetic risk AML and/or NK-AML, and/or AML comprises at least two of said cytogenetic or molecular risk factors, or at least three of said cytogenetic or molecular risk factors.

In a further embodiment, the AML comprises a mutated NPM1, a mutated FLT3 and/or a mutated DNA methylation gene e.g. DNMT3A or IDH1. In another embodiment, the AML comprises a mutated NPM1, a mutated FLT3 and a mutated DNA methylation gene, preferably the DNA methylation gene being DNMT3A. For example, the mutated FLT3 is FLT3 with internal tandem duplication (FLT3-ITD).

In yet another embodiment, the AML comprises an LSC frequency of at least about 1 LSC per $1\times10^6$ total cells, or an LSC frequency of at least about 1 LSC per $5\times10^5$ total cells. In a further embodiment, the AML comprises at least two of the above features (a) to (e), or at least three of features (a) to (e). In another embodiment, the AML is NK-AML with mutated NPM1.

According to another aspect, in the use, compound for use or method as defined herein, the compound, or pharmaceutically acceptable salt thereof, is present in a pharmaceutical composition.

In a further aspect, the present description relates to a method for determining the likelihood that a subject suffering from acute myeloid leukemia (AML) responds to a treatment with the compound or pharmaceutically acceptable salt thereof as defined herein, said method comprising determining whether AML cells from said subject comprise at least one of the features defined above, wherein the presence of said at least one of the following features in said AML cells is indicative that the subject has a high likelihood of responding to said treatment.

Additional objects and features of the present compound, compositions, methods and uses will become more apparent upon reading of the following non-restrictive description of exemplary embodiments, which should not be interpreted as limiting the scope of the invention.

BRIEF DESCRIPTION OF THE DRAWINGS

FIG. 1A: Identification of patient samples with consistent high expression of HOX-network gene members (black, upper right of each graph) and with consistent low expression of HOX-network gene members (grey, lower left of each graph) in the prognostic Leucegene AML cohort (263 AML patients) studied herein, a cohort of AML patients for which sufficient information is available to make survival studies. Values in brackets indicate the range of expression of each gene. FIG. 1B: Overall survival of AML patients belonging to HOX-network high (lower line, n=100) versus low (upper line, n=27) subgroups. FIG. 1C: Identification of a HOXA9/HOXA10 high AML sample population. FIG. 1D: Overall survival of AML patients belonging to the HOXA9/HOXA10 high group (lower line, n=131) and HOXA9/HOXA10 med/low group (upper line, n=132). In FIG. 1B and FIG. 1D, p-values were determined by log-rank test. Abbreviations: AML: Acute myeloid leukemia; HOX: Homeobox; MEIS1: MEIS Homeobox 1; RPKM: Reads Per Kilobase per Million mapped reads; Std: standard deviation.

FIG. 2A: Overview of the primary screen workflow of 60 compounds (Table 4). HOXA9 and HOXA10 were used as representative genes for the distinction between HOX-high (dark grey, n=131) versus HOX-med/low (light grey, n=132) patient samples. FIG. 2B: Summary of the results of the primary screen leading to the identification of Mubritinib as a candidate drug targeting HOX-high AML patient cells. The horizontal dashed line corresponds to p=0.05 and the vertical dashed line indicate a 2.5-fold difference in $EC_{50}$ values. FIG. 2C: AML patient samples included in the validation screen comprising HOX-high (dark grey, upper right) and HOX-med/low (light grey) specimens. FIG. 2D: Differential $EC_{50}$ values in HOX-high versus HOX-med/low AML samples measured in the validation screen. The p-value was determined by Mann-Whitney test. FIG. 2E: Frequencies of Mubritinib $EC_{50}$ values measured in 200 different AML specimens define Mubritinib-sensitive ($EC_{50}$<375 nM, n=100) and Mubritinib-resistant ($EC_{50}\geq$ 375 nM, n=100) groups. Normal primitive CD34-positive cord blood cells were moderately sensitive to Mubritinib ($EC_{50}$>375 nM). FIG. 2F: Differential overall survival of patients belonging to the Mubritinib-sensitive versus-resistant groups. The p-value was determined by log-rank test.

FIG. 2G: Transcriptomic profiles of Mubritinib-sensitive versus Mubritinib-resistant specimens, highlighting an overexpression of HOX-network genes. FIG. 2H: Transcriptomic profiles of Mubritinib-sensitive versus Mubritinib-resistant specimens, highlighting most differentially expressed genes (criteria: log (fold change)>0.8 (=6-fold), RPKM>0.1). Abbreviations: AML: Acute myeloid leukemia; ANKRD18B: Ankyrin Repeat Domain 18B; BEND6: BEN Domain Containing 6; COL4A5: Collagen Type IV Alpha 5; FDR: False Discovery Rate; HOX: Homeobox; KIRREL: Kin Of IRRE Like; LINC: Long Non Coding; LSC: leukemic stem cell; MEIS1: MEIS Homeobox 1; MIR: Micro RNA; MSLN: Mesothelin; NKX2.3: NK2 Homeobox 3; PI3K: Phosphatidylinositol-4,5-bisphosphate 3-kinase; PPBP: Pro-Platelet Basic Protein; PRDM16: PR/SET Domain 16; PRG3: Proteoglycan 3; RPKM: Reads Per Kilobase per Million mapped reads; RTK: receptor tyrosine kinase; S100A16: S100 Calcium Binding Protein A16; SNORD: Small Nucleolar RNA; ST18: Suppression Of Tumorigenicity 18, Zinc Finger; ZNF: Zinc Finger Protein.

FIG. 3A: Mubritinib $EC_{50}$ values according to cytogenetic risk classes. FIG. 3B: Mutations enriched in highly-sensitive Mubritinib AML specimens ($EC_{50}$<100 nM, n=59) versus Mubritinib highly-resistant AML specimens ($EC_{50}$>1 μM, n=58) according to a Bonferroni corrected exact Fisher's test. FIG. 3C: Mubritinib $EC_{50}$ values according to the presence of mutated genes. FIG. 3D: Mubritinib $EC_{50}$ values according to the genetic subgroups. FIG. 3E: Summary of Mubritinib-sensitive patient sample characteristics. FIG. 3F: $EC_{50}$ values of poor prognostic patient specimens carrying mutations (m) in NPM1, FLT3-ITD and DNMT3A (Papaemmanuil, E. et al. N Engl J Med 374, 2209-2221) versus other AML samples. FIG. 3G-H: Leukemic stem cell (LSC) frequencies in Mubritinib sensitive versus resistant groups of patient samples belonging to the normal karyotype (NK) subgroup (FIG. 3G) and to the NK subgroup carrying mutated NPM1 (NPM1m) (FIG. 3H). In FIGS. 3D-H, p-values were calculated by Mann-Whitney test. Horizontal lines in all panels indicate median values. Abbreviations: AML: Acute myeloid leukemia; AbnChr: abnormal chromosome; ASXL1: Additional Sex Combs Like 1, Transcriptional Regulator; CEBPA: CCAAT/Enhancer Binding Protein Alpha; Complex: complex karyotype; DNMT3A: DNA (Cytosine-5-)-Methyltransferase 3 Alpha; EVI1: Ecotropic Viral Integration Site 1; FLT3: Fms Related Tyrosine Kinase 3; HOX: Homeobox; IDH: Isocitrate Dehydrogenase (NADP(+)); Inter(AbnK): intermediate cytogenetic risk with abnormal karyotype; m: mutated; MLL: Mixed Lineage Leukemia 1; NK: normal karyotype; NPM1: Nucleophosmin (Nucleolar Phosphoprotein B23, Numatrin); NRAS: Neuroblastoma RAS Viral Oncogene Homolog; NUP98: Nucleoporin 98 kDa; RUNX1: Runt Related Transcription Factor 1; SRSF2: Serine/Arginine-Rich Splicing Factor 2; TET2: Tet Methylcytosine Dioxygenase 2; TP53: Tumor Protein P53; WT1: Wilms Tumor 1; +8: trisomy 8.

FIG. 4A: Number of viable (Propidium idodide (PI)-negative) cells after four days of treatment of OCI-AML3 with different concentrations of Mubritinib. FIG. 4B: Fold-enrichment in PI-positive cells (dead cells) compared to DMSO-treated cells after 27 hours of treatment of OCI-AML3 with different concentrations of Mubritinib. FIG. 4C: Percentage of early apoptotic and late apoptotic cells in OCI-AML3 cells after 24 hours of treatment with control DMSO, 100 nM or 10 µM Mubritinib. FIG. 4D: AML patients' cell sensitivity to Mubritinib versus Lapatinib ditosylate, an ERBB2 inhibitor. FIG. 4E: OCI-AML3 dose response curves after treatment with Mubritinib or with two known ERBB2 inhibitors: Lapatinib ditosylate or Sapitinib. FIG. 4F: ERBB2 gene expression in Mubritinib-sensitive versus Mubritinib-resistant patient samples. FIG. 4G: ERBB2 protein expression versus isotype control in ERBB2 over-expressing BT474 breast cancer cell line and in OCI-AML3 Mubritinib-sensitive AML cell line measured by flow cytometry. Samples were either treated with Mubritinib at 2 µM for 24 hours or mock-treated with DMSO. Abbreviations: AML: Acute myeloid leukemia; ERBB2: Erb-B2 Receptor Tyrosine Kinase 2; FITC: Fluorescein isothiocyanate; PE: Phycoerythrin; Pos: positive.

FIG. 5A: OCI-AML3 leukemic cells were either pre-incubated for 4 hours with 6 mM N-acetyl-cysteine (NAC), a reactive oxygen species (ROS) scavenger, or with vehicle (water) before being treated with 100 nM Mubritinib for 24 h or vehicle (DMSO). Cells underwent apoptotic death upon Mubritinib treatment as assessed by Annexin V and propidium iodide (PI) staining by flow cytometry. Mubritinib-induced cell death was reduced when cells were cultured in the presence of NAC. FIG. 5B: Flow cytometric staining using 2',7'-dichlorofluorescin diacetate (DCFDA), a fluorogenic dye that measures hydroxyl, peroxyl and other ROS activity within the cell, showing that Mubritinib treatment (500 nM, 24 h) induces ROS activity in OCI-AML3 leukemic cells. FIGS. 5C and 5D show the levels of reduced and oxidized levels of glutathione, respectively, in OCI-AML3 treated or not with Mubritinib, as detected by liquid chromatography-mass spectrometry (LC/MS). FIG. 5E shows the results of experiments assessing the effect of Mubritinib (1 µM) on oxygen consumption rate (OCR) in OCI-AML3 leukemic cells, as measured using a Seahorse XF extracellular flux analyzer (Agilent®). FIG. 5F shows the results of experiments assessing the effect of Mubritinib on the mitochondrial electron transfer chain (ETC) complex I (pivotal for mitochondrial respiration/activity), as measured using a cell free assay (MitoTox™ Complex I OXPHOS activity microplate assay, Abcam). FIG. 5G is a graph depicting dose-response curves upon Mubritinib treatment (6-day culture assay in 384-well plates) of OCI-AML3 and OCI-AML5 cell lines. FIGS. 5H-J are graphs depicting dose-response curves following treatment of OCI-AML3 and OCI-AML5 cell lines with other ETC inhibitors, namely Oligomycin (inhibitor of complex V, FIG. 5H), Rotenone (inhibitor of complex I, FIG. 5I) and Deguelin (inhibitor of complex I, FIG. 5J).

FIG. 8A: Effect on Complex I ubiquitone-dependent activity. FIG. 8B: Effect on Complex I ubiquitone-independent activity.

DETAILED DESCRIPTION

Figure 1A:
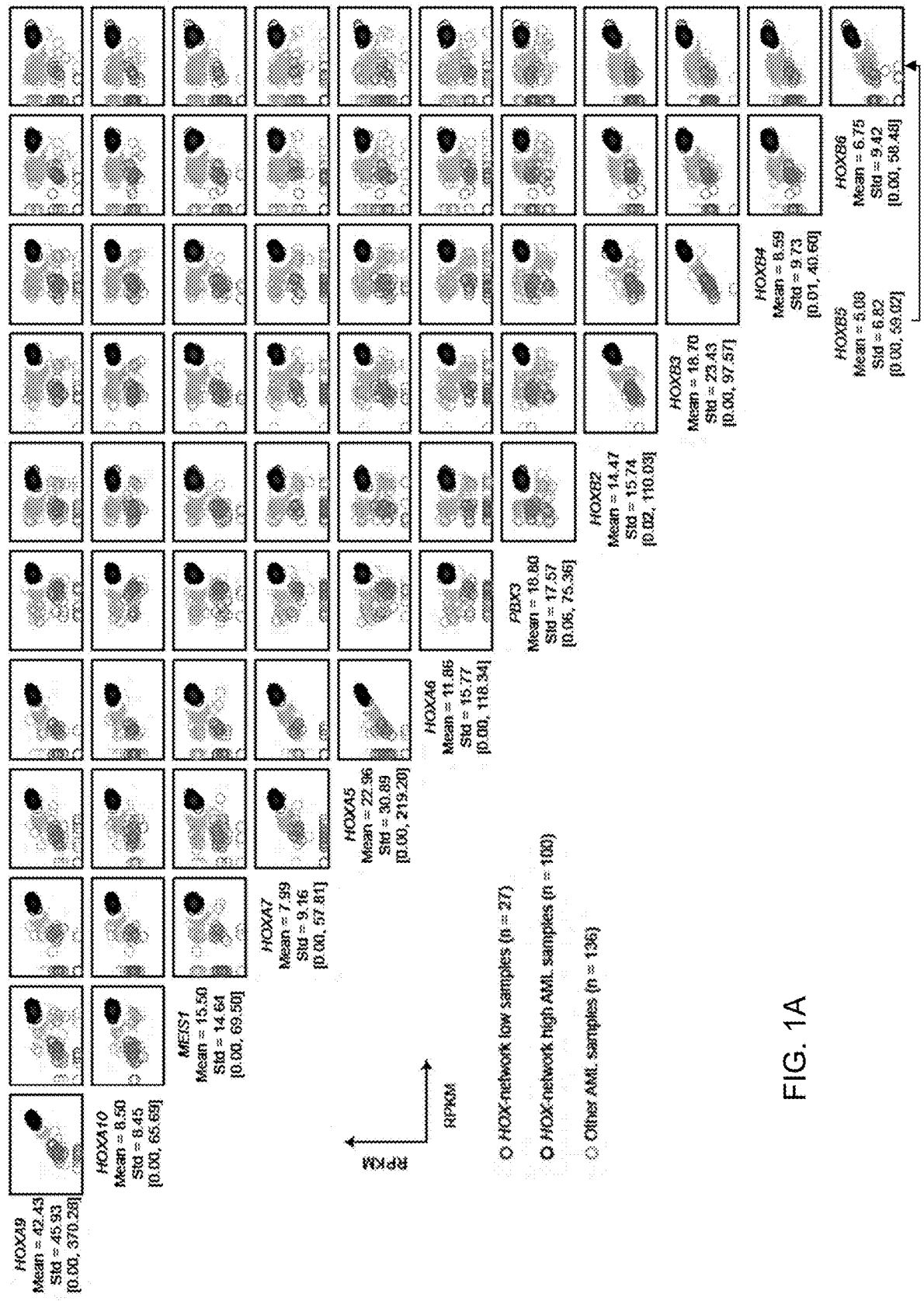
FIGS. 1A-D show the link between expression of HOX-network genes and AML prognosis.

All technical and scientific terms and expressions used herein have the same definitions as those commonly understood by a person skilled in the art to which the present technology pertains. The definition of some terms and expressions used is nevertheless provided below. To the extent the definitions of terms in the publications, patents, and patent applications incorporated herein by reference are contrary to the definitions set forth in this specification, the definitions in this specification will control. The section headings used herein are for organizational purposes only, and are not to be construed as limiting the subject matter disclosed.

i. Definitions

Chemical structures described herein are drawn according to conventional standards. Also, when an atom, such as a carbon atom, as drawn seems to include an incomplete valency, then the valency is assumed to be satisfied by one or more hydrogen atoms even though these are not necessarily explicitly drawn. Hydrogen atoms should be inferred to be part of the compound. Herein, in case of discrepancy between a chemical name and a chemical structure, the chemical structure prevails.

The terminology used herein is for the purpose of describing particular embodiments only and is not intended to be limiting. It should be noted that, the singular forms "a", "an", and "the" include plural forms as well, unless the content clearly dictates otherwise. Thus, for example, reference to a composition containing "a compound" also contemplates a mixture of two or more compounds. It should also be noted that the term "or" is generally employed in its sense including "and/or" unless the content clearly dictates otherwise. Throughout this specification, unless the context requires otherwise, the words "comprise," "comprises" and "comprising" will be understood to imply the inclusion of a stated step or element or group of steps or elements but not the exclusion of any other step or element or group of steps or elements. Furthermore, to the extent that the terms "including", "includes", "having", "has", "with", or variants thereof are used in either the detailed description and/or the claims, such terms are intended to be inclusive in a manner similar to the term "comprising".

All methods described herein can be performed in any suitable order unless otherwise indicated herein or otherwise clearly contradicted by context.

The use of any and all examples, or exemplary language ("e.g.", "such as") provided herein, is intended merely to better illustrate the invention and does not pose a limitation on the scope of the invention unless otherwise claimed.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

Unless otherwise stated, structures depicted herein are also meant to include all isomeric (e.g., enantiomeric, diastereomeric, and geometric (or conformational)) forms of the structure when applicable; for example, the R and S configurations for each asymmetric center. Therefore, single stereochemical isomers as well as enantiomeric, diastereomeric, and geometric (or conformational) mixtures of the present compounds are within the scope of the present description. The therapeutic compound unless otherwise noted, also encompasses all possible tautomeric forms of the illustrated compound, if any. The term also includes isotopically labeled compounds where one or more atoms have an atomic mass different from the atomic mass most abundantly found in nature. Examples of isotopes that may be incorporated into the present compounds include, but are not limited to, $^2$H (D), $^3$H (T), $^{11}$C, $^{13}$C, $^{14}$, $^{15}$N, $^{18}$O, $^{17}$O, any one of the isotopes of sulfur, etc. The compound may also exist in unsolvated forms as well as solvated forms, including hydrated forms. The compound may exist in multiple crystalline or amorphous forms. In general, all physical forms are equivalent for the uses contemplated herein and are intended to be within the scope of the present invention.

The expression "pharmaceutically acceptable salt" refers to those salts of the compounds of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977).

The term "solvate" refers to a physical association of one of the present compound with one or more solvent molecules, including water and non-aqueous solvent molecules. This physical association may include hydrogen bonding. In certain instances, the solvate will be capable of isolation, for example when one or more solvent molecules are incorporated in the crystal lattice of a crystalline solid. The term "solvate" encompasses both solution-phase and isolable solvates. Exemplary solvates include, without limitation, hydrates, hemihydrates, ethanolates, hemiethanolates, n-propanolates, iso-propanolates, 1-butanolates, 2-butanolate, and solvates of other physiologically acceptable solvents, such as the Class 3 solvents described in the *International Conference on Harmonization (ICH), Guide for Industry, Q3C Impurities: Residual Solvents* (1997). Accordingly, the compound as herein described also includes each of its solvates and mixtures thereof.

Herein a general chemical structure, such as Formula (I), with various substituents ($R^1$ to $R^{11}$, $X^1$ to $X^1$, etc.) and various radicals (alkyl, heterring, etc.) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

Similarly, a list of several elements, such as Compounds 1, 2, 3, etc., is intended to describe the ensemble of all elements listed as well as each individual element, which is thus incorporated into the specification as if it were individually recited herein. Further, all subsets of these listed elements are also incorporated into the specification as if they were individually recited herein.

Herein, the terms "alkyl", "alkylene", "alkenyl", "alkenylene", "alkynyl", "alkynylene" and their derivatives (such as alkoxy, alkyleneoxy, etc.) have their ordinary meaning in the art. For more certainty: alkyl is a monovalent saturated aliphatic hydrocarbon radical of general formula $C_nH_{2n+1}$ but may still be used in some circumstances to designate a multivalent group (e.g. an alkylene); alkenyl is a monovalent aliphatic hydrocarbon radical similar to an alkyl, but comprising at least one double bond; alkynyl is a monovalent aliphatic hydrocarbon radical similar to an alkyl, but comprising at least one triple bond; alkylene is a bivalent saturated aliphatic hydrocarbon radical of general formula —$C_nH_{2n}$— (also called alkanediyl); alkenylene is a bivalent aliphatic hydrocarbon radical similar to an alkylene, but comprising at least one double bond; alkynylene is a bivalent aliphatic hydrocarbon radical similar to an alkylene, but comprising at least one triple bond; alkyloxy or alkoxy is a monovalent radical of formula —O-alkyl; alkyleneoxy is a bivalent radical of formula —O-alkylene (e.g. alkyleneoxy is —O—$CH_2$—$CH_2$—, which is called ethyleneoxy, where a linear chain comprising two or more ethyleneoxy groups attached together (i.e. —O—$CH_2$—$CH_2$—]$_n$—) can be referred to as a polyethylene glycol (PEG), polyethylene oxide (PEO), or polyoxyethylene (POE) chain; alkenyloxy is a monovalent radical of formula —O-alkenyl; alkenyleneoxy is a bivalent radical of formula —O-alkenylene-; alkynyloxy is a monovalent radical of formula —O-alkynyl; and alkynyleneoxy is a bivalent radical of formula —O-alkynylene. It is to be noted that, unless otherwise specified, the hydrocarbon chains of the above groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2, or 1 carbon atom, or 2 carbon atoms.

Herein, the terms "cycloalkyl", "aryl", "heterocycloalkyl", and "heteroaryl" have their ordinary meaning in the art. For more certainty: aryl is a monovalent aromatic hydrocarbon radical presenting a delocalized conjugated π system, most commonly an arrangement of alternating single and double bonds, between carbon atoms arranged in one or more rings, wherein the rings can be fused (i.e. share two ring atoms), for example naphthalene, or linked together through a covalent bond, for example biphenyl, or linked together through a radical that allow continuation of the delocalized conjugated r system between the rings (e.g. —C(=O)—, —NRR—), for example benzophenone; heteroaryl is an aryl wherein at least one of the ring carbon atoms is replaced by a heteroatom, such as nitrogen or oxygen, where examples of heteroaryl include monocyclic or fused rings as well as and multiple rings linked together through a radical that allow continuation of the delocalized conjugated u system between the rings (e.g. —C(=O)—, —NRR—), such as indole-5-carbonylbenzene; cycloalkyl is a monovalent saturated aliphatic hydrocarbon radical of general formula $C_nH_{2n+1}$, wherein the carbon atoms are arranged in one or more rings (also called cycles) which may be spiro, fused or bridged; heterocycloalkyl is a cycloalkyl wherein at least one of the carbon atoms is replaced by a heteroatom.

Of note, term "heteroring" encompasses both non-aromatic (i.e. aliphatic), either saturated rings (i.e. heterocycloalkyls) or rings with one or more double and/or triple covalent bond (heterocycloalkenyls, heterocycloalkynyls, and heterocycloalkenynyls) as well as heteroaryls.

It is to be noted that, unless otherwise specified, the ring(s) of the above groups can each comprise between 4 and 8 ring atoms, preferably between 5 or 6 ring atoms. Also, unless otherwise specified, the above groups may preferably comprise one or more rings, preferably 1 or 2 rings, more preferably a single ring.

Examples of heteroaryl include thienyl, furanyl (furyl), pyrrolyl, imidazolyl, pyrazolyl, triazolyl, tetrazolyl, oxazolyl, isoxazolyl, oxadiazolyl, thiazolyl, isothiazolyl, thiadiazolyl, pyridinyl, pyridazinyl, pyrimidinyl, pyrazinyl, triazinyl, indolyl, 3H-indolyl, indolinyl, isoindolyl, indolizinyl, benzothienyl (benzothiophenyl), benzofuranyl, isobenzofuranyl, dibenzofuranyl, indazolyl, benzimidazolyl, benzoxazolyl, benzothiazolyl, benzotriazolyl, pyrrolopyridinyl (e.g. pyrrolo[3,2-b]pyridinyl or pyrrolo[3,2-c]pyridinyl), pyrazolopyridinyl (e.g. pyrazolo[1,5-a]pyridinyl), furopyridinyl, purinyl, imidazopyrazinyl (e.g. imidazo[4,5-b]pyrazinyl), quinolyl (quinolinyl), isoquinolyl (isoquinolinyl), quinolonyl, isoquinolonyl, cinnolinyl, phthalazinyl, quinazolinyl, quinoxalinyl, 4H-quinolizinyl, naphthyridinyl, and pteridinyl carbazolyl, acridinyl, phenanthridinyl, phenazinyl, phenothiazinyl, phenoxazinyl, tetrahydroquinolinyl, tetrahydroisoquinolinyl, and pyrido[2,3-b]-1,4-oxazin-3(4H)-one.

Herein, the term "heteroatom" means nitrogen, oxygen, sulfur (including when in —$SO_2$—), phosphorus, preferably nitrogen or oxygen.

The terms "subject" and "patient" are used interchangeably herein, and refer to an animal, preferably a mammal, most preferably a human. In an embodiment, the patient is an adult cancer (e.g., AML) patient. In an embodiment, the patient is less than 60 years old. In another embodiment, the patient is 60 years old or older. In another embodiment, the AML patient is a pediatric cancer (e.g., AML) patient.

Terms and symbols of genetics, molecular biology, biochemistry and nucleic acid used herein follow those of standard treatises and texts in the field, e.g. Green and Sambrook, Molecular Cloning: A Laboratory Manual, $4^{th}$ Edition, 2012 (Cold Spring Harbor Laboratory Press); Ausubel et al., Current Protocols in Molecular Biology (2001 and later updates thereto); Kornberg and Baker, *DNA Replication*, Second Edition (W University Science Books, 2005); Lehninger, *Biochemistry*, sixth Edition (WH Freeman & Co (Sd), New York, 2012); Strachan and Read, *Human Molecular Genetics*, Second Edition (Wiley-Liss, New York, 1999); Eckstein, editor, *Oligonucleotides and Analogs: A Practical Approach* (Oxford University Press, New York, 1991); Gait, editor, *Oligonucleotide Synthesis: A Practical Approach* (IRL Press, Oxford, 1984); and the like. All terms are to be understood with their typical meanings established in the relevant art.

Any and all combinations and subcombinations of the embodiments and features disclosed herein are also contemplated. For example, the expression of any combination of 2, 3, 4, 5 or more of the genes identified herein may be used in the methods described herein.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

In the studies described herein, it is shown that AML cells expressing high levels of HOX-network genes, which are associated with poor prognosis/survival, are sensitive to the heterocyclic compound Mubritinib. Mubritinib-sensitive AML cells were also shown to be enriched in AML samples having certain features, such as for example overexpression or underexpression of specific genes, certain cytogenetic or molecular risk factors, such as Normal Karyotype (NK), mutated NPM1, FLT3-ITD and DNMT3A specimens, and in specimens having high leukemic stem cell (LSC) frequencies. It is also demonstrated that Mubritinib, characterized as an inhibitor of the tyrosine kinase human epidermal growth factor receptor 2 (HER2/ErbB2), does not target this protein in AML cells, and compelling evidence that Mubritinib induces AML cell apoptosis through inhibition of mitochondrial activity/respiration, more particularly of the ETC, resulting in increased ROS production in sensitive AML cells, are provided. Based on these results, several heterocyclic compounds structurally related to Mubritinib were developed and shown to inhibit the growth of the tumor cell lines OCI-AML3 and MLL-AF9.

ii. Heterocyclic Compounds

The present description relates to the use of heterocyclic compounds structurally related to Mubritinib and their pharmaceutically acceptable salts, for example for the treatment of cancers, such as leukemia, including AML and more particularly Mubritinib-sensitive AML subtypes are described below. Several of the compounds described herein are novel, so the present disclosure also relates to these compounds or pharmaceutically acceptable thereof per se, i.e. independently from their use.

Examples of heterocyclic compounds are illustrated by general Formula I:

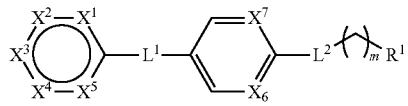

or a pharmaceutically acceptable salt thereof, wherein:
$X^1$ represents —N=, —CH=, or —O—;
$X^2$ represents —CH=, —C($R^2$)=, or a covalent bond;
$X^3$ represents —CH=, —C($R^2$)=, or a covalent bond;
$X^4$ represents —O—, —C($R^3$)=, —N=, or —S—; and
$X^5$ represents a covalent bond, —C($R^3$)=, or —O—;
provided that one of $X^2$ and $X^3$ is —C($R^2$)= and the other of $X^2$ and $X^3$ is —CH= or a covalent bond, and provided that at most only one of $X^2$, $X^3$, and $X^5$ represents a covalent bond;
$R^2$ represents ArylC($R^3$)=C(H)—, HeteroarylC($R^3$)=C(H)—, ArylN($R^3$)C(O)—, HeteroarylN($R^3$)C(O)—, Arylcyclopropyl-, Heteroarylcyclopropyl-, $R^3$OC(O)C(H)=C(H)—, $R^3$OC(O)—, Aryl-C≡C—, Heteroaryl-C≡C—, Aryl-, Heteroaryl-, Aryl-CH($R^3$)—CH($R^3$)—, or Heteroaryl-CH($R^3$)—CH($R^3$)—, wherein the Aryl group and the Heteroaryl group are optionally substituted with one to three $R^4$ groups, which are the same or different;
$R^3$ independently in each occurrence represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —$OR^6$, —N($R^6$)$_2$, —C(O)$OR^6$, —CN or —C(O)N($R^6$)$_2$;
$R^4$ independently in each occurrence represents —F, —Cl, —Br, —I, —$SR^3$, —$SOR^5$, —S(O)$_2R^5$, —S(O)$_2$N($R^3$)$_2$, -triazolyl, —CN, —C(O)$OR^3$, —C(O)$R^3$, —NO$_2$, —C(O)N($R^3$)$_2$, —$OR^3$, —C($R^3$)$_2$OH, —N($R^3$)$_2$, —N($R^3$)C(O)$R^3$, —N($R^3$)C(O)$OR^5$, —OC(O)N($R^3$)$_2$, —N$_3$, —$R^3$,

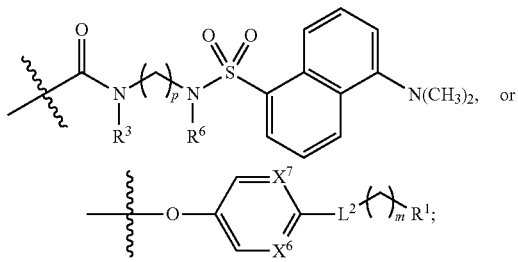

$R^5$ independently in each occurrence represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —$OR^6$, —N($R^6$)$_2$, —C(O)$OR^6$, —CN or —C(O)N($R^6$)$_2$;
$R^6$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl;
$L^1$ represents —CH$R^3$—O—, —CH$_2$—NH—, —C(O)NH—, —C(O)—CH$R^6$—, —C$R^6$=C$R^6$—, —CH$_2$—S—, —CH$_2$—, or —CH$_2$—O—CH$_2$—;

$X^6$ and $X^7$ independently represent —C$R^3$=, or —N=;
$L^2$ represents a covalent bond, —C(O)—, —C($R^3$)(OH)—, —O—, —S—, —CH$R^3$—, —CH($R^3$)—S—, or —CH($R^3$)—O—;
m independently in each occurrence represents an integer from 1 to 4;
p represents an integer from 1 to 6; and
$R^1$ represents heteroaryl, aryl, —N$_3$, —OH, —OC(O)N($R^7$)$_2$, —C(O)N($R^7$)$_2$, —N($R^7$)$_2$, —N($R^7$)C(O)$R^7$, —N($R^7$)C(O)$OR^8$, —N($R^7$)C(O)-$L^3$-$OR^7$, or —N($R^7$)C(O)-$L^3$-OC(O)N($R^7$)$_2$, the heteroaryl and aryl being optionally substituted with one or more $R^9$, which are the same or different, wherein:
$L^3$ represents $C_1$-$C_5$alkylene, $C_2$-$C_5$alkenylene, $C_2$-$C_5$alkynylene, or $C_1$-$C_4$fluoroalkylene, the alkylene, alkenylene, and alkynylene being optionally substituted with one or more $R^9$, which are the same or different;
$R^7$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl; the alkyl, alkenyl, alkynyl, and cycloalkyl being optionally substituted with one or more $R^9$, which are the same or different,
or when two $R^7$ groups are attached to a same nitrogen atom, the two $R^7$ groups together with the nitrogen atom to which they are attached optionally form a 5-7-membered heterocycloalkyl, the heterocycloalkyl optionally comprising one or more further heteroatom independently selected from —O—, —N($R^3$)—, —S—, —S(O)— and —SO$_2$—, the heterocycloalkyl being optionally substituted with one or more $R^9$, which are the same or different;
$R^8$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl; the alkyl, alkenyl, alkynyl, and cycloalkyl being optionally substituted with one or more $R^9$, which are the same or different; and
$R^9$ independently represents —$C_1$-$C_6$alkyl, —$C_0$-$C_6$alkyl-$OR^{11}$, —$C_3$-$C_6$cycloalkyl, —$C_3$-$C_6$cycloalkyl-$OR^{11}$, —$C_1$-$C_6$alkyl- OC(O)$R^{11}$, —$C_1$-$C_6$alkyl-OC(O)N($R^{11}$)$_2$, —$C_1$-$C_6$alkyl-OC(O)N($R^{11}$)-$L^4$-$OR^{11}$, —$C_0$-$C_6$alkyl-C(O)$OR^{11}$, —$C_0$-$C_6$alkyl-C(O)N($R^{11}$)$_2$, —$C_1$-$C_6$alkyl-N($R^{11}$)$_2$, —$C_1$-$C_6$alkyl-N($R^{11}$)C(O)$R^{11}$, —$C_1$-$C_6$alkyl-N($R^{11}$)C(O)-$L^4$-N($R^{11}$)—C(O)$R^{11}$, —$C_1$-$C_6$alkyl-N($R^{11}$)S(O)$_2R^{10}$, —$C_1$-$C_6$alkyl-N($R^{11}$)S(O)$_2$-$L^4$-N($R^{11}$)—C(O)$OR^{10}$, —Si($C_1$-$C_6$alkyl)$_3$, —C(O)—O—$C_1$-$C_6$alkyl, phenyl optionally substituted with $R^4$, benzyl optionally substituted with $R^4$, pyridinyl optionally substituted with $R^4$, or

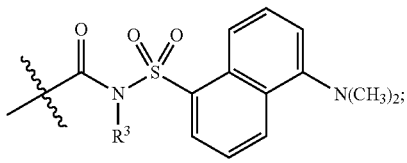

wherein:
$L^4$ represents $C_1$-$C_5$alkylene, $C_2$-$C_5$alkenylene, $C_2$-$C_5$alkynylene, or $C_1$-$C_4$fluoroalkylene; and
$R^{10}$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —$OR^6$, —N($R^6$)$_2$, —C(O)$OR^6$, —CN or —C(O)N($R^6$)$_2$;

$R^{11}$ independently represents —H, —$C_1$-$C_5$alkyl, —$C_2$-$C_5$alkenyl, —$C_2$-$C_5$alkynyl, —$C_1$-$C_4$fluoroalkyl, or —$C_3$-$C_7$cycloalkyl, the alkyl, alkenyl, alkynyl, and cycloalkyl being optionally substituted with —$OR^6$, —$N(R^6)_2$, —$C(O)OR^6$, —CN or —$C(O)N(R^6)_2$, or when two $R^{11}$ groups are attached to a same nitrogen atom, the two $R^{11}$ groups together with the nitrogen atom to which they are attached optionally form a 5-7-membered heterocycloalkyl, the heterocycloalkyl optionally comprising one or more further heteroatom independently selected from —O—, —$N(R^3)$—, —S—, —S(O)— and —$SO_2$—.

According to one example, the compound is of Formula I, wherein $R^5$, $R^8$ and $R^{10}$ are other than —H.

Herein, the following groups contained in Formula I:

(Formula II)

which is an aromatic ring, may be referred to herein as radical "Z". As will be apparent from the above, in Formula II, $X^2$, $X^3$, and $X^5$, can each represent a covalent bond, with the proviso that at most only one of $X^2$, $X^3$, and $X^5$ represents a covalent bond. In other words, the group of Formula II is a five- or six-membered aromatic ring (the term aromatic including also heteroaromatic).

Furthermore, the above general chemical formula comprises the proviso that one of $X^2$ and $X^3$ is —C(A)= and the other of $X^2$ and $X^3$ is —CH= or a covalent bond. This means that when $X^3$ represents a covalent bond, then $X^2$ and $X^5$ are not covalent bonds and $X^2$ must be —$C(R^2)$=. In other words, when $X^3$ represents a covalent bond, Formula II corresponds to the following Formula III:

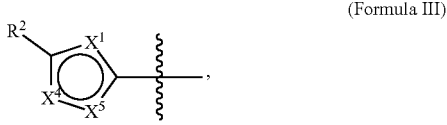
(Formula III)

wherein $X^5$ is —$C(R^3)$= or —O—. Similarly, when $X^2$ represents a covalent bond, $X^3$ and $X^5$ are not covalent bonds and $X^3$ must be —$C(R^2)$=, and thus Formula II also corresponds to formula III wherein $X^5$ is —$C(R^3)$= or —O—. Thus, in some examples, one of $X^2$ and $X^3$ represents a covalent bond, the other of $X^2$ and $X^3$ represents —$C(R^2)$=, and $X^5$ represents —$C(R^3)$=, or —O—, while $X^1$ and $X^4$ are as herein defined.

When $X^5$ represents a covalent bond, neither $X^2$ or $X^3$ can be a covalent bond, which means that one of them is —$C(R^2)$= and the other is —CH=. In other words, when $X^5$ represents a covalent bond, Formula II corresponds to the following Formulas IV and IV':

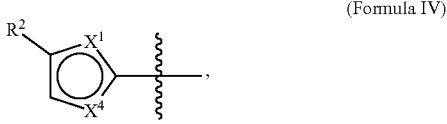
(Formula IV)

obtained when $X^2$ is —$C(R^2)$= and $X^3$ is —CH=; and

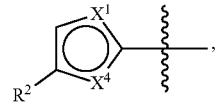
(Formula IV')

obtained when $X^2$ is —CH= and $X^3$ is —$C(R^2)$=.

Also included are compounds where in Formula II, none of $X^2$, $X^3$, and $X^5$ are covalent bonds. In which case, one of $X^2$ and $X^3$ is —$C(R^2)$= and the other is —CH=, while $X^5$ is —$C(R^3)$= or —O— and $X^1$ and $X^4$ are as defined above. Preferred such groups of Formula II include:

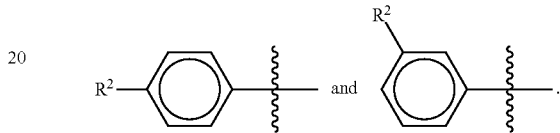

In some embodiments, $X^3$ is —CH=. In alternative embodiments, $X^3$ is a covalent bond. In yet other embodiments, $X^3$ is —$C(R^2)$=. In some other embodiments, $X^2$ is —CH=. In alternative embodiments, $X^2$ is a covalent bond. In yet other embodiments, $X^2$ is —$C(R^2)$=. In further embodiments, $X^1$ is —N= or —CH=. In other embodiments, $X^1$ is —N=. In alternative embodiments, $X^1$ is —CH=. In other embodiments, $X^1$ is —O—. In embodiments, $X^4$ is —O—. In alternative embodiments, $X^4$ is —$C(R^3)$=, for instance, wherein $R^3$ is H (i.e. $X^4$ being —CH=). In other alternative embodiments, $X^4$ is —N=. In yet other alternative embodiments, $X^4$ is —S—. In embodiments, $X^5$ is a covalent bond. In alternative embodiments, $X^5$ is —$C(R^3)$=, for instance, wherein $R^3$ is H (i.e. $X^5$ being —CH=). In other alternative embodiments, $X^5$ is —O—.

In some embodiments, in the group of Formula II, $X^1$ and $X^3$ each are —CH=, $X^2$ is —$C(R^2)$=, and $X^4$ and $X^5$ each are —$C(R^3)$=, wherein, in further embodiments, $R^3$ preferably represents H. In other embodiments, in the group of Formula II, $X^1$ and $X^3$ each represent —CH=, $X^2$ represents —$C(R^2)$=, $X^4$ is —N= and $X^5$ represents —$C(R^3)$=, wherein, in further embodiments, $R^3$ preferably represents H.

In preferred embodiments, in the group of Formula III, one of $X^2$ and $X^3$ is a covalent bond and the other is —$C(R^2)$=. In preferred such embodiments, $X^1$ represents —N=, $X^4$ represents —O— or —S—, preferably —O—, and $X^5$ represents —$C(R^3)$=, wherein, in further embodiments, $R^3$ preferably represents H.

As noted above, $R^2$ represents $ArylC(R^3)$=C(H)—, $HeteroarylC(R^3)$=C(H)—, $ArylN(R^3)C(O)$—, $HeteroarylN(R^3)C(O)$—, Arylcyclopropyl-, Heteroarylcyclopropyl-, $R^3OC(O)C(H)$=C(H)—, $R^3OC(O)$—, Aryl-C≡C—, Heteroaryl-C≡C—, Aryl-, Heteroaryl-, Aryl-$CH(R^3)$—$CH(R^3)$—, or Heteroaryl-$CH(R^3)$—$CH(R^3)$—. In preferred embodiments, $R^2$ represents $ArylC(R^3)$=C(H)—, $HeteroarylC(R^3)$=C(H)—, $ArylN(R^3)C(O)$—, Arylcyclopropyl-, $R^3OC(O)C(H)$=C(H)—, $R^3OC(O)$—, Aryl-, Heteroaryl-, or Aryl-$CH(R^3)$—$CH(R^3)$—. In more preferred embodiments, $R^2$ represents $ArylC(R^3)$=C(H)— or Heteroaryl, and more preferably $ArylC(R^3)$=C(H)—.

In preferred embodiments, the Aryl group in $R^2$ is phenyl or naphthyl, more preferably phenyl.

In preferred embodiments, the Heteroaryl group in $R^2$ is selected from:

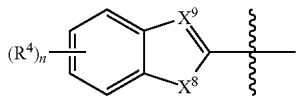

(wherein n represents an integer from 0 to 3, $X^8$ represents —NH—, —O—, or —S—, preferably —NH—, and $X^9$ is —N= or —CH=, preferably —CH=), pyridyl, pyrimidinyl, thienyl, isoxazolyl, quinolyl, isoquinolyl, indolyl, indolinyl, benzo[b]thienyl, benzimidazolyl, benzoxalolyl, benzofuranyl, isobenzofuranyl and benzothiazolyl, including any tautomer thereof. Preferably, Heteroaryl groups include

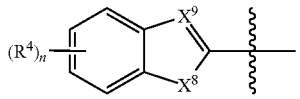

or pyridyl, and more preferably

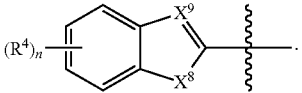

As noted above, all of these Aryl and Heteroaryl groups are optionally substituted with one to three $R^4$ groups, which are the same or different.

In $R^2$, preferred embodiments of ArylC($R^3$)=C(H)— include

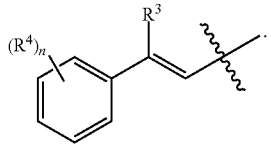

In $R^2$, preferred embodiments of HeteroarylC($R^3$)=C(H)— include

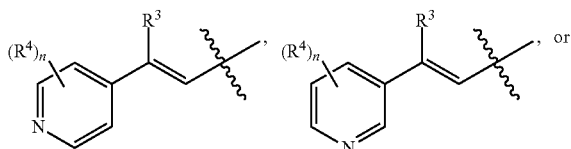

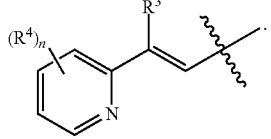

In $R^2$, preferred embodiments of Arylcyclopropyl— include

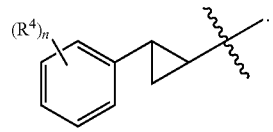

In $R^2$, preferred embodiments of ArylN($R^3$)C(O)— include

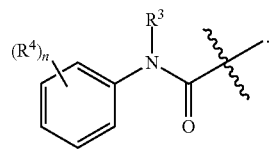

In $R^2$, preferred embodiments of $R^3$OC(O)— include MeOC(O)—.

In $R^2$, preferred embodiments of Aryl-CH($R^3$)—CH($R^3$)— include

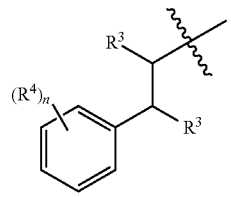

In $R^2$, preferred embodiments of Aryl include

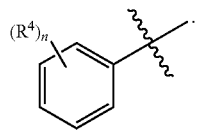

In $R^2$, preferred embodiments of Heteroaryl include

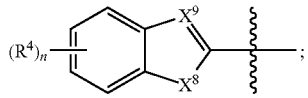

wherein n represents an integer from 0 to 3, $X^a$ represents —NH—, —O—, or —S—, preferably —NH—, and $X^9$ is —N= or —CH=, preferably —CH=.

In any and all of the above embodiments of $R^2$, $R^3$ preferably represents H or $CH_3$, more preferably H.

In any and all of the above embodiments of $R^2$, n represents an integer from 0 to 3 and $R^4$ is as defined above. In other words, the Aryl and/or the Heteroaryl contained in $R^2$ are optionally substituted with one to three (preferably one to two) $R^4$ groups, the same or different, preferably different. In other words, n is 0 to 3 in the above formula where it is present and preferably n is 0 to 2). In embodiments, these groups are unsubstituted (n=0). In alternative embodiments, these groups are substituted with one to three (i.e. n is 1 to 3), preferably one to two (n is 1 or 2), $R^4$ groups, the same or different, preferably different. In embodiments, these groups are substituted with one $R^4$ group (n=1). In embodiments, these groups are substituted with two $R^4$ groups (n=2), the same or different, preferably different. In embodiments, these groups are substituted with three $R^4$ groups (n=3), the same or different, preferably different. The $R^4$ groups optionally substituting the Aryl and/or the Heteroaryl contained in $R^2$ may be located at any position.

Examples of $R^2$ groups comprising 6-membered Aryl and Heteroaryl group in which the one $R^4$ group is preferably at position 2 include:

ArylC($R^3$)=C(H)— is preferably

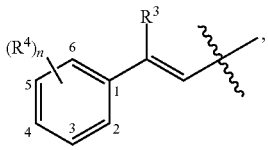

and

HeteroarylC($R^3$)=C(H)—, more preferably

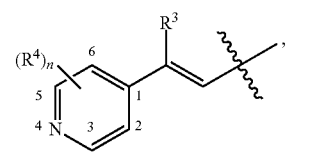

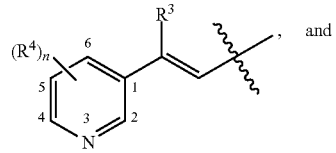, and

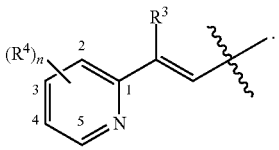

Examples of $R^2$ groups comprising 6-membered Aryl and Heteroaryl group in which the one $R^4$ group is preferably at position 3 include ArylC($R^3$)=C(H)—, preferably

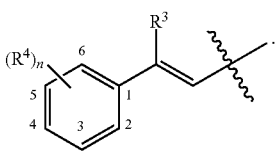

Examples of $R^2$ groups comprising 6-membered Aryl and Heteroaryl group in which the one $R^4$ group is preferably at position 4 include:

ArylC($R^3$)=C(H)—, preferably

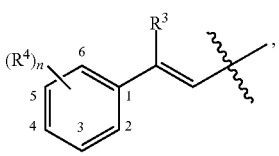

Arylcyclopropyl-, preferably

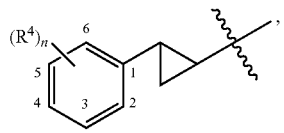

and

Aryl-, preferably

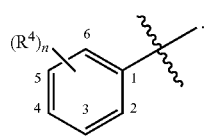

Furthermore, when the one $R^4$ group substitutes the

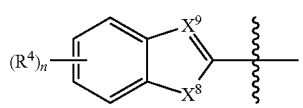

group, it is preferably at position 5 or 6, preferably 5. Such a group which is preferably substituted at position 5 or 6 is

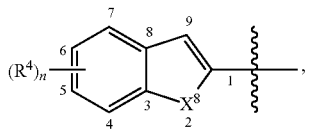

wherein $X^8$ is preferably —NH—.

Alternatively, when there are two $R^4$ groups (same or different), preferably different, substituting a 6-membered Aryl and Heteroaryl, preferably Aryl, preferably phenyl, they are preferably at positions 2 and 4, positions 3 and 4, or positions 2 and 6, more preferably at positions 2 and 4. Examples of $R^2$ groups comprising 6-membered Aryl group in which the two $R^4$ groups are thus located include ArylC($R^3$)=C(H)— and ArylN($R^3$)C(O)—, preferably ArylC($R^3$)=C(H)—, wherein Aryl is phenyl.

Furthermore, when two $R^4$ groups substitutes the

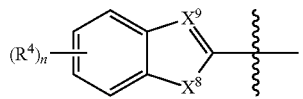

group, they are preferably at positions 5 and 7. A preferred such group which is preferably substituted at positions 5 and 7 is

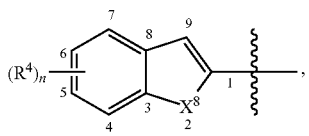

wherein $X^8$ is preferably —NH—.

Alternatively, when there are three $R^4$ groups (same or different), preferably the same, substituting a 6-membered Aryl and Heteroaryl, preferably Aryl, preferably phenyl, they are preferably at positions 3, 4, and 5. Examples of $R^2$ groups comprising 6-membered Aryl group in which the three $R^4$ group are thus located include ArylC($R^3$)=C(H)—, wherein Aryl is phenyl.

It will be noted above that the definition of $R^4$ refers in many instances to $R^3$ groups. Preferred $R^3$ groups (when in $R^4$) include —H, —$C_1$-$C_5$ alkyl, —$C_2$-$C_5$ alkynyl, or —$C_1$-$C_4$ fluoroalkyl. In such embodiments, a preferred $C_1$-$C_5$ alkyl is methyl. Furthermore, preferred $C_2$-$C_5$ alkynyl groups include —C≡CH and —$CH_2$—C≡CH. Furthermore, a preferred —$C_1$-$C_4$ fluoroalkyl is —$CF_3$.

In preferred embodiments, $R^4$ represents —F, —Cl, —Br, —I, —S(O)$_2$—$C_1$-$C_5$alkyl, -triazolyl, —CN, —C(O)O$R^3$, —NO$_2$, —C(O)N($R^3$)$_2$, —O$R^3$, —C($R^3$)$_2$OH, —N($R^3$)$_2$, —N$_3$, —$R^3$,

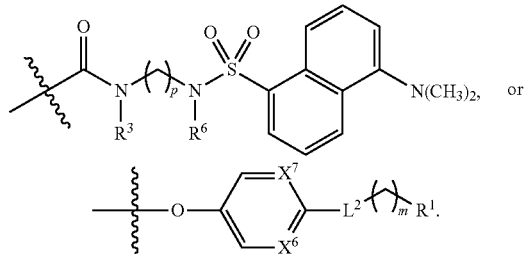

In more preferred embodiments, $R^4$ represents —F, —Br, —Cl, —CF$_3$, —S(O)$_2$Me, -triazolyl, —CN, —NO$_2$, —OCF$_3$, —OMe, —C(O)OMe, —CH$_2$OH, —OH, —C(O)NH$_2$, —NH$_2$, —N$_3$, —C(O)NHCH$_2$C≡CH, —C≡CH,

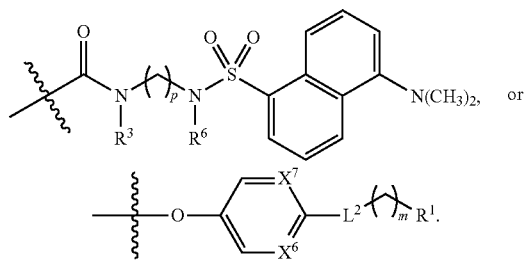

Most preferred $R^4$ groups include —F, —Br, —Cl, —CF$_3$, —S(O)$_2$Me, —CN, —NO$_2$, —OH, —OMe, —OCF$_3$, —N$_3$, CH$_2$OH, or —C(O)OMe.

When there is only one $R^4$ group, $R^4$ preferably represents F, Cl, Br, CN, CO$_2$Me, NO$_2$, OH, OCF$_3$, CH$_2$OH, or CF$_3$, preferably —F, —Cl, —Br, —CN, —CO$_2$Me, —NO$_2$, —OCF$_3$, —CH$_2$OH, or —CF$_3$, more preferably —F, —Br, —Cl, —CF$_3$, CO$_2$Me, —NO$_2$, —CN, —OCF$_3$, and —OMe, yet more preferably —F, —Br, —CF$_3$, CO$_2$Me, —NO$_2$, and —CN, even more preferably —F, CO$_2$Me, —Br, —NO$_2$, and —CN, and most preferably F or NO$_2$.

When there are two $R^4$ groups, $R^4$ preferably represents, independently is each occurrence, —F, —Br, —C, —CF$_3$, —S(O)$_2$Me, —NO$_2$, —OCF$_3$, —OMe, —C(O)OMe, —NH$_2$, —N$_3$,

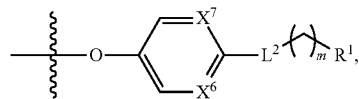

or -triazolyl, preferably F, Cl, Br, SO$_2$Me, CN, CO$_2$Me, NO$_2$, OMe, OCF$_3$, N$_3$, or CF$_3$, more preferably F, Cl, Br, CN, CO$_2$Me, NO$_2$, OCF$_3$, or CF$_3$, yet more preferably —F, —Br, —Cl, —CF$_3$, CN, NO$_2$, OCF$_3$, or —NO$_2$, and most preferably F, CN, NO$_2$, OCF$_3$, or CF$_3$. Preferred $R^4$ pairs include those wherein one of the two $R^4$ groups is F or —CF$_3$. Preferred $R^4$ pairs include Cl/Cl, F/N$_3$, F/Br, F/Cl, F/NH$_2$, F/CN, F/CF$_3$, F/S(O)$_2$Me, F/NO$_2$, F/OCF$_3$, F/OMe, F/C(O)OMe, F/F, F/triazolyl, F/N$_3$, CF$_3$/

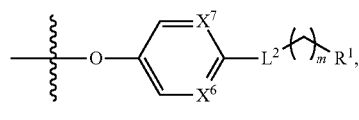

CF$_3$/NO$_2$, or NO$_2$/

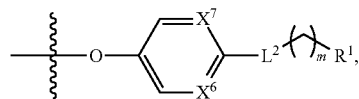

preferably F/Br, F/Cl F/CN, F/CF$_3$, F/S(O)$_2$Me, F/NO$_2$, F/OCF$_3$, F/OMe, F/C(O)OMe, F/N$_3$, F/NO$_2$ and F/F, more preferably F/F, F/Cl, F/Br, F/CN, F/CO$_2$Me, F/NO$_2$, F/OCF$_3$, or F/CF$_3$, and most preferably F/CN, F/NO$_2$, F/OCF$_3$, or F/CF$_3$.

When there are three $R^4$ groups, all $R^4$ preferably represent —F.

Herein, the term "triazolyl" indicate a monovalent radical of triazole, wherein the triazole can be any isomer and tautomer thereof. Triazoles are defined in the art as heterocyclic compounds of molecular formula $C_2H_3N_3$, having a five-membered ring of two carbon atoms and three nitrogen atoms. There are two sets of isomers that differ in the relative positions of the three nitrogen atoms. Each of these has two tautomers that differ by which nitrogen has a hydrogen bonded to it. Thus, the term "triazole" encompasses:

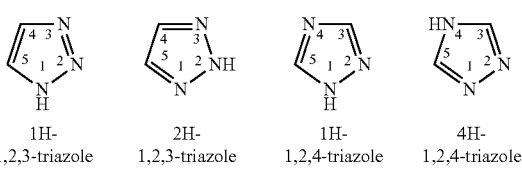

| 1H-1,2,3-triazole | 2H-1,2,3-triazole | 1H-1,2,4-triazole | 4H-1,2,4-triazole |

Herein, the triazolyl can be attached to the rest of the molecule by any of their available ring atoms. Preferred triazolyl groups include 1,2,3-triazol-1-yl, 1,2,3-triazol-2-yl, and 1,2,4-triazol-1-yl. A most preferred triazolyl (in $R^4$) include 1,2,3-triazol-2-yl.

Preferred

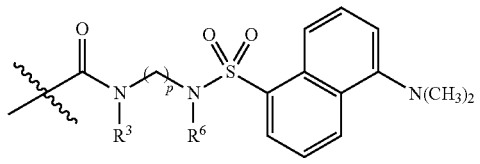

groups include those where R³ is H, p is 2, and/or R⁶ is H.

Preferred embodiments of

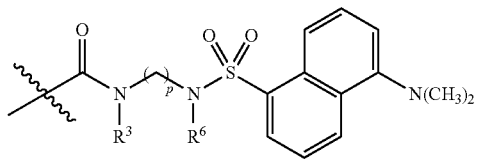

thus include

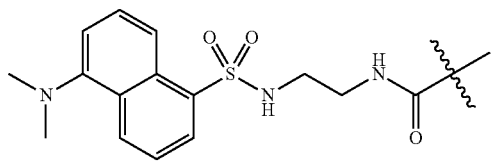

In preferred embodiments of

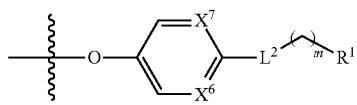

(as found in R⁴), wherein both X⁶ and X⁷ are —CH═; L² is a covalent bond, m is 1 to 4, preferably 4, and/or R¹ is a heteroaryl, more preferably a triazolyl group as defined herein. Preferred triazolyl groups include 1,2,4-triazol-1-yl and 1,2,3-triazol-1-yl. Most preferred

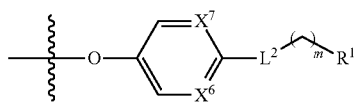

groups include:

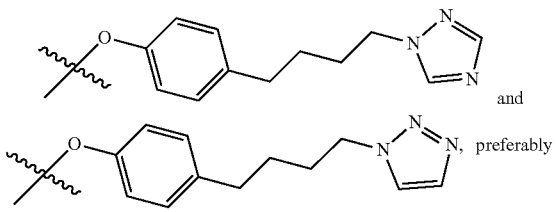

and

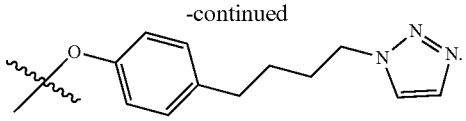

In preferred embodiments of Formula I, L¹ represents —CHR³—O—, —CH₂—NH—, —C(O)NH—, —CR⁶═CR⁶—, —CH₂—S—, or —CH₂—, preferably —CHR³—O—, —CH₂—NH—, or —CR⁶═CR⁶—, and most preferably —CHR³—O—. In preferred embodiments, in L¹, R³ is H. In preferred embodiments, in L¹, R⁶ is H.

In preferred embodiments of Formula I, both X⁶ and X⁷ represent —CR³═ or one of X⁶ and X⁷ represents —CR³═ and the other represents —NH═, preferably both X⁶ and X⁷ represent —CR³═. In preferred embodiments, in X⁶ and X⁷, R³ is H.

In preferred embodiments of Formula I, L² represents a covalent bond, —C(O)—, —C(R³)(OH)—, —O—, —S—, or —CHR³—O—, In more preferred embodiments, L² preferably represents a covalent bond, —C(O)—, —C(R³)(OH)—, or —S—, most preferably a covalent bond or —S—. In preferred embodiments, in L², R³ is H.

In preferred embodiments, m represents 2, 3 or 4, preferably 3 or 4, and more preferably 4.

In preferred embodiments of Formula I, R¹ represents heteroaryl, —N₃, —OH, —OC(O)N(R⁷)₂, —C(O)N(R⁷)₂, —N(R⁷)C(O)R⁷, —N(R⁷)C(O)OR⁸, or —N(R⁷)C(O)-L³-OC(O)N(R⁷)₂, preferably heteroaryl, —N(R⁷)C(O)R⁷, or —N(R⁷)C(O)-L³-OC(O)N(R⁷)₂, and more preferably heteroaryl, the heteroaryl being optionally substituted with one or more R⁹, which are the same or different; R⁷, R⁸, R⁹ and L³ being as defined above.

In preferred embodiments, R⁷ is —H, or —C₁-C₅alkyl, the alkyl being optionally substituted with one or more R⁹, which are the same or different, or when two R⁷ groups are attached to a same nitrogen atom, the two R⁷ groups together with the nitrogen atom to which they are attached optionally form a 5-7-membered heterocycloalkyl, the heterocycloalkyl comprising one or more further heteroatom or heteroatom-containing group independently selected from —O—, —N(R³)—, —S—, —S(O)—, and —SO₂—, the heterocycloalkyl being optionally substituted with one or more R⁹, which are the same or different.

In preferred embodiments, the alkyl in R⁷ is methyl, ethyl, or butyl (which is more preferably t-butyl).

In preferred embodiments, the heterocycloalkyl optionally formed when two R⁷ groups are attached to a same nitrogen atom, is a 6-membered heterocycloalkyl. In embodiments, the heterocycloalkyl comprises one or more, preferably one, further heteroatom. In preferred embodiments, this heteroatom is oxygen. In most preferred embodiments, the heterocycloalkyl is 4-morpholinyl. As noted above, the heterocycloalkyl being optionally substituted with one or more R⁹, which are the same or different. In preferred embodiments, the heterocycloalkyl is unsubstituted.

As noted above, the alkyl, alkenyl, alkynyl, cycloalkyl, alkylene, and heterocycloalkyl in R⁷ are optionally substituted with one or more R⁹, which are the same or different (and which are as defined above). In preferred embodiments, these groups are unsubstituted. In alternative embodiments, these groups in R¹ are substituted, preferably with one or two, more preferably with one R⁹. In such specific embodiments, $R^9$, when it substitutes the alkyl, alkenyl, alkynyl, cycloalkyl, or alkylene group, preferably the alkyl, in $R^7$ represent —OH.

In preferred embodiments, $R^8$ is —H, or —$C_1$-$C_5$alkyl, the alkyl being optionally substituted with one or more $R^9$, which are the same or different. More preferably, the alkyl in $R^8$ is methyl, ethyl, or butyl (which is more preferably t-butyl). As noted above, the alkyl, alkenyl, alkynyl, cycloalkyl, alkylene, and heterocycloalkyl in $R^8$ are optionally substituted with one or more $R^9$, which are the same or different (and which are as defined above). In preferred embodiments, these groups are unsubstituted. In alternative embodiments, these groups in $R^1$ are substituted, preferably with one or two, more preferably with one $R^9$. In such specific embodiments, $R^9$, when it substitutes the alkyl, alkenyl, alkynyl, cycloalkyl, or alkylene group, preferably the alkyl, in $R^8$ represent —OH.

In preferred embodiments, $L^3$ represents $C_1$-$C_5$ alkylene, preferably ethylene. As noted above, the alkylene, alkenylene, and alkynylene in $L^3$ are optionally substituted with one or more $R^9$, which are the same or different (and which are as defined above). In preferred embodiments, these groups are unsubstituted.

In preferred embodiments, the heteroaryl in $R^1$ is triazolyl, imidazolyl, pyrazolyl, pyridinyl, thiazolyl, pyrimidinyl, tetrazolyl, pyrazinyl, pyridazinyl, oxadiazolyl, or thiadiazolyl, preferably triazolyl, imidazolyl, pyridinyl, thiazolyl, pyrimidinyl, pyridazinyl, ortetrazolyl, more preferably triazolyl, pyridazinyl, orimidazolyl, and most preferably pyridazinyl or triazolyl, each of which being optionally substituted with one or more $R^9$, which are the same or different.

In embodiments, the triazolyl in $R^1$ is a 1,2-3-triazolyl or a 1,2-4-triazolyl, most preferably 1,2,3-triazol-1-yl or 1,2,4-triazol-1-yl—which are as noted above optionally substituted with one or more $R^9$, which are the same or different.

Herein, the term "imidazolyl" indicates a monovalent radical of imidazole and any tautomer thereof. The imidazolyl can be attached to the rest of the molecule by any of its available ring atoms. In some embodiments, the imidazolyl in $R^1$ is imidazol-1-yl (i.e. linked by one of its nitrogen atoms)—which is as noted above optionally substituted with one or more $R^9$, which are the same or different.

Herein, the term "pyrazolyl" indicates a monovalent radical of pyrazole and any tautomer thereof. The pyrazolyl can be attached to the rest of the molecule by any of its available ring atoms. In embodiments, the pyrazolyl in $R^1$ is pyrazol-1-yl (i.e. linked by one of its nitrogen atoms)—which is as noted above optionally substituted with one or more $R^9$, which are the same or different.

Herein, the terms "pyridyl" and "pyridinyl", which are synonymous, both indicate a monovalent radical of pyridine. The pyridinyl can be attached to the rest of the molecule by any of its available ring atoms. In embodiments, the pyridinyl in $R^1$ is pyridin-3-yl or pyridin-4-yl—which are as noted above optionally substituted with one or more $R^9$, which are the same or different.

Herein, the term "thiazolyl" indicates a monovalent radical of thiazole. The thiazolyl can be attached to the rest of the molecule by any of its available ring atoms. In embodiments, the thiazolyl in $R^1$ is thiazol-2-yl—which are as noted above optionally substituted with one or more $R^9$, which are the same or different.

Herein, the terms "pyrimidinyl" indicate a monovalent radical of pyrimidine. The pyrimidinyl can be attached to the rest of the molecule by any of its available ring atoms. In embodiments, the pyrimidinyl in $R^1$ is pyrimidin-5-yl—which is as noted above optionally substituted with one or more $R^9$, which are the same or different.

Herein, the term "tetrazolyl" indicates a monovalent radical of tetrazole and any tautomer thereof. The tetrazolyl can be attached to the rest of the molecule by any of its available ring atoms. In some embodiments, the tetrazolyl in $R^1$ is 1,2,3,4-tetrazol-1-yl or 1,2,3,4-tetrazol-2-yl—which are as noted above optionally substituted with one or more $R^9$, which are the same or different.

Herein, the term "pyrazinyl" indicates a monovalent radical of pyrazine. The pyrazinyl can be attached to the rest of the molecule by any of its available ring atoms. Herein, the term "pyridazinyl" indicates a monovalent radical of pyridazine. The pyridazinyl can be attached to the rest of the molecule by any of its available ring atoms.

Herein, the term "oxadiazolyl" indicates a monovalent radical of oxadiazole and any tautomer thereof. Oxadizazole is defined in the art as a heterocyclic compound of molecular formula $C_2H_2N_2O$. There are four isomers of oxadiazole:

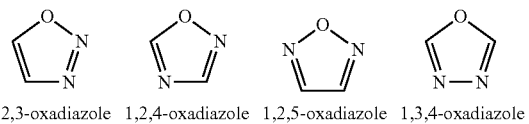

1,2,3-oxadiazole  1,2,4-oxadiazole  1,2,5-oxadiazole  1,3,4-oxadiazole

The oxadiazolyl can be attached to the rest of the molecule by any of its available ring atoms. In some embodiments, the oxadiazolyl in $R^1$ is a 1,2,4-oxadiazolyl (an example thereof being attached by the carbon between the two nitrogen atoms)—which is as noted above optionally substituted with one or more $R^9$, which are the same or different.

Herein, the term "thiadiazolyl" indicates a monovalent radical of thiadiazole and any tautomer thereof. Thiadiazole is defined in the art as a heterocyclic compound of molecular formula $C_2H_2N_2S$. There are four isomers of thiadiazole:

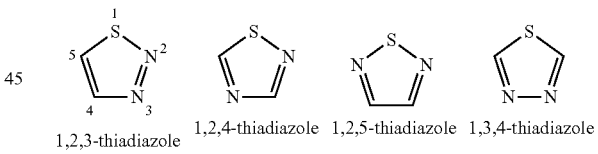

1,2,3-thiadiazole  1,2,4-thiadiazole  1,2,5-thiadiazole  1,3,4-thiadiazole

The thiadiazolyl can be attached to the rest of the molecule by any of its available ring atoms. In some embodiments, the thiadiazolyl in $R^1$ is a 1,2,4-thiadiazolyl—which is as noted above optionally substituted with one or more $R^9$, which are the same or different.

In more preferred embodiments, the heteroaryl in $R^1$ is a 1,2,3-triazolyl, a 1,2-4-triazolyl, an imidazolyl, a pyrazolyl, a pyridinyl, a pyridazinyl, a thiazolyl, a pyrimidinyl, or a 1,2,3,4-tetrazolyl, preferably an imidazolyl, a pyridazinyl, or a 1,2,3-triazolyl, more preferably a pyridazinyl or 1,2,3-triazolyl.

In yet more preferred embodiments, the heteroaryl in $R^1$ is 1,2,3-triazol-1-yl, 1,2-4-triazolyl, imidazol-1-yl, pyrazol-1-yl, pyridin-3-yl, pyridin-4-yl, pyridazin-3-yl, thiazol-2-yl, pyrimidin-5-yl, 1,2,3,4-tetrazol-1-yl, or 1,2,3,4-tetrazol-2-yl, preferably 1,3-imidazol-1-yl, pyridazin-3-yl, or 1,2,3-triazol-1-yl, more preferably pyridazin-3-yl or 1,2,3-triazol-1-yl.

As noted above, the aryl and the heteroaryl in $R^1$ are optionally substituted with one or more $R^9$, which are the same or different (and which are as defined above). In preferred embodiments, the aryl and heteroaryl in $R^1$ are unsubstituted. In alternative embodiments, the aryl and the heteroaryl in $R^1$ are substituted, preferably with one or two $R^9$, more preferably with one $R^9$. In some embodiments, $R^9$ (especially when substituting the aryl and the heteroaryl in $R^1$) is —$C_1$-$C_5$alkyl, —$C_0$-$C_6$alkyl-$OR^{11}$, —$C_3$-$C_6$cycloalkyl-$OR^{11}$, —$C_1$-$C_6$alkyl-$OC(O)N(R^{11})_2$, —$C_1$-$C_6$alkyl-$OC(O)N(R^{11})$-$L^4$-$OR^1$, —$C_0$-$C_6$alkyl-$C(O)OR^{11}$, —$C_0$-$C_6$alkyl-$C(O)N(R^{11})_2$, —$C_1$-$C_5$alkyl-$N(R^{11})_2$, —$C_1$-$C_6$alkyl-$N(R^{11})C(O)R^{11}$, —$C_1$-$C_6$alkyl-$N(R^{11})S(O)_2R^{10}$, or $Si(C_1$-$C_5$alkyl$)_3$, preferably —$C_1$-$C_5$alkyl-$OC(O)N(R^{11})_2$, —$C_1$-$C_5$alkyl-$OC(O)N(R^{11})$-$L^4$-$OR^{11}$, —$C_0$-$C_6$alkyl-$C(O)N(R^{11})_2$, —$C_1$-$C_5$alkyl-$N(R^{11})_2$, —$C_1$-$C_5$alkyl-$N(R^{11})S(O)_2R^{10}$, or $Si(C_1$-$C_5$alkyl$)_3$, more preferably —$C_1$-$C_6$alkyl-$OC(O)N(R^{11})_2$, —$C_1$-$C_5$alkyl-$OC(O)N(R^{11})$-$L^4$-$OR^{11}$, —$C_1$-$C_5$alkyl-$N(R^{11})_2$, or $Si(C_1$-$C_5$alkyl$)_3$, and most preferably $Si(C_1$-$C_5$alkyl$)_3$.

In some embodiments, the —$C_1$-$C_6$ alkyl moieties in $R^9$ are —$C_1$-$C_4$, preferably —$C_1$-$C_2$, and more preferably —$C_2$ alkyl moieties; and/or the —$C_0$-$C_6$ alkyl moieties are —$C_0$-$C_4$, preferably —$C_0$-$C_2$, and more preferably —$C_0$ (i.e. the alkyl moiety being absent) or —$C_2$ alkyl moieties.

As will be noted above, the definitions of $R^9$ (general and preferred) refer to groups $R^{10}$, $R^{11}$, and $L^4$. In $R^9$, the $R^{10}$, $R^{11}$, and $L^4$ groups are as defined above.

In more preferred embodiments, $R^{11}$ is H, —$C_1$-$C_5$alkyl, —$C_2$-$C_5$alkynyl, —$C_1$-$C_4$fluoroalkyl, or —$C_3$-$C_7$cycloalkyl or two $R^{11}$ groups together with the nitrogen atom to which they are attached optionally form a 5-7-membered heterocycloalkyl, the heterocycloalkyl optionally comprising one or more further heteroatom independently selected from —O—, —$N(R^3)$—, —S—, S(O) and $S(O)_2$.

In some embodiments, —$C_1$-$C_5$alkyl in $R^{11}$ is methyl, ethyl, propyl (preferably isopropyl), butyl (preferably tert-butyl) or pentyl. In other embodiments, the —$C_2$-$C_5$ alkynyl in $R^{11}$ is —$CH_2CH_2$—C≡CH or —$CH_2$C≡CH. In embodiments, the —$C_1$-$C_4$ fluoroalkyl in $R^{11}$ is —$CF_3$. In embodiments, the $C_3$-$C_7$ cycloalkyl in $R^{11}$ is cyclopentyl. In further embodiments, the alkyl and alkynyl groups in $R^{11}$ are unsubstituted.

In embodiments, the heterocycloalkyl optionally formed when two $R^{11}$ groups are attached to a same nitrogen atom is a 6-membered heterocycloalkyl. In embodiments, the heterocycloalkyl comprising one or more, preferably one, further heteroatom. Preferably, this heteroatom is —$SO_2$. In most preferred embodiments, the heterocycloalkyl is

In other preferred embodiments, $R^{10}$ is —$C_1$-$C_5$alkyl, —$C_2$-$C_5$alkynyl, —$C_1$-$C_4$fluoroalkyl, or —$C_3$-$C_7$cycloalkyl. In some embodiments, —$C_1$-$C_5$alkyl in $R^{10}$ is methyl, ethyl, propyl (preferably isopropyl), butyl (preferably tert-butyl) or pentyl. In other embodiments, the —$C_2$-$C_5$ alkynyl in $R^{10}$ is —$CH_2CH_2$—C≡CH or —$CH_2$C≡CH. In embodiments, the —$C_1$-$C_4$ fluoroalkyl in $R^{10}$ is —$CF_3$. In embodiments, the $C_3$-$C_7$ cycloalkyl in $R^{10}$ is cyclopentyl. In further embodiments, the alkyl and alkynyl groups in $R^{10}$ are unsubstituted.

In other embodiments, $L^4$ represents $C_1$-$C_5$ alkylene, preferably ethylene.

In embodiments, in $C_1$-$C_5$alkyl-$OR^{11}$ in $R^9$, $R^{11}$ represents H. In embodiments, in —$C_3$-$C_6$cycloalkyl-$OR^{11}$ in $R^9$, $R^{11}$ represents H. In embodiments, in —$C_1$-$C_6$alkyl-$OC(O)N(R^{11})_2$ in $R^9$, both $R^{11}$ groups represent methyl or one $R^{11}$ group represents H and the other represents propyl (preferably isopropyl), butyl (preferably tertbutyl), or cyclopentyl. In embodiments, in —$C_1$-$C_6$alkyl-$OC(O)N(R^{11})$-$L^4$-$OR^{11}$ in $R^9$, $N(R^{11})$ represents NH, $L^4$ represents ethylene and/or $OR^{11}$ represents OH. In embodiments, in —$C_0$-$C_5$alkyl-$C(O)OR^{11}$ in $R^9$, $R^{11}$ represents ethyl or tert-butyl. In embodiments, in —$C_0$-$C_6$alkyl-$C(O)N(R^{11})_2$ in $R^9$, one $R^{11}$ represents H and the other represents an alkynyl, preferably —$CH_2$—C≡CH. In embodiments, in —$C_1$-$C_6$alkyl-$N(R^{11})_2$ in $R^9$, both $R^{11}$ groups represent H, or one $R^{11}$ group represents H and the other represents methyl, or both $R^{11}$ together with the nitrogen atom to which they are attached form

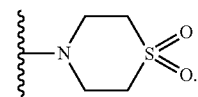

In embodiments, in —$C_1$-$C_6$alkyl-$N(R^{11})C(O)R^{11}$ in $R^9$, $N(R^{11})$ represents NH and/or $C(O)R^{11}$ represents an C(O)-alkyne, preferably $C(O)$—$CH_2CH_2$—C≡CH. In embodiments, in —$C_1$-$C_6$alkyl-$N(R^{11})S(O)_2R^{10}$ in $R^9$, $N(R^{11})$ represents NH and/or $S(O)_2R^{10}$ represents $S(O)_2$Me or $S(O)_2CF_3$.

In most preferred embodiments, $R^9$ (especially when substituting the aryl or the heteroaryl in $R^1$) represents Me, —$SiMe_3$, —$CH_2OH$, —$(CH_2)_2OH$, —$(CH_2)_3OH$, —$(CH_2)_4OH$, —$CH_2NH_2$, —$(CH_2)_2NH_2$, —$CH_2NHMe$, —$C(O)OEt$,

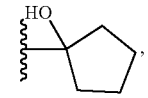

—$(CH_2)_2O$—$C(O)NMe_2$, —$(CH_2)_2NH$—$SO_2$-Me, —$(CH_2)_2NH$—$SO_2$—$CF_3$, —$(CH_2)_2O$—$C(O)NH$—$(CH_2)_2$OMe, —$(CH_2)_2O$—$C(O)NH$—isopropyl, —$(CH_2)_2O$—$C(O)NH$-cyclopentyl,

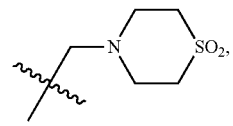

—$(CH_2)_4$—$C(O)$—NH—$CH_2$—C≡CH, —$(CH_2)_2NHC(O)(CH_2)_2$—C≡CH, or

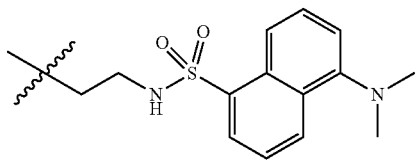

In preferred embodiments, the heteroaryl in R¹ is:

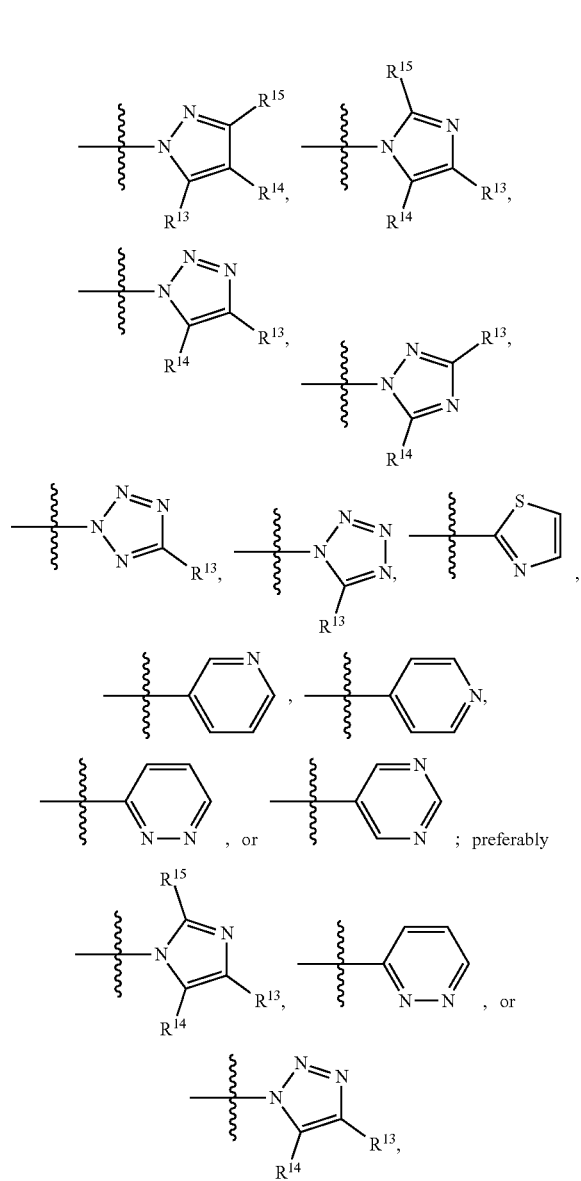

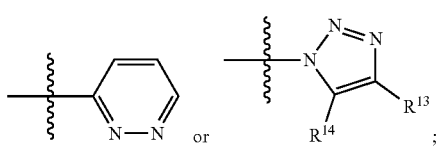

wherein $R^{13}$, $R^{14}$ and $R^{15}$ are independently H or $R^9$, wherein $R^9$ is as defined herein (including the general definition and the preferred embodiments thereof).

Overall, in more preferred embodiments, R¹ represents —N₃, —C(O)—N(H)—CH₂—C° CH, —OH, —OC(O)—(N-morpholine), —O—C(O)—NMe₂, —O—C(O)-NEt₂, —N(H)C(O)H, —N(H)—C(O)O-tert-butyl; —N(H)—C(O)—(CH₂)₂OH, —N(H)—C(O)—(CH₂)₂OC(O)NMe₂,

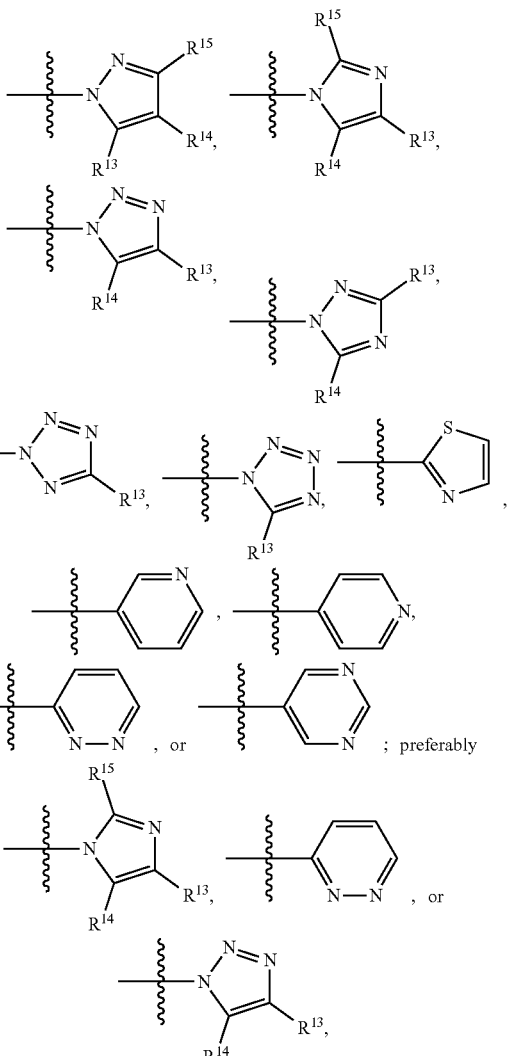

and more preferably

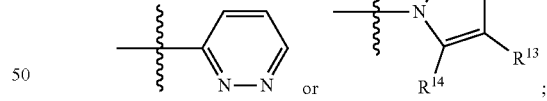

wherein $R^{13}$, $R^{14}$ and $R^{15}$ are independently H or $R^9$, wherein $R^9$ is as defined herein (including the general definition and the preferred embodiments thereof).

In preferred embodiments, $R^{13}$ represents H, Me, SiMe₃, —CH₂OH, —(CH₂)₂OH, —(CH₂)₃OH, —(CH₂)₄OH, —C(O)OEt, —CH₂NHMe,

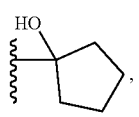 , 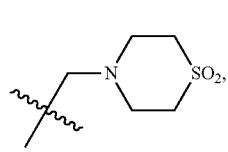

—CH$_2$NH$_2$, —(CH$_2$)$_2$NH$_2$, —(CH$_2$)$_4$—C(O)—NH—C≡CH, —(CH$_2$)$_2$NHC(O)(CH$_2$)$_2$—C≡CH, —(CH$_2$)$_2$OCONMe$_2$, —(CH$_2$)$_2$O—C(O)NH—(CH$_2$)$_2$OMe, —(CH$_2$)$_2$ O—C(O)NH-isopropyl, —(CH$_2$)$_2$O—C(O)NH-tertbutyl, or —(CH$_2$)$_2$O—C(O)NH-cyclopentyl, preferably H, —(CH$_2$)$_2$NHC(O)(CH$_2$)$_2$—C≡CH, —(CH$_2$)$_2$OCONMe$_2$, —(CH$_2$)$_2$O—C(O)NH-isopropyl, —(CH$_2$)$_2$O—C(O)NH-cyclopentyl, —(CH$_2$)$_2$O—C(O)NH—(CH$_2$)$_2$OMe,

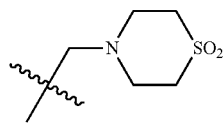 [SMILES: *CN1CCS(=O)(=O)CC1]

or —SiMe$_3$, more preferably H or —SiMe$_3$, and most preferably H.

In preferred embodiments, R$^{14}$ represents H, —C(O)OEt, —CH$_2$OH, —(CH$_2$)$_2$OH, or

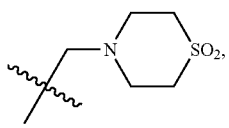

preferably H.

In preferred embodiments, R$^{15}$ represents H, —(CH$_2$)$_2$OH, —(CH$_2$)$_2$NH$_2$, —(CH$_2$)$_2$OC(O)—NMe$_2$, —(CH$_2$)$_2$NH—SO$_2$Me, or —(CH$_2$)$_2$NH—SO$_2$CF$_3$, preferably H, —(CH$_2$)$_2$OCONMe$_2$, —(CH$_2$)$_2$NH—SO$_2$Me, or —(CH$_2$)$_2$NH—SO$_2$CF$_3$, more preferably H or —(CH$_2$)$_2$OCONMe$_2$, and most preferably H.

In more preferred embodiments, especially when R$^1$ is

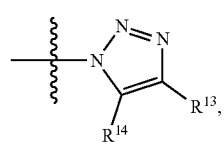

both R$^{13}$ and R$^{14}$ are H;
R$^{13}$ is R$^9$, wherein R$^9$ is as defined in any one of claims above, and R$^{14}$ is H;
both R$^{13}$ and R$^{14}$ are —C(O)OEt;
both R$^{13}$ and R$^{14}$ are —CH$_2$OH; or
R$^{13}$ is H and R$^{14}$ is

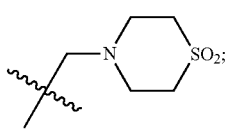 [SMILES: *CN1CCS(=O)(=O)CC1]

most preferably both R$^{13}$ and R$^{14}$ are H.

In other preferred embodiments, especially when R$^1$ is

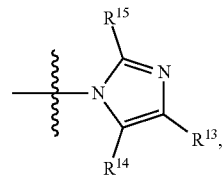

both R$^{13}$ and R$^{14}$ are H, and R$^{15}$ is H, —(CH$_2$)$_2$OH, —(CH$_2$)$_2$ NH$_2$, —(CH$_2$)$_2$OC(O)—NMe$_2$, —(CH$_2$)$_2$NH—SO$_2$Me, or —(CH$_2$)$_2$NH—SO$_2$CF$_3$, preferably H.

In other preferred embodiments, especially when R$^1$ is

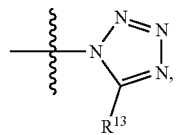

R$^{13}$ is H.

In other preferred embodiments, especially when R$^1$ is

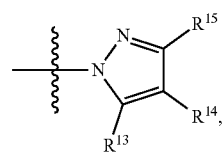

R$^{13}$, R$^{14}$, and R$^{15}$ are each H.

In other preferred embodiments, especially when R$^1$ is

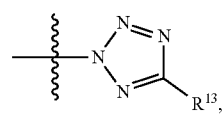

R$^{13}$ is H or methyl.

In other preferred embodiments, especially when R$^1$ is

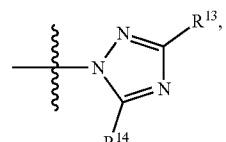

R$^{13}$ is H or methyl and R$^{14}$ is H.

In other preferred embodiments, especially when R$^1$ is

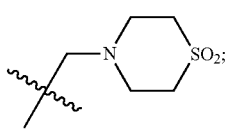 [SMILES: *CN1CCS(=O)(=O)CC1]

R$^{13}$ and R$^{14}$ are each H.

In other preferred embodiments, especially when $R^1$ is

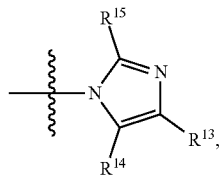

$R^{13}$, $R^{14}$, and $R^{15}$ are each H.

In some embodiments of the compounds of Formula I:
$X^1$ is —N═, $X^2$ is a covalent bond, $X^3$ is —C($R^2$)═, $X^4$ is —O— or —S—, and $X^5$ is —C($R^3$)═, wherein
$R^2$ represents ArylC($R^3$)═C(H)—, HeteroarylC($R^3$)═C(H)—, Heteroaryl-, or

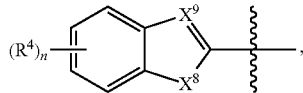

wherein:
the Aryl group and the Heteroaryl group are optionally substituted with one to three $R^4$ groups, which are the same or different;
n represents an integer from 0 to 3;
$X^8$ represents —NH—, or —O—; and
$X^9$ is —CH═;
$R^3$ independently represents —H, —$C_1$-$C_5$alkyl, —$C_1$-$C_4$fluoroalkyl, or —$C_3$-$C_7$cycloalkyl, the alkyl being optionally substituted with —$OR^6$;
$R^4$ independently represents —F, —Cl, —Br, —I, —S(O)$_2$ $R^5$, —CN, —C(O)$OR^3$, —$NO_2$, —$OR^3$, —C($R^3$)$_2$OH, —$N_3$, or —$R^3$;
$R^5$ independently represents —$C_1$-$C_5$alkyl, —$C_1$-$C_4$fluoroalkyl, or —$C_3$-$C_7$cycloalkyl, the alkyl being optionally substituted with —$OR^6$;
$R^6$ is —H;
$L^1$ represents —CH$R^3$—O—, —$CH_2$—NH—, —CH═CH— or —$CH_2$—O—$CH_2$—;
$L^2$ represents a covalent bond, —C(O)—, —CH(OH)—, or —S—;
$X^6$ and $X^7$ independently represent —CH═ or —N═;
m is an integer from 1 to 4; and
$R^1$ represents heteroaryl or —N($R^7$)C(O)$R^7$, the heteroaryl being optionally substituted with one or more $R^9$, which are the same or different, wherein:
$R^7$ independently represents —$C_1$-$C_5$alkyl;
$R^9$ independently represents —$C_1$-$C_5$alkyl, —$C_0$-$C_6$alkyl-$OR^{11}$, —$C_1$-$C_5$alkyl-OC(O)N($R^{11}$)$_2$, —$C_0$-$C_6$alkyl-C(O)N($R^{11}$)$_2$, —$C_1$-$C_6$alkyl-N($R^{11}$)S(O)$_2R^{10}$, or —Si($C_1$-$C_5$alkyl)$_3$;
$R^{10}$ independently represents —$C_1$-$C_5$alkyl, —$C_2$-$C_5$alkynyl, or —$C_3$-$C_7$cycloalkyl, the alkyl, alkynyl, and cycloalkyl being optionally substituted with —$OR^6$;
$R^{11}$ independently represents —$C_1$-$C_5$alkyl, —$C_2$-$C_5$alkynyl, or —$C_3$-$C_7$cycloalkyl, the alkyl, alkynyl, and cycloalkyl being optionally substituted with —$OR^6$, or
when two $R^{11}$ groups are attached to a same nitrogen atom, then the two $R^{11}$ groups together with the nitrogen atom to which they are attached optionally form a 5 to 7-membered heterocycloalkyl, the heterocycloalkyl optionally comprising one or more further heteroatom independently selected from —O—, —N($R^3$)—, —S—, —S(O)— and —$SO_2$—.

In additional embodiments:

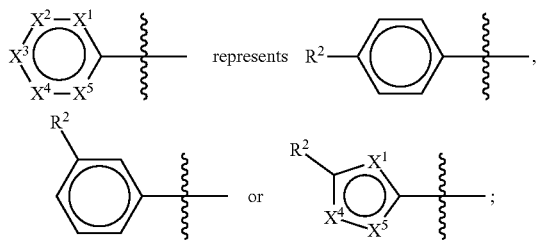

wherein $R^2$ represents:

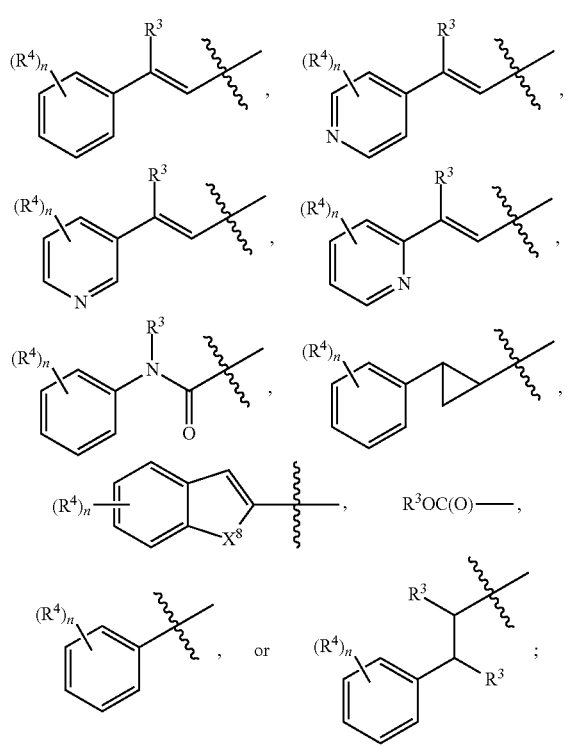

and $R^1$ represents:

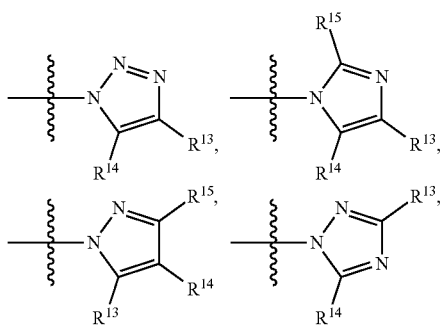

-continued

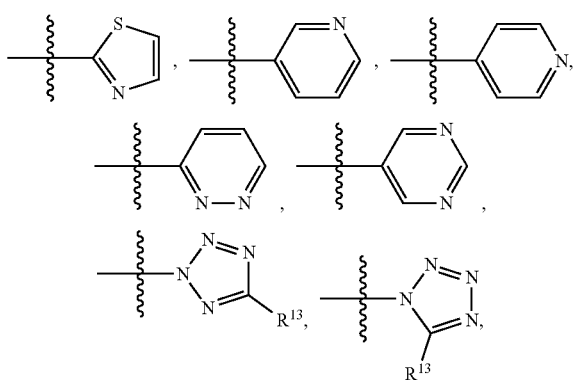

OH, —OC(O)N(R⁷)₂, —N(R⁷)C(O)R⁷, —N(R⁷)C(O)OR⁸, —N(R⁷)C(O)-L³-OR⁷, or —N(R⁷)C(O)-L³-OC(O)N(R⁷)₂, wherein R¹³, R¹⁴ and R¹⁵ are independently H or R⁹.

In preferred embodiments:

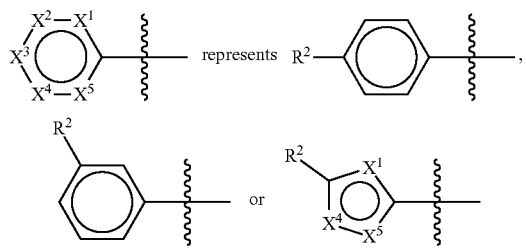

in which X¹ is —N═, X⁴ is —O— or —S—, and X⁵ is —CH═;

wherein R² represents:

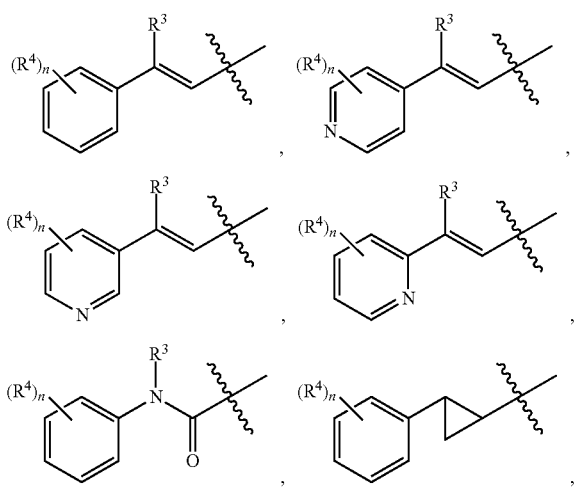

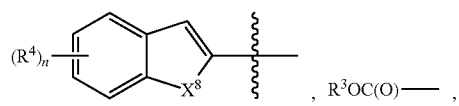, R³OC(O)—,

-continued

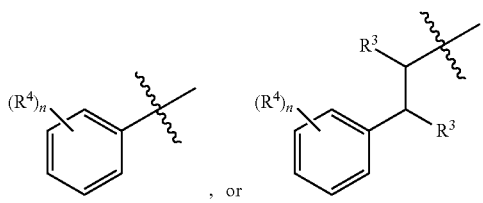, or wherein R³ is H or —C₁-C₃alkyl, and either n is 0, or n is 1 to 3 and R⁴ independently in each occurrence represents:

F, Cl, Br, I, —SR³, —SOR⁵, —S(O)₂R⁵, —S(O)₂N(R³)₂, CN, —C(O)OR³, NO₂, —C(O)NH₂, —OR³, —C(R³)₂OH, —C(O)NH—CH₂—C≡CH, OH, OMe, OCF₃, CH₂OH, —N(R³)₂, N₃, and —R³;

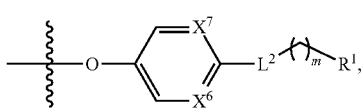

wherein X⁶ and X⁷ each represent —CH═, L² is a covalent bond, m is 4, and R¹ is

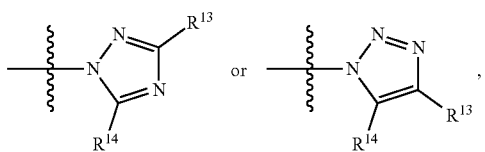

wherein R¹³ and R¹⁴ are each H; or

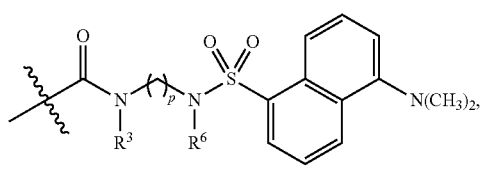

wherein R³ is H, p is 2 and R⁶ is H;

L¹ represents —CH₂—O—, —CH₂—NH—, —C(O)NH—, —CH═CH—, —CH₂—S—, or —CH₂—;

L² represents a covalent bond, —C(O)—, —CH(OH)—, —S—, or —CH₂—O—;

$X^6$ and $X^7$ each represent —CH= or one of $X^6$ and $X^7$ represents —CH= and the other represents —N=;

m is an integer from 1 to 4; and $R^1$ represents

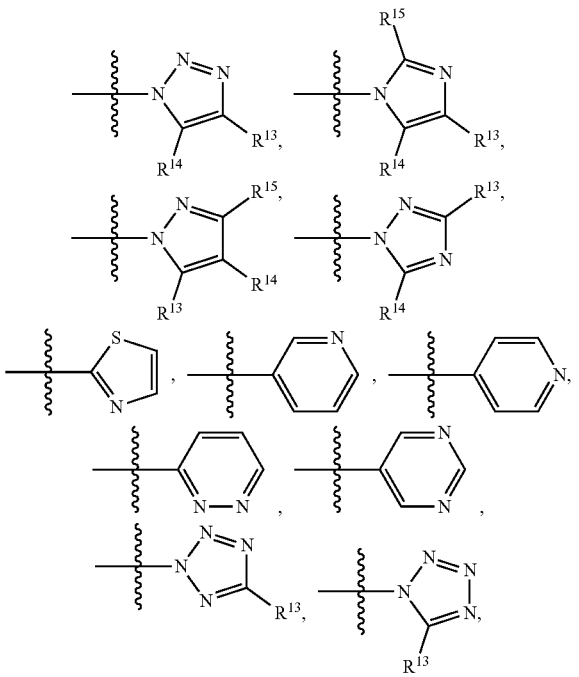

OH, —OC(O)N($R^7$)$_2$, —N($R^7$)C(O)$R^7$, —N($R^7$)C(O)O$R^8$, —N($R^7$)C(O)-$L^3$-O$R^7$, or —N($R^7$)C(O)-$L^3$-OC(O)N($R^7$)$_2$, wherein:

$R^{13}$, $R^{14}$ and $R^{15}$ are independently H, methyl, —$C_0$-$C_6$alkyl-O$R^{11}$, —$C_3$-$C_5$cycloalkyl-O$R^{11}$, —$C_0$-$C_6$alkyl-C(O)O$R^{11}$, —$C_1$-$C_6$alkyl-OC(O)N($R^{11}$)$_2$, —$C_1$-$C_5$alkyl-OC(O)N($R^{11}$)-$L^4$-O$R^{11}$, —$C_0$-$C_6$alkyl-C(O)N($R^{11}$)$_2$, —$C_1$-$C_6$alkyl-N($R^{11}$)$_2$, —$C_1$-$C_6$alkyl-N($R^{11}$)C(O)$R^{11}$, —$C_1$-$C_6$alkyl-N($R^{11}$)S(O)$_2$$R^{10}$, —SiMe$_3$, or

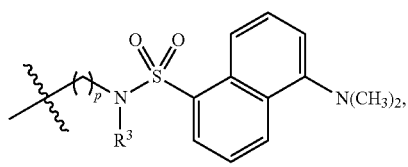

wherein $R^3$ is —H, —$C_1$-$C_5$ alkyl, or —$C_1$-$C_4$ fluoroalkyl, p is an integer from 1 to 6;

$L^3$ represents $C_1$-$C_5$alkylene;

$R^7$ independently represents —H or —$C_1$-$C_5$ alkyl, or the two $R^7$ groups together with the nitrogen atom to which they are attached optionally form a heterocycloalkyl which is

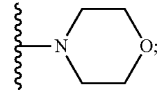

$R^8$ represents —$C_1$-$C_5$ alkyl;

$L^4$ represents $C_1$-$C_5$ alkylene;

$R^{10}$ represents —$C_1$-$C_5$ alkyl-$C_2$-$C_5$ alkynyl, or —$C_3$-$C_7$ cycloalkyl; and $R^{11}$ is —H, —$C_1$-$C_5$ alkyl, —$C_2$-$C_5$ alkynyl, or —$C_3$-$C_7$ cycloalkyl, or two $R^{11}$ groups together with the nitrogen atom to which they are attached optionally form a 5-7-membered heterocycloalkyl which is

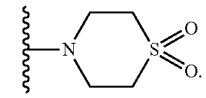

In more preferred embodiments:

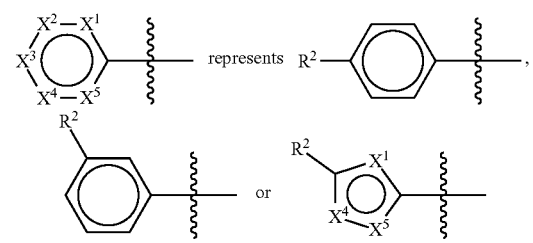

in which $X^1$ is —N=, $X^4$ is —O— or —S—, and $X^5$ is —CH=;

wherein $R^2$ represents:

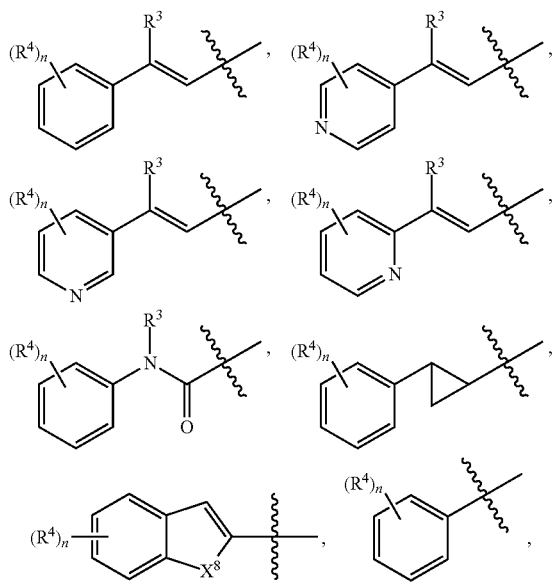

$R^3$OC(O)—, or,

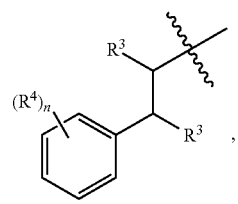

wherein R³ is H or methyl, X⁸ is —NH—, —O—, or —S—, and either n is 0, or n is 1 to 3 and R⁴ independently in each occurrence represents:
F, Cl, Br, —S(O)₂Me, CN, —CO₂Me, NO₂, —C(O)NH₂, —C(O)NH—CH₂—C≡CH, —OH, —OMe, —OCF₃, —CH₂OH, —NH₂, N₃, CF₃, —C≡CH;

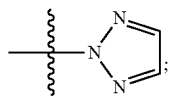

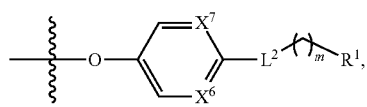

wherein X⁶ and X⁷ each represent —CH═, L² is a covalent bond,
m is 4, and R¹ is

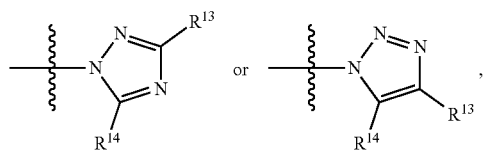

wherein R¹³ and R¹⁴ are each H; or

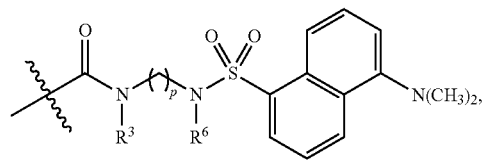

wherein R³ is H, p is 2 and R⁶ is H;
L¹ represents —CH₂—O—, —CH₂—NH—, —C(O)NH—, —CH═CH—, —CH₂—S—, or —CH₂—;
X⁶ and X⁷ each represent —CH═ or one of X⁶ and X⁷ represents —CH═ and the other is —N═;
L² represents a covalent bond and m is 3 or 4, or L² represents —C(O)—, —CH(OH)—, or —S— and m is 3, or L² represents —CH₂—O— and m is 2; and
R¹ represents

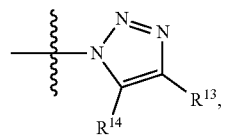

wherein R¹⁴ is H and R¹³ is selected from
H, methyl,
—C₀-C₆alkyl-OR¹¹, wherein the C₀-C₆alkyl is ethyl or butyl and R¹¹ is H,
—C₃-C₅cycloalkyl-OR¹¹, wherein the C₃-C₅ cycloalkyl is cyclopentyl and R¹¹ is H,
—C₀-C₆alkyl-C(O)OR¹¹, wherein C₀-C₆ alkyl is C₀alkyl (i.e. absent) and R¹¹ is ethyl, —C₁-C₆alkyl-OC(O)N(R¹¹)₂, wherein the C₁-C₆alkyl is ethyl and either both R¹¹ groups are methyl, or one R¹¹ group is isopropyl or cyclopentyl and the other R¹¹ group is H,
—C₁-C₆alkyl-OC(O)N(R¹¹)-L⁴-OR¹¹, wherein the C₁-C₆alkyl is ethyl, N(R¹¹) is NH, L⁴ is ethyl, and —OR¹ is —OMe,
—C₀-C₆alkyl-C(O)N(R¹¹)₂, wherein C₀-C₆alkyl is butyl and one R¹¹ group is —CH₂—C≡CH, and the other R¹¹ group is H,
—C₁-C₆alkyl-N(R¹¹)₂, wherein the C₁-C₅alkyl is methyl and both R¹¹ are H, or one R¹¹ is H and the other R¹¹ is methyl, or the two R¹¹ groups taken together with the nitrogen atom to which they are attached form a 5-7-membered heterocycloalkyl which is

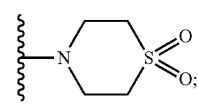

—C₁-C₆alkyl-N(R¹¹)C(O)R¹¹, wherein the C₁-C₆alkyl is ethyl, N(R¹¹) is NH, and C(O)R¹¹ is C(O)—CH₂—C≡CH,
—SiMe₃, and

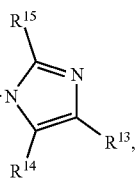

wherein R³ is —H and p is 2;
or both R¹³ and R¹⁴ are CO₂Et or CH₂OH;
or R¹³ is H and R¹⁴ is C₁-C₅alkyl-N(R¹¹)₂ wherein the C₁-C₅alkyl is methyl and the two R¹¹ groups taken together with the nitrogen atom to which they are attached form a 5-7-membered heterocycloalkyl which is

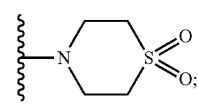

wherein R¹³ and R¹⁴ are H and R¹⁵ is selected from:
H,
—C₀-C₆alkyl-OR¹¹ wherein the C₀-C₆alkyl is ethyl and R¹¹ is H,
—C₁-C₅alkyl-OC(O)N(R¹¹)₂ wherein the C₁-C₆alkyl is ethyl and both R¹¹ groups are methyl,
—C₁-C₆alkyl-N(R¹¹)₂ wherein the C₁-C₆alkyl is ethyl and both R¹¹ groups are H, and —$C_1$-$C_6$alkyl-$N(R^{11})S(O)_2R^{10}$, wherein the $C_1$-$C_6$alkyl is ethyl, $R^{11}$ is H, and $R^{10}$ is Me or $SO_2CF_3$;

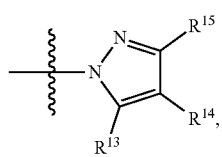

wherein $R^{13}$, $R^{14}$ and $R^{15}$ are each H;

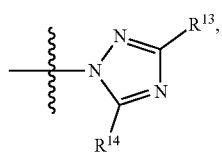

wherein $R^{13}$ is H or methyl and $R^{14}$ is H;

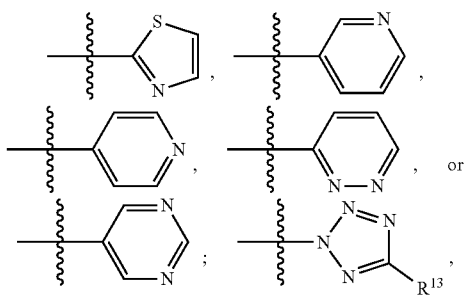

wherein $R^{13}$ is H or methyl;

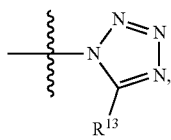

wherein $R^{13}$ is H;

OH;

—$OC(O)N(R^7)_2$, wherein both $R^7$ are methyl or ethyl or the two $R^7$ groups taken together with the nitrogen atom to which they are attached form a heterocycloalkyl which is

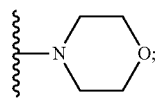

—$N(R^7)C(O)R^7$, wherein $R^7$ is H in each occurrence;
—$N(R^7)C(O)OR^8$, wherein $R^7$ is H and $R^8$ is tert-butyl;
—$N(R^7)C(O)$-$L^3$-$OR^7$, wherein $N(R^7)$ is NH, $L^3$ is ethylene, and $OR^7$ is OH; or
—$N(R^7)C(O)$-$L^3$-$OC(O)N(R^7)_2$, wherein —$N(R^7)C(O)$— is —NHC(O)—, $L^3$ is ethylene, and $N(R^7)_2$ is $NH_2$.

In yet more preferred embodiments:

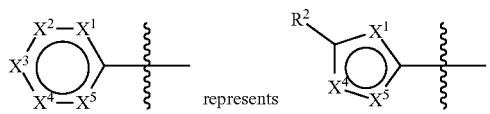  represents in which $X^1$ is —N═, $X^4$ is —O— or —S—, and $X^5$ is —CH═;

wherein $R^2$ represents:

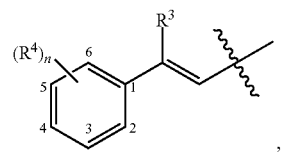

wherein $R^3$ is H and
n is 0;
n is 3 and $R^4$ is located on positions 3, 4, and 5 and is F in each occurrence;
n is 2 and $R^4$ is located on positions 2 and 4 and is independently in each occurrence selected from F, Cl, Br, $SO_2Me$, CN, $CO_2Me$, $NO_2$, OMe, $OCF_3$, $N_3$, and $CF_3$;
n is 2 and $R^4$ is located on positions 3 and 4 and is F in each occurrence; or
n is 1 and $R^4$ is located on position 2 or 4 and is selected from F, Cl, Br, CN, $CO_2Me$, $NO_2$, OH, $OCF_3$, $CH_2OH$, and $CF_3$;

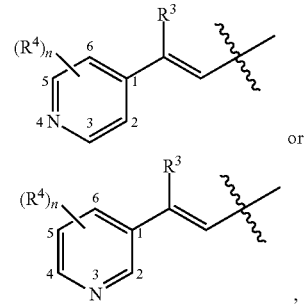

wherein $R^3$ is H and either n is 0, or n is 1 and $R^4$ is located at position 2 and is F, or

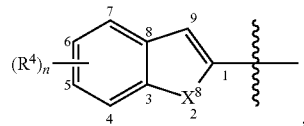

wherein $X^8$ is —NH—, —O—, or —S—, and
n is 0;
n is 2 and $R^4$ is located at positions 5 and 7 and is F in each occurrence; or
n is 1 and $R^4$ is located at position 5 or 6 and is F or $NO_2$;
$L^1$ represents —$CH_2$—O—, —$CH_2$—O—$CH_2$—, —$CH_2$—NH—, or —CH═CH—;
$X^6$ and $X^7$ each represent —CH═ or one of $X^6$ and $X^7$ represents —CH═ and the other is —N═;

$L^2$ represents a covalent bond and m is 4, or $L^2$ represents —C(O)—, —CH(OH)—, or —S— and m is 3, or $L^2$ represents —CH$_2$—O— and m is 2; and
$R^1$ represents

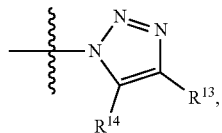

wherein $R^{14}$ is H and $R^{13}$ is selected from:
H, methyl,
—C$_1$-C$_6$alkyl-OC(O)N(R$^{11}$)$_2$, wherein the C$_1$-C$_6$alkyl is ethyl and either both R$^{11}$ groups are methyl, or one R$^{11}$ group is isopropyl or cyclopentyl and the other R$^{11}$ group is H,
—C$_1$-C$_6$alkyl-OC(O)N(R$^{11}$)-L$^4$-OR$^{11}$, wherein the C$_1$-C$_6$alkyl is ethyl, N(R$^{11}$) is NH, L$^4$ is ethyl, and —OR$^{11}$ is —OMe,
—C$_0$-C$_6$alkyl-C(O)N(R$^{11}$)$_2$, wherein C$_0$-C$_6$alkyl is butyl and one R$^{11}$ group is —CH$_2$—C≡CH, and the other R$^{11}$ group is H,
—C$_1$-C$_5$alkyl-N(R$^{11}$)$_2$, wherein the C$_1$-C$_5$alkyl is methyl and the two R$^{11}$ groups taken together with the nitrogen atom to which they are attached form a heterocycloalkyl which is

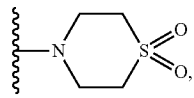

and
SiMe$_3$;

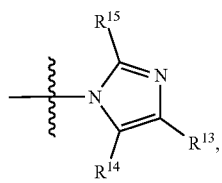

wherein $R^{13}$ and $R^{14}$ are H and $R^{15}$ is selected from:
H,
—C$_1$-C$_6$alkyl-OC(O)N(R$^{11}$)$_2$ wherein the C$_1$-C$_5$alkyl is ethyl and both R$^{11}$ groups are methyl, and
—C$_1$-C$_5$alkyl-N(R$^{11}$)S(O)$_2$R$^{10}$, wherein the C$_1$-C$_5$alkyl is ethyl, R$^{11}$ is H, and R$^{10}$ is Me or CF$_3$;

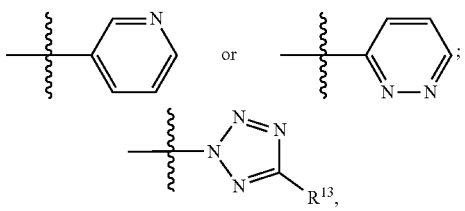

wherein $R^{13}$ is H; or
—N(R$^7$)C(O)-L$^3$-OC(O)N(R$^7$)$_2$, wherein —N(R$^7$)C(O)— is —NHC(O)—, L$^3$ is ethylene, and N(R$^7$)$_2$ is NH$_2$.

In other preferred embodiments:

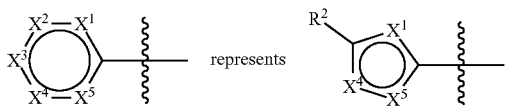

in which $X^1$ is —N=, $X^4$ is —O— or —S—, and $X^5$ is —CH=;
wherein $R^2$ represents:

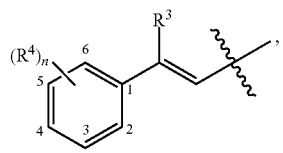

wherein $R^3$ is H and
n is 0;
n is 3 and $R^4$ is located at positions 3, 4, and 5 and is F in each occurrence;
n is 2 and $R^4$ is located at positions 2 and 4 and is:
  F at position 2 and F, Cl, Br, SO$_2$Me, CN, CO$_2$Me, NO$_2$, OMe, OCF$_3$, N$_3$, or CF$_3$ at position 4;
  Cl at position 2 and F at position 4; or
  Cl at positions 2 and 4;
n is 2 and $R^4$ is located on positions 3 and 4 and is F in each occurrence; or
n is 1 and $R^4$ is located on position 2 or 4 and is selected from F, Cl, Br, CN, CO$_2$Me, NO$_2$, OH, OCF$_3$, CH$_2$OH, and CF$_3$;

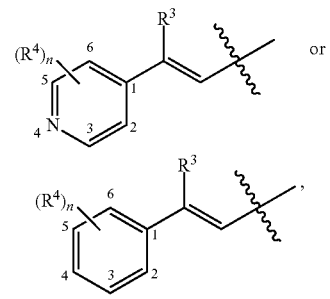

wherein $R^3$ is H and either n is 0, or n is 1 and $R^4$ is located at position 2 and is F, or

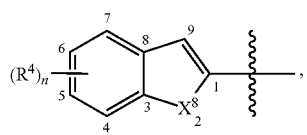

wherein $X^8$ is —NH—, —O—, or —S—, and
n is 2 and $R^4$ is located at positions 5 and 7 and is F in each occurrence; or
n is 1 and $R^4$ is located at position 5 or 6 and is F or NO$_2$;
$L^1$ represents —CH$_2$—O—, —CH$_2$—NH—, or —CH=CH—;
$X^6$ and $X^7$ each represent —CH=;

$L^2$ represents a covalent bond and m is 4, or $L^2$ represents —C(O)—, —CH(OH)—, or —S— and m is 3; and $R^1$ represents

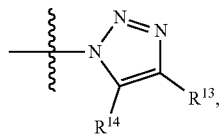

wherein $R^{14}$ is H and $R^{13}$ is selected from

H, methyl,

—$C_1$-$C_6$alkyl-OC(O)N($R^{11}$)$_2$, wherein the $C_1$-$C_6$alkyl is ethyl and either both $R^{11}$ groups are methyl, or one $R^{11}$ group is isopropyl or cyclopentyl and the other $R^{11}$ group is H, —$C_1$-$C_5$alkyl-OC(O)N($R^{11}$)-$L^4$-O$R^{11}$, wherein the $C_1$-$C_5$alkyl is ethyl, N($R^{11}$) is NH, $L^4$ is ethyl, and —O$R^1$ is —OMe, —$C_1$-$C_6$alkyl-N($R^{11}$)$_2$, wherein the $C_1$-$C_6$alkyl is methyl and the two $R^{11}$ groups taken together with the nitrogen atom to which they are attached form a heterocycloalkyl which is

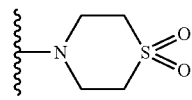

and
—SiMe$_3$;

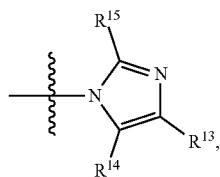

wherein $R^{13}$ and $R^{14}$ are H and $R^{15}$ is H or —$C_1$-$C_6$alkyl-OC(O)N($R^{11}$)$_2$ wherein the $C_1$-$C_6$alkyl is ethyl and both $R^{11}$ groups are methyl;

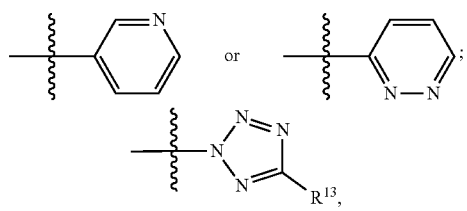

wherein $R^{13}$ is H; or
—N($R^7$)C(O)-$L^3$-OC(O)N($R^7$)$_2$, wherein —N($R^7$)C(O)— is —NHC(O)—, $L^3$ is ethylene, and N($R^7$)$_2$ is NH$_2$.

In yet other preferred embodiments:

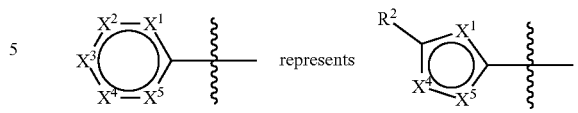

in which $X^1$ is —N=, $X^4$ is —O—, and $X^5$ is —CH=;
wherein $R^2$ represents:

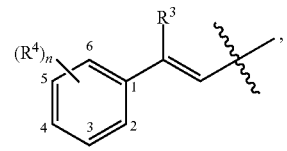

wherein $R^3$ is H and
n is 2 and $R^4$ is located at positions 2 and 4 and is F in position 2 and F, Cl, Br, SO$_2$Me, CN, CO$_2$Me, NO$_2$, OCF$_3$, or CF$_3$ in position 4;
n is 2 and $R^4$ is located at positions 3 and 4 and is F in each occurrence; or
n is 1 and $R^4$ is located at position 4 and is CN or CO$_2$Me; or

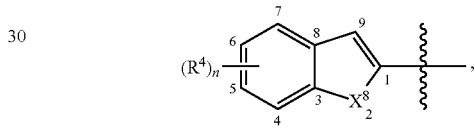

wherein $X^8$ is —NH— or —O—, and
n is 2 and $R^4$ is located at positions 5 and 7 and is F in each occurrence; or
n is 1 and $R^4$ is located at position 5 or 6 and is F or NO$_2$;
$L^1$ represents —CH$_2$—O—;
$X^6$ and $X^7$ each represent —CH=;
$L^2$ represents a covalent bond and m is 4, or $L^2$ represents —C(O)—, —CH(OH)—, or —S— and m is 3; and
$R^1$ represents:

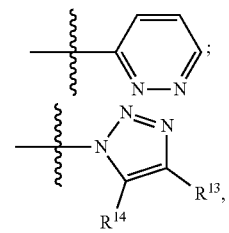

wherein $R^{14}$ is H and $R^{13}$ is H or —SiMe$_3$; or

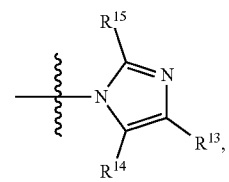

wherein $R^{13}$, $R^{14}$ and $R^{15}$ are each H.

In yet other preferred embodiments:

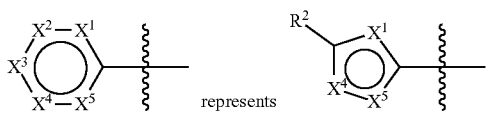 represents in which $X^1$ is —N=, $X^4$ is —O—, and $X^5$ is —CH=;
wherein $R^2$ represents:

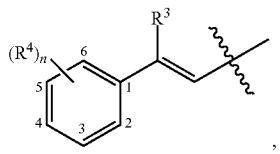

wherein $R^3$ is H, n is 2 and $R^4$ is located at positions 2 and 4, and is F in position 2 and F, Cl, Br, $SO_2Me$, CN, $CO_2Me$, $NO_2$, $OCF_3$, or $CF_3$ in position 4; or

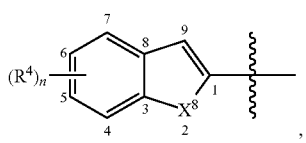

wherein $X^8$ is —NH—, and
n is 2 and $R^4$ is located at positions 5 and 7 and is F in each occurrence; or
n is 1 and $R^4$ is located at position 5 or 6 and is F or $NO_2$;
$L^1$ represents —$CH_2$—O—;
$X^6$ and $X^7$ each represent —CH=;
$L^2$ represents a covalent bond and m is 4, or $L^2$ represents —S— and m is 3; and
$R^1$ represents

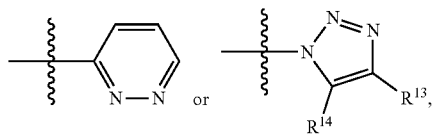

wherein $R^{13}$ and $R^{14}$ are each H.

In embodiments, the compound is one of the following (in which the compound numbers correspond to those used in Example 6) or a pharmaceutically acceptable salt thereof:

Compound 1: (E)-4-((4-(4-(1H-1,2,3-triazol-1-yl)butyl)phenoxy)methyl-2-(4-trifluoromethyl)styryl)oxazole;
Compound 2: (E)-4-((4-(4-(1H-1,2,3-triazol-1-yl-)butyl)phenoxy)methyl)-2-(4-trifluoromethoxy)styryl)oxazole;
Compound 3A: (E)-2-(4-Bromo-2-fluorostyryl)-4-((4-(4-(4-(trimethylsilyl)-1H-1,2,3-triazol-1-yl)butyl)phenoxy)methyl)oxazole;
Compound 38: (E)-((4-(4-(1H-1,2,3-triazol-1-yl)butyl)phenoxy)methyl)-2-(4-bromo-2-fluorostyryl)oxazole;
Compound 4: (E)-2-(1-(4-(4-((2-(4-Trifluoromethyl)styryl)oxazol-4-yl)methoxy)phenyl)butyl-1H-1,2,3-triazol-4-yl)ethanol;
Compound 5: (E)-4-(1-(4-(4-((2-(4-(trifluoromethyl)styryl)oxazol-4-yl-methoxy)phenyl)butyl)-1H-1,2,3-triazol-4-yl)butan-1-ol;
Compound 6: (E)-diethyl 1-(4-(4-((2-(4-(trifluoromethyl)styryl)oxazol-4-yl)methoxy)phenyl)butyl)-1H-1,2,3-triazole-4,5-dicarboxylate;
Compound 7: (E)-N-methyl-1-(1-(4-(4-((2-(4-(trifluoromethyl)oxazol-4-yl)methoxy)phenyl)butyl)-1H-1,2,3-triazol-4-yl)methanamine;
Compound 8: (E)-1-(1-(4-(4-((2-(4-(trifluoromethyl)styryl)oxazol-4-yl)methoxy)phenyl)butyl)-1H-1,2,3-triazol-4-yl)cyclopentanol;
Compound 9: (E)-(1-(4-(4-((2-(4-(trifluoromethyl)styryl)oxazol-4-yl)methoxy)phenyl)butyl)-1H-1,2,3-triazole-4,5-diyl)dimethanol;
Compound 10: (E)-4-((1-(4-(4-((2-(4-(trifluoromethyl)styryl)oxazol-4-yl)methoxy)phenyl)butyl)-1H-1,2,3-triazol-4-yl)methyl)thiomorpholine 1,1-dioxide;
Compound 11: 4-((4-(4-(1H-1,2,3-triazol-1-yl)butyl)phenoxy)methyl)-2-(2-fluoro-4-(trifluoromethyl)phenethyl)oxazole;
Compound 12: (E)-N-(prop-2-yn-1-yl)-5-(1-(4-(4-((2-(4-(trifluoromethyl)styryl)oxazol-4-yl)methoxy)phenyl)butyl)-1H-1,2,3-triazol-4-yl)pentanamide;
Compound 13: (E)-2-(1-(4-(4-((2-(4-(trifluoromethyl)styryl)oxazol-4-yl)methoxy)phenyl)butyl)-1H-1,2,3-triazol-4-yl)ethanamine;
Compound 14: (E)-N-(2-(1-(4-(4-((2-(4-(trifluoromethyl)styryl)oxazol-4-yl)methoxy)phenyl)butyl)-1H-1,2,3-triazol-4-yl)ethyl)pent-4-ynamide;
Compound 15: (E)-4-((1-(4-(4-((2-(4-(trifluoromethyl)styryl)oxazol-4-yl)methoxy)phenyl)butyl)-1H-1,2,3-triazol-5-yl)methyl)thiomorpholine 1,1-dioxide;
Compound 16: (E)-4-(1H-1,2,3-triazol-1-yl)-1-(4-((2-(4-(trifluoromethyl)styryl)oxazol-4-yl)methoxy)phenyl)butan-1-one;
Compound 17: (E)-4-(1H-1,2,3-triazol-1-yl)-1-(4-((2-(4-(trifluoromethyl)styryl)oxazol-4-yl)methoxy)phenyl)butan-1-ol;
Compound 18: (E)-4-(1H-1,2,3-triazol-1-yl)-1-(4-((2-(4-(trifluoromethoxy)styryl)oxazol-4-yl)methoxy)phenyl)butan-1-one;
Compound 19: (E)-4-(1H-1,2,3-triazol-1-yl)-1-(4-((2-(4-(trifluoromethoxy)styryl)oxazol-4-yl)methoxy)phenyl)butan-1-ol;
Compound 20: (E)-1-(4-((2-(4-bromo-2-fluorostyryl)oxazol-4-yl)methoxy)phenyl)-4-(1H-1,2,3-triazol-1-yl)butan-1-one;
Compound 21: (E)-1-(4-((2-(4-bromo-2-fluorostyryl)oxazol-4-yl)methoxy)phenyl)-4-(1H-1,2,3-triazol-1-yl)butan-1-ol;
Compound 22: (E)-1-(4-((2-(2-fluoro-4-(trifluoromethyl)styryl)oxazol-4-yl)methoxy)phenyl)-4-(1H-1,2,3-triazol-1-yl)butan-1-one;
Compound 23: (E)-1-(4-((2-(2-fluoro-4-(trifluoromethyl)styryl)oxazol-4-yl)methoxy)phenyl)-4-(1H-1,2,3-triazol-1-yl)butan-1-ol;
Compound 24: (E)-1-(4-((2-(2-fluoro-4-nitrostyryl)oxazol-4-yl)methoxy)phenyl)-4-(1H-1,2,3-triazol-1-yl)butan-1-one;
Compound 25: (E)-1-(4-((2-(2-fluoro-4-nitrostyryl)oxazol-4-yl)methoxy)phenyl)-4-(1H-1,2,3-triazol-1-yl)butan-1-ol;
Compound 26: (E)-4-(4-(1H-1,2,3-triazol-1-yl)butyl)-N-((2-(4-(trifluoromethyl)styryl)oxazol-4-yl)methyl)aniline;
Compound 27: (E)-4-(4-(1H-1,2,3-triazol-1-yl)butyl)-N-((2-(4-bromo-2-fluorostyryl)oxazol-4-yl)methyl)aniline;
Compound 28: 4-((4-(4-(1H-1,2,3-triazol-1-yl)butyl)phenoxy)methyl)-2-(4-(trifluoromethyl)phenyl)oxazole;

Compound 29: (E)-N-(4-(4-hydroxybutyl)phenyl)-2-(4-(trifluoromethyl)styryl)oxazole-4-carboxamide;
Compound 30: (E)-N-(4-(4-(1H-1,2,3-triazol-1-yl)butyl)phenyl)-2-(4-(trifluoromethyl)styryl)oxazole-4-carboxamide;
Compound 31: (E)-5-(dimethylamino)-N-(2-(1-(4-(4-((2-(4-(trifluoromethyl)styryl)oxazol-4-yl)methoxy)phenyl)butyl)-1H-1,2,3-triazol-4-yl)ethyl)naphthalene-1-sulfonamide;
Compound 32: (E)-4-((4-(4-(1H-1,2,3-triazol-1-yl)butyl)phenoxy)methyl)-2-(4-methoxystyryl)oxazole;
Compound 33: (E)-4-((4-(4-(1H-1,2,3-triazol-1-yl)butyl)phenoxy)methyl)-2-(4-bromostyryl)oxazole;
Compound 34: (E)-4-(4-((2-(4-(trifluoromethyl)styryl)oxazol-4-yl)methoxy)phenyl)butyl diethylcarbamate;
Compound 35: (E)-4-(4-((2-(4-(trifluoromethyl)styryl)oxazol-4-yl)methoxy)phenyl)butyl morpholine-4-carboxylate;
Compound 36: (E)-4-(4-((2-(4-(trifluoromethyl)styryl)oxazol-4-yl)methoxy)phenyl)butyl dimethylcarbamate;
Compound 37: (E)-4-(2-(4-((4-(4-(1H-1,2,3-triazol-1-yl)butyl)phenoxy)methyl)oxazol-2-yl)vinyl)benzonitrile;
Compound 38: (E)-4-((4-(4-(1H-1,2,3-triazol-1-yl)butyl)phenoxy)methyl)-2-(4-chlorostyryl)oxazole;
Compound 39: (E)-4-((4-(4-(1H-1,2,3-triazol-1-yl)butyl)phenoxy)methyl)-2-(4-fluorostyryl)oxazole;
Compound 40: (E)-4-((4-(4-(1H-1,2,3-triazol-1-yl)butyl)phenoxy)methyl)-2-(4-nitrostyryl)oxazole;
Compound 41: (E)-4-((4-(4-(1H-1,2,3-triazol-1-yl)butyl)phenoxy)methyl)-2-(2-fluorostyryl)oxazole;
Compound 42: (E)-4-((4-(4-(1H-1,2,3-triazol-1-yl)butyl)phenoxy)methyl)-2-(2-nitrostyryl)oxazole;
Compound 43: (E)-4-((4-(4-(1H-1,2,3-triazol-1-yl)butyl)phenoxy)methyl)-2-(3-nitrostyryl)oxazole;
Compound 44: (E)-4-((4-(4-(1H-1,2,3-triazol-1-yl)butyl)phenoxy)methyl)-2-(2-(trifluoromethyl)styryl)oxazole;
Compound 45: (E)-4-((4-(4-(1H-1,2,3-triazol-1-yl)butyl)phenoxy)methyl)-2-(2,4-difluorostyryl)oxazole;
Compound 46: (E)-4-((4-(4-(1H-1,2,3-triazol-1-yl)butyl)phenoxy)methyl)-2-(2,6-difluorostyryl)oxazole;
Compound 47: (E)-4-((4-(4-(1H-1,2,3-triazol-1-yl)butyl)phenoxy)methyl)-2-styryloxazole;
Compound 48: (E)-4-((4-(4-(1H-1,2,3-triazol-1-yl)butyl)phenoxy)methyl)-2-(2-fluoro-4-(trifluoromethyl)styryl)oxazole;
Compound 49: (E)-4-((4-(4-(1H-1,2,3-triazol-1-yl)butyl)phenoxy)methyl)-2-(3-(trifluoromethyl)styryl)oxazole;
Compound 50: (E)-4-((4-(3-(1H-1,2,3-triazol-1-yl)propyl)phenoxy)methyl)-2-(4-(trifluoromethyl)styryl)oxazole;
Compound 51: (E)-2-(1-(4-(4-((2-(4-(trifluoromethyl)styryl)oxazol-4-yl)methoxy)phenyl)butyl)-1H-imidazol-2-yl)ethanol;
Compound 52: (E)-2-(1-(4-(4-((2-(4-(trifluoromethyl)styryl)oxazol-4-yl)methoxy)phenyl)butyl)-1H-imidazol-2-yl)ethanamine;
Compound 53: (E)-2-(1-(4-(4-((2-(4-(trifluoromethyl)styryl)oxazol-4-yl)methoxy)phenyl)butyl)-1H-imidazol-2-yl)ethyl dimethylcarbamate;
Compound 54: (E)-N-(2-(1-(4-(4-((2-(4-(trifluoromethyl)styryl)oxazol-4-yl)methoxy)phenyl)butyl)-1H-imidazol-2-yl)ethyl)methanesulfonamide;
Compound 55: (E)-1,1,1-trifluoro-N-(2-(1-(4-(4-((2-(4-(trifluoromethyl)styryl)oxazol-4-yl)methoxy)phenyl)butyl)-1H-imidazol-2-yl)ethyl)methanesulfonamide;
Compound 56: (E)-1-(4-(4-((3-(4-(trifluoromethyl)styryl)benzyl)oxy)phenyl)butyl)-1H-1,2,3-triazole;
Compound 57: (E)-1-(4-(4-((4-(4-(trifluoromethyl)styryl)benzyl)oxy)phenyl)butyl)-1H-1,2,3-triazole;
Compound 58: (E)-methyl 4-(2-(4-((4-(4-(1H-1,2,3-triazol-1-yl)butyl)phenoxy)methyl)oxazol-2-yl)vinyl)benzoate;
Compound 59: (E)-4-(2-(4-((4-(4-(1H-1,2,3-triazol-1-yl)butyl)phenoxy)methyl)oxazol-2-yl)vinyl)-N-(prop-2-yn-1-yl)benzamide;
Compound 60: (E)-(4-(2-(4-((4-(4-(1H-1,2,3-triazol-1-yl)butyl)phenoxy)methyl)oxazol-2-yl)vinyl)phenyl)methanol;
Compound 61: (E)-4-((4-(4-(1H-1,2,3-triazol-1-yl)butyl)phenoxy)methyl)-2-(2-fluoro-4-methoxystyryl)oxazole;
Compound 62: (E)-4-(2-(4-((4-(4-(1H-1,2,3-triazol-1-yl)butyl)phenoxy)methyl)oxazol-2-yl)vinyl)phenol;
Compound 63: (E)-4-(2-(4-((4-(4-(1H-1,2,3-triazol-1-yl)butyl)phenoxy)methyl)oxazol-2-yl)vinyl)benzamide;
Compound 64: (E)-4-((4-(4-(1H-1,2,3-triazol-1-yl)butyl)phenoxy)methyl)-2-(4-ethynylstyryl)oxazole;
Compound 65: (E)-4-((4-(4-(1H-1,2,3-triazol-1-yl)butyl)phenoxy)methyl)-2-(2-fluoro-4-nitrostyryl)oxazole;
Compound 66: (E)-4-(2-(4-((4-(4-(1H-1,2,3-triazol-1-yl)butyl)phenoxy)methyl)oxazol-2-yl)vinyl)-3-fluoroaniline;
Compound 67: (E)-4-((4-(4-(1H-1,2,3-triazol-1-yl)butyl)phenoxy)methyl)-2-(4-azido-2-fluorostyryl)oxazole;
Compound 68: (E)-2-(1-(4-(4-((2-(4-(trifluoromethyl)styryl)oxazol-4-yl)methoxy)phenyl)butyl)-1H-1,2,3-triazol-4-yl)ethyl dimethylcarbamate;
Compound 69: (E)-2-(1-(4-(4-((2-(4-(trifluoromethyl)styryl)oxazol-4-yl)methoxy)phenyl)butyl)-1H-1,2,3-triazol-4-yl)ethyl (2-methoxyethyl)carbamate;
Compound 70: (E)-2-(1-(4-(4-((2-(4-(trifluoromethyl)styryl)oxazol-4-yl)methoxy)phenyl)butyl)-1H-1,2,3-triazol-4-yl)ethyl isopropylcarbamate;
Compound 71: (E)-4-((1-(4-(4-((2-(2-fluoro-4-(trifluoromethyl)styryl)oxazol-4-yl)methoxy)phenyl)butyl)-1H-1,2,3-triazol-4-yl)methyl)thiomorpholine 1,1-dioxide;
Compound 72: (E)-4-(2-(4-((4-(4-(1H-1,2,3-triazol-1-yl)butyl)phenoxy)methyl)oxazol-2-yl)vinyl)-N-(2-(5-(dimethylamino)naphthalene-1-sulfonamido)ethyl)benzamide;
Compound 73: 4-((4-(4-(1H-1,2,3-triazol-1-yl)butyl)phenoxy)methyl)-2-(5-fluoro-1H-indol-2-yl)oxazole;
Compound 74: (E)-4-((4-(4-(1H-1,2,3-triazol-1-yl)butyl)phenoxy)methyl)-2-(2-(4-(trifluoromethyl) phenyl)prop-1-en-1-yl)oxazole;
Compound 75: 5-((4-(4-(1H-1,2,3-triazol-1-yl)butyl)phenoxy)methyl)-2-(4-(trifluoromethyl)phenyl) pyridine;
Compound 76: 4-((4-(4-(1H-1,2,3-triazol-1-yl)butyl)phenoxy)methyl)-2-(2-(4-(trifluoromethyl)phenyl) cyclopropyl)oxazole;
Compound 77: Methyl 2-((4-(4-(1H-1,2,3-triazol-1-yl)butyl)phenoxy)methyl)oxazole-4-carboxylate;
Compound 78: 2-((4-(4-(1H-1,2,3-triazol-1-yl)butyl)phenoxy)methyl)-N-(2-nitro-4-(trifluoromethyl) phenyl)oxazole-4-carboxamide;
Compound 79: (E)-tert-butyl (4-(4-((2-(4-(trifluoromethyl)styryl)oxazol-4-yl)methoxy)phenyl)butyl) carbamate;
Compound 80: (E)-4-((4-(4-(1H-1,2,3-triazol-1-yl)butyl)phenoxy)methyl)-2-(2-(pyridin-4-yl)vinyl) oxazole;
Compound 81: (E)-4-((4-(4-(1H-1,2,3-triazol-1-yl)butyl)phenoxy)methyl)-2-(2-(3-fluoropyridin-4-yl)vinyl)oxazole;
Compound 82: (E)-4-((4-(4-(1H-1,2,3-triazol-1-yl)butyl)phenoxy)methyl)-2-(2-(pyridin-3-yl)vinyl)oxazole;

Compound 83: (E)-4-((4-(4-(1H-1,2,3-triazol-1-yl)butyl)phenoxy)methyl)-2-(2-(2-fluoropyridin-3-yl)vinyl)oxazole;

Compound 84: (E)-4-((4-(4-(1H-1,2,3-triazol-1-yl)butyl)phenoxy)methyl)-2-(2-(pyridin-2-yl)vinyl)oxazole;

Compound 85: (E)-4-((4-(4-(1H-1,2,3-triazol-1-yl)butyl)phenoxy)methyl)-2-(2-(3-fluoropyridin-2-yl)vinyl)oxazole;

Compound 86: (E)-3-hydroxy-N-(4-(4-((2-(4-(trifluoromethyl)styryl)oxazol-4-yl)methoxy)phenyl)butyl) propanamide;

Compound 87: (E)-3-oxo-3-((4-(4-((2-(4-(trifluoromethyl)styryl)oxazol-4-yl)methoxy)phenyl)butyl) amino)propyl dimethylcarbamate;

Compound 88: (E)-4-((4-(4-(1H-1,2,4-triazol-1-yl)butyl)phenoxy)methyl)-2-(2-fluoro-4-(trifluoromethyl)styryl)oxazole;

Compound 89: (E)-2-(2-(4-(4-(1H-1,2,4-triazol-1-yl)butyl)phenoxy)-4-(trifluoromethyl)styryl)-4-((4-(4-(1H-1,2,4-triazol-1-yl)butyl)phenoxy)methyl)oxazole;

Compound 90: (E)-4-((4-(4-(1H-tetrazol-1-yl)butyl)phenoxy)methyl)-2-(2-fluoro-4-(trifluoromethyl)styryl) oxazole;

Compound 91: (E)-4-((4-(4-(1H-pyrazol-1-yl)butyl)phenoxy)methyl)-2-(2-fluoro-4-(trifluoromethyl)styryl) oxazole;

Compound 92: (E)-2-(2-fluoro-4-(trifluoromethyl)styryl)-4-((4-(4-(4-methyl-1H-1,2,3-triazol-1-yl)butyl)phenoxy) methyl) oxazole;

Compound 93: (E)-2-(2-fluoro-4-(trifluoromethyl)styryl)-4-((4-(4-(3-methyl-1H-1,2,4-triazol-1-yl)butyl) phenoxy) methyl)oxazole;

Compound 94: (E)-2-(2-fluoro-4-(trifluoromethyl)styryl)-4-((4-(4-(5-methyl-2H-tetrazol-2-yl)butyl)phenoxy) methyl)oxazole;

Compound 95: (E)-2-(1-(4-(4-((2-(2-fluoro-4-(trifluoromethyl)styryl)oxazol-4-yl)methoxy)phenyl)butyl)-1H-1,2,3-triazol-4-yl)ethanol;

Compound 96: (E)-2-(1-(4-(4-((2-(2-fluoro-4-(trifluoromethyl)styryl)oxazol-4-yl)methoxy)phenyl)butyl)-1H-1,2,3-triazol-4-yl)ethyl (2-methoxyethyl)carbamate;

Compound 97: (E)-2-(1-(4-(4-((2-(2-fluoro-4-(trifluoromethyl)styryl)oxazol-4-yl)methoxy)phenyl)butyl)-1H-1,2,3-triazol-4-yl)ethyl cyclopentylcarbamate;

Compound 98: (E)-2-(1-(4-(4-((2-(2-fluoro-4-(trifluoromethyl)styryl)oxazol-4-yl)methoxy)phenyl)butyl)-1H-1,2,3-triazol-4-yl)ethyl isopropylcarbamate;

Compound 99: (E)-4-((4-(4-(1H-imidazol-1-yl)butyl)phenoxy)methyl)-2-(2-fluoro-4-nitrostyryl)oxazole;

Compound 100: (E)-4-((4-(4-(1H-imidazol-1-yl)butyl)phenoxy)methyl)-2-(2-fluoro-4-(trifluoromethyl)styryl)oxazole;

Compound 101: (E)-2-(2-(4-(4-(1H-1,2,3-triazol-1-yl)butyl)phenoxy)-4-nitrostyryl)-4-((4-(4-(1H-1,2,3-triazol-1-yl)butyl)phenoxy)methyl)oxazole;

Compound 102: (E)-2-(2-fluoro-4-(trifluoromethyl)styryl)-4-((4-(4-(pyridin-3-yl)butyl)phenoxy)methyl)oxazole;

Compound 103: (E)-2-(2-fluoro-4-nitrostyryl)-4-((4-(4-(pyridin-3-yl)butyl)phenoxy)methyl)oxazole;

Compound 104: (E)-2-(2-fluoro-4-(trifluoromethyl)styryl)-4-((4-(4-(pyridin-4-yl)butyl)phenoxy)methyl)oxazole;

Compound 105: (E)-4-((4-(3-(1H-1,2,3-triazol-1-yl)propyl)phenoxy)methyl)-2-(2-fluoro-4-(trifluoromethyl)styryl)oxazole;

Compound 106: (E)-4-((4-(3-(1H-1,2,3-triazol-1-yl)propyl)phenoxy)methyl)-2-(2-(2H-1,2,3-triazol-2-yl)-4-(trifluoromethyl)styryl)oxazole Compound 107: (E)-2-(2-fluoro-4-(trifluoromethyl)styryl)-4-((4-(4-(thiazol-2-yl)butyl)phenoxy)methyl) oxazole;

Compound 108: (E)-2-(2-fluoro-4-(trifluoromethyl)styryl)-4-((4-(4-(pyrimidin-5-yl)butyl)phenoxy) methyl)oxazole;

Compound 109: (E)-4-((4-(3-(1H-1,2,3-triazol-1-yl)propoxy)phenoxy)methyl)-2-(2-fluoro-4-(trifluoromethyl)styryl)oxazole;

Compound 110: (E)-4-((4-(4-(2H-tetrazol-2-yl)butyl)phenoxy)methyl)-2-(2-fluoro-4-(trifluoromethyl)styryl)oxazole;

Compound 111: 4-((E)-4-(4-(1H-1,2,3-triazol-1-yl)butyl)styryl)-2-((E)-2-fluoro-4-(trifluoromethyl)styryl) oxazole;

Compound 112: 4-((4-(4-(1H-1,2,3-triazol-1-yl)butyl)phenoxy)methyl)-2-(5-fluorobenzofuran-2-yl) oxazole;

Compound 113: 4-((4-(4-(1H-1,2,3-triazol-1-yl)butyl)phenoxy)methyl)-2-(5-fluorobenzo[b]thiophen-2-yl)oxazole;

Compound 114: ethyl (E)-1-(4-(4-((2-(4-(trifluoromethyl)styryl)oxazol-4-yl)methoxy)phenyl)butyl)-1H-1,2,3-triazole-4-carboxylate;

Compound 115: (E)-4-((4-((2-(1H-1,2,3-triazol-1-yl)ethoxy)methyl)phenoxy)methyl)-2-(2-fluoro-4-(trifluoromethyl)styryl)oxazole;

Compound 116: (E)-4-((4-(4-(1H-1,2,3-triazol-1-yl)butyl)phenoxy)methyl)-2-(4-chloro-2-fluorostyryl)oxazole;

Compound 117: (E)-4-((4-(4-(1H-1,2,3-triazol-1-yl)butyl)phenoxy)methyl)-2-(2-chloro-4-fluorostyryl)oxazole;

Compound 118: (E)-4-((4-(4-(1H-1,2,3-triazol-1-yl)butyl)phenoxy)methyl)-2-(2-chlorostyryl)oxazole;

Compound 119: (E)-4-((4-(4-(1H-1,2,3-triazol-1-yl)butyl)phenoxy)methyl)-2-(2,4-dichlorostyryl)oxazole;

Compound 120: (E)-4-((4-(4-(1H-1,2,3-triazol-1-yl)butyl)phenoxy)methyl)-2-(3,4,5-trifluorostyryl)oxazole;

Compound 121: (E)-4-((4-(4-(1H-1,2,3-triazol-1-yl)butyl)phenoxy)methyl)-2-(3,4-difluorostyryl)oxazole;

Compound 122: (E)-4-(2-(4-((4-(4-(1H-1,2,3-triazol-1-yl)butyl)phenoxy)methyl)oxazol-2-yl)vinyl)-3-fluorobenzonitrile;

Compound 123: (E)-4-((4-(4-(1H-1,2,3-triazol-1-yl)butyl)phenoxy)methyl)-2-(2-fluoro-4-(methylsulfonyl)styryl) oxazole;

Compound 124: (E)-4-((4-(4-(1H-1,2,3-triazol-1-yl)butyl)phenoxy)methyl)-2-(2-fluoro-4-(trifluoromethoxy)styryl) oxazole;

Compound 125: methyl (E)-4-(2-(4-((4-(4-(1H-1,2,3-triazol-1-yl)butyl)phenoxy)methyl)oxazol-2-yl)vinyl)-3-fluorobenzoate;

Compound 126: 4-((4-(4-(1H-1,2,3-triazol-1-yl)butyl)phenoxy)methyl)-2-(5-fluoro-7-nitro-1H-indol-2-yl)oxazole;

Compound 127: 4-((4-(4-(1H-1,2,3-triazol-1-yl)butyl)phenoxy)methyl)-2-(6-fluoro-1H-indol-2-yl)oxazole;

Compound 128: 4-((4-(4-(1H-1,2,3-triazol-1-yl)butyl)phenoxy)methyl)-2-(4,6-difluoro-1H-indol-2-yl)oxazole;

Compound 129: 4-((4-(4-(1H-1,2,3-triazol-1-yl)butyl)phenoxy)methyl)-2-(6-nitro-1H-indol-2-yl)oxazole;

Compound 130: (E)-4-((4-(3-(1H-1,2,3-triazol-1-yl)propyl)thio)phenoxy)methyl)-2-(2-fluoro-4-(trifluoromethyl)styryl)oxazole;

Compound 131: (E)-4-((4-(4-(1H-1,2,3-triazol-1-yl)butyl)phenoxy)methyl)-2-(2-fluoro-4-(trifluoromethyl)styryl) thiazole;

Compound 132: (E)-4-(((4-(3-(1H-1,2,3-triazol-1-yl)propyl)phenyl)thio)methyl)-2-(2-fluoro-4-(trifluoromethyl)styryl)oxazole;

Compound 133: (E)-4-(((6-(4-(1H-1,2,3-triazol-1-yl)butyl)pyridin-3-yl)oxy)methyl)-2-(2-fluoro-4-(trifluoromethyl)styryl)oxazole;

Compound 134: (E)-4-(4-(4-(1H-1,2,3-triazol-1-yl)butyl)benzyl)-2-(2-fluoro-4-(trifluoromethyl)styryl)oxazole;

Compound 135: (E)-4-((4-(4-(4H-1,2,4-triazol-4-yl)butyl)phenoxy)methyl)-2-(2-fluoro-4-(trifluoromethyl)styryl)oxazole;

Compound 136: (E)-N-(4-(4-((2-(2-fluoro-4-(trifluoromethyl)styryl)oxazol-4-yl)methoxy)phenyl)butyl)formamide;

Compound 137: (E)-4-(4-(4-((2-(2-fluoro-4-(trifluoromethyl)styryl)oxazol-4-yl)methoxy)phenyl)butyl)thiomorpholine 1,1-dioxide;

Compound 138: (E)-2-(2-fluoro-4-(trifluoromethyl)styryl)-4-((4-(4-(pyridazin-3-yl)butyl)phenoxy)methyl)oxazole;

Compound 139: (E)-2-(2-fluoro-4-(trifluoromethyl)styryl)-4-((4-(4-(pyrimidin-2-yl)butyl)phenoxy)methyl)oxazole;

Compound 140: (E)-2-(2-fluoro-4-(trifluoromethyl)styryl)-4-((4-(4-(pyridin-2-yl)butyl)phenoxy)methyl)oxazole;

Compound 141: (E)-4-(2-(4-((4-((3-(1H-1,2,3-triazol-1-yl)propyl)thio)phenoxy)methyl)oxazol-2-yl)vinyl)-3-fluorobenzonitrile;

Compound 142: 4-((4-(4-(1H-1,2,3-triazol-1-yl)butyl)phenoxy)methyl)-2-(6-fluorobenzofuran-2-yl)oxazole;

Compound 143: 4-((4-(4-(1H-1,2,3-triazol-1-yl)butyl)phenoxy)methyl)-2-(6-fluorobenzo[b]thiophen-2-yl)oxazole;

Compound 144: 4-((4-((3-(1H-1,2,3-triazol-1-yl)propyl)thio)phenoxy)methyl)-2-(4,6-difluoro-1H-indol-2-yl)oxazole;

Compound 145: (E)-4-((4-(4-(1H-1,2,3-triazol-1-yl)butyl)phenoxy)methyl)-2-(2-fluoro-4-(trifluoromethyl)styryl)-5-methyloxazole;

Compound 146: (E)-4-(((4-(4-(1H-1,2,3-triazol-1-yl)butyl)phenyl)thio)methyl)-2-(2-fluoro-4-(trifluoromethyl)styryl)oxazole; and Compound 147: (E)-4-((4-((2-(1H-1,2,3-triazol-1-yl)ethyl)thio)phenoxy)methyl)-2-(2-fluoro-4-(trifluoromethyl)styryl)oxazole.

Of note, Compound 1 above corresponds to Mubritinib (CAS Number 366017-09-6), also referred to as TAK-165 or (1-(4-{4-[(2-{(E)-2-[4-(trifluoromethyl)phenyl]ethenyl}-1,3-oxazol-4-yl)methoxy]phenyl}butyl)-1H-1,2,3-triazole, which has the following structure:

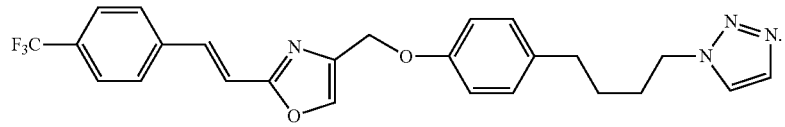 [SMILES: FC(F)(F)c1ccc(/C=C/c2nc(COc3ccc(CCCCn4ccnn4)cc3)co2)cc1]

In preferred embodiments, the compound is one of the following: Compounds 1, 2, 3A, 3B, 10, 12, 17, 19, 21 to 23, 25, 27, 33, 37 to 41, 45 to 48, 53 to 55, 58, 60 to 62, 65, 67, 68, 70, 71, 73, 80 to 83, 87, 92, 96 to 100, 102, 103, 105, 109 to 113, 115 to 125, 127 to 131, 133, 135 to 138, and 141 to 147, or a pharmaceutically acceptable salt thereof.

In more preferred embodiments, the compound is one of the following: Compounds 1, 3A, 10, 17, 19, 21, 22, 23, 25, 27, 33, 37, 38, 39, 40, 41, 45, 47, 48, 53, 58, 60, 61, 65, 67, 68, 70, 71, 73, 81, 82, 83, 87, 96 to 100, 103, 109 to 113, 116 to 125, 127 to 131, 133, 136, 138, and 141 to 147, or a pharmaceutically acceptable salt thereof.

In other more preferred embodiments, the compound is one of the following: Compounds 1, 3A, 10, 17, 21, 23, 27, 38, 40, 45, 48, 53, 65, 71, 73, 81, 98, 112, 116, 120, 121, 122, 124, 125, 127, 128, 129, 130, 133, 138, 141, 144, and 147, or a pharmaceutically acceptable salt thereof.

In yet more preferred embodiments, the compound is one of the following: Compounds 3A, 22, 23, 37, 48, 99, 112, 121, 122, 124, 125, 127, 128, 129, and 130, or a pharmaceutically acceptable salt thereof.

In yet more preferred embodiments, the compound is one of the following: Compounds 3A, 10, 65, 71, 73, 120, 122, 124, 127, 128, 129, 130, 138, 141, 144, and 147, or a pharmaceutically acceptable salt thereof.

In most preferred embodiments, the compound is one of the following: Compounds 65, 122, 124, 127, 128, 129, 130, 138, 141, 144, and 147, or a pharmaceutically acceptable salt thereof.

Other aspects also relate to a compound according to any of the embodiments defined herein, with one or more of the following provisos:

provided that

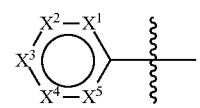

does not represent

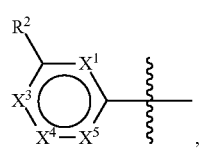

in which $X^3$ is a covalent bond, $X^1$ is —N=, $X^4$ is —O—, and $X^5$ is —CH=;

provided that $R^2$ is not ArylC($R^3$)=C(H)—, wherein $R^3$ is H and Aryl is p-trifluoromethylphenyl;

provided that $L^1$ is not —CH$_2$—O—;

provided that $X^6$ and $X^7$ are not both —CH=;

provided that $L^2$ is not a covalent bond;

provided that m is not 4;

provided that $R^1$ is not

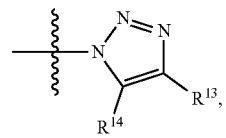

wherein $R^{13}$ and $R^{14}$ are each H; and/or provided that the compound is not Compound 1.

Alternatively, with one or more of the following provisos:
provided that

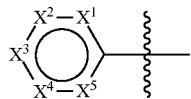

does not represent any one, any subset, or all of the following:

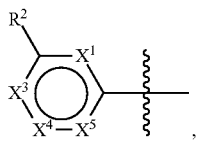

in which $X^1$ is —N=, $X^3$ is a covalent bond, $X^4$ is —O—, and $X^5$ is —CH=; and/or

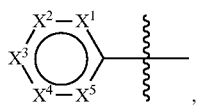

in which $X^1$ is —CH=, $X^2$ is —CH=, $X^3$ is —C($R^2$)=, $X^4$ is —N=, and $X^5$ is —CH=;

provided that $R^2$ does not represent any one, any subset, or all of the following:
ArylC($R^3$)=C(H)—;
ArylC($R^3$)=C(H)—, wherein $R^3$ is H and Aryl is p-trifluoromethylphenyl;
ArylC($R^3$)=C(H)—, wherein $R^3$ is H and Aryl is p-trifluoromethoxyphenyl;
ArylC($R^3$)=C(H)—, wherein $R^3$ is H and Aryl is p-methoxyphenyl;
ArylC($R^3$)=C(H)—, wherein $R^3$ is H and Aryl is p-fluorophenyl;
ArylC($R^3$)=C(H)—, wherein $R^3$ is H and Aryl is 2,4-difluorophenyl;
ArylC($R^3$)=C(H)—, wherein $R^3$ is H and Aryl is 2,6-difluorophenyl;
ArylC($R^3$)=C(H)—, wherein $R^3$ is H and Aryl is phenyl;
ArylC($R^3$)=C(H)—, wherein $R^3$ is H and Aryl is 2-fluoro-4-trifluoromethylphenyl;
ArylC($R^3$)=C(H)—, wherein $R^3$ is H and Aryl is 3-trifluoromethylphenyl;
Heteroaryl, optionally substituted with one to three $R^4$ groups;

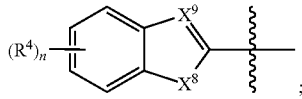

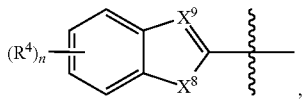

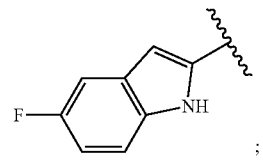

wherein $X^8$ is —NH— and/or $X^9$ is —CH=;

Aryl optionally substituted with one to three $R^4$ groups;
phenyl optionally substituted with one to three $R^4$ groups:
p-trifluoromethylphenyl;
Aryl(N($R^3$)C(O)—; and/or
Aryl(N($R^3$)C(O)—, wherein Aryl is 2-nitro-4-trifluoromethylphenyl and $R^3$ is H;
provided that $L^1$ does not represent any one, any subset, or all of the following:
—$CH_2$—O—;
—$CH_2$—NH—; and/or
—C(O)NH—;
provided that $X^6$ and $X^7$ are not both —CH=;
provided that $L^2$ does not represent any one, any subset, or all of the following:
a covalent bond;
—C(O)—;
—C($R^3$)(OH)—; and/or
—CH(OH)—;
provided that m is not 3 and/or 4;
provided that $R^1$ does not represent any one, any subset, or all of the following:

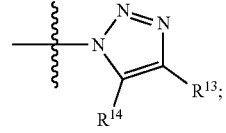

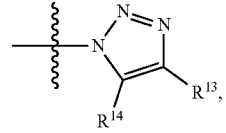

wherein $R^{13}$ and $R^{14}$ are each H;

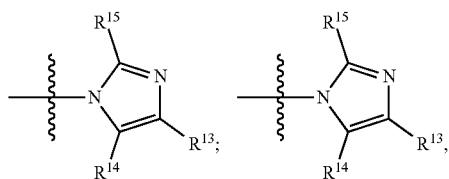

wherein $R^{13}$ and $R^{14}$ are each H;

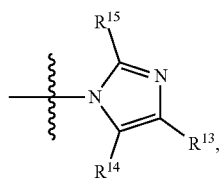

wherein $R^{13}$ and $R^{14}$ are each H and $R^{15}$ is —(CH$_2$)$_2$OH;

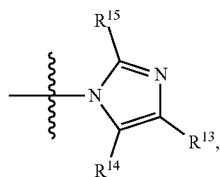

wherein $R^{13}$ and $R^{14}$ are each H and $R^{15}$ is —(CH$_2$)$_2$NH$_2$;

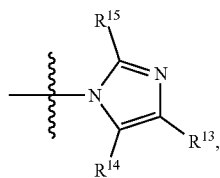

wherein $R^{13}$ and $R^{14}$ are each H and $R^{15}$ is —(CH$_2$)$_2$NHSO$_2$CH$_3$; and/or

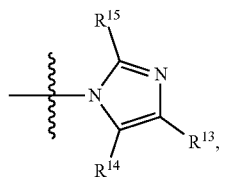

wherein $R^{13}$ and $R^{14}$ are each H and $R^{15}$ is —(CH$_2$)$_2$NHSO$_2$CF$_3$; and/or
provided that the compound is not any one, any subset, or all of the following: Compounds 1, 2, 18, 19, 26, 30, 32, 39, 45, 46, 47, 48, 49, 50, 51, 52, 54, 55, 73, 75, and/or 78.

The compound as herein defined may be in any amorphous, crystalline or polymorphic form, including their salts and/or solvates, or a combination or mixture thereof.

The compounds described herein may be prepared by any method known to a skilled medicinal chemist. Exemplary methods are presented in the Examples section.

In an embodiment, the compound or pharmaceutically acceptable salt thereof inhibits leukemic cell growth (e.g., OCI-AML3 cell growth) with an EC$_{50}$ that is about 1 µM or less, 500 nM or less, 100 nM or less, 75 nM or less, 50 nM or less, 10 nM or less, 5 nM or less, or 1 nM or less. In another embodiment, the compound or pharmaceutically acceptable salt thereof inhibits leukemic cell growth (e.g., OCI-AML3 cell growth) with an EC$_{50}$ that is about 100 nM or less, for example from about 100 nM to about 1 nM. In another embodiment, the compound or pharmaceutically acceptable salt thereof inhibits leukemic cell growth (e.g., OCI-AML3 cell growth) with an EC$_{50}$ that is about 50 nM or less, for example from about 50 nM to about 1 nM. In an embodiment, the EC$_{50}$ is assessed using the assay described in the Examples below.

iii. Methods, Uses, Formulations and Administration

Inhibitors of mitochondrial activity/respiration, such as inhibitors of the mitochondrial ETC complex I, have been shown to inhibit tumor growth in various cancers including lung, lymphoma, and breast cancers. The results described herein also show that Mubritinib and structurally-related heterocyclic compounds inhibit the growth of AML tumor cells.

Accordingly, in an aspect, the present disclosure provides a method for inhibiting tumor growth and/or inducing tumor cell death, said method comprising contacting said tumor with an effective amount of the compound of formula I or pharmaceutically acceptable thereof as described herein. The present disclosure also provides the use of the compound of formula I or pharmaceutically acceptable thereof as described herein, for inhibiting tumor growth and/or inducing tumor cell death, or for the manufacture of a medicament for inhibiting tumor growth and/or inducing tumor cell death. The present disclosure also provides the compound of formula I or pharmaceutically acceptable thereof as described herein, for inhibiting tumor growth and/or inducing tumor cell death. In an embodiment, the method/use is in vitro. In another embodiment, the method/use is in vivo.

In another aspect, the present disclosure provides a method for treating cancer in a subject, said method comprising administering to a subject in need thereof an effective amount of the compound of formula I or pharmaceutically acceptable thereof as described herein. The present disclosure also provides the use of the compound of formula I or pharmaceutically acceptable thereof as described herein, for treating a subject suffering from cancer, or for the manufacture of a medicament for treating a subject suffering from cancer. The present disclosure also provides the compound of formula I or pharmaceutically acceptable thereof as described herein, for use in the treatment of a subject suffering from cancer.

In another aspect, the present disclosure provides a method for treating AML, for example poor prognosis or poor risk AML, said method comprising administering to a subject in need thereof an effective amount of the compound of formula I or pharmaceutically acceptable thereof as described herein. The present disclosure also provides the use of the compound of formula I or pharmaceutically acceptable thereof as described herein, for treating a subject suffering from AML, for example poor prognosis or poor risk AML, or for the manufacture of a medicament for treating a subject suffering from AML, for example poor prognosis or poor risk AML. The present disclosure also provides the compound of formula I or pharmaceutically acceptable thereof as described herein, for use in the treatment of a subject suffering from AML, for example poor prognosis or poor risk AML.

In another aspect, the present disclosure provides a method for inhibiting mitochondrial activity/respiration in a cell (in vitro or in vivo), for example a cancer cell such as an AML cell (poor prognosis or poor risk AML cell), said method comprising contacting the cell with an effective amount of the compound of formula I or pharmaceutically acceptable thereof as described herein. The present disclosure also provides the use of the compound of formula I or pharmaceutically acceptable thereof as described herein, for inhibiting mitochondrial activity/respiration in a cell, or for the manufacture of a medicament for inhibiting mitochondrial activity/respiration in a cell. The present disclosure also provides the compound of formula I or pharmaceutically acceptable thereof as described herein, for use in the inhibition of mitochondrial activity/respiration in a cell.

The term "inhibition of mitochondrial activity" (or "inhibition of mitochondrial respiration") as used herein refers to the inhibition of the oxidative cellular energy production process, typically the inhibition of the aerobic cell metabolism. It includes inhibition of the cellular tricarboxylic acid (TCA) cycle (also known as the citric acid cycle, CAC, or Krebs cycle) (chemical conversion of carbohydrates, fats and proteins into carbon dioxide and water to generate a form of usable energy), and inhibition of the cellular oxidative (aerobic) glycolysis (metabolism of glucose to pyruvate in the cell cytoplasm) or of the oxidative phosphorylation of glycolysis substrate (pyruvate). The mitochondrial activity inhibition according to the present disclosure is the capacity to block the ETC or oxidative phosphorylation, leading to the production of Reactive Oxygen Species (ROS, such as $H_2O_2$) (i.e. increase in the levels of ROS in the cells), i.e., is an ROS-inducing mitochondrial activity inhibition. The effective amount of the compound of formula I or pharmaceutically acceptable salt thereof described herein is an amount that is toxic to tumor cells, such as AML cells (that inhibits tumor cell proliferation and/or induces tumor cell death) but not toxic (or significantly less toxic) for normal, non-tumor cells.

In an embodiment, the compound of formula I or pharmaceutically acceptable salt thereof inhibits the ETC, and induces the production of ROS in cells (i.e. increase the levels of ROS relative to an untreated cells), i.e. is an ROS-inducing ETC inhibitor. The ETC (also known as the respiratory chain) is a series of protein complexes located in the intermembrane space of the mitochondria of eukaryotic cells that transfer electrons from electron donors to electron acceptors via redox reactions, and couples this electron transfer with the transfer of protons ($H^+$ ions) across a membrane, which creates an electrochemical proton gradient that drives the synthesis of adenosine triphosphate (ATP). The components of the ETC are organized into 4 complexes (Complexes I to IV), and each complex contains several different electron carriers. Complex I, also known as the NADH-coenzyme Q reductase or NADH dehydrogenase) accepts electrons from NADH and serves as the link between glycolysis, the citric acid cycle, fatty acid oxidation and the ETC. Complex 11, also known as succinate-coenzyme Q reductase or succinate dehydrogenase, includes succinate dehydrogenase and serves as a direct link between the citric acid cycle and the ETC. Complexes I and II both produce reduced coenzyme Q, $CoQH_2$ which is the substrate for Complex III. Complex III, also known as coenzyme Q reductase, transfers the electrons from $CoQH_2$ to reduce cytochrome c which is the substrate for Complex IV. Finally, Complex IV, also known as cytochrome c reductase, transfers the electrons from cytochrome c to reduce molecular oxygen into water. In an embodiment, the compound of formula I or pharmaceutically acceptable salt thereof described herein inhibits the activity of the Complex I and/or Complex III of the human mitochondrial ETC, which are considered the major sites for ROS production. In a further embodiment, the compound of formula I or pharmaceutically acceptable salt thereof inhibits Complex I of the human mitochondrial ETC. In a further embodiment, the compound of formula I or pharmaceutically acceptable salt thereof described herein is a class A complex I inhibitor according to the classification of Fato et al. (*Biochim Biophys Acta*, 2009 May; 1787(5): 384-392). The term "class A complex I inhibitor" as used herein refers to an inhibitor of complex I that induces the production of ROS in cells, i.e. is an ROS-inducing complex I inhibitor.

The term cancer as used herein refers to the physiological condition in mammals that is typically characterized by unregulated cell growth/proliferation, and includes different types of cancers including carcinomas, sarcomas, gliomas, leukemias (acute and chronic leukemias), lymphomas (Hodgkin's and non-Hodgkin's lymphomas), e.g. epithelial neoplasms, squamous cell neoplasms, basal cell, neoplasms, transitional cell papillomas and carcinomas, adenomas and adenocarcinomas, adnexal and skin appendage neoplasms, mucoepidermoid neoplasms, cystic neoplasms, mucinous and serous neoplasms, ductal-, lobular and medullary neoplasms, acinar cell neoplasms, complex epithelial neoplasms, specialized gonadal neoplasms, paragangliomas and glomus tumors, naevi and melanomas, soft tissue tumors including sarcomas, fibromatous neoplasms, myxomatous neoplasms, lipomatous neoplasms, myomatous neoplasms, complex mixed and stromal neoplasms, fibroepithelial neoplasms, synovial-like neoplasms, mesothelial neoplasms, germ cell neoplasms, trophoblastic neoplasms, mesonephromas, blood vessel tumors, lymphatic vessel tumors, osseous and chondromatous neoplasms, giant cell tumors, miscellaneous bone tumors, gliomas, glioblastomas, oligodendrogliomas, neuroepitheliomatous neoplasms, meningiomas, nerve sheath tumors, granular cell tumors and alveolar soft part sarcomas, other lymphoreticular neoplasms, plasma cell tumors, and mast cell tumors. The cancer may be a cancer of any tissue/organ, e.g., lung cancer, breast cancer, colon cancer, skin cancer, liver cancer, or blood cancer. In an embodiment, the cancer/tumor cells do not express the Erb-B2 Receptor Tyrosine Kinase 2 (ERBB2 or HER2) protein. In another embodiment, the cancer is leukemia, preferably AML. In an embodiment, the cancer/tumor cells are sensitive to increased ROS levels or oxidative stress.

The studies described herein show that AML specimens more sensitive to Mubritinib have certain characteristics/features, including (i) higher expression of certain genes (see Tables 1 and 2b), notably homeobox (HOX)-network genes, relative to AML specimens more resistant to Mubritinib, (ii) lower expression of certain genes (see Tables 2 and 2a), relative to AML specimens more resistant to Mubritinib; (iii) certain cytogenetic or molecular risk factors, such as intermediate cytogenetic risk, Normal Karyotype (NK), high HOX status, mutated NPM1, mutated CEBPA, mutated FLT3, mutated DNA methylation genes (DNMT3A, TET2, IDH1, IDH2), mutated RUNX1, mutated WT1, mutated SRSF2, intermediate cytogenetic risk with abnormal karyotype (intern(abnK)), trisomy 8 (+8) and abnormal chr(5/7); and (iv) a higher leukemic stem cell (LSC) frequency, i.e. an LSC frequency of about 1 LSC per $1\times10^6$ total cells or more, relative to AML specimens more resistant.

TABLE 1

Genes overexpressed in Mubritinib sensitive versus resistant AML specimens (see Table 2b)

| | | | | | |
|---|---|---|---|---|---|
| HOXA5 | HOXA9 | PRDM16 | LOC285758 | HOXA3 | HOXA.AS3 |
| HOXB5 | HOXA11 | BEND6 | MIR4740 | COL4A5 | HOXA6 |
| HOXB9 | HOXA10.AS | LINC00982 | CYP7B1 | ANKRD18B | |
| HOXA4 | HOXA11.AS | NKX2.3 | HOXA7 | HOXB.AS3 | |

TABLE 2

Genes underexpressed in Mubritinib sensitive versus resistant AML specimens (see Table 2a)

| | | | | |
|---|---|---|---|---|
| ORM1 | SNORD116.4 | MSLN | MS4A2 | PRG3 |
| PRAME | SNORD116.24 | TINAGL1 | SNORD116.20 | ST18 |
| MYZAP | ZNF521 | S100A16 | KIRREL | SNORD116.21 |

Thus, in an embodiment, the subject treated by the method/use described herein suffers from AML characterized by at least one of the following features (i.e. the tumor cells exhibit at least one of the following features): (a) high level of expression of one or more homeobox (HOX)-network genes; (b) high level of expression of one or more of the genes depicted in Tables 1 and/or 2b; (c) low level of expression of one or more of the genes depicted in Tables 2 and/or 2a; (d) one or more of the following cytogenetic or molecular risk factor: intermediate cytogenetic risk, Normal Karyotype (NK), mutated NPM1, mutated CEBPA, mutated FLT3, mutated DNA methylation genes, mutated RUNX1, mutated WT1, mutated SRSF2, intermediate cytogenetic risk with abnormal karyotype (intern(abnK)), trisomy 8 (+8) and abnormal chr(5/7); and (e) a leukemic stem cell (LSC) frequency of about 1 LSC per $1 \times 10^6$ total cells, or more.

In another aspect, the present disclosure provides a method for treating AML, said method comprising administering to a subject in need thereof an effective amount of the compound of formula I or pharmaceutically acceptable salt thereof described herein, wherein said AML has at least one of the following features: (a) high level of expression of one or more HOX-network genes; (b) high level of expression of one or more of the genes depicted in Tables 1 and/or 2b; (c) low level of expression of one or more of the genes depicted in Tables 2 and/or 2a; (d) one or more of the following cytogenetic or molecular risk factor: intermediate cytogenetic risk, Normal Karyotype (NK), mutated NPM1, mutated CEBPA, mutated FLT3, mutated DNA methylation genes, mutated RUNX1, mutated WT1, mutated SRSF2, intermediate cytogenetic risk with abnormal karyotype (intern(abnK)), trisomy 8 (+8) and abnormal chr(5/7); and (e) a leukemic stem cell (LSC) frequency of about 1 LSC per $1 \times 10^6$ total cells, or more.

In another aspect, the present disclosure provides a use of the compound of formula I or pharmaceutically acceptable salt thereof described herein, for treating a subject suffering from AML, wherein said AML has at least one of the features (a)-(e) defined above. In another aspect, the present disclosure provides a use of the compound of formula I or pharmaceutically acceptable salt thereof described herein, for the manufacture of a medicament for treating a subject suffering from AML, wherein said AML has at least one of the features (a)-(e) defined above. In another aspect, the present disclosure provides the compound of formula I or pharmaceutically acceptable salt thereof described herein for use in the treatment of a subject suffering from AML, wherein said AML has at least one of the features (a)-(e) defined above.

In an embodiment, the subject to be treated has already been identified has having one or more of the above-noted features (a)-(e). In another embodiment, the methods further comprise a step of identifying a subject having one or more of the above-noted features, e.g. by performing a suitable assay, prior to administration of the compound of formula I or pharmaceutically acceptable salt thereof.

In another aspect, the present disclosure provides a method for determining a suitable therapy for a subject suffering from AML, the method comprising determining the presence or absence of at least one of features (a)-(e) defined herein in an AML cell sample from the subject, wherein the presence of at least one of features (a)-(e) is indicative that the subject is a suitable candidate for a therapy comprising the compound of formula I or pharmaceutically acceptable salt thereof described herein, and wherein the absence of features (a)-(e) is indicative that the subject is not a suitable candidate for a therapy comprising the compound of formula I or pharmaceutically acceptable salt thereof described herein, i.e. is a candidate for a therapy free of the compound of formula I or pharmaceutically acceptable salt thereof.

In another aspect, the present disclosure provides a method for treating poor prognosis or poor—risk AML, said method comprising administering to a subject in need thereof an effective amount of the compound of formula I or pharmaceutically acceptable salt thereof described herein. In another aspect, the present disclosure provides a use of the compound of formula I or pharmaceutically acceptable salt thereof described herein for treating poor prognosis or poor—risk AML in a subject. In another aspect, the present disclosure provides a use of the compound of formula I or pharmaceutically acceptable salt thereof described herein for the manufacture of a medicament for treating poor prognosis or poor—risk AML in a subject. In another aspect, the present disclosure provides the compound of formula I or pharmaceutically acceptable salt thereof described herein for use in the treatment of poor prognosis or poor—risk AML in a subject.

In another aspect, the present disclosure provides a method for treating intermediate—risk AML, said method comprising administering to a subject in need thereof an effective amount of the compound of formula I or pharmaceutically acceptable salt thereof described herein. In another aspect, the present disclosure provides a use of the compound of formula I or pharmaceutically acceptable salt thereof described herein for treating intermediate—risk AML in a subject. In another aspect, the present disclosure provides a use of the compound of formula I or pharmaceutically acceptable salt thereof described herein for the manufacture of a medicament for treating intermediate—risk AML in a subject. In another aspect, the present disclosure provides the compound of formula I or pharmaceutically acceptable salt thereof described herein for use in the treatment of intermediate—risk AML in a subject.

In another aspect, the present disclosure provides a method for treating poor—and/or intermediate—risk AML, said method comprising administering to a subject in need thereof an effective amount of the compound of formula I or pharmaceutically acceptable salt thereof described herein. In another aspect, the present disclosure provides a use of the compound of formula I or pharmaceutically acceptable salt thereof described herein for treating poor—and/or intermediate—risk AML in a subject. In another aspect, the present disclosure provides a use of the compound of formula I or pharmaceutically acceptable salt thereof described herein for the manufacture of a medicament for treating poor— and/or intermediate—risk AML in a subject. In another aspect, the present disclosure provides the compound of formula I or pharmaceutically acceptable salt thereof described herein for use in the treatment of poor—and/or intermediate—risk AML in a subject.

As used herein, the term "prognosis" refers to the forecast of the probable outcome or course of AML; the patient's chance of recovery or survival. The terms "poor prognosis AML" or "poor—risk AML" as used herein refer to an AML associated with long-term survival (5 years or more) of less than about 25% or 20% based on the currently available therapies. Poor prognosis AML is often associated with, for example, deletion of part of chromosome 5 or 7, translocation between chromosomes 9 and 11, translocation or inversion of chromosome 3, translocation between chromosomes 6 and 9, translocation between chromosomes 9 and 22, abnormalities of chromosome 11, FLT3 gene mutations, high EVI1 expression, complex karyotype (>3 abnormalities), and high HOX-network genes expression.

The term "intermediate—risk AML" as used herein refers to an AML is associated with long-term survival (5 years or more) of between about 60% to about 25% based on the currently available therapies. intermediate—risk AMLs are generally not associated with favorable and particular unfavorable cytogenetic aberrations (i.e. "uninformative" cytogenetic aberrations), and account for a significant proportion (approximately 55%) of AML patients. Examples of intermediate—risk AMLs include normal karyotype (NK) AML, NUP98-NSD1 fusion in AML with normal karyotype (NK), trisomy 8 alone AML, and intermediate abnormal karyotype AML.

In another aspect, the present disclosure provides a method for treating AML (e.g., poor—risk or poor prognosis AML), said method comprising administering to a subject in need thereof an effective amount of the compound of formula I or pharmaceutically acceptable salt thereof described herein, wherein said AML exhibiting high level of expression of one or more HOX-network genes (i.e. HOX-high AML). In another aspect, the present disclosure provides a use of the compound of formula I or pharmaceutically acceptable salt thereof described herein for treating AML (e.g., poor—risk or poor prognosis AML), said AML exhibiting high level of expression of one or more HOX-network genes. In another aspect, the present disclosure provides a use of the compound of formula I or pharmaceutically acceptable salt thereof described herein, for the manufacture of a medicament for treating AML (e.g., poor—risk or poor prognosis AML), said AML exhibiting high level of expression of one or more HOX-network genes. In another aspect, the present disclosure provides the compound of formula I or pharmaceutically acceptable salt thereof described herein for use in the treatment of AML (e.g., poor—risk or poor prognosis AML), said AML exhibiting high level of expression of one or more HOX-network genes.

The present disclosure also provides a method for determining the likelihood that a subject suffering from AML responds to a treatment with the compound of formula I or pharmaceutically acceptable salt thereof described herein, the method comprising determining whether AML cells from said subject exhibit high level of expression of one or more HOX-network genes, wherein high level of expression of the one or more HOX-network genes in said AML cells is indicative that the subject has a high likelihood of responding to said treatment.

Deregulation of the HOX-MEIS-PBX network (HOX network) is a common molecular anomaly in AML patients (Lawrence, H. J. et al. *Leukemia* 13, 1993-1999 (1999)). It is detected for example in two AML subtypes: in AML patients with normal karyotype (NK) carrying a mutation in nucleophosmin gene (NK NPM1m, representing around 25% of patients) and in a subgroup of patients with chromosome translocations involving the mixed lineage leukemia gene (MLL) on 11q23 (8% of patients).

The term "HOX-network gene" as used herein refers to a gene involved in the regulatory network of transcription factor (TF) family HOX and expressed in cells of the hematopoietic lineage. Members of the "HOX-network gene" expressed in cells of the hematopoietic lineage includes HOX genes of clusters A, B and C, such as HOXB1, HOXB2, HOXB3, HOXB4, HOXB5, HOXB6, HOXB7, HOXB9, HOXB-AS3, HOXA1, HOXA2, HOXA3, HOXA4, HOXA5, HOXA6, HOXA7, HOXA9, HOXA10, HOXA10-AS, HOXA11, HOXA11-AS and HOXA-AS3, as well as other genes such as MEIS1 and PBX3. In an embodiment, at least one HOX-network gene is highly expressed in the AML. In an embodiment, at least 2 HOX-network genes are highly expressed in the AML. In an embodiment, at least 3 HOX-network genes are highly expressed in the AML. In an embodiment, at least 4 HOX-network genes are highly expressed in the AML. In an embodiment, at least 5 HOX-network genes are highly expressed in the AML. In an embodiment, at least 10 HOX-network genes are highly expressed in the AML. In an embodiment, at least 15 HOX-network genes are highly expressed in the AML. In an embodiment, at least 20 HOX-network genes are highly expressed in the AML. In an embodiment, at least one of HOXA9 and HOXA10 are highly expressed in the AML. In an embodiment, both HOXA9 and HOXA10 are highly expressed in the AML. AML with high HOX gene expression defines a distinct biologic subset of AML, characterized by poor prognosis (adverse survival), intermediate risk cytogenetics, higher levels of FLT3 expression, frequent FLT3 and NPM1 mutations, and high LSC frequencies (see, e.g., Roche et al., *Leukemia* (2004) 18, 1059-1063; Kramarzova et al., *Journal of Hematology & Oncology* 2014 7:94). In an embodiment, the HOX-network gene(s) highly expressed in the AML is one or more of the HOX-network genes listed in Table 1.

In an embodiment, the above-mentioned method further comprises measuring the level of expression of one or more HOX-network genes in a sample comprising leukemic cells from the subject, and comparing the level to a reference level or control to determine whether the one or more HOX-network genes is/are highly expressed or overexpressed in the leukemic cells, and wherein if the one or more HOX-network genes is/are highly expressed or overexpressed in the leukemic cells, selecting the subject for treatment with the compound of formula I or pharmaceutically acceptable salt thereof described herein.

The present disclosure also provides a method for treating AML, said method comprising administering to a subject in need thereof an effective amount of the compound of formula I or pharmaceutically acceptable salt thereof described herein, wherein said AML exhibits high level of expression of one or more of the genes depicted in Table 1. In another aspect, the present disclosure provides a use of the compound of formula I or pharmaceutically acceptable salt thereof described herein for treating a subject suffering from AML, wherein said AML exhibits high level of expression of one or more of the genes depicted in Table 1. In another aspect, the present disclosure provides a use of the compound of formula I or pharmaceutically acceptable salt thereof described herein for the manufacture of a medicament for treating a subject suffering from AML, wherein said AML exhibits high level of expression of one or more of the genes depicted in Table 1. In another aspect, the present disclosure provides the compound of formula I or pharmaceutically acceptable salt thereof described herein for use in the treatment of a subject suffering from AML, wherein said AML exhibits high level of expression of one or more of the genes depicted in Table 1.

The present disclosure also provides a method for determining the likelihood that a subject suffering from AML responds to a treatment with the compound of formula I or pharmaceutically acceptable salt thereof described herein, the method comprising determining whether AML cells from said subject exhibit high level of expression of one or more of the genes depicted in Table 1, wherein high level of expression of the one or more genes in said AML cells is indicative that the subject has a high likelihood of responding to said treatment.

In an embodiment, at least one gene of Table 1 is highly expressed (overexpressed) in the AML. In an embodiment, at least 2 genes of Table 1 are highly expressed in the AML. In an embodiment, at least 3 genes of Table 1 are highly expressed in the AML. In an embodiment, at least 4 genes of Table 1 are highly expressed in the AML. In an embodiment, at least 5 genes of Table 1 are highly expressed in the AML. In an embodiment, at least 10 genes of Table 1 are highly expressed in the AML. In an embodiment, at least 1, 2, 3, 4, 5, 10, or more of the genes listed in Table 1 are highly expressed in the AML. In an embodiment, all the genes listed in Table 1 are highly expressed in the AML.

In an embodiment, the above-mentioned method further comprises measuring the level of expression of one or more of the genes of Table 1 in a sample comprising leukemic cells from the subject, and comparing the level to a reference level or control to determine whether the one or more genes is/are highly expressed or overexpressed in the leukemic cells, and wherein if the one or more genes is/are highly expressed or overexpressed in the leukemic cells, selecting the subject for treatment with the compound of formula I or pharmaceutically acceptable salt thereof described herein.

The present disclosure also provides a method for treating AML, said method comprising administering to a subject in need thereof an effective amount of the compound of formula I or pharmaceutically acceptable salt thereof described herein wherein said AML exhibits low level of expression of one or more of the genes depicted in Table 2. In another aspect, the present disclosure provides a use of the compound of formula I or pharmaceutically acceptable salt thereof described herein for treating a subject suffering from AML, wherein said AML exhibits low level of expression of one or more of the genes depicted in Table 2. In another aspect, the present disclosure provides a use of the compound of formula I or pharmaceutically acceptable salt thereof described herein for the manufacture of a medicament for treating a subject suffering from AML, wherein said AML exhibits low level of expression of one or more of the genes depicted in Table 2. In another aspect, the present disclosure provides the compound of formula I or pharmaceutically acceptable salt thereof described herein for use in the treatment of a subject suffering from AML, wherein said AML exhibits low level of expression of one or more of the genes depicted in Table 2.

The present disclosure also provides a method for determining the likelihood that a subject suffering from AML responds to a treatment with the compound of formula I or pharmaceutically acceptable salt thereof described herein, the method comprising determining whether AML cells from said subject exhibit low level of expression of one or more of the genes depicted in Table 2, wherein low level of expression of the one or more genes in said AML cells is indicative that the subject has a high likelihood of responding to said treatment.

In an embodiment, at least one gene of Table 2 is weakly expressed (underexpressed) in the AML. In an embodiment, at least 2 genes of Table 2 are weakly expressed in the AML. In an embodiment, at least 3 genes of Table 2 are weakly expressed in the AML. In an embodiment, at least 4 genes of Table 2 are weakly expressed in the AML. In an embodiment, at least 5 genes of Table 2 are weakly expressed in the AML. In an embodiment, at least 10 genes of Table 2 are weakly expressed in the AML. In an embodiment, all the above-noted genes are upregulated in the AML. In an embodiment, at least 1, 2, 3, 4, 5, 10, or more of the genes listed in Table 2 are weakly expressed in the AML. In an embodiment, all the genes listed in Table 2 are weakly expressed in the AML.

In an embodiment, the above-mentioned method further comprises measuring the level of expression of one or more of the genes of Table 2 in a sample comprising leukemic cells from the subject, and comparing the level to a reference level or control to determine whether the one or more genes is/are weakly expressed or underexpressed in the leukemic cells, and wherein if the one or more genes is/are weakly expressed or underexpressed in the leukemic cells, selecting the subject for treatment with the compound of formula I or pharmaceutically acceptable salt thereof.

The determination of the expression of the one or more genes or encoded gene products (e.g., mRNA, protein) disclosed herein (e.g., HOX-network genes, the genes in Tables 1 to 3) may be performed using any known methods to detect nucleic acids or proteins. In embodiments, the expression is compared to a control or reference level (e.g., the level obtained a sample from an AML subjects known to be resistant or sensitive to the compound of formula I or pharmaceutically acceptable salt thereof to assess the subject's likelihood of responding to the compound of formula I or pharmaceutically acceptable salt thereof described herein and to determine whether the subject may be treated with the compound of formula I or pharmaceutically acceptable salt thereof.

The levels of nucleic acids corresponding to the above-mentioned genes (e.g., transcripts) can then be evaluated according to commonly used methods such as those disclosed below, e.g., with or without the use of nucleic acid amplification methods. In some embodiments, nucleic acid amplification methods can be used to detect the level of expression of the one or more genes. For example, oligonucleotide primers and/or probes may be used in amplification and detection methods that use nucleic acid substrates isolated by any of a variety of well-known and established methodologies (e.g., Sambrook et al., supra; Lin et al., in *Diagnostic Molecular Microbiology, Principles and Applications*, pp. 605-16 (Persing et al., eds. (1993); Ausubel et al., *Current Protocols in Molecular Biology* (2001 and later updates thereto)). Methods for amplifying nucleic acids include, but are not limited to, for example the polymerase chain reaction (PCR) and reverse transcription PCR (RT-PCR) (see e.g., U.S. Pat. Nos. 4,683,195; 4,683,202; 4,800,159; 4,965,188), ligase chain reaction (LCR) (see, e.g., Weiss, Science 254: 1292-93 (1991)), strand displacement amplification (SDA) (see e.g., Walker et al., Proc. Natl. Acad. Sci. USA 89:392-396 (1992); U.S. Pat. Nos. 5,270,184 and 5,455,166), Thermophilic SDA (tSDA) (see e.g., European Pat. No. 0 684 315) and methods described in U.S. Pat. No. 5,130,238; Lizardi et al., *BioTechnol.* 6:1197-1202 (1988); Kwoh et al., *Proc. Natl. Acad. Sci. USA* 86:1173-77 (1989); Guatelli et al., *Proc. Natl. Acad. Sci. USA* 87:1874-78 (1990); U.S. Pat. Nos. 5,480,784; 5,399,491; U.S. Publication No. 2006/46265. The methods include the use of Transcription Mediated Amplification (TMA), which employs an RNA polymerase to produce multiple RNA transcripts of a target region (see, e.g., U.S. Pat. Nos. 5,480,784; 5,399,491 and U.S. Publication No. 2006/46265). The levels of nucleic acids may also be measured by "Next Generation Sequencing" (NGS) methods such as RNA sequencing (RNA-seq). In an embodiment, the method for measuring the level of expression of the one or more genes comprises a step of nucleic acid amplification.

The nucleic acid or amplification product may be detected or quantified by hybridizing a probe (e.g., a labeled probe) to a portion of the nucleic acid or amplified product. The primers and/or probes may be labelled with a detectable label that may be, for example, a fluorescent moiety, chemiluminescent moiety, radioisotope, biotin, avidin, enzyme, enzyme substrate, or other reactive group. As used herein, the term "detectable label" refers to a moiety emitting a signal (e.g., light) that may be detected using an appropriate detection system. Any suitable detectable label may be used in the method described herein. Detectable labels include, for example, enzyme or enzyme substrates, reactive groups, chromophores such as dyes or colored particles, luminescent moieties including bioluminescent, phosphorescent, or chemiluminescent moieties, and fluorescent moieties. In an embodiment, the detectable label is a fluorescent moiety.

Other well-known detection techniques include, for example, gel filtration, gel electrophoresis and visualization of the amplicons, and High-Performance Liquid Chromatography (HPLC). In certain embodiments, for example using real-time TMA or real-time PCR, the level of amplified product is detected as the product accumulates. In an embodiment, the method for measuring the level of expression of the one or more genes comprises a step of detection or quantification of a nucleic acid or amplification product with a probe.

In an embodiment, the above-mentioned method comprises a step of normalizing the gene expression levels, i.e. normalization of the measured levels of the above-noted genes against a stably expressed control gene (or housekeeping gene) to facilitate the comparison between different samples. "Normalizing" or "normalization" as used herein refers to the correction of raw gene expression values/data between different samples for sample to sample variations, to take into account differences in "extrinsic" parameters such as cellular input, nucleic acid (RNA) or protein quality, efficiency of reverse transcription (RT), amplification, labeling, purification, etc., i.e. differences not due to actual "intrinsic" variations in gene expression by the cells in the samples. Such normalization is performed by correcting the raw gene expression values/data for a test gene (or gene of interest) based on the gene expression values/data measured for one or more "housekeeping" or "control" genes, i.e. whose expressions are known to be constant (i.e. to show relatively low variability) between the cells of different tissues and under different experimental conditions. Thus, in an embodiment, the above-mentioned method further comprises measuring the level of expression of a housekeeping gene in the biological sample. Suitable housekeeping genes are known in the art and several examples are described in WO 2014/134728.

In an embodiment, the method for measuring the level of expression of the one or more genes further comprises measuring the level of expression of one or more housekeeping genes in a biological sample from the subject.

In another embodiment, the expression of the one or more genes or encoded gene products is measured at the protein level. Methods to measure the amount/level of proteins are well known in the art. Protein levels may be detected directly using a ligand binding specifically to the protein, such as an antibody or a fragment thereof. In embodiments, such a binding molecule or reagent (e.g., antibody) is labeled/conjugated, e.g., radio-labeled, chromophore-labeled, fluorophore-labeled, or enzyme-labeled to facilitate detection and quantification of the complex (direct detection). Alternatively, protein levels may be detected indirectly, using a binding molecule or reagent, followed by the detection of the [protein/binding molecule or reagent] complex using a second ligand (or second binding molecule) specifically recognizing the binding molecule or reagent (indirect detection). Such a second ligand may be radio-labeled, chromophore-labeled, fluorophore-labeled, or enzyme-labeled to facilitate detection and quantification of the complex. Enzymes used for labeling antibodies for immunoassays are known in the art, and the most widely used are horseradish peroxidase (HRP) and alkaline phosphatase (AP). Examples of binding molecules or reagents include antibodies (monoclonal or polyclonal), natural or synthetic ligands, and the like. Examples of methods to measure the amount/level of protein in a sample include, but are not limited to: Western blot, immunoblot, enzyme-linked immunosorbent assay (ELISA), "sandwich" immunoassays, radioimmunoassay (RIA), immunoprecipitation, surface plasmon resonance (SPR), chemiluminescence, fluorescent polarization, phosphorescence, immunohistochemical (IHC) analysis, matrix-assisted laser desorption/ionization time-of-flight (MALDI-TOF) mass spectrometry, microcytometry, microarray, antibody array, microscopy (e.g., electron microscopy), flow cytometry, proteomic-based assays, and assays based on a property or activity of the protein including but not limited to ligand binding or interaction with other protein partners, enzymatic activity, fluorescence. For example, if the protein of interest is a kinase known to phosphorylate of given target, the level or activity of the protein of interest may be determined by the measuring the level of phosphorylation of the target in the presence of the test compound. If the protein of interest is a transcription factor known to induce the expression of one or more given target gene(s), the level or activity of the protein of interest may be determined by the measuring the level of expression of the target gene(s).

"Control level" or "reference level" are used interchangeably herein and broadly refers to a separate baseline level measured in a comparable "control" sample, which is generally from a subject having a known level of expression of the gene of interest and/or whose responsiveness to the compound of formula I or pharmaceutically acceptable salt thereof is known, for example an AML sample from a subject known to not respond to the compound of formula I or pharmaceutically acceptable salt thereof. The corresponding control level may be a level corresponding to an average or median level calculated based of the levels measured in several reference or control subjects (e.g., a pre-determined or established standard level). The control level may be a pre-determined "cut-off" value recognized in the art or established based on levels measured in samples from one or a group of control subjects (e.g., a group of subject known to not respond to the compound of formula I or pharmaceutically acceptable salt thereof). For example, the "threshold reference level" may be the level corresponding the minimal level of expression (cut-off) of the gene(s) that permits to distinguish in a statistically significant manner AML subjects who are likely to respond to the compound of formula I or pharmaceutically acceptable salt thereof described herein (sensitive) from those who are unlikely to respond to the compound of formula I or pharmaceutically acceptable salt thereof described herein (resistant), which may be determined using samples from AML patients with different pharmalogical responses to the compound of formula I or pharmaceutically acceptable salt thereof described herein, for example. Alternatively, the "threshold reference level" may be the level corresponding the level of gene expression (cut-off) that permits to best or optimally distinguish in a statistically significant manner AML subjects sensitive to the compound of formula I or pharmaceutically acceptable salt thereof from AML subjects resistant a mitochondria activity inhibitor (e.g., Mubritinib). The corresponding reference/control level may be adjusted or normalized for age, gender, race, or other parameters. The "control level" can thus be a single number/value, equally applicable to every subject individually, or the control level can vary, according to specific subpopulations of patients. Thus, for example, older men might have a different control level than younger men, and women might have a different control level than men. The predetermined standard level can be arranged, for example, where a tested population is divided equally (or unequally) into groups, such as a low-likelihood group, a medium-likelihood group and/or a high-likelihood group or into quadrants or quintiles. It will also be understood that the control levels may be, in addition to predetermined levels or standards, levels measured in other samples (e.g. from a subject having a known level of expression of the gene of interest and/or whose responsiveness to the compound of formula I or pharmaceutically acceptable salt thereof is known) tested in parallel with the experimental sample. The reference or control levels may correspond to normalized levels, i.e. reference or control values subjected to normalization based on the expression of a housekeeping gene.

"Higher expression" or "higher level of expression" (overexpression) as used herein refers to (i) higher expression of the one or more of the above-mentioned genes (protein and/or mRNA) in one or more given cells present in the sample (relative to the control) and/or (ii) higher amount of cells expressing the one or more genes in the sample (relative to the control). "Low/weak expression" or "lower/weaker level of expression" (underexpression) as used herein refers to (i) lower expression of the one or more genes (protein and/or mRNA) in one or more given cells present in the sample (relative to the control) and/or (ii) lower amount of cells expressing the one or more genes in the sample (relative to the control). In an embodiment, higher or lower refers to a level of expression that is above or below the control level (e.g., the predetermined cut-off value). In another embodiment, higher or lower refers to a level of expression that is at least one standard deviation above or below the control level (e.g., the predetermined cut-off value) (e.g. that is statistically significant as determined using a suitable statistical analysis), and a "similar expression" or "similar level of expression" refers to a level of expression that is less than one standard deviation above or below the control level (e.g., the predetermined cut-off value) (e.g. that is not statistically significant as determined using a suitable statistical analysis, such as False Discovery Rate (FDR)/q-values, Student t-test/p values, Mann-Whitney test/p values). In embodiments, higher or lower refers to a level of expression that is at least 1.5, 2, 2.5, 3, 4 or 5 standard deviations above or below the control level (e.g., the predetermined cut-off value. In another embodiment, "higher expression" refers to an expression that is at least 10, 20, 30, 40, 45 or 50% higher in the test sample relative to the control level. In an embodiment, "lower expression" refers to an expression that is at least 10, 20, 25, 30, 35, 40, 45, or 50% lower in the test sample relative to the control level. In another embodiment, higher or lower refers to a level of expression that is at least 1.5, 2-, 5-, 10-, 25-, or 50-fold higher or lower in the test sample relative to the control sample.

In another aspect, the present disclosure provides a method for treating AML, said method comprising administering to a subject in need thereof an effective amount of the compound of formula I or pharmaceutically acceptable salt thereof described herein, wherein said AML exhibits one or more of the following cytogenetic or molecular risk factor: Normal Karyotype (NK), mutated NPM1, mutated CEBPA (e.g., mono- or bi-allelic), mutated FLT3, mutated DNMT3A, mutated TET2, mutated IDH1, mutated IDH2, mutated RUNX1, mutated WT1, mutated SRSF2, intermediate cytogenetic risk, intermediate cytogenetic risk with abnormal karyotype (intern(abnK)), trisomy 8 (+8) and abnormal chr(5/7). In another aspect, the present disclosure provides a use of the compound of formula I or pharmaceutically acceptable salt thereof described herein for treating a subject suffering from AML, wherein said AML exhibits one or more of the above-noted cytogenetic or molecular risk factors. In another aspect, the present disclosure provides a use of the compound of formula I or pharmaceutically acceptable salt thereof described herein for the manufacture of a medicament for treating a subject suffering from AML, wherein said AML exhibits one or more of the above-noted cytogenetic or molecular risk factors. In another aspect, the present disclosure provides the compound of formula I or pharmaceutically acceptable salt thereof described herein for use in the treatment of AML, wherein said AML exhibits one or more of the above-noted cytogenetic or molecular risk factors.

In an embodiment, the subject suffers from AML characterized by intermediate cytogenetic risk, Normal Karyotype (NK), and/or high HOX expression. In an embodiment, the subject suffers from AML with intermediate cytogenetic risk. In an embodiment, the subject suffers from AML with Normal Karyotype (NK). In an embodiment, the subject suffers from AML with high HOX expression.

The present disclosure also provides a method for determining the likelihood that a subject suffering from AML responds to a treatment the compound of formula I or pharmaceutically acceptable salt thereof described herein, the method comprising determining whether AML cells from said subject exhibit one or more of the following cytogenetic or molecular risk factor: Normal Karyotype (NK), mutated NPM1, mutated CEBPA, mutated FLT3, mutated DNMT3A, mutated TET2, mutated IDH1, mutated IDH2, mutated RUNX1, mutated WT1, mutated SRSF2, intermediate cytogenetic risk, intermediate cytogenetic risk with abnormal karyotype (intern(abnK)), trisomy 8 (+8) and abnormal chr(5/7), wherein the presence of said one or more of cytogenetic or molecular risk factor in said AML cells is indicative that the subject has a high likelihood of responding to said treatment. In an embodiment, the mutation in the above-noted mutated genes is at one or more of the positions depicted in Table 3B. In a further embodiment, the mutation in the above-noted mutated genes is one or more of the mutations depicted in Table 3B.

In an embodiment, the method/use is for treating NK-AML. In an embodiment, the method/use is for treating AML with mutated FLT3 (e.g., FLT3 with internal tandem duplications, FLT3-ITD). In an embodiment, the method/use is for treating AML with mutated CEBPA. In an embodiment, the method/use is for treating AML with mutated DNMT3A. In an embodiment, the method/use is for treating AML with mutated TET2. In an embodiment, the method/use is for treating AML with mutated IDH1. In an embodiment, the method/use is for treating AML with mutated IDH2. In an embodiment, the method/use is for treating AML with mutated RUNX1. In an embodiment, the method/use is for treating AML with mutated WT1. In an embodiment, the method/use is for treating AML with mutated SRSF2. In an embodiment, the method/use is for treating AML with intermediate cytogenetic risk with abnormal karyotype (intern(abnK)). In an embodiment, the method/use is for treating AML with trisomy 8 (+8). In an embodiment, the method/use is for treating AML with abnormal chromosome (5/7).

In an embodiment, the method is for treatment AML with any combination of 2, 3, 4, 5 or more of the above-mentioned cytogenetic or molecular risk factors.

In an embodiment, the AML is not AML with MLL translocations. In an embodiment, the AML is not EVI1-rearranged AML. In an embodiment, the AML is not Core Binding Factor (CBF) AML, for example AML with t(8:21) or inv(16) chromosomal rearrangements. In an embodiment, the AML is not AML with mutated NRAS, mutated c-KIT and/or mutated TP53.

In an embodiment, the AML is NK-AML with mutated NPM1. In an embodiment, the AML cells comprise a mutated NPM1, a mutated FLT3 (e.g., FLT3 with internal tandem duplications, FLT3-ITD) and a mutated DNA methylation gene such as DNMT3A. In a further embodiment, the AML cells comprise a mutated NPM1, a mutated FLT3 (e.g., FLT3 with internal tandem duplications, FLT3-ITD), a mutated DNA methylation gene such as DNMT3A, and do not comprise a mutated NRAS.

The cytogenetic and molecular risk factors defined herein are based on the 2008 World Health Organization (WHO) classification (Vardiman et al., *Blood* 2009 114:937-951), and recent advances in genomic classification (Papaemmanuil, E. et al. *N Engl J Med* 374, 2209-2221, 2016).

In another embodiment, the above-noted method/use further comprises determining the presence (or absence) of one or more of the cytogenetic and molecular risk factors defined herein in a sample comprising leukemic cells from the subject, wherein if one or more of the cytogenetic and molecular risk factors are present, selecting the subject for treatment with the compound of formula I or pharmaceutically acceptable salt thereof described herein.

Methods and kits to identify cytogenetic or molecular risk factors (mutation(s), translocations, fusions, chromosomal abnormalities, etc.) are well known in the art, and include, for example, karyotype, fluorescence in situ hybridization (FISH), reverse transcription polymerase chain reaction (RT-PCR), DNA sequencing, and microarray technology (see, e.g., Gulley et al., *J Mol Diagn.* 2010 January; 12(1): 3-16). The determination of the presence of the mutation(s), translocations, fusions, etc. in the sample may be performed using any suitable methods (see, e.g., Syvänen, *Nat Rev Genet.* 2001 December; 2(12):930-42). For example, the presence of the mutation(s) may be detected at the genomic DNA, transcript (RNA or cDNA) or protein level. Examples of suitable methods for determining sequences and polymorphisms at the nucleic acid level include sequencing of the nucleic acid sequence encompassing the mutation(s), e.g., in the genomic DNA or transcript (cDNA), for example by "Next Generation Sequencing" methods (e.g., genome sequencing, RNA sequencing (RNA-seq)) or other sequencing methods; hybridization of a nucleic acid probe capable of specifically hybridizing to a nucleic acid sequence comprising the mutation(s) and not to (or to a lesser extent to) a corresponding nucleic acid sequence that does not comprises the mutation(s) (under comparable hybridization conditions, such as stringent hybridization conditions) (e.g., molecular beacons); restriction fragment length polymorphism analysis (RFLP); Amplified fragment length polymorphism PCR (AFLP-PCR); amplification of a nucleic acid fragment comprising the mutation(s) using a primer specifically hybridizing to a nucleic acid sequence comprising the mutation(s), wherein the primer produces an amplified product if the mutation(s) is/are present and does not produce the same amplified product when a nucleic acid sequence not comprising the mutation(s) is used as a template for amplification, nucleic acid sequence based amplification (Nasba), primer extension assay, FLAP endonuclease assay (Invader assay, Olivier M. (2005). *Mutat Res.* 573(1-2):103-10), 5'-nuclease assay (McGuigan F. E. and Ralston S. H. (2002) *Psychiatr Genet.* 12(3):133-6), oligonucleotide ligase assay. Other methods include in situ hybridization analyses and single-stranded conformational polymorphism analyses. Several SNP genotyping platforms are commercially available. Additional methods will be apparent to one of skill in the art.

The determination of the presence of the mutation(s) and/or fusion(s) may also be achieved at the polypeptide/protein level. Examples of suitable methods for detecting alterations at the polypeptide level include sequencing of the encoded polypeptide; digestion of the encoded polypeptide followed by mass spectrometry or HPLC analysis of the peptide fragments, wherein the mutated polypeptide results in an altered mass spectrometry or HPLC spectrum as compared to the unmutated polypeptide; and immunodetection using an immunological reagent (e.g., an antibody, a ligand) which exhibits altered immunoreactivity with a mutated polypeptide relative to a corresponding unmutated polypeptide. Immunodetection can measure the amount of binding between a polypeptide molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots, and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999).

All these detection techniques may also be employed in the format of microarrays, e.g., SNP microarrays, DNA microarrays, protein-arrays, antibody microarrays, tissue microarrays, electronic biochip or protein-chip based technologies (see Schena M., Microarray Biochip Technology, Eaton Publishing, Natick, Mass., 2000).

In another embodiment, the methods described herein to identify the presence of one or more features in the AML cells further comprise obtaining or collecting a biological sample from a subject. In various embodiments, the sample can be from any source that contains biological material suitable for the detection of the mutation(s), such as genomic DNA, RNA (cDNA), and/or proteins, for example a tissue or cell sample from the subject (blood cells, immune cells (e.g., lymphocytes), etc. that comprises cancer cells, such as leukemic cells (e.g., AML cells). The sample may be subjected to cell purification/enrichment techniques to obtain a cell population enriched in a specific cell subpopulation or cell type(s). The sample may be subjected to commonly used isolation and/or purification techniques for enrichment in nucleic acids (genomic DNA, cDNA, mRNA) and/or proteins. Accordingly, in an embodiment, the method may be performed on an isolated nucleic acid and/or protein sample, such as isolated genomic DNA. The biological sample may be collected using any methods for collection of biological fluid, tissue or cell sample, such as venous puncture for collection of blood cell samples.

The present disclosure also provides a method for treating AML, said method comprising administering to a subject in need thereof an effective amount of the compound of formula I or pharmaceutically acceptable salt thereof described herein, wherein said AML exhibits a leukemic stem cell (LSC) frequency of about 1 LSC per $1 \times 10^6$ total cells, or more.

The present disclosure also provides a method for determining the likelihood that a subject suffering from AML responds to a treatment with the compound of formula I or pharmaceutically acceptable salt thereof described herein, the method comprising determining LSC frequency in the AML cells from said subject, wherein an LSC frequency of about 1 LSC per $1 \times 10^6$ total cells, or more, is indicative that the subject has a high likelihood of responding to said treatment.

In an embodiment, the AML exhibits an LSC frequency of about 1 LSC per $9 \times 10^5$ total cells, or more. In an embodiment, the AML exhibits an LSC frequency of about 1 LSC per $8 \times 10^5$ total cells, or more. In an embodiment, the AML exhibits an LSC frequency of about 1 LSC per $7 \times 10^5$ total cells, or more. In an embodiment, the AML exhibits an LSC frequency of about 1 LSC per $6 \times 10^5$ total cells, or more. In an embodiment, the AML exhibits an LSC frequency of about 1 LSC per $5 \times 10^5$ total cells, or more. In an embodiment, the AML exhibits an LSC frequency of about 1 LSC per $4 \times 10^5$ total cells, or more. In an embodiment, the AML exhibits an LSC frequency of about 1 LSC per $3 \times 10^5$ total cells, or more. In an embodiment, the AML exhibits an LSC frequency of about 1 LSC per $2 \times 10^5$ total cells, or more. In an embodiment, the AML exhibits an LSC frequency of about 1 LSC per $1 \times 10^5$ total cells, or more.

LSC frequency in an AML cell sample may be measured using methods known in the art, for example using a flow cytometric-based assay using LSC-associated markers (CD34+CD38-) and light scatter aberrancies (Terwijn et al., *PLoS One*. 2014 Sep. 22; 9(9):e107587) or using a limiting dilution assay (LDA) in a model of xenotransplantation based on NOD/SCID/IL2Rγc-deficient (NSG) mice (Sarry et al., *J Clin Invest*. 2011; 121(1):384-395; Pabst, C. et al. *Blood* 127, 2018-2027 and US Patent Publication No. 2014/0343051 A1)), as used in the studies described below. In an embodiment, the LSC frequency is as measured using the limiting dilution assay in NSG mice described in the Examples below.

In an embodiment, the above-mentioned method further comprises measuring the LSC frequency in a sample comprising leukemic cells from the subject, and wherein if the LSC frequency is about 1 LSC per $1 \times 10^6$ total cells, or more, selecting the subject for treatment with the compound of formula I or pharmaceutically acceptable salt thereof described herein.

In another aspect, the present disclosure provides a method for determining whether a subject suffering from cancer AML is likely to respond to a treatment with the compound of formula I or pharmaceutically acceptable salt thereof, said method comprising determining whether the AML has at least one of the following features: (a) high level of expression of one or more homeobox (HOX)-network genes; (b) high level of expression of one or more of the genes depicted in Table 1; (c) low level of expression of one or more of the genes depicted in Table 2; (d) one or more of the following cytogenetic or molecular risk factor: intermediate cytogenetic risk, Normal Karyotype (NK), mutated NPM1, mutated CEBPA, mutated FLT3, mutated DNA methylation genes, mutated RUNX1, mutated WT1, mutated SRSF2, intermediate cytogenetic risk with abnormal karyotype (intern(abnK)), trisomy 8 (+8) and abnormal chr(5/7); and (e) a leukemic stem cell (LSC) frequency of about 1 LSC per $1 \times 10^6$ total cells, or more; wherein the presence of at least one of these features in said AML is indicative that the patient is likely to respond to a treatment with the compound of formula I or pharmaceutically acceptable salt thereof.

Methods to measure the above-noted features are well known in the art, and representative methods are described above.

In another embodiment, the compound of formula I or pharmaceutically acceptable salt thereof described herein is administered/used as a prodrug, for example as a pharmaceutically acceptable ester. The term "prodrug" refers to analogs of an active agent (compound of formula I or pharmaceutically acceptable salt thereof) that are pharmacologically acceptable and substantially non-toxic to the subject to which they are administered. More specifically, the prodrug retains the biological effectiveness and properties of the active agent and when absorbed into the bloodstream of a warm-blooded animal, is cleaved or metabolized in such a manner as to produce the parent active agent. Methods to produce prodrugs of compounds are known in the art.

In the methods/uses of the present disclosure, the compound of formula I or pharmaceutically acceptable salt thereof may be administered using any conventional route, for example orally, intravenously, parenterally, subcutaneously, intramuscularly, intraperitoneally, intranasally or pulmonary (e.g., aerosol).

In an embodiment, the above-mentioned treatment comprises the use/administration of more than one (i.e. a combination of) active/therapeutic agent or therapy, one of which being with the compound of formula I or pharmaceutically acceptable salt thereof. The combination of prophylactic/therapeutic agents and/or compositions of the present disclosure may be administered or co-administered (e.g., consecutively, simultaneously, at different times) in any conventional dosage form. Co-administration in the context of the present disclosure refers to the administration of more than one therapeutic in the course of a coordinated treatment to achieve an improved clinical outcome. Such co-administration may also be coextensive, that is, occurring during overlapping periods of time. For example, a first agent (e.g., the compound of formula I or pharmaceutically acceptable salt thereof) may be administered to a patient before, concomitantly, before and after, or after a second active agent or therapy is administered. In an embodiment, the one or more active agent(s) is used/administered in combination with one or more agent(s) currently used to prevent or treat the disorder in question, for example chemotherapeutic drugs used for the treatment of cancers such as AML. The compound of formula I or pharmaceutically acceptable salt thereof may also be used in combination with one or more other cancer therapies, for example stem cell/bone marrow transplantation, radiation and/or surgery.

In an embodiment, the compound of Formula I or pharmaceutically acceptable salt thereof is present in a pharmaceutical composition. Thus, in another aspect, the present technology provides a composition for use in the treatment of AML in a subject, the composition comprising the compound of formula I or pharmaceutically acceptable salt thereof.

In an embodiment, the composition comprises one or more pharmaceutically acceptable carriers or excipients. Supplementary active compounds can also be incorporated into the compositions. The carrier/excipient can be suitable, for example, for intravenous, parenteral, subcutaneous, intramuscular, intraperitoneal, intranasal or pulmonary (e.g., aerosol) administration (see Remington: *The Science and Practice of Pharmacy*, by Loyd V Allen, Jr, 2012, 22$^{nd}$ edition, Pharmaceutical Press; *Handbook of Pharmaceutical Excipients*, by Rowe et al., 2012, 7$^{th}$ edition, Pharmaceutical Press). Pharmaceutical compositions may be prepared using standard methods known in the art by mixing the Mubritinib or pharmaceutically acceptable salt thereof having the desired degree of purity with one or more optional pharmaceutically acceptable carriers and/or excipients.

The term "pharmaceutically acceptable carrier or excipient" as used herein has its normal meaning in the art and refers any ingredient that is not an active ingredient (mitochondrial activity inhibitor such as Mubritinib or pharmaceutically acceptable salt thereof) itself that does not interfere with effectiveness of the biological activity of the active ingredient and that is not toxic to the subject, i.e., is a type of carrier or excipient and/or is for use in an amount which is not toxic to the subject. Excipients/carriers include for example binders, lubricants, diluents, fillers, thickening agents, disintegrants/dissolution promoting agents, plasticizers, coatings, barrier layer formulations, lubricants, surfactants, stabilizing agent, release-delaying agents, permeation enhancers, glidants, anti-caking agents, anti-tacking agents, stabilizing agents, anti-static agents, swelling agents and other components. As those of skill would recognize, a single excipient can fulfill more than two functions at once, e.g., can act as both a binding agent and a thickening agent. As those of skill will also recognize, these terms are not necessarily mutually exclusive.

Useful diluents, e.g., fillers, include, for example and without limitation, dicalcium phosphate, calcium diphosphate, calcium carbonate, calcium sulfate, lactose, cellulose, kaolin, sodium chloride, starches, powdered sugar, colloidal silicon dioxide, titanium oxide, alumina, talc, colloidal silica, microcrystalline cellulose, silicified micro crystalline cellulose and combinations thereof. Fillers that can add bulk to tablets with minimal drug dosage to produce tablets of adequate size and weight include croscarmellose sodium NF/EP (e.g., Ac-Di-Sol™); anhydrous lactose NF/EP (e.g., Pharmatose™ DCL 21); and/or povidone USP/EP.

Binder materials include, for example and without limitation, starches (including corn starch and pregelatinized starch), gelatin, sugars (including sucrose, glucose, dextrose and lactose), polyethylene glycol, povidone, waxes, and natural and synthetic gums, e.g., acacia sodium alginate, polyvinylpyrrolidone, cellulosic polymers (e.g., hydroxypropyl cellulose, hydroxypropyl methylcellulose, methyl cellulose, hydroxyethyl cellulose, carboxymethylcellulose, colloidal silicon dioxide NF/EP (e.g., Cab-O-Sil™ M5P), Silicified Microcrystalline Cellulose (SMCC), e.g., Silicified microcrystalline cellulose NF/EP (e.g., Prosolv™ SMCC 90), and silicon dioxide, mixtures thereof, and the like), veegum, and combinations thereof.

Useful lubricants include, for example, canola oil, glyceryl palmitostearate, hydrogenated vegetable oil (type 1), magnesium oxide, magnesium stearate, mineral oil, poloxamer, polyethylene glycol, sodium lauryl sulfate, sodium stearate fumarate, stearic acid, talc and, zinc stearate, glyceryl behapate, magnesium lauryl sulfate, boric acid, sodium benzoate, sodium acetate, sodium benzoate/sodium acetate (in combination), dl-leucine, calcium stearate, sodium stearyl fumarate, mixtures thereof, and the like.

Bulking agents include, for example: microcrystalline cellulose, for example, AVICEL® (FMC Corp.) or EMCOCEL® (Mendell Inc.), which also has binder properties; dicalcium phosphate, for example, EMCOMPRESS® (Mendell Inc.); calcium sulfate, for example, COMPACTROL® (Mendell Inc.); and starches, for example, Starch 1500; and polyethylene glycols (CARBOWAX®).

Disintegrating or dissolution promoting agents include: starches, clays, celluloses, alginates, gums, crosslinked polymers, colloidal silicon dioxide, osmogens, mixtures thereof, and the like, such as crosslinked sodium carboxymethyl cellulose (AC-DI-SOLO), sodium croscarmelose, sodium starch glycolate (EXPLOTAB®, PRIMO JEL®) crosslinked polyvinylpolypyrrolidone (PLASONE-XL®), sodium chloride, sucrose, lactose and mannitol.

Antiadherents and glidants employable in the core and/or a coating of the solid oral dosage form may include talc, starches (e.g., cornstarch), celluloses, silicon dioxide, sodium lauryl sulfate, colloidal silica dioxide, and metallic stearates, among others.

Examples of silica flow conditioners include colloidal silicon dioxide, magnesium aluminum silicate and guar gum.

Suitable surfactants include pharmaceutically acceptable non-ionic, ionic and anionic surfactants. An example of a surfactant is sodium lauryl sulfate. If desired, the pharmaceutical composition to be administered may also contain minor amounts of nontoxic auxiliary substances such as wetting or emulsifying agents, pH-buffering agents and the like, for example, sodium acetate, sorbitan monolaurate, triethanolamine sodium acetate, triethanolamine oleate, etc. If desired, flavoring, coloring and/or sweetening agents may be added as well.

Examples of stabilizing agents include acacia, albumin, polyvinyl alcohol, alginic acid, bentonite, dicalcium phosphate, carboxymethylcellulose, hydroxypropylcellulose, colloidal silicon dioxide, cyclodextrins, glyceryl monostearate, hydroxypropyl methylcellulose, magnesium trisilicate, magnesium aluminum silicate, propylene glycol, propylene glycol alginate, sodium alginate, carnauba wax, xanthan gum, starch, stearate(s), stearic acid, stearic monoglyceride and stearyl alcohol.

Examples of thickening agent can be for example talc USP/EP, a natural gum, such as guar gum or gum arabic, or a cellulose derivative such as microcrystalline cellulose NF/EP (e.g., Avicel™ PH 102), methylcellulose, ethylcellulose or hydroxyethylcellulose. A useful thickening agent is hydroxypropyl methylcellulose (HPMC), an adjuvant which is available in various viscosity grades.

Examples of plasticizers include: acetylated monoglycerides; these can be used as food additives; Alkyl citrates, used in food packagings, medical products, cosmetics and children toys; Triethyl citrate (TEC); Acetyl triethyl citrate (ATEC), higher boiling point and lower volatility than TEC; Tributyl citrate (TBC); Acetyl tributyl citrate (ATBC), compatible with PVC and vinyl chloride copolymers; Trioctyl citrate (TOC), also used for gums and controlled release medicines; Acetyl trioctyl citrate (ATOC); Trihexyl citrate (THC), compatible with PVC, also used for controlled release medicines; Acetyl trihexyl citrate (ATHC), compatible with PVC; Butyryl trihexyl citrate (BTHC, trihexyl o-butyryl citrate), compatible with PVC; Trimethyl citrate (TMC), compatible with PVC; alkyl sulphonic acid phenyl ester, polyethylene glycol (PEG) or any combination thereof. Optionally, the plasticizer can comprise triethyl citrate NF/EP.

Examples of permeation enhancers include: sulphoxides (such as dimethylsulphoxide, DMSO), a zones (e.g. laurocapram), pyrrolidones (for example 2-pyrrolidone, 2P), alcohols and alkanols (ethanol, or decanol), glycols (for example propylene glycol and polyethylene glycol), surfactants and terpenes.

In an embodiment, the pharmaceutical composition is an oral formulation, is for oral administration. In an embodiment, the pharmaceutical composition is in the form of a tablet or pill.

Formulations suitable for oral administration may include (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Any suitable amount of the compound of formula I or pharmaceutically acceptable salt thereof, or pharmaceutical composition comprising same, may be administered to a subject. The dosages will depend on many factors including the mode of administration. Typically, the amount of the compound contained within a single dose will be an amount that effectively prevent, delay or treat cancer (e.g., AML) without inducing significant toxicity.

For the prevention, treatment or reduction in the severity of cancer (e.g., AML), the appropriate dosage of the compound of formula I or pharmaceutically acceptable salt thereof or composition will depend, for example, on the type of cancer to be treated, the severity and course of the cancer, whether the compound of formula I or pharmaceutically acceptable salt thereof, or composition, is administered for preventive or therapeutic purposes, previous therapy, the patient's clinical history and response to the compound of formula I or pharmaceutically acceptable salt thereof and the discretion of the attending physician. The compound of formula I or pharmaceutically acceptable salt thereof, or composition, may be suitably administered to the patient at one time or over a series of treatments. Preferably, it is desirable to determine the dose-response curve in vitro, and then in useful animal models, prior to testing in humans. The present disclosure provides dosages for the compound of formula I or pharmaceutically acceptable salt thereof, and compositions comprising same. For example, depending on the type and severity of the cancer (e.g., AML), about 1 μg/kg to about 1000 mg per kg (mg/kg) of body weight of the mitochondrial activity inhibitor may be administered per day. In embodiments, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. The mitochondrial activity inhibitor, e.g., Mubritinib or pharmaceutically acceptable salt thereof, may be administered according to any suitable dosing schedule/regimen, e.g., twice-a-day, once-a-day, every 2 days, twice-a-week, weekly, etc. In an embodiment, the administration is once-a-day.

In an embodiment, the pharmaceutical composition comprises from about 0.1 mg to about 100 mg of the compound of formula I or pharmaceutically acceptable salt thereof. In further embodiments, the pharmaceutical composition comprises from about 1 mg to about 50 mg, from about 2 mg to about 30 mg, from about 5 mg to about 25 or 20 mg, or about 10 mg, of the compound of formula I or pharmaceutically acceptable salt thereof.

In an embodiment, the composition comprises the compound of formula I or pharmaceutically acceptable salt thereof and an additional active agent, e.g. a chemotherapeutic agent. The active agents are combined/formulated in a single composition, and thus administered at the same time for the methods/uses described above.

The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The following non-limiting examples are illustrative embodiments and should not be construed as further limiting the scope of the present invention. These examples will be better understood with reference to the accompanying figures.

The Examples set forth herein below provide syntheses and experimental results obtained for certain exemplary compounds. Unless otherwise indicated, all numbers expressing quantities of ingredients, reaction conditions, concentrations, properties, stabilities, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Example 1: Materials and Methods

Human Leukemia Samples

This study was approved by the Research Ethics Boards (REB) of Université de Montréal, Maisonneuve-Rosemont Hospital and Charles Lemoyne Hospital (Longueuil, QC, Canada). All AML samples were collected with an informed consent between 2001 and 2017 according to the procedures of the Banque de Cellules Leucémiques du Quebec (BCLQ). Umbilical cord blood (CB) units were collected from consenting mothers and human CD34+CB cells were isolated with the EasySep® positive selection kit (StemCell Technologies, Vancouver, Canada, catalog number 18056) (Fares et al., Science. 2014 Sep. 19; 345(6203):1509-12).

Chemical Screen

Primary cells: frozen AML mono-nucleated cells were thawed at 37° C. in Iscove's modified Dulbecco's medium (IMDM) containing 20% FBS and DNase 1(100 µg/mL). Cells were then cultured in optimized AML growth medium as previously reported (Pabst, C. et al. Nature methods 11, 436-442, 2014): IMDM, 15% BIT (bovine serum albumin, insulin, transferrin; Stem Cell Technologies®), 100 ng/mL SCF, 50 ng/mL FLT3-L, 20 ng/mL IL-3, 20 ng/mL G-CSF (Shenandoah®), $10^{-4}$ M β-mercaptoethanol, 500 nM SR1 (Alichem®), 500 nM UM729 (synthesized at the Medicinal Chemistry Core Facility at the Institute for Research in Immunology and Cancer (IRIC)), gentamicin (50 µg/mL) and ciprofloxacin (10 µg/mL).

Expanded CB cells are cells that resulted from 6 days of UM171-supplemented culture of fresh CB cells, as described in Fares et al., supra. Fresh CB cells are cells directly collected from umbilical cord blood specimens, following a positive CD34 selection (EasySep® kit, Stem-Cell Technologies, Vancouver, Canada), as described in Fares et al., Science. 2014 Sep. 19; 345(6203):1509-12. CB cells (fresh and expanded) were cultivated in StemSpan®-ACF (Stemcell Technologies 09855) containing SCF 100 ng/mL, TPO 100 ng/mL, FLT3-L 50 ng/mL (Shenandoah®), Glutamax®1X, LDL 10 µg/mL, ciprofloxacin 10 µg/mL, 500 nM SR1 (Alichem®) and 35 nM UM171 (synthesized at the Medicinal Chemistry Core Facility at the Institute for Research in Immunology and Cancer (IRIC)).

Cell lines. OCI-AML3 cells were maintained in alpha-MEM, 20% FBS whereas breast tumor BT474 cells were maintained in DMEM 10% FBS. BT474 (ATCC® HTB-20™) was a kind gift from the laboratory of Sylvie Mader, whereas OCI-AML3 and OCI-AML5 cells were purchased from the German cell bank (DSMZ, accession Nos. ACC 582 and ACC 247, respectively).

Compounds. All powders were dissolved in DMSO and diluted in culture medium immediately before use. Final DMSO concentration in all conditions was 0.1%. The 60 compounds were purchased from various suppliers including Santa Cruz, Selleckchem, Calbiochem, AdooQ Bioscience, Cayman chemical and Synkinase.

Cell dose-response viability assays. Patient cells were seeded in 384-well plates at a density of 5,000 cells in 50 µL per well. In the initial screen, compounds were added to seeded cells in serial dilutions (10 dilutions, 1:3, starting from µM or 20 µM), in duplicates. Cells treated with 0.1% DMSO without additional compound were used as negative controls. Viable cell counts per well were evaluated after 6 days of culture using the CellTiterGlo® assay (Promega®) according to the manufacturer's instruction. The percent of inhibition was calculated as follows: 100-(100×(mean luminescence(compound)/mean luminescence(DMSO)); where mean-luminescence(compound) corresponds to the average of luminescent signals obtained for the compound-treated cells, and mean-luminescence(DMSO) corresponds to the average of luminescent signals obtained for the control DMSO-treated cells.

$EC_{50}$ values (corresponding to the concentration of compound required to reach 50% of inhibition) were calculated using ActivityBase® SARview Suite (IDBS, London, UK) and GraphPad® Prism 4.03 (La Jolla, Calif., USA) by four-parameter-non-linear curve fitting methods.

Leukemic Stem Cell (LSC) Frequency Assessment.

LSC frequencies were assessed in immunocompromised NSG mice using limiting dilution assays, as detailed previously (Pabst, C. et al. Blood 127, 2018-2027, 2016). NOD.Cg-Prkdc$^{scid}$ Il2rg$^{tm1Wjl}$/SzJ (NSG) mice were purchased from Jackson Laboratory® (Bar Harbor, Me.) and bred in a pathogen-free animal facility. All AML samples were transplanted via the tail vein into 8 to 12-week old sublethally irradiated (250 cGy, $^{137}$Cs-gamma source) NSG mice. AML cells were transplanted at four different cell doses in groups of four recipient mice directly after thawing. Human leukemic engraftment in mouse bone marrow was determined by flow cytometry between 10 and 16 weeks post-transplant. On average 150,000 gated events were acquired. Mice were considered positive if human cells represented >1% of the bone marrow cell population. Mice were excluded only in case of obvious non-leukemia related death (e.g., first two weeks after irradiation). To discriminate between engraftment of leukemic and normal cells present in unsorted patient samples only recipients with proportions of CD45$^+$CD33$^+$ or CD45$^+$CD34$^+$, cells higher than proportions of CD19$^+$CD33$^-$ or CD3$^+$ were considered to harbor cells of leukemic origin.

Flow Cytometry Staining

The following FACS antibodies were used: anti-human CD45 Pacific Blue (BioLegend 304029), CD45 fluorescein isothiocyanate (FITC; BioLegend 304006), CD33 phycoerythrin (PE; BD Bioscience 555450), CD33 BV421 (BD 562854), CD34 antigen-presenting cell (APC; BD Bioscience 555824), CD34 APC (Stem Cell Technologies 10613), CD3 FITC (BD Bioscience 555332), CD4 APC-Cy7 (BD 560158), CD8 APC (BD 555369), CD3 PE-Cy5 (BD 555334), CD19 PE-Cy7(BD Bioscience 557835), anti-mouse CD45.1 APC-efluor730 (eBioscience 47-0453-82), ERBB2-PE (Biolegend®, 324406), Annexin V FITC (BD Bioscience®, 556419). Dead cells were stained using Propidium iodide at a final concentration of 1 µg/mL. For ROS quantification cells were stained with 1 µM H2DCFDA (Thermo Fisher, D399) under normal growth conditions. Cells were analyzed on LSRII® flow cytometer (BD Bioscience®), BD Canto® II cytometer (BD Bioscience) or on an IQue Screener (Intellicyt®) and results were analyzed with BD fluorescence-activated cell sorter (FACS) Diva®4.1 and FlowJo®X software.

Next-Generation Sequencing and Mutation Quantification

Workflow for sequencing, mutation analysis and transcripts quantification have been described previously (Lavallée, V.-P. et al. *Blood* 125, 140-143, 2014; Lavallée, V.-P. et al. *Nat. Genet.* 47, 1030-1037, 2015). Briefly, libraries were constructed with TruSeq® RNA/TruSeq®DNA Sample Preparation Kits (Illumina®). Sequencing was performed using an Illumina® HiSeq 2000 with 200 cycles paired end runs. Sequence data were mapped to the reference genome hg19 using the Illumina® Casava 1.8.2 package and EI and v2 mapping software according to RefSeq annotations (UCSC, Apr. 16 2014). Variants were identified using Casava 1.8.2 and fusions or larger mutations such as partial tandem duplications with Tophat 2.0.7 and Cufflinks 2.1.1.

Transcript levels are given as Reads Per Kilobase per Million mapped reads (RPKM) and genes are annotated according to RefSeq annotations (UCSC, Apr. 16 2014).

LC/MS Metabolite Measurements (Citric Acid Cycle Intermediates and Glutathione)

LC/MS metabolite measurements were carried out at the McGill Metabolomics platform. Authentic metabolite standards were purchased from Sigma-Aldrich Co., while the following LC/MS grade solvents and additives were purchased from Fisher: ammonium acetate, formic acid, water, methanol, and acetonitrile. OCI-AML3 cells (5 million cells, quadruplicates, treated with either DMSO or Mubritinib 500 nM for 20 h) were washed twice with ice-cold 150 mM ammonium formate pH 7.2. Metabolites were then extracted using 380 µl of LC/MS grade 50% methanol/50% water mixture and 220 µl of cold acetonitrile. Samples were then homogenized by 1.4 mm ceramic bead beating 2 min at 30 Hz (TissueLyser, Qiagen). A volume of 300 µl of ice-cold water and 600 µl of ice-cold methylene chloride were added to the lysates. Samples were vortexed and allowed to rest on ice for 10 min for phase separation followed by centrifugation at 4,000 rpm for 5 min. The upper aqueous layer was transferred to a fresh pre-chilled tube. Samples were eventually dried by vacuum centrifugation operating at −4° C. (Labconco) and stored at −80° C. until ready for LC-MS/MS data collection. For LC-MS/MS analysis, specimens were first re-suspended in 50 µl of water and clarified by centrifugation for 15 min at 15,000 rpm at 1° C. Samples were maintained at 4° C. for the duration of the LC-MS/MS analysis in the autosampler. Specimens were separated by U-HPLC (Ultra-High-Performance Liquid Chromatography) (1290 Infinity, Agilent Technologies) using a Scherzo SM-$C_{18}$ (3 mm×150 mm) 3 µm column and guard column (Imtakt USA) operating at 10° C.

Seahorse Metabolic Flux Experiments

Oxygen consumption rates and extracellular acidification rates were measured using a 96-well Seahorse Bioanalyzer XFe96® or XFe24® according to the manufacturer's instructions (Agilent Technologies). Seahorse XF Base medium was supplemented with 1 mM pyruvate, 2 mM glutamine and 10 mM glucose in the case of Mitochondrial Stress Test and with 1 mM pyruvate, 2 mM glutamine and no glucose in the case of Glycolytic Stress Test. The pH of the Seahorse media was then adjusted at 7.4 prior to assay. In brief, leukemic cells were seeded into Seahorse 96-well (or 24-well) plates pre-coated for 3 h with poly-lysine (Sigma-Aldrich, P4707) at a density of 75,000 cells/well in 100 µL (or 150,000 cells/well, in 150 µL) of temperature/$CO_2$ pre-adjusted Seahorse media per well. The Seahorse plates were then centrifuged at 1400 rpm for 5 min. An additional 75 µL (or 375 µL) of Seahorse media was then added and cells were eventually analyzed following the manufacturer's instructions by adding compounds in a constant volume of 25 µL (or 75 µL). Compounds were acutely injected in cells at a final concentration of 1 µM for Mubritinib, 1 µM for Oligomycin, 0.5 µM for FCCP, 0.5 µM for Rotenone/Antimycin A, Glucose 10 mM and 2-Deoxy-Glucose 50 mM.

Cell-Free Assay for ETC Complex I Activity

The cell-free kit assay for ETC complex I activity was purchased from MitoSciences (Abcam, Cambridge, UK), and used in accordance with the manufacturer's protocol. $IC_{50}$ values were calculated using GraphPad® Prism 4.03 (La Jolla, Calif., USA) by four-parameter-non-linear curve fitting methods.

Statistics

Analysis of differential gene expression was performed using the Wilcoxon rank-sum test and the false discovery rate (FDR) method was applied for global gene analysis as previously described (Lavallée, V.-P. et al. *Blood* 125, 140-143, 2014). Differential overall survival p-values were calculated by log-rank test on patients belonging to the prognostic Leucegene cohort.

Example 2: HOX-High AML Patients Generally have a Poor Disease Prognosis

Figure 1B:
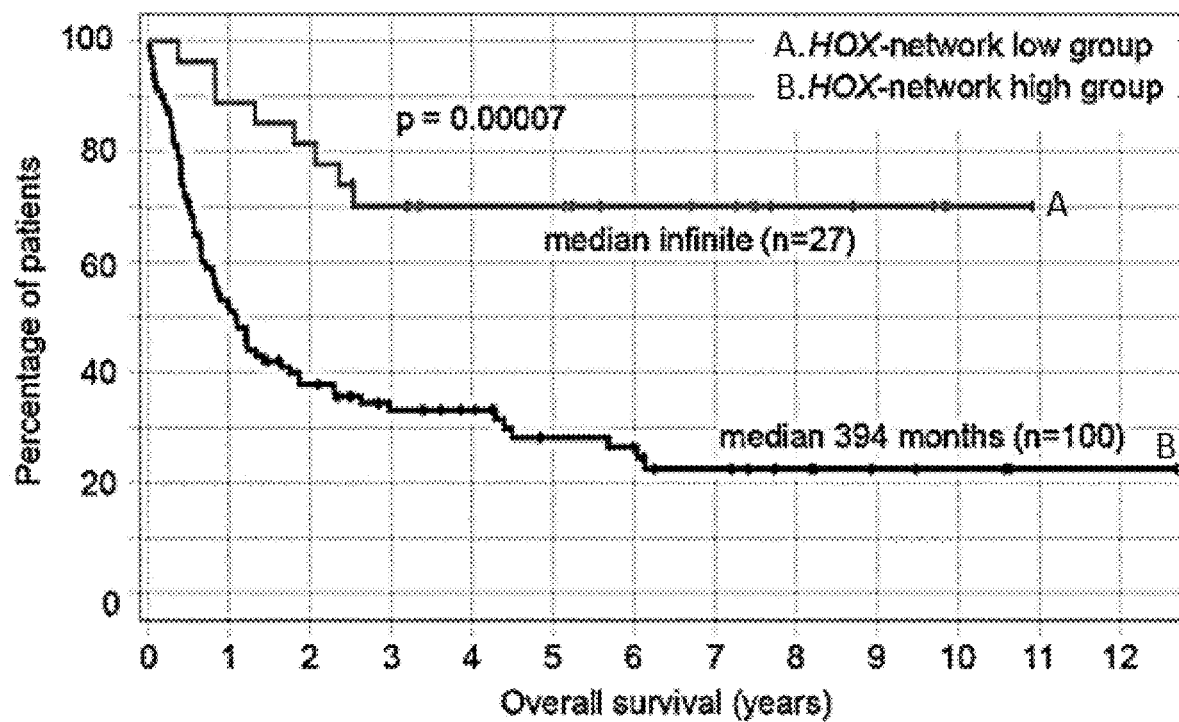
Figure 1C:
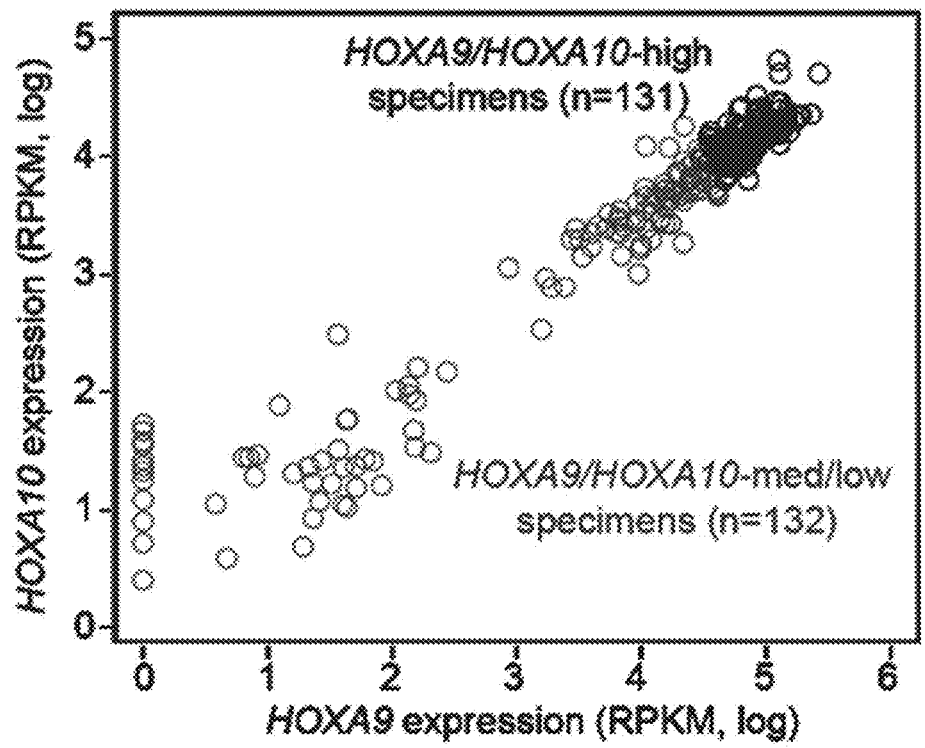
Figure 1D:
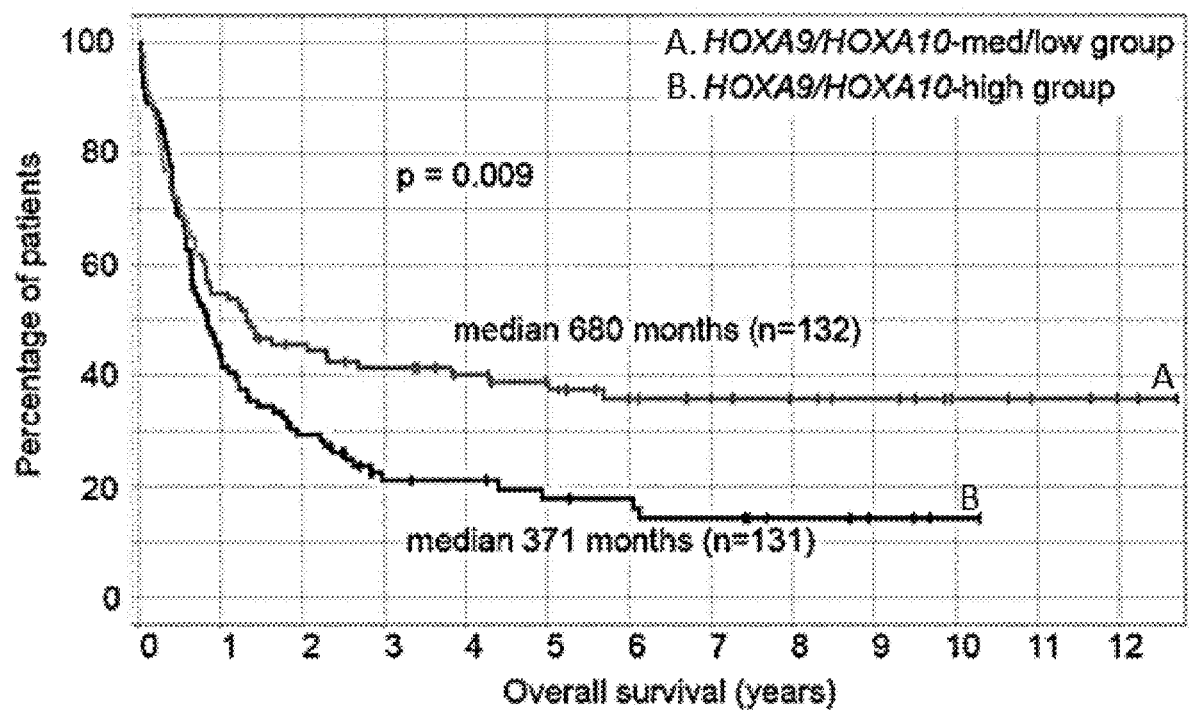

Consistent high expression of genes belonging to the HOX network (FIG. 1A) in AML cell samples was shown to be associated with a significantly decreased patient overall survival (FIG. 1B). FIG. 1C shows the correlation between HOXA9 and HOXA10 expression in leukemic cells, and FIG. 1D show that survival of AML patients belonging to the HOXA9/HOXA10 high group is similar to that of patients belonging to HOX-network high subgroup shown in FIG. 1B, indicating that high expression of HOXA9 and HOXA10 may be used as a surrogate for the detection of HOX network-high patients. Overall, these data show that patients having AML cells exhibiting high expression of HOX-network genes have a poor prognosis and would benefit from suitable AML treatments.

Example 3: Mubritinib Efficiently Inhibits HOX-High AML Cells

Figure 2A:
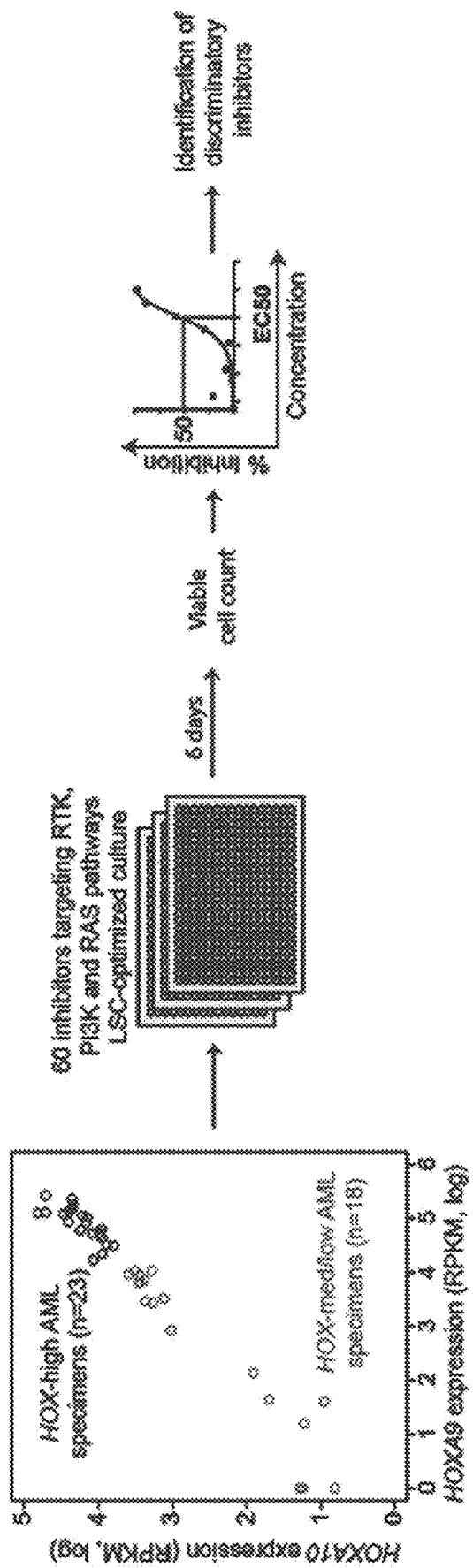
FIGS. 2A-H show the characterization of the pharmacological response of HOX-high AML cells.

Using high expression of HOXA9 and HOXA10 as a surrogate for the detection of HOX-network-high patient samples, the survival of HOX-high versus HOX-med/low specimens contacted with 60 inhibitors targeting receptor tyrosine kinases (RTK), members of the RAS and PI3K pathways, was assessed (FIG. 2A).

Figure 2B:
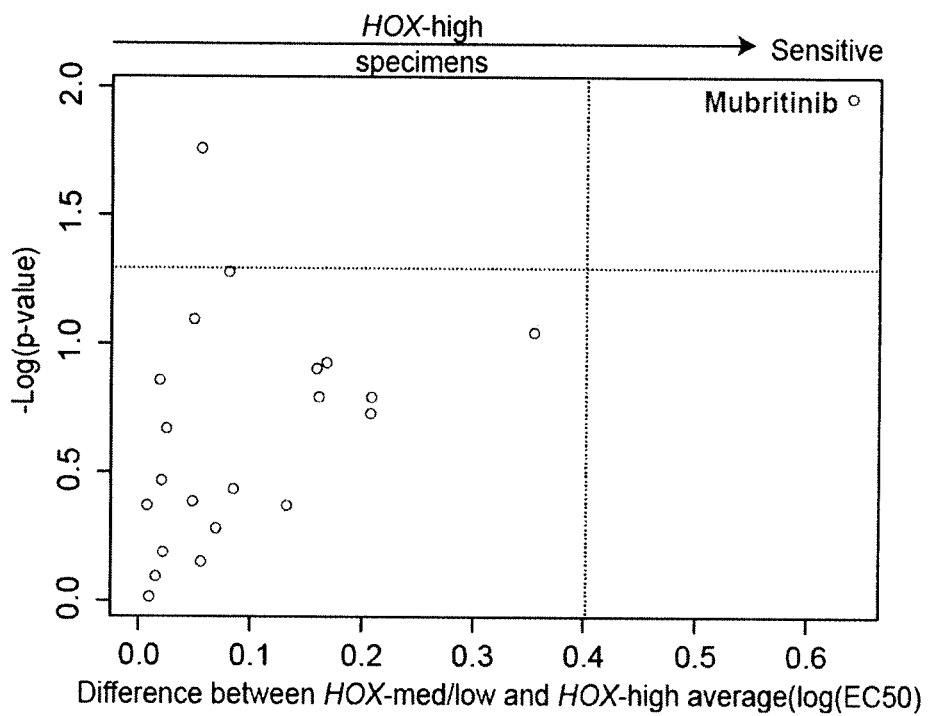

When compared to HOX-med/low samples, HOX-high patient cells were significantly more sensitive to the RTK ERBB2 inhibitor Mubritinib (FIG. 2B). No statistically significant difference in sensitivity was observed for the other compounds tested.

Figure 2C:
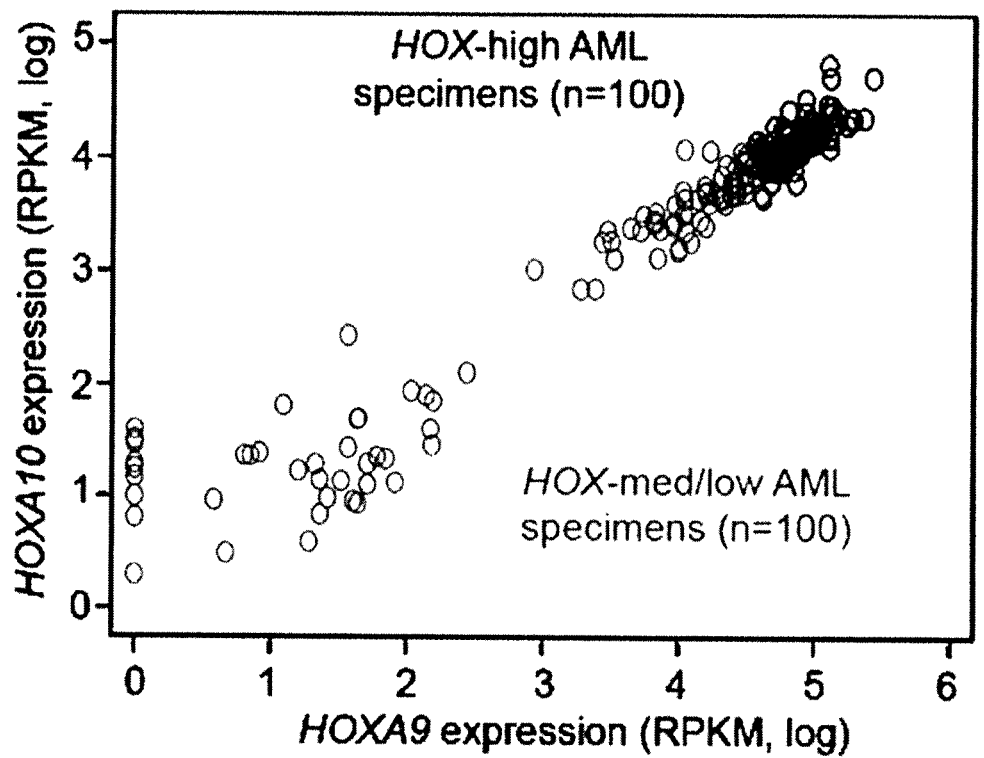
Figure 2D:
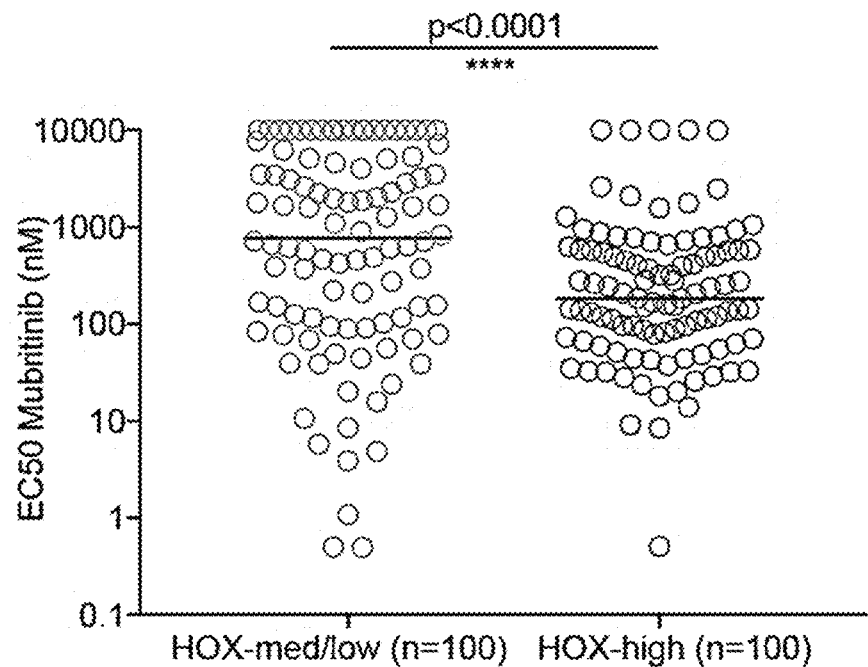
Figure 2E:
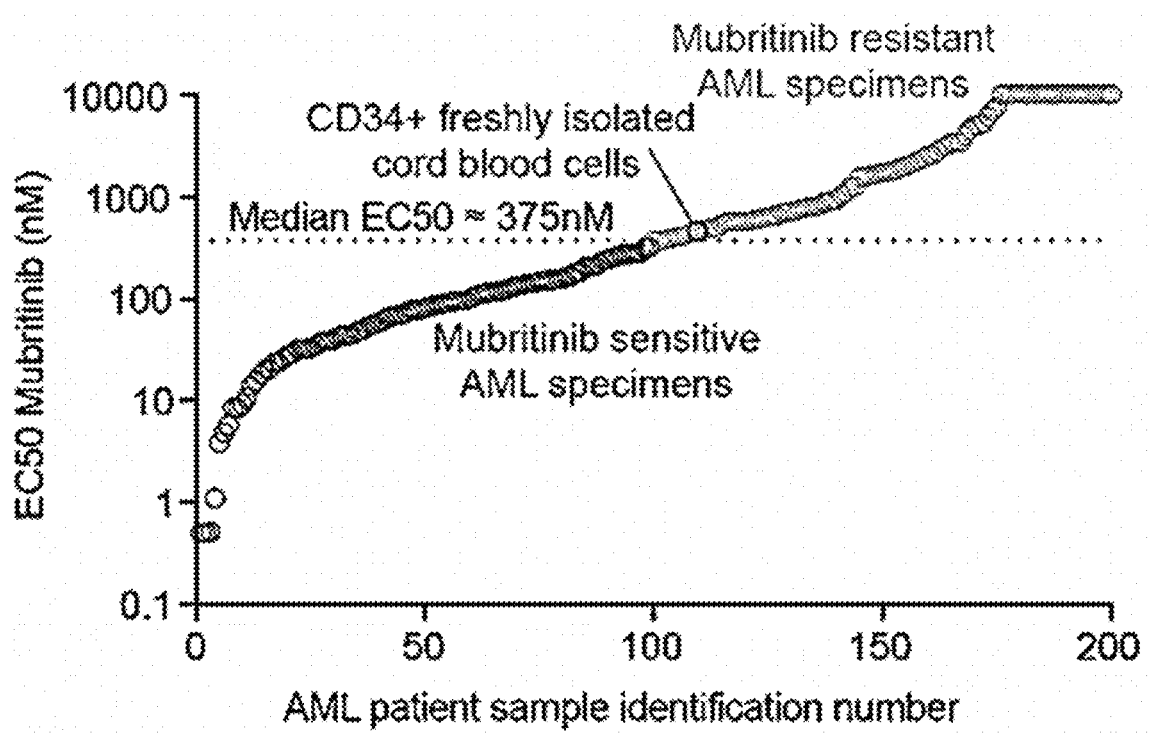
Figure 2F:
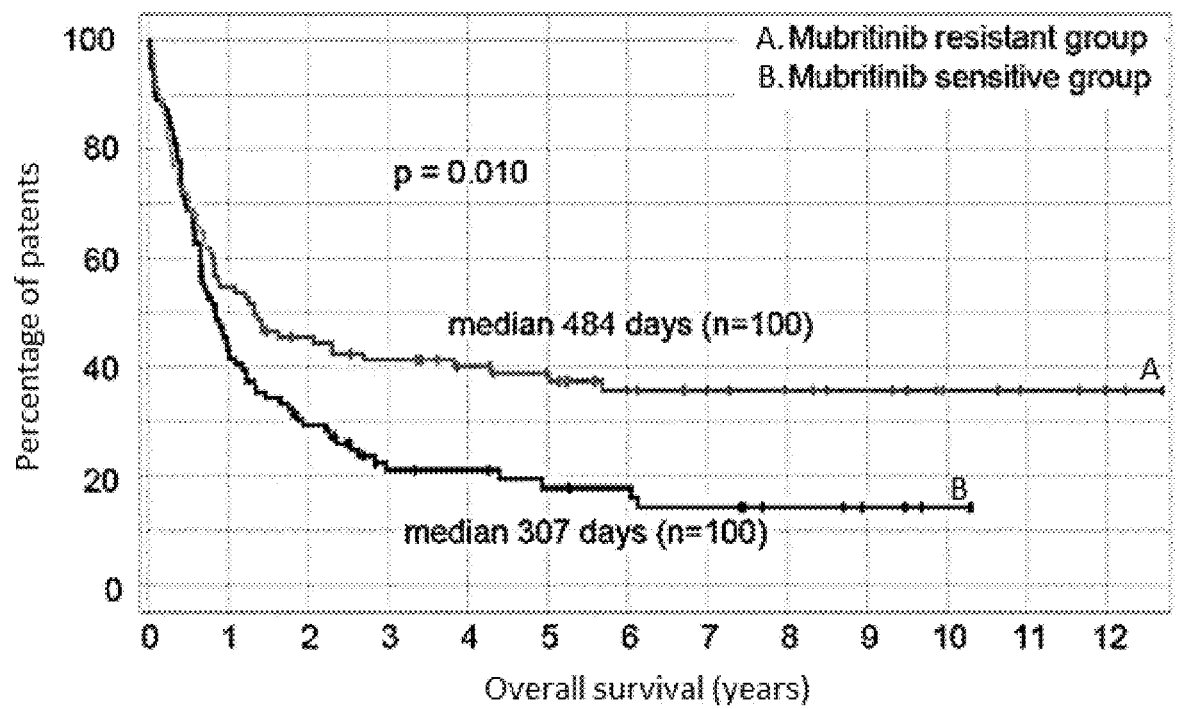
Figure 2G:
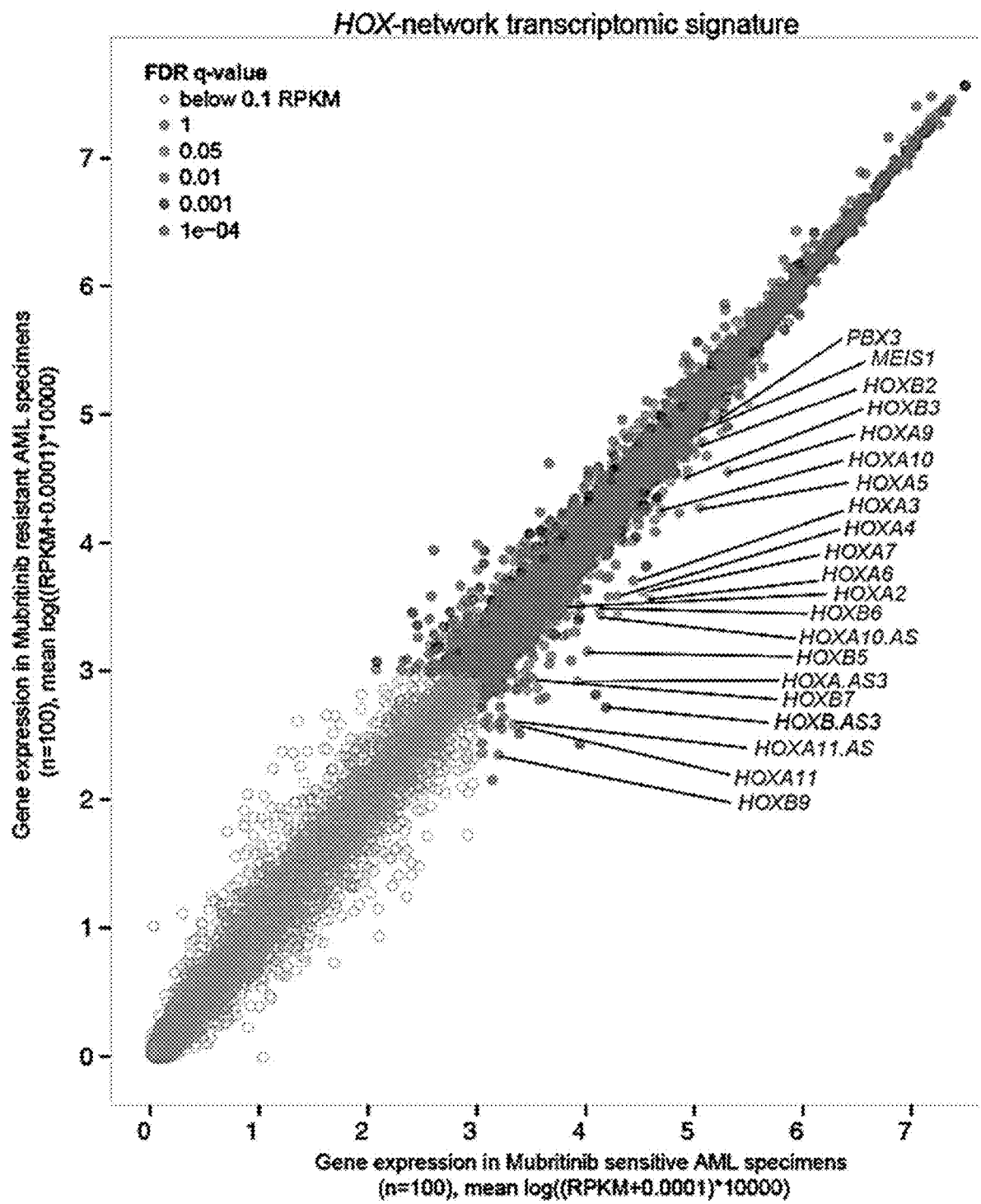
Figure 2H:
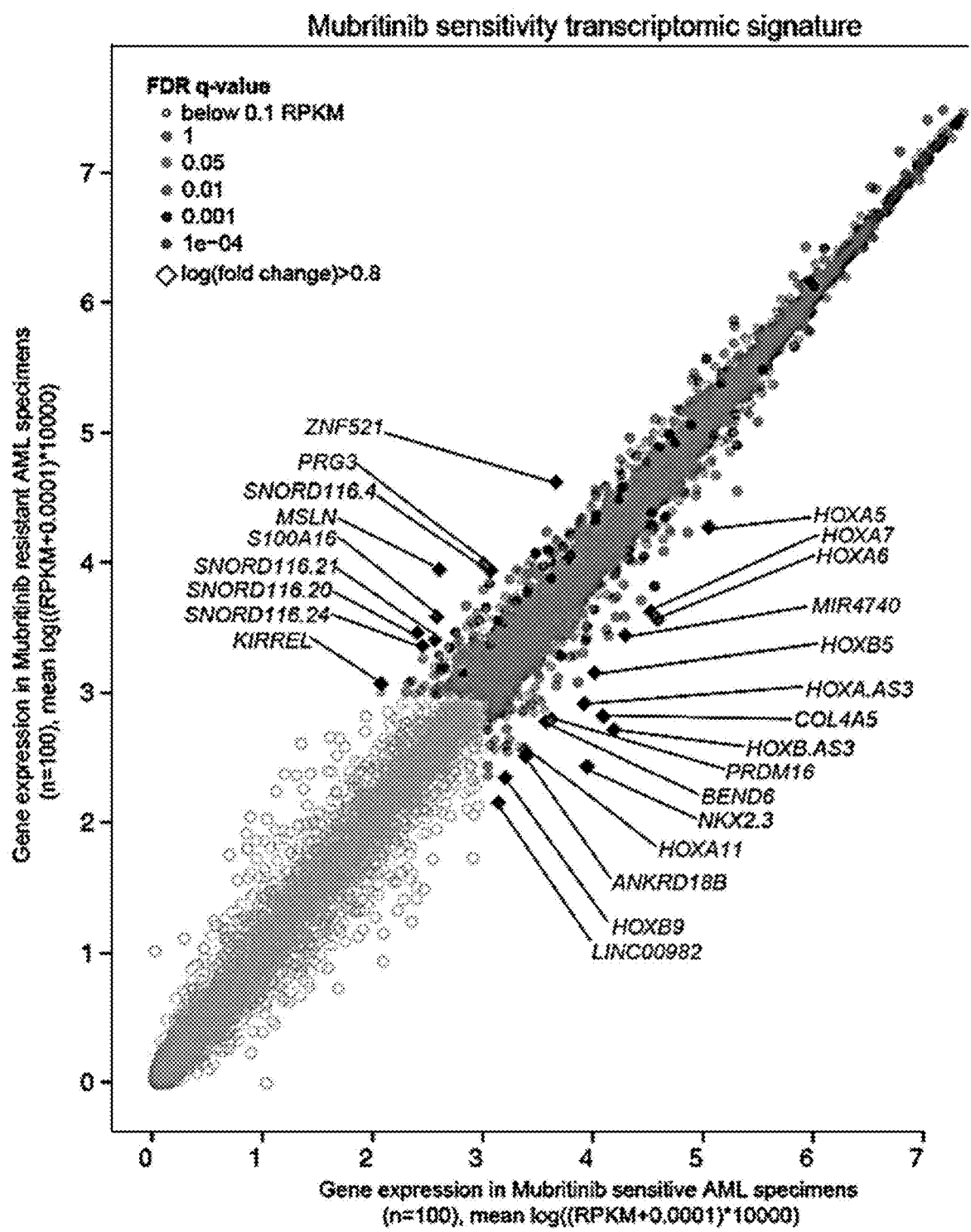

Dose response validation screening in a large cohort of AML samples confirmed that HOX-high patient cells are significantly more sensitive to Mubritinib than HOX-med/low AML cells (FIGS. 2C-D). Median Mubritinib $EC_{50}$ in the AML population tested was approximately 375 nM (FIG. 2E). Patients belonging to the Mubritinib-sensitive group ($EC_{50}$<375 nM) have a significantly decreased overall survival relative to patients of the Mubritinib-resistant group ($EC_{50}$>375 nM, FIG. 2F). Specimens belonging to the Mubritinib-sensitive group overexpress genes of the HOX network (FIG. 2G), consistent with the results presented in Example 2. The most differentially expressed genes, (6-fold difference in RPKM values, RPKM>0.1) are shown in FIG. 2H and the complete Mubritinib sensitivity transcriptomic signature in AML is displayed in Table 2b (genes overexpressed more than 5-fold in RPKM values in Mubritinib-sensitive cells, RPKM>0.1), and Table 2a (genes underexpressed more than 5-fold in RPKM values in Mubritinib-sensitive cells, RPKM>0.1). Taken together, these data demonstrate that Mubritinib is a good candidate drug for the treatment of AML patients, and particularly those with high expression of HOX-network genes.

TABLE 2a

Under-expressed genes* in Mubritinib-sensitive versus Mubritinib-resistant

| Gene | FDR q-value | Log(RPKM + 0.0001)*10000 resistant AML | Log(RPKM + 0.0001)*10000 sensitive AML |
|---|---|---|---|
| ORM1 | 0.0068 | 3.6 | 2.8 |
| PRAME | 0.0110 | 3.7 | 3.0 |
| MYZAP | 0.0019 | 3.0 | 2.3 |
| SNORD116.4 | 0.0002 | 3.9 | 3.0 |
| SNORD116.24 | 0.0008 | 3.3 | 2.4 |
| ZNF521 | 0.0031 | 4.5 | 3.6 |
| MSLN | 0.0001 | 3.9 | 2.6 |
| TINAGL1 | 0.0034 | 3.0 | 2.3 |
| S100A16 | 0.0011 | 3.5 | 2.5 |
| MS4A2 | 0.0003 | 3.8 | 3.0 |
| SNORD116.20 | 0.0003 | 3.4 | 2.4 |
| KIRREL | 0.0001 | 3.0 | 2.0 |
| PRG3 | 0.0015 | 3.9 | 3.0 |
| ST18 | 0.0062 | 3.2 | 2.4 |
| SNORD116.21 | 0.0016 | 3.4 | 2.5 |

*Mubritinib-sensitive (n = 100, separation by median of the entire cohort, $EC_{50}$ = 375 nM) versus Mubritinib-resistant (n = 100) AML specimens according to false-discovery rate (FDR) corrected multiple Mann-Whitney test applied to RNA-sequencing data. Cut-offs used: expression > 0.1 RPKM, log(fold-change) between sensitive and resistant specimens > 0.7 (=5-fold difference in gene expression).

TABLE 2b

Over-expressed genes* in Mubritinib-sensitive versus Mubritinib-resistant

| Gene | FDR q-value | Log(RPKM + 0.0001)*10000 resistant AML | Log(RPKM + 0.0001)*10000 sensitive AML |
|---|---|---|---|
| HOXA5 | 0.0065 | 4.2 | 5.0 |
| HOXB5 | 0.0074 | 3.1 | 4.0 |
| HOXB9 | 0.0078 | 2.3 | 3.2 |
| HOXA4 | 0.0081 | 3.5 | 4.2 |
| HOXA3 | 0.0088 | 3.6 | 4.4 |
| HOXA9 | 0.0101 | 4.5 | 5.3 |
| HOXA11 | 0.0206 | 2.5 | 3.3 |
| HOXA10.AS | 0.0214 | 3.4 | 4.1 |
| HOXA11.AS | 0.0313 | 2.5 | 3.3 |
| COL4A5 | 0.0006 | 2.8 | 4.0 |
| PRDM16 | 0.0024 | 2.7 | 3.5 |
| BEND6 | 0.0024 | 2.8 | 3.6 |
| LINC00982 | 0.0025 | 2.1 | 3.1 |
| NKX2.3 | 0.0002 | 2.4 | 3.9 |
| ANKRD18B | 0.0001 | 2.5 | 3.4 |
| LOC285758 | 0.0009 | 3.8 | 4.5 |
| MIR4740 | 0.0011 | 3.4 | 4.3 |
| CYP7B1 | 0.0011 | 3.0 | 3.8 |
| HOXA7 | 0.0043 | 3.6 | 4.5 |
| HOXB.AS3 | 0.0004 | 2.7 | 4.1 |

TABLE 2b-continued

Over-expressed genes* in Mubritinib-sensitive versus Mubritinib-resistant

| Gene | FDR q-value | Log(RPKM + 0.0001)*10000 resistant AML | Log(RPKM + 0.0001)*10000 sensitive AML |
|---|---|---|---|
| HOXA.AS3 | 0.0051 | 2.9 | 3.9 |
| HOXA6 | 0.0055 | 3.5 | 4.5 |

*Mubritinib-sensitive (n = 100, separation by median of the entire cohort, $EC_{50}$ = 375 nM) versus Mubritinib-resistant (n = 100) AML specimens according to false-discovery rate (FDR) corrected multiple Mann-Whitney test applied to RNA-sequencing data. Cut-offs used: expression > 0.1 RPKM, log(fold-change) between sensitive and resistant specimens > 0.7 (=5-fold difference in gene expression).

Figure 3A:
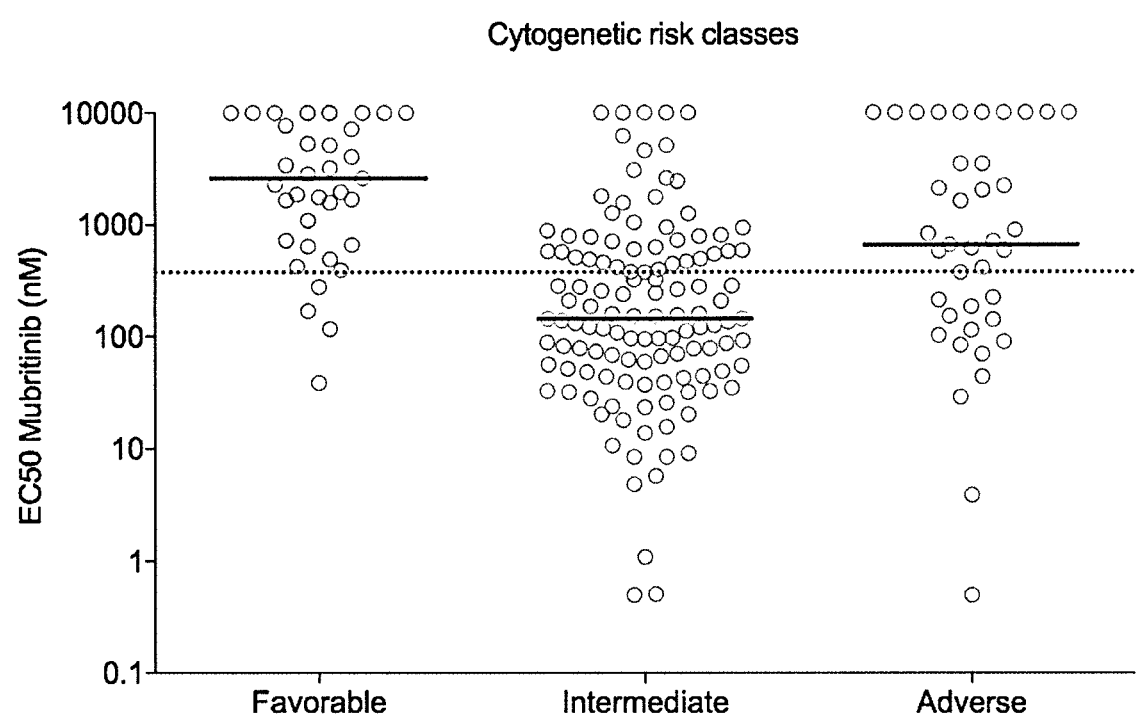
FIGS. 3A-H show a characterization of Mubritinib-sensitive AML specimens according to various genetic and clinical features.
Figure 3B:
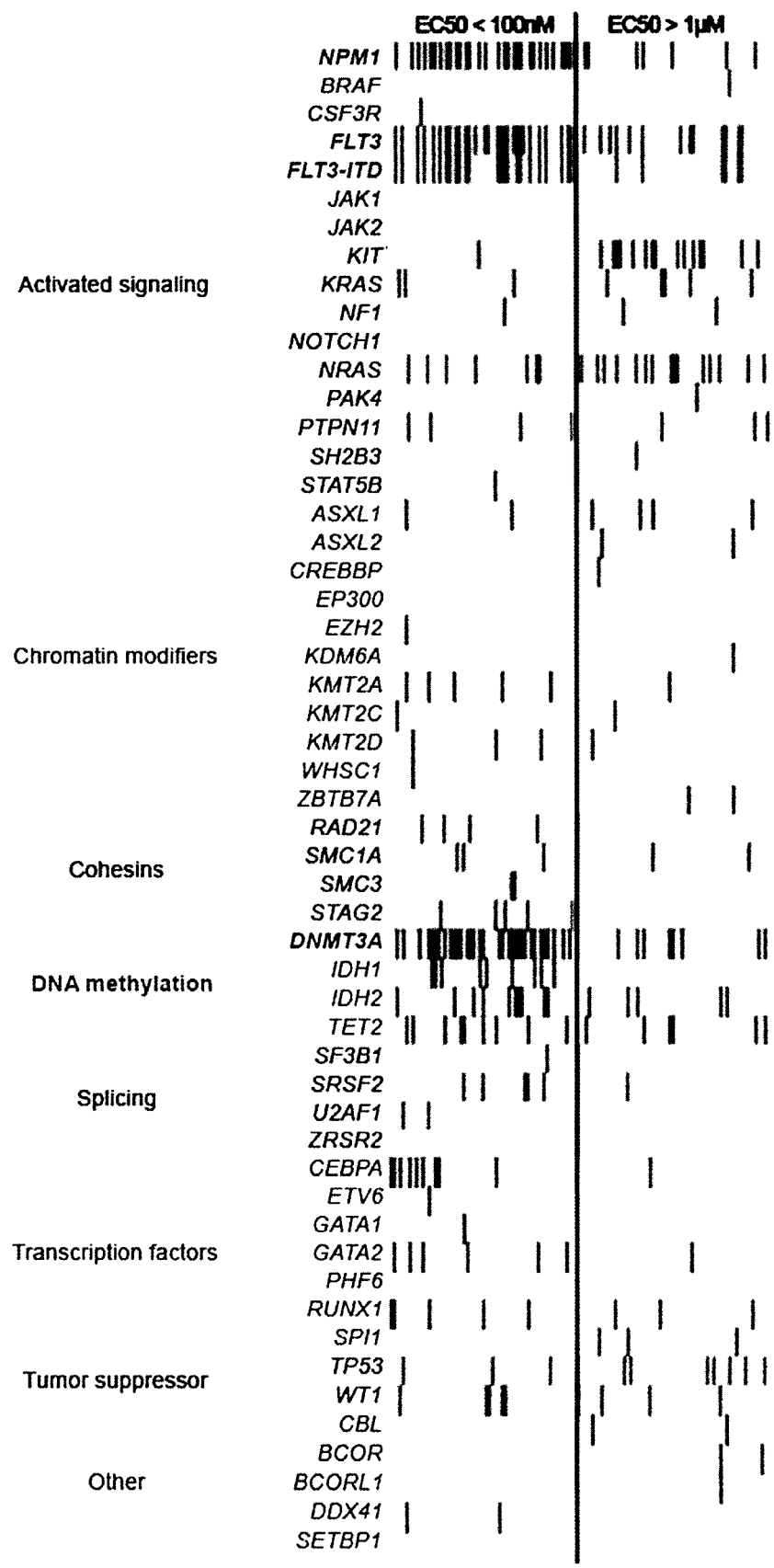
Figure 3C:
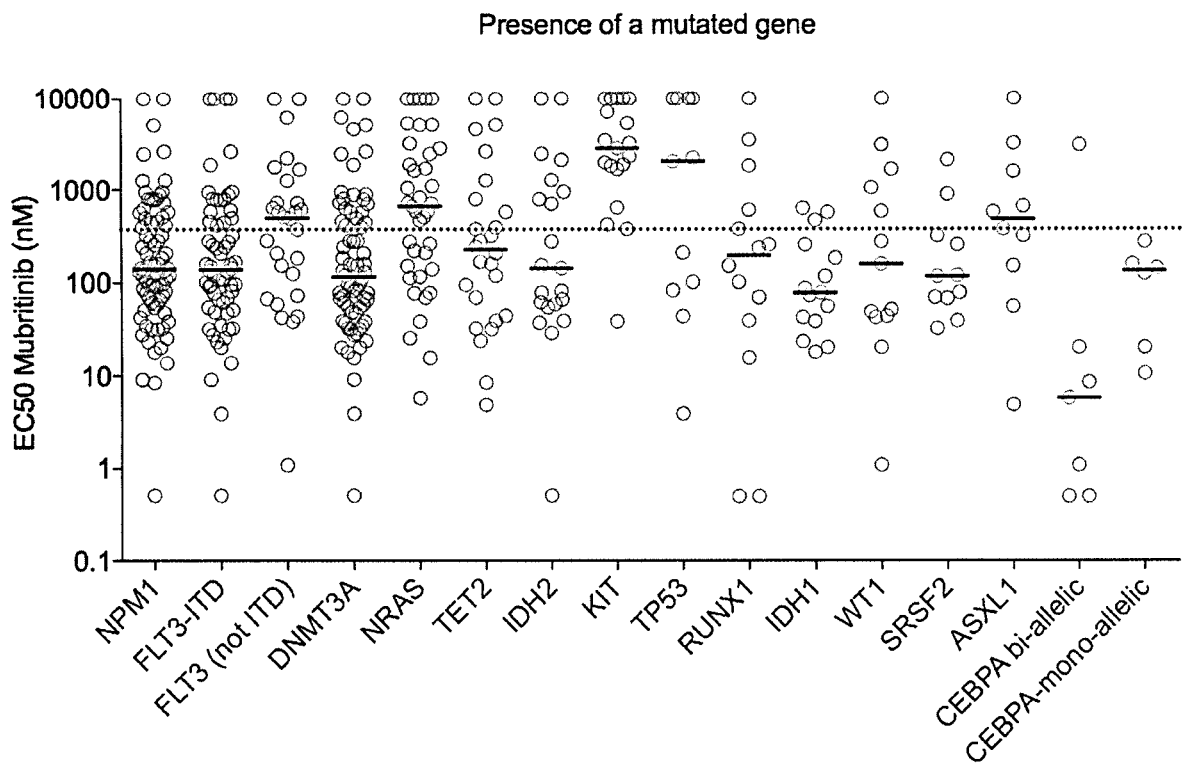
Figure 3D:
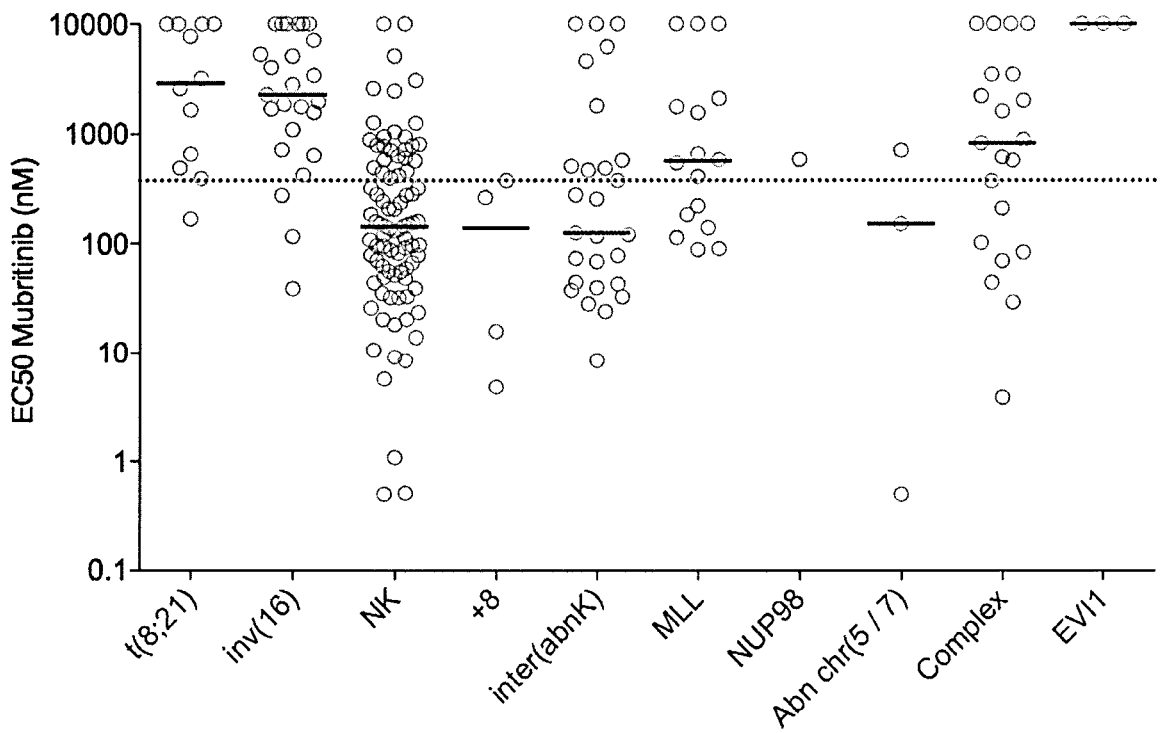
Figure 3E:
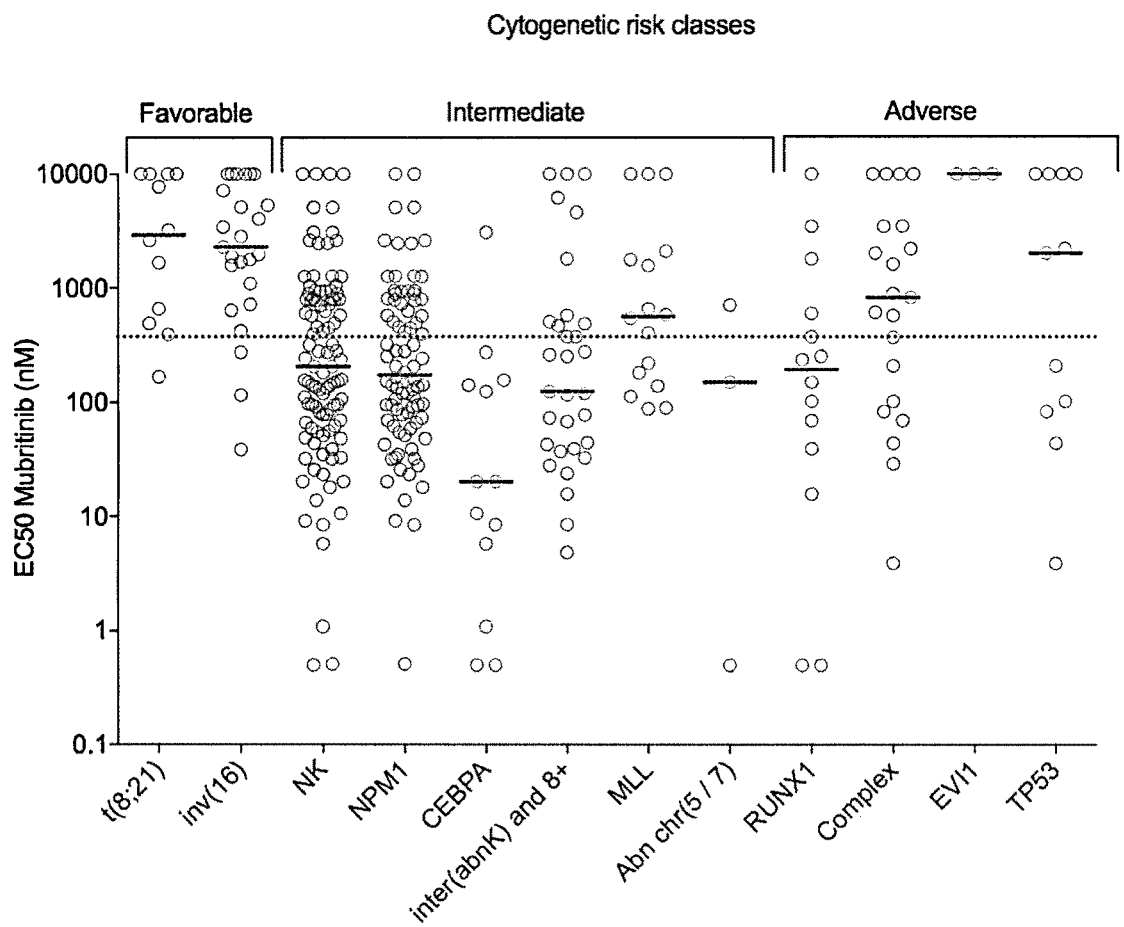
Figure 3F:
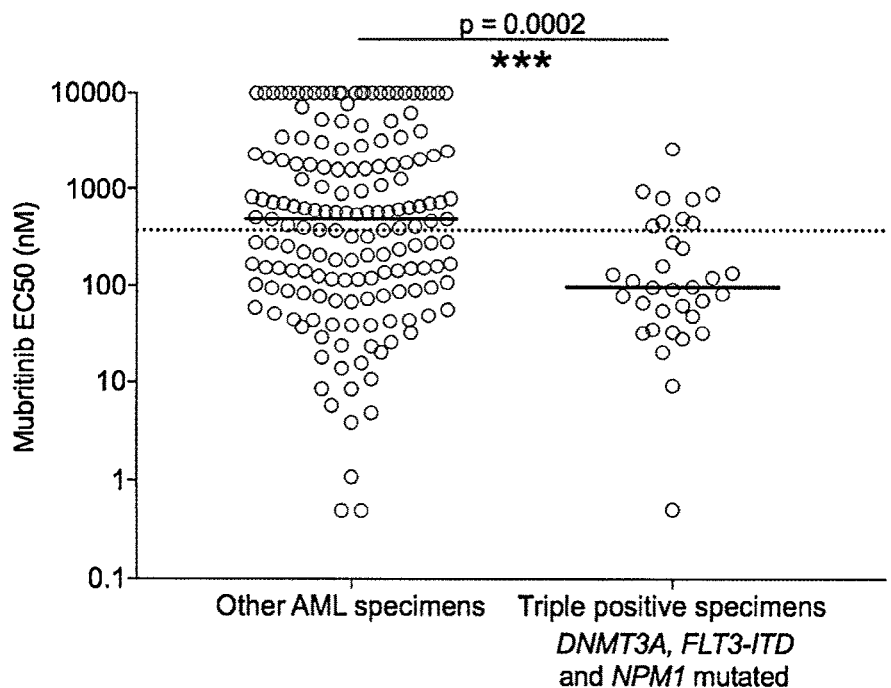

Example 4: Mubritinib Target Population According to Classical Genetic/Cytogenetic Classifications The results of a set of experiments aimed at identifying AML subtypes more sensitive to Mubritinib are depicted in FIGS. 3A-F and Tables 3A and 5A-5B. FIGS. 3A and 3E show that Mubritinib-sensitive AML cells most frequently belong to the intermediate cytogenetic risk class, often carry mutations in either NPM1, IDH1, SRSF2, CEBPA, DNMT3A or FLT3-ITD (FIGS. 3B, 3C and 3F), and generally have a normal karyotype (NK, Table 3C and FIGS. 3D and 3E). The most significantly enriched mutated in Mubritinib-sensitive versus resistant specimens were IDH1, SRSF2 and CEBPA, whereas AML samples mutations in NRAS, KIT, FLT3 not ITD and TP53 were underrepresented in the Mubritinib-sensitive group relative to the Mubritinib-resistant group (Table 3A). The detail of the mutations is depicted in Table 3B.

TABLE 3A patient sample fold-enrichment in Mubritinib-sensitive versus Mubritinib-resistant AML samples according to the presence of a mutated gene.

| Genes mutated | Mubritinib sensitive (%) | Mubritinib resistant (%) | Fold enrichment sensitive/resistant |
|---|---|---|---|
| NPM1 | 36.6 | 22.4 | 1.6 |
| FLT3-ITD | 30.3 | 17.8 | 1.7 |
| FLT3(not ITD) | 8.5 | 15.0 | 0.6 |
| DNMT3A | 31.0 | 24.3 | 1.3 |
| NRAS | 10.6 | 22.4 | 0.5 |
| TET2 | 11.3 | 9.3 | 1.2 |
| IDH2 | 9.2 | 7.5 | 1.2 |
| KIT | 0.7 | 16.8 | 0.0 |
| TP53 | 3.5 | 5.6 | 0.6 |
| RUNX1 | 6.3 | 4.7 | 1.4 |
| IDH1 | 8.5 | 2.8 | 3.0 |
| WT1 | 5.6 | 4.7 | 1.2 |
| SRSF2 | 6.3 | 1.9 | 3.4 |
| ASLX1 | 2.8 | 5.6 | 0.5 |
| CEBPA | 8.5 | 0.9 | 9.0 |

TABLE 3B

Mutations present in the AML samples.

| Sample | Mutations |
|---|---|
| ASLX1 | R417*, A472-, G643-, G645-, L696-, Q708*, C759*, P763, L775*, E824-, E1006* |
| CEBPA | L219P, E215*, R204-, L196-, V195-, K194-, Q193-, Q312-, T191-, K304-, A184D, R300S, R178L, Y62*, H6Y, A113-, G96-, A91-, A79G, F77-, F73-, P70-, D69-, G38-, A30-, P23-, Y7* |
| DNMT3A | K906Q, G890S, L888M, R882H, R882P, R882C, F870-, W795R, S786L, R771*, W753R, F752L, P743S, R736C, F732C, F731Y, N717I, D712Y, G707D, I705T, Q692-, V684-, G673S, S669-, S669F, P625-, R597-, R597P, C586Y, L566*, G543C, Q527*, L508-, R379C, H355-, W330*, R326H, S304-, E30A |
| FLT3-ITD | 575-, A680V, D586-, D593-, D600-, D835H, D835V, D835Y, D839G, E573-, E596-, F590-, F594-, G583-, I836-, K602-, L789-, M578-, M837-, N587-, N676K, Q577-, Q580-, R595-, S451F, S574-, S584-, S585-, T582-, V581-, V592-, W603-, Y572-, Y589-, Y591-, Y597-, Y599- |
| IDH1 | R132C, R132G, R132H, R132S |
| IDH2 | R172K, R140Q, R140L |
| KIT | D419-, D812V, D812Y, L416-, N818K, T417-, Y418-, Y418S |
| NPM1 | L258-, L287-, W259-, W261-, W288-, W290- |
| NRAS | G12A, G12C, G12D, G12S, G12V, G13C, G13D, G13R, Q61H, Q61K, Q61R, S17N, Y64D |
| SRSF2 | P95H, P95L, P95R |
| TET2 | A1355T, A1379V, A1837-, A991-, C1271-, C1289S, C1298-, D1384N, D1587-, D688-, E692*, G1137V, G1275R, G1288C, G1430-, G1719-, G1869W, G563-, G613-, H1219D, L1457I, L1511-, M1456-, N1102-, N1103-, N1266S, N1774-, P1115-, P408-, P818-, Q1021-, Q1501*, Q383*, Q635*, Q705*, Q744*, Q810*, R1261C, R1516* S1050*, S1449-, S1838A, S217-, S675*, Y1598- |
| TP53 | A6P, C124-, E310-, G134R, K93-, L72Q, P190-, P322-, Q4*, R116Q, R141C, R141H, R150W, R26C, R273H, R81*, S83-, T86, V140M, V25F, V84-, V84G, V84M, Y102C, Y73C, Y88C |
| WT1 | A113-, H246-, H441-, P134-, P134Q, P266-, P376-, R369-, R370-, R380-, R458*, R462L, R462P, R462Q, S138-, S381-, S381*, S381X, T385-, V368-, V379-, |

* = mutation introducing a stop codon; - = frameshift mutation
ASXL1 = NM_015338; CEBPA = NM_004364; DNMT3A = NM_022552; FLT3 = NM_004119; IDH1 = NM_005896; IDH2 = NM_002168; KIT = NM_001093772; NPM1 = NM_002520; NRAS = NM_002524; RUNX1 = NM_001754; SRSF2 = NM_003016; TET2 = NM_017628; TP53 = NM_001276760; WT1 = NM_024426.

TABLE 3C

Clinical features enriched in Mubritinib sensitive versus resistant AML specimens*

| | Mubritinib sensitive specimens (n = 100) | Mubritinib resistant specimens (n = 100) | P-value |
|---|---|---|---|
| Age | 58 (20-78) | 56 (17-75) | n.s. |
| WBC ($\times 10^9$/L) | 50 (1.6-361) | 46 (1.5-447) | n.s. |
| Gender | | | |
| Male | 49 | 62 | n.s. |
| Female | 51 | 38 | n.s. |
| Cytogenetic risk | | | |
| Favorable | 4 | 33 | n.s. |
| Intermediate | 80 | 43 | 5.6E−08 |
| Adverse | 15 | 24 | n.s. |
| Und | 1 | 0 | n.s. |
| FAB | | | |
| M0 | 1 | 7 | n.s. |
| M1 | 40 | 26 | n.s. |
| M2 | 16 | 11 | n.s. |
| M3 | 0 | 0 | n.s. |
| M4 | 11 | 9 | n.s. |
| M5 | 2 | 2 | n.s. |
| M6 | 0 | 0 | n.s. |
| M7 | 0 | 0 | n.s. |
| NC | 12 | 15 | n.s. |
| Other | 18 | 30 | n.s. |

TABLE 3C-continued

Clinical features enriched in Mubritinib sensitive versus resistant AML specimens*

| | Mubritinib sensitive specimens (n = 100) | Mubritinib resistant specimens (n = 100) | P-value |
|---|---|---|---|
| Genetic group | | | |
| t(8:21) | 1 | 11 | n.s. |
| inv(16) | 3 | 22 | n.s. |
| Normal karyotype | 59 | 25 | 8.9E−07 |
| Intermediate abnormal K | 17 | 11 | n.s. |
| NUP98-NSD1 | 2 | 2 | n.s. |
| Trisomy/tetrasomy 8 | 2 | 1 | n.s. |
| MLL | 7 | 12 | n.s. |
| Monosomy 5 | 1 | 1 | n.s. |
| Complex | 7 | 12 | n.s. |
| EVI1 | 0 | 3 | n.s. |
| Other | 1 | 0 | n.s. |
| HOX status | | | |
| high | 63 | 37 | 0.0002 |
| low | 37 | 63 | n.s. |

*Mubritinib sensitive ($EC_{50}$ < 375 nM, n = 100) versus resistant ($EC_{50}$ ≥ 375 nM, n = 100) AML specimens according to a Bonferroni corrected exact Fisher's test.

Figure 3G:
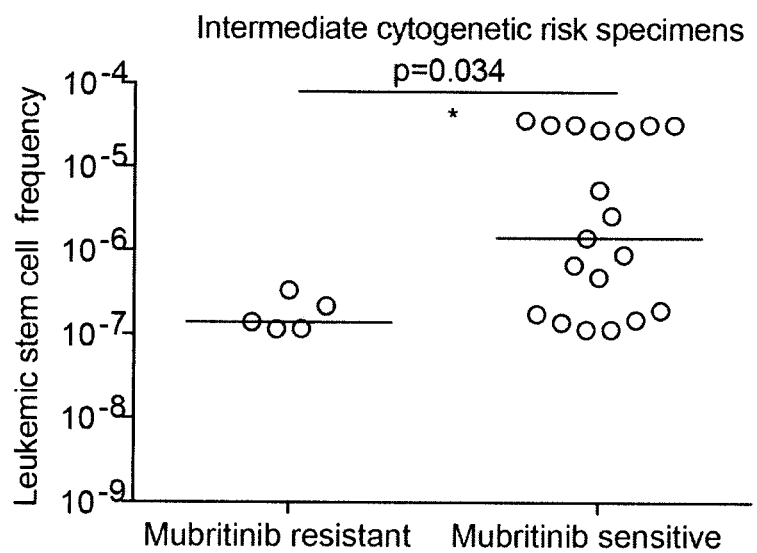
Figure 3H:
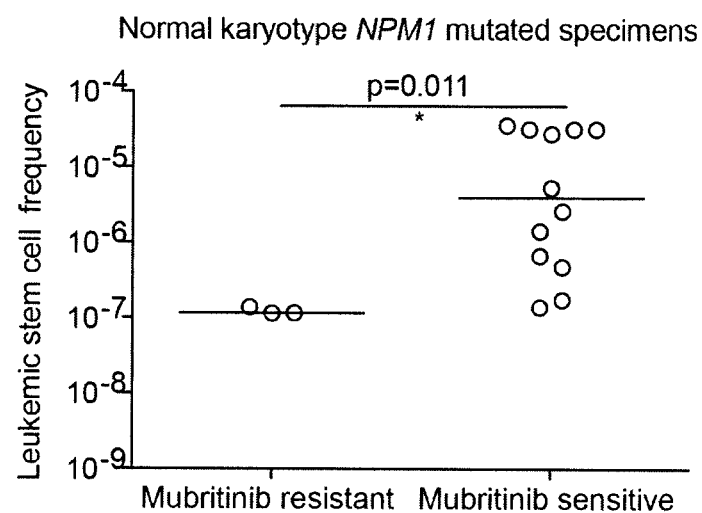

Notably, AML specimens with simultaneous mutations in NPM1, DNMT3A and FLT3-ITD, which was recently associated with a particularly adverse prognostic (Papaemmanuil, E. et al. N Engl J Med 374, 2209-2221, 2016), were shown to be particularly sensitive to Mubritinib (median $EC_{50}$ of 96 nM as compared to 423 nM in other AMLs subtypes, FIG. 3F). Focusing on specimens with a NK (representing 30% of AML patients, FIG. 3G) or on samples with a NK and mutations in NPM1 (representing 25% of AML patient samples, FIG. 3H), limiting dilution assays in immunocompromised mice demonstrate that Mubritinib-sensitive specimens have significantly higher frequencies of leukemic stem cells (LSCs) relative to Mubritinib-resistant samples. High LSC frequency has been shown to be generally associated with increased minimal residual disease (MRD) and poor prognosis (see, e.g., Moshaver B. et al., Stem Cells 26, 3059-3067 (2008)). Overall, these results provide useful indications for the selection of AML patient populations who might most benefit from treatment with Mubritinib, and provide evidence of a potential link between sensitivity to Mubritinib and the frequency of LSCs in patient samples.

Example 5: Assessment of the Mechanism of Action of Mubritinib in AML

Figure 4A:
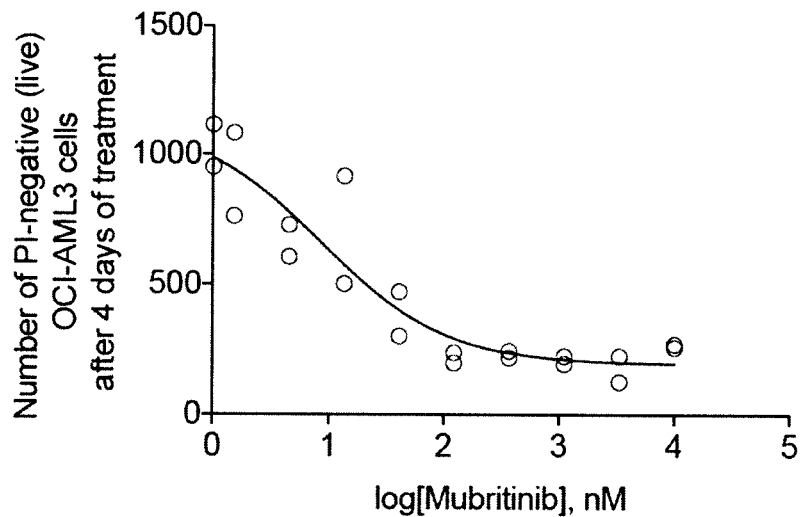
FIGS. 4A-4G show the results on experiments assessing the effect of Mubritinib on tumor cells.
Figure 4B:
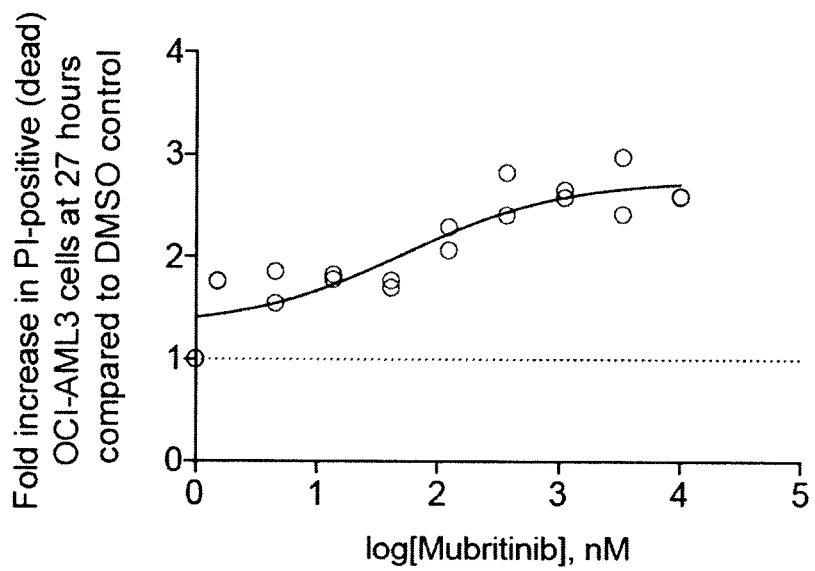
Figure 4C:
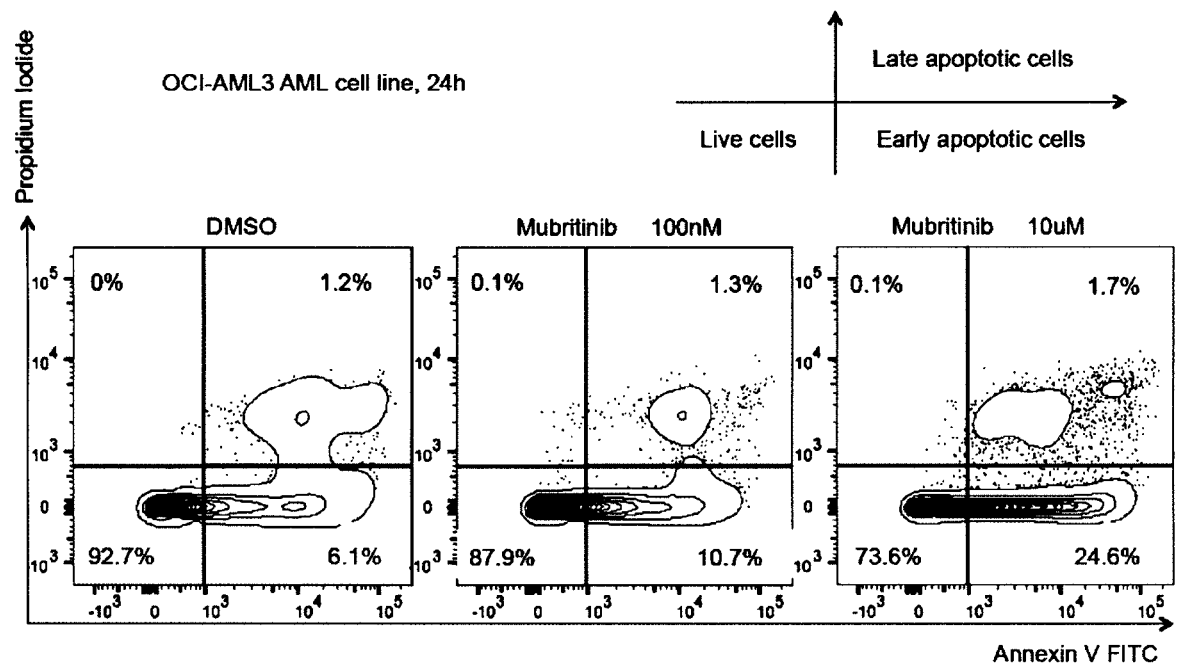

Mubritinib treatment induces a reduction of live cell counts (as measured by a decrease in Propidium Iodide (PI)-negative cells) in a dose-dependent manner (FIG. 4A). Cells are lost due to an increase in the number of dead (PI-positive) cells (FIG. 4B), which appear to die through apoptosis, as suggested by the increase in Annexin V staining (a marker of apoptosis) in a Mubritinib-sensitive AML cell line, OCI-AML3. (FIG. 4C).

Figure 4D:
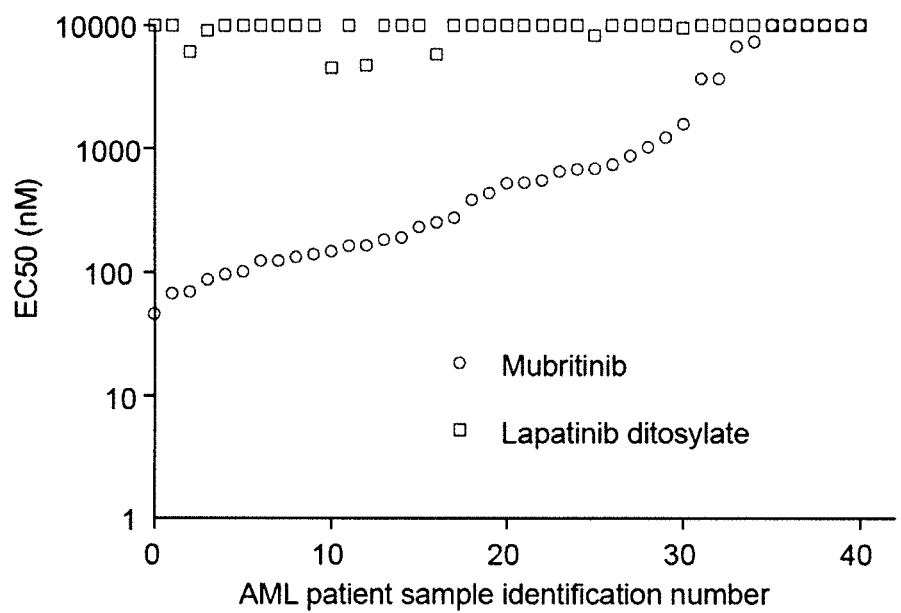
Figure 4E:
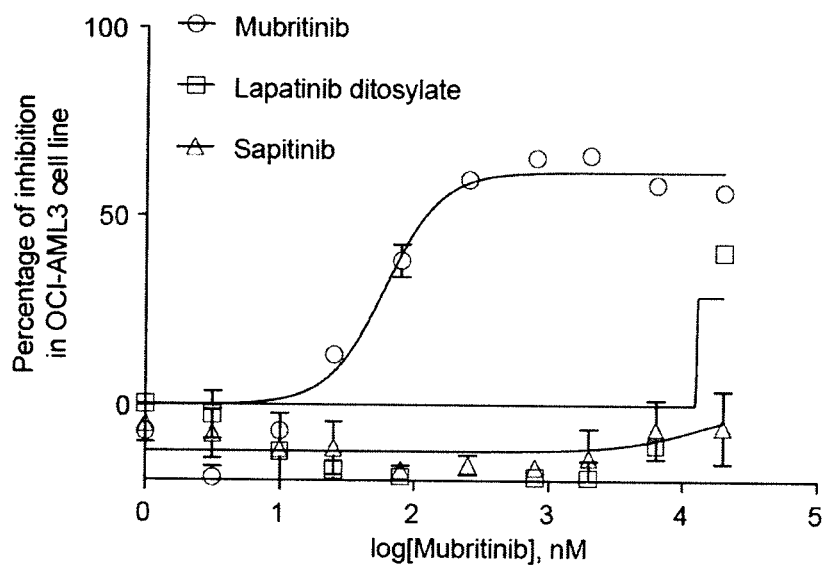
Figure 4F:
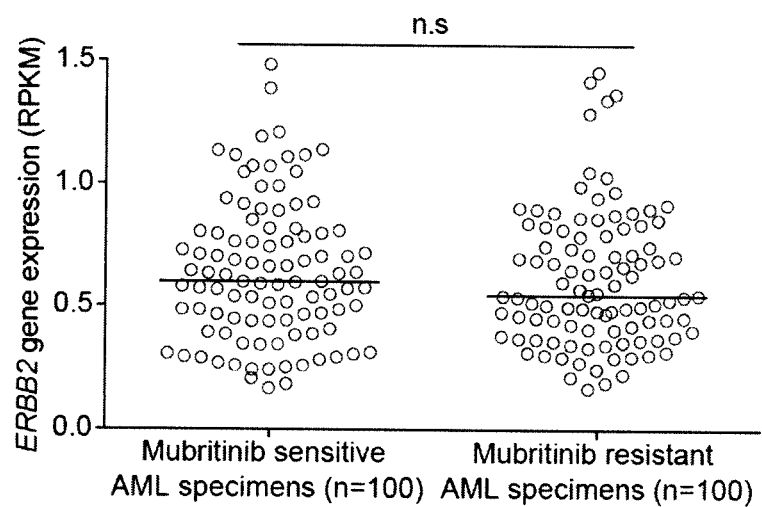
Figure 4G:
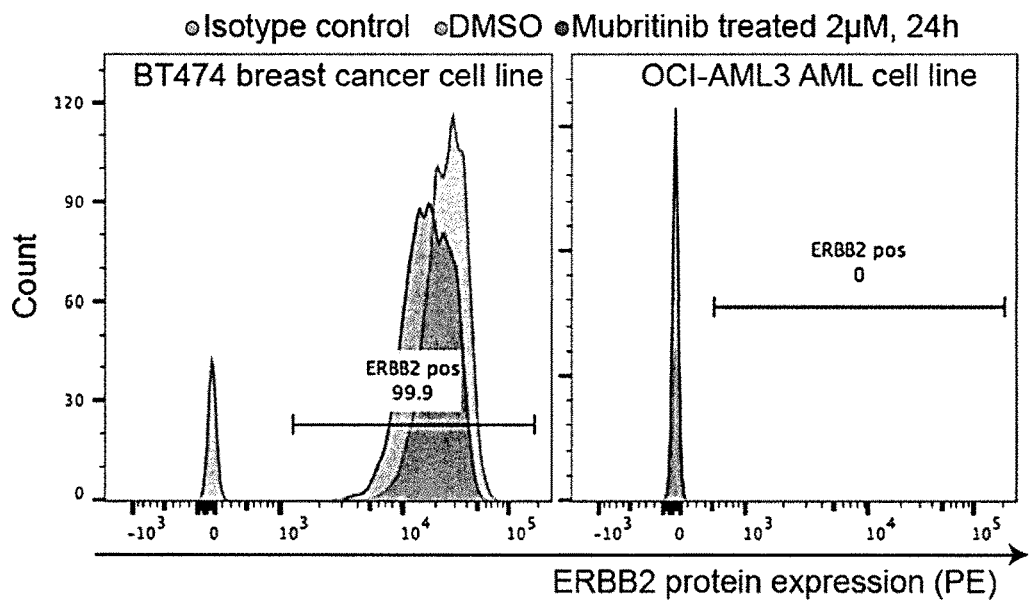

Mubritinib is described as a specific ERBB2 inhibitor (Nagasawa, J. et al. Int J Urol 13, 587-592, 2006), and it was next assessed whether Mubritinib acts through this target on AML cells. Another potent ERBB2 inhibitor, Lapatinib, was included in the primary screen (FIG. 2A); strikingly, all 41 AML patient specimens tested were resistant to Lapatinib, in contrast to Mubritinib (FIG. 4D). Similarly, OCI-AML3 cells were sensitive to Mubritinib, but not to Lapatinib or Sapitinib, two other potent ERBB2 inhibitors (FIG. 4E), providing evidence that Mubritinib effects on AML cells is not shared by the class of ERBB2 inhibitors. Overall, AML patient cells that were sensitive to Mubritinib had the same low level of ERBB2 gene expression level as Mubritinib-resistant specimens (median around 0.5 RPKM, FIG. 4F). Finally, flow cytometry analysis of ERBB2 expression have demonstrated that the Mubritinib-sensitive AML cell line OCI-AML3 does not express detectable levels of ERBB2 protein, contrary to a positive control breast cancer cell line BT474 (FIG. 4G). Taken together, these results indicate that Mubritinib induces cell death in AML cells through a target other than ERBB2.

Figure 5A:
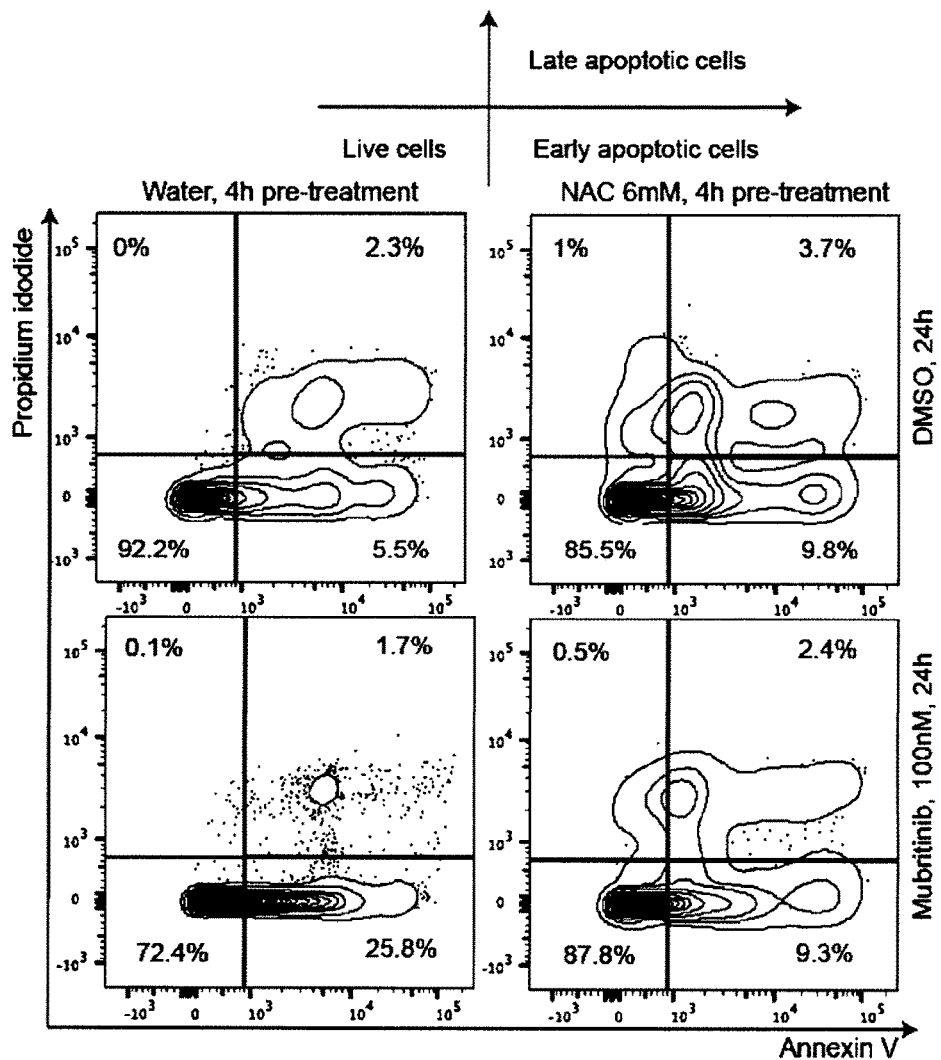
FIGS. 5A-5J show the results on experiments assessing the mode of action of Mubritinib for mediating tumor cell death.
Figure 5B:
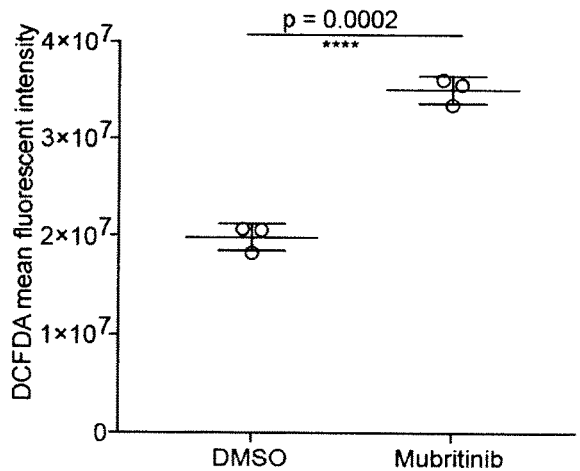
Figure 5C:
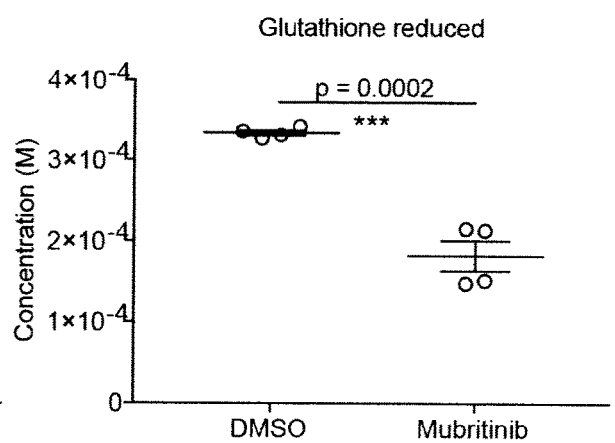
Figure 5D:
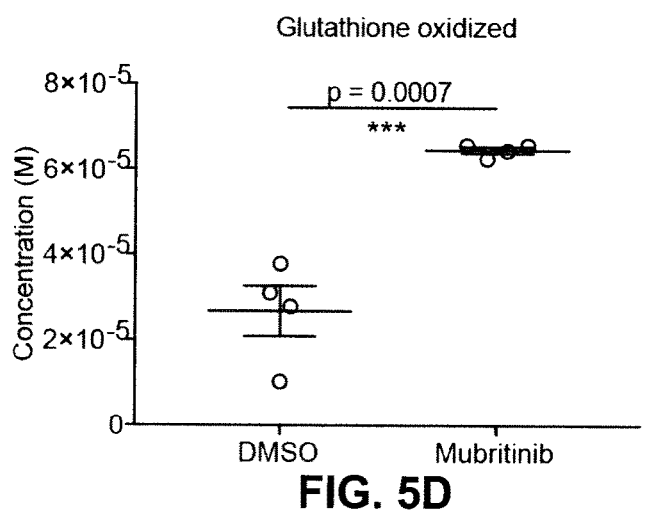

It was next assessed whether apoptosis induced by Mubritinib treatment involved oxidative stress, e.g., through the increase in reactive oxygen species (ROS). As shown in FIG. 5A, Mubritinib-induced apoptosis was significantly decreased when AML3 leukemic cells were incubated in the presence of the ROS scavenger N-acetyl-cysteine (NAC). Also, the level of ROS activity (hydroxyl, peroxyl), as assessed by the 2',7'-dichlorofluorescin diacetate (DCFDA) fluorogenic dye, was increased in AML3 cells treated with Mubritinib (FIG. 5B). Also, upon Mubritinib treatment (500 nM, 24 h), the levels of oxidized glutathione were increased (FIG. 5C), while the levels of reduced glutathione were decreased (FIG. 5D), relative to DMSO control, in these leukemic cells, indicating that Mubritinib induces oxidative stress in sensitive leukemic cells.

Figure 5E:
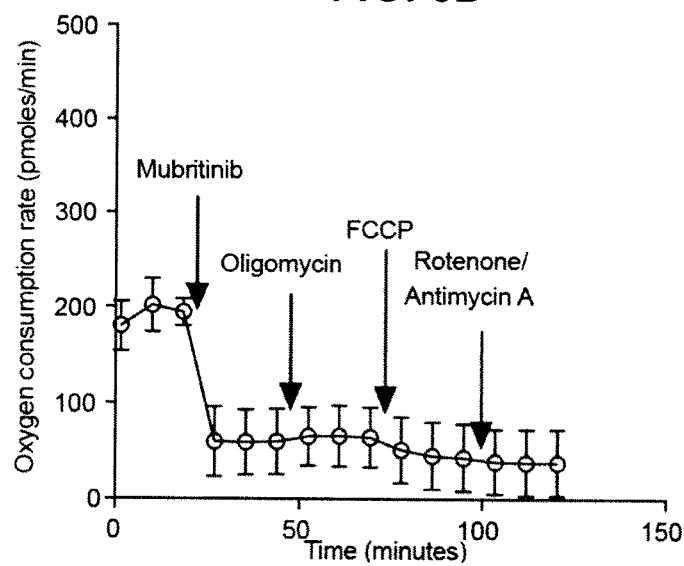
Figure 5F:
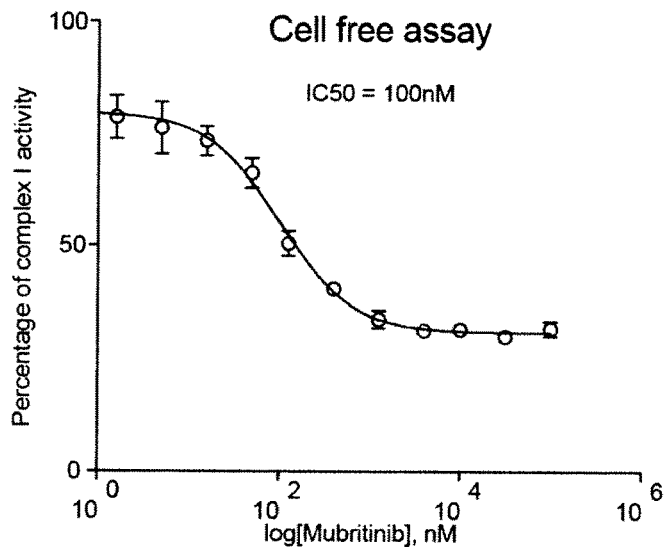
Figure 5G:
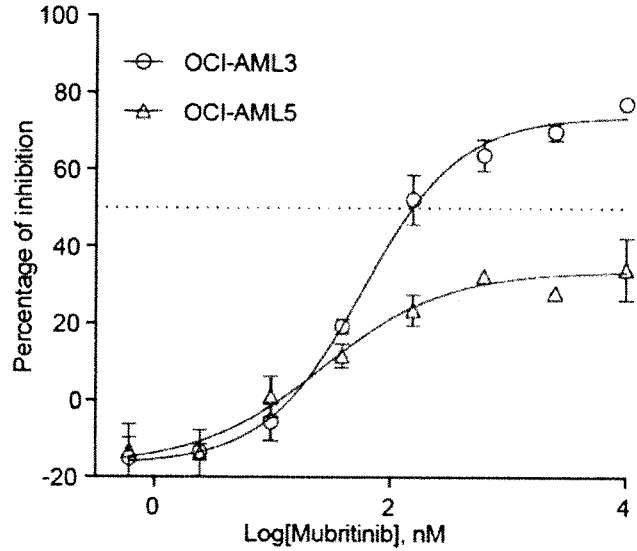
Figure 5H:
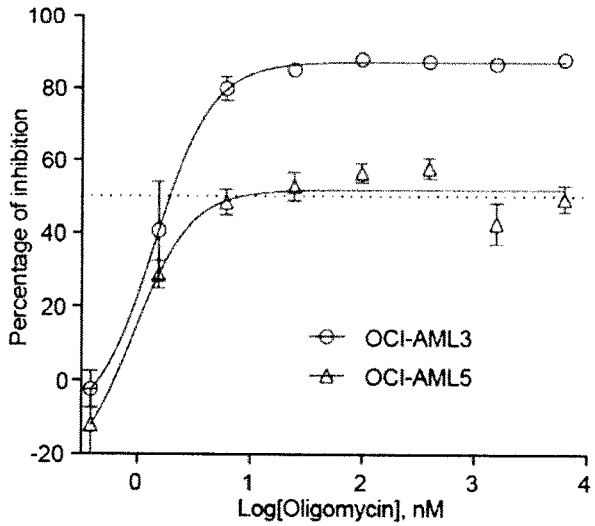
Figure 5I:
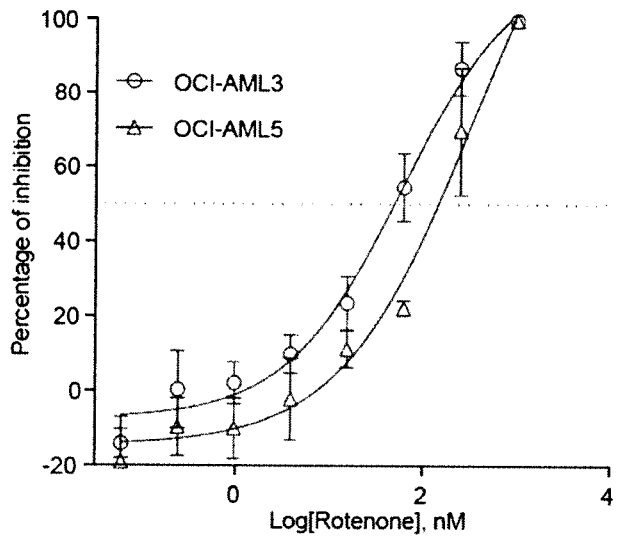
Figure 5J:
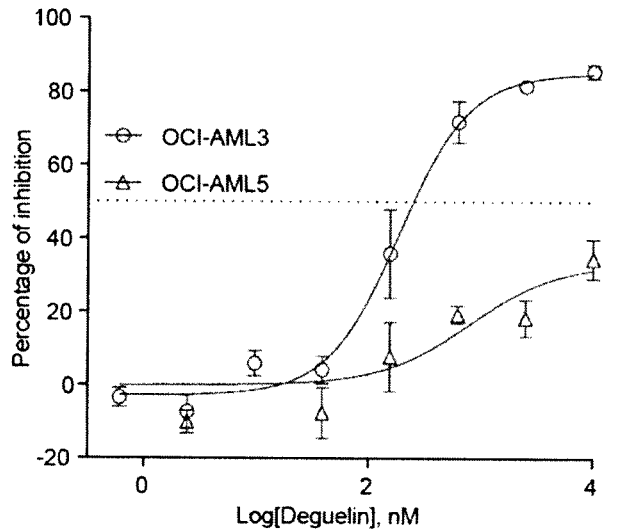
Figure 6A:
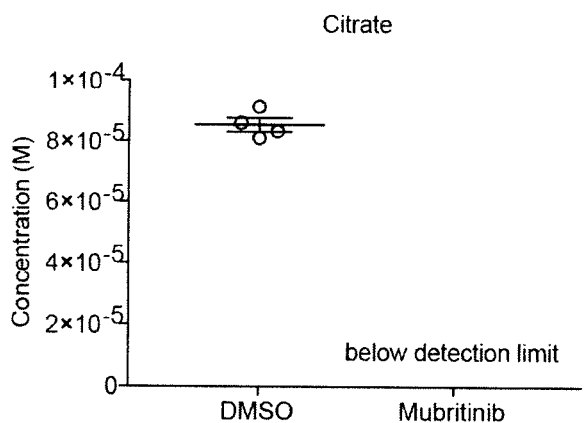
FIGS. 6A-6E are graphs showing the effects of Mubritinib treatment on the levels of different intermediates of the citric acid cycle in OCI-AML3 cells, namely citrate (FIG. 6A), alpha-ketoglutarate (FIG. 6B), succinate (FIG. 6C), fumarate (FIG. 6D), and malate (FIG. 6E).
Figure 6B:
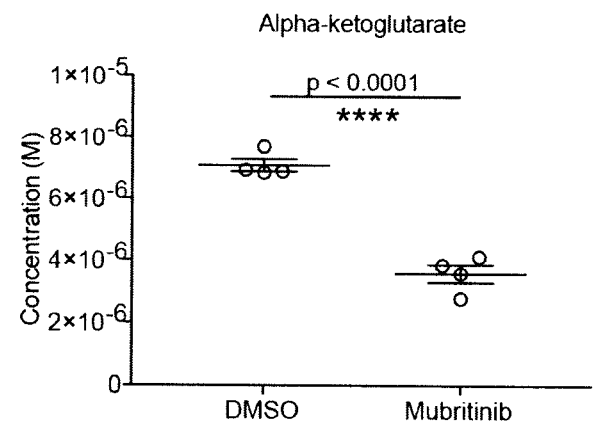
Figure 6C:
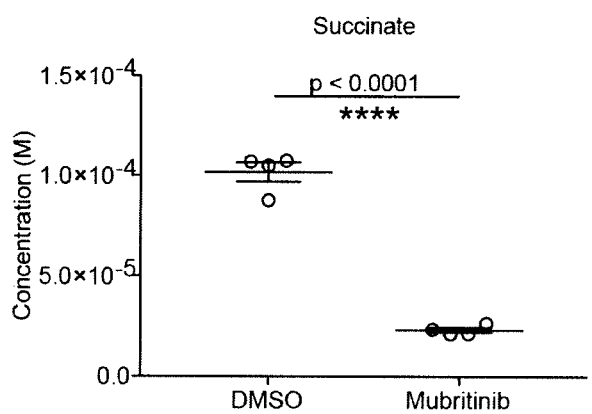
Figure 6D:
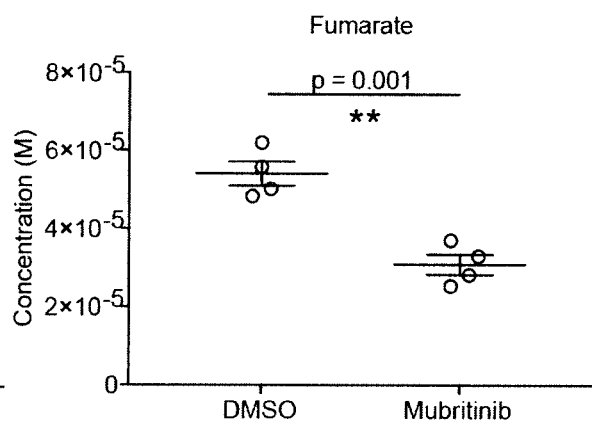
Figure 6E:
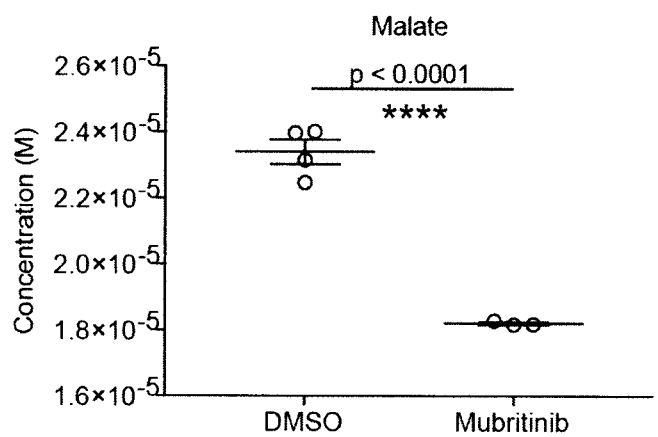

To assess whether Mubritinib-induced oxidative stress in sensitive leukemic cells involves mitochondrial activity, namely the activity of the electron transfer chain (ETC), the oxygen consumption rate was measured in cells treated with Mubritinib. As shown in FIG. 5E, acute injection of Mubritinib (1 μM) in OCI-AML3 leukemic cells impaired oxygen consumption rate in these cells. The data presented in FIG. 5F demonstrates that Mubritinib exhibits an inhibitory effect on ETC Complex I activity. FIG. 5G shows that the leukemic cell line OCI-AML5 is resistant to Mubritinib-induced cell death, in contrast to OCI-AML3 cells, which suggests that these cell lines exhibit metabolic or mitochondrial function disparities. Consistent with this hypothesis, OCI-AML3 were shown to be more sensitive than OCI-AML5 to other mitochondrial activity inhibitors such as Oligomycin (inhibitor of the $F_1$-$F_0$ ATP synthase, complex V, FIG. 5H), Rotenone (Class A inhibitor of complex I, FIG. 5I) and Deguelin (Class A inhibitor of complex I, FIG. 5J).

The results depicted in FIGS. 6A-6E show that Mubritinib treatment reduces the levels of several intermediates of the citric acid cycle in OCI-AML3 cells, namely citrate (FIG. 6A), alpha-ketoglutarate (FIG. 6B), succinate (FIG. 6C), fumarate (FIG. 6D), and malate (FIG. 6E), confirming that Mubritinib impairs mitochondrial activity/respiration in these leukemic cells. Mubritinib treatment was shown to inhibit pyruvate dehydrogenase (PDH) in an indirect fashion, and to induce a glycolytic switch in OCI-AML3 cells.

Figure 7:
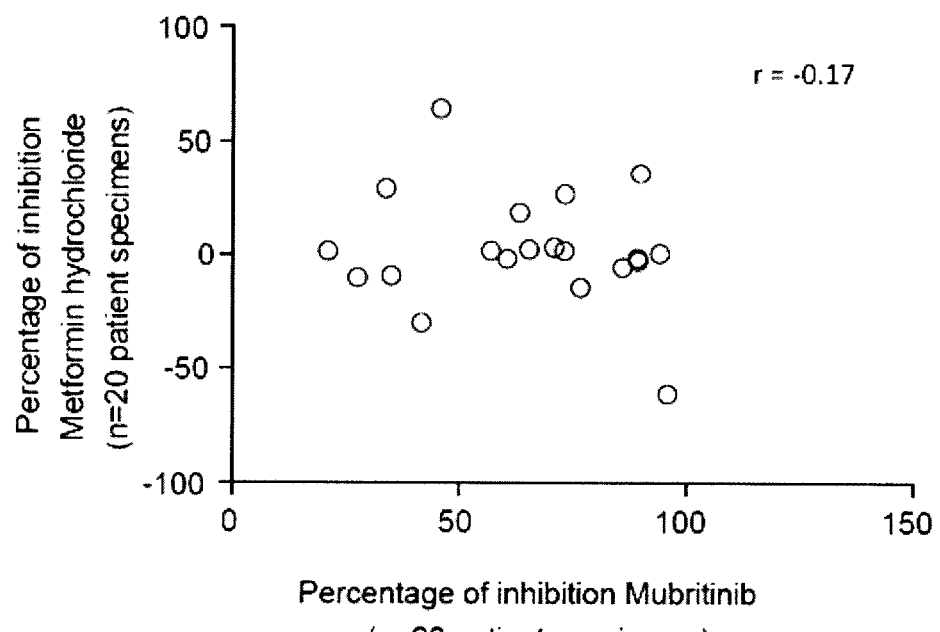
FIG. 7 is a graph showing the inhibitory effects of Mubritinib and Metformin hydrochloride on AML specimens. 20 AML specimens were tested for sensitivity to Mubritinib and Metformin hydrochloride at 1 µM in leukemic stem cell activity conservative culture conditions (Pabst et al., 2014, *Nature Methods* 11(4):436-42).

The antidiabetic drug metformin has been shown to inhibit the proliferation of tumor cell lines (prostate, malignant melanoma and breast), and to synergistically sensitize FLT3-ITD+ AML cells to the kinase inhibitor sorafenib through enhancement of autophagy (Wang et al., 2015. *Leukemia Research* 39:1421-1427). Metformin has also been shown to inhibit mitochondrial complex I in HCT116 p53$^{-/-}$ colon cancer cells, but contrary to rotenone and antimycin, it does not increase ROS ($H_2O_2$) production by these cells (Wheaton et al., 2014. *Elife.* 13(3):e02242). It was thus next tested whether there was a correlation between Mubritinib and metformin effect on AML cells. As shown in FIG. 7, comparison of the percentage of AML cell inhibition induced by each compound throughout the 20 AML specimens tested shows a lack of correlation (Pearson correlation coefficient r=−0.17) between Mubritinib's and Metformin's inhibitory effects in leukemic cells, providing evidence that these two compounds act through different mechanisms of action and target different AML cells, and that Mubritinib activity against AML cells involves induction of ROS production.

Figure 8A:
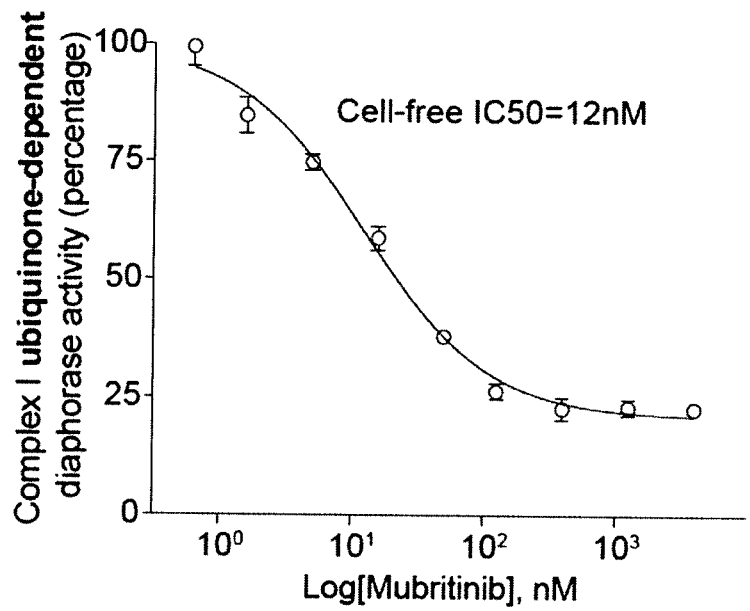
FIGS. 8A and 8B are graphs showing the effect of Mubritinib on Complex I enzyme activity (diaphorase-type activity) in OCI-AML3 cells, as assessed using the Complex I Enzyme Activity Microplate Assay Kit according to the manufacturer's instructions (Abcam, catalog No. ab109721). Complex I activity is determined by following the oxidation of NADH to NAD+ and the simultaneous reduction of a dye which leads to increased absorbance at OD=450 nm.
Figure 8B:
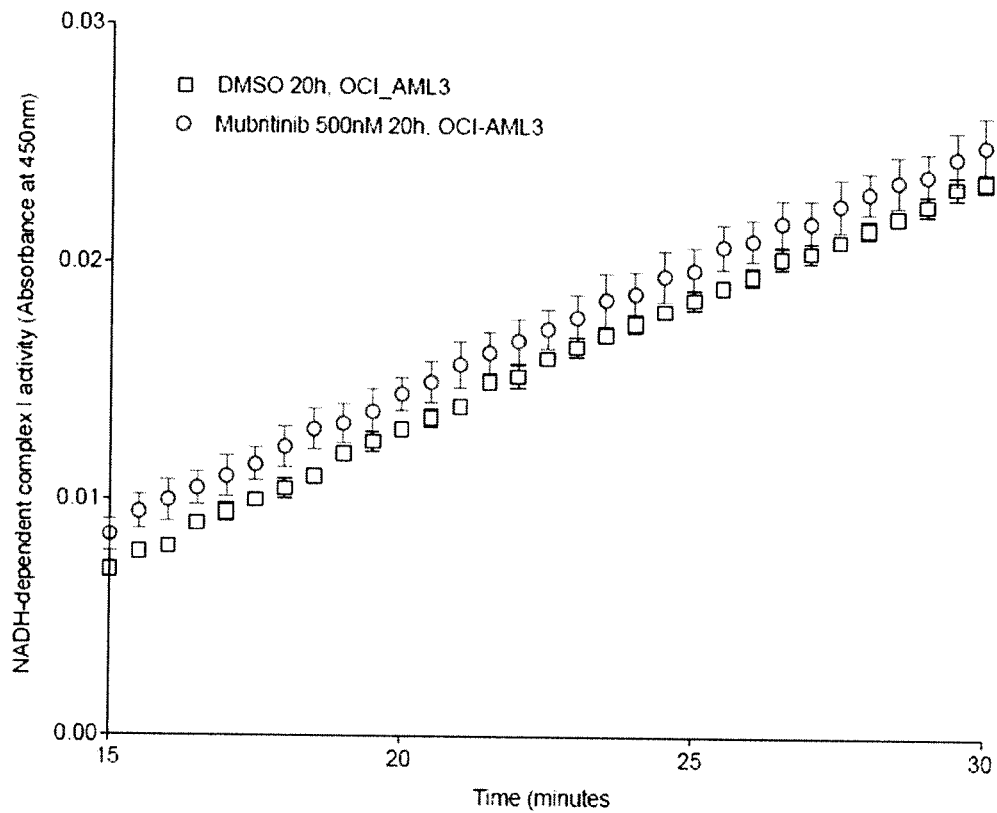
Figure 9:
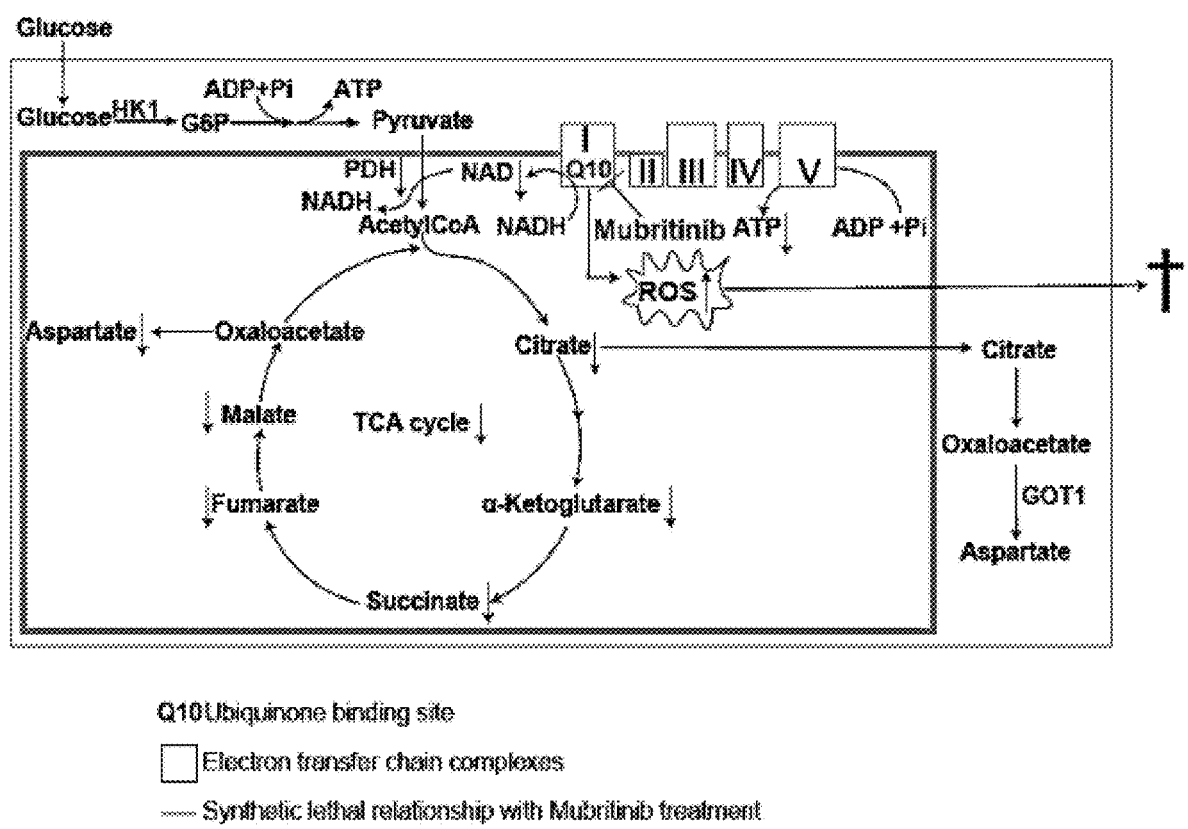
FIG. 9 is a schematic representation of the putative mechanism of action of Mubritinib for inducing tumor cell death.

The inhibitory effect of Mubritinib on Complex I enzyme activity in OCI-AML3 cells was further assessed using the Complex I Enzyme Activity Microplate Assay Kit according to the manufacturer's instructions (Abcam, catalog No. ab109721). This assay measures the diaphorase-type activity of Complex I, which is not dependant on the presence of ubiquinone, and therefore inhibitors that bind at or near the ubiquinone binding site, such as rotenone, do not inhibit this assay. The results depicted in FIGS. 8A and B show that Mubritinib's inhibitory effect on complex I is NADH-independent (i.e. ubiquinone-dependent), as is described for class A inhibitors such as rotenone (Fato et al., *Biochim Biophys Acta,* 2009 May; 1787(5): 384-392), consistent with Mubritinib's ability to increase ROS in these cells. FIG. 9 depicts the putative mechanism of action of Mubritinib for inducing tumor cell death. Mubritinib binds and inhibits Complex I in an ubiquinone-dependent manner, leading to induction of ROS production and ROS-induced cell death in sensitive cells.

In view of these results, heterocyclic compounds having structural similarities with Mubritinib were synthesized and tested for the ability to inhibit the growth of OCI-AML3 cells, which were shown to be sensitive to ROS production induced by Mubritinib.

Example 6: Synthesis of Compounds

Glossary t-BuOH: tert-butyl alcohol
DCM: dichloromethane
DIPEA: diiopropyl ethylamine
DMF: dimethylformamide
DMSO: dimethylsulfoxide
EA: ethyl acetate
EDC: (3-dimethylaminopropyl)-N'-ethylcarbodiimide hydrochloride
HATU: 1-[Bis(dimethylamino)methylene]-1H-1,2,3-triazolo[4,5-b]pyridimium 3-oxid hexafluorophosphate
Hx: hexane
HOBT: Hydroxybenzotriazole
ISCO: Teledyne ISCO combiFlash chromatography system
Me-THF: 2-methyltetrahydrofuran
min: minute
rt: room temperature Compound 1: Mubritinib, i.e. (E)-4-((4-(4-(1H-1,2, 3-triazol-1-yl)butyl)phenoxy)methyl-2-(4-trifluoromethyl)styryl)oxazole

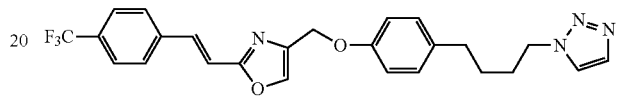

Step 1: 4-(4-Methoxyphenyl)butyl methanesulfonate

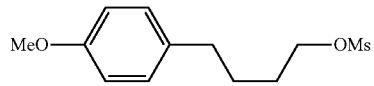 [SMILES: COc1ccc(CCCCOS(C)(=O)=O)cc1]

Methanesulfonyl chloride (2.81 ml, 36.1 mmol) was added dropwise over 5 minutes to a mixture of 4-(4-methoxyphenyl)butan-1-ol (5 g, 27.7 mmol) and triethylamine (5.22 ml, 37.4 mmol) in $CH_2Cl_2$ (75.0 ml, 1165 mmol) at 0° C. Stirred at 0° C. for 10 minutes then slowly warmed to 20° C. After 1 h, washed with water (50 mL), HCl 2% (60 mL) and $NaHCO_3$ 4% weight. (60 mL). The organic layer was dried over $MgSO_4$, filtered and concentrated to dryness to give 7.32 g (102%) of the title compound.

Step 2: 1-(4-Azidobutyl)-4-methoxybezene

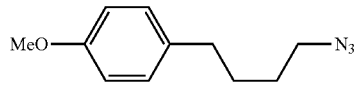 [SMILES: COc1ccc(CCCCN=[N+]=[N-])cc1]

Method A: Sodium azide (2.346 g, 36.1 mmol) was added to a solution of added 4-(4-methoxyphenyl)butyl methanesulfonate (7.17 g, 27.8 mmol) in DMF and stirred overnight at rt. Then, it was heated to 40° C. for 48 h. The reaction mixture was cooled to 20° C. and quenched with water (10 mL) and extracted with $Et_2O$ (3×50 mL). The combined organic phases were washed with water (50 mL) and then with brine (50 mL). The organic layer was dried over $MgSO_4$, filtered and concentrated to give a tan oil. The residue was purified on ISCO using a RediSep® column (Hex/EtOAc) to give 5.45 g of 1-(4-azidobutyl)-4-methoxybenzene.

Method B: Alternatively preparation: Diisopropyl azodicarboxy (DIAD) (13.46 g, 66.6 mmol) was added dropwise to a cold solution of triphenylphosphine (17.46 g, 66.6 mmol) in THE (77 ml). After 20 min, 4-(4-methoxyphenyl)

butan-1-ol (9.60 ml, 55.5 mmol) in THF (77 ml) was added dropwise and stirred 40 min then diphenyl phosphorazidate (15.54 ml, 72.1 mmol) was added dropwise. The mixture was brought to rt and let go overnight. The reaction was concentrated under reduced pressure and the crude compound was first purified with a pad of silica gel (eluent: Hex/EtOAc (95/5) then by ISCO using a RediSep® column (Hex/EtOAc (0-10%)) to give 5.36 g of the title compound.

Step 3:
1-(4-(4-Methoxyphenyl)butyl-1H-1,2,3-triazole

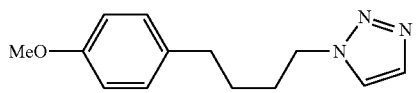 [SMILES: COc1ccc(CCCCn2ccnn2)cc1]

A mixture of 1-(4-azidobutyl)-4-methoxybenzene (3.0 g, 14.62 mmol) in vinyl acetate (45.0 ml, 488 mmol) in a sealed tube was heated to 120° C. overnight. The solution was concentrated to dryness and the residue purified on ISCO using a RediSep® column (DCM/EA) to give 3.38 g (92%) of the title compound. LRMS+H+=232.1.

Step 4: 4-(4-(1H-1,2,3-triazol-1-yl)butyl)phenol

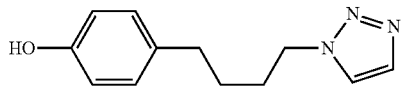 [SMILES: Oc1ccc(CCCCn2ccnn2)cc1]

1-(4-(4-methoxyphenyl)butyl)-1H-1,2,3-triazole (3.38 g, 14.61 mmol) in HBr-water 48% wt. (9.57 ml, 85 mmol) was heated to 90° C. and stirred overnight. Sodium hydroxide 4M in water (38.3 ml, 153 mmol) was added dropwise and the aqueous layer was washed with toluene (15 mL). The aqueous layer was adjusted to pH 6.0-6.5 by addition of HCl 6M in water (7.79 ml, 46.8 mmol) and the mixture extracted with a mixture of EA (35.9 ml, 367 mmol) and THF (17.94 ml, 219 mmol). The organic layer was washed with water (15 mL) and to the organic layer was added activated charcoal (270 mg). It was stirred for 15 minutes, filtered and concentrated to dryness. Crystallization from ethyl acetate-hexane gave 2.80 g (88%) of the title product.

Step 5: (E)-4-((4-(4-(1H-1,2,3-triazol-1-yl)butyl)
phenoxy)methyl-2-(4-trifluoromethyl)styryl)oxazole

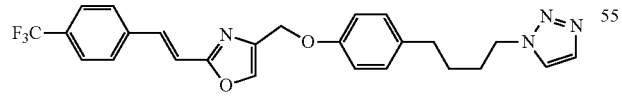

A mixture of (E)-4-(chloromethyl)-2-(4-(trifluoromethyl) styryl)oxazole (0.058 g, 0.203 mmol), prepared according to International patent publication no. WO 01/77107, potassium carbonate (0.038 g, 0.276 mmol) and the previous phenol (0.040 g, 0.184 mmol) in DMF (0.368 ml) was heated at 80° C. for 5 h. It was cooled to rt and quenched with 1 ml water-MeOH (3-1). The precipitate was filtered and purified on ISCO using a RediSep® column (DCM/MeOH; 0-10%) to give 0.040 g (46%) of the title compound. LRMS+H+=469.1; (see WO 01/77107 A1)

Compound 2: (E)-4-((4-(1H-1,2,3-triazol-1-yl-) butyl)phenoxy)methyl)-2-(4-trifluoromethoxy) styryl)oxazole

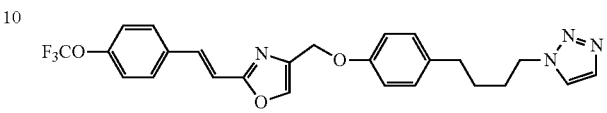

Step 1: 1-(4-(4-Methoxyphenyl)butyl)-4-(trimethyl-silyl)-1H-1,2,3-triazole

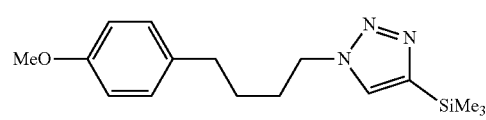

To a solution of ethynyltrimethylsilane (0.700 g, 7.12 mmol) in DCM (5 ml)-tBuOH (5 ml)-water (5 ml) was added 1-(4-azidobutyl)-4-methoxybenzene (0.87 g, 4.24 mmol, step 2 of compound 1, followed by CuSO₄·5H₂O (0.159 g, 0.636 mmol) and sodium ascorbate (0.378 g, 1.907 mmol). The mixture was stirred overnight, filtered and most of the solvent removed. It was then extracted with in EA (2×), combined, dried over Na₂SO₄, filtered and the solvent removed. Purification on ISCO using a RediSep® column (Hx/EA; 0-80%) gave 0.22 g (17%) of the title compound.

Step 2: 4-(4-(4-(trimethylsilyl)-1H-1,2,3-triazol-1-yl)butyl)phenol

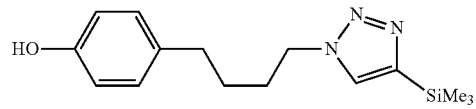

BBr₃ (2.17 ml, 2.17 mmol) was added dropwise to a −78° C. sol. of 1-(4-(4-methoxyphenyl)butyl)-4-(trimethylsilyl)-1H-1,2,3-triazole (0.22 g, 0.72 mmol) in DCM (5.0 ml). After 45 min at −78° C. the solution was brought to 0° C. and left overnight at the same temperature. The reaction was quenched with 2 ml of MeOH and stirred with a saturated solution of NaHCO₃ for 1 h. It was diluted with DCM and the organic phase was separated, dried over Na₂SO₄, filtered and the solvent removed to give 0.175 g (83%) of crude material.

Step 3: (E)-4-((4-(1H-1,2,3-triazol-1-yl-)butyl)phenoxy)methyl)-2-(4-trifluoromethoxy)styryl)oxazole

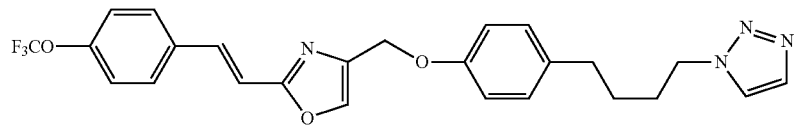

NaH 60% (7.90 mg, 0.198 mmol) was added to a solution of 4-(4-(4-(trimethylsilyl)-1H-1,2,3-triazol-1-yl)butyl)phenol (0.052 g, 0.181 mmol) in THF (0.823 ml) at 0° C. After 10 min, (E)-4-(chloromethyl)-2-(4-(trifluoromethoxy)styryl)oxazole (0.050 g, 0.165 mmol) was added and heated overnight at 80° C. The mixture was quenched with a NH₄Cl solution and extracted 2× with EA. The combined organic solution was dried over Na₂SO₄, filtered and purified on preparative HPLC (water-MeOH, 5% HCO₂H; 35%-100%) to give 0.024 g (30%) of the title compound. ¹H NMR (400 MHz, CDCl₃) δ ppm 1.61-1.67 (m, 2H) 1.89-2.00 (m, 2H) 2.58-2.65 (m, 2H) 4.40 (t, J=7.04 Hz, 2H) 5.02 (d, J=0.78 Hz, 2H) 6.88-6.95 (m, 3H) 7.08 (d, J=8.61 Hz, 2H) 7.25 (d, J=9.00 Hz, 2H) 7.49-7.59 (m, 4H) 7.69 (d, J=13.69 Hz, 2H). LRMS+H⁺: 485.2.

Compounds 3A and 3B: (E)-2-(4-Bromo-2-fluorostyryl)-4-((4-(4-(4-(trimethylsilyl)-1H-1,2,3-triazol-1-yl)butyl)phenoxy)methyl)oxazole and (E)-((4-(4-(1H-1,2,3-triazol-1-yl)butyl)phenoxy)methyl)-2-(4-bromo-2-fluorostyryl)oxazole

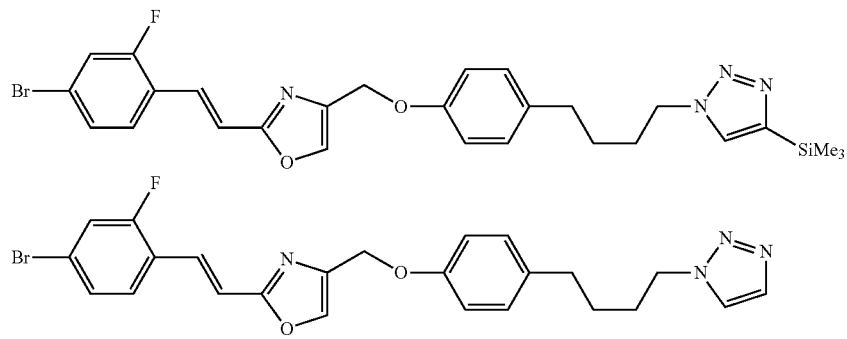

Step 1: (E)-3-(4-bromo-2-fluorophenyl)acylamide

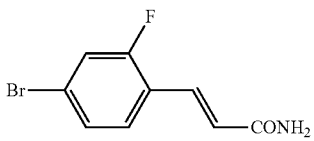

Oxalyl chloride (0.429 ml, 4.90 mmol) was added to a suspension of (E)-3-(4-bromo-2-fluorophenyl)acrylic acid (1 g, 4.08 mmol) in DCM (27.2 ml) at 0° C. and DMF (8.74 µl, 0.122 mmol) was added. Bring to rt and let go 2 h. The solvent removed, the residue taken in EA and the solvent removed. It was taken in EA and NH₄OH conc. (6.15 ml, 86 mmol) was added slowly. It was stirred 30 minutes and diluted with EA. The organic phase was separated and washed with brine, dried over Na₂SO₄, filtered and the solvent removed to give 0.88 g of the title compound. ¹H NMR (400 MHz, CCCl₃) δ ppm 5.60 (br. s., 2H) 6.59 (d, J=16.04 Hz, 1H) 7.28-7.34 (m, 2H) 7.35-7.42 (m, 1H) 7.66 (d, J=16.04 Hz, 1H).

Step 2: (E)-2-(4-Bromo-2-fluorostyryl)-4-(chloromethyl)oxazole

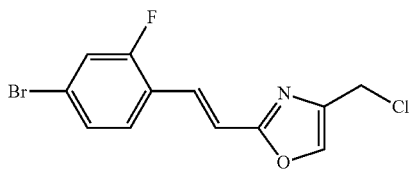 [SMILES: Fc1cc(Br)ccc1/C=C/c1nc(CCl)co1]

A mixture of (E)-3-(4-bromo-2-fluorophenyl)acrylamide (0.876 g, 3.59 mmol) and 1,3-dichloropropan-2-one (0.911 g, 7.18 mmol) in toluene (7.18 ml) was heated to reflux with a Dean-Stark for 24 h. The solvent was removed and the residue absorbed on SiO₂ with DCM. Purification on ISCO using a RediSep® column (Hx-EA; 0-40%) gave 0.61 g of the title compound. LRMS+H⁺: 315.9.

Step 3: (E)-2-(4-Bromo-2-fluorostyryl)-4-((4-(4-(4-(trimethylsilyl)-1H-1,2,3-triazol-1-yl)butyl)phenoxy)methyl)oxazole and (E)-((4-(4-(1H-1,2,3-triazol-1-yl)butyl)phenoxy)methyl)-2-(4-bromo-2-fluorostyryl)oxazole NaH 60% (6.89 mg, 0.172 mmol) was added to a solution of adduct from compound 2 step 2 (0.042 g, 0.144 mmol) in DMF (0.718 ml). Then at 0° C. was added the previous oxazole (0.050 g, 0.158 mmol). Bring to rt for 3 h later it was quenched with a NH₄Cl solution. Extracted 2× with EA, dried with Na₂SO₄, filtered and purified on ISCO using a RediSep® column (Hx-EA; 0-100%) to give 0.010 g of (E)-((4-(4-(1H-1,2,3-triazol-1-yl)butyl)phenoxy)methyl)-2-

(4-bromo-2-fluorostyryl)oxazole 3A. ¹H NMR (400 MHz, CDCl₃) δ ppm 1.61-1.67 (m, 2H) 1.89-2.00 (m, 2H) 2.58-2.65 (m, 2H) 4.40 (t, J=7.04 Hz, 2H) 5.02 (d, J=0.78 Hz, 2H) 6.88-6.95 (m, 3H) 7.08 (d, J=8.61 Hz, 2H) 7.25 (d, J=9.00 Hz, 2H) 7.49-7.59 (m, 4H) 7.69 (d, J=13.69 Hz, 2H). HRMS+H⁺: 499.0946.

The second adduct needed more purification on preparative HPLC (water-MeOH, 5% HCO₂H, 35%-100%) to give 0.036 g of (E)-2-(4-Bromo-2-fluorostyryl)-4-((4-(4-(4-(trimethylsilyl)-1H-1,2,3-triazol-1-yl)butyl)phenoxy)methyl)oxazole 3B. ¹H NMR (400 MHz, CDCl₃) δ 0.31 (s, 9H) 1.58-1.70 (m, 2H) 1.85-1.98 (m, 2H) 2.60 (t, J=7.63 Hz, 2H) 4.37 (t, J=7.24 Hz, 2H) 5.01 (s, 2H) 6.91 (d, J=8.61 Hz, 2H) 7.05-7.10 (m, 3H) 7.28-7.34 (m, 2H) 7.41 (d, J=7.83 Hz, 1H) 7.45 (s, 1H) 7.57 (d, J=16.82 Hz, 1H) 7.67 (s, 1H). HRMS+H⁺: 571.1344.

Compound 4: (E)-2-(1-(4-(4-((2-(4-Trifluoromethyl)styryl)oxazol-4-yl)methoxy)phenyl)butyl-1H-1,2,3-triazol-4-yl)ethanol

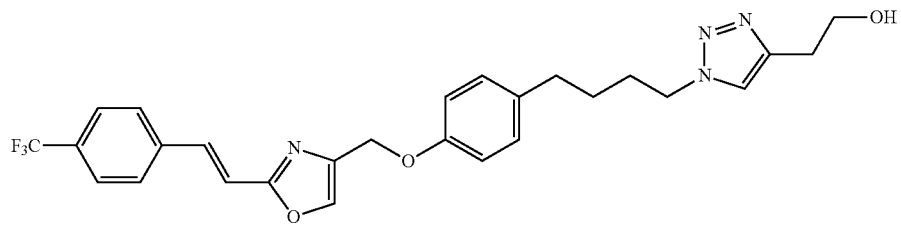 [SMILES: OCCc1cn(CCCCc2ccc(OCc3coc(/C=C/c4ccc(C(F)(F)F)cc4)n3)cc2)nn1]

Step 1: (E)-4-(4-((2-(4-Trifluoromethyl)styryl)oxazol-4-yl)methoxy)phenyl)butan-1-ol

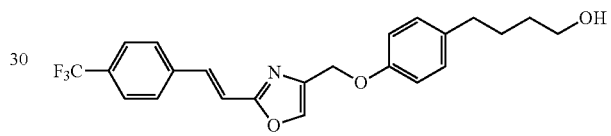

A mixture of (E)-4-(chloromethyl)-2-(4-(trifluoromethyl)styryl)oxazole (0.249 g, 0.866 mmol), 4-(4-hydroxybutyl)phenol (0.12 g, 0.722 mmol), K₂CO₃ (0.120 g, 0.866 mmol) and NaI (0.108 g, 0.722 mmol) in acetone (3.61 ml) was heated at reflux for 6 h. The reaction was diluted with EA and water. The organic phase was separated and the aqueous was extracted with EA and combined with the previous one. It was then dried on Na₂SO₄, filtered and the solvent removed. Purification on ISCO using a RediSep® column (Tol-EA; 0-100%) gave 0.115 g of the title compound. ¹H NMR (400 MHz, DMSO-d₆) δ ppm 1.33-1.47 (m, 2H) 1.49-1.62 (m, 2H) 3.39 (q, J=6.26 Hz, 2H) 4.34 (t, J=5.28 Hz, 1H) 4.99 (s, 2H) 6.90-6.97 (m, 2H) 7.11 (m, J=8.61 Hz, 2H) 7.34 (d, J=16.82 Hz, 1H) 7.62 (d, J=16.43 Hz, 1H) 7.76 (m, J=8.22 Hz, 2H) 7.95 (m, J=8.22 Hz, 2H), 8.24 (s, 1H).

Step 2: (E)-4((4-(4-azidobutyl)phenoxy)methyl)-2-(4-(trifluoromethyl)styryl)oxazole

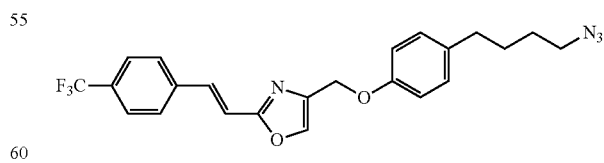

This compound was prepared in a similar fashion as compound 1 step 2 (method B). ¹H NMR (400 MHz, CDCl₃) δ ppm 1.58-1.75 (m, 4H) 2.61 (t, J=7.24 Hz, 2H) 3.29 (t, J=6.65 Hz, 2H) 5.04 (d, J=0.78 Hz, 2H) 6.90-6.97 (m, 2H) 7.03 (d, J=16.43 Hz, 1H) 7.12 (m, J=8.61 Hz, 2H) 7.56 (d, J=16.43 Hz, 1H) 7.61-7.68 (m, 4H) 7.69 (s, 1H).

Step 3: (E)-2-(1-(4-(4-((2-(4-Trifluoromethyl)styryl)oxazol-4-yl)methoxy)phenyl)butyl-1H-1,2,3-triazol-4-yl)ethanol

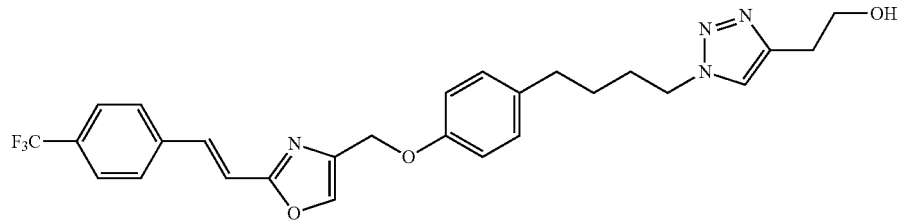 [SMILES: OCCc1cn(CCCCc2ccc(OCc3coc(/C=C/c4ccc(C(F)(F)F)cc4)n3)cc2)nn1]

CuSO$_4$·5H$_2$O (2.1 mg, 8.4 μmol) and but-3-yn-1-ol (3.9 mg, 0.05 mmol) in THF (0.28 ml) and triethylamine (9.4 μl, 0.06 mmol) were stirred for 15 min then, the previous azido analogue (0.025 g, 0.057 mmol) was added and the reaction was stirred overnight. SiO$_2$ was added and the solvent removed. Purification on ISCO using a RediSep® column (Hx-EA; 0-100%) gave 0.012 g of the title compound. $^1$H NMR (400 MHz, DMSO-d6) δ ppm 1.42-1.55 (m, 2H) 1.71-1.84 (m, 2H) 2.51-2.57 (m, 2H) 2.74 (t, J=7.04 Hz, 2H) 3.61 (q, J=5.80 Hz, 2H) 4.31 (t, J=7.04 Hz, 2H) 4.67 (t, J=5.28 Hz, 1H) 4.98 (s, 2H) 6.94 (m, J=8.61 Hz, 2H) 7.10 (m, J=8.22 Hz, 2H) 7.34 (d, J=16.43 Hz, 1H) 7.62 (d, J=16.43 Hz, 1H) 7.76 (m, J=8.22 Hz, 2H) 7.83 (s, 1H) 7.95 (m, J=8.22 Hz, 2H) 8.24 (s, 1H). HRMS+H$^+$: 513.2129.

Compound 5: (E)-4-(1-(4-(4-((2-(4-(trifluoromethyl)styryl)oxazol-4-yl-methoxy)phenyl)butyl-1H-1,2,3-triazol-4-yl)butan-1-ol

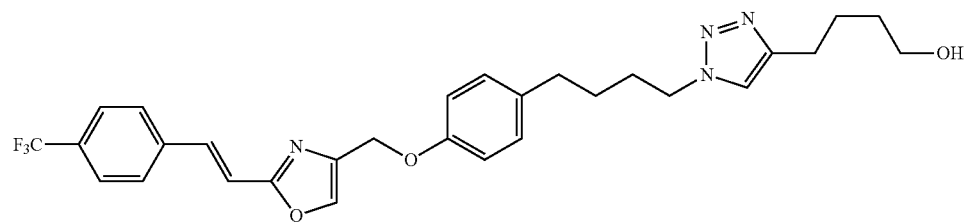 [SMILES: OCCCCc1cn(CCCCc2ccc(OCc3coc(/C=C/c4ccc(C(F)(F)F)cc4)n3)cc2)nn1]

This compound was prepared in a similar fashion as compound 4 with hex-5-yn-1-ol. $^1$H NMR (400 MHz, DMSO-d$_6$) δ ppm 1.46 (quin, J=7.60 Hz, 2H) 1.72-1.82 (m, 2H) 3.97 (s, 2H) 4.31 (t, J=7.04 Hz, 2H) 4.98 (s, 2H) 6.93 (m, 2H) 7.07 (m, 2H) 7.15-7.31 (m, 5H) 7.34 (d, J=16.43 Hz, 1H) 7.62 (d, J=16.43 Hz, 1H) 7.76 (m, 2H) 7.82 (s, 1H) 7.95 (m, 2H) 8.24 (s, 1H). LRMS+H$^+$: 541.2.

Compound 6: (E)-diethyl 1-(4-(4-((2-(4-(trifluoromethyl)styryl)oxazol-4-yl)methoxy)phenyl)butyl)-1H-1,2,3-triazole-4,5-dicarboxylate

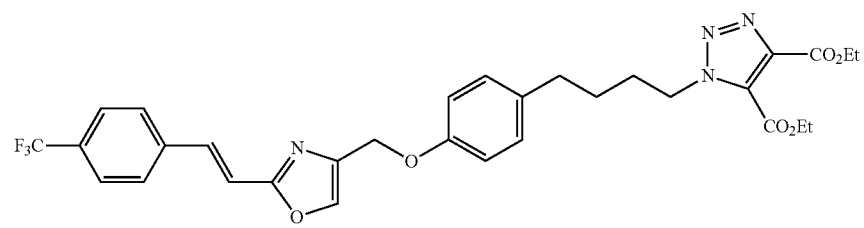 [SMILES: CCOC(=O)c1nnn(CCCCc2ccc(OCc3coc(/C=C/c4ccc(C(F)(F)F)cc4)n3)cc2)c1C(=O)OCC]

(E)-4-((4-(4-azidobutyl)phenoxy)methyl)-2-(4-(trifluoromethyl)styryl)oxazole (0.025 g, 0.057 mmol) and diethyl but-2-ynedioate (0.019 g, 0.113 mmol) in toluene (0.283 ml) were heated to 105° C. overnight. Purification on preparative HPLC (water-MeOH, 5% HCOOH; 35%-100%) gave 0.015 g of the title compound. ¹H NMR (400 MHz, DMSO-d₆) δ ppm 1.21-1.31 (m, 6H) 1.51 (quin, J=7.40 Hz, 2H) 1.83 (quin, J=7.24 Hz, 2H) 2.52-2.58 (m, 2H) 4.26-4.40 (m, 4H) 4.56 (t, J=7.04 Hz, 2H) 4.98 (s, 2H) 6.94 (d, J=8.61 Hz, 1H) 7.09 (d, J=8.61 Hz, 1H) 7.34 (d, J=16.43 Hz, 1H) 7.61 (d, J=16.43 Hz, 1H) 7.76 (d, J=8.22 Hz, 2H) 7.95 (d, J=8.22 Hz, 2H) 8.23 (s, 1H). LRMS+H⁺: 613.2.

Compound 7: (E)-N-methyl-1-(1-(4-(4-((2-(4-(trifluoromethyl)styryl)oxazol-4-yl)methoxy)phenyl)butyl)-1H-1,2,3-triazol-4-yl)methanamine

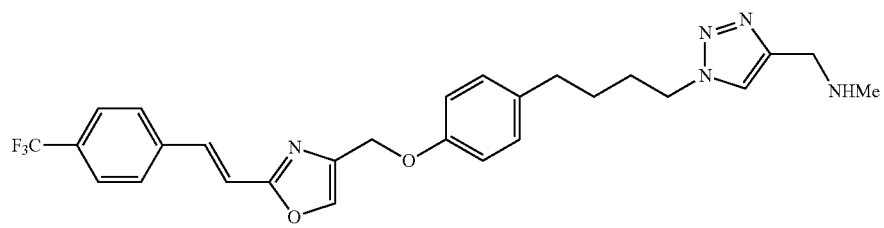 [SMILES: CNCc1cn(CCCCc2ccc(OCc3coc(/C=C/c4ccc(C(F)(F)F)cc4)n3)cc2)nn1]

To a solution of N-methylprop-2-yn-1-amine (0.016 g, 0.226 mmol) in DCM (0.251 ml), tBuOH (0.251 ml) and water (0.251 ml) was added (E)-4-((4-(4-azidobutyl)phenoxy)methyl)-2-(4-(trifluoromethyl)styryl)oxazole (0.050 g, 0.113 mmol) followed by CuSO₄·5H₂O (0.021 g, 0.085 mmol) and by sodium ascorbate (0.034 g, 0.170 mmol). It was stirred overnight, diluted with 2-methyltetrahyfrofuran and heated to get a solution. This was quenched with a NH₄C₁ solution and the organic phase was separated and extracted with 2-methyltetrahyfrofuran. The combined organic phases were dried over Na₂SO₄, filtered and purified on ISCO using a RediSep® column DCM-MeOH—NH₄OH (77.5-22-2.5%) to give 0.016 g of the title compound. ¹H NMR (400 MHz, DMSO-d6) δ ppm 1.40-1.63 (m, 4H) 2.51-2.56 (m, 2H) 2.72 (t, J=7.04 Hz, 2H) 4.99 (s, 2H) 6.95 (d, J=8.61 Hz, 2H) 7.13 (d, J=8.61 Hz, 2H) 7.34 (d, J=16.43 Hz, 1H) 7.61 (d, J=16.82 Hz, 1H) 7.76 (d, J=8.61 Hz, 2H) 7.95 (d, J=8.22 Hz, 2H) 8.24 (s, 1H) 8.43 (br. s., 1H). LRMS+H⁺: 512.2.

Compound 8: (E)-1-(1-(4-(4-((2-(4-(trifluoromethyl)styryl)oxazol-4-yl)methoxy)phenyl)butyl)-1H-1,2,3-triazol-4-yl)cyclopentanol

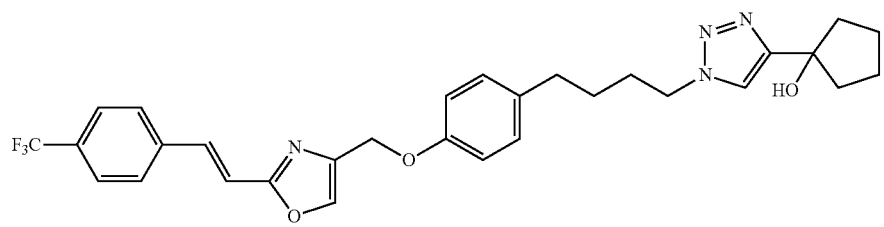 [SMILES: OC1(c2cn(CCCCc3ccc(OCc4coc(/C=C/c5ccc(C(F)(F)F)cc5)n4)cc3)nn2)CCCC1]

To a solution of 1-ethynylcyclopentanol (0.025 g, 0.226 mmol) in DCM (0.251 ml)-tBuOH (0.251 ml)-water (0.251 ml) was added first (E)-4-((4-(4-azidobutyl)phenoxy)methyl)-2-(4-(trifluoromethyl)styryl)oxazole (0.050 g, 0.113 mmol) followed by CuSO$_4$·5H$_2$O (0.021 g, 0.085 mmol) and sodium ascorbate (0.034 g, 0.170 mmol). This was stirred overnight. It was taken in 2-methyltetrahydrofuran and heated to get a solution and quenched with a NH$_4$Cl solution. Separated and extracted with Me-THF. Combined, Na$_2$SO4 dried and the solvent removed. It was absorbed on SiO$_2$ and purified on ISCO using a RediSep® column Hx-EA (30-100%) to give 40 mg of the title compound. $^1$H NMR (400 MHz, DMSO-d$_6$) δ ppm 1.51 (quin, J=7.60 Hz, 2H) 1.61-1.71 (m, 2H) 1.74-1.86 (m, 6H) 1.89-2.00 (m, 2H) 2.54 (t, J=7.63 Hz, 2H) 4.32 (t, J=7.04 Hz, 2H) 4.93 (s, 1H) 4.99 (s, 2H) 6.94 (d, J=8.61 Hz, 2H) 7.10 (d, J=8.61 Hz, 2H) 7.34 (d, J=16.43 Hz, 1H) 7.62 (d, J=16.43 Hz, 1H) 7.76 (d, J=8.22 Hz, 2H) 7.85 (s, 1H) 7.95 (d, J=8.22 Hz, 2H) 8.24 (s, 1H). LRMS+H$^+$: 553.2.

Compound 9: (E)-(1-(4-(4-((2-(4-(trifluoromethyl)styryl)oxazol-4-yl)methoxy)phenyl)butyl)-1H-1,2,3-triazole-4,5-diyl)dimethanol

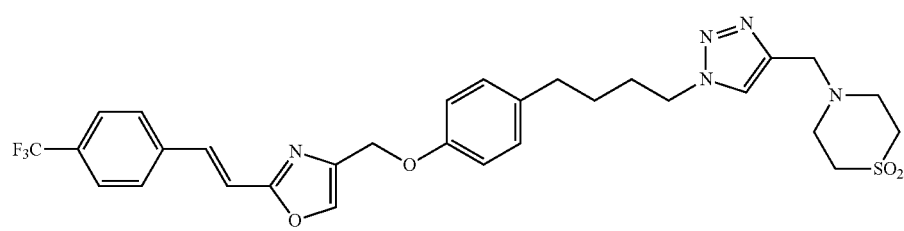

A mixture of (E)-4((4-(4-azidobutyl)phenoxy)methyl)-2-(4-(trifluoromethyl)styryl)oxazole (0.030 g, 0.068 mmol) and but-2-yne-1,4-diol (0.025 ml, 0.339 mmol) were heated to 90° C. 8 h. The crude was purified on ISCO using a RediSep® column (DCM-MeOH; 0-10%%) to give 0.016 g of the title compound. $^1$H NMR (400 MHz, DMSO-d$_6$) δ ppm 1.55 (quin, J=7.80 Hz, 2H) 1.83 (quin, J=7.20 Hz, 1H) 2.55 (t, J=7.43 Hz, 2H) 4.34 (t, J=7.24 Hz, 2H) 4.49 (d, J=5.48 Hz, 2H) 4.58 (d, J=5.48 Hz, 2H) 4.95-5.03 (m, 3H) 5.31 (t, J=5.48 Hz, 1H) 6.94 (m, J=8.61 Hz, 2H) 7.11 (m, J=8.61 Hz, 2H) 7.34 (d, J=16.43 Hz, 1H) 7.62 (d, J=16.43 Hz, 1H) 7.76 (m, J=8.22 Hz, 2H) 7.95 (m, J=8.22 Hz, 2H) 8.24 (s, 1H). LRMS+H$^+$: 529.2.

Compound 10: (E)-4-((1-(4-(4-((2-(4-(trifluoromethyl)styryl)oxazol-4-yl)methoxy)phenyl)butyl)-1H-1,2,3-triazol-4-yl)methyl)thiomorpholine 1,1-dioxide

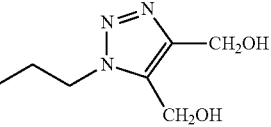

This compound was prepared in a similar fashion as compound 7 with 4-(prop-2-yn-1-yl)thiomorpholine 1,1-dioxide. $^1$H NMR (400 MHz, DMSO-d$_6$) δ ppm 1.48 (quin, J=7.53 Hz, 2H) 1.80 (quin, J=7.34 Hz, 2H) 2.52-2.57 (m, 2H) 2.83-2.90 (m, 4H) 3.05-3.12 (m, 4H) 3.75 (s, 2H) 4.35 (t, J=7.04 Hz, 2H) 4.98 (s, 2H) 6.94 (d, J=9.00 Hz, 2H) 7.09 (d, J=8.61 Hz, 2H) 7.34 (d, J=16.43 Hz, 1H) 7.62 (d, J=16.43 Hz, 1H) 7.76 (d, J=8.22 Hz, 2H) 7.95 (d, J=8.22 Hz, 2H) 8.01 (s, 1H) 8.23 (s, 1H). LRMS+H$^+$: 616.1.

Compound 11: 4-((4-(4-(1H-1,2,3-triazol-1-yl)butyl)phenoxy)methyl)-2-(2-fluoro-4-(trifluoromethyl)phenethyl)oxazole

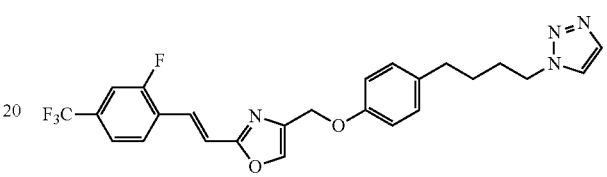

A suspension of compound 48 (31 mg, 0.064 mmol) and Pd—C 10%, Degussa type, 50% wet (5.43 mg, 2.55 µmol) in EA (2 ml) was stirred under a hydrogen atmosphere for 1.5 h. The mixture was filtered and reloaded with more Pd—C 10%, Degussa type, 50% wet (5.43 mg, 2.55 µmol), EA (2 ml) and MeOH (2 ml) and stirred under a hydrogen atmosphere for 5 h. The mixture was filtered on a 45 µm syringe filter, washed with MeOH (1 ml) then EA (2 ml) and concentrated to afford the title compound. $^1$H NMR (500 MHz, CCCl$_3$) δ ppm 1.59-1.67 (m, 2H) 1.94 (dt, J=14.98, 7.33 Hz, 2H) 2.61 (t, J=7.57 Hz, 2H) 3.06-3.15 (m, 2H) 3.16-3.24 (m, 2H) 4.40 (t, J=7.25 Hz, 2H) 4.95 (d, J=0.95 Hz, 2H) 6.86-6.92 (m, 2H) 7.03-7.09 (m, 2H) 7.28-7.35 (m, 3H) 7.50 (s, 1H) 7.59 (s, 1H) 7.70 (s, 1H). LRMS+H$^+$: 489.3.

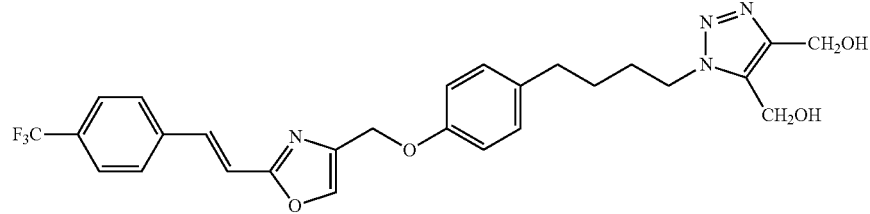 [SMILES: OCc1nnn(CCCCc2ccc(OCc3coc(/C=C/c4ccc(C(F)(F)F)cc4)n3)cc2)c1CO]

Compound 12: (E)-N-(prop-2-yn-1-yl)-5-(1-(4-(4-((2-(4-(trifluoromethyl)styryl)oxazol-4-yl)methoxy)phenyl)butyl)-1H-1,2,3-triazol-4-yl)pentanamide

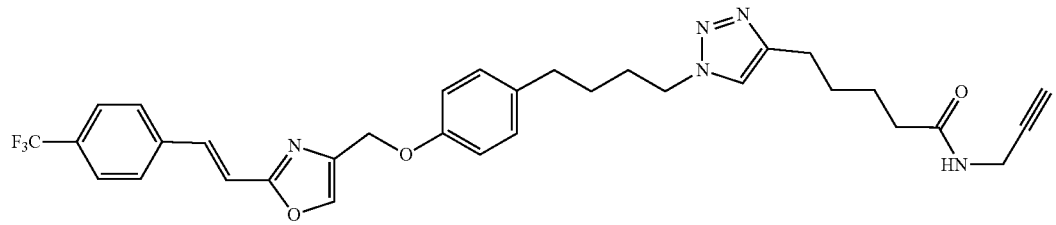 [SMILES: C#CCNC(=O)CCCCc1cn(CCCCc2ccc(OCc3coc(/C=C/c4ccc(C(F)(F)F)cc4)n3)cc2)nn1]

Step 1: (E)-5-(1-(4-(4-((2-(4-(trifluoromethyl)styryl)oxazol-4-yl)methoxy)phenyl)butyl)-1H-1,2,3-triazol-4-yl)pentanoic acid

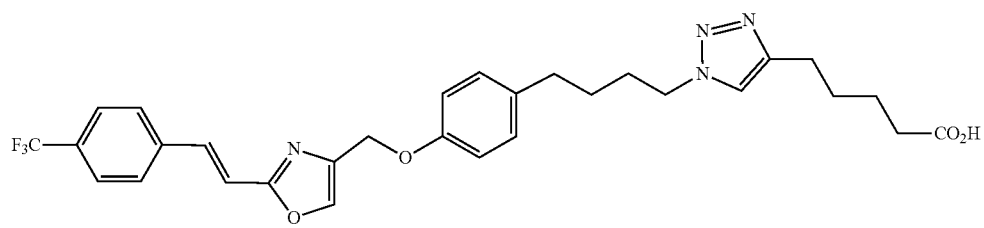 [SMILES: O=C(O)CCCCc1cn(CCCCc2ccc(OCc3coc(/C=C/c4ccc(C(F)(F)F)cc4)n3)cc2)nn1]

To (E)-4((4-(4-azidobutyl)phenoxy)methyl)-2-(4-(trifluoromethyl)styryl)oxazole (0.150 g, 0.339 mmol) and hept-6-ynoic acid (0.064 g, 0.509 mmol) in tBuOH (2.5 ml)-DCM (2.500 ml)-water (2.500 ml) was added first copper(II) sulfate pentahydrate (0.063 g, 0.254 mmol) followed by sodium ascorbate (0.101 g, 0.509 mmol). After 1 h, it was diluted with EA-water and filtered on celite. The organic phase was separated and the aqueous extracted with EA. The organic phases were combined, $Na_2SO_4$ dried, filtered and the solvent removed. The crude residue was absorbed on $SiO_2$ and purified on a short pad of $SiO_2$ with 100% EA followed by 5% MeOH in EA to give 0.146 g of the title compound. $^1$H NMR (400 MHz, DMSO-$d_6$) δ ppm 1.43-1.63 (m, 6H) 1.72-1.84 (m, 2H) 2.23 (t, J=6.85 Hz, 2H) 2.52-2.56 (m, 2H) 2.59 (t, J=7.24 Hz, 2H) 4.30 (t, J=7.04 Hz, 2H) 4.98 (s, 2H) 6.94 (d, J=8.61 Hz, 2H) 7.09 (d, J=8.61 Hz, 2H) 7.34 (d, J=16.43 Hz, 1H) 7.62 (d, J=16.43 Hz, 1H) 7.76 (d, J=8.22 Hz, 2H) 7.82 (s, 1H) 7.95 (d, J=7.83 Hz, 2H) 8.24 (s, 1H) 11.99 (br. s., 1H).

Step 2: (E)-N-(prop-2-yn-1-yl)-5-(1-(4-(4-((2-(4-(trifluoromethyl)styryl)oxazol-4-yl)methoxy)phenyl)butyl)-1H-1,2,3-triazol-4-yl)pentanamide

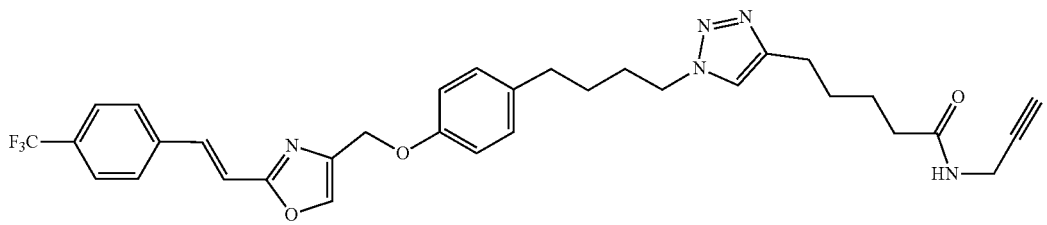 [SMILES: C#CCNC(=O)CCCCc1cn(CCCCc2ccc(OCc3coc(/C=C/c4ccc(C(F)(F)F)cc4)n3)cc2)nn1]

HATU (0.067 g, 0.176 mmol) was added to (E)-5-(1-(4-(4-((2-(4-(trifluoromethyl)styryl)oxazol-4-yl)methoxy)phenyl)butyl)-1H-1,2,3-triazol-4-yl)pentanoic acid (0.080 g, 0.141 mmol) in DMF (1.0 ml). After 10 min Hunig's Base (0.074 ml, 0.422 mmol) was added followed by prop-2-yn-1-amine (9.69 mg, 0.176 mmol) and let go overnight. It was then diluted with EA-NaHCO$_3$ solution and the organic phase separated and the aqueous phase extracted with EA. The combined phases were dried over Na$_2$SO$_4$, filtered and absorbed on SiO$_2$ to purify on ISCO using a RediSep® column using DCM-MeOH—NH$_4$OH (77.5-20-2.5) to give 0.056 g of the title compound. $^1$H NMR (400 MHz, DMSO-d$_6$) δ ppm 1.43-1.59 (m, 6H) 1.78 (quin, J=7.40 Hz, 2H) 2.10 (t, J=6.85 Hz, 2H) 2.52-2.55 (m, 2H) 2.58 (t, J=6.85 Hz, 2H) 3.07 (t, J=2.35 Hz, 1H) 3.83 (dd, J=5.28, 2.54 Hz, 2H) 4.30 (t, J=7.04 Hz, 2H) 4.98 (s, 2H) 6.94 (d, J=8.61 Hz, 2H) 7.09 (d, J=8.61 Hz, 2H) 7.34 (d, J=16.82 Hz, 1H) 7.62 (d, J=16.43 Hz, 1H) 7.76 (d, J=8.22 Hz, 2H) 7.81 (s, 1H) 7.95 (d, J=8.22 Hz, 2H) 8.19-8.29 (m, 2H). LRMS+H$^+$: 606.6.

Compound 13: (E)-2-(1-(4-(4-((2-(4-(trifluoromethyl)styryl)oxazol-4-yl)methoxy)phenyl)butyl)-1H-1,2,3-triazol-4-yl)ethanamine

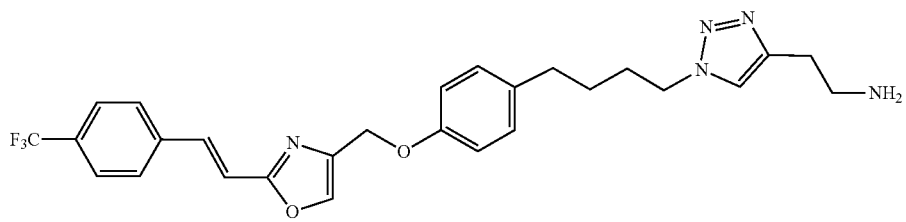 [SMILES: NCCc1cn(CCCCc2ccc(OCc3coc(/C=C/c4ccc(C(F)(F)F)cc4)n3)cc2)nn1]

This compound was prepared in a similar fashion as compound 7 with but-3-yn-1-amine. $^1$H NMR (400 MHz, DMSO-d) δ ppm 1.49 (dt, J=15.06, 7.73 Hz, 2H) 1.78 (quin, J=7.34 Hz, 2H) 2.52-2.56 (m, 2H) 2.66 (br. s., 2H) 2.78 (br.s., 2H) 4.31 (t, J=7.04 Hz, 2H) 4.98 (s, 2H) 6.94 (d, J=8.61 Hz, 2H) 7.10 (d, J=8.61 Hz, 2H) 7.34 (d, J=16.43 Hz, 1H) 7.62 (d, J=16.43 Hz, 1H) 7.76 (d, J=8.22 Hz, 2H) 7.84 (s, 1H) 7.95 (d, J=8.22 Hz, 2H) 8.24 (s, 1H). HRMS+H$^+$: 512.2280.

Compound 14: (E)-N-(2-(1-(4-(4-((2-(4-(trifluoromethyl)styryl)oxazol-4-yl)methoxy)phenyl)butyl)-1H-1,2,3-triazol-4-yl)ethyl)pent-4-ynamide

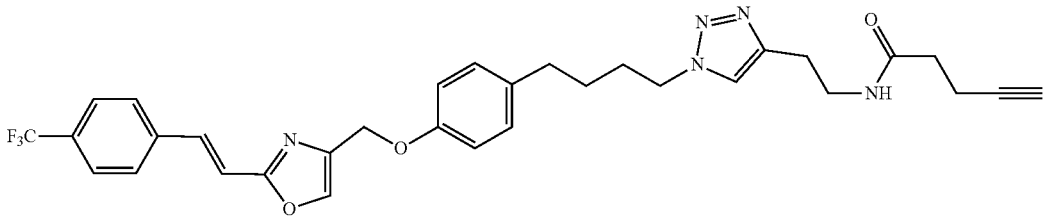 [SMILES: C#CCCC(=O)NCCc1cn(CCCCc2ccc(OCc3coc(/C=C/c4ccc(C(F)(F)F)cc4)n3)cc2)nn1]

This compound was prepared in a similar fashion as compound 12 step 2 with pent-4-ynoic acid and compound 13. $^1$H NMR (400 MHz, DMSO-d$_6$) δ ppm 1.49 (quin, J=7.20 Hz, 2H) 1.78 (quin, J=7.40 Hz, 2H) 2.20-2.27 (m, 2H) 2.30-2.37 (m, 2H) 2.52-2.58 (m, 2H) 2.69-2.78 (m, 3H) 3.25-3.31 (m, 2H) 4.31 (t, J=7.04 Hz, 2H) 4.98 (s, 2H) 6.94 (d, J=8.61 Hz, 2H) 7.10 (d, J=8.22 Hz, 2H) 7.34 (d, J=16.43 Hz, 1H) 7.62 (d, J=16.43 Hz, 1H) 7.76 (d, J=8.22 Hz, 2H) 7.85 (s, 1H) 7.91-8.02 (m, 3H) 8.24 (s, 1H). LRMS+H$^+$: 592.2.

Compound 15: (E)-4-((1-(4-(4-((2-(4-(trifluoromethyl)styryl)oxazol-4-yl)methoxy)phenyl)butyl)-1H-1,2,3-triazol-5-yl)methyl)thiomorpholine 1,1-dioxide

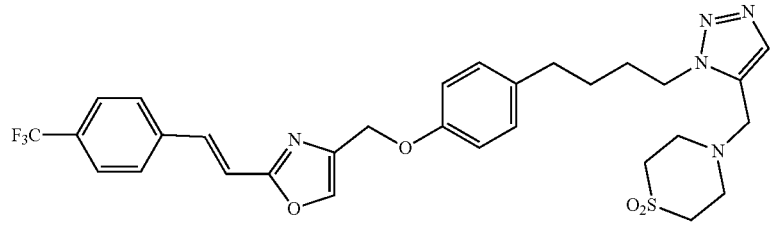 [SMILES: O=S1(=O)CCN(Cc2cnnn2CCCCc2ccc(OCc3coc(/C=C/c4ccc(C(F)(F)F)cc4)n3)cc2)CC1]

Step 1: 4-((1-(4-(4-methoxyphenyl)butyl)-1H-1,2,3-triazol-5-yl)methyl)thiomorpholine 1,1-dioxide

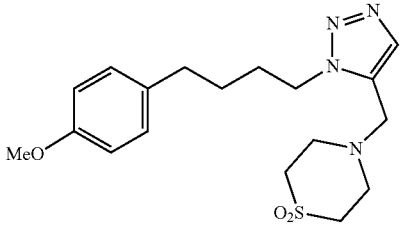 [SMILES: COc1ccc(CCCCn2nncc2CN2CCS(=O)(=O)CC2)cc1]

Chloro(pentamethylcyclopentadienyl)ruthenium(II) tetramer (0.039 g, 0.036 mmol) was added to a degassed solution of intermediate of step 2 compound 1 and 4-(prop-2-yn-1-yl)thiomorpholine 1,1-dioxide (0.169 g, 0.974 mmol) in DMF (6.50 ml) at rt. After 1 h the mixture was diluted with EA-water. The organic phase was separated and the aqueous extracted with EA. They were then combined, Na$_2$SO$_4$ dried, filtered and the solvent removed. It was absorbed on SiO$_2$ and purified on ISCO using a RediSep® column (DCM-MeOH—NH$_4$OH; 77.5-20-2.5) to give 0.160 g of a 1:1 mixture of the title compound with the starting alkyne.

Step 2: 4-((1-(4-(4-hydroxyphenyl)butyl)-1H-1,2,3-triazol-5-yl)methyl)thiomorpholine 1,1-dioxide

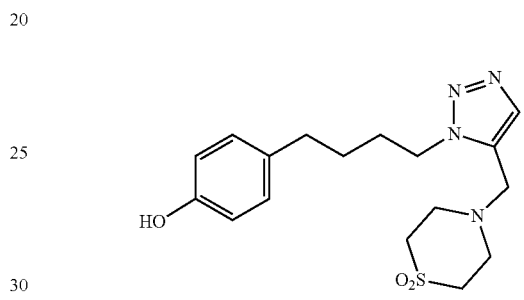

A mixture of the previous mixture in HBr (48% in water; 2.5 ml) was heated at 95° C. for 3.5 h. It was then diluted with toluene and the solvents were removed. The residue was taken in DCM and quenched with a NaHCO$_3$ solution. The organic phase was separated and the aqueous extracted with DCM. They were combined, Na$_2$SO$_4$, dried, filtered and the solvent removed. It was then absorbed on SiO2 and purified on ISCO using a RediSep® column (DCM/MeOH; 0-10%) to give 0.036 g of the title compound.

Step 3: (E)-4-((1-(4-(4-((2-(4-(trifluoromethyl)styryl)oxazol-4-yl)methoxy)phenyl)butyl)-1H-1,2,3-triazol-5-yl)methyl)thiomorpholine 1,1-dioxide

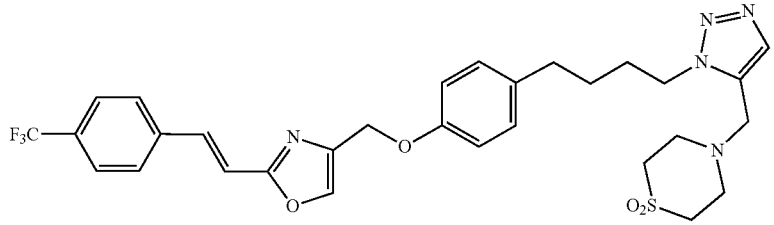 [SMILES: O=S1(=O)CCN(Cc2cnnn2CCCCc2ccc(OCc3coc(/C=C/c4ccc(C(F)(F)F)cc4)n3)cc2)CC1]

This compound was prepared in a similar fashion as compound 1 step 5 with the previous phenol and (E)-4-(chloromethyl)-2-(4-(trifluoromethyl)styryl)oxazole. ° H NMR (400 MHz, DMSO-d$_6$) b ppm 1.55 (quin, J=7.30 Hz, 2H) 1.80 (quin, J=7.34 Hz, 2H) 2.55 (t, J=7.63 Hz, 2H) 2.86 (br. s., 4H) 3.02-3.11 (m, 4H) 3.77 (s, 2H) 4.35 (t, J=7.24 Hz, 2H) 4.99 (s, 2H) 6.94 (d, J=8.61 Hz, 2H) 7.11 (d, J=8.61 Hz, 2H) 7.34 (d, J=16.43 Hz, 1H) 7.57-7.66 (d, 2H) 7.76 (d, J=8.22 Hz, 2H) 7.95 (d, J=8.22 Hz, 2H) 8.23 (s, 1H). LRMS+H$^+$: 616.1.

Compound 16: (E)-4-(1H-1,2,3-triazol-1-yl)-1-(4-((2-(4-(trifluoromethyl)styryl)oxazol-4-yl)methoxy)phenyl)butan-1-one

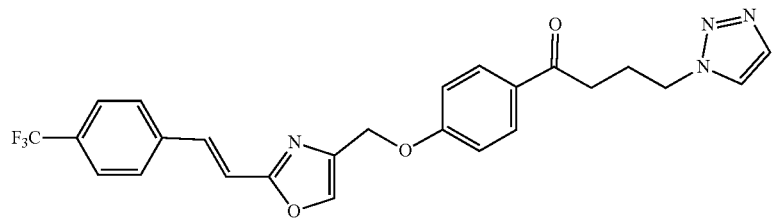 [SMILES: O=C(CCCn1ccnn1)c1ccc(OCc2coc(/C=C/c3ccc(C(F)(F)F)cc3)n2)cc1]

Step 1: 1-(4-methoxyphenyl)-4-(1H-1,2,3-triazol-1-yl)butan-1-one

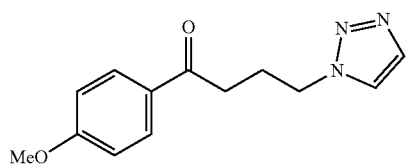 [SMILES: COc1ccc(C(=O)CCCn2ccnn2)cc1]

4-azido-1-(4-methoxyphenyl)butan-1-one (1.32 g, 6.02 mmol), prepared from International Patent Publication no. WO 2006/032453 in vinyl acetate (100 ml) was heated in the microwave for 14 h at 120° C. in three separate experiment and combined at the end of the experiments. The solvent was removed and the crude purified on ISCO using a RediSep® column (Hx-EA; 25-100%) to give 1.22 g of the title compound.

Step 2: 1-(4-hydroxyphenyl)-4-(1H-1,2,3-triazol-1-yl)butan-1-one

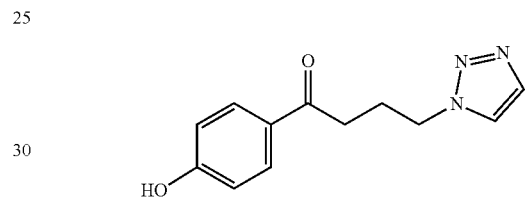

A mixture of the previous ketone (0.500 g, 2.039 mmol) in HBr 48% in water (5.0 ml, 92 mmol) was heated at 90° C. for 24 h. The solvent was removed and the residue diluted with EA. The solution was neutralized with a NaHCO₃ solution and acidified with a tartaric acid solution. The organic phase was separated and the aqueous was extracted 3 times with EA. The organic phases were combined, Na₂SO₄ dried, filtered and the solvent removed to give 0.25 g of the crude title compound.

Step 3: (E)-4-(1H-1,2,3-triazol-1-yl)-1-(4-((2-(4-(trifluoromethyl)styryl)oxazol-4-yl)methoxy)phenyl)butan-1-one

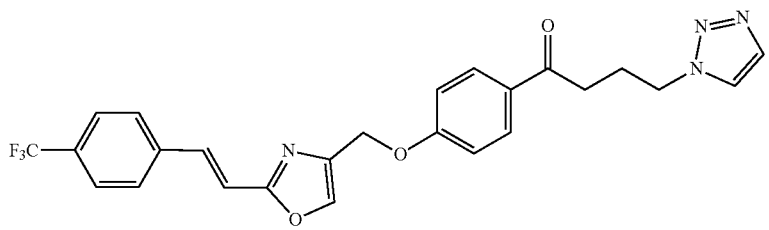 [SMILES: O=C(CCCn1ccnn1)c1ccc(OCc2coc(/C=C/c3ccc(C(F)(F)F)cc3)n2)cc1]

This compound was prepared in a similar fashion as compound 1 step 5 with the previous phenol and (E)-4-(chloromethyl)-2-(4-(trifluoromethyl)styryl)oxazole. $^1$H NMR (400 MHz, DMSO-$d_6$) δ ppm 2.15 (quin, J=7.00 Hz, 2H) 3.00 (t, J=7.04 Hz, 2H) 4.45 (t, J=7.04 Hz, 2H) 7.16 (d, J=8.61 Hz, 2H) 7.34 (d, J=16.43 Hz, 1H) 7.63 (d, J=16.82 Hz, 1H) 7.73 (s, 1H) 7.76 (d, J=8.22 Hz, 2H) 7.87-7.99 (m, 4H) 8.17 (s, 1H) 8.30 (s, 1H). LRMS+H$^+$:483.3.

Compound 17: (E)-4-(1H-1,2,3-triazol-1-yl)-1-(4-((2-(4-(trifluoromethyl)styryl)oxazol-4-yl)methoxy)phenyl)butan-1-ol

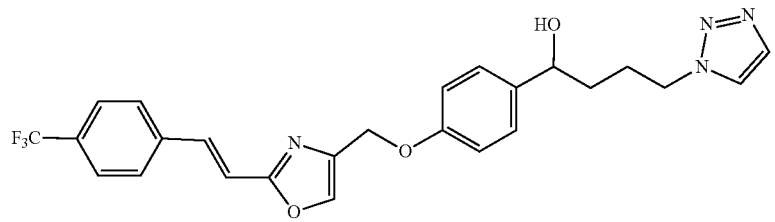 [SMILES: OC(CCCn1ccnn1)c1ccc(OCc2coc(/C=C/c3ccc(C(F)(F)F)cc3)n2)cc1]

The previous ketone (0.013 g, 0.027 mmol) in MeOH (1.5 ml) was heated in the microwave for 4 minutes at 140° C. to get the product in solution. Then at rt, NaBH$_4$ (0.005 mg, 0.132 µmol) was added. The mixture was quenched with HOAc and the solvent removed. Purification on ISCO using a RediSep® column (Hx-EA; 80-100%) gave 0.0044 g of the title compound. $^1$H NMR (400 MHz, DMSO-d$_6$) δ ppm 1.42-1.60 (m, 2H) 1.68-1.82 (m, 1H) 1.82-1.95 (m, 1H) 4.37 (t, J=7.04 Hz, 2H) 4.45-4.54 (m, 1H) 5.00 (s, 2H) 5.14 (d, J=4.70 Hz, 1H) 6.97 (d, J=9.00 Hz, 2H) 7.21 (d, J=8.61 Hz, 2H) 7.34 (d, J=16.43 Hz, 1H) 7.62 (d, J=16.83 Hz, 1H) 7.70 (s, 1H) 7.76 (d, J=8.22 Hz, 2H) 7.95 (d, J=8.22 Hz, 2H) 8.09 (s, 1H) 8.24 (s, 1H). HRMS+H$^+$: 485.1774.

Compound 18: (E)-4-(1H-1,2,3-triazol-1-yl)-1-(4-((2-(4-(trifluoromethoxy)styryl)oxazol-4-yl)methoxy)phenyl)butan-1-one

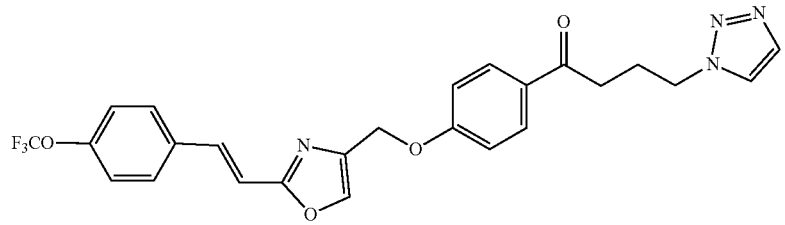 [SMILES: O=C(CCCn1ccnn1)c1ccc(OCc2coc(/C=C/c3ccc(OC(F)(F)F)cc3)n2)cc1]

This compound was synthesized as described in Example 1 (page 20) of International Patent Publication no. WO 2006/032453.

Compound 19: (E)-4-(1H-1,2,3-triazol-1-yl)-1-(4-((2-(4-(trifluoromethoxy)styryl)oxazol-4-yl)methoxy)phenyl)butan-1-ol

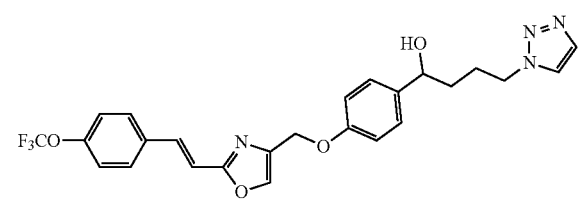 [SMILES: OC(CCCn1ccnn1)c1ccc(OCc2coc(/C=C/c3ccc(OC(F)(F)F)cc3)n2)cc1]

This compound was synthesized as described in Example 2 (page 22 and compound 22) of International Patent Publication no. WO 2006/032453. LRMS+H$^+$: 501.2.

Compound 20: (E)-1-(4-((2-(4-bromo-2-fluorostyryl)oxazol-4-yl)methoxy)phenyl)-4-(1H-1,2,3-triazol-1-yl)butan-1-one

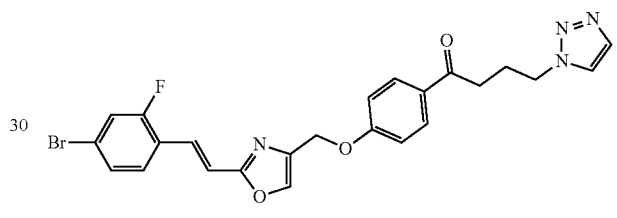

Step 1: (E)-3-(4-bromo-2-fluorophenyl)acrylamide

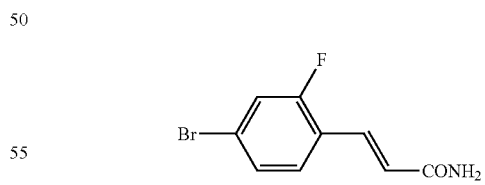

Oxalyl chloride (0.429 ml, 4.90 mmol) was added to a suspension of (E)-3-(4-bromo-2-fluorophenyl)acrylic acid (1 g, 4.08 mmol) in DCM (27.2 ml) at 0° C. and DMF (8.74 µl, 0.122 mmol) was added. The temperature was brought to rt and let go for 2 h. The solvent was removed and the residue taken in EA and the solvent was removed. It was taken again in EA and NH$_4$OH., (6.15 ml, 86 mmol) was added slowly. After stirring for 30 min it was diluted with EA and the organic phase separated. It was washed with brine, Na₂SO₄ dried, filtered and the solvent removed to give 0.88 g of the title compound.

Step 2: (E)-2-(4-bromo-2-fluorostyryl)-4-(chloromethyl)oxazole

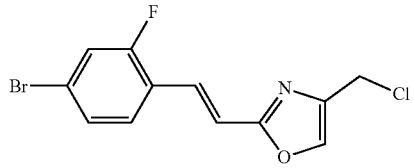 [SMILES: Fc1cc(Br)ccc1/C=C/c1nc(CCl)co1]

A mixture of (E)-3-(4-bromo-2-fluorophenyl)acrylamide (0.876 g, 3.59 mmol) and 1,3-dichloropropan-2-one (0.911 g, 7.18 mmol) in toluene (7.18 ml) was heated to reflux with a Dean-Stark for 24 h. The solvent was removed and the residue absorbed on SiO₂. Purification on ISCO using a RediSep® column (Hx-EA; 0-40%) gave 0.61 g of the title compound. ¹H NMR (400 MHz, CDCl₃) δ ppm 4.55 (d, J=0.78 Hz, 2H) 7.03 (d, J=16.82 Hz, 1H) 7.28-7.35 (m, 2H) 7.38-7.47 (m, 1H) 7.58 (d, J=16.82 Hz, 1H) 7.66 (s, 1H).

Step 3: (E)-1-(4-((2-(4-bromo-2-fluorostyryl)oxazol-4-yl)methoxy)phenyl)-4-(1H-1,2,3-triazol-1-yl)butan-1-one

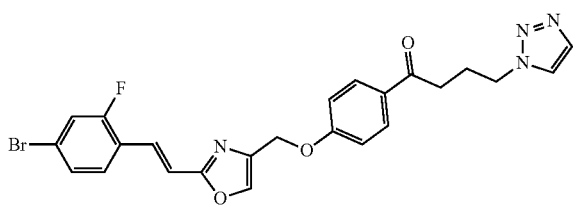 [SMILES: O=C(CCCn1ccnn1)c1ccc(OCc2coc(/C=C/c3ccc(Br)cc3F)n2)cc1]

This compound was prepared from the previous chloride and 1-(4-hydroxyphenyl)-4-(1H-1,2,3-triazol-1-yl)butan-1-one in a similar fashion as compound 1 step 5. ¹H NMR (400 MHz, DMSO-d₆) δ ppm 2.15 (quint, J=7.20, Hz, 2H) 3.00 (t, J=7.24 Hz, 2H) 4.45 (t, J=7.24 Hz, 2H) 5.14 (s, 2H) 7.15 (d, J=9.00 Hz, 2H) 7.27 (d, J=16.43 Hz, 1H) 7.45-7.55 (m, 2H) 7.66 (dd, J=10.56, 1.96 Hz, 1H) 7.73 (s, 1H) 7.85-7.91 (m, 1H) 7.92 (d, J=9.00 Hz, 2H) 8.17 (s, 1H) 8.29 (s, 1H). LRMS+H⁺: 511.1.

Compound 21: (E)-1-(4-((2-(4-bromo-2-fluorostyryl)oxazol-4-yl)methoxy)phenyl)-4-(1H-1,2,3-triazol-1-yl)butan-1-ol

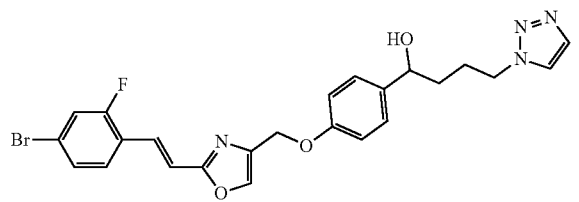 [SMILES: OC(CCCn1ccnn1)c1ccc(OCc2coc(/C=C/c3ccc(Br)cc3F)n2)cc1]

This compound was prepared in a similar fashion as compound 17. ¹H NMR (400 MHz, DMSO-d₆) δ ppm 1.42-1.62 (m, 2H) 1.68-1.81 (m, 1H) 1.81-1.94 (m, 1H) 4.37 (t, J=7.04 Hz, 2H) 4.46-4.53 (m, 1H) 4.99 (s, 2H) 5.14 (d, J=4.30 Hz, 1H) 6.97 (d, J=8.61 Hz, 2H) 7.21 (d, J=8.61 Hz, 2H) 7.27 (d, J=16.43 Hz, 1H) 7.49 (s, 2H) 7.66 (dd, J=10.56, 1.96 Hz, 1H) 7.69 (d, J=0.78 Hz, 1H) 7.88 (t, J=8.41 Hz, 1H) 8.09 (s, 1H) 8.23 (s, 1H). LRMS+H⁺: 515.0913.

Compound 22: (E)-1-(4-((2-(2-fluoro-4-(trifluoromethyl)styryl)oxazol-4-yl)methoxy)phenyl)-4-(1H-1,2,3-triazol-1-yl)butan-1-one

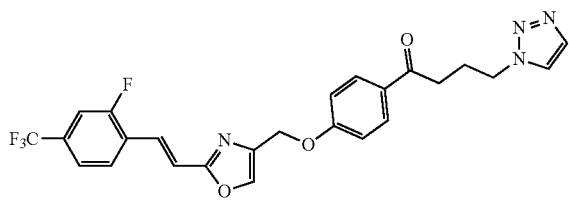 [SMILES: O=C(CCCn1ccnn1)c1ccc(OCc2coc(/C=C/c3ccc(C(F)(F)F)cc3F)n2)cc1]

This compound was prepared in a similar fashion as compound 20 with (E)-4-(chloromethyl)-2-(2-fluoro-4-(trifluoromethyl)styryl)oxazole (see compound 48). ¹H NMR (400 MHz, DMSO-d₆) δ ppm 2.15 (quin, J=7.00 Hz, 2H) 3.00 (t, J=7.04 Hz, 2H) 4.45 (t, J=7.04 Hz, 2H) 5.15 (s, 2H) 7.16 (d, J=9.00 Hz, 2H) 7.40 (d, J=16.82 Hz, 1H) 7.60 (d, J=16.43 Hz, 1H) 7.65 (d, J=8.61 Hz, 1H) 7.72 (s, 1H) 7.78 (d, J=10.96 Hz, 1H) 7.93 (d, J=8.61 Hz, 2H) 8.12-8.20 (m, 2H) 8.32 (s, 1H). LRMS+H⁺: 501.0.

Compound 23: (E)-1-(4-((2-(2-fluoro-4-(trifluoromethyl)styryl)oxazol-4-yl)methoxy)phenyl)-4-(1H-1,2,3-triazol-1-yl)butan-1-ol

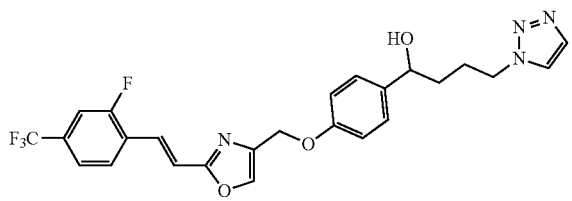 [SMILES: OC(CCCn1ccnn1)c1ccc(OCc2coc(/C=C/c3ccc(C(F)(F)F)cc3F)n2)cc1]

NaBH₄ (2.4 mg, 0.064 mmol) was added to a solution of (E)-1-(4-((2-(2-fluoro-4-(trifluoromethyl)styryl)oxazol-4-yl)methoxy)phenyl)-4-(1H-1,2,3-triazol-1-yl)butan-1-one (0.016 g, 0.032 mmol) in MeOH (2.0 ml)-THF (2.0 ml). After 30 min, the solvent was removed and the residue taken in EA and a NH₄Cl solution. The organic phase was separated, Na₂SO₄ dried, filtered and absorbed on SiO2. Purification on ISCO using a RediSep® column (Hx-EA; 40-100%) gave 0.010 g of the title compound. ¹H NMR (400 MHz, DMSO-d₆) δ ppm 1.44-1.58 (m, 2H) 1.68-1.81 (m, 1H) 1.82-1.95 (m, 1H) 4.37 (t, J=7.04 Hz, 2H) 4.45-4.54 (m, 1H) 5.01 (s, 2H) 5.14 (d, J=4.30 Hz, 1H) 6.97 (d, J=8.61 Hz, 2H) 7.18-7.25 (m, 2H) 7.39 (d, J=16.43 Hz, 1H) 7.59 (d, J=16.83 Hz, 1H) 7.65 (d, J=8.22 Hz, 1H) 7.69 (s, 1H) 7.78 (d, J=10.17 Hz, 1H) 8.09 (s, 1H) 8.16 (t, J=7.63 Hz, 1H) 8.27 (s, 1H). LRMS+H⁺-H₂O: 485.0.

Compound 24: (E)-1-(4-((2-(2-fluoro-4-nitrostyryl)oxazol-4-yl)methoxy)phenyl)-4-(1H-1,2,3-triazol-1-yl)butan-1-one

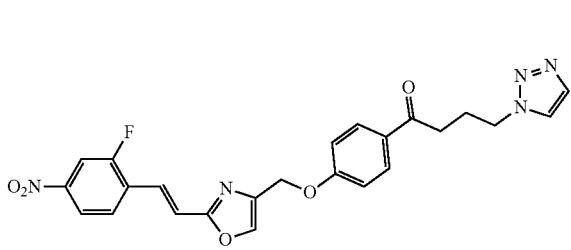 [SMILES: O=C(CCCn1ccnn1)c1ccc(OCc2coc(/C=C/c3ccc([N+](=O)[O-])cc3F)n2)cc1]

Step 1: (E)-ethyl 3-(2-fluoro-4-nitrophenyl)acrylate

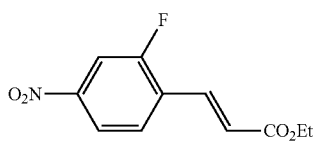

Ethyl 2-(tiphenylphosphoranylidene)acetate (4.12 g, 11.83 mmol) was added to a solution of 2-fluoro-4-nitrobenzaldehyde (1.00 g, 5.91 mmol) in THF (11.83 ml) and this was heated for 5 h. The solvent was removed and the residue diluted in toluene and purified on a short pad of SiO2 Hx-EA (9-1). This was then treated with 5% mol of iodine in 50 ml of toluene at 100° C. overnight. The solvent was removed to give 1.25 g of the title compound. $^1$H NMR (400 MHz, CDCl3d) δ ppm 1.37 (t, J=7.24 Hz, 3H) 4.31 (q, J=7.17 Hz, 2H) 6.68 (d, J=16.43 Hz, 1H) 7.68-7.76 (m, 1H) 7.69-7.76 (m, 1H) 8.00 (dd, J=9.98, 2.15 Hz, 1H) 8.07 (dd, J=8.41, 2.15 Hz, 1H).

Step 2: (E)-3-(2-fluoro-4-nitrophenyl)acrylamide

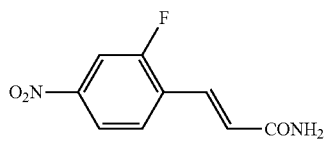

NaOH (3.92 ml, 7.84 mmol) was added to a solution of (E)-ethyl 3-(2-fluoro-4-nitrophenyl)acrylate (1.25 g, 5.23 mmol) in THF (10.45 ml) followed by a few drop of MeOH until one phase was obtained. It was heated to 50° C. for 1 h. Then, HCl 10% quenched, diluted with EA, extracted 4× with EA and washed the combined organic phase with brine. The organic phase was Na2SO4 dried, filtered, absorbed on SiO2 and the solvent removed. This crude carboxylic acid was then converted to the title compound according to the procedure for the compound 20 step 1. $^1$H NMR (400 MHz, DMSO-d$_6$) δ ppm 6.90 (d, J=16.04 Hz, 1H) 7.36 (br. s., 1H) 7.52 (d, J=16.04 Hz, 1H) 7.77 (br. s., 1H) 7.95 (t, J=8.02 Hz, 1H) 8.13 (dd, J=8.61, 1.96 Hz, 1H) 8.19 (dd, J=10.56, 2.35 Hz, 1H).

Step 3: (E)-4-(chloromethyl)-2-(2-fluoro-4-nitrostyryl)oxazole

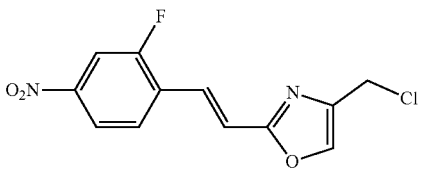 [SMILES: O=[N+]([O-])c1ccc(/C=C/c2nc(CCl)co2)c(F)c1]

A mixture of (E)-3-(2-fluoro-4-nitrophenyl)acrylamide (0.100 g, 0.47 mmol), and 1,3-dichloropropan-2-one (0.181 g, 1.42 mmol) in toluene (0.25 ml) was heated to 120° C. for 8 h. It was diluted with EA and absorbed on SiO2. Purification on ISCO using a RediSep® column (Hx-EA; 0-70%) gave 0.071 g of the title compound. $^1$H NMR (400 MHz, DMSO-d$_6$) δ ppm 4.73 (s, 2H) 7.47 (d, J=16.43 Hz, 1H) 7.62 (d, J=16.43 Hz, 1H) 8.09-8.15 (m, 2H) 8.18-8.29 (m, 3H).

Step 4: (E)-1-(4-((2-(2-fluoro-4-nitrostyryl)oxazol-4-yl)methoxy)phenyl)-4-(1H-1,2,3-triazol-1-yl)butan-1-one

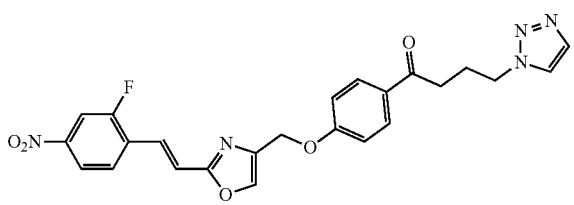 [SMILES: O=C(CCCn1ccnn1)c1ccc(OCc2coc(/C=C/c3ccc([N+](=O)[O-])cc3F)n2)cc1]

This compound was prepared in a similar fashion as compound 25 with (E)-4-(chloromethyl)-2-(2-fluoro-4-nitrostyryl)oxazole and 1-(4-hydroxyphenyl)-4-(1H-1,2,3-triazol-1-yl)butan-1-one. $^1$H NMR (400 MHz, DMSO-d$_6$) δ ppm 2.15 (quin, J=7.00 Hz, 2H) 3.00 (t, J=7.04 Hz, 2H) 4.45 (t, J=7.24 Hz, 2H) 5.16 (s, 2H) 7.16 (d, J=8.61 Hz, 2H) 7.48 (d, J=16.83 Hz, 1H) 7.62 (d, 0.1=16.43 Hz, 1H) 7.72 (s, 1H) 7.93 (d, J=8.61 Hz, 2H) 8.09-8.14 (d, 1H) 8.17 (s, 1H) 8.18-8.26 (d, 2H) 8.35 (s, 1H). HRMS+H$^+$:478.1503

Compound 25: (E)-1-(4-((2-(2-fluoro-4-nitrostyryl)oxazol-4-yl)methoxy)phenyl)-4-(1H-1,2,3-triazol-1-yl)butan-1-ol

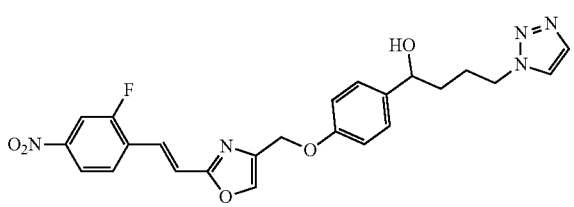 [SMILES: O=[N+]([O-])c1ccc(/C=C/c2nc(COc3ccc(C(O)CCCn4ccnn4)cc3)co2)c(F)c1]

This compound was prepared in a similar fashion as compound 23 from the previous ketone (no need of the microwave). $^1$H NMR (400 MHz, DMSO-d$_6$) δ ppm 1.44-1.58 (m, 2H) 1.68-1.81 (m, 1H) 1.82-1.95 (m, 1H) 4.37 (t, J=7.04 Hz, 2H) 4.45-4.54 (m, 1H) 5.01 (s, 2H) 5.14 (d, J=4.30 Hz, 1H) 6.97 (d, J=8.61 Hz, 2H) 7.18-7.25 (m, 2H)

7.39 (d, J=16.43 Hz, 1H) 7.59 (d, J=16.83 Hz, 1H) 7.65 (d, J=8.22 Hz, 1H) 7.69 (s, 1H) 7.78 (d, J=10.17 Hz, 1H) 8.09 (s, 1H) 8.16 (t, J=7.63 Hz, 1H) 8.27 (s, 1H). LRMS+H⁺ −H₂O: 462.0.

Compound 26: (E)-4-(4-(1H-1,2,3-triazol-1-yl)butyl)-N-((2-(4-(trifluoromethyl)styryl)oxazol-4-yl)methyl)aniline

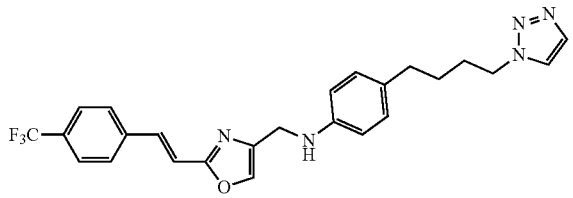 [SMILES: FC(F)(F)c1ccc(/C=C/c2nc(CNc3ccc(CCCCn4ccnn4)cc3)co2)cc1]

Step 1: 4-(4-nitrophenyl)but-3-yn-1-ol

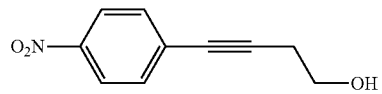

To a degassed solution of Ph₃P (0.130 g, 0.495 mmol), 1-bromo-4-nitrobenzene (5.00 g, 24.75 mmol) and 4-(4-nitrophenyl)but-3-yn-1-ol (4.55 g, 23.80 mmol, 96% yield) in Et₃N (103 ml)-toluene (165 ml) was added copper (1) iodide (0.236 g, 1.238 mmol) and PdCl₂(PPh₃)₂ (0.521 g, 0.743 mmol). The mixture was heated to 90° C. for 24 h at the end of which it was filtered and the solvent removed. The residue was diluted with a NH₄Cl solution and EA. The organic phase was separated and the aqueous phase extracted 2× with EA. The combined organic phases was washed with water, Na₂SO₄ dried, filtered and absorbed on SiO₂. Purification on ISCO using a RediSep® column (Hx-EA; 10-1000%) gave 4.55 g of the title compound.

Step 2: 4-(4-aminophenyl)butan-1-ol

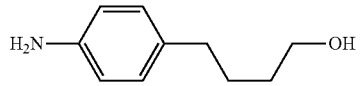

A mixture of 4-(4-nitrophenyl)but-3-yn-1-ol (1.00 g, 5.23 mmol) and PtO₂ (0.125 g) in EtOH (52 ml) was hydrogenated at 1 atmosphere and rt for 4 h. The reaction was filtered and the solvent removed to give 0.77 g of the title compound. ¹H NMR (400 MHz, DMSO-d₆) δ ppm 1.34-1.44 (m, 2H) 1.44-1.53 (m, 2H) 2.38 (t, J=7.43 Hz, 2H) 3.35-3.41 (m, 2H) 4.32 (t, J=5.09 Hz, 1H) 4.77 (s, 1H) 6.41-6.51 (m, 2H) 6.82 (m, J=8.22 Hz, 2H).

Step 3: (E)-4-(4-(((2-(4-(trifluoromethyl)styryl)oxazol-4-yl)methyl)amino)phenyl)butan-1-ol

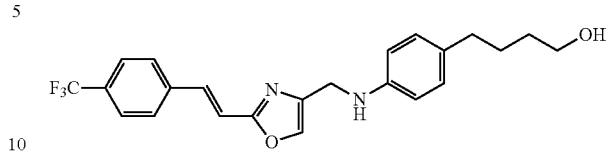

A mixture of (E)-4-(chloromethyl)-2-(4-(trifluoromethyl)styryl)oxazole (0.100 g, 0.348 mmol), 4-(4-aminophenyl)butan-1-ol (0.057 g, 0.348 mmol) and K₂CO₃ (0.072 g, 0.521 mmol) in DMF (0.695 ml) was heated at 75° C. overnight. It was diluted with a NH₄Cl solution and EA. The organic phase was separated and the aqueous extracted 2× with EA. They were combined and washed with water, Na₂SO₄ dried, filtered, absorbed on SiO₂. Purification on ISCO using a RediSep® column (Hx-EA; 10-100%) gave 0.077 g of the title compound. ¹H NMR (400 MHz, DMSO-d₆) δ ppm 1.35-1.44 (m, 2H) 1.45-1.55 (m, 2H) 2.40 (t, J=7.43 Hz, 2H) 3.38 (q, J=6.00 Hz, 2H) 4.14 (d, J=5.87 Hz, 2H) 4.32 (t, J=5.09 Hz, 1H) 5.81 (t, J=5.87 Hz, 1H) 6.56 (d, J=8.61 Hz, 2H) 6.90 (d, J=8.22 Hz, 2H) 7.30 (d, J=16.43 Hz, 1H) 7.56 (d, J=16.43 Hz, 1H) 7.75 (d, J=8.22 Hz, 2H) 7.90-8.00 (m, 3H).

Step 4: (E)-4-(4-azidobutyl)-N-((2-(4-(trifluoromethyl)styryl)oxazol-4-yl)methyl)aniline

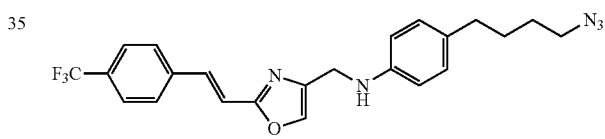

This compound was prepared in a similar fashion as compound 1 step 2 (method B) with (E)-4-(4-(((2-(4-(trifluoromethyl)styryl)oxazol-4-yl)methyl)amino)phenyl)butan-1-ol to give the title compound. LRMS+H⁺: 442.3

Step 5: (E)-4-(4-(1H-1,2,3-triazol-1-yl)butyl)-N-((2-(4-(trifluoromethyl)styryl)oxazol-4-yl)methyl)aniline

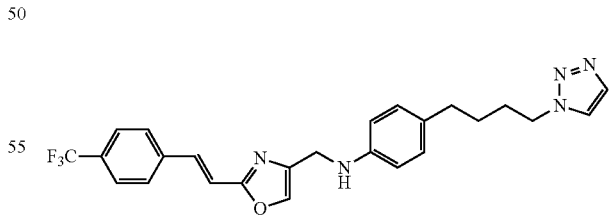

This compound was prepared in a similar fashion as compound 1 step 3 with vinyl acetate and (E)-4-(4-azidobutyl)-N-((2-(4-(trifluoromethyl)styryl)oxazol-4-yl)methyl)aniline. ¹H NMR (400 MHz, DMSO-d₆) δ ppm 1.51 (quin, J=7.63 Hz, 2H) 1.83 (quin, J=7.34 Hz, 2H) 2.57 (t, J=7.43 Hz, 2H) 4.40 (t, J=7.04 Hz, 2H) 7.11-7.22 (m, 3H) 7.37-7.49 (m, 3H) 7.61-7.78 (m, 6H) 8.09-8.16 (m, 1H) 8.76 (s, 1H) 10.07 (s, 1H). LRMS+H⁺: 468.1.

Compound 27: (E)-4-(4-(1H-1,2,3-triazol-1-yl) butyl)-N-((2-(4-bromo-2-fluorostyryl)oxazol-4-yl) methyl)aniline

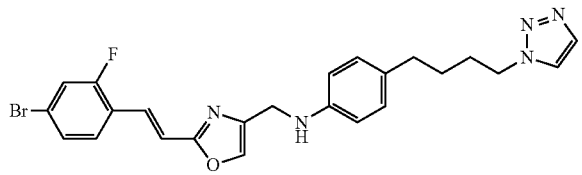 [SMILES: Fc1cc(Br)ccc1/C=C/c1nc(CNc2ccc(CCCCn3ccnn3)cc2)co1]

Step 1: (E)-4-(4-(((2-(4-bromo-2-fluorostyryl)oxazol-4-yl)methyl)amino)phenyl)butan-1-ol

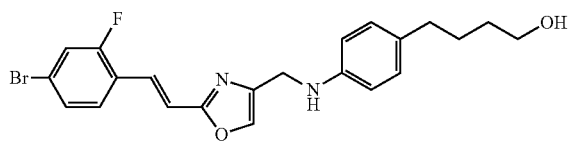 [SMILES: OCCCCc1ccc(NCc2coc(/C=C/c3ccc(Br)cc3F)n2)cc1]

This compound was prepared in a similar fashion as compound 26 step 3 with (E)-2-(4-bromo-2-fluorostyryl)-4-(chloromethyl)oxazole. $^1$H NMR (400 MHz, DMSO-$d_6$) δ ppm 1.34-1.45 (m, 2H) 1.45-1.55 (m, 2H) 2.40 (t, J=7.43 Hz, 2H) 3.38 (q, J=6.26 Hz, 2H) 4.14 (d, J=6.26 Hz, 2H) 4.32 (t, J=5.28 Hz, 1H) 5.82 (t, J=1.00 Hz, 1H) 6.56 (d, J=8.22 Hz, 2H) 6.89 (d, J=8.22 Hz, 2H) 7.23 (d, J=16.43 Hz, 1H) 7.42-7.52 (m, 2H) 7.65 (dd, J=10.56, 1.96 Hz, 1H) 7.86 (t, J=1.00 Hz, 1H) 7.96 (s, 1H).

Step 2: (E)-4-(4-azidobutyl)-N-((2-(4-bromo-2-fluorostyryl)oxazol-4-yl)methyl)aniline

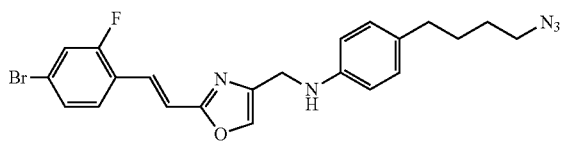 [SMILES: [N-]=[N+]=NCCCCc1ccc(NCc2coc(/C=C/c3ccc(Br)cc3F)n2)cc1]

This compound was prepared in a similar fashion as compound 1 step 2 (method B).

Step 3: (E)-4-(4-(1H-1,2,3-triazol-1-yl)butyl)-N-((2-(4-bromo-2-fluorostyryl)oxazol-4-yl)methyl)aniline

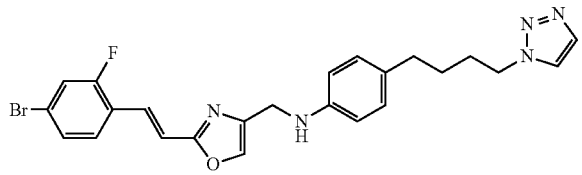 [SMILES: Fc1cc(Br)ccc1/C=C/c1nc(CNc2ccc(CCCCn3ccnn3)cc2)co1]

This compound was prepared in a similar fashion as compound 1 step 3 with (E)-4-(4-azidobutyl)-N-((2-(4-bromo-2-fluorostyryl)oxazol-4-yl)methyl)anilin. $^1$H NMR (400 MHz, DMSO-$d_6$) δ ppm 1.32-1.48 (m, 2H) 1.72-1.81 (m, 2H) 2.41 (t, J=7.63 Hz, 2H) 4.11 (d, J=5.87 Hz, 2H) 4.35 (t, J=7.04 Hz, 2H) 5.82 (t, J=5.87 Hz, 1H) 6.54 (d, J=8.22 Hz, 2H) 6.86 (d, J=8.61 Hz, 2H) 7.17-7.25 (m, 1H) 7.38-7.53 (m, 2H) 7.61-7.66 (m, 1H) 7.68 (s, 1H) 7.79-7.89 (m, 1H) 7.94 (s, 1H) 8.08 (s, 1H). LRMS+H$^+$: 496.1.

Compound 28: 4-((4-(4-(1H-1,2,3-triazol-1-yl)butyl) phenoxy)methyl)-2-(4-(trifluoromethyl)phenyl)oxazole

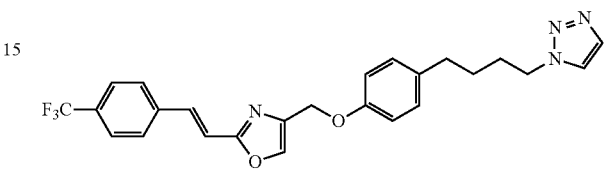

Step 1: 4-(chloromethyl)-2-(4-(trifluoromethyl)phenyl)oxazole

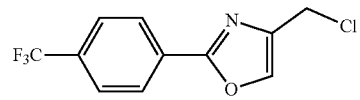

A mixture of 4-(trifluoromethyl)benzamide (1.00 g, 5.29 mmol) and 1,3-dichloropropan-2-one (1.343 g, 10.57 mmol) in toluene (15.11 ml) was heated to reflux 24 h. Added 0.5 eq more of 1,3-dichloropropan-2-one and let go overnight at reflux. The solvent was removed, the residue absorbed on SiO$_2$ and purified on ISCO using a RediSep® column (Hx-EA; 0-70%). This gave 0.62 g of the title compound. $^1$H NMR (400 MHz, CDCl$_3$) δ ppm 4.60 (d, =0.78 Hz, 2H) 7.74 (d, J=8.22 Hz, 2H) 7.76-7.78 (d, 1H) 8.17 (d, J=7.83 Hz, 2H).

Step 2: 4-((4-(4-(1H-1,2,3-triazol-1-yl)butyl)phenoxy)methyl)-2-(4-(trifluoromethyl)phenyl)oxazole

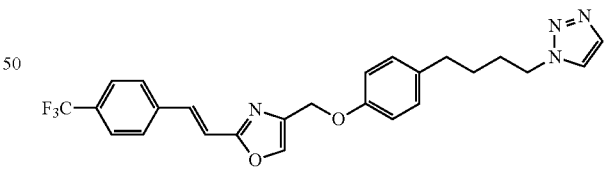

NaH 60% (6.6 mg, 0.16 mmol) was added to a solution of 4-(4-(1H-1,2,3-triazol-1-yl)butyl)phenol (0.030 g, 0.138 mmol) in DMF (0.690 ml) at 0° C. Bring to rt and 4-(chloromethyl)-2-(4-(trifluoromethyl)phenyl)oxazole (0.042 g, 0.159 mmol) was added and let go overnight. The reaction was quenched with a NH$_4$Cl solution and diluted with EA. The organic phase was separated and the aqueous phase extracted with EA. They were combined and washed with brine, dried over Na$_2$SO$_4$, filtered and absorbed on SiO$_2$. Purification on ISCO using a RediSep® column (Hx-EA; 0-100%) gave 0.042 g of the title compound. $^1$H NMR (400 MHz, CDCl$_3$) δ ppm 1.58-1.70 (m, 2H) 1.88-2.00 (m, 1H)

2.62 (t, J=7.43 Hz, 2H) 4.40 (t, J=7.24 Hz, 2H) 5.08 (d, J=0.78 Hz, 2H) 6.90-6.97 (m, 2H) 7.09 (d, J=8.61 Hz, 2H) 7.50 (d, J=0.78 Hz, 1H) 7.70-7.74 (m, 2H) 7.75 (s, 1H) 7.79 (s, 1H) 8.18 (d, J=8.22 Hz, 2H).

Compound 29: (E)-N-(4-(4-hydroxybutyl)phenyl)-2-(4-(trifluoromethyl)styryl)oxazole-4-carboxamide

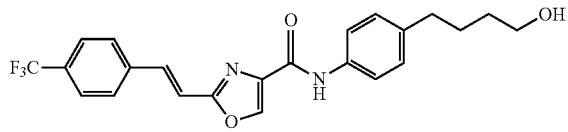 [SMILES: O=C(Nc1ccc(CCCCO)cc1)c1coc(/C=C/c2ccc(C(F)(F)F)cc2)n1]

To a mixture of (E)-2-(4-(trifluoromethyl)styryl)oxazole-4-carboxylic acid (0.263 g, 0.929 mmol) from PCT Int. Appl., 2004096796, triethylamine (0.25 ml, 1.85 mmol), 4-(4-aminophenyl)butan-1-ol (0.184 g, 1.11 mmol) and HOBT (0.171 g, 1.114 mmol) in DMF (1.857 ml) was added EDC (0.196 g, 1.022 mmol). After 5 h it was diluted with a NH$_4$Cl solution and EA. The organic phase was separated and the aqueous extracted 2× with EA. They were combined and washed with water, It was dried over Na$_2$SO$_4$, filtered and absorbed on SiO$_2$. Purification on ISCO using a RediSep® column (Hx-EA; 10-100%) gave 0.174 g of the title compound. $^1$H NMR (400 MHz, DMSO-d$_6$) δ ppm 1.36-1.48 (m, 2H) 1.52-1.63 (m, 2H) 2.55 (t, J=7.63 Hz, 2H) 3.37-3.44 (m, 2H) 4.36 (t, J=5.09 Hz, 1H) 7.17 (d, J=8.61 Hz, 2H) 7.36 (d, J=16.43 Hz, 1H) 7.70 (d, J=8.61 Hz, 2H) 7.74 (d, J=16.43 Hz, 1H) 7.79 (m, J=8.22 Hz, 2H) 7.98 (m, J=8.22 Hz, 2H) 8.81 (s, 1H) 10.08 (s, 1H).

Compound 30: (E)-N-(4-(4-(1H-1,2,3-triazol-1-yl)butyl)phenyl)-2-(4-(trifluoromethyl)styryl)oxazole-4-carboxamide

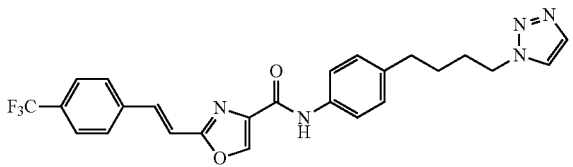 [SMILES: O=C(Nc1ccc(CCCCn2ccnn2)cc1)c1coc(/C=C/c2ccc(C(F)(F)F)cc2)n1]

Step 1: (E)-N-(4-(4-azidobutyl)phenyl)-2-(4-(trifluoromethyl)styryl)oxazole-4-carboxamide

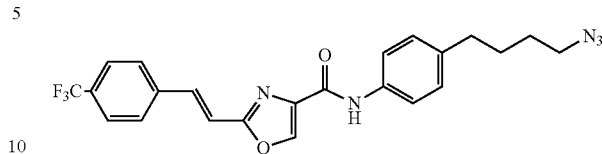

This compound was prepared according to Method B of compound 1 step 2 and (E)-N-(4-(4-hydroxybutyl)phenyl)-2-(4-(trifluoromethyl)styryl)oxazole-4-carboxamide. $^1$H NMR (400 MHz, DMSO-d6) δ ppm 1.43-1.68 (m, 4H) 2.58 (t, J=7.24 Hz, 2H) 3.35 (t, J=6.65 Hz, 2H) 7.18 (d, J=8.22 Hz, 2H) 7.36 (d, J=16.43 Hz, 1H) 7.69-7.77 (m, 3H) 7.80 (m, J=8.22 Hz, 2H) 7.98 (m, J=8.22 Hz, 2H) 8.82 (s, 1H) 10.09 (s, 1H).

Step 2: (E)-N-(4-(4-(1H-1,2,3-triazol-1-yl)butyl)phenyl)-2-(4-(trifluoromethyl)styryl)oxazole-4-carboxamide

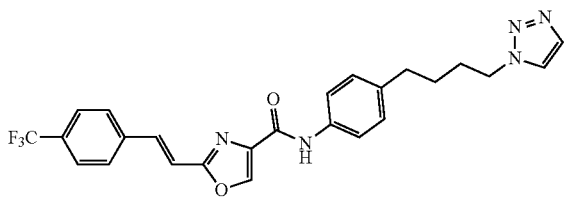 [SMILES: O=C(Nc1ccc(CCCCn2ccnn2)cc1)c1coc(/C=C/c2ccc(C(F)(F)F)cc2)n1]

This compound was prepared according to the procedure described for compound 1 step 3 with the previous intermediate. $^1$H NMR (400 MHz, DMSO-d$_6$) δ ppm 1.51 (quin, J=7.40 Hz, 2H) 1.83 (quin, J=7.34 Hz, 1H) 2.57 (t, J=7.63 Hz, 2H) 4.40 (t, J=6.85 Hz, 2H) 7.15 (d, J=8.22 Hz, 2H) 7.36 (d, J=16.43 Hz, 1H) 7.67-7.77 (m, 4H) 7.79 (d, J=8.61 Hz, 2H) 7.98 (d, J=8.22 Hz, 2H) 8.12 (s, 1H) 8.81 (s, 1H) 10.08 (s, 1H). LRMS+H$^+$: 482.1.

Compound 31: (E)-5-(dimethylamino)-N-(2-(1-(4-(4-((2-(4-(trifluoromethyl)styryl)oxazol-4-yl)methoxy)phenyl)butyl)-1H-1,2,3-triazol-4-yl)ethyl)naphthalene-1-sulfonamide

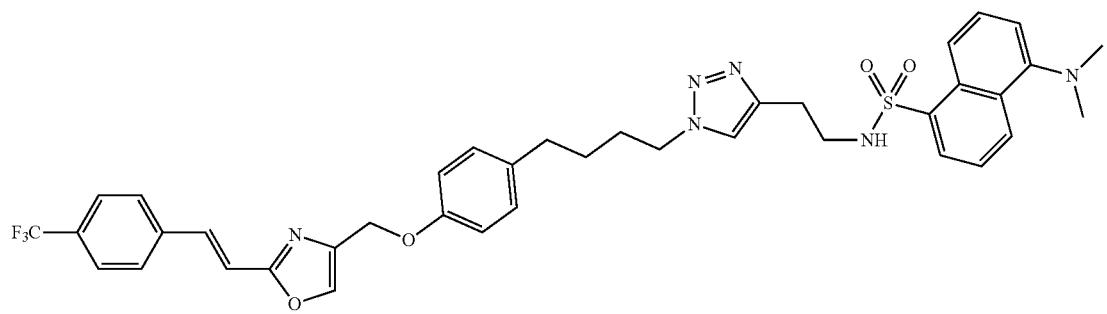 [SMILES: CN(C)c1cccc2c(S(=O)(=O)NCCc3cn(CCCCc4ccc(OCc5coc(/C=C/c6ccc(C(F)(F)F)cc6)n5)cc4)nn3)cccc12]

123

Step 1: N-(but-3-yn-1-yl)-5-(dimethylamino)naphthalene-1-sulfonamide

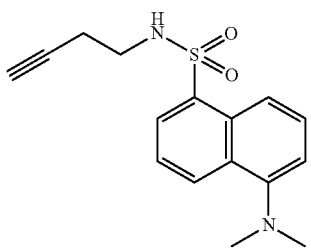 [SMILES: C#CCCNS(=O)(=O)c1cccc2c(N(C)C)cccc12]

MeOH (0.013 ml, 0.315 mmol) was added to a mixture of but-3-yn-1-amine hydrochloride (0.075 g, 0.710 mmol), triethylamine (1.0 ml, 7.14 mmol) and 5-(dimethylamino)naphthalene-1-sulfonyl chloride (0.085 g, 0.315 mmol) in THF (2.5 ml).

After 5 min it was diluted with EA-water and the organic phase was separated and washed with water. It was then dried over $Na_2SO_4$, filtered and the solvent removed. Purification on ISCO using a RediSep® column (Hx-EA; 0-60%) gave 0.055 g of the title compound. LRMS+H$^+$: 303.1.

Step 2: (E)-5-(dimethylamino)-N-(2-(1-(4-(4-((2-(4-(trifluoromethyl)styryl)oxazol-4-yl)methoxy)phenyl)buy)-1H-1,2,3-triazol-4-yl)ethyl)naphthalene-1-sulfonamide

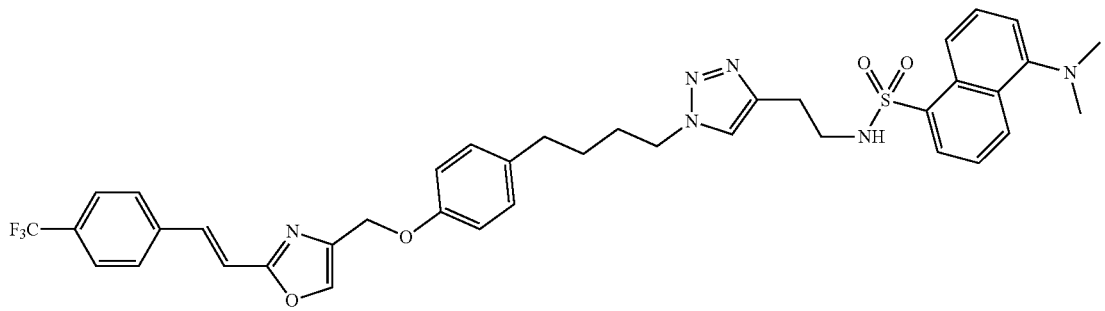 [SMILES: CN(C)c1cccc2c(S(=O)(=O)NCCc3cn(CCCCc4ccc(OCc5coc(/C=C/c6ccc(C(F)(F)F)cc6)n5)cc4)nn3)cccc12]

This compound was prepared in a similar fashion as compound 8 with (E)-4((4-(4-azidobutyl)phenoxy)methyl)-2-(4-(trifluoromethyl)styryl)oxazole and the previous intermediate. $^1$H NMR (400 MHz, DMSO-d$_6$) δ ppm 1.45 (quin, J=7.20 Hz, 2H) 1.71 (quin, J=7.34 Hz, 2H) 2.68 (t, J=7.43 Hz, 2H) 3.04 (q, J=6.70 Hz, 2H) 4.22 (t, J=7.04 Hz, 2H) 4.98 (s, 2H) 6.93 (d, J=8.61 Hz, 2H) 7.08 (d, J=8.61 Hz, 2H) 7.24 (d, J=7.43 Hz, 1H) 7.34 (d, J=16.43 Hz, 1H) 7.53-7.64 (m, 3H) 7.67 (s, 1H) 7.76 (d, J=8.61 Hz, 2H) 7.95 (d, J=8.22 Hz, 2H) 8.05 (t, J=5.67 Hz, 1H) 8.10 (dd, J=7.43, 1.17 Hz, 1H) 8.23 (s, 1H) 8.27 (d, J=8.61 Hz, 1H) 8.45 (d, J=8.61 Hz, 1H). LRMS+H$^+$: 745.2.

124

Compound 32: (E)-4-((4-(4-(1H-1,2,3-triazol-1-yl)butyl)phenoxy)methyl)-2-(4-methoxystyryl)oxazole

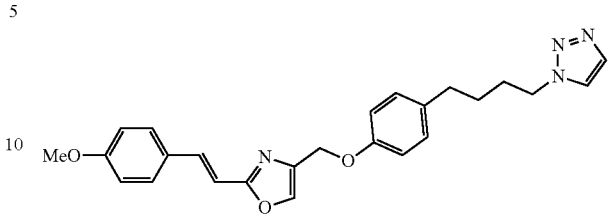

Step 1: (E)-4-(chloromethyl)-2-(4-methoxystyryl)oxazole

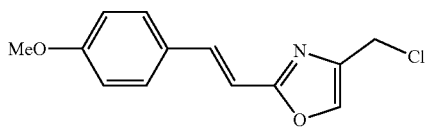 [SMILES: COc1ccc(/C=C/c2nc(CCl)co2)cc1]

(E)-3-(4-methoxyphenyl)acrylamide, prepared from the corresponding carboxylic acid according to compound 3 step 1, (359 mg, 2,026 mmol) and 1,3-dichloropropan-2-one (514 mg, 4.05 mmol) in toluene (6.2 ml) was heated at 145° C. with a Dean-Stark for 17 h. The mixture was concentrated under reduced pressure and the residue was absorbed on silica gel and purified on ISCO using a RediSep® column (Hx-EA; 0-35%) to give 420 mg of the title compound. $^1$H NMR (400 MHz, CDCl$_3$) δ ppm 3.85 (s, 3H) 4.54 (d, J=0.78 Hz, 2H) 6.79 (d, J=16.43 Hz, 1H) 6.90-6.95 (m, 2H) 7.45-7.53 (m, 3H) 7.61 (s, 1H)

Step 2: (E)-4-((4-(4-(1H-1,2,3-triazol-1-yl)butyl)phenoxy)methyl)-2-(4-methoxystyryl)oxazole

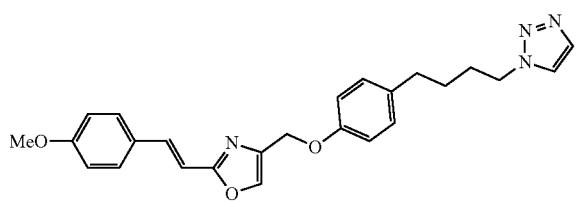 [SMILES: COc1ccc(/C=C/c2nc(COc3ccc(CCCCn4ccnn4)cc3)co2)cc1]

A mixture of (E)-4-(chloromethyl)-2-(4-methoxystyryl)oxazole (100 mg, 0.400 mmol), 4-(4-(1H-1,2,3-triazol-1-yl)butyl)phenol (96 mg, 0.441 mmol) and K$_2$CO$_3$ (60.9 mg, 0.441 mmol) in DMF (653 μl, 8.43 mmol) was heated at 75° C. for 3 hrs. It was cooled to rt and the compound precipitated. It was heated to obtain a solution and MeOH (653 μl, 16.14 mmol) and water (1088 μl, 60.4 mmol) were added. Cooled to 20° C. and stirred for 45 min. The solids were collected on Buchner and the cake was washed with water (2×1 mL) and dried at 35° C. to give 0.144 g of the title compound. $^1$H NMR (400 MHz, DMSO-d6) δ ppm 1.40-1.54 (m, 2H) 1.81 (quin, J=7.34 Hz, 2H) 2.52-2.57 (m, 2H) 3.79 (s, 3H) 4.39 (t, J=7.04 Hz, 2H) 4.95 (s, 2H) 6.89-7.04 (m, 5H) 7.06-7.13 (m, 2H) 7.47 (d, J=16.43 Hz, 1H) 7.62-7.72 (m, 3H) 8.09-8.17 (m, 2H). LRMS+H): 431.1.

Compound 33: (E)-4-((4-(4-(1H-1,2,3-triazol-1-yl)butyl)phenoxy)methyl)-2-(4-bromostyryl)oxazole

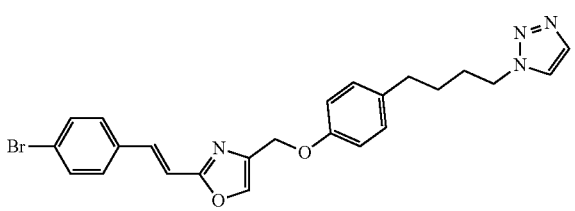

Step 1: (E)-2-(4-bromostyryl)-4-(chloromethyl)oxazole

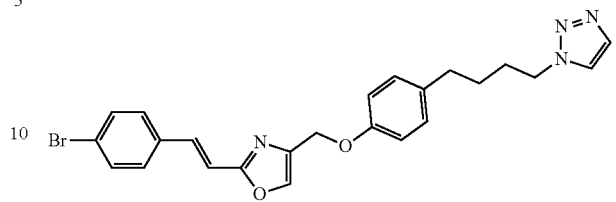

(E)-3-(4-bromophenyl)acrylamide prepared from the corresponding carboxylic acid according to compound 3 step 1 and 1,3-dichloropropan-2-one gave the title compound according to compound 32 step 1. $^1$H NMR (400 MHz, CDCl$_3$) δ ppm 4.54 (d, J=0.78 Hz, 2H) 6.91 (d, J=16.04 Hz, 1H) 7.39 (m, J=8.61 Hz, 2H) 7.48 (d, J=16.43 Hz, 1H) 7.53 (m, J=8.61 Hz, 2H) 7.64 (s, 1H).

Step 2: (E)-4-((4-(4-(1H-1,2,3-triazol-1-yl)butyl)phenoxy)methyl)-2-(4-bromostyryl)oxazole (E)-2-(4-bromostyryl)-4-(chloromethyl)oxazole was reacted with 4-(4-(1H-1,2,3-triazol-1-yl)butyl)phenol according to the procedure for compound 1 step 5. $^1$H NMR (400 MHz, DMSO-d$_6$) δ ppm 1.48 (quin, J=7.63 Hz, 2H) 1.81 (quin, J=7.34 Hz, 2H) 2.52-2.58 (m, 2H) 4.39 (t, J=7.04 Hz, 2H) 4.97 (s, 2H) 6.93 (d, J=8.61 Hz, 2H) 7.09 (d, J=8.61 Hz, 2H) 7.21 (d, J=16.43 Hz, 1H) 7.51 (d, J=16.43 Hz, 1H) 7.57-7.65 (m, 2H) 7.69 (d, J=8.61 Hz, 3H) 8.11 (d, J=0.78 Hz, 1H) 8.20 (s, 1H). HRMS+H$^+$: 481.1037.

Compound 34: (E)-4-(4-((2-(4-(trifluoromethyl)styryl)oxazol-4-yl)methoxy)phenyl)butyl diethylcarbamate

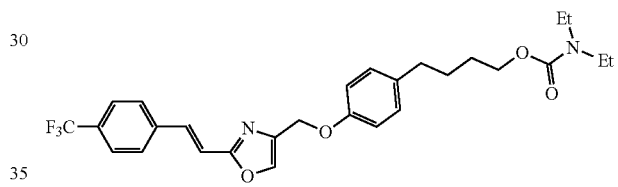

Diethylcarbamic chloride (6.8 μl, 0.054 mmol) was added to a suspension of (E)-4-(4-((2-(4-(trifluoromethyl)styryl)oxazol-4-yl)methoxy)phenyl)butan-1-ol (0.015 g, 0.036 mmol) in pyridine (0.012 ml) and the solution was heated 8 h at 100° C. The solvent was removed and the residue purified on ISCO using a RediSep® column (DCM-MeOH; 0-20%) to give 0.012 g of the title compound. $^1$H NMR (400 MHz, DMSO-d$_6$) δ ppm 1.03 (t, J=7.04 Hz, 6H) 1.46-1.65 (m, 4H) 2.51-2.58 (m, 2H) 3.19 (q, J=7.04 Hz, 4H) 3.99 (t, J=6.06 Hz, 2H) 4.99 (s, 2H) 6.95 (d, J=8.61 Hz, 2H) 7.12 (d, J=8.61 Hz, 2H) 7.34 (d, J=16.43 Hz, 1H) 7.62 (d, J=16.43 Hz, 1H) 7.76 (d, J=8.22 Hz, 2H) 7.95 (d, J=8.22 Hz, 2H) 8.24 (s, 1H). LRMS+H$^+$: 517.2.

Compound 35: (E)-4-(4-((2-(4-(trifluoromethyl)styryl)oxazol-4-yl)methoxy)phenyl)butyl morpholine-4-carboxylate

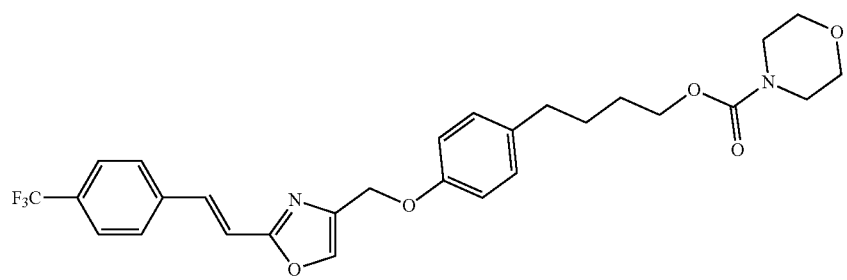 [SMILES: O=C(OCCCCc1ccc(OCc2coc(/C=C/c3ccc(C(F)(F)F)cc3)n2)cc1)N1CCOCC1]

This compound was prepared in a similar fashion as compound 34 with morpholine-4-carbonyl chloride. ¹H NMR (400 MHz, DMSO-d₆) δ ppm 1.43-1.64 (m, 4H) 2.51-2.57 (m, 2H) 3.53 (t, J=4.89 Hz, 4H) 3.95-4.04 (m, 2H) 4.99 (s, 2H) 6.95 (d, J=8.61 Hz, 2H) 7.12 (d, J=8.22 Hz, 2H) 7.34 (d, J=16.43 Hz, 1H) 7.62 (d, J=16.43 Hz, 1H) 7.76 (d, J=8.22 Hz, 2H) 7.95 (d, J=7.83 Hz, 2H). LRMS+H⁺: 531.2.

Compound 36: (E)-4-(4-((2-(4-(trifluoromethyl)styryl)oxazol-4-yl)methoxy)phenyl)butyl dimethylcarbamate

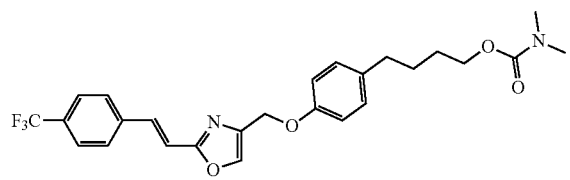 [SMILES: CN(C)C(=O)OCCCCc1ccc(OCc2coc(/C=C/c3ccc(C(F)(F)F)cc3)n2)cc1]

This compound was prepared in a similar fashion as compound 34 with dimethylcarbamic chloride. ¹H NMR (400 MHz, DMSO-d₆) δ ppm ppm 1.47-1.64 (m, 4H) 2.51-2.57 (m, 2H) 2.81 (br. s., 6H) 3.93-4.00 (m, 2H) 4.99 (s, 2H) 6.95 (d, J=8.61 Hz, 2H) 7.12 (d, J=8.61 Hz, 2H) 7.34 (d, J=16.43 Hz, 1H) 7.62 (d, J=16.43 Hz, 1H) 7.76 (d, J=8.61 Hz, 2H) 7.95 (d, J=8.22 Hz, 2H) 8.24 (s, 1H). LRMS+H⁺: 489.2.

Compounds 37 to 48

The following compounds (37-48) were prepared in three steps according to the following procedure. Step 1: the acrylamide is prepared from the corresponding carboxylic acid according to the procedure of compound 3 step 1; the chloromethyl oxazole is prepared from the corresponding acrylamide according to the procedure of compound 3 step 2 (or it could be prepared without solvent at 130° C. until completion). The last step is done with 4-(4-(1H-1,2,3-triazol-1-yl)butyl)phenol and the corresponding chloromethyl oxazole according to Compound 1 step 5.

Compound 37

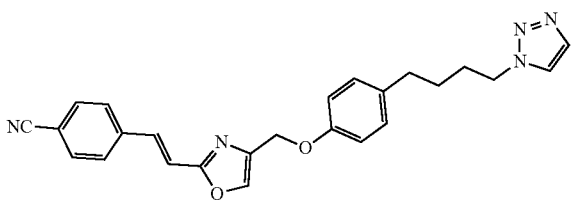

Compound 38

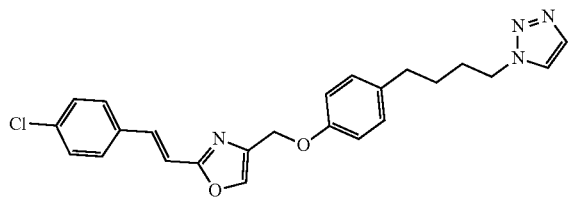

Compound 39

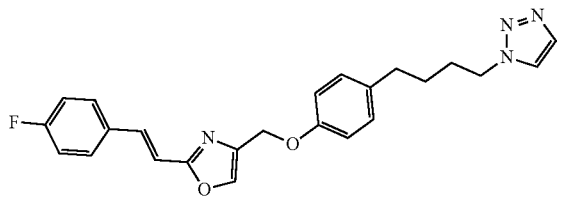

Compound 40

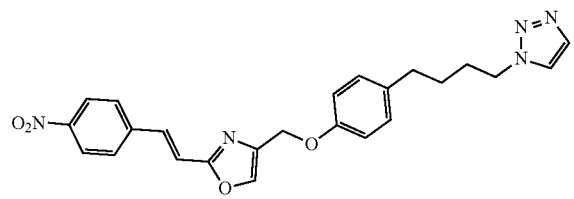

Compound 41

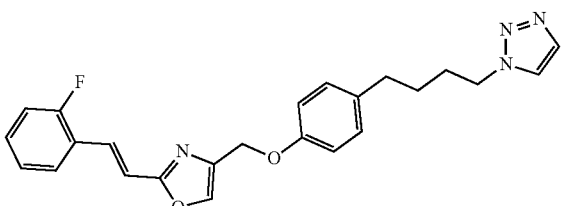

Compound 42

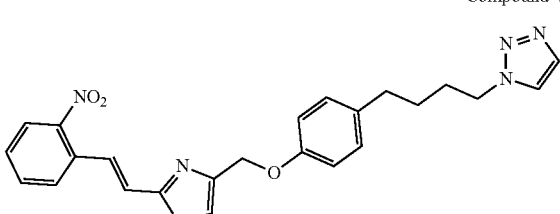

Compound 43

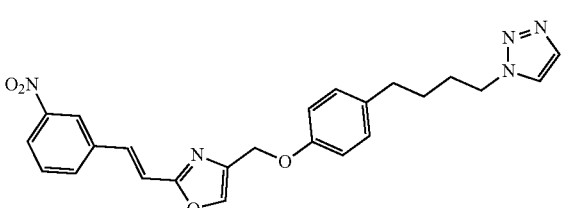

Compound 44

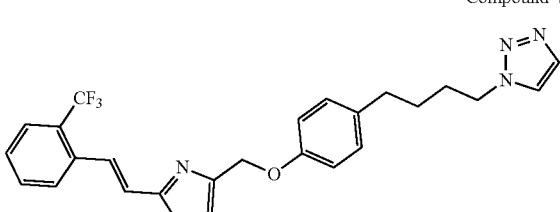

Compound 45

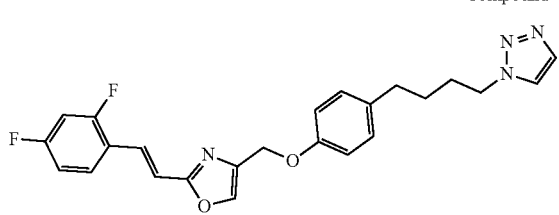

-continued

Compound 46

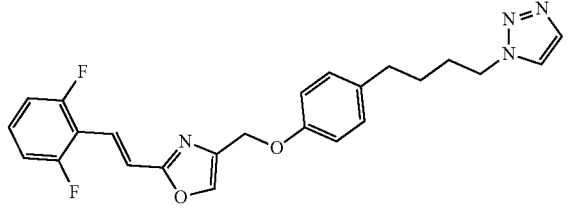

Compound 47

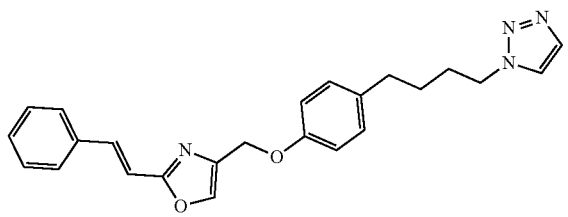

Compound 48

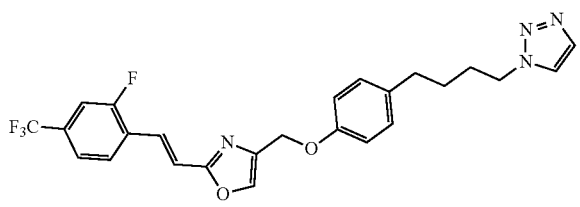

Compound 37: (E)-4-(2-(4-((4-(4-(1H-1,2,3-triazol-1-yl)butyl)phenoxy)methyl)oxazol-2-yl)vinyl)benzonitrile

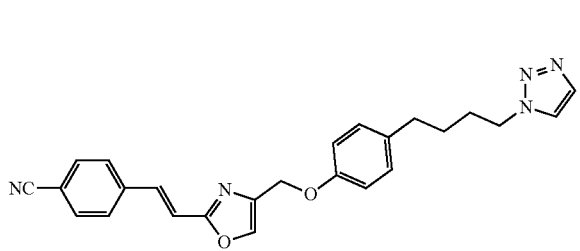 [SMILES: N#Cc1ccc(/C=C/c2nc(COc3ccc(CCCCn4ccnn4)cc3)co2)cc1]

$^1$H NMR (400 MHz, DMSO-$d_6$) δ ppm 1.48 (quin, J=7.63 Hz, 2H) 1.81 (quin, J=7.24 Hz, 2H) 2.52-2.57 (m, 2H) 4.39 (t, J=7.04 Hz, 2H) 4.98 (s, 2H) 6.94 (m, J=8.61 Hz, 2H) 7.09 (m, J=8.61 Hz, 2H) 7.37 (d, J=16.43 Hz, 1H) 7.60 (d, J=16.43 Hz, 1H) 7.70 (s, 1H) 7.87 (d, J=8.61 Hz, 2H) 7.93 (d, J=8.22 Hz, 2H) 8.11 (s, 1H) 8.24 (s, 1H). LRMS+H$^+$: 426.2.

Compound 38: (E)-4-((4-(4-(1H-1,2,3-triazol-1-yl)butyl)phenoxy)methyl)-2-(4-chlorostyryl)oxazole

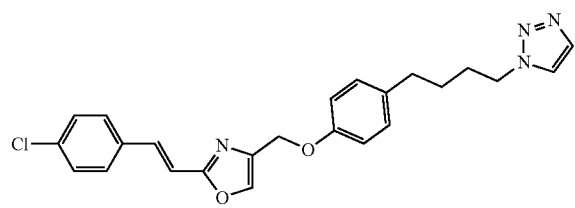 [SMILES: Clc1ccc(/C=C/c2nc(COc3ccc(CCCCn4ccnn4)cc3)co2)cc1]

$^1$H NMR (400 MHz, DMSO-$d_6$) δ ppm 1.48 (quin, J=7.63 Hz, 2H) 1.81 (quin, J=7.34 Hz, 2H) 2.52-2.57 (m, 2H) 4.39 (t, J=7.04 Hz, 2H) 4.97 (s, 2H) 6.93 (m, J=8.61 Hz, 2H) 7.09 (d, J=8.61 Hz, 2H) 7.19 (d, J=16.43 Hz, 1H) 7.47 (d, J=8.61 Hz, 2H) 7.53 (d, J=16.43 Hz, 1H) 7.68-7.72 (m, 1H) 7.76 (d, J=8.61 Hz, 2H) 8.11 (s, 1H) 8.19 (s, 1H). LRMS+H$^+$: 435.1.

Compound 39: (E)-4-((4-(4-(1H-1,2,3-triazol-1-yl)butyl)phenoxy)methyl)-2-(4-fluorostyryl)oxazole

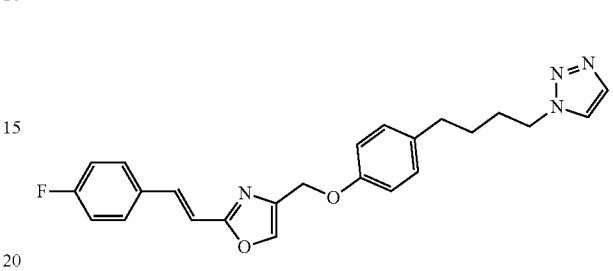

$^1$H NMR (400 MHz, DMSO-$d_6$) δ ppm 1.48 (quin, J=7.63 Hz, 2H) 1.81 (quin, J=7.34 Hz, 2H) 2.52-2.57 (m, 2H) 4.39 (t, J=7.04 Hz, 2H) 4.96 (s, 2H) 6.93 (d, J=8.22 Hz, 2H) 7.05-7.18 (m, 3H) 7.25 (t, J=8.80 Hz, 2H) 7.53 (d, J=16.43 Hz, 1H) 7.70 (s, 1H) 7.79 (dd, J=8.61, 5.87 Hz, 2H) 8.11 (s, 1H) 8.18 (s, 1H). LRMS+H$^+$: 419.1.

Compound 40: (E)-4-((4-(4-(1H-1,2,3-triazol-1-yl)butyl)phenoxy)methyl)-2-(4-nitrostyryl)oxazole

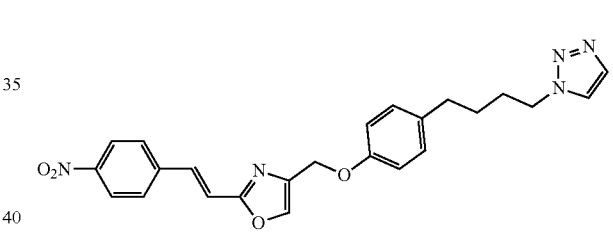

$^1$H NMR (400 MHz, DMSO-$d_6$) δ ppm 1.48 (quin, J=7.63 Hz, 2H) 1.81 (quin, J=7.34 Hz, 2H) 2.52-2.58 (m, 2H) 4.39 (t, J=7.04 Hz, 2H) 4.99 (s, 2H) 6.94 (d, J=8.61 Hz, 2H) 7.09 (d, J=8.61 Hz, 2H) 7.42 (d, J=16.82 Hz, 1H) 7.66 (d, J=16.43 Hz, 1H) 7.70 (s, 1H) 8.01 (d, J=9.00 Hz, 2H) 8.11 (s, 1H) 8.20-8.31 (m, 3H). LRMS+H$^+$: 446.1.

Compound 41: (E)-4-((4-(4-(1H-1,2,3-triazol-1-yl)butyl)phenoxy)methyl)-2-(2-fluorostyryl)oxazole

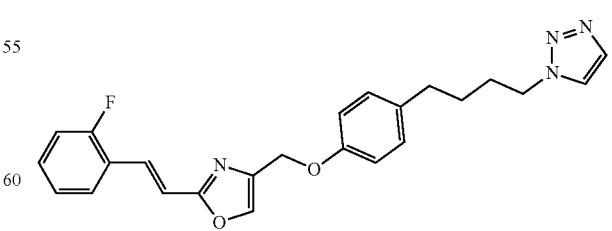

$^1$H NMR (400 MHz, DMSO-$d_6$) δ ppm 1.48 (quin, J=7.63 Hz, 2H) 1.81 (quin, J=7.24 Hz, 2H) 2.51-2.57 (m, 2H) 4.39 (t, J=7.04 Hz, 2H) 4.98 (s, 2H) 6.94 (d, J=8.61 Hz, 2H) 7.09 (d, J=8.61 Hz, 2H) 7.23 (d, J=16.82 Hz, 1H) 7.26-7.33 (m, 2H) 7.39-7.48 (m, 1H) 7.58 (d, J=16.82 Hz, 1H) 7.70 (s, 1H) 7.91 (t, J=7.83 Hz, 1H) 8.11 (s, 1H) 8.21 (s, 1H). LRMS+H⁺: 419.1.

Compound 42: (E)-4-((4-(4-(1H-1,2,3-triazol-1-yl)butyl)phenoxy)methyl)-2-(2-nitrostyryl)oxazole

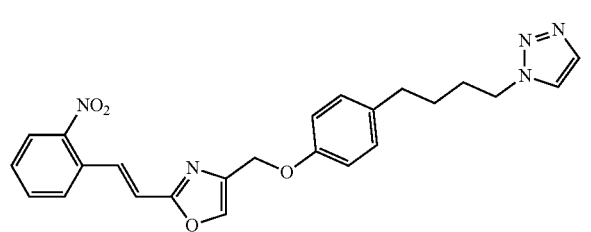 [SMILES: O=[N+]([O-])c1ccccc1/C=C/c1nc(COc2ccc(CCCCn3ccnn3)cc2)co1]

¹H NMR (400 MHz, DMSO-d₆) δ ppm 1.48 (quin, J=7.63 Hz, 2H) 1.81 (quin, J=7.34 Hz, 2H) 2.52-2.58 (m, 2H) 4.39 (t, J=7.04 Hz, 2H) 4.99 (s, 2H) 6.94 (d, J=8.61 Hz, 2H) 7.09 (d, J=8.22 Hz, 2H) 7.24 (d, J=16.04 Hz, 1H) 7.59-7.67 (m, 1H) 7.70 (s, 1H) 7.74-7.83 (m, 2H) 8.06 (d, J=8.22 Hz, 2H) 8.11 (s, 1H) 8.25 (s, 1H). LRMS+H⁺: 446.1.

Compound 43: (E)-4-((4-(4-(1H-1,2,3-triazol-1-yl)butyl)phenoxy)methyl)-2-(3-nitrostyryl)oxazole

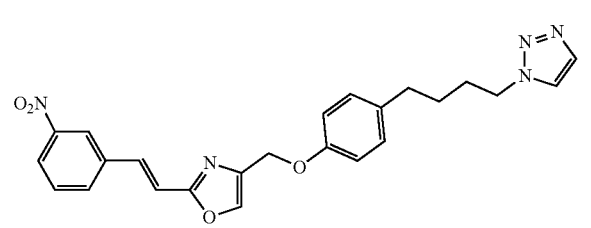 [SMILES: O=[N+]([O-])c1cccc(/C=C/c2nc(COc3ccc(CCCCn4ccnn4)cc3)co2)c1]

¹H NMR (400 MHz, DMSO-d₆) δ ppm 1.48 (quin, J=7.63 Hz, 2H) 1.81 (quin, J=7.24 Hz, 2H) 2.52-2.57 (m, 2H) 4.39 (t, J=7.04 Hz, 2H) 4.99 (s, 2H) 6.94 (d, J=8.61 Hz, 2H) 7.10 (d, J=8.61 Hz, 2H) 7.41 (d, J=16.43 Hz, 1H) 7.63-7.76 (m, 3H) 8.11 (s, 1H) 8.16-8.28 (m, 3H) 8.57 (s, 1H). LRMS+H⁺: 446.1.

Compound 44: (E)-4-((4-(4-(1H-1,2,3-triazol-1-Yl)butyl)phenoxy)methyl)-2-(2-(trifluoromethyl)styryl)oxazole

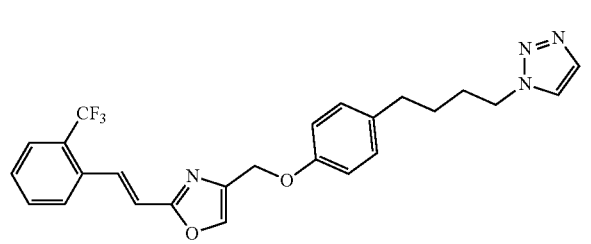 [SMILES: Fc1cccc(F)c1/C=C/c1nc(COc2ccc(CCCCn3ccnn3)cc2)co1]

¹H NMR (400 MHz, DMSO-d₆) δ ppm 1.48 (quin, J=7.63 Hz, 2H) 1.81 (quin, J=7.34 Hz, 2H) 2.52-2.57 (m, 2H) 4.39 (t, J=7.04 Hz, 2H) 4.99 (s, 2H) 6.94 (d, J=8.61 Hz, 2H) 7.09 (d, J=8.61 Hz, 2H) 7.31 (d, J=16.04 Hz, 1H) 7.55-7.63 (m, 1H) 7.66-7.78 (m, 3H) 7.81 (d, J=7.83 Hz, 1H) 8.07-8.17 (m, 2H) 8.24 (s, 1H). LRMS+H⁺: 469.1.

Compound 45: (E)-4-((4-(4-(1H-1,2,3-triazol-1-yl)butyl)phenoxy)methyl)-2-(2,4-difluorostyryl)oxazole

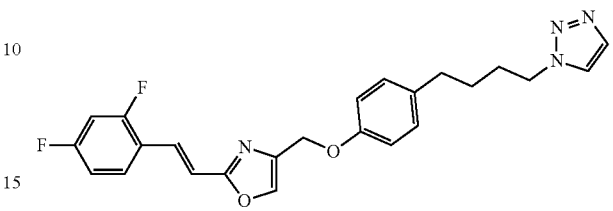

¹H NMR (400 MHz, DMSO-d₆) δ ppm 1.48 (quin, J=7.63 Hz, 2H) 1.81 (quin, J=7.24 Hz, 2H) 2.52-2.57 (m, 2H) 4.39 (t, J=7.04 Hz, 2H) 4.97 (s, 2H) 6.94 (d, J=8.61 Hz, 2H) 7.09 (d, J=8.61 Hz, 2H) 7.14-7.25 (m, 2H) 7.36 (ddd, J=11.35, 9.19, 2.54 Hz, 1H) 7.52 (d, J=16.82 Hz, 1H) 7.70 (s, 1H) 7.99 (td, J=8.80, 7.04 Hz, 1H) 8.11 (s, 1H) 8.21 (s, 1H). LRMS+H⁺: 437.1.

Compound 46: (E)-4-((4-(4-(1H-1,2,3-triazol-1-yl)butyl)phenoxy)methyl)-2-(2,6-difluorostyryl)oxazole

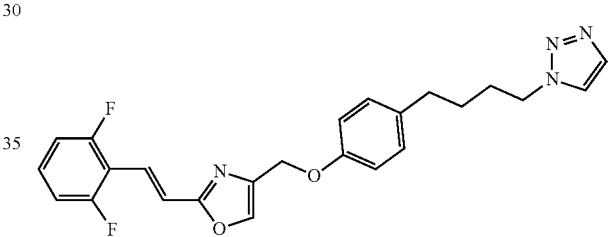

¹H NMR (400 MHz, DMSO-d₆) δ ppm 1.48 (quin, J=7.63 Hz, 2H) 1.81 (quin, J=7.34 Hz, 2H) 2.52-2.56 (m, 2H) 4.39 (t, J=7.04 Hz, 2H) 4.98 (s, 2H) 6.94 (d, J=8.61 Hz, 2H) 7.09 (d, J=8.61 Hz, 2H) 7.16 (d, J=16.82 Hz, 1H) 7.23 (t, J=8.80 Hz, 2H) 7.42-7.54 (m, 2H) 7.70 (s, 1H) 8.08-8.13 (m, 1H) 8.25 (s, 1H). LRMS+H⁺: 437.1.

Compound 47: (E)-4-((4-(4-(1H-1,2,3-triazol-1-yl)butyl)phenoxy)methyl)-2-styryloxazole

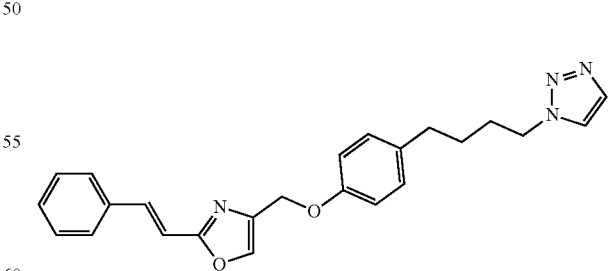

¹H NMR (400 MHz, DMSO-d₆) δ ppm 1.48 (quin, J=7.63 Hz, 2H) 1.81 (quin, J=7.34 Hz, 2H) 2.52-2.57 (m, 2H) 4.39 (t, J=7.04 Hz, 2H) 4.97 (s, 2H) 6.94 (d, J=8.61 Hz, 2H) 7.09 (d, J=8.22 Hz, 2H) 7.16 (d, J=16.43 Hz, 1H) 7.33-7.47 (m, 3H) 7.53 (d, J=16.43 Hz, 1H) 7.66-7.77 (m, 3H) 8.11 (s, 1H) 8.18 (s, 1H). LRMS+H⁺: 401.2.

Compound 48: (E)-4-((4-(4-(1H-1,2,3-triazol-1-yl)butyl)phenoxy)methyl)-2-(2-fluoro-4-(trifluoromethyl)styryl)oxazole

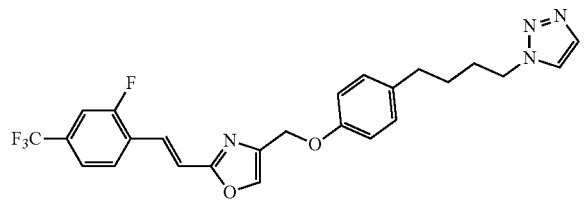 [SMILES: Fc1cc(C(F)(F)F)ccc1/C=C/c1nc(COc2ccc(CCCCn3ccnn3)cc2)co1]

¹H NMR (500 MHz, CDCl₃) δ ppm 1.60-1.67 (m, 2H) 1.95 (dt, J=15.05, 7.45 Hz, 2H) 2.61 (t, J=7.57 Hz, 2H) 4.40 (t, J=7.09 Hz, 2H) 5.03 (d, J=0.95 Hz, 2H) 6.91-6.94 (m, 2H) 7.06-7.10 (m, 2H) 7.14 (d, J=16.71 Hz, 1H) 7.39 (d, J=10.40 Hz, 1H) 7.45 (d, J=8.51 Hz, 1H) 7.50 (d, J=0.95 Hz, 1H) 7.62-7.72 (m, 4H). LRMS+H⁺: 487.3.

Compound 49: (E)-4-((4-(4-(1H-1,2,3-triazol-1-yl)butyl)phenoxy)methyl)-2-(3-(trifluoromethyl)styryl)oxazole

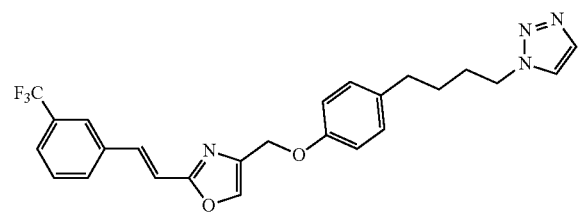 [SMILES: FC(F)(F)c1cccc(/C=C/c2nc(COc3ccc(CCCCn4ccnn4)cc3)co2)c1]

Step 1: (E)-3-(3-(trifluoromethyl)phenyl)acrylamide

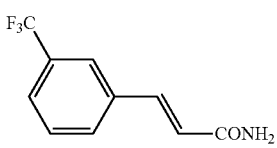

This compound was prepared in a similar fashion as compound 3 step 1 starting with (E)-3-(3-(trifluoromethyl)phenyl)acrylic acid. LRMS+H⁺: 216.2.

Step 2: (E)-4-(chloromethyl)-2-(3-(trifluoromethyl)styryl)oxazole

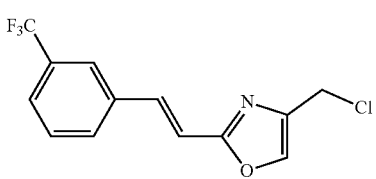 [SMILES: FC(F)(F)c1cccc(/C=C/c2nc(CCl)co2)c1]

This compound was prepared in a similar fashion as compound 3 step 2. LRMS+H⁺: 288.1.

Step 3: (E)-4-((4-(4-(1H-1,2,3-triazol-1-yl)butyl)phenoxy)methyl)-2-(3-(trifluoromethyl)styryl)oxazole

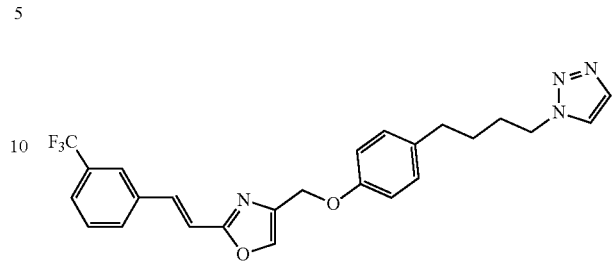

This compound was prepared in a similar fashion as compound 3 step 3 with the previous intermediate and 4-(4-(1H-1,2,3-triazol-1-yl)butyl)phenol. ¹H NMR (500 MHz, CDCl₃) δ ppm 1.60-1.68 (m, 2H) 1.95 (dt, J=14.90, 7.53 Hz, 2H) 2.62 (t, J=7.57 Hz, 2H) 4.40 (t, J=7.09 Hz, 2H) 5.03 (d, J=0.95 Hz, 2H) 6.93 (d, J=8.50 Hz, 2H) 7.01 (d, J=16.39 Hz, 1H) 7.08 (d, J=8.50 Hz, 2H) 7.50 (d, J=0.95 Hz, 1H) 7.53 (t, J=7.60 Hz, 1H) 7.56 (d, J=16.71 Hz, 1H) 7.59-7.62 (m, 1H) 7.67-7.73 (m, 3H) 7.77 (s, 1H). LRMS+H⁺: 469.3.

Compound 50: (E)-4-((4-(3-(1H-1,2,3-triazol-1-yl)propyl)phenoxy)methyl)-2-(4-(trifluoromethyl)styryl)oxazole

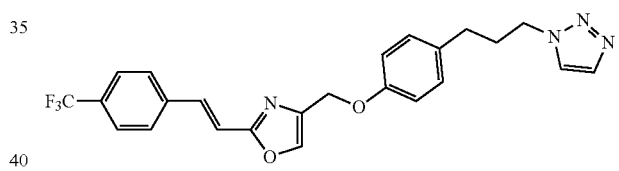

Step 1: (E)-3-(4-((2-(4-(trifluoromethyl)styryl)oxazol-4-yl)methoxy)phenyl)propan-1-ol

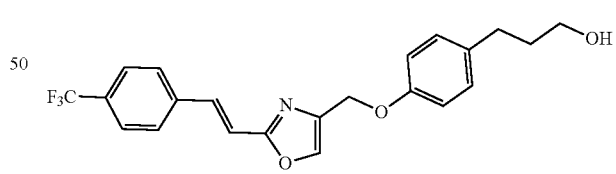

To a solution of 4-(3-hydroxypropyl)phenol (116 mg, 0.765 mmol) in DMF (6953 μl) was added NaH (64.0 mg, 1.599 mmol). After 30 min, (E)-4-(chloromethyl)-2-(4-(trifluoromethyl)styryl)oxazole (200 mg, 0.695 mmol) was added to the chilled solution. After 2 h at rt the mixture was poured into water and extracted with EA. The organic layer was washed with water, 1N NaOH then brine, dried over Na₂SO₄, filtered and concentrated. The residue was adsorbed onto silica gel and purified by ISCO using a RediSep® column (Hx_EA; 0-100%) to afford 0.186 mg of the title compound. LRMS+H⁺: 404.3.

Step 2: (E)-4-((4-(3-iodopropyl)phenoxy)methyl)-2-(4-(trifluoromethyl)styryl)oxazole

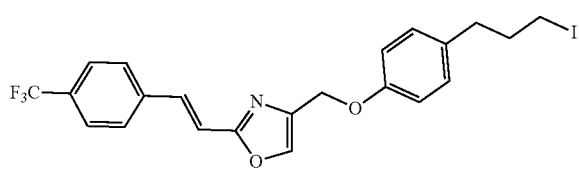 [SMILES: FC(F)(F)c1ccc(/C=C/c2nc(COc3ccc(CCCI)cc3)co2)cc1]

To a chilled solution of (E)-3-(4-((2-(4-(trifluoromethyl)styryl)oxazol-4-yl)methoxy)phenyl)propan-1-ol (186 mg, 0.461 mmol) in EA (4.61 ml) was added triethylamine (96 μl, 0.692 mmol) and methanesulfonyl chloride (53.9 μl, 0.692 mmol) dropwise. After 30 min at 0° C., the mixture was allowed to warm to rt. After 1 h more methanesulfonyl chloride (6 μl) and triethylamine (10 μl) were added and stirred overnight at rt. More methanesulfonyl chloride (10 μl) and triethylamine (20 μl) were added and stirred 1.5 h. The mixture was washed with ice water and then brine. The organic layer was dried over $Na_2SO_4$, filtered and concentrated to afford (E)-3-(4-((2-(4-(trifluoromethyl)styryl)oxazol-4-yl)methoxy)phenyl)propyl methanesulfonate (235 mg). To solution of the previous adduct in acetone (2.102 ml) was added NaI (366 mg, 2.440 mmol) and the mixture was stirred at reflux for 1.5 h. The concentrated residue was dissolved in ethyl acetate (20 ml), washed with water, aq. sodium thiosulfate then brine. The organic layer was dried over $Na_2SO_4$, filtered and concentrated to afford 251 mg of the title compound. LRMS+H$^+$: 5142.

Step 3: (E)-4-((4-(3-(1H-1,2,3-triazol-1-yl)propyl)phenoxy)methyl)-2-(4-(trifluoromethyl)styryl)oxazole

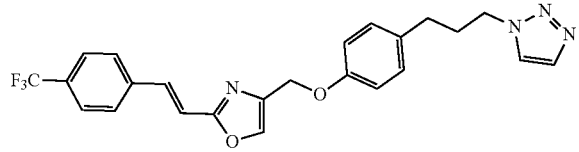 [SMILES: FC(F)(F)c1ccc(/C=C/c2nc(COc3ccc(CCCn4ccnn4)cc3)co2)cc1]

To solution of (E)-4-((4-(3-iodopropyl)phenoxy)methyl)-2-(4-(trifluoromethyl)styryl)oxazole (250 mg, 0.488 mmol) and 1H-1,2,3-triazole (42.4 μl, 0.732 mmol) in DMF (4880 μl) was added $K_2CO_3$ (101 mg, 0.732 mmol). The mixture was stirred at 60° C. over the weekend for 48 h. The mixture was diluted with ethyl acetate (20 ml), washed with water then brine. The organic layer was dried over $Na_2SO_4$, filtered and concentrated. The residue was purified by ISCO using a RediSep® column (Hx-EA; 0-100%) to give 0.095 g of the title compound. $^1$H NMR (500 MHz, CDCl$_3$) δ ppm 2.25 (quin, J=7.25 Hz, 2H) 2.62 (t, J=7.41 Hz, 2H) 4.40 (t, J=7.09 Hz, 2H) 5.04 (d, J=0.95 Hz, 2H) 6.93-6.97 (m, 2H) 7.03 (d, J=16.39 Hz, 1H) 7.10-7.14 (m, 2H) 7.53 (s, 1H) 7.57 (d, J=16.39 Hz, 1H) 7.61-7.69 (m, 4H) 7.73 (s, 1H) 7.70 (s, 1H). LRMS+H$^+$: 455.3.

Compound 51: (E)-2-(1-(4-(4-((2-(4-(trifluoromethyl)styryl)oxazol-4-yl)methoxy)phenyl)butyl)-1H-imidazol-2-yl)ethanol

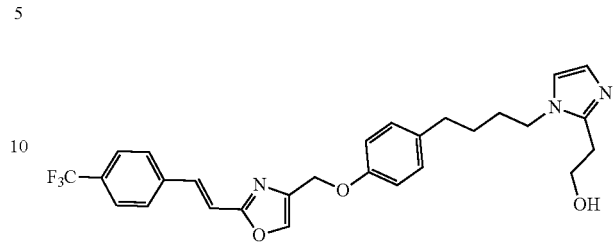

This compound was prepared according to Example 17 (page 98) of International Patent Publication no. WO 01/77107. LRMS+H$^+$: 512.3.

Compound 52: (E)-2-(1-(4-(4-((2-(4-(trifluoromethyl)styryl)oxazol-4-yl)methoxy)phenyl)butyl)-1H-imidazol-2-yl)ethanamine

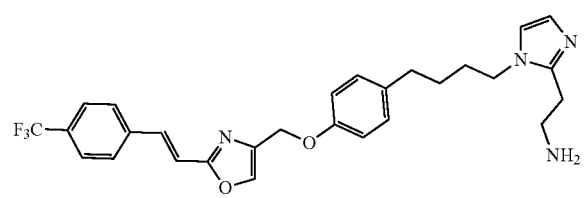 [SMILES: NCCc1nccn1CCCCc1ccc(OCc2coc(/C=C/c3ccc(C(F)(F)F)cc3)n2)cc1]

To a solution of (E)-2-(1-(4-(4-((2-(4-(trifluoromethyl)styryl)oxazol-4-yl)methoxy)phenyl)butyl)-1H-imidazol-2-yl)ethanol (100 mg, 0.195 mmol), triphenylphosphine (56.4 mg, 0.215 mmol) and isoindoline-1,3-dione (31.6 mg, 0.215 mmol) in THF (1.955 ml) was added DIAD (119 mg, 0.586 mmol). The mixture was stirred at rt for 3 h. The reaction was diluted with EA and washed with 1N NaOH aq., brine, dried over $Na_2SO_4$, filtered and concentrated. This residue was suspended in EtOH (5 ml, 86 mmol) and treated with 2-aminoethanol (11.94 mg, 0.195 mmol) at reflux for 1 h and the suspension was left at rt over the weekend. The mixture was concentrated, diluted with EA, washed with water then brine, dried over $Na_2SO_4$, filtered and concentrated. The residue was purified by ISCO using a RediSep® column (DCM-MeOH; 0-30%) to give 0.065 g of the title compound. Reference: PCT 2003031442. $^1$H NMR (500 MHz, CDCl$_3$) δ ppm 1.57-1.65 (m, 2H) 1.71-1.79 (m, 2H) 2.60 (t, J=7.41 Hz, 2H) 2.76 (t, J=6.62 Hz, 2H) 3.15 (t, J=6.46 Hz, 2H) 3.85 (t, J=7.25 Hz, 2H) 5.03 (d, J=0.95 Hz, 2H) 6.81 (d, J=1.26 Hz, 1H) 6.90-6.97 (m, 3H) 7.02 (d, J=16.39 Hz, 1H) 7.06-7.11 (m, 2H) 7.56 (d, J=16.71 Hz, 1H) 7.61-7.68 (m, 4H) 7.69 (s, 1H).

Compound 53: (E)-2-(1-(4-(4-((2-(4-(trifluoromethyl)styryl)oxazol-4-yl)methoxy)phenyl)butyl)-1H-imidazol-2-yl)ethyl dimethylcarbamate

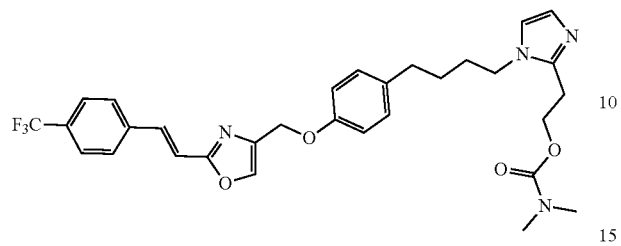

To a chilled solution of (E)-2-(1-(4-(4-((2-(4-(trifluoromethyl)styryl)oxazol-4-yl)methoxy)phenyl)butyl)-1H-imidazol-2-yl)ethanol (16 mg, 0.031 mmol) and triethylamine (6.50 μL, 0.047 mmol) in THF (2 ml) was added dimethylcarbamic chloride (3.15 μL, 0.034 mmol). The mixture was allowed to stir at RT for 5 h. Added more Et₃N (43.3 μL, 0.311 mmol) and dimethylcarbamic chloride (14.31 μL, 0.155 mmol) and stirred for two days. It was then heated to 50° C. for 10 h. The mixture was partitioned between EA and dilute NaHCO₃ then extracted with EA (3×50 ml). The combined organic phases were dried over Na₂SO₄, filtered and concentrated. The residue was purified by ISCO using a RediSep® column (Hx-EA; 0-100%) then switch to DCM-MeOH (0-60%) to give 0.0055 g of the title compound. $^1$H NMR (500 MHz, CDCl₃) δ ppm 1.57-1.66 (m, 2H) 1.71-1.81 (m, 2H) 2.59 (t, J=7.57 Hz, 2H) 2.84-2.97 (m, 6H) 3.02 (t, J=7.25 Hz, 2H) 3.89 (t, J=7.09 Hz, 2H) 4.42 (t, J=7.25 Hz, 2H) 5.03 (d, J=0.95 Hz, 2H) 6.81 (d, J=1.26 Hz, 1H) 6.89-6.96 (m, 2H) 6.97 (d, J=1.26 Hz, 1H) 7.02 (d, J=16.39 Hz, 1H) 7.05-7.12 (m, 2H) 7.56 (d, J=16.39 Hz, 1H) 7.60-7.67 (m, 4H) 7.69 (s, 1H). LRMS+H⁺: 583.3.

Compound 54: (E)-N-(2-(1-(4-(4-((2-(4-(trifluoromethyl)styryl)oxazol-4-yl)methoxy)phenyl)butyl)-1H-imidazol-2-yl)ethyl)methanesulfonamide

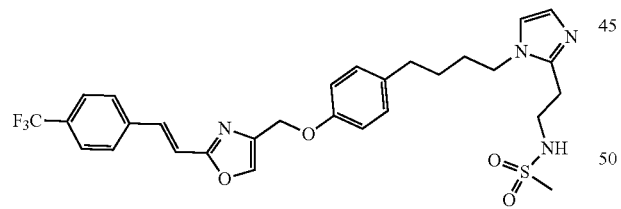

To a solution of (E)-2-(1-(4-(4-((2-(4-(trifluoromethyl)styryl)oxazol-4-yl)methoxy)phenyl)butyl)-1H-imidazol-2-yl)ethanamine (35 mg, 0.069 mmol) in pyridine (0.5 ml) was added methanesulfonyl chloride (6.68 μl, 0.086 mmol). The milky suspension was stirred at rt for 1.5 h and heated to 50° C. for 1 h. Added more methanesulfonyl chloride (6.68 μl, 0.086 mmol) and stirred at rt for 2 h then heated to 50° C. for 1 h and let go overnight at rt. The mixture was partitioned with EA and water then extracted with EA twice. The combine organic phases were dried over Na₂SO₄, filtered and concentrated. The residue was purified by ISCO using a RediSep® column with DCM-MeOH (0-30%) to give 0.025 g of the title compound. $^1$H NMR (500 MHz, CDCl₃) δ ppm 1.55-1.69 (m, 2H) 1.69-1.80 (m, 2H) 2.60 (t, J=7.41 Hz, 2H) 2.89 (br. s., 2H) 2.96 (s, 3H) 3.52-3.64 (m, 2H) 3.83 (t, J=7.09 Hz, 2H) 5.03 (d, J=0.95 Hz, 2H) 6.12 (br. s., 1H) 6.83 (s, 1H) 6.86-6.98 (m, 3H) 7.02 (d, J=16.39 Hz, 1H) 7.05-7.12 (m, 2H) 7.56 (d, J=16.39 Hz, 1H) 7.59-7.68 (m, 4H) 7.70 (s, 1H). LRMS+H⁺: 589.3.

Compound 55: (E)-1,1,1-trifluoro-N-(2-(1-(4-(4-((2-(4-(trifluoromethyl)styryl)oxazol-4-yl)methoxy)phenyl)butyl)-1H-imidazol-2-yl)ethyl)methanesulfonamide

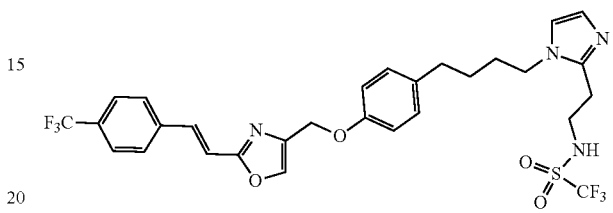

To a chilled solution of (E)-2-(1-(4-(4-((2-(4-(trifluoromethyl)styryl)oxazol-4-yl)methoxy)phenyl)butyl)-1H-imidazol-2-yl)ethanamine (29 mg, 0.057 mmol) in pyridine (0.5 ml) was added trifluoromethanesulfonic anhydride (0.048 ml, 0.284 mmol). It was stirred at rt for 1.5 h and the mixture diluted with water and extracted with EA twice. The aqueous layer was saturated with NH₄Cl and extracted with EA twice more. The combined organic layers were dried over Na₂SO₄, filtered and concentrated. The crude was purified by ISCO using a RediSep® column (DCM-MeOH; 0-50%) to give 0.005 g of the title compound. $^1$H NMR (500 MHz, CDCl₃) δ ppm 1.21-1.32 (m, 2H) 1.60-1.70 (m, 2H) 1.72-1.82 (m, 2H) 2.62 (t, J=7.41 Hz, 2H) 2.89 (t, J=5.83 Hz, 1H) 3.72 (t, J=5.83 Hz, 1H) 3.84 (t, J=7.25 Hz, 2H) 5.04 (d, J=0.95 Hz, 2H) 6.85 (s, 1H) 6.90-6.99 (m, 3H) 7.04 (d, J=16.39 Hz, 1H) 7.07-7.14 (m, 2H) 7.58 (d, J=16.39 Hz, 1H) 7.61-7.69 (m, 5H) 7.69-7.73 (m, 1H). LRMS+H⁺: 643.3.

Compound 56: (E)-1-(4-(4-((3-(4-(trifluoromethyl)styryl)benzyl)oxy)phenyl)butyl)-1H-1,2,3-triazole

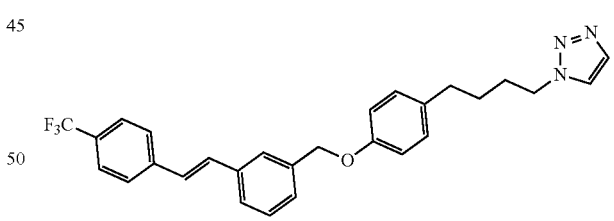

Step 1: (3-methylbenzyl)triphenylphosphonium chloride

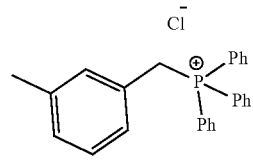 [SMILES: [Cl-] ; Cc1cccc(C[P+](c2ccccc2)(c2ccccc2)c2ccccc2)c1]

A mixture of 1-(chloromethyl)-3-methylbenzene (10 ml, 76 mmol) and triphenylphosphine (22.82 g, 87 mmol) in xylene (106 ml, 288 mmol) was heated to reflux overnight. It was cooled to 20° C. and stirred for 1 hour. The solids were collected on Buchner and the cake washed with 0-xylene (4×25 mL) and dried at 20° C. under high vacuum until constant weight. This gave 28 g of the title compound. LRMS 367.1.

Step 2: (E)-1-methyl-3-(4-(trifluoromethyl)styryl) benzene

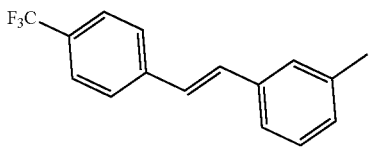 [SMILES: Cc1cccc(/C=C/c2ccc(C(F)(F)F)cc2)c1]

Potassium t-butoxide (2.198 g, 19.59 mmol) was added to (3-methylbenzyl)triphenylphosphonium chloride (7.52 g, 18.67 mmol) and 4-(trifluoromethyl)benzaldehyde (2.5 mL, 18.31 mmol) in ethanol (21.91 mL, 375 mmol). After 1 h, water (8.79 mL, 488 mmol) was added and the resulting white suspension was stirred for 30 minutes. The solids were collected on Buchner and the cake washed with EtOH:water (7:4, 2×5 mL) and dried at 20° C. under high vacuum until constant weight.

This gave 2.52 g og the title compound. $^1$H NMR (500 MHz, CDCl$_3$) δ ppm 2.40 (s, 3H) 7.18 (d, J=16.43 Hz, 1H) 7.13 (d, J=7.04 Hz, 1H) 7.12 (d, J=16.43 Hz, 1H) 7.26-7.31 (m, 1H) 7.37 (s, 1H) 7.34 (s, 1H) 7.61 (s, 4H).

Step 3: (E)-1-(bromomethyl)-3-(4-(trifluoromethyl) styryl)benzene

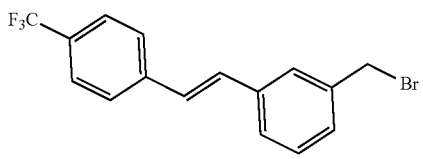 [SMILES: FC(F)(F)c1ccc(/C=C/c2cccc(CBr)c2)cc1]

(E)-1-methyl-3-(4-(trifluoromethyl)styryl)benzene (1 g, 3.81 mmol) in CCl$_4$ (11.41 ml, 118 mmol) was heated to 70° C. for 30 minutes and N-bromosuccinimide (0.780 g, 4.38 mmol) and AIBN (0.063 g, 0.381 mmol) were added. After 6 hrs, cooled to 65° C. and filtered to remove the succinimide. The filtrate was concentrated and the residue purified on ISCO using a RediSep® column (Hex/EtOAc; 0-30) to give 0.753 g of the title compound.

Step 4: (E)-1-(4-(4-((3-(4-(trifluoromethyl)styryl) benzyl)oxy)phenyl)butyl)-1H-1,2,3-triazole

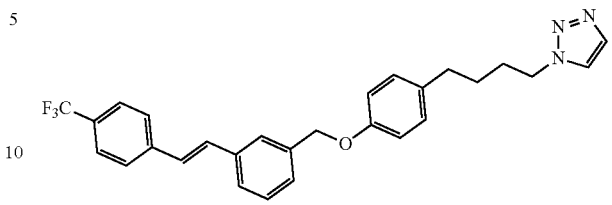

4-(4-(1H-1,2,3-triazol-1-yl)butyl)phenol and (E)-1-(bromomethyl)-3-(4-(trifluoromethyl)styryl)benzene gave the title compound following a procedure similar to compound 3. $^1$H NMR (400 MHz, DMSO-d$_6$) δ ppm 1.47 (quin, J=7.63 Hz, 2H) 1.80 (quin, J=7.34 Hz, 2H) 2.52-2.56 (m, 2H) 4.38 (t, J=7.04 Hz, 2H) 5.09 (s, 2H) 6.94 (d, J=8.61 Hz, 2H) 7.09 (d, J=8.61 Hz, 2H) 7.33-7.51 (m, 4H) 7.61 (d, J=7.43 Hz, 1H) 7.67-7.76 (m, 4H) 7.83 (d, J=8.22 Hz, 2H) 8.10 (s, 1H). LRMS+H$^+$: 478.1.

Compound 57: (E)-1-(4-(4-((4-(4-(trifluoromethyl) styryl)benzyl)oxy)phenyl)butyl)-1H-1,2,3-triazole

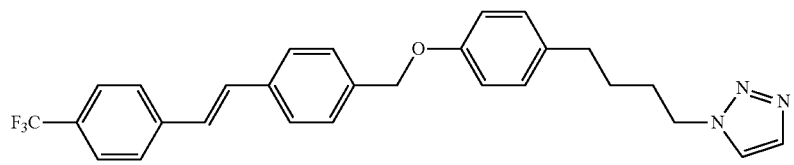

Step 1: (4-methylbenzyl)triphenylphosphonium chloride

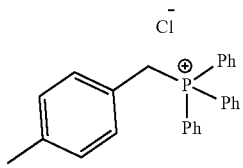 [SMILES: [Cl-] ; Cc1ccc(C[P+](c2ccccc2)(c2ccccc2)c2ccccc2)cc1]

This compound was prepared in a similar fashion as the compound 56 step 1. LRMS+367.1.

Step 2: (E)-1-methyl-4-(4-(trifluoromethyl)styryl) benzene

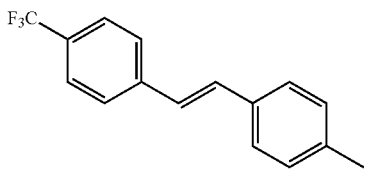 [SMILES: Cc1ccc(/C=C/c2ccc(C(F)(F)F)cc2)cc1]

This compound was prepared in a similar fashion as the compound 56 step 2 after a thermodynamic equilibrium with 3% iodine in refluxing toluene (0.2M) overnight. $^1$H NMR (500 MHz, CDCl$_3$) δ ppm 2.38 (s, 3H) 7.08 (d, J=16.43 Hz, 1H) 7.18 (d, J=16.40 Hz, 1H) 7.20 (d, J=7.83 Hz, 2H) 7.44 (d, J=8.22 Hz, 2H) 7.60 (s, 4H).

Step 3: (E)-1-(bromomethyl)-4-(4-(trifluoromethyl) styryl)benzene

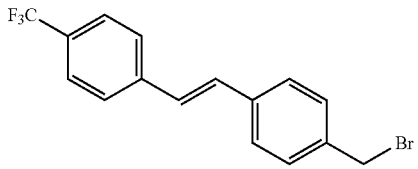 [SMILES: FC(F)(F)c1ccc(/C=C/c2ccc(CBr)cc2)cc1]

This compound was prepared in a similar fashion as the compound 56 step 3. $^1$H NMR (500 MHz, CDCl$_3$) δ ppm 4.53 (s, 2H) 7.10-7.22 (m, 2H) 7.39-7.45 (m, 2H) 7.52 (d, J=8.22 Hz, 2H) 7.58-7.64 (m, 4H).

Step 4: (E)-1-(4-(4-((4-(4-(trifluoromethyl)styryl) benzyl)oxy)phenyl)butyl)-1H-1,2,3-triazole

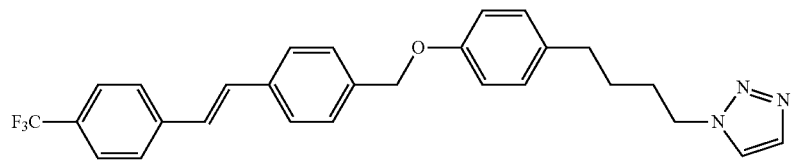 [SMILES: FC(F)(F)c1ccc(/C=C/c2ccc(COc3ccc(CCCCn4ccnn4)cc3)cc2)cc1]

This compound was prepared in a similar fashion as the compound 56 step 4. $^1$H NMR (400 MHz, DMSO-d$_6$) δ ppm 1.47 (quin, J=7.53 Hz, 2H) 1.80 (quin, J=7.34 Hz, 2H) 2.52-2.56 (m, 2H) 4.38 (t, J=7.04 Hz, 2H) 5.08 (s, 2H) 6.92 (d, J=8.61 Hz, 2H) 7.08 (d, J=8.61 Hz, 2H) 7.15 (s, 1H) 7.32-7.50 (m, 4H) 7.63-7.76 (m, 4H) 7.79-7.86 (m, 2H) 8.11 (d, J=0.78 Hz, 1H). LRMS+H$^+$: 478.1.

Compound 58: (E)-methyl 4-(2-(4-((4-(4-(1H-1,2,3-triazol-1-yl)butyl)phenoxy)methyl)oxazol-2-yl)vinyl)benzoate

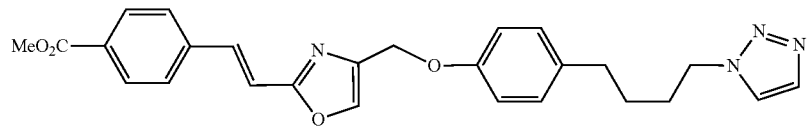 [SMILES: COC(=O)c1ccc(/C=C/c2nc(COc3ccc(CCCCn4ccnn4)cc3)co2)cc1]

Step 1: (E)-3-(4-(methoxycarbonyl)phenyl)acrylic acid

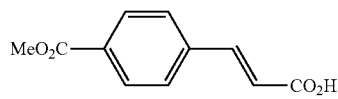

A mixture of methyl 4-formylbenzoate (5 g, 30.5 mmol), malonic acid (4.75 g, 45.7 mmol) and piperidine (0.244 ml, 2.467 mmol) in pyridine (30.5 ml, 377 mmol) was heated to 85-90° C. After 3 hrs cooled to 20° C. and poured into HCl 2M in water (305 ml, 609 mmol). The resulting white suspension was cooled to 0° C. and stirred for 45 minutes. The solids were collected on Buchner and the cake was washed with water (15 mL) and then CH$_3$CN (2×15 mL). The product was dried at 20° C. under high vacuum until constant weight. This gave 5.94 g of the title product. $^1$H NMR (400 MHz, DMSO-d$_6$) δ ppm 3.86 (s, 3H) 6.66 (d, J=16.04 Hz, 1H) 7.64 (d, J=16.04 Hz, 1H) 7.84 (d, J=8.61 Hz, 2H) 7.97 (d, J=8.22 Hz, 2H) 12.58 (s, 1H).

Step 2: (E)-methyl 4-(3-amino-3-oxoprop-1-en-1-yl) benzoate

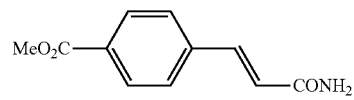

This compound was prepared in a similar fashion as compound 3 step 1 with the previous intermediate. $^1$H NMR (400 MHz, DMSO-d$_6$) δ ppm 3.86 (s, 3H) 6.73 (d, J=16.04 Hz, 1H) 7.21 (br. s., 1H) 7.46 (d, J=16.04 Hz, 1H) 7.61 (br. s., 1H) 7.70 (d, J=8.22 Hz, 2H) 7.98 (d, J=8.22 Hz, 2H).

Step 3: (E)-methyl 4-(2-(4-(chloromethyl)oxazol-2-yl)vinyl)benzoate

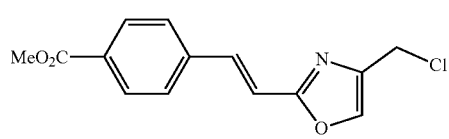 [SMILES: COC(=O)c1ccc(/C=C/c2nc(CCl)co2)cc1]

In a microwave vial were added (E)-methyl 4-(3-amino-3-oxoprop-1-en-1-yl)benzoate (0.750 g, 3.65 mmol) and 1,3-dichloropropan-2-one (0.557 g, 4.39 mmol) were heated at 130° C. After 1 hr, cooled to 20° C. and the resulting solid was dissolved in CH$_2$Cl$_2$ (10 mL) and filtered over glass wool to remove dark insoluble solid. After removal of the solvent the residue was purified on ISCO using a RediSep® column (Hex/EtOAc; 0-50%) to gibe 0.258 g of the title compound. $^1$H NMR (400 MHz, DMSO-d$_6$) δ ppm 3.87 (s, 3H) 4.71 (s, 2H) 7.31 (d, J=16.43 Hz, 1H) 7.60 (d, J=16.43 Hz, 1H) 7.88 (d, J=8.22 Hz, 2H) 7.97 (d, J=8.22 Hz, 2H) 8.22 (s, 1H).

Step 4: (E)-methyl 4-(2-(4-((4-(4-(1H-1,2,3-triazol-1-yl)butyl)phenoxy)methyl)oxazol-2-yl)vinyl)benzoate

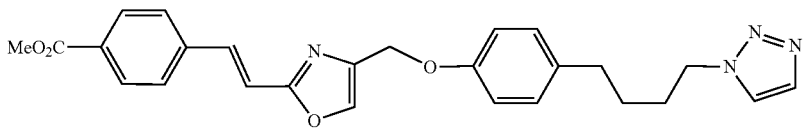 [SMILES: COC(=O)c1ccc(/C=C/c2nc(COc3ccc(CCCCn4ccnn4)cc3)co2)cc1]

This compound was prepared in a similar fashion as the compound 32 step 2 from (E)-methyl 4-(2-(4-(chloromethyl)oxazol-2-yl)vinyl)benzoate and 4-(4-(1H-1,2,3-triazol-1-yl)butyl)phenol. $^1$H NMR (400 MHz, DMSO-d$_6$) δ ppm 1.48 (quin, J=7.63 Hz, 2H) 1.81 (quin, J=7.34 Hz, 2H) 2.52-2.57 (m, 2H) 3.86 (s, 3H) 4.39 (t, J=7.04 Hz, 2H) 4.98 (s, 2H) 6.94 (m, J=8.22 Hz, 2H) 7.09 (m, J=8.61 Hz, 2H) 7.31 (d, J=16.43 Hz, 1H) 7.59 (d, J=16.43 Hz, 1H) 7.70 (s, 1H) 7.87 (d, J=8.22 Hz, 2H) 7.97 (d, J=8.22 Hz, 2H) 8.11 (s, 1H) 8.23 (s, 1H). LRMS+H$^+$: 459.1

Compound 59: (E)-4-(2-(4-((4-(4-(1H-1,2,3-triazol-1-yl)butyl)phenoxy)methyl)oxazol-2-yl)vinyl)-N-(prop-2-yn-1-yl)benzamide

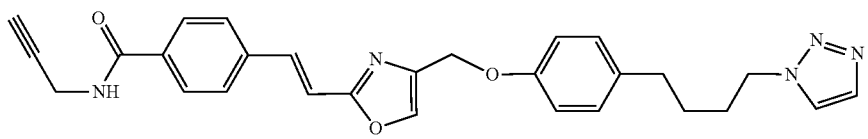 [SMILES: C#CCNC(=O)c1ccc(/C=C/c2nc(COc3ccc(CCCCn4ccnn4)cc3)co2)cc1]

Step 1: (E)-4-(2-(4-((4-(4-(1H-1,2,3-triazol-1-yl)butyl)phenoxy)methyl)oxazol-2-yl)vinyl)benzoic acid

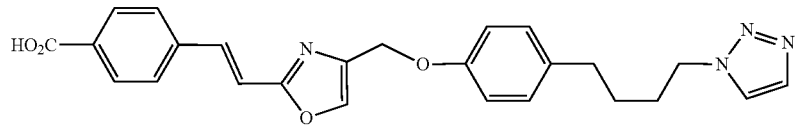 [SMILES: O=C(O)c1ccc(/C=C/c2nc(COc3ccc(CCCCn4ccnn4)cc3)co2)cc1]

NaOH 0.5M (0.654 ml, 0.327 mmol) was added to (E)-methyl 4-(2-(4-((4-(4-(1H-1,2,3-triazol-1-yl)butyl)phenoxy)methyl)oxazol-2-yl)vinyl)benzoate (0.150 g, 0.327 mmol) in THF (1.5 ml). After 48 hrs, NaOH 0.5M in water (0.294 ml, 0.147 mmol) was added. After 68 hrs, HCl 0.5M in water (0.981 ml, 0.491 mmol) was added and the resulting suspension was stirred for 1 h. The solids were collected on Buchner and the cake was washed with water (3×1 mL) and dried at 40° C. under high vacuum until constant weight. This gave 0.132 g of the title compound. $^1$H NMR (400 MHz, DMSO-d$_6$) δ ppm 1.48 (quin, J=7.63 Hz, 2H) 1.81 (quin, J=7.24 Hz, 2H) 2.52-2.57 (m, 2H) 4.39 (t, J=7.04 Hz, 2H) 4.98 (s, 2H) 6.94 (d, J=8.61 Hz, 2H) 7.09 (d, J=8.61 Hz, 2H) 7.30 (d, J=16.43 Hz, 1H) 7.59 (d, J=16.43 Hz, 1H) 7.70 (s, 1H) 7.84 (d, J=8.22 Hz, 2H) 7.95 (d, J=8.61 Hz, 2H) 8.11 (s, 1H) 8.23 (s, 1H) 13.03 (br. s., 1H). LRMS+H$^+$: 445.2.

Step 2: (E)-4-(2-(4-((4-(4-(1H-1,2,3-triazol-1-yl)
butyl)phenoxy)methyl)oxazol-2-yl)vinyl)-N-(prop-2-
yn-1-yl)benzamide yl)benzamide

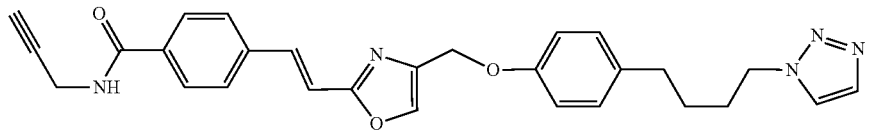

EDC (19.41 mg, 0.101 mmol) was added to (E)-4-(2-(4-((4-(4-(1H-1,2,3-triazol-1-yl)butyl)phenoxy)methyl)oxazol-2-yl)vinyl)benzoic acid (30 mg, 0.067 mmol) and propargyl amine (10.81 µl, 0.169 mmol) in DMF (500 µl, 6.45 mmol) and let go overnight.

MeOH (500 µl, 12.35 mmol) and water (850 µl, 47.2 mmol) were added and the resulting suspension stirred for 1 hour. The solids were collected on Buchner and the cake was washed with water (3×0.5 mL) and dried at 40° C. under high vacuum to give 0.022 g of the title compound. $^1$H NMR (400 MHz, DMSO-$d_6$) & ppm 1.48 (quin, J=7.63 Hz, 2H) 1.81 (dt, J=14.97, 7.19 Hz, 2H) 2.52-2.58 (m, 2H) 3.13 (t, J=2.54 Hz, 1H) 4.07 (dd, J=5.28, 2.54 Hz, 2H) 4.39 (t, J=7.04 Hz, 2H) 4.98 (s, 2H) 6.94 (d, J=8.61 Hz, 2H) 7.09 (d, J=8.61 Hz, 2H) 7.28 (d, J=16.43 Hz, 1H) 7.57 (d, J=16.43 Hz, 1H) 7.70 (s, 1H) 7.82 (d, J=8.61 Hz, 2H) 7.89 (d, J=8.61 Hz, 2H) 8.11 (s, 1H) 8.22 (s, 1H) 8.98 (t, J=5.48 Hz, 1H). LRMS+H$^+$: 482.2.

Compound 60: (E)-(4-(2-(4-((4-(4-(1H-1,2,3-triazol-1-yl)butyl)phenoxy)methyl)oxazol-2-yl)vinyl)phenyl)methanol

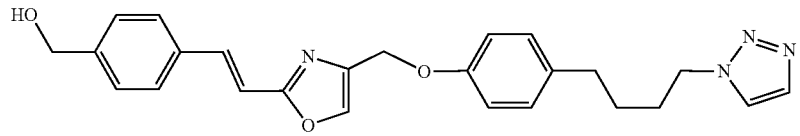 [SMILES: OCc1ccc(/C=C/c2nc(COc3ccc(CCCCn4ccnn4)cc3)co2)cc1]

LiAlH$_4$ (9.1 mg, 0.24 mmol) was added to (E)-methyl 4-(2-(4-((4-(4-(1H-1,2,3-triazol-1-yl)butyl)phenoxy)methyl)oxazol-2-yl)vinyl)benzoate (0.050 g, 0.109 mmol) in THF (3.00 ml, 36.6 mmol) and the reaction stirred overnight. To the reaction mixture was added water (9 µL), NaOH 3M (11.3 µL) and water (27 µL). After 15 minutes of stirring anhydrous MgSO$_4$ was added and stirred for 15 minutes. It was filtered and the solvent removed. This gave 0.042 g of the title compound. $^1$H NMR (400 MHz, DMSO-$d_6$) δ ppm 1.48 (quin, J=7.60 Hz, 2H) 1.81 (quin, J=7.30 Hz, 2H) 2.52-2.57 (m, 2H) 4.39 (t, J=7.04 Hz, 2H) 4.52 (d, J=5.48 Hz, 2H) 4.96 (s, 2H) 5.24 (t, J=5.50 Hz, 1H) 6.94 (d, J=8.61 Hz, 2H) 7.06-7.16 (m, 3H) 7.35 (d, J=7.83 Hz, 2H) 7.51 (d, J=16.43 Hz, 1H) 7.67 (d, J=8.22 Hz, 2H) 7.70 (s, 1H) 8.11 (s, 1H) 8.17 (s, 1H). LRMS+H$^+$: 431.2.

Compound 61: (E)-4-((4-(4-(1H-1,2,3-triazol-1-yl)butyl)phenoxy)methyl)-2-(2-fluoro-4-methoxystyryl)oxazole

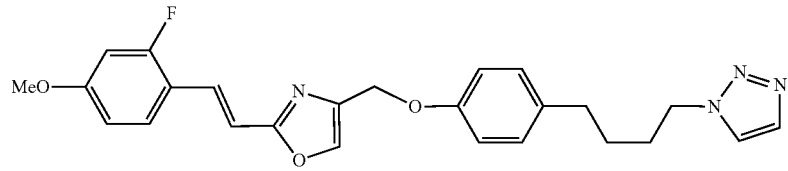 [SMILES: COc1ccc(/C=C/c2nc(COc3ccc(CCCCn4ccnn4)cc3)co2)c(F)c1]

Step 1: (E)-3-(2-fluoro-4-methoxyphenyl)acrylic acid

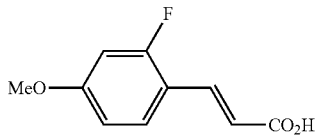

This compound was prepared in a similar fashion as compound 58 step 1 with 2-fluoro-4-(trifluoromethoxy) benzaldehyde. LRMS−H$^+$: 249.1

Step 2: (E)-3-(2-fluoro-4-methoxyphenyl)acrylamide

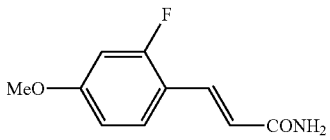

This compound was in a similar fashion as compound 3 step 1 with the previous intermediate. $^1$H NMR (400 MHz, DMSO-d$_6$) δ ppm 3.80 (s, 3H) 6.56 (d, J=16.04 Hz, 1H) 6.84 (dd, J=8.61, 2.74 Hz, 1H) 6.91 (dd, J=12.91, 2.35 Hz, 1H) 7.08 (br. s., 1H) 7.41 (d, J=16.04 Hz, 1H) 7.50-7.60 (m, 2H).

Step 3: (E)-4-(chloromethyl)-2-(2-fluoro-4-methoxystyryl)oxazole

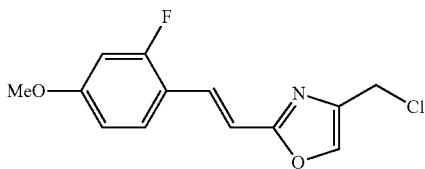 [SMILES: COc1ccc(/C=C/c2nc(CCl)co2)c(F)c1]

(E)-3-(2-fluoro-4-methoxyphenyl)acrylamide (0.250 g, 1.281 mmol) and 1,3-dichloropropan-2-one (0.195 g, 1.537 mmol) were heated to 130° C. for 1 hr. Cooled to 20° C. and the resulting black solid was dissolved in CH$_2$Cl$_2$ (4 mL) and filtered over glass wool to remove the dark insoluble solid. Concentrated to dryness and the residue was purified on ISCO using a RediSep® column (Hex/EtOAc; 0-50%) to give 89 mg of the title compound. $^1$H NMR (400 MHz, DMSO-d$_6$) δ ppm 3.82 (s, 3H) 4.69 (s, 2H) 6.86 (dd, J=8.61, 2.35 Hz, 1H) 6.93 (dd, J=13.11, 2.54 Hz, 1H) 7.06 (d, J=16.43 Hz, 1H) 7.51 (d, J=16.43 Hz, 1H) 7.83 (t, J=9.00 Hz, 1H) 8.15 (s, 1H).

Step 4: (E)-4-((4-(4-(1H-1,2,3-triazol-1-yl)butyl)phenoxy)methyl)-2-(2-fluoro-4-methoxystyryl)oxazole

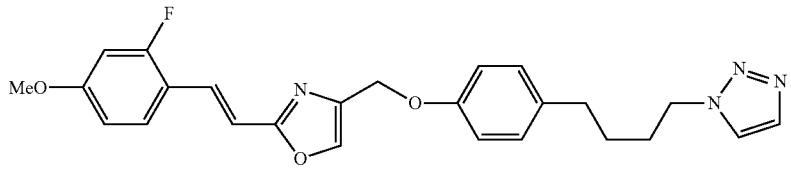 [SMILES: COc1ccc(/C=C/c2nc(COc3ccc(CCCCn4ccnn4)cc3)co2)c(F)c1]

(E)-4-(chloromethyl)-2-(2-fluoro-4-methoxystyryl)oxazole (30 mg, 0.112 mmol), 4-(4-(1H-1,2,3-triazol-1-yl)butyl)phenol (26.8 mg, 0.123 mmol) and K$_2$CO$_3$ (17.04 mg, 0.123 mmol) in DMF (183 µl, 2.360 mmol) were heated to 75° C. for 5 hrs. It was cooled to 20° C. and MeOH (183 µl, 4.52 mmol) and water (305 µl, 16.90 mmol) were added. The mixture was stirred overnight. The solids were collected on Buchner and the cake was washed with water (3×0.5 mL) and dried at 40° C. to give 0.042 g of the title compound. $^1$H NMR (400 MHz, DMSO-d$_6$) δ ppm 1.48 (quin, J=7.63 Hz, 2H) 1.81 (quin, J=7.34 Hz, 2H) 2.52-2.56 (m, 2H) 3.82 (s, 3H) 4.39 (t, J=7.04 Hz, 2H) 4.96 (s, 2H) 6.81-6.97 (m, 4H) 7.02-7.12 (m, 3H) 7.50 (d, J=16.82 Hz, 1H) 7.70 (s, 1H) 7.82 (t, J=9.00 Hz, 1H) 8.11 (s, 1H) 8.17 (s, 1H). LRMS+H$^+$: 449.2.

Compound 62: (E)-4-(2-(4-((4-(4-(1H-1,2,3-triazol-1-yl)butyl)phenoxy)methyl)oxazol-2-yl)vinyl)phenol

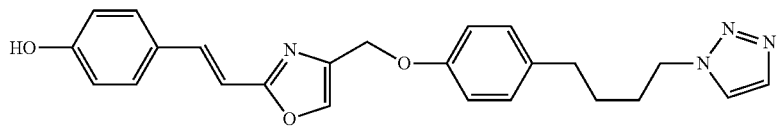

A mixture of (E)-4-((4-(4-(1H-1,2,3-triazol-1-yl)butyl)phenoxy)methyl)-2-(4-methoxystyryl)oxazole (50 mg, 0.116 mmol) in HBr 48% wt in water (201 µl, 1.777 mmol) was heated to 90° C. After 2 hrs water (1 mL) and MeOH (1 mL) were added and extracted the mixture with $CH_2Cl_2$ (3×2 mL). The organic phases were combined and the solvent removed. The residue was purified on ISCO using a RediSep® column ($CH_2Cl_2$/MeOH; 0-100%). The solid thus obtained was suspended in $CH_3CN$ (0.5 mL) and heated to reflux for 15 minutes. It was cooled to 20° C. and stirred for 1 hour. The solids were collected on Buchner and the cake was washed with $CH_3CN$ (2×0.15 mL) and dried at 40° C. under high vacuum. This gave 0.006 g of the title compound. $^1$H NMR (400 MHz, DMSO-$d_6$) δ ppm 1.48 (quin, J=7.70 Hz, 2H) 1.81 (quin, J=7.34 Hz, 2H) 2.52-2.56 (m, 2H) 4.39 (t, J=7.04 Hz, 2H) 4.94 (s, 2H) 6.79 (m, J=8.61 Hz, 2H) 6.85-6.97 (m, 3H) 7.09 (m, J=8.61 Hz, 2H) 7.42 (d, J=16.43 Hz, 1H) 7.54 (d, J=8.61 Hz, 2H) 7.70 (s, 1H) 8.11 (s, 1H) 8.11 (s, 1H) 9.85 (s, 1H). LRMS+H$^+$: 417.1.

Compound 63: (E)-4-(2-(4-((4-(4-(1H-1,2,3-triazol-1-yl)butyl)phenoxy)methyl)oxazol-2-yl)vinyl)benzamide

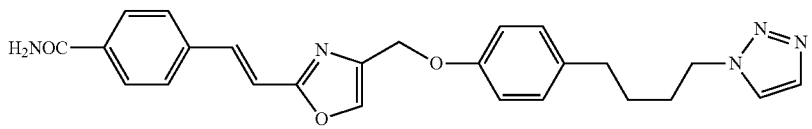 [SMILES: NC(=O)c1ccc(/C=C/c2nc(COc3ccc(CCCCn4ccnn4)cc3)co2)cc1]

(E)-4-(2-(4-((4-(4-(1H-1,2,3-triazol-1-yl)butyl)phenoxy)methyl)oxazol-2-yl)vinyl)benzonitrile (50 mg, 0.118 mmol) in EtOH (1777 µl, 30.4 mmol) and DMF (901 µl, 11.63 mmol) was heated to 50° C. for 5 minutes to obtain a solution. NaOH 3M in water (96 µl, 0.288 mmol) and hydrogen peroxide 30% wt. in water (48.0 µl, 0.470 mmol) were then added. After 3 hours then cooled to 20° C. and continued stirring. Water (900 µl, 49.9 mmol) was added the suspension was stirred for 1 hour. The solids were then collected on Buchner and the cake was washed with water (3×0.5 mL) and dried at 40° C. under high vacuum until. This gave 0.044 g of the title compound. $^1$H NMR (400 MHz, DMSO-$d_6$) δ ppm 1.48 (quin, J=7.63 Hz, 2H) 1.81 (quin, J=7.34 Hz, 2H) 2.52-2.57 (m, 2H) 4.39 (t, J=7.04 Hz, 2H) 4.98 (s, 2H) 6.94 (d, J=8.61 Hz, 2H) 7.09 (d, J=8.22 Hz, 2H) 7.27 (d, J=16.43 Hz, 1H) 7.41 (br. s., 1H) 7.57 (d, J=16.43 Hz, 1H) 7.70 (s, 1H) 7.80 (d, J=8.61 Hz, 2H) 7.90 (d, J=8.22 Hz, 2H) 8.02 (br. s., 1H) 8.11 (s, 1H) 8.21 (s, 1H).

Compound 64: (E)-4-((4-(4-(1H-1,2,3-triazol-1-yl)butyl)phenoxy)methyl)-2-(4-ethynylstyryl)oxazole

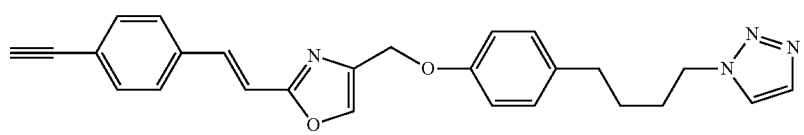 [SMILES: C#Cc1ccc(/C=C/c2nc(COc3ccc(CCCCn4ccnn4)cc3)co2)cc1]

To a $N_2$ flush vial containing (E)-4-((4-(4-(1H-1,2,3-triazol-1-yl)butyl)phenoxy)methyl)-2-(4-bromostyryl)oxazole (75 mg, 0.156 mmol), copper (1) iodide (2.9 mg, 0.016 mmol) and $(Ph_3P)_2PdCl_2$ (10.98 mg, 0.016 mmol) was added DMF (608 µl, 7.85 mmol), triethylamine (607 µl, 4.36 mmol) and trimethylsilylacetylene (110 µl, 0.782 mmol). The reaction was heated to 60° C. overnight and filtered over 0.45 µm filter and the solvent removed. The residue was dissolved in THF (3000 µl, 36.6 mmol) and cooled to 0° C. TBAF 1M in THF (203 µl, 0.203 mmol) was added and 30 minutes later, $CH_2Cl_2$ (20 mL) was added. This was washed with water (20 mL) and the organic layer dried over MgSO₄, filtered and concentrated. The residue was purified on ISCO using a RediSep® column (CH₂Cl₂/MeOH; 0-10%) to give 0.024 g of ta solid that was suspended in CH₃CN (0.5 mL) and heated to reflux for 15 minutes. Cooled to 20° C. and stirred for 30 minutes. The solids were collected on Buchner and the cake was washed with CH₃CN (1×0.5 mL) and dried at 40° C. under high vacuum to give 0.0045 g of the title compound. $^1$H NMR (400 MHz, DMSO-d₆) δ ppm 1.48 (quin, J=7.70 Hz, 2H) 1.81 (quin, J=7.34 Hz, 2H) 2.52-2.58 (m, 2H) 4.39 (t, J=7.04 Hz, 2H) 4.97 (d, J=2.35 Hz, 2H) 6.94 (d, J=8.61 Hz, 2H) 7.09 (d, J=8.22 Hz, 2H) 7.21 (d, J=16.43 Hz, 1H) 7.27 (d, J=16.43 Hz, 1H) 7.46-7.61 (m, 2H) 7.65 (d, J=8.22 Hz, 1H) 7.70 (s, 1H) 7.74 (d, J=8.22 Hz, 1H) 7.80 (d, J=8.22 Hz, 1H) 8.11 (s, 1H) 8.21 (d, J=6.26 Hz, 1H).

Compound 65: (E)-4-((4-(4-(1H-1,2,3-triazol-1-yl)butyl)phenoxy)methyl)-2-(2-fluoro-4-nitrostyryl)oxazole

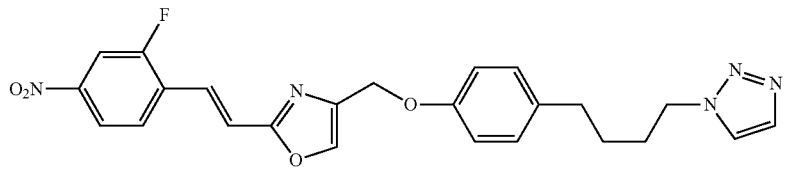

A mixture of (E)-4-(chloromethyl)-2-(2-fluoro-4-nitrostyryl)oxazole (0.118 g, 0.418 mmol), 4-(4-(1H-1,2,3-triazol-1-yl)butyl)phenol (0.100 g, 0.460 mmol) and K₂CO₃ (0.069 g, 0.502 mmol) was heated in DMF (0.837 ml) at 75° C. overnight. The temperature was brought to 50° C. and MeOH (0.677 ml, 16.74 mmol) was added followed by water (1.131 ml, 62.8 mmol). The temperature was brought to rt and the mixture filtered and absorbed on SiO₂ and purified on ISCO using a RediSep® column (DCM-MeOH; 0-10%) to give 0.099 g of the title compound. $^1$H NMR (400 MHz, DMSO-d₆) δ ppm 1.48 (quin, J=7.60 Hz, 2H) 1.81 (quin, J=7.60 Hz, 2H) 2.53 (t, J=7.60 Hz, 2H) 4.39 (t, J=7.04 Hz, 2H) 5.00 (s, 2H) 6.94 (2, J=8.61 Hz, 2H) 7.10 (2, J=8.61 Hz, 2H) 7.47 (d, J=16.82 Hz, 1H) 7.61 (d, J=16.82 Hz, 1H) 7.70 (s, 1H) 8.09-8.15 (m, 2H) 8.17-8.26 (m, 2H) 8.29 (s, 1H).

Compound 66: (E)-4-(2-(4-((4-(4-(1H-1,2,3-triazol-1-yl)butyl)phenoxy)methyl)oxazol-2-yl)vinyl)-3-fluoroaniline

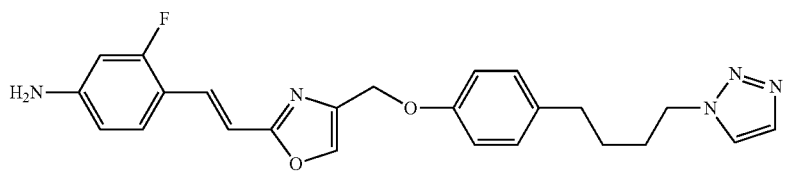 [SMILES: O=[N+]([O-])c1ccc(/C=C/c2nc(COc3ccc(CCCCn4ccnn4)cc3)co2)c(F)c1]

To a mixture of (E)-4-((4-(4-(1H-1,2,3-triazol-1-yl)butyl)phenoxy)methyl)-2-(2-fluoro-4-nitrostyryl)oxazole (0.096 g, 0.207 mmol) in THF (3.0 ml)-EtOAc (4.0 ml) was added SnCl₂·H₂O (0.234 g, 1.036 mmol) and it was heated to 75° C. for 5 h. After a quenched with a solution of NaHCO₃ sol, it was diluted with EA, filtered on celite and the organic phase separated. The aqueous was extracted with EA and the combined organic phases washed with brine and dried over Na₂SO₄ dried. After filtration the solvent was removed. This gave 0.069 g of the title compound. $^1$H NMR (400 MHz, DMSO-d₆) δ ppm 1.48 (quin, J=7.63 Hz, 2H) 1.81 (quin, J=7.34 Hz, 2H) 2.52-2.56 (m, 2H) 4.39 (t, J=7.04 Hz, 2H) 4.93 (s, 2H) 5.95 (s, 2H) 6.34 (dd, J=13.89, 2.15 Hz, 1H) 6.42 (dd, J=8.61, 1.96 Hz, 1H) 6.79 (d, J=16.43 Hz, 1H) 6.93 (d, J=8.61 Hz, 2H) 7.09 (d, J=8.61 Hz, 2H) 7.40 (d, J=16.43 Hz, 1H) 7.49 (t, J=8.80 Hz, 1H) 7.70 (s, 1H) 8.10 (d, J=8.22 Hz, 2H).

Compound 67: (E)-4-((4-(4-(1H-1,2,3-triazol-1-yl)butyl)phenoxy)methyl)-2-(4-azido-2-fluorostyryl)oxazole

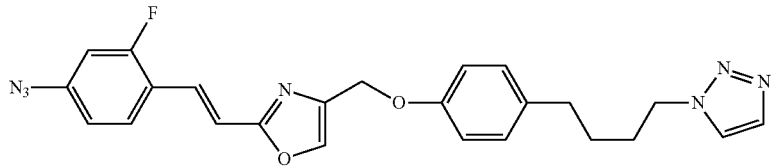 [SMILES: [N-]=[N+]=Nc1ccc(/C=C/c2nc(COc3ccc(CCCCn4ccnn4)cc3)co2)c(F)c1]

To a 0° C. suspension of (E)-4-(2-(4-((4-(4-(1H-1,2,3-triazol-1-yl)butyl)phenoxy)methyl)oxazol-2-yl)vinyl)-3-fluoroaniline (0.068 g, 0.157 mmol) in acetonitrile (1.05 ml) was added tert-butyl nitrite (0.026 ml, 0.220 mmol) followed by trimethylsilyl azide (0.025 ml, 0.188 mmol). This was brought to it and after 3 h the solvent was removed. Purification on ISCO using a RediSep® column (DCM-MeOH) gave 0.039 g of the title compound. 1H NMR (400 MHz, DMSO-$d_6$) δ ppm 1.48 (quin, J=7.63 Hz, 2H) 1.81 (quin, J=7.60 Hz, 2H) 2.52-2.57 (m, 2H) 4.39 (t, J=7.04 Hz, 2H) 4.97 (s, 2H) 6.93 (d, J=8.61 Hz, 2H) 7.05 (dd, J=8.22, 2.35 Hz, 1H) 7.09 (d, J=8.61 Hz, 2H) 7.12-7.24 (m, 2H) 7.52 (d, J=16.43 Hz, 1H) 7.70 (s, 1H) 7.95 (t, J=8.61 Hz, 1H) 8.11 (s, 1H) 8.20 (s, 1H).

Compound 68: (E)-2-(1-(4-(4-((2-(4-(trifluoromethyl)styryl)oxazol-4-yl)methoxy)phenyl)butyl)-1H-1,2,3-triazol-4-yl)ethyl dimethylcarbamate

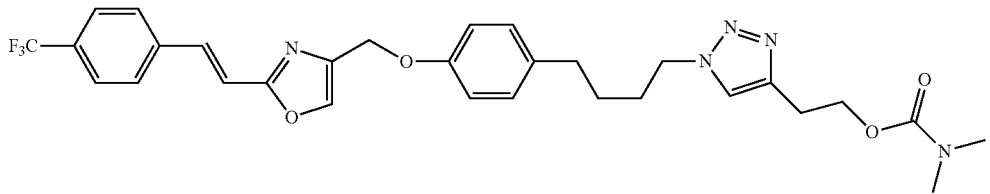 [SMILES: CN(C)C(=O)OCCc1cn(CCCCc2ccc(OCc3coc(/C=C/c4ccc(C(F)(F)F)cc4)n3)cc2)nn1]

Dimethylcarbamic chloride (5.43 μl, 0.059 mmol) was added to compound 4 (0.020 g, 0.039 mmol) in pyridine (0.013 ml) and brought to 100° C. for 10 h. It was then diluted with EA and quenched with a CuSO$_4$ solution. The phases were separated and the aqueous extracted 2× with EA. They were combined, Na$_2$SO$_4$ dried, filtered and purified on preparative HPLC (35-100% MeOH (5% HCO$_2$H)-water (5% HCO$_2$H) to give 0.007 g of the title compound. $^1$H NMR (400 MHz, DMSO-$d_6$) δ ppm 1.47 (quin, J=7.53 Hz, 2H) 1.78 (quin, J=7.60 Hz, 2H) 2.51-2.56 (m, 2H) 2.76 (br. s., 6H) 2.91 (t, J=6.65 Hz, 2H) 4.17 (t, J=6.65 Hz, 2H) 4.33 (t, J=7.04 Hz, 2H) 4.98 (s, 2H) 6.94 (d, J=8.61 Hz, 2H) 7.09 (d, J=8.61 Hz, 2H) 7.34 (d, J=16.43 Hz, 1H) 7.61 (d, J=16.43 Hz, 1H) 7.76 (d, J=8.22 Hz, 2H) 7.89 (s, 1H) 7.95 (d, J=7.83 Hz, 2H) 8.24 (s, 1H).

Compound 69: (E)-2-(1-(4-(4-((2-(4-(trifluoromethyl)styryl)oxazol-4-yl)methoxy)phenyl)butyl)-1H-1,2,3-triazol-4-yl)ethyl (2-methoxyethyl)carbamate

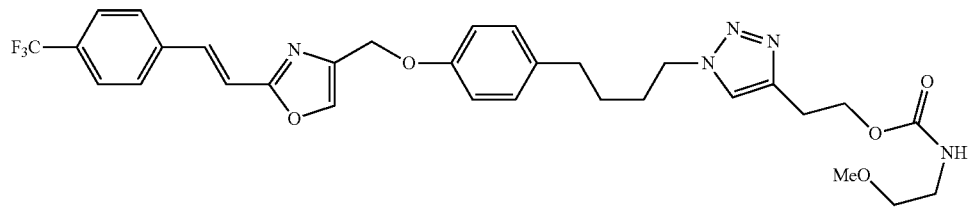 [SMILES: COCCNC(=O)OCCc1cn(CCCCc2ccc(OCc3coc(/C=C/c4ccc(C(F)(F)F)cc4)n3)cc2)nn1]

1-isocyanato-2-methoxyethane (7.89 mg, 0.078 mmol) was added to a suspension of compound 4 (0.020 g, 0.039 mmol) and Hunig's Base (0.014 ml, 0.078 mmol) in DCM (0.098 ml) at rt. After 3 h the solvent was removed and the residue absorbed on SiO$_2$. Purification on ISCO using a RediSep® column (Hx-EA; 20-100%) gave 0.017 g of the title compound. $^1$H NMR (400 MHz, DMSO-d$_6$) δ ppm 1.49 (quin, J=7.20 Hz, 2H) 1.79 (quin, J=7.24 Hz, 2H) 2.52-2.57 (m, 2H) 2.89 (t, J=6.85 Hz, 2H) 3.07-3.15 (m, 2H) 3.21 (s, 3H) 3.27-3.31 (m, 2H) 4.16 (t, J=6.85 Hz, 2H) 4.32 (t, J=6.85 Hz, 2H) 4.98 (s, 2H) 6.94 (d, J=8.61 Hz, 2H) 7.10 (d, J=8.22 Hz, 2H) 7.15 (t, J=5.67 Hz, 1H) 7.34 (d, J=16.43 Hz, 1H) 7.62 (d, J=16.43 Hz, 1H) 7.76 (d, J=8.22 Hz, 2H) 7.90 (s, 1H) 7.95 (d, J=8.22 Hz, 2H) 8.23 (s, 1H).

Compound 70: (E)-2-(1-(4-(4-((2-(4-(trifluoromethyl)styryl)oxazol-4-yl)methoxy)phenyl)butyl)-1H-1,2,3-triazol-4-yl)ethyl isopropylcarbamate

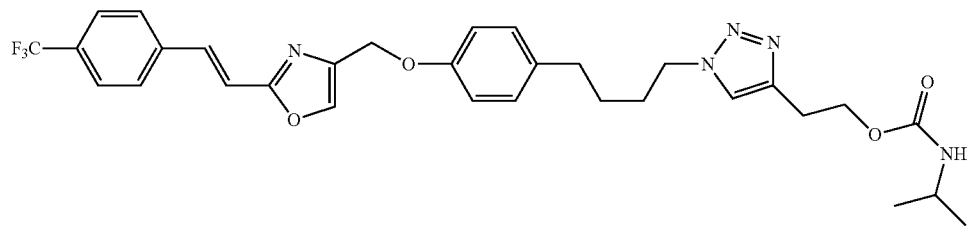 [SMILES: CC(C)NC(=O)OCCc1cn(CCCCc2ccc(OCc3coc(/C=C/c4ccc(C(F)(F)F)cc4)n3)cc2)nn1]

This compound was prepared in a similar fashion as compound 69 with 2-isocyanatopropane. $^1$H NMR (400 MHz, DMSO-d$_6$) δ ppm 1.02 (d, J=6.26 Hz, 6H) 1.49 (quin, J=7.40 Hz, 2H) 1.78 (quin, J=7.24 Hz, 2H) 2.51-2.56 (m, 2H) 2.89 (t, J=6.65 Hz, 2H) 3.48-3.63 (m, 1H) 4.15 (t, J=6.85 Hz, 2H) 4.32 (t, J=7.04 Hz, 2H) 4.98 (s, 2H) 6.94 (d, J=8.22 Hz, 2H) 7.01 (d, J=7.04 Hz, 1H) 7.10 (d, J=8.61 Hz, 2H) 7.34 (d, J=16.83 Hz, 1H) 7.62 (d, J=16.43 Hz, 1H) 7.76 (d, J=8.61 Hz, 2H) 7.89 (s, 1H) 7.95 (d, J=8.22 Hz, 2H) 8.24 (s, 1H).

Compound 71: (E)-4-((1-(4-(4-((2-(2-fluoro-4-(trifluoromethyl)styryl)oxazol-4-yl)methoxy)phenyl)butyl)-1H-1,2,3-triazol-4-yl)methyl)thiomorpholine 1,1-dioxide

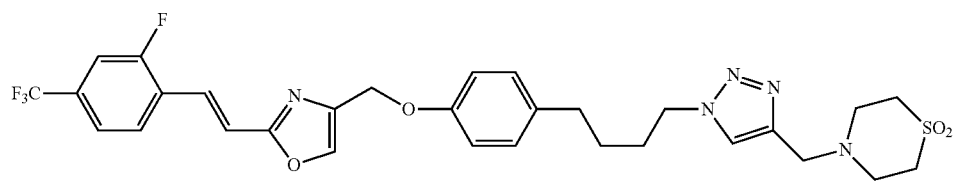 [SMILES: O=S1(=O)CCN(Cc2cn(CCCCc3ccc(OCc4coc(/C=C/c5ccc(C(F)(F)F)cc5F)n4)cc3)nn2)CC1]

Step 1: (E)-4-(4-((2-(2-fluoro-4-(trifluoromethyl)styryl)oxazol-4-yl)methoxy)phenyl)butan-1-ol

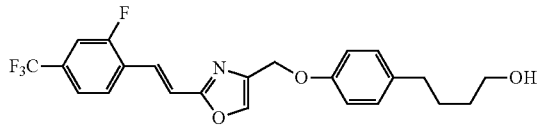 [SMILES: OCCCCc1ccc(OCc2coc(/C=C/c3ccc(C(F)(F)F)cc3F)n2)cc1]

A mixture of (E)-4-(chloromethyl)-2-(2-fluoro-4-(trifluoromethyl)styryl)oxazole (1.159 g, 3.79 mmol), K$_2$CO$_3$ (0.786 g, 5.69 mmol) and 4-(4-hydroxybutyl)phenol (0.63 g, 3.79 mmol) in DMF (12 ml) was heated overnight at 75° C. The solvent removed and the residue was purified on ISCO using a RediSep® column (Hx-EA; 20-100%) to give 1.00 g of the title compound. $^1$H NMR (400 MHz, DMSO-d$_6$) δ ppm 1.42 (s, 2H) 1.49-1.61 (m, 2H) 3.39 (q, J=5.50 Hz, 2H) 4.35 (t, J=5.28 Hz, 1H) 4.99 (s, 2H) 6.94 (d, J=8.61 Hz, 2H) 7.11 (d, J=8.22 Hz, 2H) 7.39 (d, J=16.43 Hz, 1H) 7.59 (d, J=16.82 Hz, 1H) 7.64 (d, J=8.22 Hz, 1H) 7.77 (s, 1H) 8.16 (t, J=7.83 Hz, 1H) 8.26 (s, 1H).

Step 2: (E)-4-((4-(4-azidobutyl)phenoxy)methyl)-2-(2-fluoro-4-(trifluoromethyl)styryl)oxazole

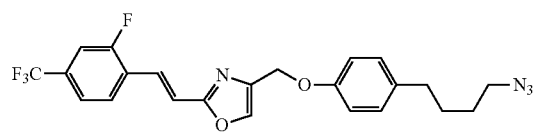 [SMILES: [N-]=[N+]=NCCCCc1ccc(OCc2coc(/C=C/c3ccc(C(F)(F)F)cc3F)n2)cc1]

This compound was prepared in a similar fashion as compound 1 step 2 with (E)-4-(4-((2-(2-fluoro-4-(trifluoromethyl)styryl)oxazol-4-yl)methoxy)phenyl)butan-1-ol, method B. LRMS+H$^+$: 461.0.

Step 3: (E)-4-((1-(4-(4-((2-(2-fluoro-4-(trifluoromethyl)styryl)oxazol-4-yl)methoxy)phenyl)butyl)-1H-1,2,3-triazol-4-yl)methyl)thiomorpholine 1,1-dioxide

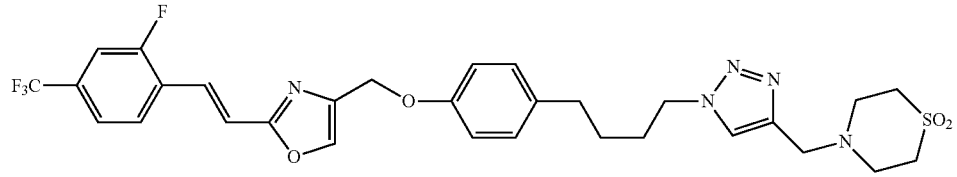 [SMILES: O=S1(=O)CCN(Cc2cn(CCCCc3ccc(OCc4coc(/C=C/c5ccc(C(F)(F)F)cc5F)n4)cc3)nn2)CC1]

This compound was prepared in a similar way as compound 12 step 1 with the previous intermediate and 4-(prop-2-yn-1-yl)thiomorpholine 1,1-dioxide. $^1$H NMR (400 MHz, DMSO-d$_6$) δ ppm 1.48 (quin, J=7.20 Hz, 2H) 1.80 (quin, J=7.24 Hz, 2H) 2.51-2.57 (m, 2H) 2.89 (br. s., 4H) 3.09 (br. s., 4H) 3.76 (br. s., 2H) 4.36 (t, J=7.04 Hz, 2H) 4.99 (s, 2H) 6.94 (d, J=8.22 Hz, 2H) 7.09 (d, J=8.61 Hz, 2H) 7.39 (d, J=16.43 Hz, 1H) 7.59 (d, J=16.43 Hz, 1H) 8.02 (s, 1H) 8.16 (s, 1H) 8.26 (s, 1H).

Compound 72: (E)-4-(2-(4-(((4-(4-(1H-1,2,3-triazol-1-yl)butyl)phenoxy)methyl)oxazol-2-yl)vinyl)-N-(2-(5-(dimethylamino)naphthalene-1-sulfonamido)ethyl)benzamide

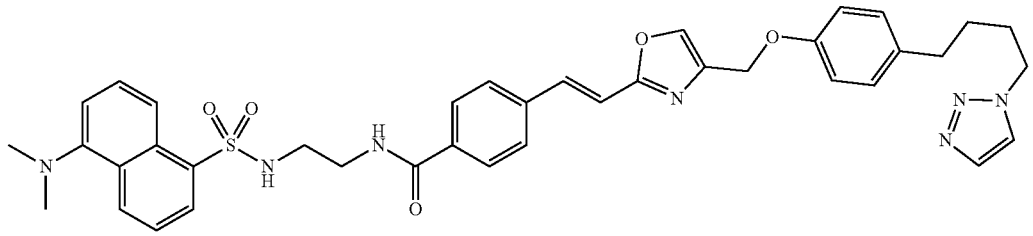 [SMILES: CN(C)c1cccc2c(S(=O)(=O)NCCNC(=O)c3ccc(/C=C/c4nc(COc5ccc(CCCCn6ccnn6)cc5)co4)cc3)cccc12]

Step 1: N-(2-aminoethyl)-5-(dimethylamino)naphthalene-1-sulfonamide

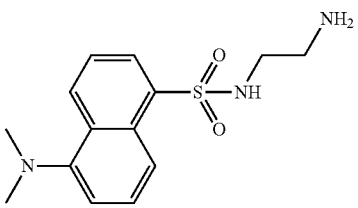 [SMILES: CN(C)c1cccc2c(S(=O)(=O)NCCN)cccc12]

In a 100 mL round-bottomed flask was added ethylenediamine (2.503 ml, 37.1 mmol) in CH$_2$C$_2$(13.75 ml) to give a colorless solution. Cooled to 0° C. A solution of 5-(dimethylamino)naphthalene-1-sulfonyl chloride (0.5 g, 1.854 mmol) in CH$_2$Cl$_2$ (15.00 ml) was added dropwise over 45 minutes. Warmed to 20° C. and stirred o/n. After 22 hrs, HCl 2M in water (46.3 ml, 93 mmol) was added and stirred vigorously for 10 minutes. Separated layers. The aqueous layer was washed with CH$_2$Cl$_2$ (10 mL). Basified the aqueous layer to pH 9 with KOH 45% wt. in water (5.00 ml, 58.4 mmol). Extracted the aqueous layer with CH$_2$Cl$_2$ (2×15 mL). The combined organic layers was dried over MgSO4, filtered and concentrated to dryness to give N-(2-aminoethyl)-5-(dimethylamino)naphthalene-1-sulfonamide (457 mg, 1.558 mmol, 84% yield) as a yellow foam. $^1$H NMR (400 MHz, DMSO-d$_6$) δ ppm 2.47 (m, J=6.30 Hz, 2H) 2.77 (m, J=12.90, 6.30 Hz, 2H) 2.83 (s, 6H) 3.35 (br. s., 2H) 7.26 (d, J=7.43 Hz, 1H) 7.36 (s, 1H) 7.55-7.67 (m, 2H) 8.06-8.13 (m, 1H) 8.30 (d, J=8.61 Hz, 1H) 8.46 (d, J=8.61 Hz, 1H).

Step 2: (E)-4-(2-(4-((4-(4-(1H-1,2,3-triazol-1-yl)butyl)phenoxy)methyl)oxazol-2-yl)vinyl)-N-(2-(5-(dimethylamino)naphthalene-1-sulfonamido)ethyl)benzamide

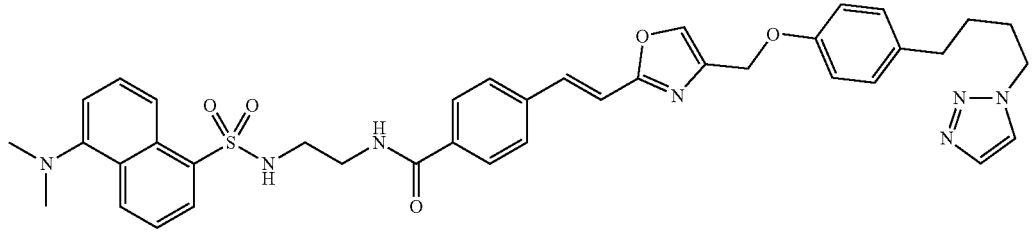 [SMILES: CN(C)c1cccc2c(S(=O)(=O)NCCNC(=O)c3ccc(/C=C/c4nc(COc5ccc(CCCCn6ccnn6)cc5)co4)cc3)cccc12]

This compound was prepared in a similar fashion as the compound 59 step 2 using (E)-4-(2-(4-((4-(4-(1H-1,2,3-triazol-1-yl)butyl)phenoxy)methyl)oxazol-2-yl)vinyl)benzoic acid and the previous amine. $^1$H NMR (400 MHz, DMSO-d$_6$) δ ppm 1.48 (quin, J=7.50 Hz, 2H) 1.81 (quin, J=7.50 Hz, 2H) 2.52-2.58 (m, 2H) 2.81 (s, 6H) 2.95 (q, J=6.52 Hz, 2H) 3.22-3.31 (m, 2H) 4.39 (t, J=7.04 Hz, 2H) 4.97 (s, 2H) 6.94 (m, J=8.61 Hz, 2H) 7.09 (m, J=8.61 Hz, 2H) 7.20-7.32 (m, 2H) 7.51-7.65 (m, 3H) 7.70 (s, 1H) 7.73-7.81 (m, 4H) 8.03-8.14 (m, 3H) 8.21 (s, 1H) 8.28 (d, J=8.61 Hz, 1H) 8.39-8.49 (m, 2H).

Compound 73: 4-((44-(1H-1,2,3-triazol-1-yl)butyl)phenoxy)methyl)-2-(5-fluoro-1H-indol-2-yl)oxazole

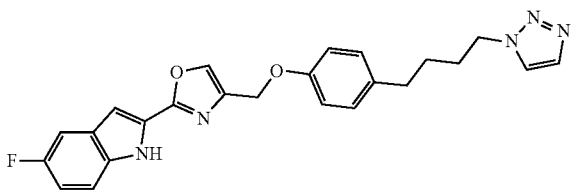 [SMILES: Fc1ccc2[nH]c(-c3nc(COc4ccc(CCCCn5ccnn5)cc4)co3)cc2c1]

This compound was prepared as described in Example 3 (page 18) of US patent application publication no. 2006/0063812. LRMS+H$^+$: 432.1.

Compound 74: (E)-4-((4-(4-(1H-1,2,3-triazol-1-yl)butyl)phenoxy)methyl)-2-(2-(4-(trifluoromethyl)phenyl)prop-1-en-1-yl)oxazole

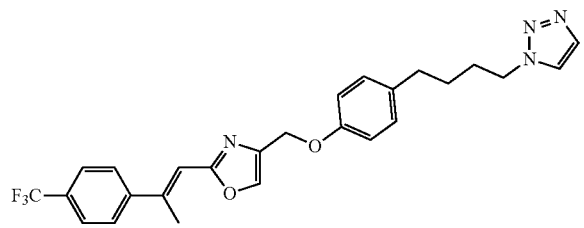 [SMILES: C/C(=C\c1nc(COc2ccc(CCCCn3ccnn3)cc2)co1)c1ccc(C(F)(F)F)cc1]

In a 5 mL round-bottomed flask was added NaH 60% wt. in mineral oil (8.53 mg, 0.213 mmol) in DMSO (500 µl) to give a grey suspension. Trimethylsulfoxonium iodide (46.9 mg, 0.213 mmol) was added in one portion. The reaction mixture was stirred at 20° C. for 30 minutes. (E)-4-((4-(4-(1H-1,2,3-triazol-1-yl)butyl)phenoxy)methyl)-2-(4-(trifluoro-methyl)styryl)oxazole (42.5 mg, 0.091 mmol) was added. Heated to 35° C. for 22 hours. In a 5 mL vial was added NaH 60% wt. in mineral oil (8.53 mg, 0.213 mmol) in DMSO (500 µl) to give a gray suspension. Trimethylsulfoxonium iodide (100 mg, 0.454 mmol) was added. Stirred for 30 minutes. Added the ylide mixture to the reaction flask and rinsed vial with DMSO (500 µl). Continued stirring at 35° C. for 12 days. Poured the reaction mixture in Water (5 mL) and rinsed flask with MeOH (1.5 mL) and added to the resulting suspension. Stirred the suspension o/n. The mixture was extracted with CH$_2$Cl$_2$ (2×5 mL). The combined organic layers were washed with water (10 mL). The organic layer was dried over MgSO$_4$, filtered and concentrated and the residue was purified on ISCO using a RediSep® column (Hex-EtOAc; 0-100%) to give (E)-4-((4-(4-(1H-1,2,3-triazol-1-yl)butyl)phenoxy)methyl)-2-(2-(4-(trifluoromethyl)phenyl) prop-1-en-1-yl)oxazole (8 mg, 0.017 mmol, 18.28% yield). $^1$H NMR (400 MHz, DMSO-d$_6$) δ ppm 8.22 (s, 1H), 8.11 (s, 1H), 7.86 (d, J=8.2 Hz, 2H), 7.77 (d, J=8.6 Hz, 2H), 7.70 (s, 1H), 7.07-7.13 (m, J=8.6 Hz, 2H), 6.91-6.99 (m, J=8.6 Hz, 2H), 6.82 (s, 1H), 5.01 (s, 2H), 4.39 (t, J=7.0 Hz, 2H), 2.61-2.69 (m, 2H), 2.52-2.58 (m, 3H), 1.81 (quin, J=7.2 Hz, 2H), 1.40-1.54 (m, 2H).

Compound 75: 5-((4-(41H-1,2,3-triazol-1-yl)butyl)phenoxy)methyl)-2-(4-(trifluoromethyl)phenyl) pyridine

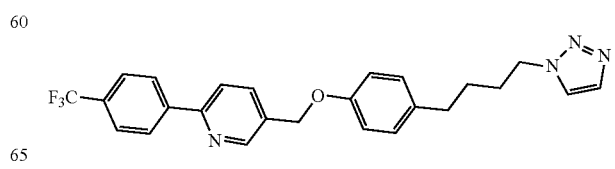

Step 1: Methyl 6-(4-(trifluoromethyl)phenyl)nicotinate

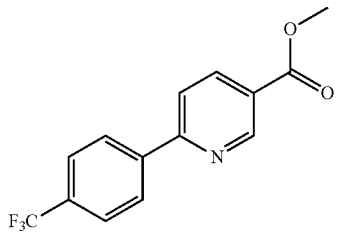 [SMILES: COC(=O)c1ccc(-c2ccc(C(F)(F)F)cc2)nc1]

In a 200 mL round-bottomed flask were added methyl 6-chloronicotinate (2 g, 11.66 mmol) and (4-(trifluoromethyl)phenyl)boronic acid (2.435 g, 12.82 mmol) in dioxane (43.7 ml) to give a tan solution. Cesium fluoride (6.20 g, 40.8 mmol) was added. Nitrogen was bubbled in the flask for 5 minutes. Pd(dppf)Cl$_2$·DCM (0.286 g, 0.350 mmol) was added. Nitrogen was bubbled in the flask for 5 minutes. Heated to 100° C. for 2 days. Diluted the reaction mixture with EtOAc (50 mL). Filtered the mixture over celite and rinsed with EtOAc (2×25 mL). Concentrated to dryness and the residue was purified on ISCO using a RediSep® Gold column (Hex-EtOAc; 0-40%) to give 2.35 g of the title compound. $^1$H NMR (400 MHz, DMSO-d$_6$) δ ppm 9.21 (d, J=2.0 Hz, 1H), 8.34-8.46 (m, 3H), 8.25 (d, J=8.6 Hz, 1H), 7.90 (d, J=8.2 Hz, 2H), 3.92 (s, 3H).

Step 2: (6-(4-(trifluoromethyl)phenyl)pyridin-3-yl)methanol

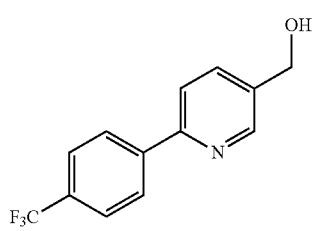

To a 0-5° C. solution of methyl 6-(4-(trifluoromethyl) phenyl) nicotinate (2.35 g, 8.36 mmol) in THF (25.7 ml) was added LiAlH$_4$ (0.327 g, 8.61 mmol. It was stirred at 0° C. for 1 hour and diluted with Et$_2$O (75 mL). Water (0.327 ml) was then added slowly followed by NaOH 15% wt. in water (0.327 ml) then by water (0.980 ml). Warmed to 20° C. and stirred for 15 minutes. Added anhydrous MgSO$_4$ and stirred for 15 minutes. Filtered the mixture to remove the salts and rinsed with Et$_2$O (3×15 mL). Concentrated to dryness to give 2.05 g of the title compound. $^1$H NMR (400 MHz, DMSO-d$_6$) δ ppm 8.66 (d, J=2.0 Hz, 1H), 8.30 (d, J=8.2 Hz, 2H), 8.05 (d, J=7.8 Hz, 1H), 7.80-7.90 (m, 3H), 5.39 (t, J=5.8 Hz, 1H), 4.60 (d, J=5.8 Hz, 2H).

Step 3: 5-(chloromethyl)-2-(4-(trifluoromethyl)phenyl)pyridine

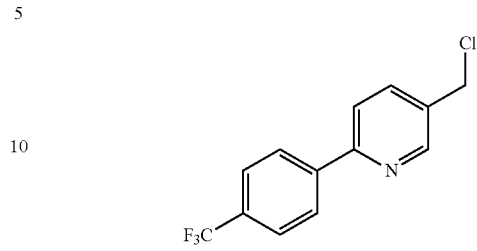

In a 100 mL round-bottomed flask was added (6-(4-(trifluoromethyl)phenyl)pyridin-3-yl)methanol (1 g, 3.95 mmol) in CH$_2$Cl$_2$ (19 ml). Cooled to 0° C. and SOCl$_2$ (0.576 ml, 7.90 mmol) was added dropwise. Stirred at 0° C. for 5 minutes then warmed to 20° C. After 30 minutes, poured reaction mixture into ice+sat. NaHCO$_3$ (10 g+30 mL). Stirred for 5 minutes. Extracted with EtOAc (2×30 mL). The combined organic layers were washed with water (30 mL) then brine (25 mL). The organic layer was dried over MgSO$_4$, filtered and concentrated to give 1.07 g of the title compound. $^1$H NMR (400 MHz, DMSO-d$_6$) δ ppm 8.79 (d, J=2.3 Hz, 1H), 8.29-8.35 (m, J=8.2 Hz, 2H), 8.12 (d, J=8.2 Hz, 1H), 8.02 (dd, J=8.2, 2.3 Hz, 1H), 7.83-7.90 (m, J=8.2 Hz, 2H), 4.90 (s, 2H).

Step 4: 5-((4-(4-(1H-1,2,3-triazol-1-yl)butyl)phenoxy)methyl)-2-(4-(trifluoromethyl)phenyl)pyridine

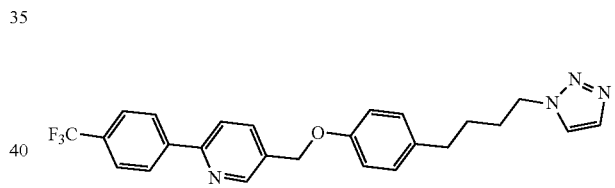

This compound was prepared according to compound 1 step 5. $^1$H NMR (400 MHz, DMSO-d$_6$) δ ppm 8.79 (d, J=1.6 Hz, 1H), 8.28-8.36 (m, J=8.2 Hz, 2H), 8.08-8.14 (m, 2H), 8.00 (dd, J=8.2, 2.0 Hz, 1H), 7.83-7.89 (m, J=8.2 Hz, 2H), 7.70 (s, 1H), 7.06-7.14 (m, J=8.6 Hz, 2H), 6.92-6.99 (m, J=8.6 Hz, 2H), 5.18 (s, 2H), 4.39 (t, J=7.0 Hz, 2H), 2.52-2.58 (m, 2H), 1.80 (quin, J=7.3 Hz, 2H), 1.48 (quin, J=7.6 Hz, 2H).

Compound 76: 4-((4-(4-(1H-1,2,3-triazol-1-yl)butyl)phenoxy)methyl)-2-(2-(4-(trifluoromethyl)phenyl)cyclopropyl)oxazole

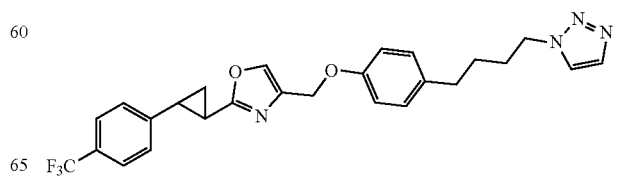

Step 1: (E)-ethyl 3-(4-(trifluoromethyl)phenyl)acrylate

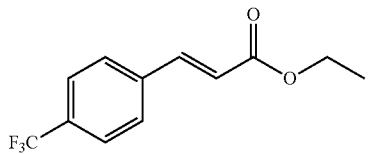 [SMILES: CCOC(=O)/C=C/c1ccc(C(F)(F)F)cc1]

In a 100 mL round-bottomed flask were added (E)-3-(4-(trifluoromethyl)phenyl)acrylic acid (2 g, 9.25 mmol) and sulfuric acid (0.200 ml, 3.75 mmol) in anhydrous ethanol (20.00 ml) to give a white suspension. Heated to reflux and stirred 19 hours. Concentrated the reaction mixture to dryness. The residue was neutralized with sat. NaHCO$_3$ (15 mL). Extracted with EtOAc (3×15 mL). The combined organic layers were washed with brine (15 mL). The organic layer was dried over MgSO$_4$, filtered and concentrated to give (E)-ethyl 3-(4-(trifluoromethyl)phenyl)acrylate (2.20 g, 9.01 mmol, 97% yield) as a white solid. $^1$H NMR (400 MHz, DMSO-d$_6$) δ ppm 7.95 (d, J=8.2 Hz, 2H), 7.77 (d, J=8.2 Hz, 2H), 7.72 (d, J=16.0 Hz, 1H), 6.79 (d, J=16.0 Hz, 1H), 4.21 (q, J=7.0 Hz, 2H), 1.27 (t, J=7.0 Hz, 3H).

Step 2: Ethyl 2-(4-(trifluoromethyl)phenyl)cyclopropanecarboxylate

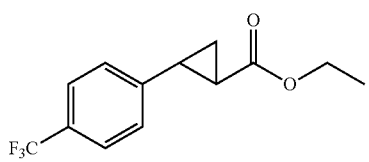

In a 100 mL round-bottomed flask was added NaH 60% wt. in mineral oil (0.649 g, 16.22 mmol) in DMSO (22 ml) to give a grey suspension. Trimethylsulfoxonium iodide (3.57 g, 16.22 mmol) was added in portions. Stirred for 30 minutes. A solution of (E)-ethyl 3-(4-(trifluoromethyl)phenyl)acrylate (2.2 g, 9.01 mmol) in DMSO (9 ml) and THF (9 ml) was added. Stirred at 20° C. for 19 hours. The reaction mixture was quenched with HCl 1M (10 mL). The mixture was extracted with EtOAc (2×20 mL). The combined organic layers were washed with water (3×20 mL) then with Brine (20 mL). The organic layer was dried over MgSO$_4$, filtered and concentrated to give 1.8 g as an orange oil. The residue was purified on ISCO using a RediSep® column (Hexane-Et$_2$O; 0-50%) to give 0.703 g of the title compound. $^1$H NMR (400 MHz, DMSO-d$_6$) δ ppm 7.57-7.66 (m, J=8.2 Hz, 2H), 7.37-7.45 (m, J=7.8 Hz, 2H), 4.11 (q, J=7.3 Hz, 2H), 2.51-2.59 (m, 1H), 2.00-2.09 (m, 1H), 1.52 (dt, J=9.5, 4.8 Hz, 1H), 1.41-1.49 (m, 1H), 1.20 (t, J=7.2 Hz, 3H).

Step 3: 2-(4-(trifluoromethyl)phenyl)cyclopropanecarboxylic acid

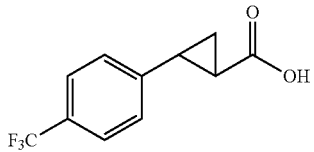

In a 50 mL round-bottomed flask was added ethyl 2-(4-(trifluoromethyl)phenyl) cyclopropanecarboxylate (0.700 g, 2.71 mmol) in ethanol (7 ml) to give a colorless solution. NaOH 1M in water (7.00 ml, 7.00 mmol) was added. The resulting mixture was stirred at 20° C. for 1.5 hour. Concentrated to ca. 5 mL on rotovap. Acidified to pH 3 with HCl 2M in water (2.60 ml, 5.20 mmol). Extracted the aqueous layer with EtOAc (2×15 mL). The combined organic layers were washed with Brine (15 mL). The organic layer was dried over MgSO$_4$, filtered and concentrated to give 2-(4-(trifluoromethyl)phenyl) cyclopropanecarboxylic acid (582 mg, 2.53 mmol, 93% yield). $^1$H NMR (400 MHz, DMSO-d$_6$) δ ppm 12.42 (br. s., 1H), 7.58-7.65 (m, J=8.2 Hz, 2H), 7.36-7.44 (m, J=8.2 Hz, 2H), 2.52-2.54 (m, 1H), 1.87-1.96 (m, 1H), 1.49 (dt, J=9.2, 4.8 Hz, 1H), 1.41 (ddd, J=8.4, 6.3, 4.5 Hz, 1H).

Step 4: 2-(4-(trifluoromethyl)phenyl)cyclopropanecarboxamide

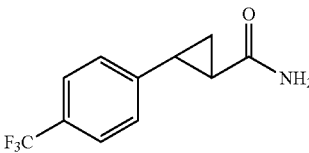 [SMILES: NC(=O)C1CC1c1ccc(C(F)(F)F)cc1]

In a 100 mL round-bottomed flask were added 2-(4-(trifluoromethyl)phenyl) cyclopropanecarboxylic acid (0.58 g, 2.52 mmol) and DMF (9.76 µl, 0.126 mmol) in CH$_2$Cl$_2$ (16 ml) to give a light yellow solution. Cooled to 0° C. Oxalyl chloride (0.287 ml, 3.28 mmol) was added slowly. Warmed to 20° C. and stirred for 1 hour. Concentrated the reaction mixture to dryness. The resulting residue was dissolved in CH$_2$Cl$_2$ (13 ml) and cooled to 0° C. NH$_4$OH$_{conc}$ (0.851 ml, 12.60 mmol) was added. After 30 minutes, concentrated to dryness on rotovap. The resulting solid was suspended in EtOH (6 mL) and heated to reflux to obtain a solution. Added slowly water (6 mL). The resulting slurry was cooled to 20° C. Water (6 mL) was added and stirred the resulting suspension for 1 hour. The solids were collected on Buchner and the cake was washed with water (3×3 mL). Dried the product at 20° C. under high vacuum until constant weight to give 2-(4-(trifluoromethyl) phenyl)cyclopropanecarboxamide (525 mg, 2.291 mmol, 91% yield). $^1$H NMR (400 MHz, DMSO-d$_6$) δ ppm 7.62 (d, J=8.2 Hz, 3H), 7.35 (d, J=8.2 Hz, 2H), 6.95 (br. s., 1H), 2.26-2.37 (m, 1H), 1.86-1.96 (m, 1H), 1.39 (dt, J=9.1, 4.6 Hz, 1H), 1.28 (ddd, J=8.3, 5.8, 4.3 Hz, 1H).

Step 5: 4-(chloromethyl)-2-(2-(4-(trifluoromethyl)phenyl)cyclopropyl)oxazole

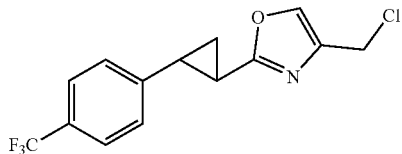

In a 15 mL sealed tube were added 2-(4-(trifluoromethyl)phenyl) cyclopropanecarboxamide (0.250 g, 1.091 mmol) and 1,3-dichloropropan-2-one (0.208 g, 1.636 mmol) in toluene (1.5 ml) and DMF (0.3 ml) to give a tan solution. Sealed the vial and heated to 120° C. for 22 hours. Cooled the mixture to 20° C., added CH$_2$Cl$_2$ (5 mL) and stirred for 15 minutes. Filtered over glass wool in pipet to remove dark unsoluble solid. Concentrated to dryness. The residue was purified on ISCO using a RediSep® column (Hex-EtOA: 0-50%) to give 4-(chloromethyl)-2-(2-(4-(trifluoromethyl)phenyl) cyclopropyl)oxazole (187 mg, 0.620 mmol, 56.8% yield). $^1$H NMR (400 MHz, DMSO-d$_6$) δ ppm 8.04 (s, 1H), 7.60-7.68 (m, J=8.2 Hz, 2H), 7.43-7.49 (m, J=8.2 Hz, 2H), 4.62 (s, 2H), 2.59-2.69 (m, 1H), 2.52-2.59 (m, 1H), 1.66-1.73 (m, 1H), 1.63 (dt, J=8.9, 5.5 Hz, 1H).

Step 6: 4-((4-(4-(1H-1,2,3-triazol-1-yl)butyl)phenoxy)methyl)-2-(2-(4-(trifluoromethyl)phenyl)cyclopropyl)oxazole

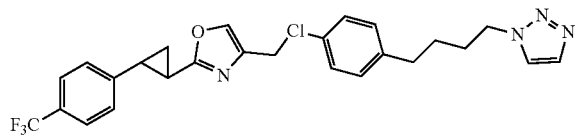

This compound was prepared according to compound 1 step 5. $^1$H NMR (400 MHz, DMSO-d$_6$) δ ppm 8.24 (s, 1H), 8.11 (s, 1H), 7.91-8.00 (m, J=8.2 Hz, 2H), 7.73-7.81 (m, J=8.2 Hz, 2H), 7.70 (s, 1H), 7.62 (d, J=16.4 Hz, 1H), 7.34 (d, J=16.4 Hz, 1H), 7.05-7.13 (m, J=8.2 Hz, 2H), 6.90-6.98 (m, J=8.6 Hz, 2H), 4.98 (s, 2H), 4.39 (t, J=7.0 Hz, 2H), 2.52-2.57 (m, 2H), 1.81 (quin, J=7.3 Hz, 2H), 1.48 (quin, J=7.6 Hz, 2H).

Compound 77: Methyl 2-((4-(4-(1H-1,2,3-triazol-1-yl)butyl)phenoxy)methyl)oxazole-4-carboxylate

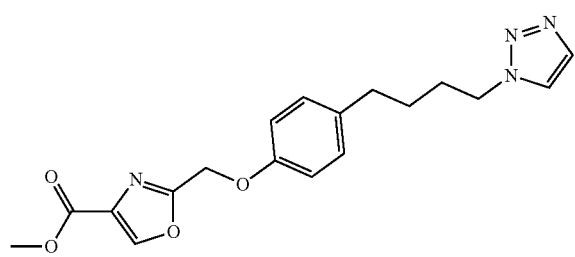 [SMILES: COC(=O)c1coc(COc2ccc(CCCCn3ccnn3)cc2)n1]

Step 1: Methyl 2-(dichloromethyl)-4,5-dihydrooxazole-4-carboxylate

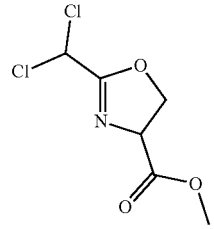

In a 200 mL round-bottomed flask was added sodium methoxide 30% wt. in MeOH (1.690 ml, 9.10 mmol) in MeOH (18 ml) to give a colorless solution. Cooled to −10° C. 2,2-dichloroacetonitrile (7.30 ml, 91 mmol) was added dropwise over 15 minutes. Continued stirring at that temperature for 20 minutes. A suspension of methyl 2-amino-3-hydroxypropanoate hydrochloride (14.15 g, 91 mmol) in MeOH (15 ml) was added to the reaction mixture. Slowly warmed to 20° C. and stirred for 19.5 hours. CH$_2$Cl$_2$ (51 ml) and water (29 ml) were added. Stirred vigorously for 5 minutes. Separated layers. The organic layer was concentrated to dryness on rotovap. The aqueous layer was extracted 2 times with CH$_2$Cl$_2$ (29 ml). The combined extracts were added to the concentrated 1st organic layer. The organic layer was dried over MgSO$_4$, filtered and concentrated to dryness to give methyl 2-(dichloromethyl)-4,5-dihydrooxazole-4-carboxylate (17.64 g, 83 mmol, 91% yield). $^1$H NMR (400 MHz, CDCl$_3$) δ ppm 6.29 (s, 1H), 4.85-4.96 (m, 1H), 4.76 (t, J=8.6 Hz, 1H), 4.61-4.72 (m, 1H), 3.83 (s, 3H).

Step 2: Methyl 2-(chloromethyl)-4-methoxy-4,5-dihydrooxazole-4-carboxylate

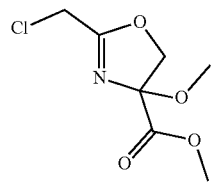

In a 200 mL round-bottomed flask was added methyl 2-(dichloromethyl)-4,5-dihydrooxazole-4-carboxylate (17.64 g, 83 mmol) in MeOH (19 ml) to give an orange solution. Cooled to 0° C. Sodium methoxide 30% wt. in methanol (15.46 ml, 83 mmol) was added dropwise over 50 minutes. Slowly warmed the resulting light orange suspension to 20° C. and stirred for 18 hours. CH$_2$Cl$_2$ (54 ml) and water (30 ml) were added. Stirred vigorously for 5 minutes. Separated layers. The organic layer was concentrated to dryness on rotovap. The aqueous layer was extracted 2 times with CH$_2$Cl$_2$ (30 ml). The combined extracts were added to the concentrated 1st organic layer. The organic layer was dried over MgSO$_4$, filtered and concentrated to give methyl 2-(chloromethyl)-4-methoxy-4,5-dihydrooxazole-4-carboxylate (16.25 g, 78 mmol, 94% yield). $^1$H NMR (400 MHz, CDCl$_3$) δ ppm 4.59 (d, J=10.6 Hz, 1H), 4.39 (d, J=10.6 Hz, 1H), 4.15-4.27 (m, 2H), 3.85 (s, 3H), 3.41 (s, 3H).

Step 3: Methyl 2-(chloromethyl)oxazole-4-carboxylate

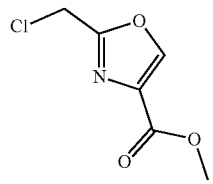

In a 200 mL round-bottomed flask was added methyl 2-(chloromethyl)-4-methoxy-4,5-dihydrooxazole-4-carboxylate (16.25 g, 78 mmol) in toluene (38 ml) to give an orange solution. CSA (2.73 g, 11.74 mmol) was added. Heated to 70° C. for 1 hour then cooled to 20° C. The organic layer was washed with $K_2CO_3$ 10% wt. in water (23 ml) then with water (30 ml). Combined the aqueous layers and back extracted with toluene (45 ml). The combined organic layers were dried over $MgSO_4$, filtered and concentrated to give 9.8 g as a brown solid. The residue was purified on ISCO using a RediSep® column (Hexane-$Et_2O$; 0-90%) to give methyl 2-(chloromethyl)oxazole-4-carboxylate (4.94 g, 28.1 mmol, 35.9% yield). $^1$H NMR (400 MHz, DMSO-$d_6$) δ ppm 8.93 (s, 1H), 4.95 (s, 2H), 3.82 (s, 3H).

Step 4: Methyl 2-((4-(4-(1H-1,2,3-triazol-1-yl)butyl)phenoxy)methyl)oxazole-4-carboxylate

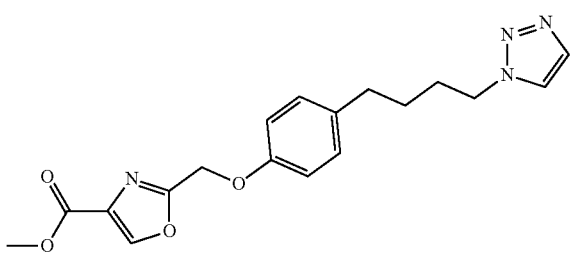 [SMILES: COC(=O)c1coc(COc2ccc(CCCCn3ccnn3)cc2)n1]

This compound was prepared according to compound 1 step 5. $^1$H NMR (400 MHz, DMSO-$d_6$) δ ppm 8.91 (s, 1H), 8.10 (s, 1H), 7.70 (s, 1H), 7.07-7.15 (m, J=8.6 Hz, 2H), 6.90-6.97 (m, J=8.6 Hz, 2H), 5.25 (s, 2H), 4.38 (t, J=7.0 Hz, 2H), 3.81 (s, 3H), 2.52-2.57 (m, 2H), 1.80 (quin, J=7.3 Hz, 2H), 1.47 (quin, J=7.7 Hz, 2H).

Compound 78: 2-((4-(4-(1H-1,2,3-triazol-1-yl)butyl)phenoxy)methyl)-N-(2-nitro-4-(trifluoromethyl) phenyl)oxazole-4-carboxamide

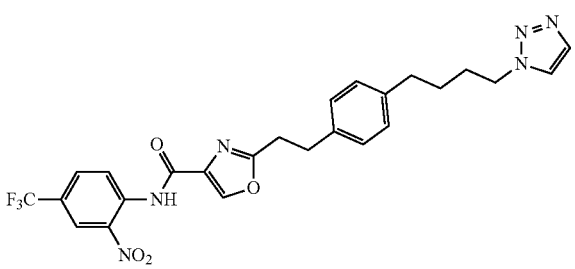 [SMILES: O=C(Nc1ccc(C(F)(F)F)cc1[N+](=O)[O-])c1coc(CCc2ccc(CCCCn3ccnn3)cc2)n1]

Step 1: 2-((4-(4-(1H-1,2,3-triazol-1-yl)butyl)phenoxy)methyl)oxazole-4-carboxylicacid

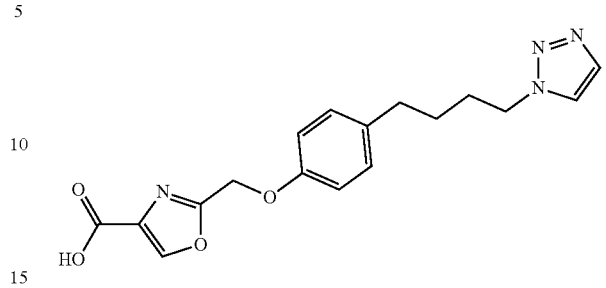

In a 10 mL round-bottomed flask was added methyl 2-((4-(4-(1H-1,2,3-triazol-1-yl)butyl)phenoxy)methyl)oxazole-4-carboxylate (0.23 g, 0.645 mmol) in THF (2.3 ml) to give a tan suspension. NaOH 0.5M in water (1.291 ml, 0.645 mmol) was added. Stirred at 20° C. for 17 hours. More NaOH 0.5M in water (0.581 ml, 0.290 mmol) was added. After 19 hours, acidified by slow addition of HCl 0.5M in water (1.936 ml, 0.968 mmol) (after addition of 1 mL, the resulting suspension was stirred for 15 minutes before adding the remaining HCl). The resulting white suspension was stirred for 2 hours. Water (1 ml) was added and continued stirring for 1 hour. The solids were collected on Buchner and the cake was washed with water (2×1 mL). Dried the product at 30° C. under high vacuum until constant weight to give 2-((4-(4-(1H-1,2,3-triazol-1-yl)phenoxy)methyl)oxazole-4-carboxylic acid (208 mg, 0.608 mmol, 94% yield). $^1$H NMR (400 MHz, DMSO-$d_6$) δ ppm 13.14 (br. s., 1H), 8.77 (s, 1H), 8.09 (s, 1H), 7.68 (s, 1H), 7.04-7.13 (m, J=8.2 Hz, 2H), 6.87-6.97 (m, J=8.6 Hz, 2H), 5.21 (s, 2H), 4.37 (t, J=7.0 Hz, 2H), 2.50-2.56 (m, 2H), 1.78 (quin, J=7.3 Hz, 2H), 1.46 (quin, J=7.6 Hz, 2H).

Step 2: 2-((4-(4-(1H-1,2,3-triazol-1-yl)butyl)phenoxy)methyl)-N-(2-nitro-4-(trifluoromethyl) phenyl)oxazole-4-carboxamide

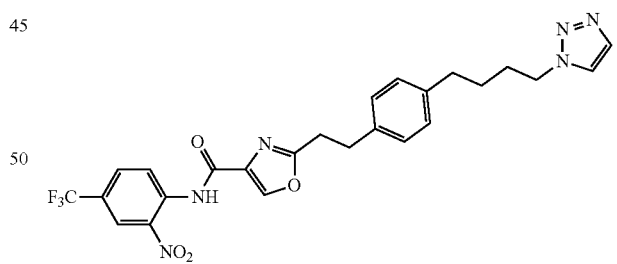

In a 10 mL round-bottomed flask were added 2-((4-(4-(1H-1,2,3-triazol-1-yl)butyl)phenoxy)methyl)oxazole-4-carboxylic acid (75 mg, 0.219 mmol) in THF (750 µl) and $CH_2Cl_2$ (750 µl, 11.65 mmol) to give a white suspension. CDI (39.1 mg, 0.241 mmol) was added. Heated to 40-45° C. After 45 minutes, more CDI (39.1 mg, 0.241 mmol) was added. 2-nitro-4-(trifluoromethyl)aniline (49.7 mg, 0.241 mmol) was added and cooled to 20° C. After 19.5 hours, more 2-nitro-4-(trifluoromethyl)aniline (49.7 mg, 0.241 mmol) was added. After 26.5 hrs, added DBU (16.51 µl, 0.110 mmol) in 2-Me THF (2 mL). Heated to 65° C. for 30 minutes then for 18 hours at 20° C. Cooled the suspension to 0° C. and stirred for 1 hour. The solids were collected on Buchner and the cake was washed with cold 2-Me THF (3×0.5 mL). Dried the product at 40° C. under high vacuum until constant weight to give 2-((4-(4-(1H-1,2,3-triazol-1-yl)butyl)phenoxy)methyl)-N-(2-nitro-4-(trifluoromethyl)phenyl)oxazole-4-carboxamide (61 mg, 0.115 mmol, 52.5% yield). $^1$H NMR (400 MHz, DMSO-d$_6$) δ ppm 11.44 (s, 1H), 9.02 (s, 1H), 8.60 (d, J=8.6 Hz, 1H), 8.44 (s, 1H), 8.16-8.22 (m, 1H), 8.10 (s, 1H), 7.70 (s, 1H), 7.09-7.16 (m, J=8.6 Hz, 2H), 6.96-7.02 (m, J=8.6 Hz, 2H), 5.32 (s, 2H), 4.39 (t, J=7.0 Hz, 2H), 2.54 (t, J=7.4 Hz, 2H), 1.81 (quin, J=7.3 Hz, 2H), 1.48 (quin, J=7.6 Hz, 2H).

Compound 79: (E)-tert-butyl (4-(4-((2-(4-(trifluoromethyl)styryl)oxazol-4-yl)methoxy)phenyl)butyl)carbamate In a 50 mL round-bottomed flask was added 4-(4-methoxyphenyl)butan-1-amine (1.5 g, 8.37 mmol) in HBr 48% wt. in water (15 ml, 133 mmol) to give a white suspension. Heated to reflux (120° C.) for 4 hours. Cooled to 0° C. and stirred the resulting suspension for 1 hour. The solids were collected on Buchner. Dried the product at 20° C. under high vacuum until constant weight to give 4-(4-aminobutyl)phenol hydrobromide (1.40 g, 5.69 mmol, 68.0% yield). $^1$H NMR (400 MHz, DMSO-d$_6$) δ ppm 9.13 (s, 1H), 7.60 (br. s., 3H), 6.94-7.01 (m, J=8.2 Hz, 2H), 6.64-6.69 (m, J=8.6 Hz, 2H), 2.70-2.84 (m, 2H), 2.43-2.48 (m, 2H), 1.42-1.62 (m, 4H).

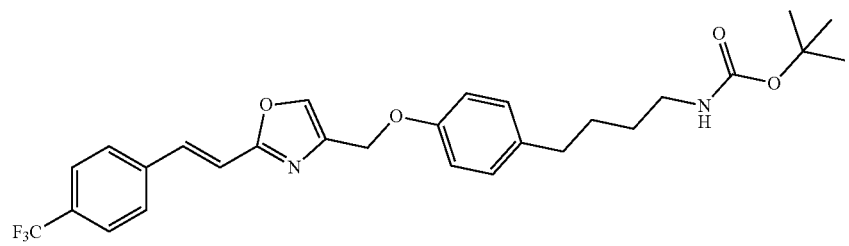 [SMILES: CC(C)(C)OC(=O)NCCCCc1ccc(OCc2coc(/C=C/c3ccc(C(F)(F)F)cc3)n2)cc1]

Step 1: 4-(4-methoxyphenyl)butan-1-amine

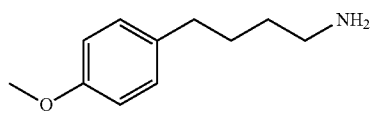

In a 25 mL round-bottomed flask was added 1-(4-azidobutyl)-4-methoxybenzene (1.75 g, 8.53 mmol) in THF (4.7 ml) to give a colorless solution. Triphenylphosphine (3.35 g, 12.79 mmol) and water (0.230 ml, 12.79 mmol) were added. Stirred at 20° C. for 22 hours. Concentrated to dryness on rotovap. The residue was purified on ISCO using a RediSep® column (DCM-DCM//MeOH/NH$_4$OH (77.5-22-2.5%); 0-100%) to give 4-(4-methoxyphenyl)butan-1-amine (1.51 g, 8.42 mmol, 99% yield). $^1$H NMR (400 MHz, DMSO-d$_6$) δ ppm 7.04-7.13 (m, J=8.2 Hz, 2H), 6.78-6.86 (m, 2H), 3.71 (s, 3H), 2.43-2.59 (m, 4H), 1.53 (quin, J=7.6 Hz, 2H), 1.32 (quin, J=7.2 Hz, 2H).

Step 2: 4-(4-aminobutyl)phenol hydrobromide

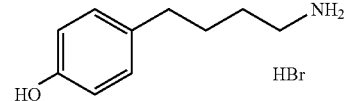 [SMILES: NCCCCc1ccc(O)cc1 ; Br]

Step 3: tert-butyl (4-(4-hydroxyphenyl)butyl)carbamate

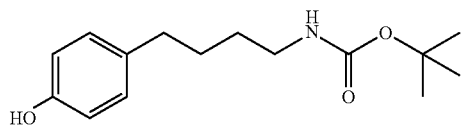 [SMILES: CC(C)(C)OC(=O)NCCCCc1ccc(O)cc1]

In a 250 mL round-bottomed flask was added 4-(4-aminobutyl)phenol hydrobromide (1.4 g, 5.69 mmol) in dioxane (56 ml) to give a tan suspension. A solution of sodium bicarbonate (1.911 g, 22.75 mmol) in water (56 ml) was added. Cooled to 0° C. BOC-Anhydride (1.453 ml, 6.26 mmol) was added. Slowly warmed to 20° C. After 21 hours, diluted the reaction mixture with EtOAc (209 ml). Separated layers. Washed organic layer with water (75 mL) then with Brine (75 mL). The organic layer was dried over MgSO$_4$, filtered and concentrated to give 1.89 g as a colorless oil. The residue was purified on ISCO using a RediSep® column (Hex-EtOAc; 0-60%) to give tert-butyl (4-(4-hydroxyphenyl)butyl)carbamate (1.23 g, 4.64 mmol, 81% yield). $^1$H NMR (400 MHz, DMSO-d$_6$) δ ppm 9.08 (s, 1H), 6.92-6.99 (m, J=8.2 Hz, 2H), 6.77 (t, J=5.7 Hz, 1H), 6.61-6.67 (m, J=8.2 Hz, 2H), 2.90 (q, J=6.7 Hz, 2H), 2.43 (t, J=7.4 Hz, 2H), 1.46 (quin, J=7.3 Hz, 2H), 1.29-1.41 (m, 11H).

Step 4: (E)-tert-butyl (4-(4-((2-(4-(trifluoromethyl)styryl)oxazol-4-yl)methoxy)phenyl)butyl) carbamate

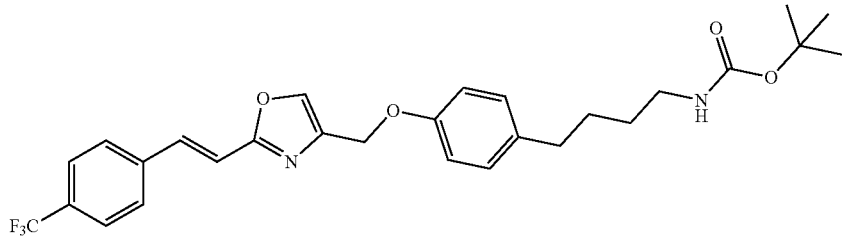 [SMILES: CC(C)(C)OC(=O)NCCCCc1ccc(OCc2coc(/C=C/c3ccc(C(F)(F)F)cc3)n2)cc1]

In a 25 mL round-bottomed flask were added (E)-4-(chloromethyl)-2-(4-(trifluoromethyl)styryl)oxazole (500 mg, 1.738 mmol), tert-butyl (4-(4-hydroxyphenyl)butyl)carbamate (484 mg, 1.825 mmol) and K$_2$CO$_3$ (264 mg, 1.912 mmol) in DMF (2.8 ml) to give a yellow suspension. Heated to 75° C. for 48 hours. Cooled to 20° C. MeOH (2.8 ml) and water (4.7 ml) were added. Stirred 5 hours. The solids were collected on Buchner and the cake was washed with water (3×3 mL). The wet solid was dissolved in warm DMF (2.8 ml). MeOH (2.8 ml) was added followed by slow addition of water (4.7 ml). Stirred the resulting suspension for 2 days. Added MeOH (2.8 mL). Stirred for 2 hours. The solids were collected on Buchner and the cake was washed with MeOH (3×1.5 mL). Dried the product at 30° C. under high vacuum until constant weight to give (E)-tert-butyl (4-(4-((2-(4-(trifluoromethyl)styryl)oxazol-4-yl)methoxy)phenyl)butyl) carbamate (352 mg, 0.681 mmol, 39.2% yield). $^1$H NMR (400 MHz, DMSO-d$_6$) δ ppm 8.24 (s, 1H), 7.91-8.00 (m, J=8.2 Hz, 2H), 7.73-7.81 (m, J=8.2 Hz, 2H), 7.62 (d, J=16.4 Hz, 1H), 7.34 (d, J=16.4 Hz, 1H), 7.06-7.16 (m, J=8.2 Hz, 2H), 6.88-6.98 (m, J=8.6 Hz, 2H), 6.73-6.82 (m, 1H), 4.99 (s, 2H), 2.92 (q, J=6.7 Hz, 2H), 2.47-2.49 (m, 2H), 1.43-1.56 (m, 2H), 1.28-1.43 (m, 11H).

Compound 80: (E)-4-((4-(4-(1H-1,2,3-triazol-1-yl)butyl)phenoxy)methyl)-2-(2-(pyridin-4-yl)vinyl)oxazole

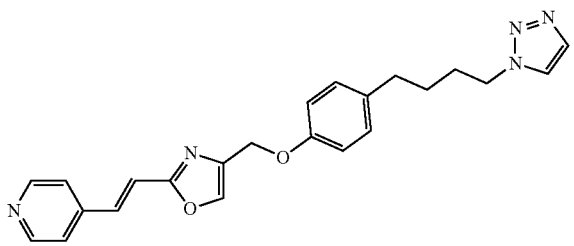 [SMILES: C(=C\c1nc(COc2ccc(CCCCn3ccnn3)cc2)co1)/c1ccncc1]

Step 1: Methyl 2-((diethoxyphosphoryl)methyl)oxazole-4-carboxylate

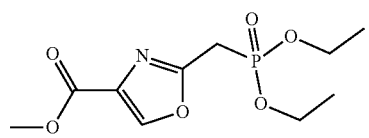 [SMILES: CCOP(=O)(Cc1nc(C(=O)OC)co1)OCC]

In a 15 mL round-bottomed flask were added methyl 2-(chloromethyl)oxazole-4-carboxylate (compound 85 step 3) (2.0 g, 11.39 mmol) in triethyl phosphite (3.59 ml, 20.50 mmol) to give a white suspension. Heated to 150° C. for 5.5 hours then cooled to 20° C. and stirred for 16 hours. The residue was purified on ISCO using a RediSep® column (Hexane-Et$_2$O; 0-100%) to give methyl 2-((diethoxyphosphoryl)methyl)oxazole-4-carboxylate (2.95 g, 10.64 mmol, 93% yield). $^1$H NMR (400 MHz, DMSO-d$_6$) δ ppm 8.80-8.85 (m, 1H), 4.05 (quin, J=7.3 Hz, 4H), 3.80 (s, 3H), 3.69 (s, 1H), 3.64 (s, 1H), 1.22 (t, J=7.0 Hz, 6H).

Step 2: (E)-methyl 2-(2-(pyridin-4-yl)vinyl)oxazole-4-carboxylate

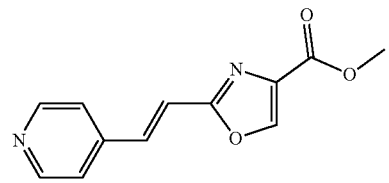 [SMILES: COC(=O)c1coc(/C=C/c2ccncc2)n1]

In a 15 mL round-bottomed flask was added NaH 60% wt. in mineral oil (0.063 g, 1.587 mmol) in THF (1.9 ml) to give a grey suspension. Cooled to −15° C. A solution of methyl 2-((diethoxyphosphoryl)methyl)oxazole-4-carboxylate (0.4 g, 1.443 mmol) in THF (2.8 ml) was added dropwise. Stirred at −15° C. for 10 minutes. Isonicotinaldehyde (0.140 ml, 1.486 mmol) was added in one portion. Slowly warmed to 0° C. After 2.5 hours, quenched by adding MeOH (1.0 ml). Warmed to 20° C. and stirred for 30 minutes. Concentrated to dryness on rotovap. The residue was purified on ISCO using a RediSep® column (CH$_2$Cl$_2$-MeOH; 0-100%) to give (E)-methyl 2-(2-(pyridin-4-yl)vinyl)oxazole-4-carboxylate (320 mg, 1.390 mmol, 96% yield). $^1$H NMR (400 MHz, DMSO-d$_6$) δ ppm 8.94 (s, 1H), 8.62 (d, J=5.9 Hz, 2H), 7.72 (d, J=6.3 Hz, 2H), 7.61 (d, J=16.4 Hz, 1H), 7.50 (d, J=16.4 Hz, 1H), 3.84 (s, 3H).

Step 3: (E)-(2-(2-(pyridin-4-yl)vinyl)oxazol-4-yl)methanol

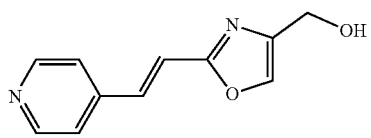 [SMILES: OCc1coc(/C=C/c2ccncc2)n1]

In a 15 mL round-bottomed flask was added (E)-methyl 2-(2-(pyridin-4-yl)vinyl)oxazole-4-carboxylate (0.15 g, 0.652 mmol) in $CH_2Cl_2$ (4 ml) to give a colorless solution. Cooled to −78° C. DIBAL-H 1M in dichloromethane (1.955 ml, 1.955 mmol) was added slowly to the white suspension. Stirred the resulting orange solution for 30 minutes at −78° C. then warmed to 0° C. After 30 minutes, poured reaction mixture in a biphasic mixture of $CH_2Cl_2$ (7.5 mL) and sat. Rochelle's salt solution (13.5 mL) and stirred vigorously for 1 hour. Separated layers. Extracted aqueous layer with $CH_2Cl_2$ (2×10 mL). The combined organic layers were dried over $MgSO_4$, filtered and concentrated to give 108 mg as a white solid. The residue was purified on ISCO using a RediSep® column (DCM-DCM (20% MeOH; 0-100%) to give (E)-(2-(2-(pyridin-4-yl)vinyl)oxazol-4-yl)methanol (54 mg, 0.267 mmol, 41.0% yield). $^1$H NMR (400 MHz, DMSO-$d_6$) δ ppm 8.60 (d, J=6.3 Hz, 2H), 7.99 (s, 1H), 7.68 (d, J=5.9 Hz, 2H), 7.36-7.51 (m, 2H), 5.23 (t, J=5.6 Hz, 1H), 4.41 (d, J=5.6 Hz, 2H).

Step 4: (E)-4-(chloromethyl)-2-(2-(pyridin-4-yl)vinyl)oxazole

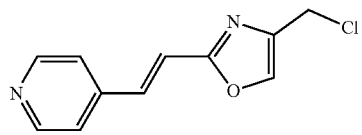 [SMILES: ClCc1coc(/C=C/c2ccncc2)n1]

In a 10 mL round-bottomed flask was added (E)-(2-(2-(pyridin-4-yl)vinyl)oxazol-4-yl)methanol (54 mg, 0.267 mmol) in $CH_2Cl_2$ (2.5 ml) to give a white suspension. Cooled to 0° C. $SOCl_2$ (58.5 µl, 0.801 mmol) was added. Stirred at 0° C. for 5 minutes then warmed to 20° C. After 30 minutes, quenched the reaction mixture with sat. $NaHCO_3$ (5 mL). Extracted the mixture with EtOAc (2×5 mL). The combined organic layers were washed with water (5 mL) then with brine (5 mL). The organic layer was dried over $MgSO_4$, filtered and concentrated to give (E)-4-(chloromethyl)-2-(2-(pyridin-4-yl)vinyl)oxazole (55 mg, 0.249 mmol, 93% yield). $^1$H NMR (400 MHz, DMSO-$d_6$) δ ppm 8.61 (d, J=5.9 Hz, 2H), 8.24 (s, 1H), 7.70 (d, J=5.9 Hz, 2H), 7.40-7.56 (m, 2H), 4.72 (s, 2H).

Step 5: (E)-4-((4-(4-(1H-1,2,3-triazol-1-yl)butyl)phenoxy)methyl)-2-(2-(pyridin-4-yl)vinyl) oxazole

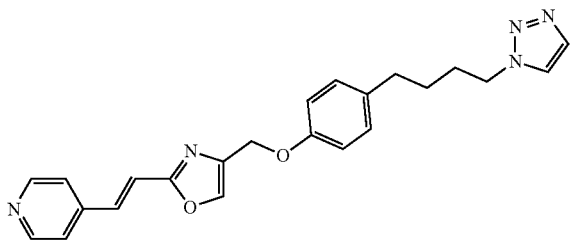 [SMILES: C(=C\c1nc(COc2ccc(CCCCn3ccnn3)cc2)co1)/c1ccncc1]

In a 10 mL round-bottomed flask was added NaH 60% wt. in mineral oil (9.71 mg, 0.243 mmol) in DMF (0.75 ml) to give a grey suspension. Cooled to 0° C. 4-(4-(1H-1,2,3-triazol-1-yl)butyl)phenol (52.7 mg, 0.243 mmol) was added. Warmed to 20° C. and stirred for 30 minutes. Cooled to 0° C. (E)-4-(chloromethyl)-2-(2-(pyridin-4-yl)vinyl)oxazole (51 mg, 0.231 mmol) was added. Stirred at 0° C. for ca. 1 hour then slowly warmed to 20° C. and stirred for 17 hours. Added DMF (0.25 ml) and heated to 40° C. for 4 hours. Cooled to 20° C. and added ca. 5 mg NaH 60% wt in mineral oil. After 23 hours, MeOH (1 ml) was added followed by water (1 ml). Stirred the resulting suspension for 17 hours. The solids were collected on Buchner the cake was washed with water (3×1 mL) then with hexane (1 mL). Dried the product at 40° C. under high vacuum until constant weight to give (E)-4-((4-(4-(1H-1,2,3-triazol-1-yl)butyl)phenoxy)methyl)-2-(2-(pyridin-4-yl)vinyl)oxazole 49.5 mg, 0.123 mmol, 53.3% yield). $^1$H NMR (400 MHz, DMSO-$d_6$) δ ppm 8.60 (d, J=5.9 Hz, 2H), 8.26 (s, 1H), 8.11 (s, 1H), 7.66-7.73 (m, 3H), 7.40-7.56 (m, 2H), 7.05-7.14 (m, J=8.6 Hz, 2H), 6.90-6.98 (m, J=8.6 Hz, 2H), 4.99 (s, 2H), 4.39 (t, J=7.0 Hz, 2H), 2.52-2.58 (m, 2H), 1.81 (quin, J=7.3 Hz, 2H), 1.48 (quin, J=7.6 Hz, 2H).

Compounds 81-85

Compounds 81-85 were prepared according to the procedure for compound 80 steps 1 to 5 from the appropriate starting pyridine.

Compound 81: (E)-4-((4-(4-(1H-1,2,3-triazol-1-yl)butyl)phenoxy)methyl)-2-(2-(3-fluoropyridin-4-yl)vinyl)oxazole

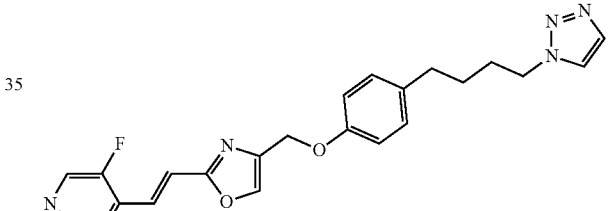

$^1$H NMR (400 MHz, DMSO-$d_6$) δ ppm 8.65 (d, J=2.0 Hz, 1H), 8.48 (d, J=5.1 Hz, 1H), 8.29 (s, 1H), 8.11 (s, 1H), 7.88-7.96 (m, 1H), 7.70 (s, 1H), 7.42-7.58 (m, 2H), 7.04-7.14 (m, J=8.6 Hz, 2H), 6.91-6.99 (m, J=8.6 Hz, 2H), 5.00 (s, 2H), 4.39 (t, J=7.0 Hz, 2H), 2.52-2.58 (m, 2H), 1.81 (quin, J=7.3 Hz, 2H), 1.48 (quin, J=7.6 Hz, 2H).

Compound 82: (E)-4-((4-(4-(1H-1,2,3-triazol-1-yl)butyl)phenoxy)methyl)-2-(2-(pyridin-3-yl)vinyl)oxazole

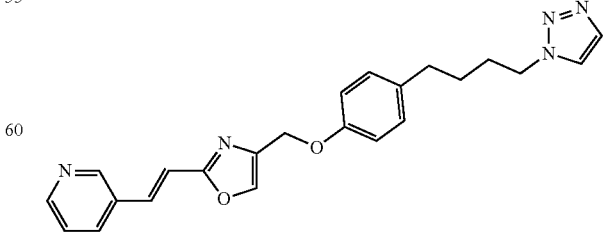

$^1$H NMR (400 MHz, DMSO-$d_6$) δ ppm 8.84-8.91 (m, 1H), 8.54 (dd, J=4.7, 0.8 Hz, 1H), 8.22 (s, 1H), 8.19 (d, J=7.8 Hz, 1H), 8.11 (s, 1H), 7.70 (s, 1H), 7.56 (d, J=16.4 Hz, 1H), 7.44 (dd, J=8.0, 4.9 Hz, 1H), 7.32 (d, J=16.8 Hz, 1H), 7.06-7.13 (m, J=8.6 Hz, 2H), 6.90-6.98 (m, J=8.2 Hz, 2H), 4.98 (s, 2H), 4.39 (t, J=7.0 Hz, 2H), 2.52-2.58 (m, 2H), 1.81 (quin, J=7.2 Hz, 2H), 1.48 (quin, J=7.6 Hz, 2H).

Compound 83: (E)-4-((4-(4-(1H-1,2,3-triazol-1-yl)butyl)phenoxy)methyl)-2-(2-(2-fluoropyridin-3-yl)vinyl)oxazole

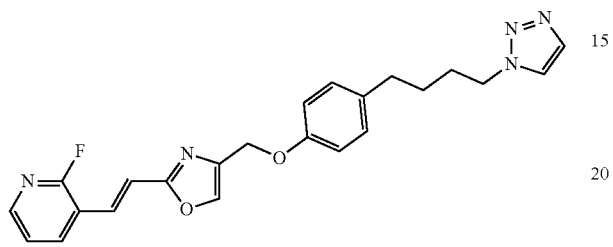

¹H NMR (400 MHz, DMSO-d₆) δ ppm 8.42-8.50 (m, 1H), 8.20-8.28 (m, 2H), 8.11 (s, 1H), 7.70 (s, 1H), 7.50 (d, J=16.4 Hz, 1H), 7.41-7.47 (m, 1H), 7.33 (d, J=16.4 Hz, 1H), 7.06-7.12 (m, J=8.2 Hz, 2H), 6.91-6.97 (m, J=8.6 Hz, 2H), 4.99 (s, 2H), 4.39 (t, J=7.0 Hz, 2H), 2.52-2.56 (m, 2H), 1.81 (quin, J=7.3 Hz, 2H), 1.48 (quin, J=7.6 Hz, 2H).

Compound 84: (E)-4-((4-(4-(1H-1,2,3-triazol-1-yl)butyl)phenoxy)methyl)-2-(2-(pyridin-2-yl)vinyl)oxazole

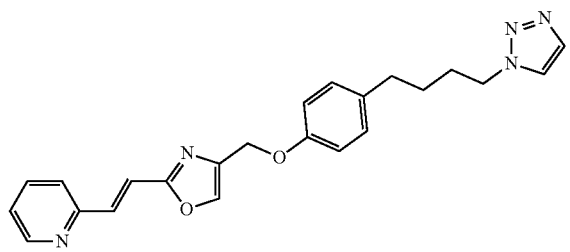 [SMILES: C(=C\c1nc(COc2ccc(CCCCn3ccnn3)cc2)co1)/c1ccccn1]

¹H NMR (400 MHz, DMSO-d₆) δ ppm 8.63 (d, J=4.3 Hz, 1H), 8.24 (s, 1H), 8.11 (s, 1H), 7.85 (td, J=7.6, 1.6 Hz, 1H), 7.67-7.74 (m, 2H), 7.57 (d, J=16.0 Hz, 1H), 7.44 (d, J=16.0 Hz, 1H), 7.36 (dd, J=7.2, 4.9 Hz, 1H), 7.05-7.14 (m, J=8.6 Hz, 2H), 6.91-6.98 (m, J=8.6 Hz, 2H), 4.98 (s, 2H), 4.39 (t, J=7.0 Hz, 2H), 2.52-2.58 (m, 2H), 1.81 (quin, J=7.3 Hz, 2H), 1.48 (quin, J=7.6 Hz, 2H).

Compound 85: (E)-4-((4-(4-(1H-1,2,3-triazol-1-yl)butyl)phenoxy)methyl)-2-(2-(3-fluoropyridin-2-yl)vinyl)oxazole

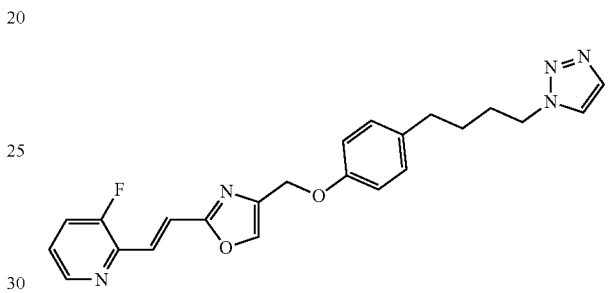

¹H NMR (400 MHz, DMSO-d₆) δ ppm 8.52 (d, J=4.7 Hz, 1H), 8.27 (s, 1H), 8.11 (s, 1H), 7.78-7.85 (m, 1H), 7.60-7.72 (m, 2H), 7.43-7.54 (m, 2H), 7.06-7.14 (m, J=8.6 Hz, 2H), 6.90-6.98 (m, J=8.6 Hz, 2H), 4.99 (s, 2H), 4.39 (t, J=7.0 Hz, 2H), 2.52-2.57 (m, 2H), 1.81 (quin, J=7.3 Hz, 2H), 1.48 (quin, J=7.6 Hz, 2H).

Compound 86: (E)-3-hydroxy-N-(4-(4-((2-(4-(trifluoromethyl)styryl)oxazol-4-yl)methoxy)phenyl)butyl) propanamide

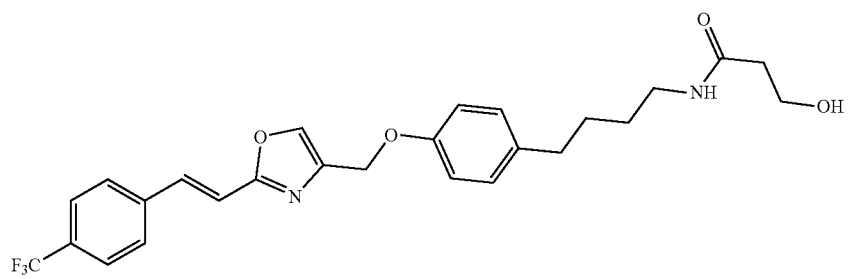 [SMILES: O=C(CCO)NCCCCc1ccc(OCc2coc(/C=C/c3ccc(C(F)(F)F)cc3)n2)cc1]

Step 1: tert-butyl 3-(trityloxy)propanoate

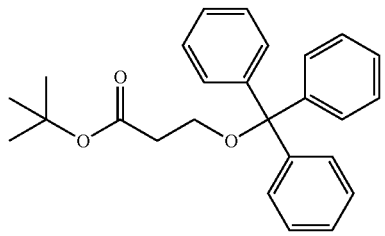 [SMILES: CC(C)(C)OC(=O)CCOC(c1ccccc1)(c1ccccc1)c1ccccc1]

In a 50 mL round-bottomed flask were added tert-butyl 3-hydroxypropanoate (0.55 g, 3.76 mmol) and pyridine (0.913 ml, 11.29 mmol) in $CH_2Cl_2$ (14 ml) to give a colorless solution. Cooled to 0° C. Trityl chloride (1.049 g, 3.76 mmol) was added in portions. Slowly warmed to 20° C. After 22 hours, concentrated to dryness on rotovap. The resulting white solid was suspended in EtOAc (30 mL). Washed with water (15 mL), 5% citric acid (20 mL) and brine (10 mL). The organic layer was dried over $MgSO_4$, filtered and concentrated to give 1.45 g as a white oily solid. The residue was purified on ISCO using a RediSep® column (Hex-EtOAc; 0-20%) to give tert-butyl 3-(trityloxy)propanoate (915 mg, 2.355 mmol, 62.6% yield). $^1$H NMR (400 MHz, DMSO-$d_6$) δ ppm 7.30-7.41 (m, 12H), 7.22-7.30 (m, 3H), 3.17 (t, J=6.1 Hz, 2H), 2.45 (t, J=6.1 Hz, 2H), 1.40 (s, 9H).

Step 2: 3-(trityloxy)propanoic acid

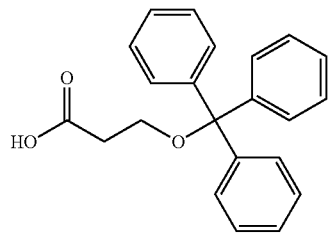 [SMILES: O=C(O)CCOC(c1ccccc1)(c1ccccc1)c1ccccc1]

In a 25 mL round-bottomed flask were added tert-butyl 3-(trityloxy)propanoate (0.915 g, 2.355 mmol) in EtOH (9 ml) to give a colorless solution. NaOH 6M in water (0.785 ml, 4.71 mmol) was added. Heated to reflux. After 4.5 hours, concentrated to dryness on rotovap. The residue was dissolved in $CH_2Cl_2$ (40 mL) and washed with 3% citric acid solution (30 mL). Washed organic layer with brine (20 mL). The organic layer was dried over $MgSO_4$, filtered and concentrated to dryness. The resulting white solid was suspended in i-$Pr_2O$ (20 mL) and stirred at 20° C. for 18 hours. The solids were collected on Buchner and the cake was washed with i-$Pr_2O$ (3×3 mL). Dried the product at 30° C. under high vacuum until constant weight to give 3-(trityloxy)propanoic acid (575 mg, 1.730 mmol, 73.4% yield). $^1$H NMR (400 MHz, DMSO-$d_6$) δ ppm 12.22 (br. s., 1H), 7.30-7.41 (m, 12H), 7.22-7.30 (m, 3H), 3.19 (t, J=6.5 Hz, 2H), 2.47 (s, 2H).

Step 3: (E)-4-(4-((2-(4-(trifluoromethyl)styryl)oxazol-4-yl)methoxy)phenyl)butan-1-amine hydrochloride

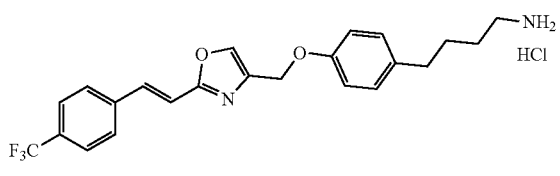 [SMILES: NCCCCc1ccc(OCc2coc(/C=C/c3ccc(C(F)(F)F)cc3)n2)cc1 ; Cl]

In a 15 mL round-bottomed flask was added (E)-tert-butyl (4-(4-((2-(4-(trifluoromethyl)styryl)oxazol-4-yl)methoxy)phenyl)butyl)carbamate (0.3 g, 0.581 mmol) in MeOH (1.5 ml) to give a white suspension. HCl 4M in dioxane (0.726 ml, 2.90 mmol) was added. Stirred the resulting thin tan suspension for 3 hours. EtOAc (4.5 ml) was added and stirred the suspension for 1 hour. The solids were collected on Buchner and the cake was washed with EtOAc (3×1 mL). Dried the product at 20° C. under high vacuum until constant weight to give (E)-4-(4-((2-(4-(trifluoromethyl)styryl)oxazol-4-yl)methoxy)phenyl)butan-1-amine hydrochloride (232 mg, 0.512 mmol, 88% yield). $^1$H NMR (400 MHz, DMSO-$d_6$) δ ppm 8.25 (s, 1H), 7.95 (d, J=8.2 Hz, 2H), 7.72-7.89 (m, 5H), 7.61 (d, J=16.4 Hz, 1H), 7.34 (d, J=16.4 Hz, 1H), 7.10-7.17 (m, J=8.6 Hz, 2H), 6.92-7.00 (m, J=8.6 Hz, 2H), 4.99 (s, 2H), 2.77 (br. s., 2H), 2.52-2.57 (m, 2H), 1.45-1.65 (m, 4H).

Step 4: (E)-N-(4-(4-((2-(4-(trifluoromethyl)styryl)oxazol-4-yl)methoxy)phenyl)butyl)-3-(trityloxy)propanamide

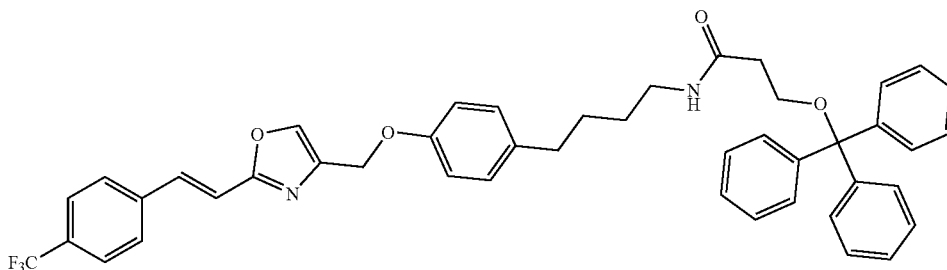

In a 15 mL round-bottomed flask were added (E)-4-(4-((2-(4-(trifluoromethyl)styryl)oxazol-4-yl)methoxy)phenyl)butan-1-amine hydrochloride (0.150 g, 0.331 mmol) and 3-(trityloxy)propanoic acid (0.121 g, 0.364 mmol) in DMF (2.25 ml). DIPEA (0.145 ml, 0.828 mmol) and EDC (0.079 g, 0.414 mmol) were added. Stirred at 20° C. for 20 hours. 3-(trityloxy)propanoic acid (compound 94 step 2) (0.220 g, 0.662 mmol), DIPEA (0.260 ml, 1.490 mmol) and EDC (0.140 g, 0.729 mmol) were added. After 43 hours, the reaction mixture was poured into EtOAc (25 mL) and washed with water (10 mL) then HCl 0.5M (10 mL) then 10% $KHCO_3$ (10 mL) then brine (10 mL). The organic layer was dried over $MgSO_4$, filtered and concentrated to give a colorless oil. The residue was purified on ISCO using a RediSep® column (Hex-EtOAc; 0-100%) to give (E)-N-(4-(4-((2-(4-(trifluoromethyl)styryl)oxazol-4-yl)methoxy)phenyl)butyl)-3-trityloxy)propanamide (223 mg, 0.305 mmol, 92% yield). $^1$H NMR (400 MHz, DMSO-$d_6$) δ ppm 8.23 (s, 1H), 7.95 (d, J=7.8 Hz, 3H), 7.76 (d, J=8.2 Hz, 2H), 7.61 (d, J=16.4 Hz, 1H), 7.33-7.39 (m, 7H), 7.30 (t, J=7.6 Hz, 6H), 7.20-7.27 (m, 3H), 7.02-7.10 (m, J=8.6 Hz, 2H), 6.87-6.94 (m, J=8.6 Hz, 2H), 4.98 (s, 2H), 3.04-3.17 (m, 4H), 2.45-2.48 (m, 2H), 2.34 (t, J=6.3 Hz, 2H), 1.49-1.61 (m, 2H), 1.36-1.49 (m, 2H).

Step 5: (E)-3-hydroxy-N-(4-(4-((2-(4-(trifluoromethyl)styryl)oxazol-4-yl)methoxy)phenyl)butyl) propanamide

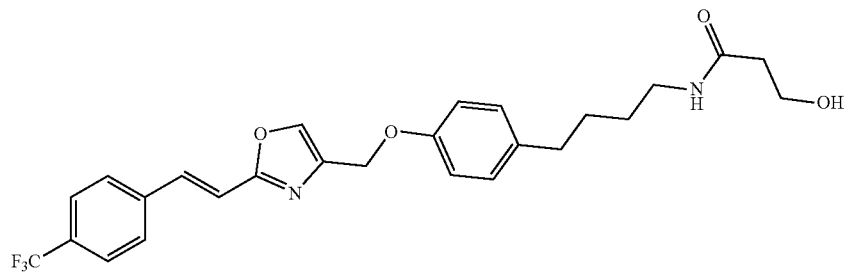 [SMILES: O=C(CCO)NCCCCc1ccc(OCc2coc(/C=C/c3ccc(C(F)(F)F)cc3)n2)cc1]

In a 25 mL round-bottomed flask were added (E)-N-(4-(4-((2-(4-(trifluoromethyl)styryl)oxazol-4-yl)methoxy)phenyl)butyl)-3-(trityloxy)propanamide (0.22 g, 0.301 mmol) in MeOH (3 ml) and $CHCl_3$ (3 ml). p-TsOH (5.73 mg, 0.030 mmol) was added. Stirred at 20° C. for 3.5 hours. Concentrated the reaction mixture to dryness on rotovap. The residue was purified on ISCO using a RediSep® column ($CH_2Cl_2$-MeOH) to give (E)-3-hydroxy-N-(4-(4-((2-(4-(trifluoromethyl) styryl)oxazol-4-yl)methoxy)phenyl)butyl) propanamide (142 mg, 0.291 mmol, 97% yield). $^1$H NMR (400 MHz, DMSO-$d_6$) δ ppm 8.24 (s, 1H), 7.95 (d, J=8.2 Hz, 2H), 7.71-7.80 (m, 3H), 7.62 (d, J=16.4 Hz, 1H), 7.34 (d, J=16.8 Hz, 1H), 7.07-7.15 (m, J=8.6 Hz, 2H), 6.90-6.98 (m, J=8.6 Hz, 2H), 4.99 (s, 2H), 4.52 (t, J=5.3 Hz, 1H), 3.54-3.61 (m, 2H), 3.04 (q, J=6.7 Hz, 2H), 2.52-2.56 (m, 2H), 2.20 (t, J=6.7 Hz, 2H), 1.52 (quin, J=7.4 Hz, 2H), 1.38 (quin, J=7.4 Hz, 2H).

Compound 87: (E)-3-oxo-3-((4-(4-((2-(4-(trifluoromethyl)styryl)oxazol-4-yl)methoxy)phenyl)butyl) amino)propyl dimethylcarbamate

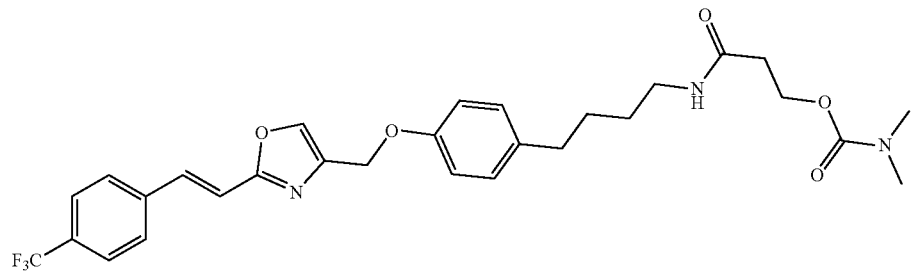 [SMILES: CN(C)C(=O)OCCC(=O)NCCCCc1ccc(OCc2coc(/C=C/c3ccc(C(F)(F)F)cc3)n2)cc1]

In a 5 mL round-bottomed flask was added NaH 60% wt. in mineral oil (3.60 mg, 0.090 mmol) in DMF (0.5 ml) to give a grey suspension. (E)-3-hydroxy-N-(4-(4-((2-(4-(trifluoromethyl)styryl)oxazol-4-yl)methoxy)phenyl)butyl)propanamide (compound 94) (40 mg, 0.082 mmol) was added. Stirred at 20° C. for 30 minutes. Cooled to 0° C. Dimethylcarbamoyl chloride (8.28 μl, 0.090 mmol) was added dropwise. After 30 minutes, dimethylcarbamoyl chloride (8.28 μl, 0.090 mmol) was added. After 1 hour, added NaH 60% wt. in mineral oil (1.638 mg, 0.041 mmol) followed by dimethylcarbamoyl chloride (8.28 μl, 0.090 mmol). After 1.5 hour, MeOH (0.5 ml) was added followed by dropwise addition of water (0.5 ml). The white suspension was stirred for 1 hour. The solids were collected on Buchner and the cake was washed with MeOH:Water (1:1, 3×0.75 mL) followed by Hexane (2×0.5 mL). Dried the product at 30° C. under high vacuum until constant weight to give (E)-3-oxo-3-((4-(4-((2-(4-(trifluoromethyl)styryl)oxazol-4-yl)methoxy)phenyl)butyl)amino)propyl dimethylcarbamate (40 mg, 0.071 mmol, 87% yield) as a white solid. $^1$H NMR (400 MHz, DMSO-$d_6$) δ ppm 8.24 (s, 1H), 7.92-8.00 (m, J=8.2 Hz, 2H), 7.89 (t, J=5.5 Hz, 1H), 7.73-7.80 (m, J=8.2 Hz, 2H), 7.61 (d, J=16.4 Hz, 1H), 7.34 (d, J=16.8 Hz, 1H), 7.06-7.15 (m, J=8.2 Hz, 2H), 6.90-6.98 (m, J=8.6 Hz, 2H), 4.99 (s, 2H), 4.13 (t, J=6.3 Hz, 2H), 3.06 (q, J=6.5 Hz, 2H), 2.70-2.83 (m, 6H), 2.52 (br. s., 2H), 2.35 (t, J=6.3 Hz, 2H), 1.52 (quin, J=7.5 Hz, 2H), 1.38 (quin, J=7.1 Hz, 2H).

Compound 88: (E)-4-((4-(4-(1H-1,2,4-triazol-1-yl)butyl)yl)phenoxy)methyl)-2-(2-fluoro-4-(trifluoromethyl)styryl)oxazole added to a solution of 4-(4-methoxyphenyl)butyl methanesulfonate (600 mg, 2.323 mmol) in DMF (4.00 ml) and THF (3.0 ml) in a microwave tube which was sealed and heated to 60° C. for 3 h. The mixture was diluted with EA (20 ml), filtered through a pad of celite. The filtrate was concentrated to dryness and the residue was purified using ISCO column (DCM to 40% AcOEt in DCM) to give title compound (0.45 g, 84% yield) as a colorless oil. $^1$H NMR (400 MHz, CDCl$_3$) δ ppm 1.59 (t, J=7.63 Hz, 2H) 1.83-2.00 (m, 2H) 2.58 (t, J=7.63 Hz, 2H) 3.78 (s, 3H) 4.16 (t, J=7.24 Hz, 2H) 6.82 (m, J=8.61 Hz, 2H) 7.05 (m, J=8.61 Hz, 2H) 7.93 (s, 1H) 8.00 (s, 1H).

Step 2: 4-(4-(1H-1,2,4-triazol-1-yl)butyl)phenol

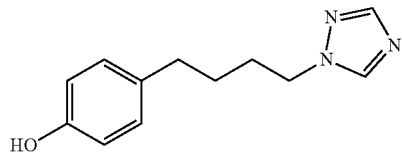

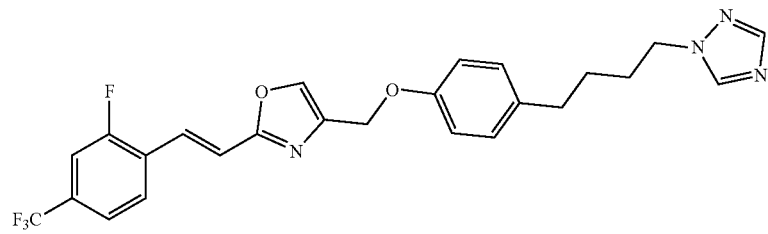 [SMILES: Fc1cc(C(F)(F)F)ccc1/C=C/c1nc(COc2ccc(CCCCn3cncn3)cc2)co1]

Step 1:
1-(4-(4-methoxyphenyl)butyl)-1H-1,2,4-triazole

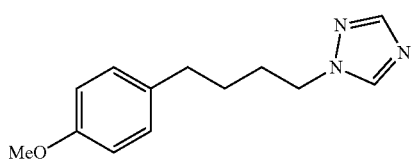 [SMILES: COc1ccc(CCCCn2cncn2)cc1]

1H-1,2,4-triazole (802 mg, 11.61 mmol) was dissolved in THF (15 ml) and cooled to 0° C., NaH 60% (418 mg, 10.45 mmol) was added and stirred for 1 h at rt. This mixture was In a 25 ml flask was added 1-(4-(4-methoxyphenyl)butyl)-1H-1,2,4-triazole (0.52 g, 2.248 mmol) in hydrogen bromide 48% in water (1.526 ml, 13.49 mmol) to give a light yellow solution. The reaction mixture was heated to 90° C. and stirred for 18 h, then cooled to rt. EtOAc (30 ml) and THF (20 ml) was added. The organic layer was washed with saturated NaHCO$_3$ solution (10 ml) and water (10 ml), dried and concentrated to give title compound 0.48 g. $^1$H NMR (400 MHz, CDCl$_3$) δ ppm 1.53 (t, J=7.63 Hz, 2H), 1.77-1.93 (m, 2H), 2.52 (t, J=7.43 Hz, 2H), 4.11 (t, J=7.04 Hz, 2H), 6.70 (d, J=8.22 Hz, 2H), 6.93 (d, J=8.61 Hz, 2H) 7.88 (s, 1H), 7.97 (s, 1H).

Step 3: (E)-4-((4-(4-(1H-1,2,4-triazol-1-yl)butyl)
phenoxy)methyl)-2-(2-fluoro-4-(trifluoromethyl)
styryl) oxazole

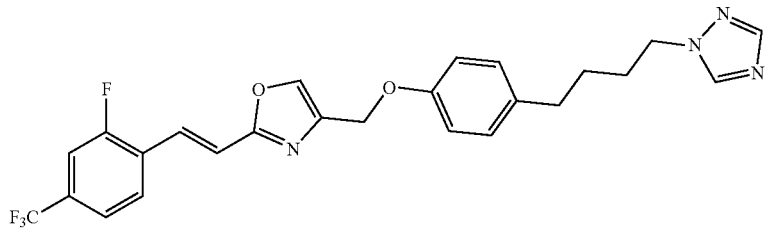 [SMILES: Fc1cc(C(F)(F)F)ccc1/C=C/c1nc(COc2ccc(CCCCn3cncn3)cc2)co1]

In a 8 ml vial were added (E)-4-(chloromethyl)-2-(2-fluoro-4-(trifluoromethyl)styryl)oxazole (40 mg, 0.131 mmol) and K$_2$CO$_3$ (19.90 mg, 0.144 mmol) in DMF (253 µl, 3.27 mmol) to give a yellow suspension. The mixture was heated to 75° C. for 6 h, then cooled to 20° C. MeOH (220 µl) and H$_2$O (360 µl) were added, stirred for 10 min. The solid were collected, washed with water (3×0.5 mL), dried under high vacuum. The crude was purified using an ISCO column (A: Pure DCM, B: 20% MeOH in DCM. 0% B to 30% B) to give title compound (40 mg, 62.8% yield) as beige solid, $^1$H NMR (400 MHz, DMSO-d6) δ ppm 1.44 (t, J=7.43 Hz, 2H) 1.66-1.83 (m, 2H) 2.50-2.54 (m, 2H) 4.16 (t, J=6.85 Hz, 2H) 4.97 (s, 2H) 6.92 (d, J=8.61 Hz, 2H) 7.08 (d, J=8.22 Hz, 2H) 7.37 (d, J=16.43 Hz, 1H) 7.52-7.67 (m, 2H), 7.76 (d, J=10.56 Hz, 1H) 7.92 (s, 1H) 8.07-8.19 (m, 1H) 8.24 (s, 1H) 8.48 (s, 1H) and Compound 89: (E)-2-(2-(4-(4-(1H-1,2,4-triazol-1-yl)butyl)phenoxy)-4-(trifluoromethyl)styryl)-4-((4-(4-(1H-1,2,4-triazol-1-yl)butyl)phenoxy)methyl) oxazole

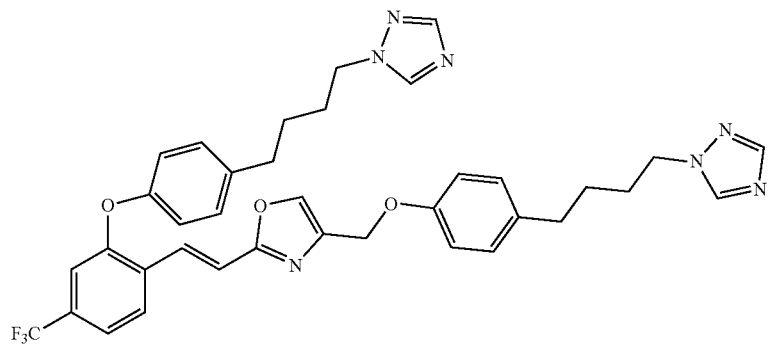 [SMILES: FC(F)(F)c1ccc(/C=C/c2nc(COc3ccc(CCCCn4cncn4)cc3)co2)c(Oc2ccc(CCCCn3cncn3)cc2)c1]

(5 mg, 5.6% yield)$^1$H NMR (400 MHz, CD$_3$OD) δ ppm 1.49-1.67 (m, 4H) 1.88 (dt, J=15.75, 7.97 Hz, 4H) 2.57 (t, J=7.43 Hz, 2H) 2.66 (t, J=7.63 Hz, 2H) 4.23 (dt, J=11.05, 6.99 Hz, 4H) 4.96 (s, 2H) 6.90 (d, J=8.22 Hz, 2H) 6.97 (m, J=8.22 Hz, 2H) 7.03 (s, 1H) 7.07 (m, J=8.22 Hz, 2H) 7.20-7.27 (m, 3H) 7.42 (d, J=7.83 Hz, 1H) 7.86 (d, J=16.83 Hz, 1H) 7.92 (s, 1H) 7.96 (d, J=2.74 Hz, 3H) 8.43 (d, J=9.00 Hz, 2H)

Compound 90: (E)-4-((4-(4-(1H-tetrazol-1-yl)butyl)
phenoxy)methyl)-2-(2-fluoro-4-(trifluoromethyl)
styryl) oxazole

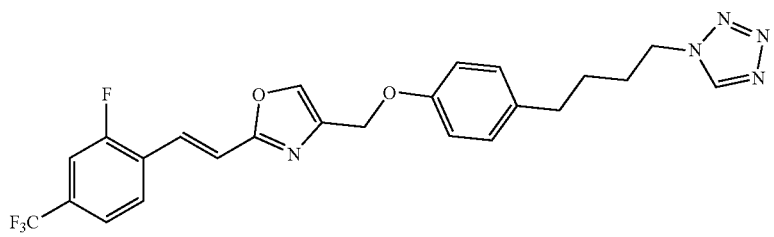 [SMILES: Fc1cc(C(F)(F)F)ccc1/C=C/c1nc(COc2ccc(CCCCn3cnnn3)cc2)co1]

Step 1: 1-(4-(4-methoxyphenyl)butyl)-1H-tetrazole

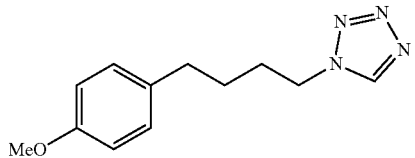 [SMILES: COc1ccc(CCCCn2cnnn2)cc1]

1H-tetrazole (987 mg, 14.09 mmol) was dissolved in THF (15 ml) and cooled to 0° C., NaH (499 mg, 12.46 mmol) was added and stirred for 1 h at rt. This mixture was added to a solution of 4-(4-methoxyphenyl)butyl methanesulfonate (700 mg, 2.71 mmol) in DMF (3.00 ml) and THF (3.00 ml) in a microwave tube that was sealed and heated to 60° C. for 3 h. The mixture was diluted with EA (20 ml) and filtered through a pad of celite. The filtrate was concentrated to dryness, and the residue was purified using an ISCO column (DCM to 40% AcOEt in DCM) to give 0.17 g of the title compound. 20 $^1$H NMR (400 MHz, CDCl$_3$) δ ppm 1.63 (t, J=7.63 Hz, 2H) 1.88-2.06 (m, 2H) 2.61 (t, J=7.43 Hz, 2H) 3.78 (s, 2H) 4.41 (t, J=7.24 Hz, 2H) 6.76-6.89 (m, 2H) 7.05 (m, J=8.61 Hz, 2H) 8.51 (s, 1H) and the regioisomer, 2-(4-(4-methoxyphenyl)butyl)-2H-tetrazole.

$^1$H NMR (400 MHz, CDCl$_3$) δ ppm 1.62 (t, J=7.63 Hz, 2H) 1.95-2.15 (m, 2H) 2.60 (t, J=7.63 Hz, 2H) 3.78 (s, 2H) 4.65 (t, J=7.04 Hz, 2H) 6.73-6.89 (m, 2H) 7.06 (m, J=8.61 Hz, 2H) 8.49 (s, 1H)

Step 2: 4-(4-(1H-tetrazol-1-yl)butyl)phenol

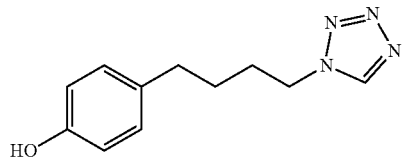 [SMILES: Oc1ccc(CCCCn2cnnn2)cc1]

This compound was prepared in a similar fashion as compound 1 step 4 with the previous intermediate. $^1$H NMR (400 MHz, CDCl$_3$) δ ppm 1.50-1.66 (m, 2H) 1.85-1.97 (m, 2H) 2.54 (t, J=7.43 Hz, 2H) 4.36 (t, J=7.04 Hz, 2H) 6.71 (m, J=8.61 Hz, 2H) 6.92 (m, J=8.22 Hz, 2H) 8.54 (s, 1H)

Step 3: (E)-4-((4-(4-(1H-tetrazol-1-yl)butyl)phenoxy)methyl)-2-(2-fluoro-4-(trifluoromethyl)styryl) oxazole

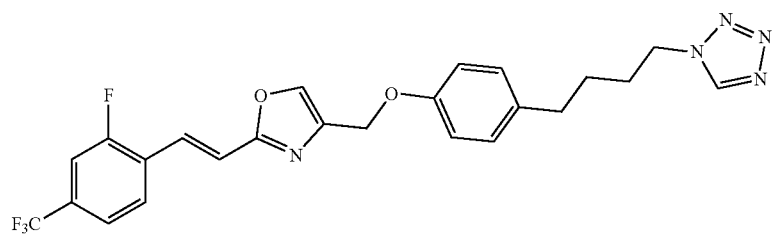 [SMILES: Fc1cc(C(F)(F)F)ccc1/C=C/c1nc(COc2ccc(CCCCn3cnnn3)cc2)co1]

This compound was prepared in a similar fashion as compound 1 step 5 with the previous intermediate. 1H NMR (400 MHz, DMSO-d$_6$) δ ppm 1.47 (t, J=7.63 Hz, 2H) 1.73-1.92 (m, 2H) 2.50-2.55 (m, 2H) 4.45 (t, J=7.04 Hz, 2H) 4.97 (s, 2H) 6.93 (m, J=8.61 Hz, 2H) 7.08 (m, J=8.61 Hz, 2H) 7.37 (d, J=16.43 Hz, 1H) 7.57 (d, J=16.43 Hz, 1H) 7.63 (d, J=8.22 Hz, 1H) 7.77 (d, J=10.96 Hz, 1H) 8.14 (t, J=8.02 Hz, 1H) 8.24 (s, 1H) 9.38 (s, 1H)

Compound 91: (E)-4-((4-(4-(1H-pyrazol-1-yl)butyl) phenoxy)methyl)-2-(2-fluoro-4-(trifluoromethyl) styryl) oxazole

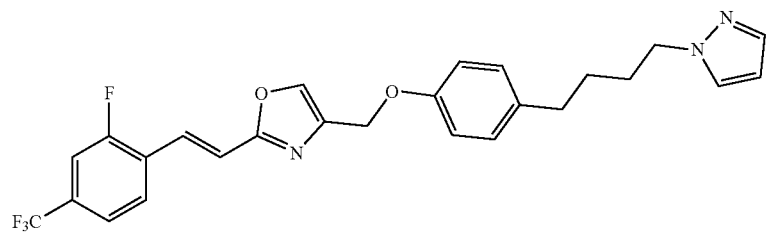

Step 1: 1-(4-(4-methoxyphenyl)butyl)-1H-pyrazole

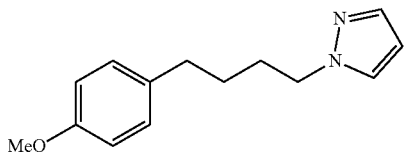 [SMILES: COc1ccc(CCCCn2cccn2)cc1]

This compound was prepared in a similar fashion as compound 88 step 1 with 1H-pyrazole. ¹H NMR (400 MHz, CDCl₃) δ ppm 1.60 (br. s., 2H) 1.81-1.97 (m, 2H) 2.57 (t, J=7.63 Hz, 2H) 3.78 (s, 3H) 4.13 (t, J=7.04 Hz, 2H) 6.22 (t, J=1.96 Hz, 1H) 6.81 (m, J=8.61 Hz, 2H) 7.06 (m, J=8.61 Hz, 2H) 7.34 (d, J=2.35 Hz, 1H) 7.49 (d, J=1.57 Hz, 1H)

Step 2: 4-(4-(1H-pyrazol-1-yl)butyl)phenol

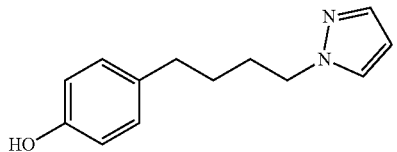 [SMILES: Oc1ccc(CCCCn2cccn2)cc1]

This compound was prepared in a similar fashion as compound 88 step 2 with the previous intermediate. ¹H NMR (400 MHz, CD₃OD) δ ppm 1.41-1.61 (m, 2H) 1.73-1.92 (m, 2H) 2.51 (t, J=7.63 Hz, 2H) 4.14 (t, J=7.04 Hz, 2H) 6.25 (t, J=1.96 Hz, 1H) 6.61-6.70 (m, 2H) 6.95 (m, J=8.61 Hz, 2H) 7.45 (d, J=1.96 Hz, 1H) 7.57 (d, J=2.35 Hz, 1H)

Step 3: (E)-4-((4-(4-(1H-pyrazol-1-yl)butyl)phenoxy)methyl)-2-(2-fluoro-4-(trifluoromethyl)styryl)oxazole

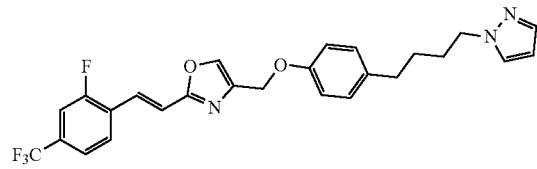 [SMILES: Fc1cc(C(F)(F)F)ccc1/C=C/c1nc(COc2ccc(CCCCn3cccn3)cc2)co1]

This compound was prepared in a similar fashion as compound 88 step 3 with the previous intermediate. ¹H NMR (400 MHz, CDCl₃) δ ppm 1.59-1.65 (m, 2H) 1.81-1.98 (m, 2H) 2.58 (t, J=7.43 Hz, 2H) 4.13 (t, J=7.04 Hz, 2H) 5.02 (s, 2H) 6.16-6.32 (m, 1H) 6.90 (m, J=8.61 Hz, 2H) 7.07 (m, J=8.61 Hz, 2H) 7.13 (d, J=16.43 Hz, 1H) 7.34 (d, J=1.96 Hz, 1H) 7.38 (d, J=10.56 Hz, 1H) 7.44 (d, J=8.22 Hz, 1H) 7.47-7.53 (m, 1H) 7.60-7.68 (m, 2H) 7.69 (s, 1H)

Compound 92: (E)-2-(2-fluoro-4-(trifluoromethyl)styryl)-4-((4-(4-(4-methyl-1H-1,2,3-triazol-1-yl)butyl)phenoxy)methyl) oxazole

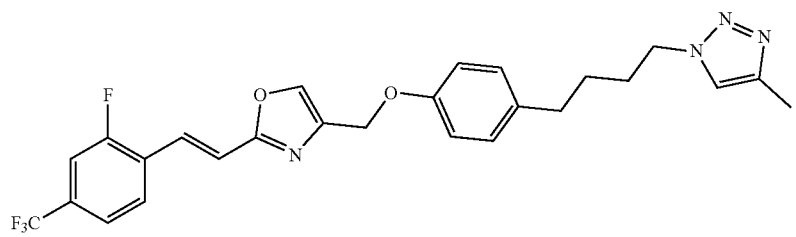

Step 1: 1-(4-(4-methoxyphenyl)butyl)-4-methyl-1H-1,2,3-triazole

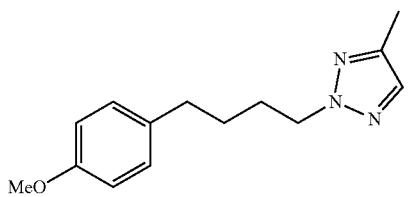 [SMILES: COc1ccc(CCCCn2ncc(C)n2)cc1]

Into a macrowave tube, 4-methyl-1H-1,2,3-triazole (473 mg, 5.69 mmol) was dissolved in THF (10 ml) and cooled to 0° C., NaH (341 mg, 8.54 mmol) was added and stirred for 1 h at rt. A solution of 4-(4-methoxyphenyl)butyl methanesulfonate (490 mg, 1.897 mmol) in DMF (2.00 ml) and THF (1.0 ml) was then added and heated to 60° C. for 3 h. The mixture was diluted with EA (20 ml) and filtered through a pad of celite. The filtrate was concentrated to dryness. The crude was purified using ISCO column (DCM to 40% EA in DCM) to give two isomers. The title compound (0.13 g), ¹H NMR (400 MHz, CDCl₃) δ ppm 1.57-1.64 (m, 2H) 1.88-2.02 (m, 2H) 2.29 (s, 2H) 2.57 (t, J=7.63 Hz, 2H) 3.78 (s, 3H) 4.35 (t, J=7.04 Hz, 2H) 6.76-6.86 (m, 2H) 7.06 (m, J=8.22 Hz, 2H) 7.31 (s, 1H) and 2-(4-(4-methoxyphenyl)butyl)-4-methyl-2H-1,2,3-triazole (0.18 g). ¹H NMR (400 MHz, CDCl₃) δ ppm 1.60-1.68 (m, 2H) 1.80-1.97 (m, 2H) 2.26 (s, 1H) 2.33 (s, 2H) 2.52-2.66 (m, 2H) 3.78 (s, 3H) 4.16-4.36 (m, 2H) 6.82 (m, J=8.22 Hz, 2H) 7.05 (d, J=8.61 Hz, 2H) 7.32 (m, 1H)

Step 2: 4-(4-(4-methyl-1H-1,2,3-triazol-1-yl)butyl)phenol

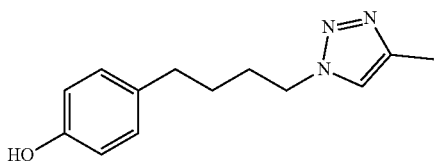 [SMILES: Cc1cn(CCCCc2ccc(O)cc2)nn1]

This compound was prepared in a similar fashion as compound 88 step 2 with 1-(4-(4-methoxyphenyl)butyl)-4-methyl-1H-1,2,3-triazole. $^1$H NMR (400 MHz, CD$_3$OD) δ ppm 1.44-1.58 (m, 2H) 1.78-1.97 (m, 2H) 2.26 (s, 3H) 2.51 (t, J=7.63 Hz, 2H) 4.34 (t, J=7.04 Hz, 2H) 6.62-6.71 (m, 2H) 6.94 (d, J=8.22 Hz, 2H) 7.40 (s, 1H)

Step 3: (E)-2-(2-fluoro-4-(trifluoromethyl)styryl)-4-((4-(4-(4-methyl-1H-1,2,3-triazol-1-yl)butyl)phenoxy)methyl)oxazole

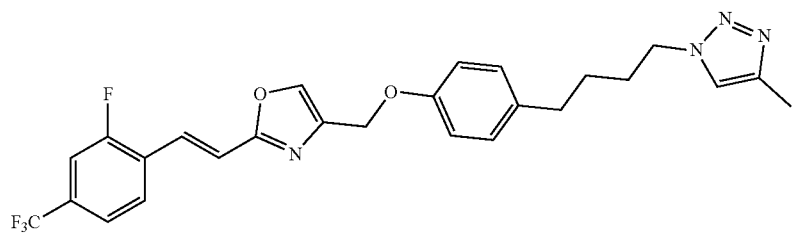

This compound was prepared in a similar fashion as compound 88 step 3 with the previous intermediate. $^1$H NMR (400 MHz, CDCl$_3$) δ ppm 1.63-1.68 (m, 2H) 1.81-1.97 (m, 2H) 2.26 (s, 1H) 2.33 (s, 2H) 2.59 (td, J=7.43, 2.74 Hz, 2H) 4.18-4.38 (m, 2H) 5.02 (s, 2H) 6.91 (d, J=8.61 Hz, 2H) 7.06 (s, 1H) 7.09 (d, J=9.00 Hz, 1H) 7.15 (s, 1H) 7.21 (s, 1H) 7.37 (d, J=10.56 Hz, 1H) 7.41-7.47 (m, 1H) 7.60-7.68 (m, 2H) 7.69 (s, 1H)

Compound 93: (E)-2-(2-fluoro-4-(trifluoromethyl)styryl)-4-((4-(4-(3-methyl-1H-1,2,4-triazol-1-yl)butyl) phenoxy)methyl)oxazole

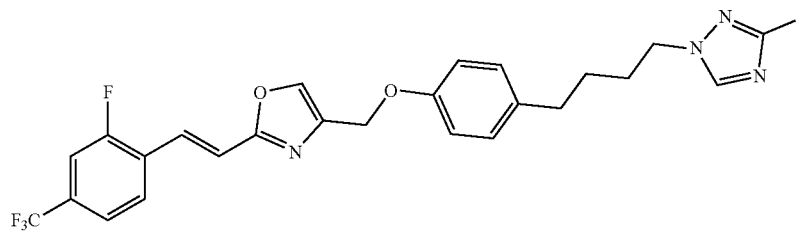 [SMILES: Cc1ncn(CCCCc2ccc(OCc3coc(/C=C/c4ccc(C(F)(F)F)cc4F)n3)cc2)n1]

Step 1: 1-(4-(4-methoxyphenyl)butyl)-3-methyl-1H-1,2,4-triazole

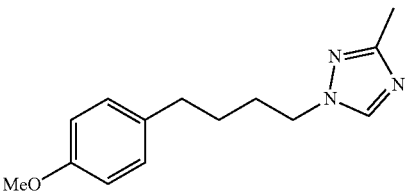 [SMILES: COc1ccc(CCCCn2cnc(C)n2)cc1]

This compound was prepared in a similar fashion as compound 88 step 1 with 3-methyl-1H-1,2,4-triazole. $^1$H NMR (400 MHz, CDCl$_3$) δ ppm 1.76-1.96 (m, 2H) 2.40 (d, J=10.56 Hz, 2H) 2.58 (t, J=7.63 Hz, 2H) 3.78 (s, 3H) 4.05 (q, J=7.17 Hz, 2H) 6.82 (m, J=8.61 Hz, 2H) 7.06 (m, J=8.22 Hz, 2H)

191

Step 2: 4-(4-(3-methyl-1H-1,2,4-triazol-1-yl)butyl)phenol

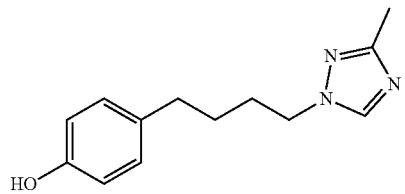 [SMILES: Cc1ncn(CCCCc2ccc(O)cc2)n1]

This compound was prepared in a similar fashion as compound 88 step 2 with the previous intermediate. ¹H NMR (400 MHz, METHANOL-d4) δ ppm 1.45-1.64 (m, 2H) 1.82 (dd, J=15.06, 7.24 Hz, 2H) 2.32 (s, 2H) 2.41 (s, 1H) 2.53 (td, J=7.53, 3.33 Hz, 2H) 4.12 (td, J=6.95, 4.11 Hz, 2H) 6.67 (d, J=8.22 Hz, 2H) 6.90-7.01 (m, 2H) 7.77-7.79 (m, 1H)

Step 3: (E)-2-(2-fluoro-4-(trifluoromethyl)styryl)-4-((4-(4-(3-methyl-1H-1,2,4-triazol-1-yl)butyl)phenoxy)methyl)oxazole

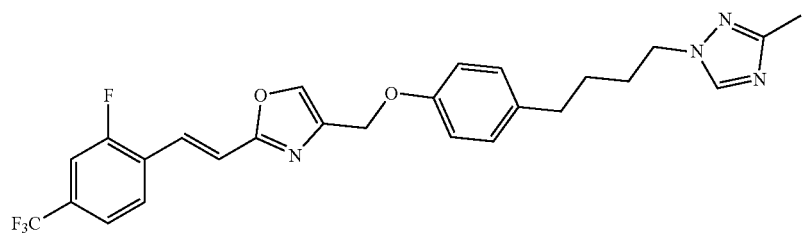 [SMILES: Cc1ncn(CCCCc2ccc(OCc3coc(/C=C/c4ccc(C(F)(F)F)cc4F)n3)cc2)n1]

This compound was prepared in a similar fashion as compound 88 step 3 with the previous intermediate. ¹H NMR (400 MHz, CDCl₃) δ ppm 1.59-1.67 (m, 2H) 1.79-1.96 (m, 2H) 2.40 (d, J=11.35 Hz, 3H) 2.59 (t, J=7.63 Hz, 2H) 4.06 (q, J=7.43 Hz, 2H) 5.02 (s, 2H) 6.91 (m, J=8.61 Hz, 2H) 7.07 (m, J=8.61 Hz, 2H) 7.13 (d, J=16.43 Hz, 1H) 7.38 (d, J=10.56 Hz, 1H) 7.44 (d, J=8.22 Hz, 1H) 7.60-7.68 (m, 2H) 7.69 (s, 1H)

Compound 94: (E)-2-(2-fluoro-4-(trifluoromethyl)styryl)-4-((4-(4-(5-methyl-2H-tetrazol-2-yl)butyl)phenoxy)methyl)oxazole

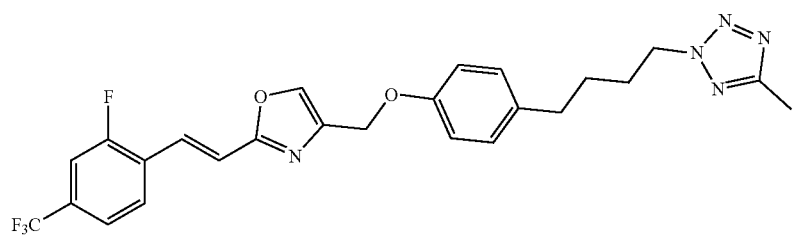

192

Step 1: 1-(4-(4-methoxyphenyl)butyl)-5-methyl-1H-tetrazole and 2-(4-(4-methoxyphenyl)butyl)-5-methyl-2H-tetrazole

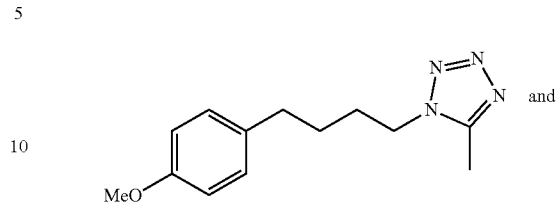

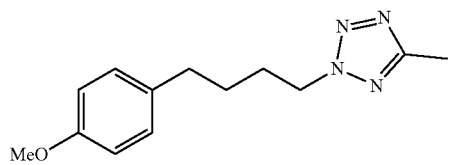

Into a microwave tube, 5-methyl-1H-tetrazole (797 mg, 9.48 mmol) was dissolved in THF (10 ml) and cooled to 0° C., NaH 60% (341 mg, 8.54 mmol) was added and stirred for 1 h at rt. A solution of 4-(4-methoxyphenyl)butyl methanesulfonate (490 mg, 1.897 mmol) in DMF (2.00 ml) and THF (1.0 ml) was then added and heated to 6° C. for 3 h. The mixture was diluted with EA (20 ml) and filtered through a pad of celite. The filtrate was concentrated to dryness, and the residue was purified using ISCO column (DCM to 40% EA in DCM) to give a mixture of 2-(4-(4-methoxyphenyl)butyl)-5-methyl-2H-tetrazole and 1-(4-(4-methoxyphenyl)butyl)-5-methyl-1H-tetrazole (0.34 g), LRMS+H⁺=247.2

Step 2: 4-(4-(5-methyl-1H-tetrazol-1-yl)butyl)phenol and 4-(4-(5-methyl-2H-tetrazol-2-yl)butyl)phenol

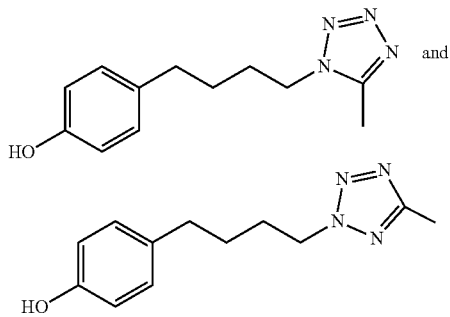

In a 25 ml flask was added a mix of 1-(4-(4-methoxyphenyl)butyl)-5-methyl-1H-tetrazole and 2-(4-(4-methoxyphenyl)butyl)-5-methyl-2H-tetrazole (0.340 g, 1.380 mmol) in hydrogen bromide 48% in water (0.937 ml, 8.28 mmol) to give a light yellow solution. The reaction mixture was heated to 90° C. and stirred for 18 h, then cooled to rt. EA (20 ml) and THF (10 ml) were added. The organic layer was washed with sat. NaHCO$_3$ (5 ml) and water (10 ml). It was dried and concentrated to dryness to give a mixture of 4-(4-(5-methyl-2H-tetrazol-2-yl)butyl)phenol and 4-(4-(5-methyl-1H-tetrazol-1-yl)butyl)phenol (0.32 g). LRMS+H$^+$: 233.1

Step 3: (E)-2-(2-fluoro-4-(trifluoromethyl)styryl)-4-((4-(4-(5-methyl-2H-tetrazol-2-yl)butyl)phenoxy)methyl)oxazole

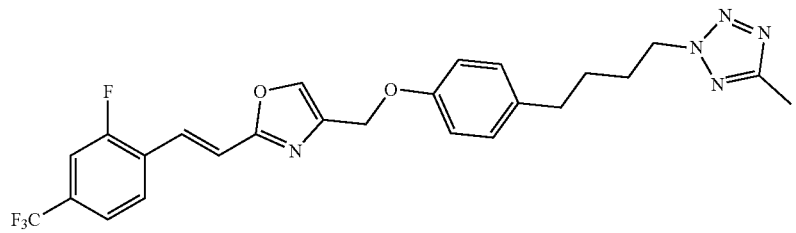 [SMILES: Cc1nnn(CCCCc2ccc(OCc3coc(/C=C/c4ccc(C(F)(F)F)cc4F)n3)cc2)n1]

In a 8 ml vial were added the mix of (E)-4-(chloromethyl)-2-(2-fluoro-4-(trifluoromethyl)styryl)oxazole and (E)-4-(chloromethyl)-2-(2-fluoro-4-(trifluoromethyl)styryl)oxazole (40 mg, 0.131 mmol), K$_2$CO$_3$ (19.90 mg, 0.144 mmol) in DMF (300 μl) to give a yellow suspension. The reaction mixture was heated to 75° C. for 6 h and then cooled to 20° C. Methanol (220 μl) and water (360 μl) were added. The solid was collected, washed with water (3×0.5 mL). The crude was further purified by preparative HPLC (MeOH-water 5% HCO$_2$H; 35%-100%) to give 20 mg of the title compound. $^1$H NMR (400 MHz, CDCl$_3$) δ ppm 1.59-1.68 (m, 2H) 2.01 (quin, J=7.43 Hz, 2H) 2.47-2.54 (m, 3H) 2.55-2.66 (m, 2H) 4.55 (t, J=7.04 Hz, 2H) 5.02 (s, 2H) 6.85-6.97 (m, 2H) 7.05-7.10 (m, 2H) 7.13 (d, J=16.43 Hz, 1H) 7.38 (d, J=10.56 Hz, 1H) 7.44 (d, J=8.22 Hz, 1H) 7.61-7.68 (m, 2H) 7.69 (s, 1H).

Compound 95: (E)-2-(1-(4-(4-((2-(2-fluoro-4-(trifluoromethyl)styryl)oxazol-4-yl)methoxy)phenyl)butyl)-1H-1,2,3-triazol-4-yl)ethanol

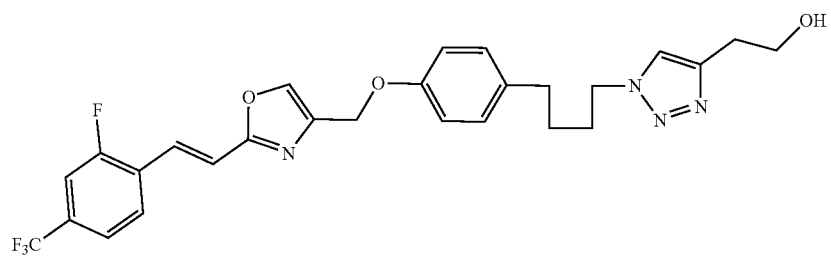 [SMILES: OCCc1cn(CCCCc2ccc(OCc3coc(/C=C/c4ccc(C(F)(F)F)cc4F)n3)cc2)nn1]

This compound was prepared in a similar fashion as compound 8 with but-3-yn-1-ol and (E)-4-((4-(4-azidobutyl) phenoxy)methyl)-2-(2-fluoro-4-(trifluoromethyl)styryl)oxazole. ¹H NMR (400 MHz, DMSO-d6) δ ppm 1.49 (quin, J=7.60 Hz, 2H) 1.78 (quin, J=7.24 Hz, 2H) 2.51-2.57 (m, 2H) 2.74 (t, J=7.04 Hz, 2H) 3.56-3.65 (m, 2H) 4.31 (t, J=7.04 Hz, 2H) 4.66 (t, J=5.28 Hz, 1H) 4.99 (s, 2H) 6.94 (m, J=8.61 Hz, 2H) 7.10 (m, J=8.61 Hz, 2H) 7.39 (d, J=16.43 Hz, 1H) 7.59 (d, J=16.82 Hz, 1H) 7.64 (d, J=8.61 Hz, 1H) 7.78 (d, J=10.96 Hz, 1H) 7.83 (s, 1H) 8.16 (t, J=7.63 Hz, 1H) 8.26 (s, 1H). LRMS+H⁺: 531.0.

Compound 96: (E)-2-(1-(4-(4-((2-(2-fluoro-4-(trifluoromethyl)styryl)oxazol-4-yl)methoxy)phenyl)butyl)-1H-1,2,3-triazol-4-yl)ethyl (2-methoxyethyl) carbamate

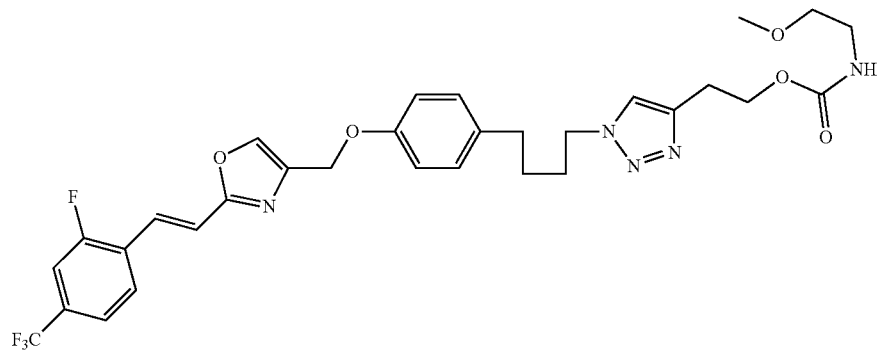 [SMILES: COCCNC(=O)OCCc1cn(CCCCc2ccc(OCc3coc(/C=C/c4ccc(C(F)(F)F)cc4F)n3)cc2)nn1]

This compound was prepared in a similar fashion as compound 69 with compound 95 and 1-isocyanato-2-methoxyethane. ¹H NMR (400 MHz, DMSO-d₆) δ ppm 1.49 (quin, J=7.20 Hz, 2H) 1.78 (quin, J=7.24 Hz, 2H) 2.52-2.58 (m, 2H) 2.89 (t, J=6.85 Hz, 2H) 3.07-3.14 (m, 2H) 3.21 (s, 3H) 4.15 (t, J=6.85 Hz, 2H) 4.32 (t, J=7.04 Hz, 2H) 4.99 (s, 2H) 6.94 (m, J=8.61 Hz, 2H) 7.10 (m, J=8.61 Hz, 2H) 7.15 (t, J=5.48 Hz, 1H) 7.39 (d, J=16.43 Hz, 1H) 7.59 (d, J=16.43 Hz, 1H) 7.65 (d, J=8.22 Hz, 1H) 7.79 (d, J=10.96 Hz, 1H) 7.90 (s, 1H) 8.16 (t, J=7.63 Hz, 1H) 8.26 (s, 1H).

Compound 97: (E)-2-(1-(4-(4-((2-(2-fluoro-4-(trifluoromethyl)styryl)oxazol-4-yl)methoxy)phenyl)butyl)-1H-1,2,3-triazol-4-yl)ethyl cyclopentylcarbamate

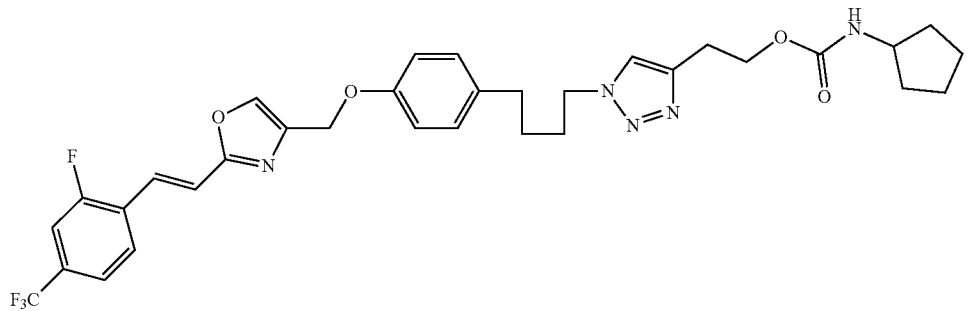 [SMILES: O=C(NC1CCCC1)OCCc1cn(CCCCc2ccc(OCc3coc(/C=C/c4ccc(C(F)(F)F)cc4F)n3)cc2)nn1]

This compound was prepared in a similar fashion as compound 69 with compound 95 and isocyanatocyclopentane. ¹H NMR (400 MHz, DMSO-d₆) δ ppm 1.30-1.63 (m, 8H) 1.68-1.84 (m, 4H) 2.51-2.57 (m, 2H) 2.89 (t, J=6.85 Hz, 2H) 4.15 (t, J=6.65 Hz, 2H) 4.32 (t, J=7.04 Hz, 2H) 4.99 (s, 2H) 6.94 (d, J=8.61 Hz, 2H) 7.02-7.15 (m, 3H) 7.39 (d, J=16.43 Hz, 1H) 7.59 (d, J=16.43 Hz, 1H) 7.64 (d, J=7.83 Hz, 1H) 7.78 (d, J=10.96 Hz, 1H) 7.89 (s, 1H) 8.16 (t, J=7.83 Hz, 1H) 8.26 (s, 1H).

Compound 98: (E)-2-(1-(4-(4-((2-(2-fluoro-4-(trifluoromethyl)styryl)oxazol-4-yl)methoxy)phenyl)butyl)-1H-1,2,3-triazol-4-yl)ethyl isopropylcarbamate

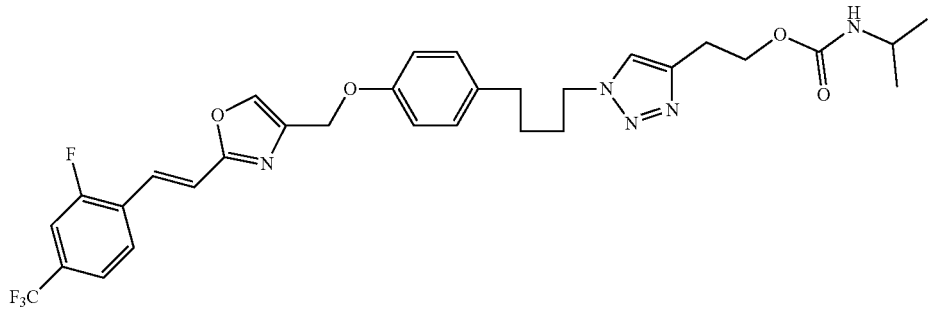 [SMILES: CC(C)NC(=O)OCCc1cn(CCCCc2ccc(OCc3coc(/C=C/c4ccc(C(F)(F)F)cc4F)n3)cc2)nn1]

This compound was prepared in a similar fashion as compound 69 with compound 95 and 2-isocyanatopropane. $^1$H NMR (400 MHz, DMSO-d$_6$) δ ppm 1.02 (d, J=6.26 Hz, 6H) 1.49 (quin, J=7.40 Hz, 2H) 1.78 (quin, J=7.40 Hz, 1H) 2.51-2.57 (m, 2H) 2.89 (t, J=6.85 Hz, 2H) 3.51-3.64 (m, 1H) 4.15 (t, J=6.65 Hz, 2H) 4.32 (t, J=7.04 Hz, 2H) 4.99 (s, 2H) 6.94 (m, J=8.61 Hz, 2H) 7.01 (d, J=7.04 Hz, 1H) 7.10 (m, J=8.61 Hz, 2H) 7.39 (d, J=16.43 Hz, 1H) 7.59 (d, J=16.43 Hz, 1H) 7.64 (d, J=8.22 Hz, 1H) 7.78 (d, J=10.56 Hz, 1H) 7.89 (s, 1H) 8.16 (t, J=7.63 Hz, 1H) 8.26 (s, 1H).

Compound 99: (E)-4-((4-(4-(1H-imidazol-1-yl)butyl)phenoxy)methyl)-2-(2-fluoro-4-nitrostyryl)oxazole

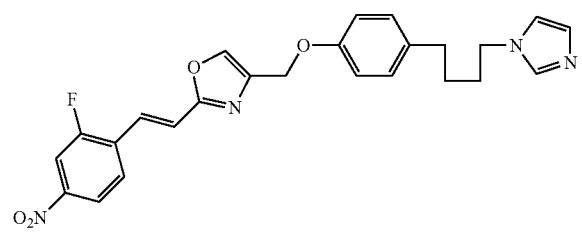 [SMILES: O=[N+]([O-])c1ccc(/C=C/c2nc(COc3ccc(CCCCn4ccnc4)cc3)co2)c(F)c1]

Step 1: 1-(4-(4-(benzyloxy)phenyl)butyl)-1H-imidazole

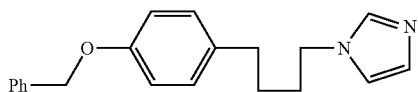

NaH 60% (0.074 g, 1.843 mmol) was added to a solution of imidazole (0.125 g, 1.843 mmol) in DMF (2.5 ml) at 0° C. and stirred 30 min at 0° C. Then, 1-(benzyloxy)-4-(4-iodobutyl)benzene (See the method described in WO 01/77107A1) (0.54 g, 1.474 mmol) in DMF (2.5 ml) was added slowly. It was brought to rt for 3 h and quenched with a NH$_4$Cl solution and extracted 3× with EA. The organic phases were combined and washed with water, Na$_2$SO$_4$ dried, filtered and the solvent removed to give 0.45 g of the title compound crude. LRMS+H$^+$307.0.

Step 2: 4-(4-(1H-imidazol-1-yl)butyl)phenol

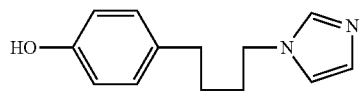 [SMILES: Oc1ccc(CCCCn2ccnc2)cc1]

A mixture of 1-(4-(4-(benzyloxy)phenyl)butyl)-1H-imidazole (0.45 g, 1.47 mmol) and Pd 10% (0.67 g) in MeOH-EA (7.2 ml) was hydrogenated at rt for 3 h. The reaction was filtered and the solvent removed to give 0.31 g of the title compound. $^1$H NMR (400 MHz, DMSO-d$_6$) δ ppm 1.42 (quin, J=7.63 Hz, 2H) 1.67 (quin, J=7.34 Hz, 2H) 2.45 (t, J=7.63 Hz, 2H) 3.95 (t, J=7.04 Hz, 2H) 6.64 (d, J=8.22 Hz, 2H) 6.86 (s, 1H) 6.94 (d, J=8.22 Hz, 2H) 7.13 (s, 1H) 7.60 (s, 1H) 9.11 (s, 1H).

Step 3: (E)-4-((4-(4-(1H-imidazol-1-yl)butyl)phenoxy)methyl)-2-(2-fluoro-4-nitrostyryl)oxazole

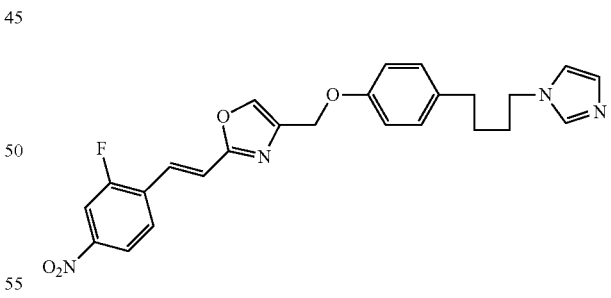

This compound was prepared in a similar fashion as compound 1 step 5 with (E)-4-(chloromethyl)-2-(2-fluoro-4-nitrostyryl)oxazole. $^1$H NMR (400 MHz, DMSO-d$_6$) δ ppm 1.49 (quin, J=7.40 Hz, 2H) 1.81 (quin, J=7.43 Hz, 2H) 2.55 (t, J=7.63 Hz, 2H) 4.20 (t, J=7.04 Hz, 2H) 5.00 (s, 2H) 6.95 (d, J=8.61 Hz, 2H) 7.11 (d, J=8.61 Hz, 2H) 7.47 (d, J=16.43 Hz, 1H) 7.61 (d, J=16.82 Hz, 1H) 7.68 (s, 1H) 7.78 (s, 1H) 8.12 (dd, J=8.61, 2.35 Hz, 1H) 8.18-8.27 (m, 2H) 8.29 (s, 1H) 9.11 (s, 1H).

Compound 100: (E)-4-((4-(4-(1H-imidazol-1-yl)butyl)phenoxy)methyl)-2-(2-fluoro-4-(trifluoromethyl)styryl)oxazole

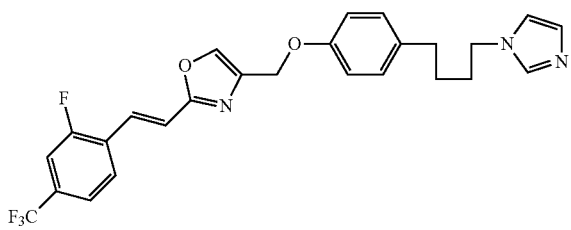

This compound was prepared as a TFA salt from the preparative HPLC (water-MeOH, 5% trifluoroacetic acid; 35-100%) in a similar fashion as compound 99 with (E)-4-(chloromethyl)-2-(2-fluoro-4-(trifluoromethyl)styryl)oxazole. 1H NMR (400 MHz, DMSO-$d_6$) δ ppm 1.47 (quin, J=7.63 Hz, 2H) 1.78 (quin, J=7.34 Hz, 2H) 2.44-2.49 (m, 2H) 4.21 (t, J=7.24 Hz, 2H) 5.42 (s, 2H) 6.59-6.68 (m, 2H) 6.95 (d, J=8.22 Hz, 2H) 7.37 (d, J=16.43 Hz, 1H) 7.59 (d, J=16.43 Hz, 1H) 7.65 (d, J=8.22 Hz, 1H) 7.74-7.84 (m, 3H) 8.14 (t, J=7.83 Hz, 1H) 8.33 (s, 1H) 9.14 (br. s., 1H) 9.27 (s, 1H).

Compound 101: (E)-2-(2-(4-(4-(1H-1,2,3-triazol-1-yl)butyl)phenoxy)-4-nitrostyryl)-4-((4-(4-(1H-1,2,3-triazol-1-yl)butyl)phenoxy)methyl)oxazole

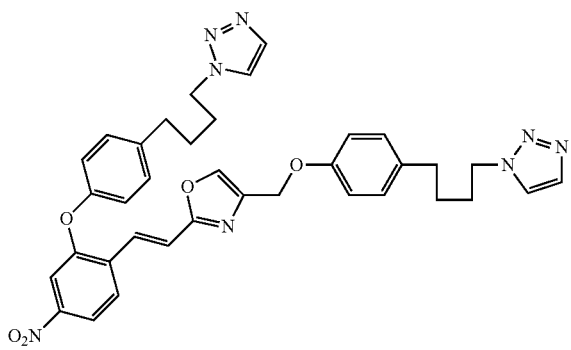 [SMILES: O=[N+]([O-])c1ccc(/C=C/c2nc(COc3ccc(CCCCn4ccnn4)cc3)co2)c(Oc2ccc(CCCCn3ccnn3)cc2)c1]

NaH 60% (0.017 g, 0.421 mmol) was added to a 0° C. solution of 4-(4-(1H-1,2,3-triazol-1-yl)butyl)phenol (0.080 g, 0.39 mmol) in DMF (0.876 ml). It was brought to rt 20 minutes then back to 0° C. (E)-4-(chloromethyl)-2-(2-fluoro-4-nitrostyryl)oxazole (0.104 g, 0.368 mmol) in DMF (0.876 ml) was added to the solution and brought to rt overnight. The mixture was quenched with a NH$_4$Cl solution and extracted 2× with EA. The combined organic solution was dried over Na$_2$SO$_4$, filtered and purified on ISCO using a RediSep® column (DCM-MeOH; 0-10%) to give 0.038 g of the bis-addition product. $^1$H NMR (400 MHz, DMSO-$d_6$) δ ppm 1.35-1.61 (m, 4H) 1.67-1.90 (m, 4H) 2.51-2.56 (m, 2H) 2.64 (t, J=7.63 Hz, 2H) 4.32-4.45 (m, 4H) 4.97 (s, 2H) 6.93 (d, J=8.61 Hz, 2H) 7.09 (t, J=8.22 Hz, 4H) 7.29 (d, J=8.61 Hz, 2H) 7.44-7.53 (m, 2H) 7.70 (d, J=3.91 Hz, 2H) 7.78 (d, J=16.43 Hz, 1H) 8.00 (dd, J=8.61, 2.35 Hz, 1H) 8.11 (d, J=7.04 Hz, 2H) 8.21-8.29 (m, 2H).

Compound 102: (E)-2-(2-fluoro-4-(trifluoromethyl)styryl)-4-((4-(4-(pyridin-3-yl)butyl)phenoxy)methyl)oxazole

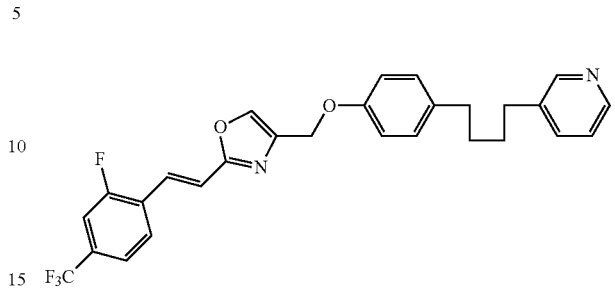

Step 1: 3-(4-(4-(benzyloxy)phenyl)but-1-yn-1-yl)pyridine

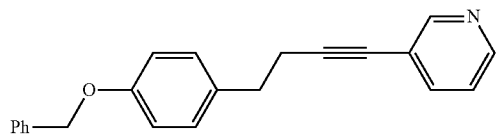 [SMILES: C(#Cc1cccnc1)CCc1ccc(OCc2ccccc2)cc1]

To a degassed mixture of 3-iodopyridine (0.109 g, 0.533 mmol) and 1-(benzyloxy)-4-(but-3-yn-1-yl)benzene (J. Org. Chem. 2017, 82, 7070, (0.120 g, 0.508 mmol) in triethylamine (2.83 ml, 20.31 mmol) was added copper(I) iodide (2.90 mg, 0.015 mmol) and PdCl$_2$(PPh$_3$)$_2$ (10.69 mg, 0.015 mmol) and heated at 80° C. overnight. It was then cooled, diluted with EA, filtered, absorbed on SiO$_2$ and the solvent removed. Purification on ISCO using a RediSep® column (Hx-EA; 0-50%) gave 0.117 g of the title compound.

Step 2: 4-(4-(pyridin-3-yl)butyl)phenol

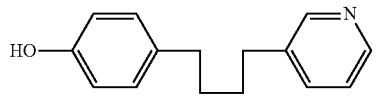 [SMILES: Oc1ccc(CCCCc2cccnc2)cc1]

A mixture of 3-(4-(4-(benzyloxy)phenyl)but-1-yn-1-yl)pyridine (0.117 g, 0.37 mmol) and Pd 10% (0.023 g) in MeOH-EA (2.5 ml) was hydrogenated at rt overnight. The reaction was filtered and the solvent removed to give 0.070 g of the title compound. $^1$H NMR (400 MHz, CDCl$_3$) δ ppm 1.58-1.71 (m, 4H) 2.56 (t, J=7.24 Hz, 2H) 2.67 (t, J=7.43 Hz, 2H) 3.91 (s, 3H) 4.58 (s, 1H) 6.74 (d, J=8.61 Hz, 2H) 7.02 (d, J=8.61 Hz, 2H) 7.31-7.38 (m, 2H) 7.79-7.88 (m, 2H).

Step 3: (E)-2-(2-fluoro-4-(trifluoromethyl)styryl)-4-((4-(4-(pyridin-3-yl)butyl)phenoxy)methyl)oxazole

Compound 104: (E)-2-(2-fluoro-4-(trifluoromethyl)styryl)-4-((4-(4-(pyridin-4-yl)butyl)phenoxy)methyl)oxazole

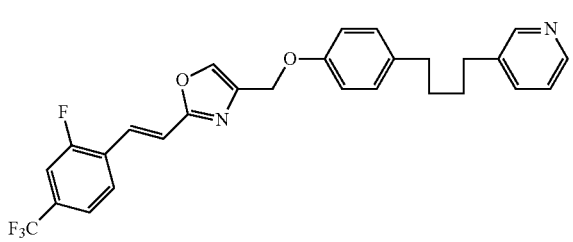 [SMILES: Fc1cc(C(F)(F)F)ccc1/C=C/c1nc(COc2ccc(CCCCc3cccnc3)cc2)co1]

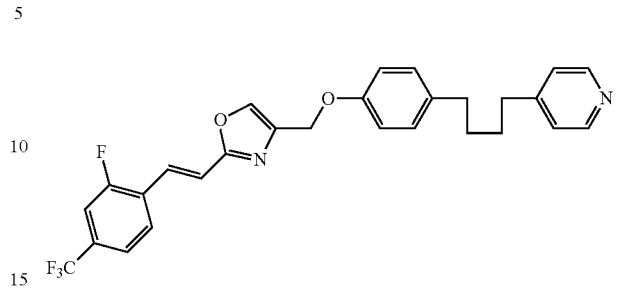

NaH (8.01 mg, 0.200 mmol) was added to 4-(4-(pyridin-3-yl)butyl)phenol (0.035 g, 0.154 mmol) in DMF (0.513 ml) followed by (E)-4-(chloromethyl)-2-(2-fluoro-4-(trifluoromethyl)styryl)oxazole (0.052 g, 0.169 mmol) was added and let stirred overnight. The mixture was quenched with a NH$_4$Cl solution and extracted 2× with EA. The combined organic solution was dried over Na$_2$SO$_4$, filtered and purified on ISCO using a RediSep® column (Hx-EA; 15-100%) to give 0.036 g of the title compound. $^1$H NMR (400 MHz, DMSO-d$_6$) δ ppm 1.47-1.60 (m, 4H) 2.52 (t, J=7.04 Hz, 2H) 2.59 (t, J=7.00 Hz, 1H) 4.97 (s, 2H) 6.92 (m, J=8.61 Hz, 2H) 7.08 (m, J=8.61 Hz, 2H) 7.27 (dd, J=7.83, 4.70 Hz, 1H) 7.37 (d, J=16.43 Hz, 1H) 7.54-7.60 (m, 2H) 7.63 (d, J=8.61 Hz, 1H) 7.77 (d, J=10.56 Hz, 1H) 8.14 (t, J=7.43 Hz, 1H) 8.24 (s, 1H) 8.36 (d, J=4.70 Hz, 1H) 8.39 (d, J=2.35 Hz, 1H).

Compound 103: (E)-2-(2-fluoro-4-nitrostyryl)-4-((4-(4-(pyridin-3-yl)butyl)phenoxy)methyl)oxazole

Step 1: 4-(4-(pyridin-4-yl)butyl)phenol

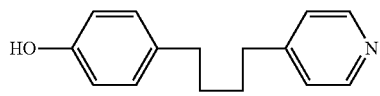

This compound was prepared in a similar fashion as compound 102 step 1 and 2 starting with 4-iodopyridine. 1H NMR (400 MHz, CDCl3) δ ppm 1.58-1.71 (m, 4H) 2.56 (t, J=7.24 Hz, 2H) 2.67 (t, J=7.43 Hz, 2H) 3.91 (s, 3H) 4.58 (s, 1H) 6.74 (d, J=8.61 Hz, 2H) 7.02 (d, J=8.61 Hz, 2H) 7.31-7.38 (m, 2H) 7.79-7.88 (m, 2H).

Step 2: (E)-2-(2-fluoro-4-(trifluoromethyl)styryl)-4-((4-(4-(pyridin-4-yl)butyl)phenoxy)methyl)oxazole

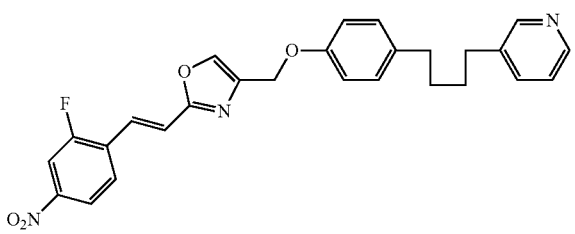 [SMILES: O=[N+]([O-])c1ccc(/C=C/c2nc(COc3ccc(CCCCc4cccnc4)cc3)co2)c(F)c1]

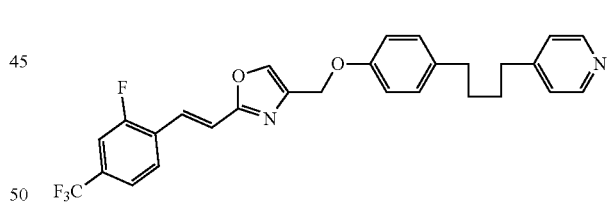

This compound was prepared in a similar fashion as compound 102 with (E)-4-(chloromethyl)-2-(2-fluoro-4-nitrostyryl)oxazole and 4-(4-(pyridin-3-yl)butyl)phenol. $^1$H NMR (400 MHz, DMSO-d$_6$) δ ppm 1.47-1.61 (m, 4H) 2.53 (t, J=6.85 Hz, 2H) 2.59 (t, J=7.04 Hz, 2H) 4.98 (s, 2H) 6.92 (m, J=8.61 Hz, 2H) 7.09 (m, J=8.22 Hz, 2H) 7.27 (dd, J=7.83, 4.70 Hz, 1H) 7.42-7.50 (m, 1H) 7.54-7.64 (m, 2H) 8.10 (dd, J=8.61, 1.96 Hz, 1H) 8.16-8.24 (m, 1H) 8.27 (s, 1H) 8.34-8.43 (m, 2H).

This compound was prepared in a similar fashion as compound 102 step 3 with (E)-4-(chloromethyl)-2-(2-fluoro-4-(trifluoromethyl)styryl)oxazole and 4-(4-(pyridin-4-yl)butyl)phenol. $^1$H NMR (400 MHz, DMSO-d$_6$) δ ppm 1.46-1.61 (m, 4H) 2.52 (t, J=7.04 Hz, 2H) 2.59 (t, J=7.04 Hz, 2H) 4.97 (s, 2H) 6.92 (m, J=8.61 Hz, 2H) 7.08 (m, J=8.22 Hz, 2H) 7.18 (d, J=5.48 Hz, 2H) 7.37 (d, J=16.43 Hz, 1H) 7.57 (d, J=16.43 Hz, 1H) 7.62 (d, J=8.22 Hz, 1H) 7.76 (d, J=10.56 Hz, 1H) 8.14 (t, J=7.83 Hz, 1H) 8.24 (s, 1H) 8.41 (d, J=5.48 Hz, 2H).

Compound 105: (E)-4-((4-(3-(1H-1,2,3-triazol-1-yl)propyl)phenoxy)methyl)-2-(2-fluoro-4-(trifluoromethyl)styryl)oxazole

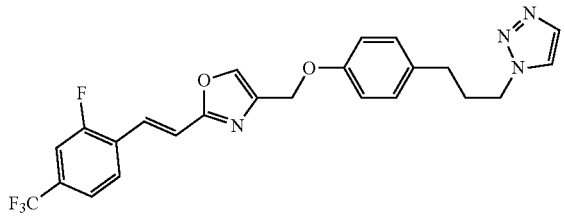 [SMILES: Fc1cc(C(F)(F)F)ccc1/C=C/c1nc(COc2ccc(CCCn3ccnn3)cc2)co1]

This compound was prepared in a similar fashion as compound 50 with (E)-4-(chloromethyl)-2-(2-fluoro-4-(trifluoromethyl)styryl)oxazole and was further purified on preparative HPLC (water-MeOH, 5% trifluoroacetic acid; 40-100%). $^1$H NMR (500 MHz, CDCL$_3$) δ ppm 1.59-1.67 (m, 2H) 1.94 (dt, J=14.98, 7.33 Hz, 2H) 2.61 (t, J=7.57 Hz, 2H) 3.06-3.15 (m, 2H) 3.16-3.24 (m, 2H) 4.40 (t, J=7.25 Hz, 2H) 4.95 (d, J=0.95 Hz, 2H) 6.86-6.92 (m, 2H) 7.03-7.09 (m, 2H) 7.28-7.35 (m, 3H) 7.50 (s, 1H) 7.59 (s, 1H) 7.70 (s, 1H). LRMS+H$^+$: 473.3.

Compound 106: (E)-4-((4-(3-(1H-1,2,3-triazol-1-yl)propyl)phenoxy)methyl)-2-(2-(2H-1,2,3-triazol-2-yl)-4-(trifluoromethyl)styryl)oxazole When preparing compound 105, a second adduct, compound 106 was also isolated:

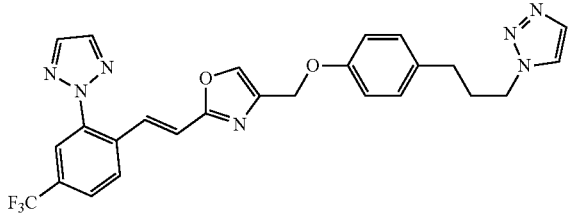 [SMILES: FC(F)(F)c1ccc(/C=C/c2nc(COc3ccc(CCCn4ccnn4)cc3)co2)c(-n2nccn2)c1]

$^1$H NMR (500 MHz, CDCl$_3$) δ ppm 2.19-2.31 (m, 2H) 2.62 (t, J=7.57 Hz, 2H) 4.39 (t, J=7.09 Hz, 2H) 5.02 (s, 2H) 6.94 (m, J=8.51 Hz, 2H) 6.99 (d, J=15.76 Hz, 1H) 7.11 (m, J=8.51 Hz, 2H) 7.53 (br. s., 1H) 7.66 (s, 1H) 7.70-7.77 (m, 2H) 7.85 (d, J=16.08 Hz, 1H) 7.90 (d, J=8.20 Hz, 1H) 7.93-7.99 (m, 2H) 8.05 (s, 1H).

Compound 107: (E)-2-(2-fluoro-4-(trifluoromethyl)styryl)-4-((4-(4-(thiazol-2-yl)butyl)phenoxy)methyl)oxazole

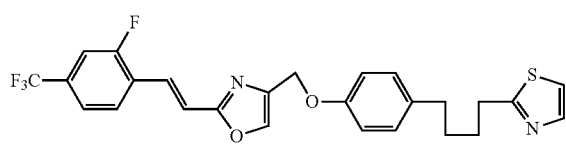 [SMILES: Fc1cc(C(F)(F)F)ccc1/C=C/c1nc(COc2ccc(CCCCc3nccs3)cc2)co1]

Step 1: 1-(4-(benzyloxy)phenyl)but-3-yn-1-ol

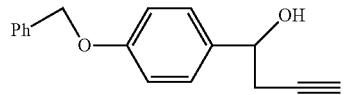 [SMILES: C#CCC(O)c1ccc(OCc2ccccc2)cc1]

To 4-(benzyloxy)benzaldehyde (4.0 g, 18.85 mmol) in THF (37.7 ml) was added 3-bromoprop-1-yne (3.16 ml, 28.3 mmol) and then activate zinc (3.70 g, 56.5 mmol) and the suspension stirred 24 h. It was then diluted with a NH4Cl solution, filtered and the solid washed with EA. The organic phase was separated, dried over Na$_2$SO$_4$ filtered and the solvent removed. Purification on ISCO using a RediSep® column (Hexane-EA; 0-40%) gave 4.8 g of the title compound. $^1$H NMR (400 MHz, CDCl$_3$) δ ppm 2.07 (t, J=2.74 Hz, 1H) 2.27 (d, J=3.52 Hz, 1H) 2.57-2.67 (m, 2H) 4.84 (td, J=6.36, 3.33 Hz, 1H) 5.07 (s, 2H) 6.87-7.00 (m, 2H) 7.29-7.35 (m, 3H) 7.35-7.45 (m, 4H).

Step 2: 1-(benzyloxy)-4-(but-3-yn-1-yl)benzene

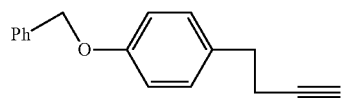

To a 0° C. solution of triethylsilane (6.08 ml, 38.0 mmol) and 1-(4-(benzyloxy)phenyl)but-3-yn-1-ol (4.8 g, 19.02 mmol) in DCM (190 ml) was added BF$_3$·OEt$_2$ (4.82 ml, 38.0 mmol) and stirred for 2 h30. It was diluted with DCM and quenched with a NaHCO$_3$ solution. The organic phase was separated, dried over Na$_2$SO$_4$ filtered and the solvent removed. Purification on ISCO using a RediSep® column (Hexane-EA; 0-50%) gave 3.14 g of the title compound. $^1$H NMR (400 MHz, CDCl$_3$) δ ppm 1.98 (t, J=2.54 Hz, 1H) 2.46 (td, J=7.53, 2.54 Hz, 2H) 2.80 (t, J=7.43 Hz, 2H) 5.06 (s, 2H) 6.87-6.96 (m, 2H) 7.13-7.18 (m, 2H) 7.30-7.36 (m, 1H) 7.39 (t, J=7.24 Hz, 2H) 7.42-7.48 (m, 2H)

Step 3: 2-(4-(4-(benzyloxy)phenyl)but-1-yn-1-yl)thiazole

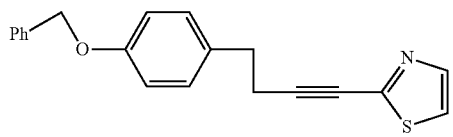 [SMILES: C(#Cc1nccs1)CCc1ccc(OCc2ccccc2)cc1]

This compound was prepared in a similar fashion as compound 102, step 1 with the previous alkyne and 2-bromothiazole. LRMS+H$^+$: 320.0.

Step 4: 4-(4-(thiazol-2-yl)butyl)phenol

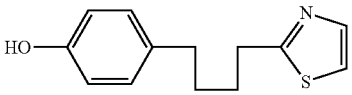 [SMILES: Oc1ccc(CCCCc2nccs2)cc1]

The previous alkyne was hydrogenated with Pd/C in MeOH-EA at 1 atmosphere and the residue then deprotected by the addition of 2.8 equivalent BCl₃ (1.0 M) to a −78° C. solution of the residue (0.05M) in DCM containing 5.0 equivalent of pentamethyl benzene for 1 h. The mixture was quenched with a NaHCO₃ solution and brought to rt. The phases were separated and the aqueous extracted with DCM and combined. It was then dried over Na₂SO₄ filtered and the solvent removed. Purification on ISCO using a RediSep® column (Hexane-EA; 0-70%) to give the title compound. ¹H NMR (400 MHz, CDCl₃) δ ppm 1.62-1.72 (m, 2H) 1.83 (quin, J=7.63 Hz, 2H) 2.58 (t, J=7.63 Hz, 2H) 3.05 (t, J=7.43 Hz, 2H) 5.41 (br. s., 1H) 6.65-6.77 (m, 2H) 7.01 (m, J=8.61 Hz, 2H) 7.18 (d, J=3.13 Hz, 1H) 7.67 (d, J=3.52 Hz, 1H).

Step 5: (E)-2-(2-fluoro-4-(trifluoromethyl)styryl)-4-((4-(4-(thiazol-2-yl)butyl)phenoxy)methyl)oxazole

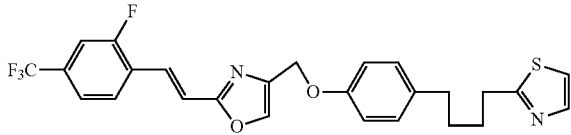

This compound was prepared in a similar fashion as compound 102, step 3 with the previous phenol and the corresponding oxazol. ¹H NMR (400 MHz, DMSO-d6) δ ppm 1.58 (m, J=7.04 Hz, 2H) 1.64-1.74 (m, 2H) 2.53 (t, J=7.43 Hz, 2H) 2.98 (t, J=7.43 Hz, 2H) 4.97 (s, 2H) 6.92 (m, J=8.61 Hz, 2H) 7.09 (m, J=8.61 Hz, 2H) 7.37 (d, J=16.80 Hz, 1H) 7.52 (d, J=3.52 Hz, 1H) 7.57 (d, J=16.80 Hz, 1H) 7.62 (br. d, J=8.50 Hz, 1H) 7.65 (d, J=3.13 Hz, 1H) 7.76 (br. d, J=11.00 Hz, 1H) 8.14 (t, J=8.00 Hz, 1H) 8.24 (s, 1H). LRMS+H⁺=503.1.

Compound 108: (E)-2-(2-fluoro-4-(trifluoromethyl)styryl)-4-((4-(4-(pyrimidin-5-yl)butyl)phenoxy)methyl)oxazole

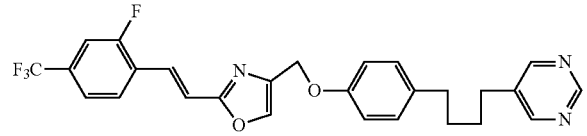 [SMILES: Fc1cc(C(F)(F)F)ccc1/C=C/c1nc(COc2ccc(CCCCc3cncnc3)cc2)co1]

Step 1: 2-(4-(4-(benzyloxy)phenyl)but-1-yn-1-yl)pyrimidine

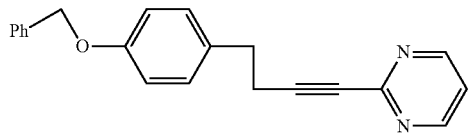 [SMILES: C(#Cc1ncccn1)CCc1ccc(OCc2ccccc2)cc1]

This compound was prepared in a similar fashion as compound 107, step 3 with 2-bromopyrimidine. LRMS+H⁺= 315.0.

Step 2: 4-(4-(pyrimidin-5-yl)butyl)phenol

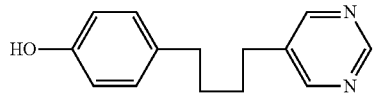

This compound was prepared in a similar fashion as compound 107, step 4. LRMS+H⁺=229.2.

Step 3: (E)-2-(2-fluoro-4-(trifluoromethyl)styryl)-4-((4-(4-(pyrimidin-5-yl)butyl)phenoxy)methyl)oxazole

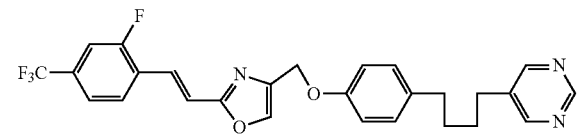 [SMILES: Fc1cc(C(F)(F)F)ccc1/C=C/c1nc(COc2ccc(CCCCc3cncnc3)cc2)co1]

This compound was prepared in a similar fashion as compound 102, step 3 with the previous phenol. ¹H NMR (400 MHz, DMSO-d6) δ ppm 1.55 (quint, J=7.40 Hz, 2H) 1.73 (quint, J=7.60 Hz, 2H) 2.53 (t, J=7.63 Hz, 2H) 2.85 (t, J=7.43 Hz, 2H) 4.97 (s, 2H) 6.92 (m, J=8.61 Hz, 2H) 7.08 (m, J=8.22 Hz, 2H) 7.29 (t, J=4.89 Hz, 1H) 7.37 (d, J=16.43 Hz, 1H) 7.57 (d, J=16.82 Hz, 1H) 7.62 (d, J=8.22 Hz, 1H) 7.76 (d, J=10.96 Hz, 1H) 8.14 (t, J=7.63 Hz, 1H) 8.24 (s, 1H) 8.68 (d, J=4.70 Hz, 2H). LRMS+H⁺=498.2.

Compound 109: (E)-4-((4-(3-(1H-1,2,3-triazol-1-yl)propoxy)phenoxy)methyl)-2-(2-fluoro-4-(trifluoromethyl)styryl)oxazole

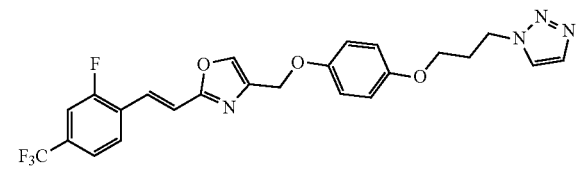 [SMILES: Fc1cc(C(F)(F)F)ccc1/C=C/c1nc(COc2ccc(OCCCn3ccnn3)cc2)co1]

Step 1: 3-(4-methoxyphenoxy)propyl methanesulfonate

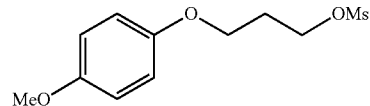 [SMILES: COc1ccc(OCCCOS(C)(=O)=O)cc1]

This compound was prepared in a similar fashion as compound 1, step 1 starting with 3-(4-methoxyphenoxy)propan-1-ol (1.045 g, 5.73 mmol). ¹H NMR (400 MHz, CDCl₃) δ ppm 2.20 (t, J=6.06 Hz, 2H) 2.99 (s, 3H) 3.77 (s, 3H) 4.04 (t, J=5.87 Hz, 2H) 4.44 (t, J=6.26 Hz, 2H) 6.83 (s, 4H).

Step 2: 1-(3-azidopropoxy)-4-methoxybenzene

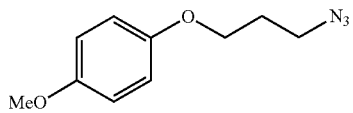 [SMILES: COc1ccc(OCCCN=[N+]=[N-])cc1]

Sodium azide (0.225 g, 3.46 mmol) was added to 3-(4-methoxyphenoxy)propyl methanesulfonate (0.6 g, 2.305 mmol) in N,N-dimethylformamide (1 ml). The reaction mixture was heated to 50° C. for 16 hr, then cooled to 20° C. and quenched with water (3 ml). The reaction mixture was extracted with $Et_2O$ (3×10 ml) and the organic layer was washed with water (10 ml) and brine (10 ml), dried over $MgSO_4$, filtered and concentrated to give title compound (0.46 g, 96%) as an oil. $^1$H NMR (400 MHz, MeOH-d4) δ ppm 2.03 (t, J=6.26 Hz, 2H) 3.51 (t, J=6.65 Hz, 2H) 3.77 (s, 2H) 4.00 (t, J=5.87 Hz, 2H) 6.84 (s, 3H).

Step 3: 1-(3-(4-methoxyphenoxy)propyl)-1H-1,2,3-triazole

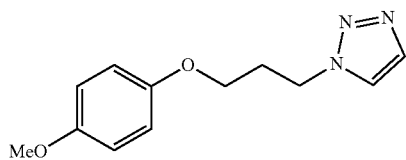 [SMILES: COc1ccc(OCCCn2ccnn2)cc1]

A mixture of 1-(3-azidopropoxy)-4-methoxybenzene (0.3 g, 1.45 mmol) and vinyl acetate (3.96 ml, 43.4 mmol) in a microwave tube was heated to 120° C. for 21 h. The mixture was concentrated to dryness and the residue was purified on ISCO using a RediSep® column (DCM to 40% AcOEt in DCM) to give title compound (0.27 g, 80% yield) as a colorless oil. $^1$H NMR (400 MHz, $CDCl_3$) δ ppm 2.38 (quin, J=6.26 Hz, 2H) 3.77 (s, 2H) 3.89 (t, J=5.87 Hz, 2H) 4.62 (t, J=6.85 Hz, 2H) 6.76-6.88 (m, 3H) 7.54 (s, 1H) 7.69 (s, 1H).

Step 4: 4-(3-(1H-1,2,3-triazol-1-yl)propoxy)phenol

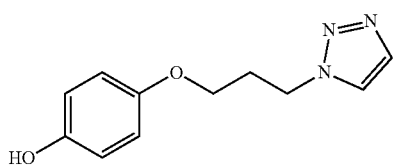 [SMILES: Oc1ccc(OCCCn2ccnn2)cc1]

This compound was prepared in a similar fashion as compound 1, step 4. $^1$H NMR (400 MHz, $CDCl_3$) δ ppm 2.32 (t, J=5.87 Hz, 2H) 3.83 (t, J=5.67 Hz, 2H) 4.58 (t, J=6.85 Hz, 2H) 6.71 (d, J=1.57 Hz, 4H) 7.55 (s, 1H) 7.64 (s, 1H).

Step 5: (E)-4-((4-(3-(1H-1,2,3-triazol-1-yl)propoxy)phenoxy)methyl)-2-(2-fluoro-4-(trifluoromethyl)styryl) oxazole

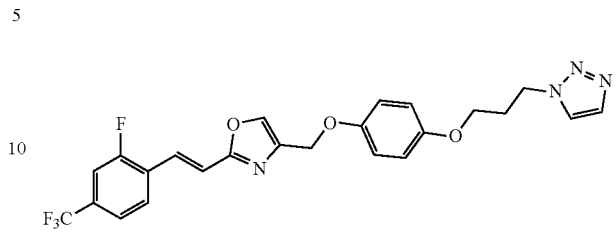

This compound was prepared in a similar fashion as compound 1, step 5. $^1$H NMR (400 MHz, $CDCl_3$) δ ppm 2.39 (t, J=6.06 Hz, 2H) 3.90 (t, J=5.67 Hz, 2H) 4.62 (t, J=6.85 Hz, 2H) 4.99 (s, 2H) 6.76-6.86 (m, 2H) 6.88-6.99 (m, 2H) 7.13 (d, J=16.82 Hz, 1H) 7.33-7.48 (m, 2H) 7.55 (s, 1H) 7.59-7.72 (m, 3H). LRMS+H$^+$=489.1.

Compound 110: (E)-4-((4-(4-(2H-tetrazol-2-yl)butyl)phenoxy)methyl)-2-(2-fluoro-4-(trifluoromethyl)styryl)oxazole

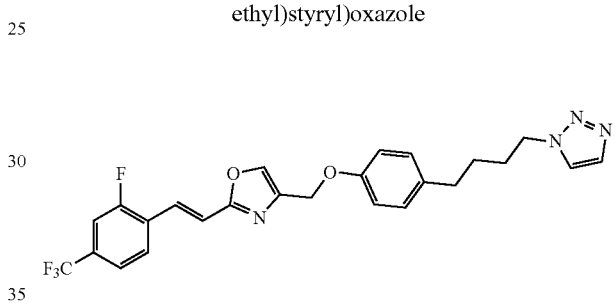

Step 1: 2-(4-(4-methoxyphenyl)butyl)-2H-tetrazole

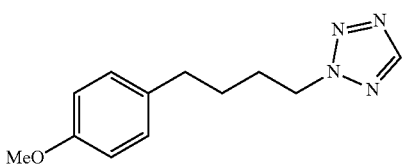 [SMILES: COc1ccc(CCCCn2ncnn2)cc1]

This compound was isolated as a regioisomer in the preparation of compound 90. LRMS+H$^+$=233.1.

Step 2: 4-(4-(2H-tetrazol-2-yl)butyl)phenol

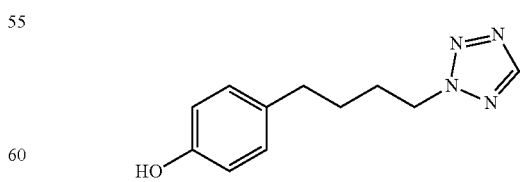

This compound was prepared in a similar fashion as compound 1, step 3. $^1$H NMR (400 MHz, $CDCl_3$) δ ppm 1.58-1.68 (m, 2H) 1.92-2.11 (m, 2H) 2.56-2.63 (m, 2H) 4.78 (s, 0H) 4.65 (t, J=7.04 Hz, 2H) 6.69-6.80 (m, 2H) 7.01 (m, J=8.61 Hz, 2H) 8.49 (s, 1H).

Step 3: (E)-4-((4-(4-(2H-tetrazol-2-yl)butyl)phenoxy)methyl)-2-(2-fluoro-4-(trifluoromethyl)styryl) oxazole

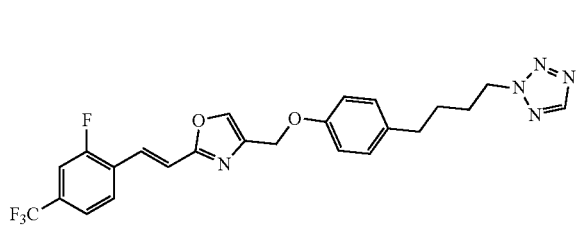 [SMILES: Fc1cc(C(F)(F)F)ccc1/C=C/c1nc(COc2ccc(CCCCn3ncnn3)cc2)co1]

This compound was prepared in a similar fashion as compound 1, step 5. ¹H NMR (400 MHz, CDCl₃) δ ppm 1.63 (t, J=7.63 Hz, 2H) 1.95-2.15 (m, 2H) 2.61 (t, J=7.43 Hz, 2H) 4.65 (t, J=7.04 Hz, 2H) 5.02 (s, 2H) 6.91 (d, J=8.22 Hz, 2H) 7.03-7.19 (m, 3H) 7.33-7.49 (m, 2H) 7.57-7.76 (m, 3H) 8.49 (s, 1H). HRMS+H⁺: 488.1747.

Compound 111: 4-((E)-4-(4-(1H-1,2,3-triazol-1-yl) butyl)styryl)-2-((E)-2-fluoro-4-(trifluoromethyl) styryl) oxazole

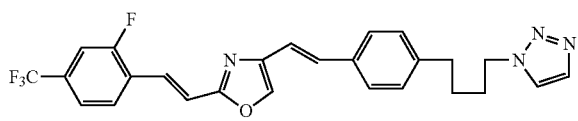 [SMILES: Fc1cc(C(F)(F)F)ccc1/C=C/c1nc(/C=C/c2ccc(CCCCn3ccnn3)cc2)co1]

Step 1: (E)-((2-(2-fluoro-4-(trifluoromethyl)styryl) oxazol-4-yl)methyl)triphenylphosphonium chloride

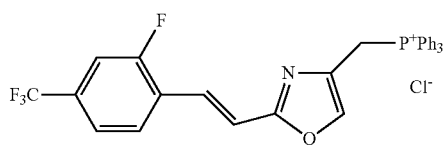

A mixture of triphenylphosphine (0.113 g, 0.429 mmol) and (E)-4-(chloromethyl)-2-(2-fluoro-4-(trifluoromethyl) styryl)oxazole (0.125 g, 0.409 mmol) in ACN (4.09 ml) was heated to 95° C. overnight. The solvent was removed and the residue taken in EA and the solvent removed again. A solid was obtained and stirred in ethyl ether with 2-3% EA. The solid was filtered and dried under high vacuum to give 0.092 g of the title compound. LRMS+H⁺: 532.2.

Step 2: 4-(4-hydroxybut-1-yn-1-yl)benzaldehyde

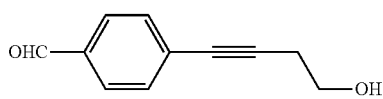

This compound was prepared in a similar fashion as compound 102, step 1 with 4-bromobenzaldehyde.

Step 3: 4-(4-hydroxybutyl)benzaldehyde

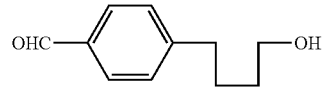 [SMILES: O=Cc1ccc(CCCCO)cc1]

A Mixture of the previous aldehyde (0.400 g, 2.3 mmol) and Pd/C (0.040 g) in EA (23 ml) was hydrogenated until completion. The mixture was filtered and the solvent removed. Purification on ISCO using a RediSep® column (Hx-EA; 0-60%) gave 0.147 g of the title compound. ¹H NMR (400 MHz, CDCl₃) δ ppm 1.59-1.66 (m, 2H) 1.68-1.80 (m, 2H) 2.73 (t, J=7.63 Hz, 2H) 3.68 (t, J=6.26 Hz, 2H) 7.35 (m, J=7.83 Hz, 2H) 7.80 (m, J=8.22 Hz, 2H) 9.97 (s, 1H).

Step 4: 4-(4-(1H-1,2,3-triazol-1-yl)butyl)benzaldehyde

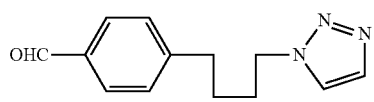

This compound was prepared in a similar fashion as compound 109, step 1, 2 and 3 from the previous alcohol and used directly for the next step.

Step 5: 4-((E)-4-(4-(1H-1,2,3-triazol-1-yl)butyl) styryl)-2-((E)-2-fluoro-4-(trifluoromethyl)styryl) oxazole

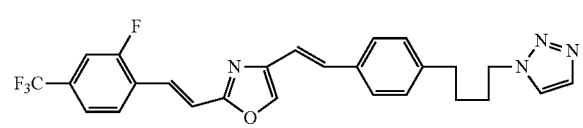 [SMILES: Fc1cc(C(F)(F)F)ccc1/C=C/c1nc(/C=C/c2ccc(CCCCn3ccnn3)cc2)co1]

To a solution of (E)-((2-(2-fluoro-4-(trifluoromethyl) styryl)oxazol-4-yl)methyl)triphenylphosphonium chloride (0.092 g, 0.161 mmol) and 4-(4-(1H-1,2,3-triazol-1-yl) butyl)benzaldehyde (0.037 g, 0.161 mmol) in EtOH (0.538 ml) at rt was added solid potassium t-butoxide (0.020 g, 0.178 mmol). Let go for 4 h. The reaction was quenched with water and diluted with EA. The layers were separated and the aqueous extracted with EA, combined, Na₂SO₄ dried, filtered and the solvent removed. The residues was absorbed on SiO2 and purified on ISCO using a RediSep® column (Hexane-EA; 0-100%) to give 0.041 g of a mixture of cis and trans. 6 mg of the mixture was taken in a 5% solution of iodine in toluene and heated at 100 C overnight. The solvent was removed and the residue taken in EA and solvent removed again to give 4.5 mg of the trans adduct. ¹H NMR (400 MHz, DMSO-d6) δ ppm 1.55 (quint, J=7.40 Hz, 2H) 1.73 (quint, J=7.60 Hz, 2H) 2.53 (t, J=7.63 Hz, 2H) 2.85 (t, J=7.43 Hz, 2H) 4.97 (s, 2H) 6.92 (m, J=8.61 Hz, 2H) 7.08 (m, J=8.22 Hz, 2H) 7.29 (t, J=4.89 Hz, 1H) 7.37 (d, J=16.43 Hz, 1H) 7.57 (d, J=16.82 Hz, 1H) 7.62 (d, J=8.22 Hz, 1H) 7.76 (d, J=10.96 Hz, 1H) 8.14 (t, J=7.63 Hz, 1H) 8.24 (s, 1H) 8.68 (d, J=4.70 Hz, 2H). LRMS+H⁺=483.1.

Compound 112: 4-((4-(4-(1H-1,2,3-triazol-1-yl)butyl)phenoxy)methyl)-2-(5-fluorobenzofuran-2-yl)oxazole

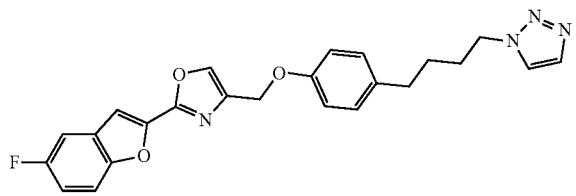 [SMILES: Fc1ccc2oc(-c3nc(COc4ccc(CCCCn5ccnn5)cc4)co3)cc2c1]

Step 1: 5-fluorobenzofuran-2-carboxamide

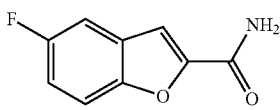 [SMILES: NC(=O)c1cc2cc(F)ccc2o1]

This compound was prepared in a similar fashion as compound 76 step 4 using 5-fluorobenzofuran-2-carboxylic acid. $^1$H NMR (400 MHz, DMSO-d$_6$) δ ppm 8.14 (br. s., 1H), 7.72 (br. s., 1H), 7.67 (dd, J=9.0, 4.3 Hz, 1H), 7.59 (dd, J=8.6, 2.7 Hz, 1H), 7.52 (s, 1H), 7.30 (td, J=9.2, 2.7 Hz, 1H).

Step 2: 4-(chloromethyl)-2-(5-fluorobenzofuran-2-yl)oxazole

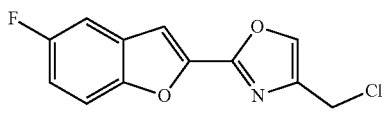 [SMILES: Fc1ccc2oc(-c3nc(CCl)co3)cc2c1]

This compound was prepared in a similar fashion as compound 61 step 3 using the previous intermediate. $^1$H NMR (400 MHz, DMSO-d$_6$) δ ppm 8.39 (s, 1H), 7.78 (dd, J=9.0, 4.3 Hz, 1H), 7.65 (s, 1H), 7.59 (dd, J=8.8, 2.5 Hz, 1H), 7.33 (td, J=9.4, 2.7 Hz, 1H), 4.78 (s, 2H).

Step 3: 4-((4-(4-(1H-1,2,3-triazol-1-yl)butyl)phenoxy)methyl)-2-(5-fluorobenzofuran-2-yl)oxazole

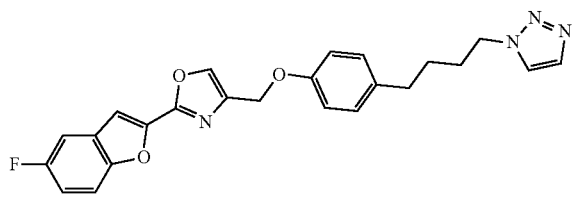 [SMILES: Fc1ccc2oc(-c3nc(COc4ccc(CCCCn5ccnn5)cc4)co3)cc2c1]

This compound was prepared according to compound 1 step 5. $^1$H NMR (400 MHz, DMSO-d$_6$) δ ppm 8.40 (s, 1H), 8.11 (s, 1H), 7.77 (dd, J=9.0, 4.3 Hz, 1H), 7.70 (s, 1H), 7.63 (s, 1H), 7.58 (dd, J=8.8, 2.5 Hz, 1H), 7.32 (td, J=9.2, 2.7 Hz, 1H), 7.07-7.14 (m, J=8.6 Hz, 2H), 6.91-7.00 (m, J=8.6 Hz, 2H), 5.05 (s, 2H), 4.39 (t, J=7.0 Hz, 2H), 2.54 (t, J=7.8 Hz, 2H), 1.81 (quin, J=7.3 Hz, 2H), 1.48 (quin, J=7.6 Hz, 2H).

Compound 113: 4-((4-(4-(1H-1,2,3-triazol-1-yl)butyl)phenoxy)methyl)-2-(5-fluorobenzo[b]thiophen-2-yl)oxazole

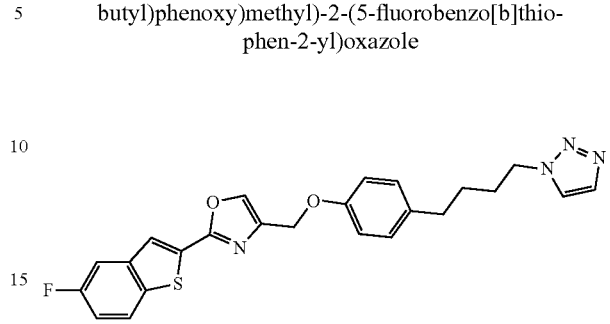

Step 1: 5-fluorobenzo[b]thiophene-2-carboxamide

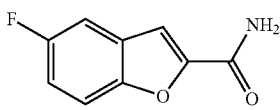 [SMILES: NC(=O)c1cc2cc(F)ccc2o1]

This compound was prepared in a similar fashion as compound 76 step 4 using 5-fluorobenzo[b]thiophene-2-carboxylic acid. $^1$H NMR (400 MHz, DMSO-d$_6$) δ ppm 8.26 (br. s., 1H), 8.00-8.09 (m, 2H), 7.77 (dd, J=9.8, 2.7 Hz, 1H), 7.65 (br. s., 1H), 7.34 (td, J=9.0, 2.7 Hz, 1H).

Step 2: 4-(chloromethyl)-2-(5-fluorobenzo[b]thiophen-2-yl)oxazole

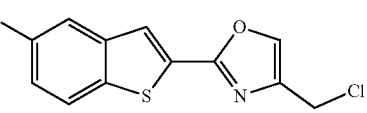

This compound was prepared in a similar fashion as compound 61 step 3 using the previous intermediate. $^1$H NMR (400 MHz, DMSO-d$_6$) δ ppm 8.34 (s, 1H), 8.13 (dd, J=8.8, 4.9 Hz, 1H), 8.08 (s, 1H), 7.81 (dd, J=9.6, 2.5 Hz, 1H), 7.38 (td, J=9.0, 2.3 Hz, 1H), 4.76 (s, 2H).

Step 3: 4-((4-(4-(1H-1,2,3-triazol-1-yl)butyl)phenoxy)methyl)-2-(5-fluorobenzo[b]thiophen-2-yl)oxazole

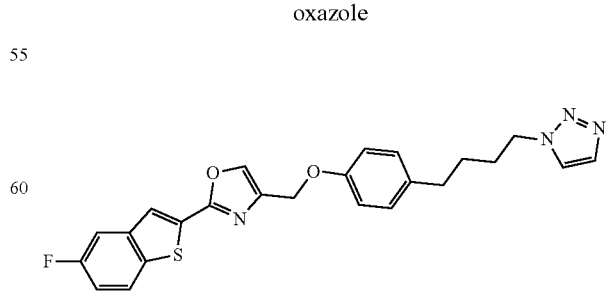

This compound was prepared according to compound 1 step 5. $^1$H NMR (400 MHz, DMSO-d$_6$) δ ppm 8.36 (s, 1H), 8.09-8.15 (m, 2H), 8.06 (s, 1H), 7.81 (dd, J=9.6, 2.5 Hz, 1H), 7.70 (s, 1H), 7.37 (td, J=9.0, 2.7 Hz, 1H), 7.07-7.14 (m, J=8.6 Hz, 2H), 6.92-6.99 (m, J=8.6 Hz, 2H), 5.03 (s, 2H), 4.39 (t, J=7.0 Hz, 2H), 2.54 (t, J=7.4 Hz, 2H), 1.81 (quin, J=7.3 Hz, 2H), 1.48 (quin, J=7.5 Hz, 2H).

Compound 114: ethyl (E)-1-(4-(4-((2-(4-(trifluoromethyl)styryl)oxazol-4-yl)methoxy)phenyl)butyl)-1H-1,2,3-triazole-4-carboxylate

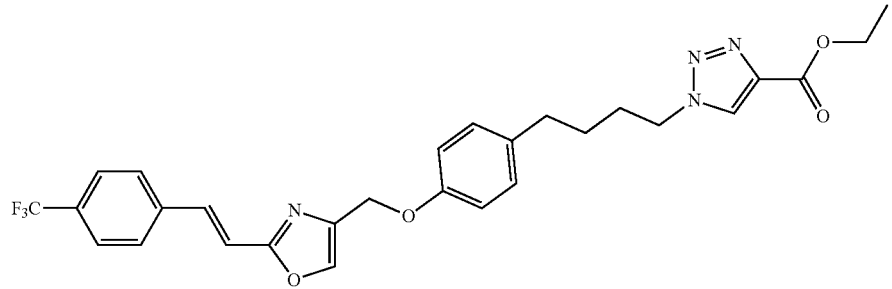 [SMILES: CCOC(=O)c1cn(CCCCc2ccc(OCc3coc(/C=C/c4ccc(C(F)(F)F)cc4)n3)cc2)nn1]

This compound was prepared in a similar fashion as compound 4 with (E)-4((4-(4-azidobutyl)phenoxy)methyl)-2-(4-(trifluoromethyl)styryl)oxazole and ethyl propiolate. $^1$H NMR (400 MHz, DMSO-d$_6$) δ ppm 1.29 (t, J=7.04 Hz, 3H) 1.47 (quin, J=7.60 Hz, 2H) 1.84 (quin, J=7.40 Hz, 2H) 2.51-2.57 (m, 2H) 4.30 (q, J=7.17 Hz, 2H) 4.43 (t, J=7.04 Hz, 2H) 4.98 (s, 2H) 6.94 (d, J=8.61 Hz, 2H) 7.10 (d, J=8.61 Hz, 2H) 7.34 (d, J=16.43 Hz, 1H) 7.61 (d, J=16.43 Hz, 1H) 7.76 (m, J=8.22 Hz, 2H) 7.95 (d, J=8.22 Hz, 2H) 8.23 (s, 1H) 8.78 (s, 1H). LRMS+H$^+$=541.1.

Compound 115: (E)-4-((4-((2-(1H-1,2,3-triazol-1-yl)ethoxy)methyl)phenoxy)methyl)-2-(2-fluoro-4-(trifluoromethyl)styryl)oxazole

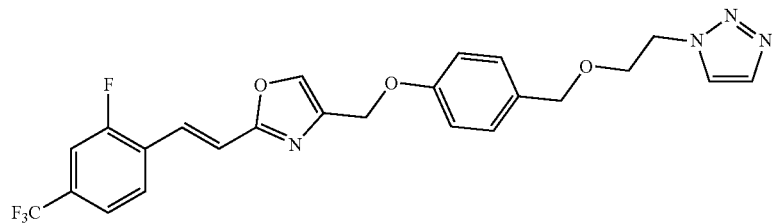 [SMILES: Fc1cc(C(F)(F)F)ccc1/C=C/c1nc(COc2ccc(COCCn3ccnn3)cc2)co1]

Step 1: (4-(chloromethyl)phenoxy)triisopropylsilane

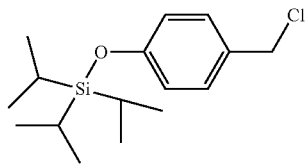 [SMILES: CC(C)[Si](Oc1ccc(CCl)cc1)(C(C)C)C(C)C]

To a solution of (4-((triisopropylsilyl)oxy)phenyl)methanol (1.5 g, 5.35 mmol) in DCM (10.70 ml) was added thionyl chloride (0.624 ml, 8.56 mmol) dropwise at 0° C. After the addition the ice bath was removed and the reaction mixture was stirred at room temperature for 2 h. The mixture was diluted with DCM (20 ml), washed with water (3×10 ml), dried and concentrated. The residue was-purified using ISCO column (Hx to 20% AcOEt) to give title compound (1.3 g, 81% yield). $^1$H NMR (400 MHz, CDCl$_3$) δ ppm 1.09 (d, J=7.04 Hz, 18H) 1.19-1.30 (m, 3H) 4.55 (s, 2H) 6.84 (d, J=8.61 Hz, 2H) 7.23 (d, J=8.61 Hz, 2H).

Step 2: 4-((2-azidoethoxy)methyl)phenol

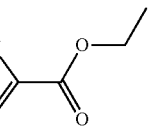

Sodium hydride (0.039 g, 1.606 mmol) was added to a cold solution of 2-azidoethanol (0.140 g, 1.606 mmol) in DMF (3 ml), followed by Bu4NI (9.42 mg, 0.067 mmol). After 15 min, (4-(chloromethyl)phenoxy)triisopropylsilane (0.4 g, 1.3 mmol) was added and the reaction mixture was stirred overnight. The mixture was diluted with AcOEt (20 ml), filtered through a pad of celite and the filtrate was concentrated to dryness. The residue was purified on ISCO using a RediSep® column (DCM/EA; 0-40%) to give 0.060 g (23%) of the title compound. 1H NMR (400 MHz, CDCl3) δ ppm 3.39 (t, J=5.09 Hz, 2H) 3.63 (t, J=5.09 Hz, 2H) 3.81 (s, 2H) 4.51 (s, 2H) 6.89 (d, J=8.61 Hz, 1H) 7.28 (d, J=8.61 Hz, 1H).

Step 3: 4-((2-(1H-1,2,3-triazol-1-yl)ethoxy)methyl) phenol

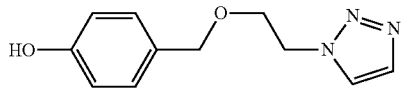

A mixture of 4-((2-azidoethoxy)methyl)phenol (0.06 g, 0.311 mmol) in vinyl acetate (0.851 ml, 9.32 mmol) was heated to 120° C. for 21 h in a microwave tube. The mixture was concentrated to dryness under high vacuum to give desired 4-((2-(1H-1,2,3-triazol-1-yl)ethoxy)methyl)phenol (64 mg, 0.29 mmol, 94% yield) as a colorless oil, which was pure enough for next reaction without further purification. $^1$H NMR (400 MHz, CDCl$_3$) δ ppm 3.82 (t, J=5.09 Hz, 2H) 4.41 (s, 2H) 4.58 (t, J=5.09 Hz, 2H) 5.09 (s, 1H) 6.80 (m, J=8.22 Hz, 2H) 7.11 (m, J=8.22 Hz, 2H) 7.69 (d, J=4.30 Hz, 2H).

Step 4: (E)-4-((4-((2-(1H-1,2,3-triazol-1-yl)ethoxy)methyl)phenoxy)methyl)-2-(2-fluoro-4-(trifluoromethyl)styryl)oxazole

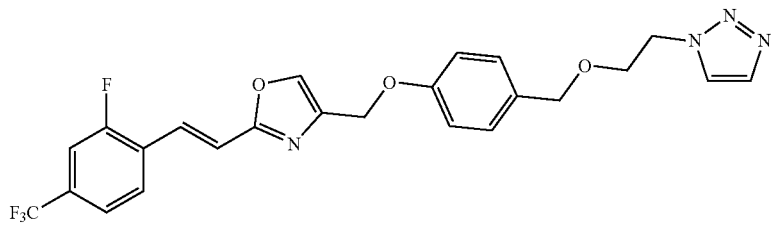 [SMILES: Fc1cc(C(F)(F)F)ccc1/C=C/c1nc(COc2ccc(COCCn3ccnn3)cc2)co1]

This compound was prepared in a similar fashion as compound 32 from the previous phenol and (E)-4-(chloromethyl)-2-(2-fluoro-4-(trifluoromethyl)styryl)oxazole. $^1$H NMR (400 MHz, CDCl$_3$) δ ppm 3.83 (t, J=5.09 Hz, 2H) 4.44 (s, 2H) 4.58 (t, J=5.09 Hz, 2H) 5.04 (s, 2H) 6.96 (d, J=8.61 Hz, 2H) 7.09-7.21 (m, 3H) 7.38 (d, J=10.56 Hz, 1H) 7.44 (d, J=8.22 Hz, 1H) 7.58-7.75 (m, 5H). LRMS+H$^+$=489.2.

Compound 116: (E)-4-((4-(4-(1H-1,2,3-triazol-1-yl)butyl)phenoxy)methyl)-2-(4-chloro-2-fluorostyryl)oxazole

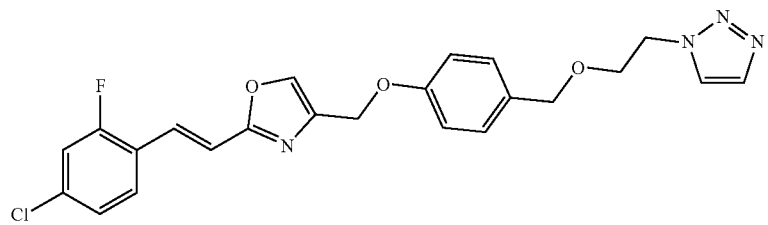 [SMILES: Fc1cc(Cl)ccc1/C=C/c1nc(COc2ccc(COCCn3ccnn3)cc2)co1]

Step 1: (E)-2-(4-chloro-2-fluorostyryl)-4-(chloromethyl)oxazole

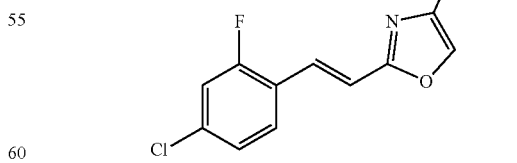

This compound was prepared in a similar fashion as compound 3A/B step 1 and 2 from the corresponding (E)-3-(4-chloro-2-fluorophenyl)acrylic acid. 1H NMR (DMSO-d$_6$) δ: 8.21 (s, 1H), 7.96 (t, J=8.4 Hz, 1H), 7.48-7.58 (m, 2H), 7.37 (dd, J=8.6, 1.6 Hz, 1H), 7.25 (d, J=16.8 Hz, 1H), 4.71 (s, 2H).

Step 2: (E)-4-((4-(4-(1H-1,2,3-triazol-1-yl)butyl)
phenoxy)methyl)-2-(4-chloro-2-fluorostyryl)oxazole

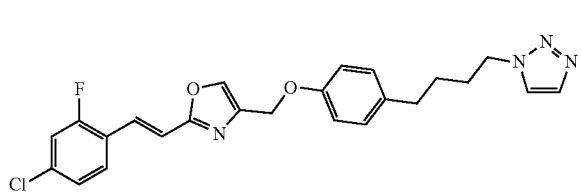 [SMILES: Fc1cc(Cl)ccc1/C=C/c1nc(COc2ccc(CCCCn3ccnn3)cc2)co1]

This compound was prepared in a similar fashion as compound 32 step 2 from the previous chloride and the corresponding phenol. 1H NMR (DMSO-$d_6$) δ: 8.22 (s, 1H), 8.11 (s, 1H), 7.95 (t, J=8.4 Hz, 1H), 7.70 (s, 1H), 7.48-7.58 (m, 2H), 7.37 (d, J=8.6 Hz, 1H), 7.25 (d, J=16.8 Hz, 1H), 7.05-7.14 (d, J=8.6 Hz, 2H), 6.90-6.98 (d, J=8.2 Hz, 2H), 4.98 (s, 2H), 4.39 (t, J=7.0 Hz, 2H), 2.52-2.58 (m, 2H), 1.81 (quin, J=7.2 Hz, 2H), 1.48 (quin, J=7.5 Hz, 2H). LRMS+H$^+$=453.1.

Compound 117: (E)-4-((4-(4-(1H-1,2,3-triazol-1-yl)
butyl)phenoxy)methyl)-2-(2-chloro-4-fluorostyryl)
oxazole

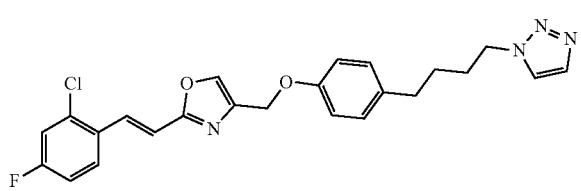 [SMILES: Fc1ccc(/C=C/c2nc(COc3ccc(CCCCn4ccnn4)cc3)co2)c(Cl)c1]

Step 1: (E)-2-(2-chloro-4-fluorostyryl)-4-(chloromethyl)oxazole

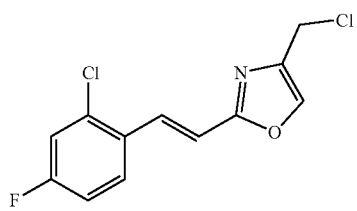 [SMILES: Fc1ccc(/C=C/c2nc(CCl)co2)c(Cl)c1]

(E)-2-(2-chloro-4-fluorostyryl)-4-(chloromethyl)
oxazole

This compound was prepared in a similar fashion as compound 3A/B step 1 and 2 from the corresponding (E)-3-(2-chloro-4-fluorophenyl)acrylic acid. 1H NMR (DMSO-$d_6$) δ: 8.21 (s, 1H), 8.09 (dd, J=8.6, 6.3 Hz, 1H), 7.72 (d, J=16.0 Hz, 1H), 7.56 (dd, J=8.8, 2.5 Hz, 1H), 7.32 (td, J=8.6, 2.7 Hz, 1H), 7.25 (d, J=16.0 Hz, 1H), 4.72 (s, 2H).

Step 2: (E)-4-((4-(4-(1H-1,2,3-triazol-1-yl)butyl)
phenoxy)methyl)-2-(2-chloro-4-fluorostyryl)oxazole

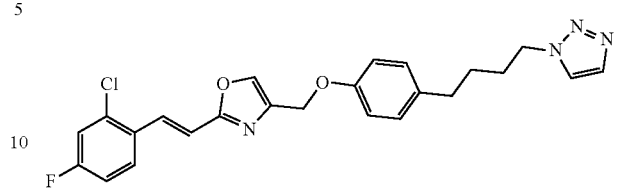

This compound was prepared in a similar fashion as compound 32 step 2 from the previous chloride and the corresponding phenol. $^1$H NMR (DMSO-$d_6$) δ: 8.22 (s, 1H), 8.04-8.13 (m, 2H), 7.67-7.76 (m, 2H), 7.56 (dd, J=8.6, 2.3 Hz, 1H), 7.32 (td, J=8.5, 2.5 Hz, 1H), 7.25 (d, J=16.4 Hz, 1H), 7.06-7.13 (d, J=8.6 Hz, 2H), 6.90-6.97 (d, J=8.6 Hz, 2H), 4.98 (s, 2H), 4.39 (t, J=7.0 Hz, 2H), 2.52-2.58 (m, 2H), 1.81 (quin, J=7.3 Hz, 2H), 1.48 (quin, J=7.5 Hz, 2H). LRMS+H$^+$=453.1. LRMS+H$^+$=453.1.

Compound 118: (E)-4-((4-(4-(1H-1,2,3-triazol-1-yl)
butyl)phenoxy)methyl)-2-(2-chlorostyryl)oxazole

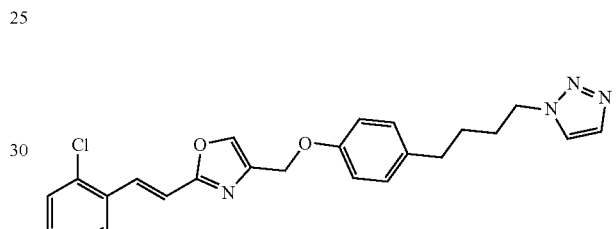

Step 1: (E)-4-(chloromethyl)-2-(2-chlorostyryl)oxazole

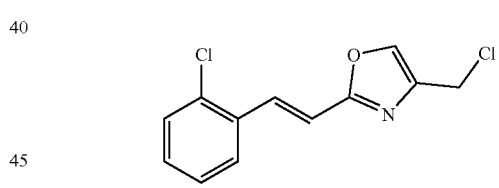

This compound was prepared in a similar fashion as compound 3A/B step 1 and 2 from the corresponding (E)-3-(2-chlorophenyl)acrylic acid. $^1$H NMR (DMSO-$d_6$) δ: 8.21 (s, 1H), 8.09 (dd, J=8.6, 6.3 Hz, 1H), 7.72 (d, J=16.0 Hz, 1H), 7.56 (dd, J=8.8, 2.5 Hz, 1H), 7.32 (td, J=8.6, 2.7 Hz, 1H), 7.25 (d, J=16.0 Hz, 1H), 4.72 (s, 2H).

Step 2: (E)-4-((4-(4-(1H-1,2,3-triazol-1-yl)butyl)
phenoxy)methyl)-2-(2-chlorostyryl)oxazole

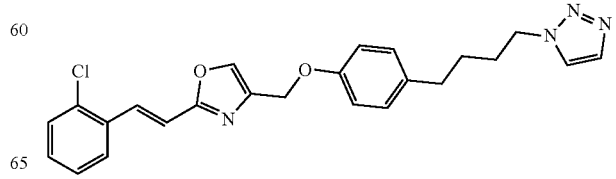

This compound was prepared in a similar fashion as compound 32 step 2 from the previous chloride and the corresponding phenol. $^1$H NMR (DMSO-d$_6$) δ: 8.23 (s, 1H), 8.11 (s, 1H), 7.98-8.05 (m, 1H), 7.78 (d, J=16.4 Hz, 1H), 7.70 (s, 1H), 7.50-7.58 (m, 1H), 7.36-7.44 (m, 2H), 7.27 (d, J=16.4 Hz, 1H), 7.05-7.14 (d, J=8.6 Hz, 2H), 6.91-6.98 (d, J=8.6 Hz, 2H), 4.99 (s, 2H), 4.39 (t, J=7.0 Hz, 2H), 2.52-2.58 (m, 2H), 1.81 (quin, J=7.3 Hz, 2H), 1.48 (quin, J=7.6 Hz, 2H). LRMS+H$^+$=435.1.

Compound 119: (E)-4-((4-(4-(1H-1,2,3-triazol-1-yl)butyl)phenoxy)methyl)-2-(2,4-dichlorostyryl)oxazole Step 1: (E)-4-(chloromethyl)-2-(2,4-dichlorostyryl)oxazole

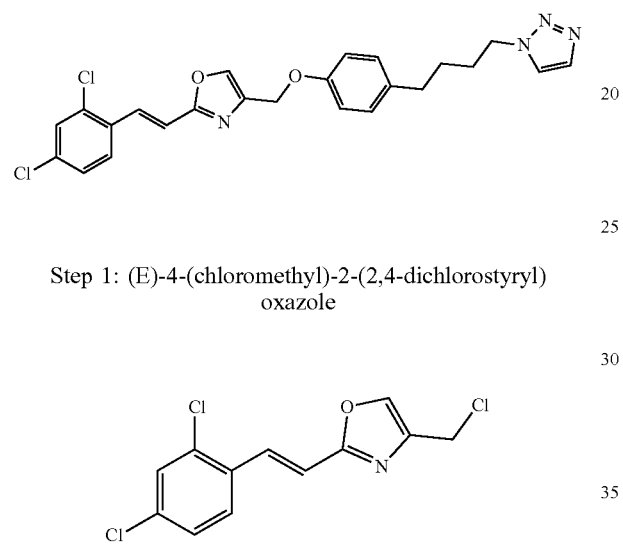

This compound was prepared in a similar fashion as compound 3A/B step 1 and 2 from the corresponding (E)-3-(2,4-dichlorophenyl)acrylic acid. $^1$H NMR (DMSO-d$_6$) δ: 8.22 (s, 1H), 8.05 (d, J=8.6 Hz, 1H), 7.67-7.76 (m, 2H), 7.50 (dd, J=8.6, 2.3 Hz, 1H), 7.30 (d, J=16.4 Hz, 1H), 4.72 (s, 2H).

Step 2: (E)-4-((4-(4-(1H-1,2,3-triazol-1-yl)butyl)phenoxy)methyl)-2-(2,4-dichlorostyryl)oxazole

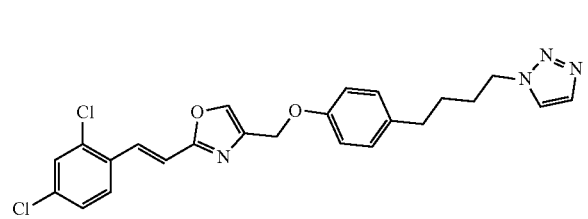 [SMILES: Clc1ccc(/C=C/c2nc(COc3ccc(CCCCn4ccnn4)cc3)co2)c(Cl)c1]

This compound was prepared in a similar fashion as compound 32 step 2 from the previous chloride and the corresponding phenol. $^1$H NMR (DMSO-d$_6$) δ: 8.24 (s, 1H), 8.11 (s, 1H), 8.05 (d, J=8.6 Hz, 1H), 7.67-7.75 (m, 3H), 7.50 (dd, J=8.6, 2.0 Hz, 1H), 7.31 (d, J=16.4 Hz, 1H), 7.06-7.13 (d, J=8.6 Hz, 2H), 6.90-6.98 (d, J=8.2 Hz, 2H), 4.99 (s, 2H), 4.39 (t, J=7.0 Hz, 2H), 2.52-2.57 (m, 2H), 1.80 (quin, J=7.2 Hz, 2H), 1.47 (quin, J=7.6 Hz, 2H). LRMS+H$^+$=469.1.

Compound 120: (E)-4-((4-(4-(1H-1,2,3-triazol-1-yl)butyl)phenoxy)methyl)-2-(3,4,5-trifluorostyryl)oxazole

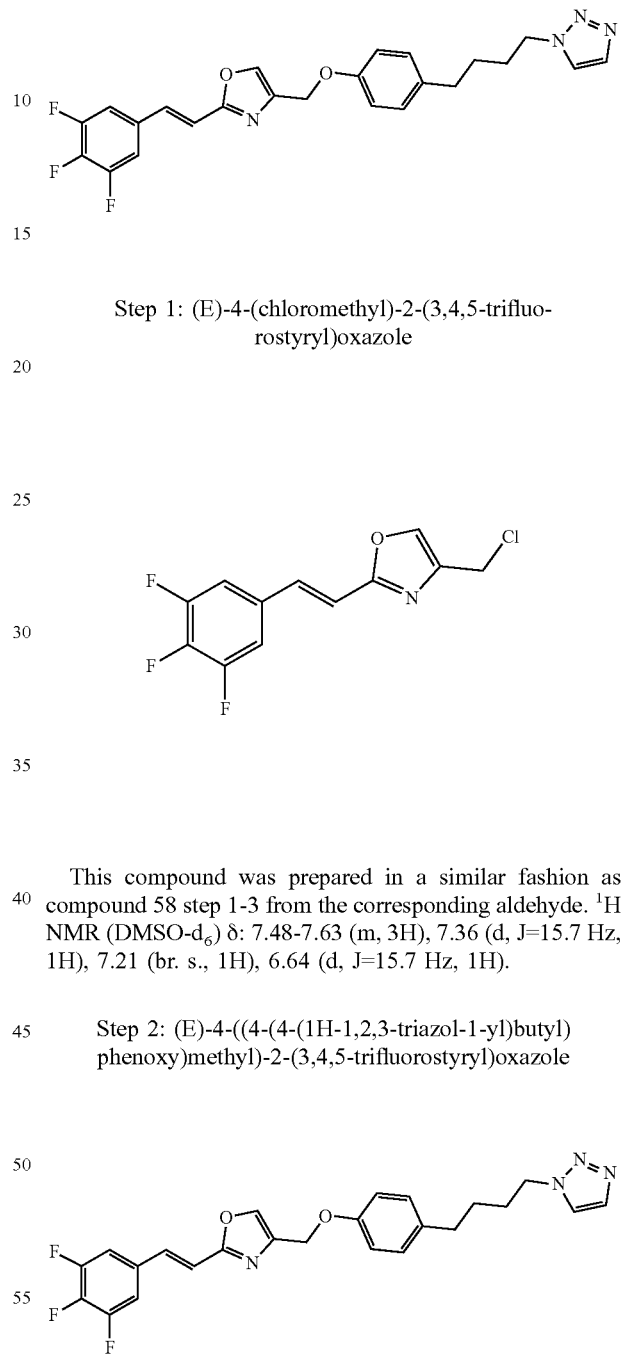

Step 1: (E)-4-(chloromethyl)-2-(3,4,5-trifluorostyryl)oxazole

This compound was prepared in a similar fashion as compound 58 step 1-3 from the corresponding aldehyde. $^1$H NMR (DMSO-d$_6$) δ: 7.48-7.63 (m, 3H), 7.36 (d, J=15.7 Hz, 1H), 7.21 (br. s., 1H), 6.64 (d, J=15.7 Hz, 1H).

Step 2: (E)-4-((4-(4-(1H-1,2,3-triazol-1-yl)butyl)phenoxy)methyl)-2-(3,4,5-trifluorostyryl)oxazole This compound was prepared in a similar fashion as compound 32 step 2 from the previous chloride and the corresponding phenol. $^1$H NMR (DMSO-d$_6$) δ: 8.22 (s, 1H), 8.11 (s, 1H), 7.80 (dd, J=9.0, 7.0 Hz, 2H), 7.70 (s, 1H), 7.49 (d, J=16.4 Hz, 1H), 7.30 (d, J=16.4 Hz, 1H), 7.05-7.14 (m, J=8.6 Hz, 2H), 6.89-6.98 (m, J=8.2 Hz, 2H), 4.97 (s, 2H), 4.39 (t, J=7.0 Hz, 2H), 2.52-2.58 (m, 2H), 1.81 (quin, J=7.2 Hz, 2H), 1.48 (quin, J=7.6 Hz, 2H). LRMS+H$^+$=455.2.

Compound 121: (E)-4-((4-(4-(1H-1,2,3-triazol-1-yl)butyl)phenoxy)methyl)-2-(3,4-difluorostyryl)oxazole

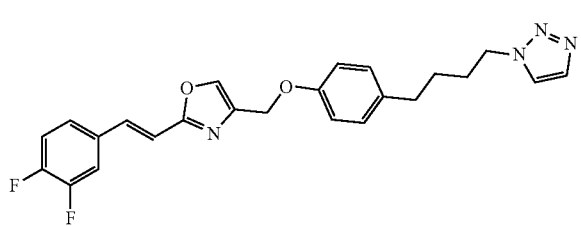 [SMILES: Fc1ccc(/C=C/c2nc(COc3ccc(CCCCn4ccnn4)cc3)co2)cc1F]

Step 1: (E)-4-(chloromethyl)-2-(3,4-difluorostyryl)oxazole

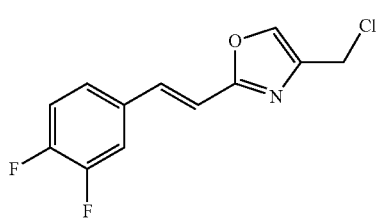 [SMILES: Fc1ccc(/C=C/c2nc(CCl)co2)cc1F]

This compound was prepared in a similar fashion as compound 58 step 1-3 from the corresponding aldehyde. $^1$H NMR (DMSO-d$_6$) δ: 8.18 (s, 1H), 7.93 (ddd, J=12.1, 7.8, 2.0 Hz, 1H), 7.56-7.62 (m, 1H), 7.42-7.56 (m, 2H), 7.21 (d, J=16.4 Hz, 1H), 4.70 (s, 2H).

Step 2: (E)-4-((4-(4-(1H-1,2,3-triazol-1-yl)butyl)phenoxy)methyl)-2-(3,4-difluorostyryl)oxazole

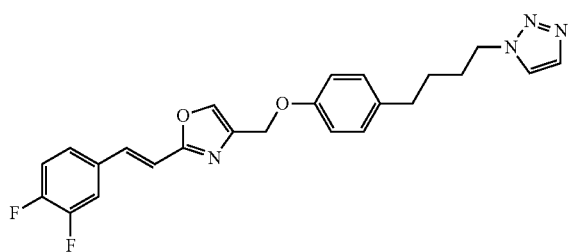 [SMILES: Fc1ccc(/C=C/c2nc(COc3ccc(CCCCn4ccnn4)cc3)co2)cc1F]

This compound was prepared in a similar fashion as compound 32 step 2 from the previous chloride and the corresponding phenol. $^1$H NMR (DMSO-d$_6$) δ:8.20 (s, 1H), 8.11 (d, J=0.8 Hz, 1H), 7.92 (ddd, J=12.1, 7.8, 2.0 Hz, 1H), 7.70 (d, J=0.8 Hz, 1H), 7.55-7.62 (m, 1H), 7.41-7.55 (m, 2H), 7.22 (d, J=16.4 Hz, 1H), 7.05-7.13 (d, J=8.6 Hz, 2H), 6.88-6.98 (m, 2H), 4.97 (s, 2H), 4.39 (t, J=7.0 Hz, 2H), 2.52-2.57 (m, 2H), 1.81 (quin, J=7.3 Hz, 2H), 1.42-1.54 (m, 2H). LRMS+H$^+$=437.2.

Compound 122: (E)-4-(2-(4-((4-(4-(1H-1,2,3-triazol-1-yl)butyl)phenoxy)methyl)oxazol-2-yl)vinyl)-3-fluorobenzonitrile

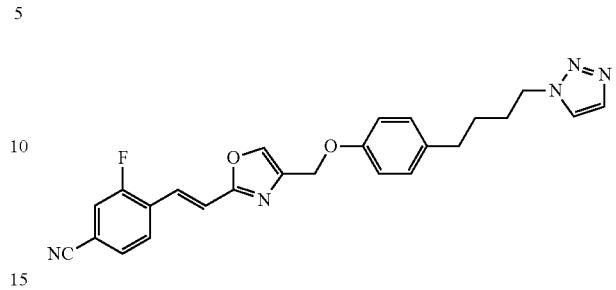

Step 1: (E)-4-(2-(4-(chloromethyl)oxazol-2-yl)vinyl)-3-fluorobenzonitrile

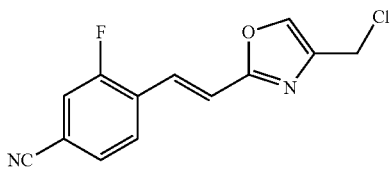 [SMILES: N#Cc1ccc(/C=C/c2nc(CCl)co2)c(F)c1]

This compound was prepared in a similar fashion as compound 58 step 1-3 from the corresponding aldehyde. $^1$H NMR (DMSO-d$_6$) δ: 8.25 (s, 1H), 8.14 (t, J=7.8 Hz, 1H), 7.96 (dd, J=11.0, 1.2 Hz, 1H), 7.77 (d, J=9.0 Hz, 1H), 7.58 (d, J=16.8 Hz, 1H), 7.42 (d, J=16.8 Hz, 1H), 4.72 (s, 2H).

Step 2: (E)-4-(2-(4-((4-(4-(1H-1,2,3-triazol-1-yl)butyl)phenoxy)methyl)oxazol-2-yl)vinyl)-3-fluorobenzonitrile This compound was prepared in a similar fashion as compound 32 step 2 from the previous chloride and the corresponding phenol. $^1$H NMR (DMSO-d$_6$) δ: 8.27 (s, 1H), 8.14 (t, J=8.0 Hz, 1H), 8.11 (d, J=0.8 Hz, 1H), 7.95 (dd, J=10.6, 1.2 Hz, 1H), 7.76 (dd, J=8.2, 1.2 Hz, 1H), 7.68-7.72 (m, 1H), 7.57 (d, J=16.8 Hz, 1H), 7.42 (d, J=16.8 Hz, 1H), 7.06-7.12 (d, J=8.6 Hz, 2H), 6.90-6.97 (m, 2H), 4.99 (s, 2H), 4.39 (t, J=7.0 Hz, 2H), 2.52-2.56 (m, 2H), 1.81 (quin, J=7.2 Hz, 2H), 1.41-1.54 (m, 2H). LRMS+H*=444.2.

Compound 123: (E)-4-((4-(4-(1H-1,2,3-triazol-1-yl)butyl)phenoxy)methyl)-2-(2-fluoro-4-(methylsulfonyl)styryl)oxazole

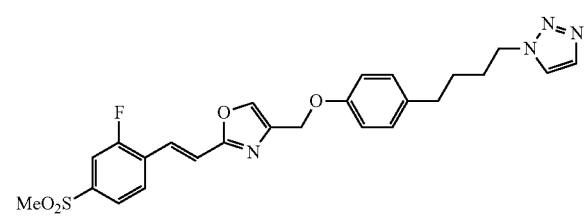 [SMILES: CS(=O)(=O)c1ccc(/C=C/c2nc(COc3ccc(CCCCn4ccnn4)cc3)co2)c(F)c1]

223

Step 1: (E)-4-(chloromethyl)-2-(2-fluoro-4-(methyl-sulfonyl)styryl)oxazole

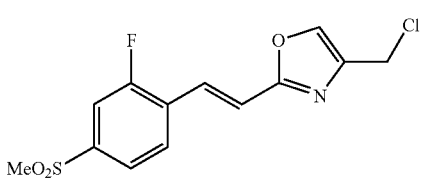

This compound was prepared in a similar fashion as compound 58 step 1-3 from the corresponding aldehyde. $^1$H NMR (DMSO-$d_6$) δ: 8.26 (s, 1H), 8.22 (t, J=7.6 Hz, 1H), 7.86 (dd, J=10.0, 1.4 Hz, 1H), 7.80 (dd, J=8.0, 1.4 Hz, 1H), 7.61 (d, J=16.4 Hz, 1H), 7.42 (d, J=16.8 Hz, 1H), 4.73 (s, 2H), 3.30 (s, 3H).

Step 2: (E)-4-((4-(4-(1H-1,2,3-triazol-1-yl)butyl) phenoxy)methyl)-2-(2-fluoro-4-(methylsulfonyl) styryl)oxazole

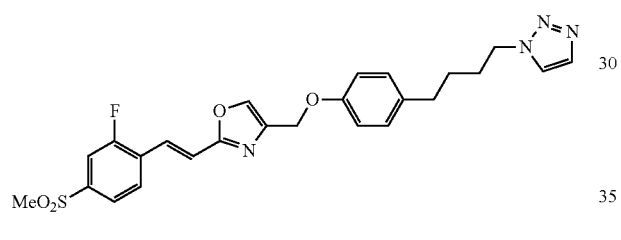

This compound was prepared in a similar fashion as compound 32 step 2 from the previous chloride and the corresponding phenol. $^1$H NMR (DMSO-$d_6$) δ: 8.27 (s, 1H), 8.22 (t, J=7.8 Hz, 1H), 8.08-8.13 (m, 1H), 7.86 (dd, J=10.0, 1.8 Hz, 1H), 7.80 (dd, J=8.2, 1.6 Hz, 1H), 7.70 (d, J=0.8 Hz, 1H), 7.60 (d, J=16.8 Hz, 1H), 7.43 (d, J=16.4 Hz, 1H), 7.05-7.13 (d, J=8.6 Hz, 2H), 6.90-6.98 (m, 2H), 5.00 (s, 2H), 4.39 (t, J=7.0 Hz, 2H), 3.30 (s, 3H), 2.52-2.57 (m, 2H), 1.81 (quin, J=7.2 Hz, 2H), 1.48 (quin, J=7.6 Hz, 2H). LRMS+H$^+$=497.2.

Compound 124: (E)-4-((4-(4-(1H-1,2,3-triazol-1-yl) butyl)phenoxy)methyl)-2-(2-fluoro-4-(trifluo-romethoxy)styryl)oxazole

224

Step 1: (E)-4-(chloromethyl)-2-(2-fluoro-4-(trifluo-romethoxy)styryl)oxazole

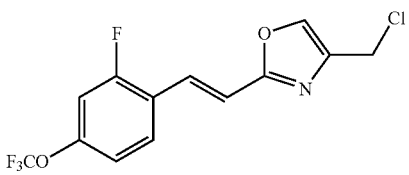 [SMILES: Fc1cc(OC(F)(F)F)ccc1/C=C/c1nc(CCl)co1]

This compound was prepared in a similar fashion as compound 58 step 1-3 from the corresponding aldehyde. $^1$H NMR (DMSO-$d_6$) δ: 8.22 (s, 1H), 8.07 (t, J=8.6 Hz, 1H), 7.55 (d, J=16.4 Hz, 1H), 7.50 (d, J=12.5 Hz, 1H), 7.32 (d, J=9.0 Hz, 1H), 7.27 (d, J=16.8 Hz, 1H), 4.71 (s, 2H).

Step 2: (E)-4-((4-(4-(1H-1,2,3-triazol-1-yl)butyl) phenoxy)methyl)-2-(2-fluoro-4-(trifluoromethoxy) styryl)oxazole

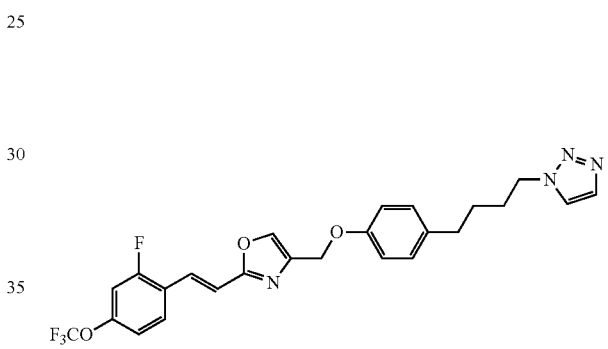

This compound was prepared in a similar fashion as compound 32 step 2 from the previous chloride and the corresponding phenol. $^1$H NMR (DMSO-$d_6$) δ: 8.23 (s, 1H), 8.09-8.13 (m, 1H), 8.06 (t, J=8.8 Hz, 1H), 7.67-7.73 (m, 1H), 7.46-7.59 (m, 2H), 7.23-7.35 (m, 2H), 7.05-7.14 (d, J=8.6 Hz, 2H), 6.89-6.98 (d, 2H), 4.98 (s, 2H), 4.39 (t, J=7.0 Hz, 2H), 2.52-2.57 (m, 2H), 1.81 (quin, J=7.3 Hz, 2H), 1.42-1.54 (m, 2H). LRMS+H$^+$=503.1.

Compound 125: methyl (E)-4-(2-(4-((4-(4-(1H-1,2, 3-triazol-1-yl)butyl)phenoxy)methyl)oxazol-2-yl) vinyl)-3-fluorobenzoate

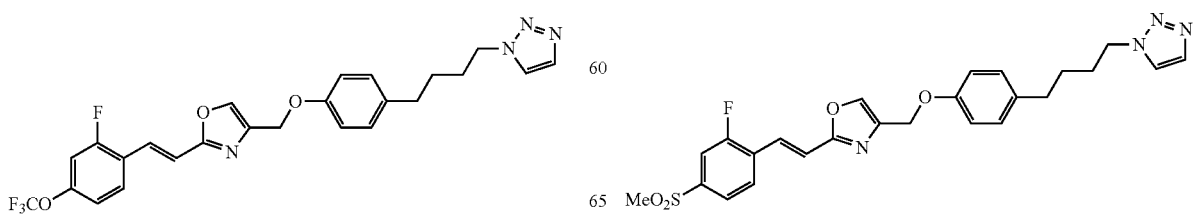

Step 1: methyl (E)-4-(2-(4-(chloromethyl)oxazol-2-yl)vinyl)-3-fluorobenzoate

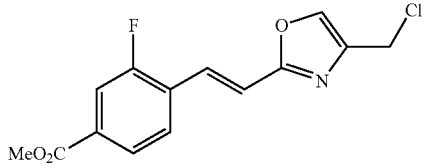 [SMILES: COC(=O)c1ccc(/C=C/c2nc(CCl)co2)c(F)c1]

This compound was prepared in a similar fashion as compound 58 step 1-3 from the corresponding aldehyde. ¹H NMR (DMSO-d$_6$) δ: 8.24 (s, 1H), 8.08 (t, J=7.8 Hz, 1H), 7.73-7.84 (m, 2H), 7.60 (d, J=16.4 Hz, 1H), 7.37 (d, J=16.8 Hz, 1H), 4.72 (s, 2H), 3.88 (s, 3H).

Step 2: methyl (E)-4-(2-(4-((4-(4-(1H-1,2,3-triazol-1-yl)butyl)phenoxy)methyl)oxazol-2-yl)vinyl)-3-fluorobenzoate

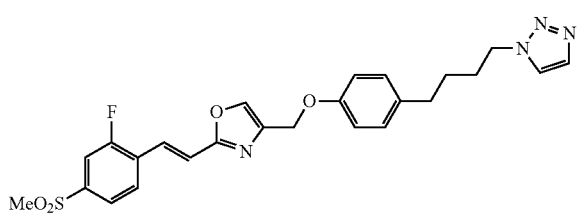 [SMILES: CS(=O)(=O)c1ccc(/C=C/c2nc(COc3ccc(CCCCn4ccnn4)cc3)co2)c(F)c1]

This compound was prepared in a similar fashion as compound 32 step 2 from the previous chloride and the corresponding phenol. ¹H NMR (DMSO-d$_6$) δ: 8.26 (s, 1H), 8.04-8.12 (m, 2H), 7.82 (dd, J=8.0, 1.4 Hz, 1H), 7.77 (dd, J=11.2, 1.4 Hz, 1H), 7.70 (s, 1H), 7.59 (d, J=16.4 Hz, 1H), 7.38 (d, J=16.4 Hz, 1H), 7.06-7.12 (d, J=8.2 Hz, 2H), 6.90-6.97 (d, J=8.6 Hz, 2H), 4.99 (s, 2H), 4.39 (t, J=7.0 Hz, 2H), 3.88 (s, 3H), 2.52-2.58 (m, 2H), 1.81 (quin, J=7.2 Hz, 2H), 1.48 (quin, J=7.6 Hz, 2H). LRMS+H⁺=477.2.

Compound 126: 4-((4-(4-(1H-1,2,3-triazol-1-yl)butyl)phenoxy)methyl)-2-(5-fluoro-7-nitro-1H-indol-2-yl)oxazole

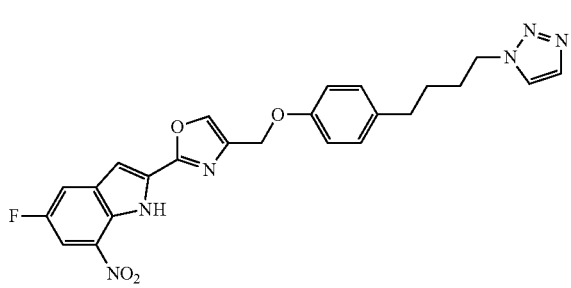 [SMILES: O=[N+]([O-])c1cc(F)cc2cc(-c3nc(COc4ccc(CCCCn5ccnn5)cc4)co3)[nH]c12]

Step 1: ethyl 5-fluoro-7-nitro-1H-indole-2-carboxylate

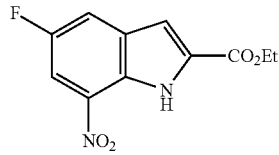

A solution of NaNO$_2$ (2.320 g, 33.6 mmol) in water (NaNO2) (8.69 ml, 482 mmol) was added dropwise over 20 minutes to 4-fluoro-2-nitroaniline (5 g, 32.0 mmol) in water (aniline) (11.14 ml, 618 mmol) and HCl conc. (13.15 ml, 160 mmol. In a separate containing ethyl 2-methylacetoacetate (4.66 ml, 32.0 mmol) in EtOH (33.1 ml, 567 mmol) cooled to 0-5° C. was added dropwise KOH 45% wt. in water (8.23 ml, 96 mmol) followed by ice-cold water (66.1 ml, 3667 mmol) and It was stirred for 10 minutes. To this solution was added the 1st solution dropwise and stirred overnight An orange suspension and big black chunks were formed. The reaction mixture was extracted with Et2O (3×100 mL) and the combined organic layers were washed with water (2×100 mL) then with brine (100 mL). The organic layer was dried over MgSO$_4$, filtered and concentrated to dryness to give crude ethyl (E)-ethyl 2-(2-(4-fluoro-2-nitrophenyl)hydrazono)propanoate (7.30 g, 27.1 mmol, 85% yield).

The previous compound in polyphosphoric acid (41.5 ml, 873 mmol) was heated to 110° C. for 1 hour then cooled to 75° C. After 3 hrs, the mixture was cooled to 20° C. and water (100 mL) was added and stirred for 30 minutes. EA was then added (600 mL) and the aqueous phase was neutralized with sat. NaHCO$_3$(300 mL) (not close to neutral pH). More water was added (500 mL) and then solid NaHCO$_3$(ca. 250 g). More water (500 mL) and EtOAc (500 mL) were added and the mixture was filtered. The solid was washed solids with Water (500 mL) and EtOAc (500 mL). The layers were separated and the organic layer was washed with water (500 mL) and with brine (300 mL). The organic layer was dried over MgSO$_4$, filtered and concentrated to give 3.42 g as a brown solid. The residue was purified on ISCO using a RediSep Gold column (Hex/EtOAc). The crude product was dissolved and loaded onto a pre-column (dissolved crude in EtOAc). A second purification was needed to yield ethyl 5-fluoro-7-nitro-1H-indole-2-carboxylate (585 mg, 8.55% yield). ¹H NMR (DMSO-d$_6$) δ:11.59 (br. s., 1H), 8.18 (dd, J=9.0, 2.3 Hz, 1H), 8.12 (dd, J=8.6, 2.3 Hz, 1H), 7.44 (s, 1H), 4.39 (q, J=7.0 Hz, 2H), 1.36 (t, J=7.0 Hz, 3H).

Step 2: 5-fluoro-7-nitro-1H-indole-2-carboxylic acid

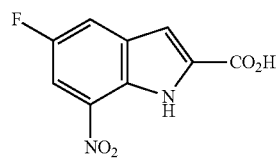

To ethyl 5-fluoro-7-nitro-1H-indole-2-carboxylate (0.585 g, 2.320 mmol) in ethanol (5.76 ml, 99 mmol) was added a solution of potassium hydroxide (0.390 g, 6.96 mmol) in water (1.529 ml, 85 mmol). Stirred at 20° C. After 1 hr at rt it was heated to 60° C. for 2 hrs. It was concentrated to dryness and the crude dissolved in water (30 mL) by heating to 60° C. HCl (3.02 ml, 6.03 mmol) was added and crystallization started. Cooled to 20° C. and stirred for 1 hour. The solids were filtered and the cake was washed with water (2×2.5 mL) and dried under high vacuum until constant weight (500 mg, 96% yield). $^1$H NMR (DMSO-d$_6$) δ: 10.80 (br. s., 1H), 8.05-8.08 (m, J=2.3, 2.3, 2.3 Hz, 1H), 8.02-8.05 (m, 1H), 7.12 (s, 1H)

Step 3: 4-(chloromethyl)-2-(5-fluoro-7-nitro-1H-indol-2-yl)oxazole

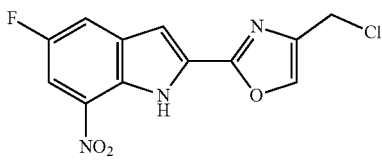 [SMILES: O=[N+]([O-])c1cc(F)cc2cc(-c3nc(CCl)co3)[nH]c12]

This compound was prepared in a similar fashion as compound 3A/B step 1 and 2 from the previous carboxylic acid. $^1$H NMR (DMSO-d$_6$) δ: 11.95 (br. s., 1H), 8.40 (s, 1H), 8.03-8.13 (m, 2H), 7.39 (s, 1H), 4.80 (s, 2H).

Step 4: 4-((4-(4-(1H-1,2,3-triazol-1-yl)butyl)phenoxy)methyl)-2-(5-fluoro-7-nitro-1H-indol-2-yl)oxazole

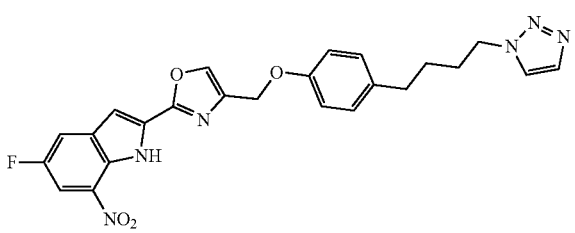 [SMILES: O=[N+]([O-])c1cc(F)cc2cc(-c3nc(COc4ccc(CCCCn5ccnn5)cc4)co3)[nH]c12]

To a cooled 0° C. suspension of NaH 60% wt. (6.39 mg, 0.160 mmol) in DMF (565 µl, 7.29 mmol) was added 4-(4-(1H-1,2,3-triazol-1-yl)butyl)phenol (26.2 mg, 0.121 mmol). It was warmed to 20° C. and stirred for 30 minutes and cooled back to 0° C. 4-(chloromethyl)-2-(5-fluoro-7-nitro-1H-indol-2-yl)oxazole (35 mg, 0.118 mmol) was added and this was stirred at 0° C. for 1 hour and slowly warmed to 20° C. overnight. Added more NaH 60% wt ca. until completion. After 42 hours, HPLCI. MeOH (565 µl, 13.97 mmol) was added followed by water (565 µl, 31.4 mmol) and crystallization started. After 3 h of stirring the solids were collected and the cake was washed with MeOH: water (1:1, 3×0.5 mL) then with Hexane (3×1 mL). The product was dried under high vacuum until constant weight. (47 mg, 83% yield). $^1$H NMR (DMSO-d$_6$) δ: 11.97 (br. s., 1H), 8.41 (s, 1H), 8.10-8.13 (m, 1H), 8.06 (dq, J=9.0, 2.1 Hz, 2H), 7.68-7.73 (m, 1H), 7.36 (s, 1H), 7.08-7.14 (d, J=8.6 Hz, 2H), 6.93-7.01 (m, 2H), 5.06 (s, 2H), 4.39 (t, J=7.0 Hz, 2H), 2.54 (t, J=7.8 Hz, 2H), 1.81 (quin, J=7.3 Hz, 2H), 1.48 (quin, J=7.6 Hz, 2H). LRMS+H$^+$=477.2.

Compound 127:4-((4-(4-(H-1,2,3-triazol-1-yl)butyl)phenoxy)methyl)-2-(6-fluoro-1H-indol-2-yl)oxazole

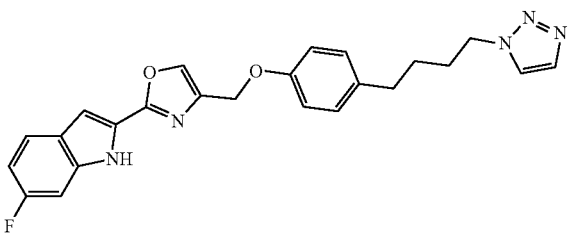 [SMILES: Fc1ccc2cc(-c3nc(COc4ccc(CCCCn5ccnn5)cc4)co3)[nH]c2c1]

Step 1: 4-(chloromethyl)-2-(6-fluoro-1H-indol-2-yl)oxazole

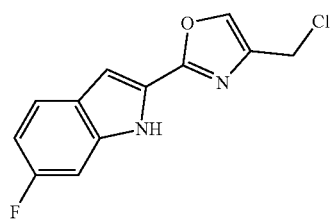 [SMILES: Fc1ccc2cc(-c3nc(CCl)co3)[nH]c2c1]

This compound was prepared in a similar fashion as compound 3A/B step 1 and 2 from 4-(chloromethyl)-2-(6-fluoro-1H-indol-2-yl)oxazole. $^1$H NMR (DMSO-d$_6$) δ: 12.19 (br. s., 1H), 8.27 (s, 1H), 7.65 (dd, J=8.6, 5.5 Hz, 1H), 7.15 (dd, J=10.0, 2.2 Hz, 1H), 7.11 (d, J=1.6 Hz, 1H), 6.90-6.99 (m, 1H), 4.77 (s, 2H).

Step 2: 4-((4-(4-(1H-1,2,3-triazol-1-yl)butyl)phenoxy)methyl)-2-(6-fluoro-1H-indol-2-yl)oxazole

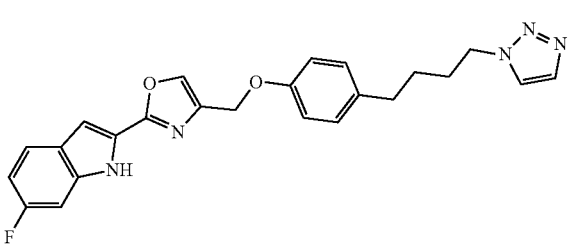 [SMILES: Fc1ccc2cc(-c3nc(COc4ccc(CCCCn5ccnn5)cc4)co3)[nH]c2c1]

This compound was prepared in a similar fashion as compound 32 step 2 from the previous chloride and the corresponding phenol. $^1$H NMR (DMSO-d$_6$) δ: 12.18 (s, 1H), 8.30 (s, 1H), 8.11 (s, 1H), 7.70 (s, 1H), 7.65 (dd, J=8.8, 5.7 Hz, 1H), 7.14 (dd, J=10.0, 2.2 Hz, 1H), 7.10 (d, J=8.2 Hz, 3H), 6.90-6.99 (m, 3H), 5.03 (s, 2H), 4.39 (t, J=7.0 Hz, 2H), 2.52-2.57 (m, 2H), 1.81 (quin, J=7.3 Hz, 2H), 1.48 (quin, J=7.6 Hz, 2H). LRMS+H$^+$=432.1.

Compound 128: 4-((4-(4-(1H-1,2,3-triazol-1-yl)butyl)phenoxy)methyl)-2-(4,6-difluoro-1H-indol-2-yl)oxazole

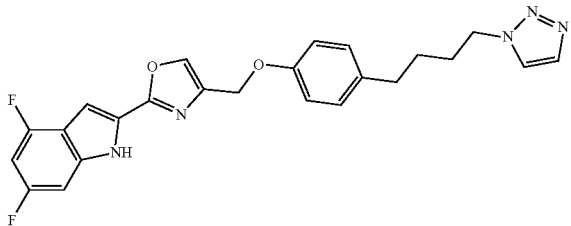 [SMILES: Fc1cc(F)c2cc(-c3nc(COc4ccc(CCCCn5ccnn5)cc4)co3)[nH]c2c1]

This compound was prepared in a similar fashion as compound 127 starting with 4,6-difluoro-1H-indole-2-carboxylic acid. $^1$H NMR (DMSO-d$_6$) δ: 12.56 (s, 1H), 8.33 (s, 1H), 8.11 (s, 1H), 7.70 (s, 1H), 7.07-7.14 (m, 3H), 7.04 (dd, J=9.2, 1.8 Hz, 1H), 6.88-6.99 (m, 3H), 5.04 (s, 2H), 4.39 (t, J=7.0 Hz, 2H), 2.52-2.57 (m, 2H), 1.81 (quin, J=7.3 Hz, 2H), 1.48 (quin, J=7.6 Hz, 2H). LRMS+H$^+$=450.1.

Compound 129: 4-((4-(4-(1H-1,2,3-triazol-1-yl)butyl)phenoxy)methyl)-2-(6-nitro-1H-indol-2-yl)oxazole

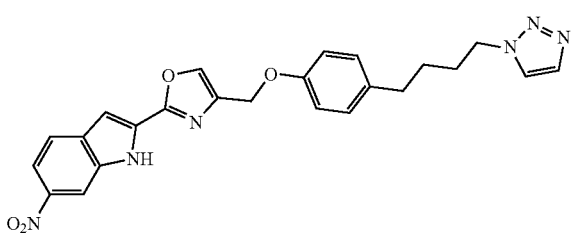 [SMILES: O=[N+]([O-])c1ccc2cc(-c3nc(COc4ccc(CCCCn5ccnn5)cc4)co3)[nH]c2c1]

This compound was prepared in a similar fashion as compound 127 starting with 6-nitro-1H-indole-2-carboxylic acid. $^1$H NMR (DMSO-d$_6$) δ: 12.90 (br. s., 1H), 8.42 (s, 1H), 8.31 (d, J=1.6 Hz, 1H), 8.11 (s, 1H), 7.95 (dd, J=8.8, 2.2 Hz, 1H), 7.85 (d, J=9.0 Hz, 1H), 7.70 (s, 1H), 7.29 (s, 1H), 7.07-7.13 (d, J=8.2 Hz, 2H), 6.93-6.99 (d, J=8.2 Hz, 2H), 5.07 (s, 2H), 4.39 (t, J=7.0 Hz, 2H), 2.52-2.57 (m, 2H), 1.81 (quin, J=7.3 Hz, 2H), 1.48 (quin, J=7.5 Hz, 2H). LRMS+H$^+$=459.1.

Compound 130: (E)-4-((4-((3-(1H-1,2,3-triazol-1-yl)propyl)thio)phenoxy)methyl)-2-(2-fluoro-4-(trifluoromethyl)styryl)oxazole

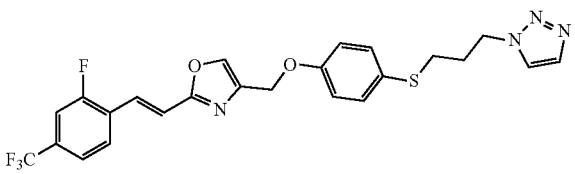 [SMILES: Fc1cc(C(F)(F)F)ccc1/C=C/c1nc(COc2ccc(SCCCn3ccnn3)cc2)co1]

Step 1: 3-(1H-1,2,3-triazol-1-yl)propan-1-ol and 3-(4-(trimethylsilyl)-1H-1,2,3-triazol-1-yl)propan-1-ol

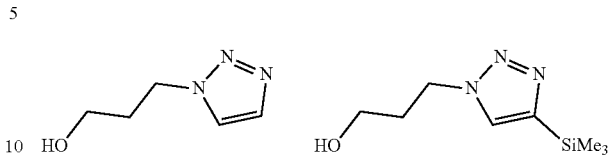

These compounds were prepared in a similar fashion as compound 2 step 1 and used as a mixture for the next step. $^1$H NMR (CDCl$_3$) for the first compound δ 2.00 (br. s., 1H) 2.14 (quin, J=6.20 Hz, 2H) 3.65 (t, J=5.87 Hz, 2H) 4.56 (t, J=6.65 Hz, 2H) 7.59 (s, 1H) 7.71 (s, 1H) and for the second compound δ ppm 0.32 (s, 9H) 2.13 (quint, J=6.20, 2H) 3.65 (t, J=5.67 Hz, 2H) 4.54 (t, J=6.65 Hz, 2H) 7.54 (s, 1H).

Step 2: 4-((3-(1H-1,2,3-triazol-1-yl)propyl)thio)phenol

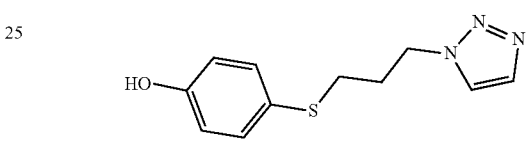

A mixture of the previous alcohols was converted to the methanesulfonate according to a similar procedure described for compound 1 step 1 and the crude was heated in DMF at 60° C. overnight with 4-methoxybenzenethiol and potassium carbonate. It was then diluted with water-EA, separated and the aqueous layer extracted with EA. The combined organic layers were dried over Na$_2$SO$_4$, filtered and the solvent removed. The obtained crude was heated in aqueous HBr (48%) overnight and then the solvent was removed. The residue was diluted in EA-NaHCO3 (water) and the pH adjusted to almost neutral. The organic phase was separated, dried and the solvent removed. Purification on ISCO using a RediSep® column (Hx/EA; 20-100%) gave the title compound. LRMS+H$^+$=236.1.

Step 3: (E)-4-((4-((3-(1H-1,2,3-triazol-1-yl)propyl)thio)phenoxy)methyl)-2-(2-fluoro-4-(trifluoromethyl)styryl)oxazole

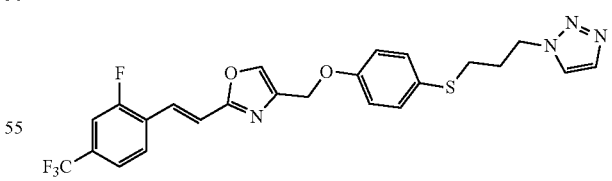

This compound was prepared in a similar fashion as compound 32 step 2 from the previous phenol and the corresponding chloride. $^1$H NMR (DMSO-d$_6$) δ: 2.01 (quint, J=7.00, 7.00, 7.00, 7.00, 7.00, 7.00 Hz, 2H) 2.80 (t, J=7.24 Hz, 2H) 4.46 (t, J=6.85 Hz, 2H) 5.02 (s, 2H) 6.98-7.03 (m, 2H) 7.28-7.34 (m, 2H) 7.38 (d, J=16.82 Hz, 1H) 7.58 (d, J=16.43 Hz, 1H) 7.63 (d, J=7.83 Hz, 1H) 7.68-7.71 (m, 1H) 7.76 (d, J=9.78 Hz, 1H) 8.09 (d, J=0.78 Hz, 1H) 8.14 (t, J=8.02 Hz, 1H) 8.26 (s, 1H). LRMS+H$^+$=504.9.

Compound 131: (E)-4-((4-(4-(1H-1,2,3-triazol-1-yl)butyl)phenoxy)methyl)-2-(2-fluoro-4-(trifluoromethyl)styryl)thiazole

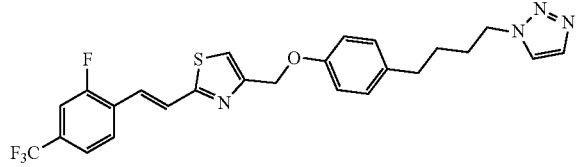 [SMILES: Fc1cc(C(F)(F)F)ccc1/C=C/c1nc(COc2ccc(CCCCn3ccnn3)cc2)cs1]

Step 1: (E)-3-(2-fluoro-4-(trifluoromethyl)phenyl)acrylamide

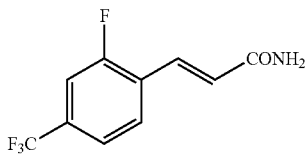 [SMILES: NC(=O)/C=C/c1ccc(C(F)(F)F)cc1F]

This compound was prepared in a similar fashion as compound 3A/B step 1 from the corresponding carboxylic acid. $^1$H NMR (DMSO-d$_6$) δ: 6.83 (d, J=16.04 Hz, 1H) 7.31 (br. s., 1H) 7.50 (d, J=16.04 Hz, 1H) 7.64 (d, J=7.83 Hz, 1H) 7.68-7.80 (m, 2H) 7.85-7.93 (m, 1H).

Step 2: (E)-3-(2-fluoro-4-(trifluoromethyl)phenyl)prop-2-enethioamide

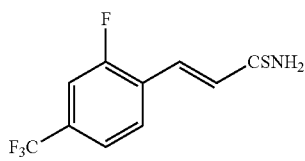

In a 25 mL round-bottomed flask were added (E)-3-(2-fluoro-4-(trifluoromethyl)phenyl)acrylamide (0.4 g, 1.716 mmol) in THF (7.80 ml, 95 mmol) to give a colorless solution. Lawesson's reagent (0.416 g, 1.029 mmol) was added to the previous amide (0.4 g, 1.716 mmol) in THF (7.80 ml, 95 mmol) and stirred overnight at rt. It was then heated to reflux for 48 h. Continued stirring for an extra 16 hours at reflux then cooled to 20° C. and concentrated to dryness. The crude was dissolved in CH$_2$Cl$_2$ (7.78 ml, 121 mmol) and silica gel was added (3 g). Concentrated under reduced pressure and the residue was purified on ISCO using a RediSep column (Hex/EtOAc; 0-100%) to give the title compound (245 mg, 0.983 mmol, 57.3% yield) as a yellow solid. $^1$H NMR (DMSO-d$_6$) δ: 9.78 (br. s., 1H), 9.46 (br. s., 1H), 7.92 (t, J=7.8 Hz, 1H), 7.79 (d, J=10.6 Hz, 1H), 7.74 (d, J=15.7 Hz, 1H), 7.65 (d, J=8.2 Hz, 1H), 7.18 (d, J=15.7 Hz, 1H).

Step 3: (E)-4-(chloromethyl)-2-(2-fluoro-4-(trifluoromethyl)styryl)thiazole

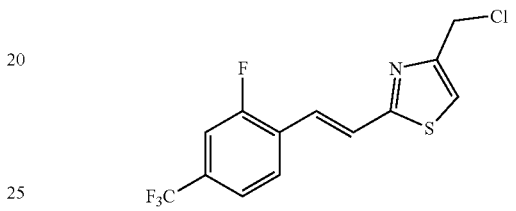

A mixture of (E)-3-(2-fluoro-4-(trifluoromethyl)phenyl)prop-2-enethioamide (100 mg, 0.401 mmol) and 1,3-dichloropropan-2-one (61.1 mg, 0.481 mmol) in EtOH (820 µl, 14.04 mmol) in a sealed vial was heated to reflux (ca. 85° C.) for 1 hr. The solvent was removed and the residue was purified on ISCO using a RediSep column (Hex/EtOAc; 0-50%) to yield the title compound (69 mg, 0.214 mmol, 53.5% yield). $^1$H NMR (DMSO-d$_6$) δ:8.13 (t, J=7.8 Hz, 1H), 7.84 (s, 1H), 7.77 (d, J=11.0 Hz, 1H), 7.73 (d, J=16.4 Hz, 1H), 7.64 (d, J=7.8 Hz, 1H), 7.58 (d, J=16.4 Hz, 1H), 4.87 (s, 2H).

Step 4: (E)-4-((4-(4-(1H-1,2,3-triazol-1-yl)butyl)phenoxy)methyl)-2-(2-fluoro-4-(trifluoromethyl)styryl)thiazole

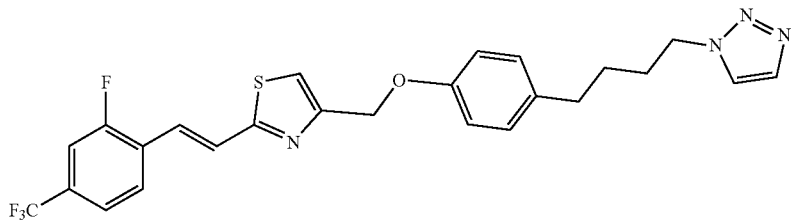

This compound was prepared in a similar fashion as compound 32 step 2 from the previous chloride the corresponding phenol. $^1$H NMR (DMSO-d$_6$) δ: 8.08-8.17 (m, 2H), 7.69-7.80 (m, 4H), 7.64 (d, J=7.8 Hz, 1H), 7.58 (d, J=16.4 Hz, 1H), 7.06-7.14 (d, J=8.6 Hz, 2H), 6.91-6.99 (d, J=8.6 Hz, 2H), 5.16 (s, 2H), 4.39 (t, J=7.0 Hz, 2H), 2.52-2.57 (m, 2H), 1.81 (quin, J=7.3 Hz, 2H), 1.48 (quin, J=7.6 Hz, 2H). LRMS+H$^+$=503.1.

Compound 132: (E)-4-(((4-(3-(1H-1,2,3-triazol-1-yl)propyl)phenyl)thio)methyl)-2-(2-fluoro-4-(trifluoromethyl)styryl)oxazole

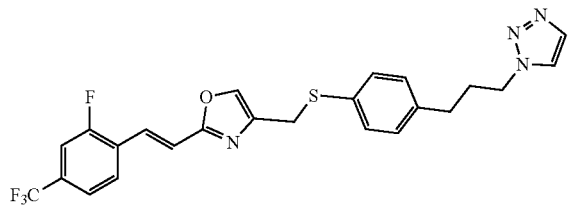 [SMILES: Fc1cc(C(F)(F)F)ccc1/C=C/c1nc(CSc2ccc(CCCn3ccnn3)cc2)co1]

Step 1: 0-(4-(3-(1H-1,2,3-triazol-1-yl)propyl)phenyl) dimethylcarbamothioate

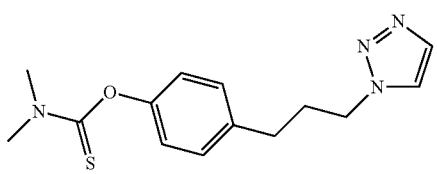 [SMILES: CN(C)C(=S)Oc1ccc(CCCn2ccnn2)cc1]

Dimethylthiocarbamoyl chloride (0.365 g, 2.95 mmol) was added to 4-(4-(1H-1,2,3-triazol-1-yl)butyl)phenol (0.3 g, 1.476 mmol) in DMF (5.88 ml, 76 mmol) and this was heated to 70° C. overnight. The reaction mixture was poured into water (18 mL) and extracted with Et$_2$O (5×15 mL). The combined organic layers were washed with 1% wt. NaOH (10 mL) then with brine (10 mL). The organic layer was dried over MgSO$_4$, filtered and concentrated to give a yellow oil. The residue was purified on ISCO using a RediSep column (Hex/EtOAc; 0-100%) to give the title compound (236 mg, 0.813 mmol, 55.1% yield). $^1$H NMR (DMSO-d$_6$) δ: 8.17 (s, 1H), 7.74 (s, 1H), 7.16-7.27 (d, J=8.2 Hz, 2H), 6.93-7.02 (d, J=8.2 Hz, 2H), 4.39 (t, J=7.0 Hz, 2H), 3.35 (s, 3H), 3.29 (s, 3H), 2.52-2.59 (m, 2H), 2.14 (quin, J=7.4 Hz, 2H).

Step 2: S-(4-(3-(1H-1,2,3-triazol-1-yl)propyl)phenyl) dimethylcarbamothioate

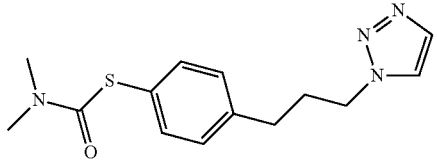 [SMILES: CN(C)C(=O)Sc1ccc(CCCn2ccnn2)cc1]

A solution of 0-(4-(3-(1H-1,2,3-triazol-1-yl)propyl)phenyl) dimethylcarbamothioate (230 mg, 0.792 mmol) in diphenyl lether (1206 μl, 7.58 mmol) was placed in the microwave and heated to 250° C. for 10 h. The residue was purified on ISCO using a RediSep column (Hexane). The crude product was dissolved and loaded onto a pre-column (medium, 10 g SiO$_2$, dissolved crude in MeOH). Collected fractions: none. This was done to remove PhOPh. The residue was purified on ISCO using a RediSep 12 g column (Hex/EtOAc) with the drypack prepared above to give the title compound (129 mg, 56.1% yield). $^1$H NMR (DMSO-d$_6$) δ: 8.17 (s, 1H), 7.74 (s, 1H), 7.32-7.38 (d, J=7.8 Hz, 2H), 7.22-7.28 (d, J=7.8 Hz, 2H), 4.40 (t, J=7.0 Hz, 2H), 3.03 (br. s., 3H), 2.92 (br. s., 3H), 2.55-2.62 (m, 2H), 2.14 (quin, J=7.4 Hz, 2H).

Step 3: 4-(3-(1H-1,2,3-triazol-1-yl)propyl)benzenethiol

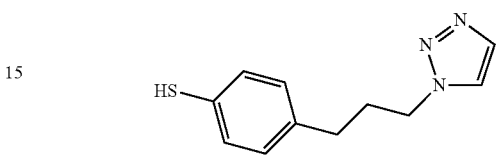

To a solution of S-(4-(3-(1H-1,2,3-triazol-1-yl)propyl)phenyl) dimethylcarbamothioate (130 mg, 0.448 mmol) in THF (578 μl, 7.05 mmol) was added a solution of KOH (60.3 mg, 1.074 mmol) in MeOH (230 μl, 5.69 mmol). This was stirred overnight and the end of which the mixture was poured in water (5 mL) and acidified with HCl (187 μl, 1.119 mmol). The aqueous layer was extracted with EtOAc (10 mL) and the organic layer washed with water (5 mL) and then with brine (5 mL). The organic layer was dried over MgSO$_4$, filtered and concentrated to dryness. The residue was purified on ISCO using a RediSep column (CH$_2$Cl$_2$/MeOH; 0-50%). The crude product was dissolved and loaded onto a pre-column (small, 4 g SiO$_2$, dissolved crude in CH$_2$Cl$_2$) to give the title compound (56 mg, 57.0% yield). $^1$H NMR (DMSO-d$_6$) δ: 8.15 (s, 1H), 7.73 (s, 1H), 7.18-7.23 (m, J=8.2 Hz, 2H), 7.05-7.12 (m, 2H), 5.28 (s, 1H), 4.36 (t, J=7.2 Hz, 2H), 2.43-2.48 (m, 2H), 2.09 (quin, J=7.5 Hz, 2H). LRMS+H$^+$=220.1.

Step 4: (E)-4-(((4-(3-(1H-1,2,3-triazol-1-yl)propyl)phenyl)thio)methyl)-2-(2-fluoro-4-(trifluoromethyl)styryl)oxazole

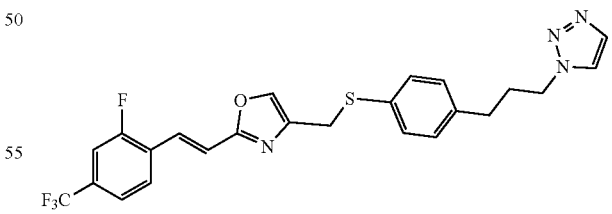

This compound was prepared in a similar fashion as compound 32 step 2 from the previous thiol the corresponding chloride. $^1$H NMR (DMSO-d$_6$) δ: 8.09-8.18 (m, 2H), 7.97 (s, 1H), 7.77 (d, J=10.6 Hz, 1H), 7.72 (s, 1H), 7.63 (d, J=8.2 Hz, 1H), 7.53 (d, J=16.4 Hz, 1H), 7.28-7.38 (m, 3H), 7.16 (d, J=8.2 Hz, 2H), 4.37 (t, J=7.0 Hz, 2H), 4.12 (s, 2H), 2.52-2.56 (m, 2H), 2.11 (quin, J=7.4 Hz, 2H). LRMS+H$^+$= 489.2.

Compound 133: (E)-4-(((6-(4-(1H-1,2,3-triazol-1-yl)butyl)pyridin-3-yl)oxy)methyl)-2-(2-fluoro-4-(trifluoromethyl)styryl)oxazole

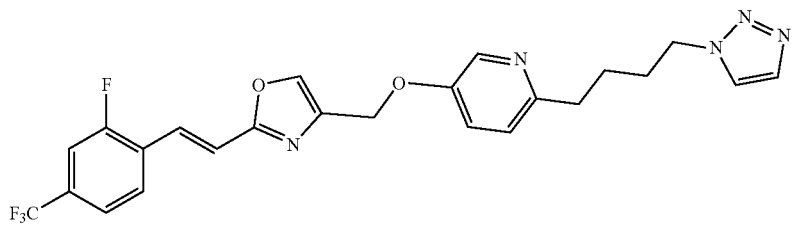 [SMILES: Fc1cc(C(F)(F)F)ccc1/C=C/c1nc(COc2ccc(CCCCn3ccnn3)nc2)co1]

Step 1: 4-(4-methoxyphenyl)but-3-yn-1-ol

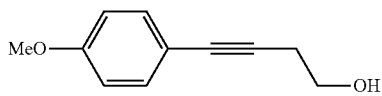

To a degassed solution of 2-bromo-5-methoxypyridine (1.00 g, 5.3 mmol) and but-3-yn-1-ol (0.224 g, 3.19 mmol) in Et$_3$N (17.79 ml, 128 mmol) was added copper (I) iodide (0.018 g, 0.096 mmol) and PdCl$_2$(PPh$_3$)$_2$ (0.067 g, 0.096 mmol). This was stirred overnight at 80° C. It was then filtered and the solvent removed. The crude was purified using ISCO column (DCM-MeOH; 0-15%) to give title compound (1.3 g, 81% yield). $^1$H NMR (400 MHz, CDCl$_3$) δ 2.70 (t, J=6.26 Hz, 2H) 3.74-3.92 (m, 5H) 7.13 (dd, J=8.61, 2.74 Hz, 1H) 7.34 (d, J=8.61 Hz, 1H) 8.23 (br. s., 1H).

Step 2: 4-(4-methoxyphenyl)butan-1-ol

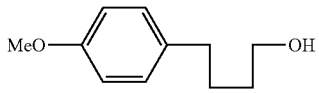 [SMILES: COc1ccc(CCCCO)cc1]

The previous alkyne (0.41 g, 2.3 mmol) was hydrogenated with a hydrogen balloon overnight in methanol-ethyl acetate (1/1; 158 ml) with palladium on charcoal 10%. The mixture was filtered and the solvent removed to give the title compound (0.33 g, 79%). $^1$H NMR (DMSO-d$_6$) δ:1.31-1.46 (m, 2H) 1.57 (quin, J=7.63 Hz, 2H) 2.54 (t, J=7.63 Hz, 2H) 3.39 (q, J=6.26 Hz, 2H) 4.36 (t, J=5.28 Hz, 1H) 7.16 (m, J=8.22 Hz, 2H) 7.45 (m, J=8.22 Hz, 2H).

Step 3: 1-(4-(4-methoxyphenyl)butyl)-1H-1,2,3-triazole

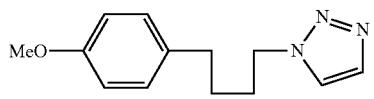 [SMILES: COc1ccc(CCCCn2ccnn2)cc1]

1-(4-azidobutyl)-4-methoxybenzene was prepared in a similar fashion as compound 1, step 2, method B from the previous alcohol and then treated with vinyl acetate in a similar fashion manner as compound 1 step 3 to yield the title compound. $^1$H NMR (DMSO-d$_6$) δ: 1.55 (quint, J=7.60 Hz, 2H) 1.80 (quin, J=7.34 Hz, 1H) 2.66 (t, J=7.63 Hz, 2H) 3.76 (d, J=1.57 Hz, 3H) 4.37 (t, J=6.85 Hz, 2H) 7.13 (d, J=8.22 Hz, 1H) 7.27 (dd, J=8.61, 3.13 Hz, 1H) 7.68 (s, 1H) 8.09 (s, 1H) 8.15 (d, J=3.13 Hz, 1H).

Step 4: 4-(4-(1H-1,2,3-triazol-1-yl)butyl)phenol

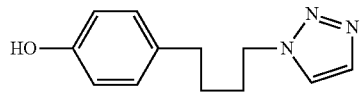 [SMILES: Oc1ccc(CCCCn2ccnn2)cc1]

A mixture of 2-(4-(1H-1,2,3-triazol-1-yl)butyl)-5-methoxypyridine (0.074, 0.319 mmol) in HBr (2 ml, 17.68 mmol) was heated at 105° C. overnight and then 8 h at 120 C. Nitrogen was bubbled for 15 min then EA was added and the mixture was quenched with solid Na$_2$CO$_3$. The layers were separated and the aqueous layer extracted with EA. The organic layers were combined, washed with brine, Na$_2$SO$_4$ dried, filtered and the solvent removed to give the title compound (0.060 g, 86%). $^1$H NMR (DMSO-d$_6$) δ: 1.55 (quint, J=7.60 Hz, 2H) 1.81 (quint, J=7.40, Hz, 2H) 2.62 (t, J=7.63 Hz, 2H) 4.38 (t, J=7.04 Hz, 2H) 6.91-7.08 (m, 2H) 7.70 (d, J=0.78 Hz, 1H) 8.01 (d, J=1.96 Hz, 1H) 8.10 (d, J=0.78 Hz, 1H) 9.59 (s, 1H).

Step 5: (E)-4-(chloromethyl)-2-(2-fluoro-4-(trifluoromethyl)styryl)oxazole

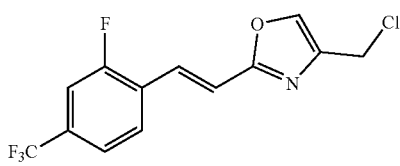 [SMILES: Fc1cc(C(F)(F)F)ccc1/C=C/c1nc(CCl)co1]

This compound was prepared in a similar fashion as compound 3A/B step 1-2 from (E)-3-(2-fluoro-4-(trifluoromethyl)phenyl)acrylic acid. $^1$H NMR (DMSO-d$_6$) δ: 4.70 (s, 2H) 7.36 (d, J=16.43 Hz, 1H) 7.57 (d, J=16.82 Hz, 1H) 7.62 (d, J=8.22 Hz, 1H) 7.75 (d, J=9.78 Hz, 1H) 8.13 (t, J=7.83 Hz, 1H) 8.22 (s, 1H).

Step 6: (E)-4-(((6-(4-(1H-1,2,3-triazol-1-yl)butyl)pyridin-3-yl)oxy)methyl)-2-(2-fluoro-4-(trifluoromethyl)styryl)oxazole

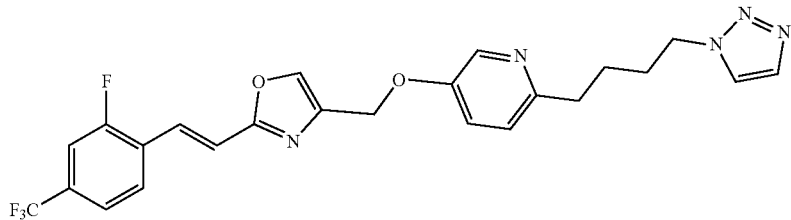 [SMILES: Fc1cc(C(F)(F)F)ccc1/C=C/c1nc(COc2ccc(CCCCn3ccnn3)nc2)co1]

This compound was prepared in a similar fashion as compound 32 step 2 from the previous phenol (step 4) and the chloride of step 5. $^1$H NMR (DMSO-$d_6$) δ: 1.58 (quin, J=7.63 Hz, 2H) 1.82 (quin, J=7.34 Hz, 2H) 2.69 (t, J=7.63 Hz, 2H) 4.39 (t, J=6.85 Hz, 2H) 5.09 (s, 2H) 7.35-7.44 (m, 2H) 7.60 (d, J=16.20 Hz, 1H) 7.65 (d, J=8.22 Hz, 1H) 7.70 (s, 1H) 7.79 (d, J=10.96 Hz, 1H) 8.11 (s, 1H) 8.16 (t, J=7.83 Hz, 1H) 8.26 (d, J=3.13 Hz, 1H) 8.30 (s, 1H). LRMS+H$^+$= 488.0.

Compound 134: (E)-4-(4-(4-(1H-1,2,3-triazol-1-yl)butyl)benzyl)-2-(2-fluoro-4-(trifluoromethyl)styryl)oxazole

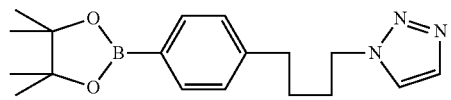

Step 1: 4-(4-bromophenyl)butan-1-ol

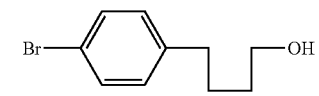 [SMILES: OCCCCc1ccc(Br)cc1]

BH$_3$·THF (6.17 ml, 6.17 mmol) was added to a 0° C. solution of 4-(4-bromophenyl)butanoic acid (1.0 g, 4.11 mmol) in THF (13.71 ml) and let go to rt overnight. It was cooled back and the same quantities of BH$_3$·THF was added and let go overnight at rt. The mixture was quenched with HOAc (2.5 mL) and brought to rt for 30 min. It was diluted with EA and the layers separated. The aqueous was extracted with EA, the organic combined and washed with brine. After drying over Na$_2$SO$_4$, it was filtered and the solvent removed to give the title compound (0.85 g, 90%). $^1$H NMR (DMSO-$d_6$) δ: 1.31-1.46 (m, 2H) 1.57 (quin, J=7.63 Hz, 2H) 2.54 (t, J=7.63 Hz, 2H) 3.39 (q, J=6.26 Hz, 2H) 4.36 (t, J=5.28 Hz, 1H) 7.16 (m, J=8.22 Hz, 2H) 7.45 (m, J=8.22 Hz, 2H).

Step 2: 1-(4-(4-bromophenyl)butyl)-1H-1,2,3-triazole

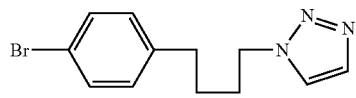 [SMILES: Brc1ccc(CCCCn2ccnn2)cc1]

This compound was prepared in a similar fashion as for compound 133 step 3. $^1$H NMR (DMSO-$d_6$) δ: 1.42-1.56 (m, 2H) 1.74-1.85 (m, 2H) 2.57 (t, J=7.83 Hz, 2H) 4.39 (t, J=7.04 Hz, 2H) 7.09-7.16 (m, 2H) 7.40-7.48 (m, 2H) 7.70 (d, J=0.78 Hz, 1H) 8.11 (d, J=0.78 Hz, 1H).

Step 3: 1-(4-(4-(4,4,5,5-tetramethyl-1,3,2-dioxaborolan-2-yl)phenyl)butyl)-1H-1,2,3-triazole A degassed mixture of the previous bromide (1.0 eq.), potassium acetate (5.0 eq.), bis(pinacolato)diboron (1.5 eq.) and PdCl$_2$·dppf (0.2 eq.) was heated at 100° C. 2 h. The mixture was quenched with NH$_4$Cl solution and diluted with EA. The layers were separated and the aqueous was extracted with EA. The combined organic layers were washed with brine, Na$_2$SO$_4$ dried, filtered and solvent removed. Purification on ISCO using a RediSep® column (Hx/EA; 20-100%) gave the title compound (0.072 g, 61%). $^1$H NMR (DMSO-$d_6$) δ: 1.28 (s, 12H) 1.51 (quin, J=7.53 Hz, 2H) 1.80 (quin, J=7.34 Hz, 1H) 2.61 (s, 2H) 4.39 (t, J=7.04 Hz, 2H) 7.18 (m, J=7.83 Hz, 2H) 7.58 (m, J=7.43 Hz, 2H) 7.70 (s, 1H) 8.10 (s, 1H).

Step 4: Compound 134: (E)-4-(4-(4-(1H-1,2,3-triazol-1-yl)butyl)benzyl)-2-(2-fluoro-4-(trifluoromethyl)styryl)oxazole

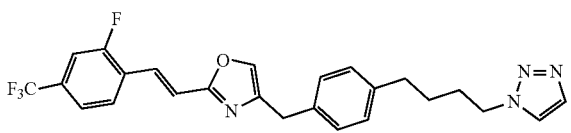 [SMILES: Fc1cc(C(F)(F)F)ccc1/C=C/c1nc(Cc2ccc(CCCCn3ccnn3)cc2)co1]

A degassed mixture of the previous triazole (1.0 eq.), sodium carbonate (1.0 eq.), (Ph₃)P)₄Pd (0.05 eq) and (E)-4-(chloromethyl)-2-(2-fluoro-4-(trifluoromethyl)styryl)oxazole was heated overnight at 80° C. The mixture was quenched with NH₄Cl solution and diluted with EA. The layers were separated and the aqueous was extracted with EA. The combined organic layers were washed with brine, Na₂SO₄ dried, filtered and solvent removed. Purification on ISCO using a RediSep® column (Hx/EA; 5-100%) gave an impure compound. A second purification with toluene-EA (0-70%) was necessary to give the title compound (0.015 g, 14%). ¹H NMR (DMSO-d₆) δ: 1.49 (quin, J=7.63 Hz, 2H) 1.81 (quin, J=7.60 Hz, 2H) 2.56 (t, J=7.63 Hz, 2H) 3.82 (s, 2H) 4.39 (t, J=7.04 Hz, 2H) 7.10 (d, J=8.22 Hz, 2H) 7.18 (d, J=7.83 Hz, 2H) 7.33 (d, J=16.43 Hz, 1H) 7.51 (d, J=16.43 Hz, 1H) 7.62 (d, J=8.22 Hz, 1H) 7.70 (s, 1H) 7.76 (d, J=9.78 Hz, 1H) 7.92 (s, 1H) 8.07-8.19 (m, 2H). LRMS+H⁺=471.1.

Compound 135: (E)-4-((4-(4-(4H-1,2,4-triazol-4-yl) butyl)phenoxy)methyl)-2-(2-fluoro-4-(trifluoromethyl)styryl)oxazole and Compound 136: (E)-N-(4-(4-((2-(2-fluoro-4-(trifluoromethyl)styryl)oxazol-4-yl)methoxy)phenyl)butyl) formamide

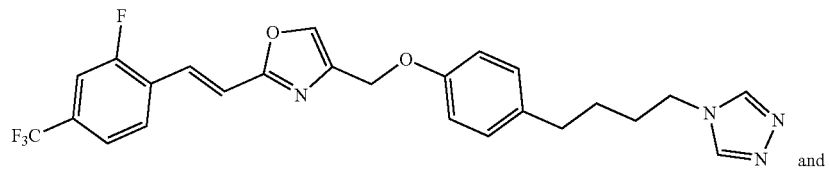

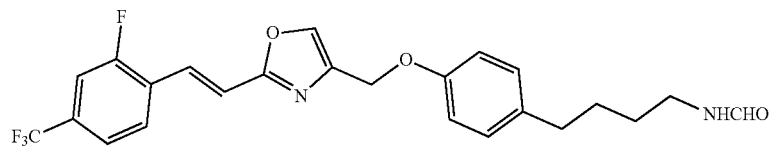

Step 1: (E)-4-(4-((2-(2-fluoro-4-(trifluoromethyl) styryl)oxazol-4-yl)methoxy)phenyl)butan-1-amine

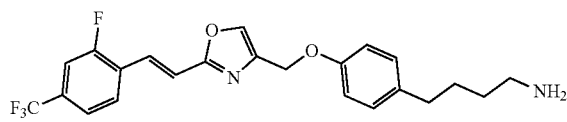 [SMILES: NCCCCc1ccc(OCc2coc(/C=C/c3ccc(C(F)(F)F)cc3F)n2)cc1]

To (E)-4-((4-(4-azidobutyl)phenoxy)methyl)-2-(2-fluoro-4-(trifluoromethyl)styryl)oxazole (0.200 g, 0.43 mmol) in THF (0.29 ml) was added Ph₃P (0.171 g, 0.65 mmol) and water (0.012 ml, 0.65 mmol). The mixture was stirred 18 h and the solvent was removed. Purification on ISCO using a RediSep® column (DCM-MeOH—NH₄OH; 77.5-22-2.5%; 0-70%) gave 0.168 g of the amine product.

Step 2: (E)-N-(4-(4-((2-(2-fluoro-4-(trifluoromethyl) styryl)oxazol-4-yl)methoxy)phenyl)butyl) formamide

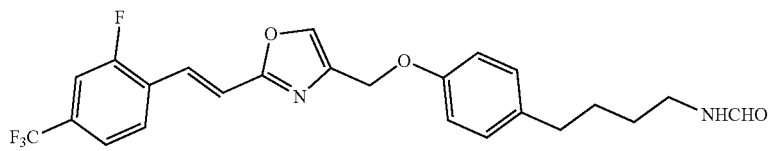

Triethyl orthoformate (0.055 ml, 0.33 mmol) and formohydrazide (0.013 g, 0.22 mmol) in MeOH (0.12 ml) was heated to 70° C. for 2.5 h. Then the previous amine (0.080 g, 0.184 mmol) was added and the mixture heated overnight. It was absorbed on SiO₂ and purified on ISCO using a RediSep® column (Hex/EtOAc; 0-100%) followed by MeOH (7%) in EA to give 12 mg of compound 135; ¹H NMR (400 MHz, DMSO-d₆) δ ppm 1.32-1.45 (m, 2H) 1.47-1.58 (m, 2H) 3.09 (q, J=6.65 Hz, 2H) 5.00 (s, 2H) 6.91-6.98 (m, 2H) 7.12 (m, J=8.61 Hz, 2H) 7.39 (d, J=16.43 Hz, 1H) 7.59 (d, J=16.82 Hz, 1H) 7.65 (d, J=8.22 Hz, 1H) 7.78 (d, J=9.78 Hz, 1H) 7.93-8.05 (m, 2H) 8.16 (t, J=7.83 Hz, 1H) 8.27 (s, 1H) and 54 mg of compound 136 (E)-N-(4-(4-((2-(2-fluoro-4-(trifluoromethyl)styryl)oxazol-4-yl) methoxy)phenyl)butyl)formamide ¹H NMR (400 MHz, DMSO-d6) δ ppm 1.32-1.45 (m, 2H) 1.47-1.58 (m, 2H) 3.09 (q, J=6.65 Hz, 2H) 5.00 (s, 2H) 6.91-6.98 (m, 2H) 7.12 (d, J=8.61 Hz, 2H) 7.39 (d, J=16.43 Hz, 1H) 7.59 (d, J=16.82 Hz, 1H) 7.65 (d, J=8.22 Hz, 1H) 7.78 (d, J=9.78 Hz, 1H) 7.93-8.05 (m, 2H) 8.16 (t, J=7.83 Hz, 1H) 8.27 (s, 1H).

Compound 137: (E)-4-(4-(4-((2-(2-fluoro-4-(trifluoromethyl)styryl)oxazol-4-yl)methoxy)phenyl)butyl)thiomorpholine 1,1-dioxide

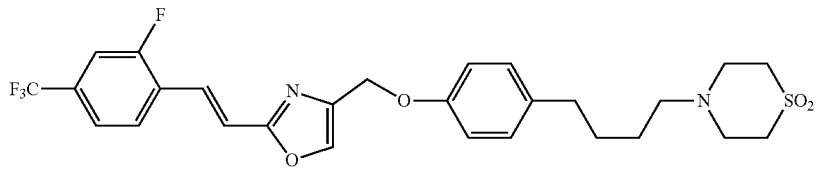 [SMILES: O=S1(=O)CCN(CCCCc2ccc(OCc3coc(/C=C/c4ccc(C(F)(F)F)cc4F)n3)cc2)CC1]

(vinylsulfonyl)ethene (5.7 µl, 0.058 mmol) in toluene (2.5 ml) was added portionwise to a 80° C. solution of (E)-4-(4-((2-(2-fluoro-4-(trifluoromethyl)styryl)oxazol-4-yl)methoxy)phenyl)butan-1-amine (0.025 g, 0.058 mmol) in i-propanol (5.7 ml). After 5 h of heating the solvent was removed and the crude purified on ISCO using a RediSep® column Hex/EtOAc; 0-100%) to give 22 mg of the title compound. $^1$H NMR (400 MHz, DMSO-$d_6$) δ ppm 1.33-1.46 (m, 2H) 1.48-1.59 (m, 2H) 2.45 (t, J=7.24 Hz, 2H) 2.51-2.56 (m, 2H) 2.83 (br. s., 4H) 3.04 (d, J=5.09 Hz, 4H) 5.00 (s, 2H) 6.94 (d, J=8.61 Hz, 2H) 7.12 (d, J=8.61 Hz, 2H) 7.39 (d, J=16.43 Hz, 1H) 7.59 (d, J=16.43 Hz, 1H) 7.66 (s, 1H) 8.16 (t, J=7.83 Hz, 1H) 8.27 (s, 1H).

Compound 138: (E)-2-(2-fluoro-4-(trifluoromethyl)styryl)-4-((4-(4-(pyridazin-3-yl)butyl)phenoxy)methyl)oxazole

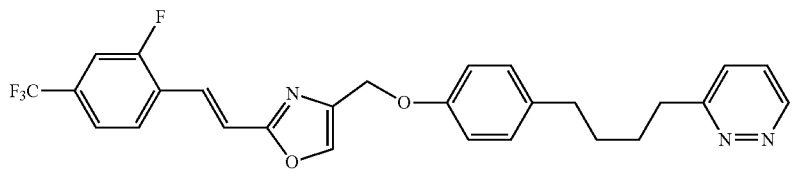 [SMILES: Fc1cc(C(F)(F)F)ccc1/C=C/c1nc(COc2ccc(CCCCc3cccnn3)cc2)co1]

Step 1: 3-(4-(4-(benzyloxy)phenyl)but-1-yn-1-yl)pyridazine

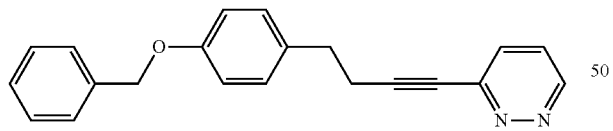

A degassed mixture of 1-(benzyloxy)-4-(but-3-yn-1-yl)benzene (0.250 g; 1.06 mmol), 3-bromopyridazine (0.185 g; 1.16 mmol), copper iodide (0.008 g; 0.042 mmol) and PdCl$_2$(Ph$_3$P)$_2$ (0.030 g, 0.042 mmol) in triethylamine (5.3 ml) was heated overnight at 85° C. It was then diluted with water-EA and the organic phase separated. The aqueous phase was extracted twice with EA and then were combined, fried and the solvent removed. Purification on ISCO using a RediSep® column Hex/EtOAc; 0-100%) to give 163 mg of the title compound. $^1$H NMR (400 MHz, DMSO-$d_6$) δ ppm 2.72-2.79 (m, 2H) 2.80-2.87 (m, 2H) 5.05 (s, 2H) 6.84-6.98 (m, 2H) 7.23 (d, J=8.61 Hz, 2H) 7.31 (s, 1H) 7.36 (t, J=7.24 Hz, 2H) 7.39-7.44 (m, 2H) 7.58-7.71 (m, 2H) 9.14 (dd, J=4.11, 2.54 Hz, 1H).

Step 2: 3-(4-(4-(benzyloxy)phenyl)butyl)pyridazine

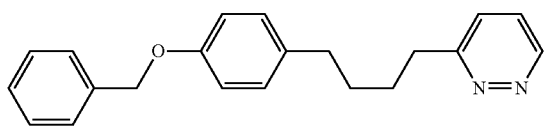 [SMILES: c1ccc(COc2ccc(CCCCc3cccnn3)cc2)cc1]

The previous alkyne was hydrogenated according to step 2 of compound 99 in MeOH. LRMS+H$^+$: 319.1.

Step 3: 4-(4-(pyridazin-3-yl)butyl)phenol

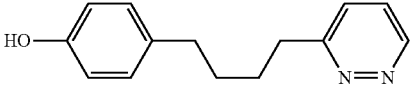 [SMILES: Oc1ccc(CCCCc2cccnn2)cc1]

Debenzylation was done according to step 4 compound 107. $^1$H NMR (400 MHz, CDCl$_3$) δ ppm 1.62-1.72 (m, 2H) 1.83 (quin, J=7.63 Hz, 2H) 2.58 (t, J=7.63 Hz, 2H) 3.05 (t, J=7.43 Hz, 2H) 5.41 (br. s., 1H) 6.65-6.77 (m, 2H) 7.01 (d, J=8.61 Hz, 2H) 7.18 (d, J=3.13 Hz, 1H) 7.67 (d, J=3.52 Hz, 1H).

Step 4: (E)-2-(2-fluoro-4-(trifluoromethyl)styryl)-4-((4-(4-(pyridazin-3-yl)butyl)phenoxy)methyl)oxazole

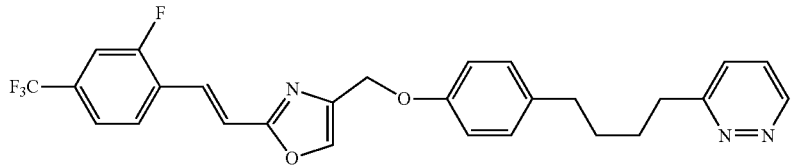 [SMILES: Fc1cc(C(F)(F)F)ccc1/C=C/c1nc(COc2ccc(CCCCc3cccnn3)cc2)co1]

This compound was prepared from the previous phenol according to step 3 of compound 88. $^1$H NMR (400 MHz, DMSO-$d_6$) δ ppm 1.56 (quin, J=7.34 Hz, 2H) 1.69 (quin, J=7.40 Hz, 2H) 2.54 (t, J=7.43 Hz, 2H) 2.90 (t, J=7.63 Hz, 2H) 4.97 (s, 2H) 6.92 (d, J=8.61 Hz, 2H) 7.09 (d, J=8.61 Hz, 2H) 7.37 (d, J=16.60 Hz, 1H) 7.51-7.65 (m, 4H) 7.76 (d, J=10.17 Hz, 1H) 8.14 (t, J=7.63 Hz, 1H) 8.24 (s, 1H) 9.04 (dd, J=4.70, 1.96 Hz, 1H).

Compound 139: (E)-2-(2-fluoro-4-(trifluoromethyl)styryl)-4-((4-(4-(pyrimidin-2-yl)butyl)phenoxy)methyl)oxazole

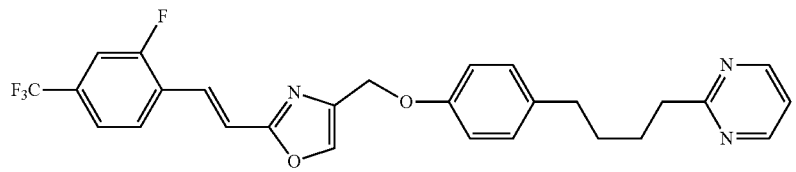 [SMILES: Fc1cc(C(F)(F)F)ccc1/C=C/c1nc(COc2ccc(CCCCc3ncccn3)cc2)co1]

Step 1: 2-(4-(4-(benzyloxy)phenyl)but-1-yn-1-yl)pyrimidine

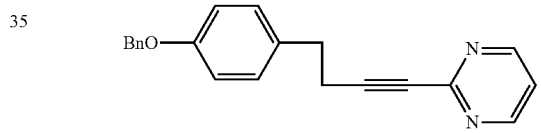

This compound was prepared in a similar fashion as compound 108 step 1 with 2-iodopyrimidine. LRMS+H$^+$: 315.1.

Step 2: 4-(4-(pyrimidin-2-yl)butyl)phenol

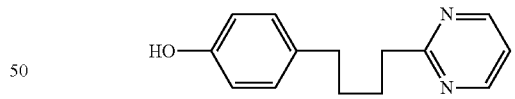

This compound was prepared by hydrogenation with Pd/C in MeOH-EA at 1 atmosphere in methanol. LRMS+H$^+$: 229.1.

Step 3: (E)-2-(2-fluoro-4-(trifluoromethyl)styryl)-4-((4-(4-(pyrimidin-2-yl)butyl)phenoxy)methyl) oxazole

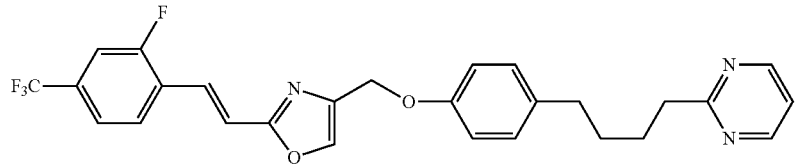 [SMILES: Fc1cc(C(F)(F)F)ccc1/C=C/c1nc(COc2ccc(CCCCc3ncccn3)cc2)co1]

This compound was prepared with the previous phenol and (E)-4-(chloromethyl)-2-(2-fluoro-4-(trifluoromethyl)styryl)oxazole in a similar fashion as compound 26, step 3. $^1$H NMR (400 MHz, DMSO-d$_6$) δ ppm 1.55 (quin, J=7.50 Hz, 2H) 1.72 (quin, J=7.53 Hz, 2H) 2.53 (t, J=7.63 Hz, 2H) 2.85 (t, J=7.43 Hz, 2H) 4.97 (s, 2H) 6.92 (d, J=8.61 Hz, 2H) 7.08 (d, J=8.61 Hz, 2H) 7.29 (t, J=4.89 Hz, 1H) 7.37 (d, J=16.43 Hz, 1H) 7.57 (d, J=16.43 Hz, 1H) 7.62 (d, J=8.22 Hz, 1H) 7.76 (d, J=10.56 Hz, 1H) 8.14 (t, J=7.83 Hz, 1H) 8.24 (s, 1H) 8.68 (d, J=4.70 Hz, 2H). LRMS+H$^+$=498.0.

Compound 140: (E)-2-(2-fluoro-4-(trifluoromethyl)styryl)-4-((4-(4-(pyridin-2-yl)butyl)phenoxy)methyl)oxazole

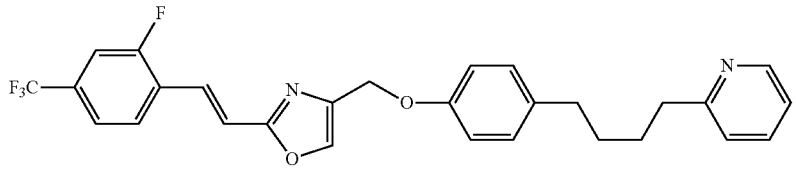 [SMILES: Fc1cc(C(F)(F)F)ccc1/C=C/c1nc(COc2ccc(CCCCc3ccccn3)cc2)co1]

This compound was prepared in a similar fashion as compound 138 starting with 2-bromopyridine. $^1$H NMR (400 MHz, DMSO-d$_6$) δ 1.47-1.59 (m, 2H) 1.59-1.70 (m, 2H) 2.52 (t, J=7.40 Hz, 2H) 2.71 (t, J=7.43 Hz, 2H) 4.97 (s, 2H) 6.91 (d, J=8.22 Hz, 2H) 7.08 (d, J=8.22 Hz, 2H) 7.15 (dd, J=6.65, 5.09 Hz, 1H) 7.20 (d, J=7.83 Hz, 1H) 7.37 (d, J=16.43 Hz, 1H) 7.57 (d, J=16.43 Hz, 1H) 7.60-7.68 (m, 2H) 7.77 (d, J=10.17 Hz, 1H) 8.14 (t, J=7.83 Hz, 1H) 8.24 (s, 1H) 8.43 (d, J=4.70 Hz, 1H). LRMS+H$^+$=497.0.

Compound 141: (E)-4-(2-(4-((4-((3-(1H-1,2,3-triazol-1-yl)propyl)thio)phenoxy)methyl)oxazol-2-yl)vinyl)-3-fluorobenzonitrile

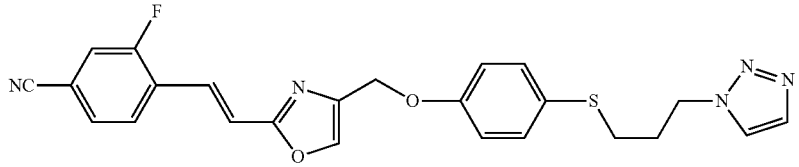 [SMILES: N#Cc1ccc(/C=C/c2nc(COc3ccc(SCCCn4ccnn4)cc3)co2)c(F)c1]

This compound was prepared from (E)-4-(2-(4-(chloromethyl)oxazol-2-yl)vinyl)-3-fluorobenzonitrile and 4-((3-(1H-1,2,3-triazol-1-yl)propyl)thio)phenol according to compound 130, step 3. $^1$H NMR (400 MHz, DMSO-d$_6$) δ 8.29 (s, 1H), 8.09-8.17 (m, 2H), 7.95 (d, J=10.6 Hz, 1H), 7.76 (d, J=8.2 Hz, 1H), 7.71 (s, 1H), 7.57 (d, J=16.4 Hz, 1H), 7.43 (d, J=16.4 Hz, 1H), 7.30-7.36 (d, J=8.6 Hz, 2H), 6.99-7.06 (d, J=8.6 Hz, 2H), 5.03 (s, 2H), 4.48 (t, J=6.8 Hz, 2H), 2.82 (t, J=7.0 Hz, 2H), 2.03 (quin, J=7.0 Hz, 2H). LRMS+H$^+$=462.1.

Compound 142: 4-((4-(4-(1H-1,2,3-triazol-1-yl)butyl)phenoxy)methyl)-2-(6-fluorobenzofuran-2-yl)oxazole

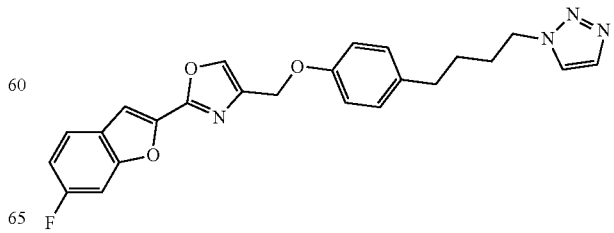

Step 1: 6-fluorobenzofuran-2-carboxamide

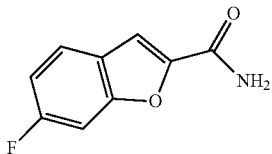 [SMILES: NC(=O)c1cc2ccc(F)cc2o1]

This compound was prepared from hydrolysis (KOH) of ethyl 6-fluorobenzofuran-2-carboxylate followed the procedure used to prepared compound 3, step 1. $^1$H NMR (400 MHz, DMSO-d$_6$) δ 8.10 (br. s., 1H), 7.80 (dd, J=8.8, 5.7 Hz, 1H), 7.67 (br. s., 1H), 7.58 (dd, J=9.4, 2.0 Hz, 1H), 7.55 (d, J=0.8 Hz, 1H), 7.23 (ddd, J=9.8, 8.8, 2.2 Hz, 1H).

Step 2: 4-(chloromethyl)-2-(6-fluorobenzofuran-2-yl)oxazole

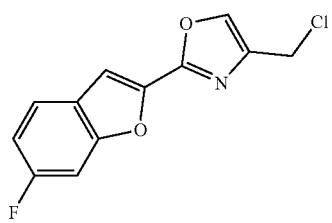 [SMILES: Fc1ccc2cc(-c3nc(CCl)co3)oc2c1]

This compound was prepared from the previous intermediate in a similar fashion as compound 58, step 3. $^1$H NMR (400 MHz, DMSO-d$_6$) δ 8.37 (s, 1H), 7.81 (dd, J=8.8, 5.7 Hz, 1H), 7.72 (dd, J=9.4, 2.0 Hz, 1H), 7.69 (s, 1H), 7.22-7.31 (m, 1H), 4.77 (s, 2H).

Step 3: 4-((4-(4-(1H-1,2,3-triazol-1-yl)butyl)phenoxy)methyl)-2-(6-fluorobenzofuran-2-yl)oxazole

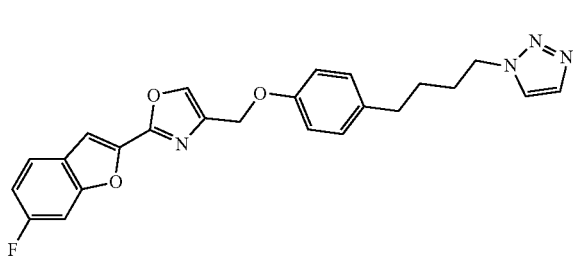 [SMILES: Fc1ccc2cc(-c3nc(COc4ccc(CCCCn5ccnn5)cc4)co3)oc2c1]

This compound was prepared in a similar fashion as compound 113, step 3 with the previous intermediate and 4-(4-(1H-1,2,3-triazol-1-yl)butyl)phenol. $^1$H NMR (400 MHz, DMSO-d$_6$) δ 8.39 (s, 1H), 8.11 (s, 1H), 7.80 (dd, J=8.6, 5.5 Hz, 1H), 7.65-7.75 (m, 3H), 7.26 (td, J=9.3, 2.2 Hz, 1H), 7.07-7.13 (d, J=8.2 Hz, 2H), 6.93-6.99 (d, J=8.6 Hz, 2H), 5.04 (s, 2H), 4.39 (t, J=7.0 Hz, 2H), 2.52-2.58 (m, 2H), 1.81 (quin, J=7.3 Hz, 2H), 1.48 (quin, J=7.6 Hz, 2H).

Compound 143: 4-((4-(4-(1H-1,2,3-triazol-1-yl)butyl)phenoxy)methyl)-2-(6-fluorobenzo[b]thiophen-2-yl)oxazole

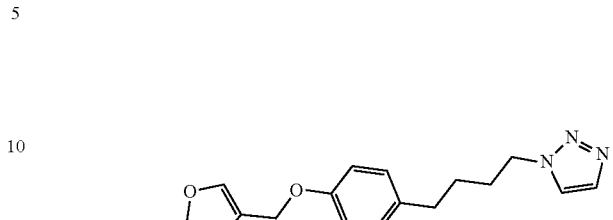

This compound was prepared in a similar fashion as compound 140 starting with ethyl 6-fluorobenzo[b]thiophene-2-carboxylate. $^1$H NMR (400 MHz, DMSO-d$_6$) δ 8.34 (s, 1H), 8.10 (d, J=7.0 Hz, 2H), 7.97-8.05 (m, 2H), 7.70 (s, 1H), 7.36 (td, J=9.1, 2.2 Hz, 1H), 7.07-7.14 (d, J=8.6 Hz, 2H), 6.93-7.00 (d, J=8.6 Hz, 2H), 5.02 (s, 2H), 4.39 (t, J=6.8 Hz, 2H), 2.52-2.57 (m, 2H), 1.81 (quin, J=7.3 Hz, 2H), 1.48 (quin, J=7.6 Hz, 2H). LRMS+H$^+$=449.1.

Compound 144: 4-((4-((3-(1H-1,2,3-triazol-1-yl)propyl)thio)phenoxy)methyl)-2-(4,6-difluoro-1H-indol-2-yl)oxazole

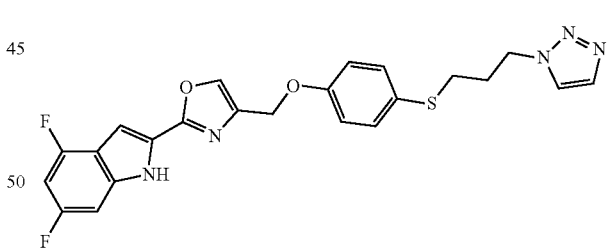

This compound was prepared in a similar fashion as compound 128 with 4-(chloromethyl)-2-(4,6-difluoro-1H-indol-2-yl)oxazole and 4-((3-(1H-1,2,3-triazol-1-yl)propyl)thio)phenol. $^1$H NMR (400 MHz, DMSO-d$_6$) δ 12.56 (br. s., 1H), 8.35 (s, 1H), 8.11 (s, 1H), 7.71 (s, 1H), 7.34 (d, J=8.6 Hz, 2H), 7.12 (s, 1H), 7.04 (d, J=8.6 Hz, 3H), 6.93 (td, J=10.4, 2.0 Hz, 1H), 5.08 (s, 2H), 4.48 (t, J=7.0 Hz, 2H), 2.82 (t, J=7.2 Hz, 2H), 2.04 (quin, J=7.0 Hz, 2H). LRMS+H$^+$=468.1.

Compound 145: (E)-4-((4-(4-(1H-1,2,3-triazol-1-yl)butyl)phenoxy)methyl)-2-(2-fluoro-4-(trifluoromethyl)styryl)-5-methyloxazole

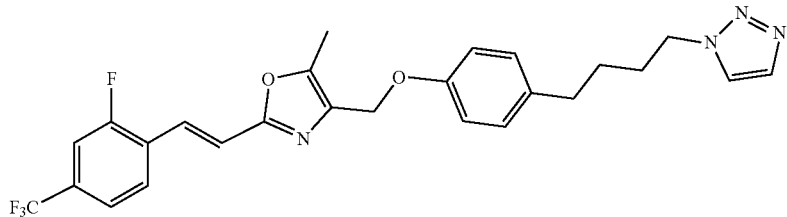 [SMILES: Cc1oc(/C=C/c2ccc(C(F)(F)F)cc2F)nc1COc1ccc(CCCCn2ccnn2)cc1]

Step 1: (E)-ethyl 2-(3-(2-fluoro-4-(trifluoromethyl)phenyl)acrylamido)-3-oxobutanoate

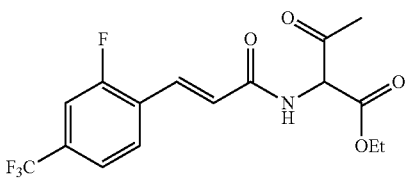 [SMILES: CCOC(=O)C(NC(=O)/C=C/c1ccc(C(F)(F)F)cc1F)C(C)=O]

Trietylamine (1.34 ml, 9.2 mmol) was added to a solution of (E)-3-(2-fluoro-4-(trifluoromethyl)phenyl)acryloyl chloride (1.08 g, 4.28 mmol) and ethyl 2-amino-3-oxobutanoate hydrochloride (0.971 g, 5.34 mmol) in dichloromethane (25.03 ml, 389 mmol) at 0° C. After 30 minutes, the mixture was poured into water (15 mL) and stirred vigorously. The layers were separated and the organic layer was dried over $MgSO_4$, filtered and concentrated. The residue was purified on ISCO using a RediSep 80 g column (Hex/EtOAc; 0-100%) to yield the title product (145 mg). LRMS+H$^+$= 362.1.

Step 2: (E)-ethyl 2-(2-fluoro-4-(trifluoromethyl)styryl)-5-methyloxazole-4-carboxylate

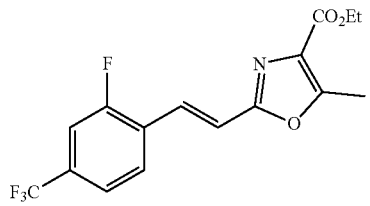

(E)-ethyl 2-(3-(2-fluoro-4-(trifluoromethyl)phenyl)acrylamido)-3-oxobutanoate (0.145 g, 0.40 mmol) in phosphorus oxychloride (2.00 ml, 21.47 mmol) was heated to 105° C. for 2 hr. The mixture was concentrated, neutralized with sat. $NaHCO_3$ (10 mL) and extracted with $CH_2Cl_2$ (10 mL). The aqueous layer was extracted with $CH_2Cl_2$ (5 mL) and the combined organic layers were washed with water (5 mL). The organic layer was dried over $MgSO_4$, filtered and concentrated. to give a dark orange oil. The residue was purified on ISCO using a RediSep 24 g column (Hex/EtOAc; 0-60%) to give 80 mg of the title compound. $^1$H NMR (DMSO-d$_6$) δ: 8.15 (t, J=7.8 Hz, 1H), 7.79 (d, J=11.0 Hz, 1H), 7.65 (d, J=8.6 Hz, 1H), 7.57 (d, J=16.4 Hz, 1H), 7.37 (d, J=16.8 Hz, 1H), 4.29 (q, J=7.2 Hz, 2H), 2.65 (s, 3H), 1.31 (t, J=7.0 Hz, 3H).

Step 3: (E)-(2-(2-fluoro-4-(trifluoromethyl)styryl)-5-methyloxazol-4-yl)methanol

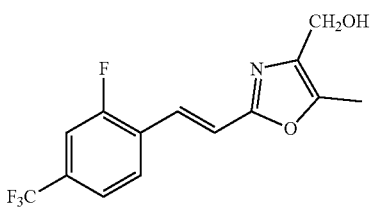 [SMILES: Cc1oc(/C=C/c2ccc(C(F)(F)F)cc2F)nc1CO]

To LiAlH$_4$ (0.011 g, 0.303 mmol) in Et$_2$O (1.50 ml, 14.43 mmol) at 0° C. was added a solution of (E)-ethyl 2-(2-fluoro-4-(trifluoromethyl)styryl)-5-methyloxazole-4-carboxylate (0.080 g, 0.233 mmol) in THF (0.50 ml, 6.11 mmol) and Et$_2$O (1.000 ml, 9.62 mmol). After 30 minutes, it was warmed to 20° C. and stirred for 15 minutes. Some $MgSO_4$ was added and the mixture filtered. The filtrate was concentrated to dryness to yield the title compound (53 mg, 75% yield). LRMS+H$^+$=302.1.

Step 4: (E)-4-(chloromethyl)-2-(2-fluoro-4-(trifluoromethyl)styryl)-5-methyloxazole

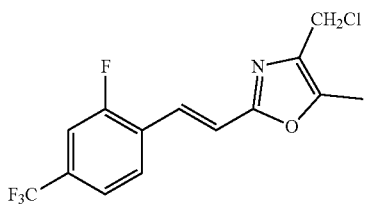

Thionyl chloride (0.064 ml, 0.88 mmol) was added dropwise to a solution of (E)-(2-(2-fluoro-4-(trifluoromethyl)styryl)-5-methyloxazol-4-yl)methanol (0.053 g, 0.176 mmol) in dichloromethane (2.50 ml, 38.8 mmol) at 0° C. After 15 minutes it was then warmed to 20° C. for 45 minutes. After removal of the solvent the residue was purified on ISCO using a RediSep 12 g column (Hex/EtOAc; 0-30%) to yield the title compound (37 mg, 65.8% yield). 1H NMR (DMSO-d$_6$) δ: 8.14 (t, J=7.6 Hz, 1H), 7.77 (d, J=11.0 Hz, 1H), 7.64 (d, J=8.2 Hz, 1H), 7.51 (d, J=16.8 Hz, 1H), 7.32 (d, J=16.4 Hz, 1H), 4.73 (s, 2H), 2.43 (s, 3H).

Step 5: (E)-4-((4-(4-(1H-1,2,3-triazol-1-yl)butyl)phenoxy)methyl)-2-(2-fluoro-4-(trifluoromethyl)styryl)-5-methyloxazole

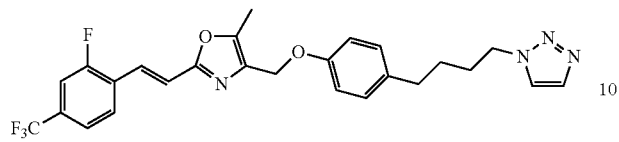

This compound was prepared in a similar fashion as compound 88, step 3 with the previous chloride. ¹H NMR (DMSO-d₆) δ: 8.14 (t, J=8.0 Hz, 1H), 8.08-8.12 (m, 1H), 7.77 (d, J=10.2 Hz, 1H), 7.70 (s, 1H), 7.63 (d, J=7.8 Hz, 1H), 7.50 (d, J=16.4 Hz, 1H), 7.33 (d, J=16.4 Hz, 1H), 7.06-7.13 (d, J=8.6 Hz, 2H), 6.89-6.96 (d, J=8.6 Hz, 2H), 4.94 (s, 2H), 4.39 (t, J=7.0 Hz, 2H), 2.52-2.57 (m, 2H), 2.42 (s, 3H), 1.81 (quin, J=7.2 Hz, 2H), 1.48 (quin, J=7.6 Hz, 2H). LRMS+H⁺=501.2.

Compound 146: (E)-4-(((4-(4-(1H-1,2,3-triazol-1-yl)butyl)phenyl)thio)methyl)-2-(2-fluoro-4-(trifluoromethyl)styryl)oxazole

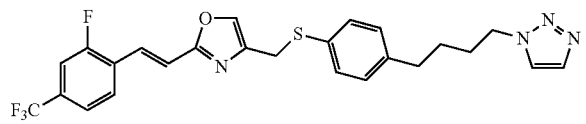 [SMILES: Fc1cc(C(F)(F)F)ccc1/C=C/c1nc(CSc2ccc(CCCCn3ccnn3)cc2)co1]

Step 1: O-(4-(4-(1H-1,2,3-triazol-1-yl)butyl)phenyl) dimethylcarbamothioate

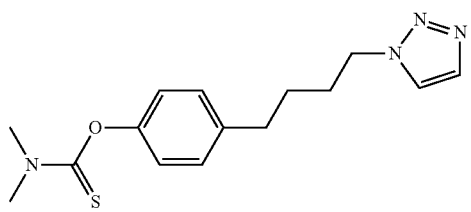 [SMILES: CN(C)C(=S)Oc1ccc(CCCCn2ccnn2)cc1]

This compound was prepared in a similar fashion as compound 132, step 1 with 4-(4-(1H-1,2,3-triazol-1-yl)butyl)phenol. ¹H NMR (DMSO-d6) δ: 8.12 (s, 1H), 7.68-7.73 (m, 1H), 7.13-7.21 (m, 2H), 6.91-6.97 (m, 2H), 4.41 (t, J=7.0 Hz, 2H), 3.35 (s, 3H), 3.29 (s, 3H), 2.60 (t, J=7.8 Hz, 2H), 1.83 (quin, J=7.3 Hz, 2H), 1.47-1.58 (m, 2H).

Step 2: S-(4-(4-(1H-1,2,3-triazol-1-yl)butyl)phenyl) dimethylcarbamothioate

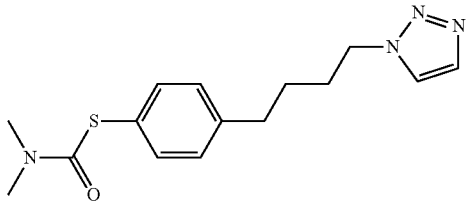 [SMILES: CN(C)C(=O)Sc1ccc(CCCCn2ccnn2)cc1]

This compound was prepared in a similar fashion as compound 132, step 2 from the previous intermediate. ¹H NMR (DMSO-d₆) δ: 8.09-8.13 (m, 1H), 7.70 (d, J=0.8 Hz, 1H), 7.29-7.35 (d, 2H), 7.18-7.24 (d, J=8.2 Hz, 2H), 4.40 (t, J=7.0 Hz, 2H), 2.85-3.09 (m, 6H), 2.62 (t, J=7.6 Hz, 2H), 1.83 (quin, J=7.3 Hz, 2H), 1.45-1.58 (m, 2H).

Step 3: 4-(4-(1H-1,2,3-triazol-1-yl)butyl)benzenethiol

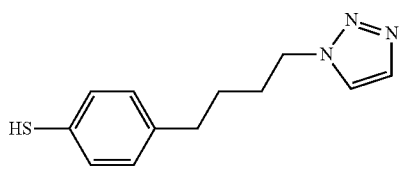 [SMILES: Sc1ccc(CCCCn2ccnn2)cc1]

This compound was prepared in a similar fashion as compound 132, step 3 from the previous intermediate. ¹H NMR (DMSO-d₆) δ: 8.10 (s, 1H), 7.70 (s, 1H), 7.14-7.22 (d, J=7.8 Hz, 2H), 7.00-7.09 (d, J=8.2 Hz, 2H), 5.23 (s, 1H), 4.38 (t, J=7.0 Hz, 2H), 2.52-2.56 (m, 2H), 1.79 (quin, J=7.3 Hz, 2H), 1.47 (quin, J=7.6 Hz, 2H).

Step 4: (E)-4-(((4-(4-(1H-1,2,3-triazol-1-yl)butyl)phenyl)thio)methyl)-2-(2-fluoro-4-(trifluoromethyl)styryl)oxazole

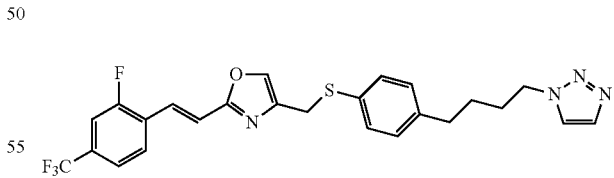

This compound was prepared in a similar fashion as compound 132, step 4 from the previous intermediate. ¹H NMR (DMSO-d₆) δ: 8.14 (t, J=7.8 Hz, 1H), 8.10 (s, 1H), 7.96 (s, 1H), 7.77 (d, J=11.0 Hz, 1H), 7.70 (s, 1H), 7.64 (d, J=8.2 Hz, 1H), 7.53 (d, J=16.8 Hz, 1H), 7.34 (d, J=16.8 Hz, 1H), 7.25-7.31 (d, J=8.2 Hz, 2H), 7.08-7.16 (d, J=8.2 Hz, 2H), 4.39 (t, J=7.0 Hz, 2H), 4.11 (s, 2H), 2.56 (t, J=7.6 Hz, 2H), 1.81 (quin, J=7.3 Hz, 2H), 1.48 (quin, J=7.6 Hz, 2H). LRMS+H⁺=503.2.

Compound 147: (E)-4-((4-((2-(1H-1,2,3-triazol-1-yl)ethyl)thio)phenoxy)methyl)-2-(2-fluoro-4-(trifluoromethyl)styryl)oxazole

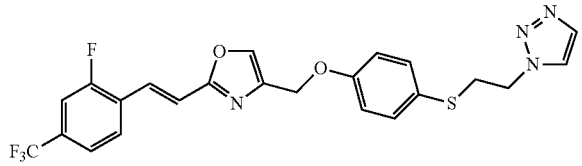 [SMILES: Fc1cc(C(F)(F)F)ccc1/C=C/c1nc(COc2ccc(SCCn3ccnn3)cc2)co1]

Step 1: (2-azidoethyl)(4-methoxyphenyl)sulfane

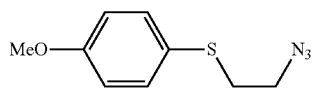

2-((4-methoxyphenyl)thio)ethanol was treated with methanesulfonyl chloride and trietylamine in dichloromethane as described in to yield the crude mesylate which was in turned converted to the corresponding azide in a similar fashion as compound 109, step 2 at 70° C. The crude is taken for the net step. $^1$H NMR (400 MHz, DMSO-d$_6$) δ ppm 3.04 (t, J=6.46 Hz, 2H) 3.40 (t, J=6.65 Hz, 2H) 3.73 (s, 3H) 6.84-6.96 (m, 2H) 7.25-7.41 (m, 2H).

Step 2: 1-(2-((4-methoxyphenyl)thio)ethyl)-1H-1,2,3-triazole

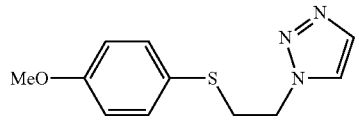 [SMILES: COc1ccc(SCCn2ccnn2)cc1]

This compound was prepared in a similar fashion as compound 1, step 3. The crude was used for the next step. $^1$H NMR (400 MHz, DMSO-d$_6$) δ 0 ppm 3.32 (t, J=7.00 Hz, 1H) 3.74 (s, 3H) 4.47 (t, J=6.85 Hz, 1H) 6.80-6.97 (m, 2H) 7.29-7.41 (m, 2H) 7.69 (d, J=1.17 Hz, 1H) 8.12 (d, J=0.78 Hz, 1H).

Step 3: 4-((2-(1H-1,2,3-triazol-1-yl)ethyl)thio)phenol

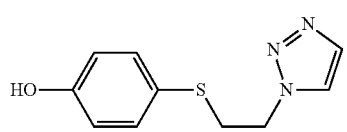

This compound was prepared in a similar fashion as compound 15, step 2. The crude was used for the next step. LRMS–H$^+$=220.0.

Step 4: (E)-4-((4-((2-(1H-1,2,3-triazol-1-yl)ethyl)thio)phenoxy)methyl)-2-(2-fluoro-4-(trifluoromethyl)styryl)oxazole

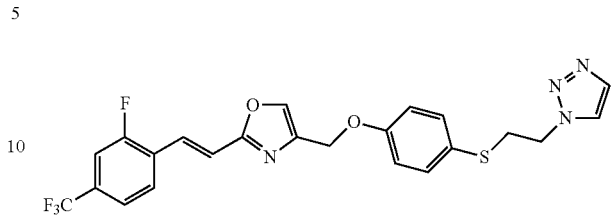

This compound was prepared in a similar fashion as compound 32, step 2. $^1$H NMR (400 MHz, DMSO-d$_6$) δ ppm 3.34 (t, J=6.85 Hz, 2H) 4.49 (t, J=6.85 Hz, 2H) 5.03 (s, 2H) 6.96-7.07 (m, 2H) 7.33-7.44 (m, 3H) 7.58 (d, J=16.43 Hz, 1H) 7.63 (d, J=7.83 Hz, 1H) 7.69 (d, J=1.17 Hz, 1H) 7.76 (d, J=9.78 Hz, 1H) 8.10-8.18 (m, 2H) 8.28 (s, 1H).

Example 7: Biological Activity of the Heterocyclic Compounds of Example 6

The potency of the compounds of Example 6 at inhibiting OCI-AML3 cell growth was tested using a procedure similar to that described for Mutritinib in Example 1. Briefly, OCI-AML3 cells purchased from the German cell bank (DSMZ, accession Nos. ACC 582) were maintained in alpha-MEM, 20% FBS. Murine MLL-AF9 leukemia cells (female cells) were generated by infection with VSV-G-pseudotyped MSCV MLL-AF9 IRES Puro (subcloned from a construct by Frédéric Barabé, Laval U, Quebec, QC, Canada).

OCI-AML3 cells were seeded in 384-well plates at a density of 150 cells in 50 μL per well and MLL-AF9 cells at 90 cells per well. Compounds were added to seeded cells in serial dilutions from 10 μM to 0.5 nM, in duplicates or quadruplicates. Cells treated with 0.1% DMSO without additional compound were used as negative controls. Viable cell counts per well were evaluated after 6 days of culture for OCI-AML3 and 5 days for MLL-AF9 cells using the Cell-TiterGlo® assay (Promega®) according to the manufacturer's instruction. The percent of inhibition was calculated as follows: 100-(100×(mean luminescence(compound)/mean luminescence(DMSO)); where mean-luminescence(compound) corresponds to the average of luminescent signals obtained for the compound-treated cells, and mean-luminescence(DMSO) corresponds to the average of luminescent signals obtained for the control DMSO-treated cells. EC$_{50}$ values (corresponding to the concentration of compound required to reach 50% of inhibition) were calculated using ActivityBase® SARview Suite (IDBS, London, UK) and GraphPad® Prism 4.03 (La Jolla, Calif., USA) by four-parameter-non-linear curve fitting methods. The results are summarized in Table 4 below.

TABLE 4

Potency of the heterocyclic compounds tested at inducing OCI-AML3 and MLL-AF9 cell death

| Compound | AML-3 EC50 | MLL-AF9 EC50 |
|---|---|---|
| 1 | +++ | ++++ |
| 2 | +++ | +++ |
| 3A | +++++ | +++++ |

TABLE 4-continued

Potency of the heterocyclic compounds tested at inducing OCI-AML3 and MLL-AF9 cell death

| Compound | AML-3 EC50 | MLL-AF9 EC50 |
|---|---|---|
| 3B | ++ | +++ |
| 4 | + | ++ |
| 5 | + | +++ |
| 6 | + | + |
| 7 | + | ++ |
| 8 | ++ | +++ |
| 9 | + | ++ |
| 10 | +++ | +++++ |
| 11 | + | + |
| 12 | ++ | +++ |
| 13 | + | + |
| 14 | + | ++ |
| 15 | ++ | +++ |
| 16 | + | +++ |
| 17 | +++ | ++++ |
| 18 | + | ++ |
| 19 | +++ | +++ |
| 20 | ++ | +++ |
| 21 | +++ | ++++ |
| 22 | ++ | +++ |
| 23 | +++ | ++++ |
| 24 | + | ++ |
| 25 | + | ++ |
| 26 | + | +++ |
| 27 | ++ | ++++ |
| 28 | + | +++ |
| 29 | + | +++ |
| 30 | ++ | +++ |
| 31 | + | ++ |
| 32 | +++ | +++ |
| 33 | +++ | +++ |
| 34 | + | + |
| 35 | + | ++ |
| 36 | + | + |
| 37 | +++ | +++ |
| 38 | ++++ | +++ |
| 39 | +++ | +++ |
| 40 | ++++ | +++ |
| 41 | +++ | +++ |
| 42 | ++ | +++ |
| 43 | + | + |
| 44 | + | − |
| 45 | ++++ | +++ |
| 46 | ++ | + |
| 47 | +++ | +++ |
| 48 | ++++ | +++++ |
| 49 | + | + |
| 50 | + | +++ |
| 51 | + | ++ |
| 52 | + | + |
| 53 | +++ | ++++ |
| 54 | +++ | +++ |
| 55 | ++ | +++ |
| 56 | + | + |
| 57 | + | ++ |
| 58 | ++ | + |
| 59 | ++ | +++ |
| 60 | + | + |
| 61 | +++ | +++ |
| 62 | +++ | +++ |
| 63 | ++ | + |
| 64 | + | ++ |
| 65 | ++++ | +++++ |
| 66 | + | + |
| 67 | +++ | +++ |
| 68 | ++ | +++ |
| 69 | ++ | +++ |
| 70 | ++ | +++ |
| 71 | +++ | +++++ |
| 72 | + | ++ |
| 73 | +++ | +++++ |
| 74 | + | +++ |
| 75 | + | + |
| 76 | + | + |
| 77 | + | − |
| 78 | + | − |
| 79 | + | + |
| 80 | ++ | +++ |
| 81 | ++++ | ++++ |
| 82 | +++ | +++ |
| 83 | ++ | +++ |
| 84 | + | + |
| 85 | + | + |
| 86 | + | +++ |
| 87 | ++ | +++ |
| 88 | + | ++ |
| 89 | + | + |
| 90 | + | +++ |
| 91 | + | ++ |
| 92 | ++ | +++ |
| 93 | + | ++ |
| 94 | + | + |
| 95 | + | +++ |
| 96 | ++ | +++ |
| 97 | +++ | +++ |
| 98 | +++ | ++++ |
| 99 | +++ | +++ |
| 100 | ++ | ++ |
| 101 | + | + |
| 102 | +++ | +++ |
| 103 | +++ | +++ |
| 104 | + | + |
| 105 | +++ | ++ |
| 106 | + | + |
| 107 | + | + |
| 108 | + | + |
| 109 | ++ | +++ |
| 110 | + | + |
| 111 | + | ++ |
| 112 | +++ | ++++ |
| 113 | ++ | +++ |
| 114 | + | + |
| 115 | ++ | +++ |
| 116 | ++++ | ++++ |
| 117 | +++ | +++ |
| 118 | +++ | +++ |
| 119 | +++ | +++ |
| 120 | +++ | +++++ |
| 121 | ++++ | ++++ |
| 122 | +++++ | +++++ |
| 123 | +++ | +++ |
| 124 | +++++ | ++++ |
| 125 | ++++ | +++ |
| 126 | + | − |
| 127 | +++++ | +++++ |
| 128 | +++++ | +++++ |
| 129 | +++++ | +++++ |
| 130 | +++++ | +++++ |
| 131 | +++ | +++ |
| 132 | + | ++ |
| 133 | +++ | ++++ |
| 134 | + | ++ |
| 135 | NT | ++ |
| 136 | NT | +++ |
| 137 | NT | ++ |
| 138 | +++++ | ++++ |
| 139 | − | + |
| 140 | − | + |
| 141 | +++++ | ++++ |
| 142 | ++ | +++ |
| 143 | + | +++ |
| 144 | +++++ | +++++ |
| 145 | ++ | +++ |

TABLE 4-continued

Potency of the heterocyclic compounds tested at inducing OCI-AML3 and MLL-AF9 cell death

| Compound | AML-3 EC50 | MLL-AF9 EC50 |
|---|---|---|
| 146 | + | +++ |
| 147 | +++++ | +++++ |

Activities presented as using the symbol "−" for $EC_{50} > 10$ µM; + for $1$ µM $< EC_{50} \leq 10$ µM; ++ for $0.5$ µM $< EC_{50} \leq 1$ µM; +++ for $0.1$ µM $< EC_{50} \leq 0.5$ µM; ++++ for $0.05$ µM $< EC_{50} \leq 0.1$ µM; +++++ for $EC_{50} \leq 0.05$ µM; NT for not tested.

Numerous modifications could be made to any of the embodiments described above without departing from the scope of the present invention. Any references, patents or scientific literature documents referred to in the present document are incorporated herein by reference in their entirety for all purposes.

The invention claimed is:

1. A compound having one of the following structures:

Compound 122

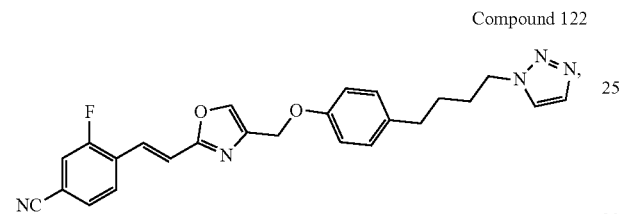

Compound 130

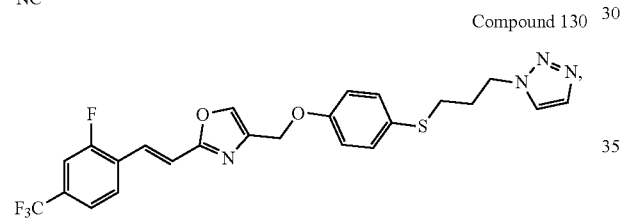

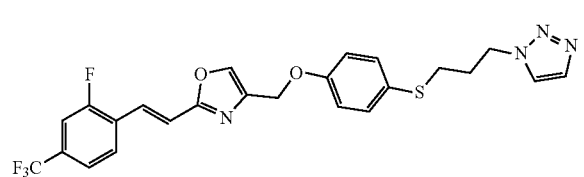

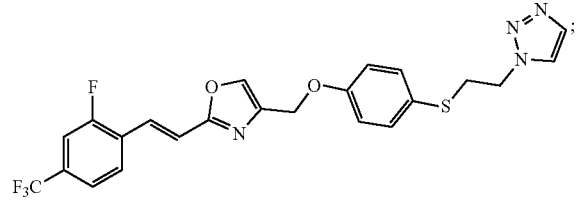

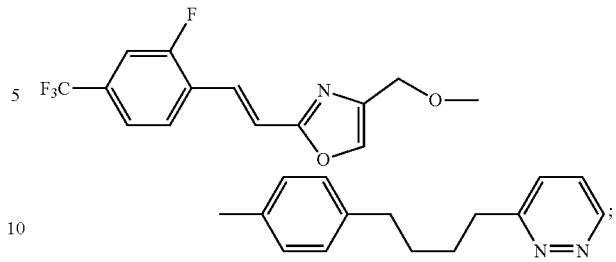

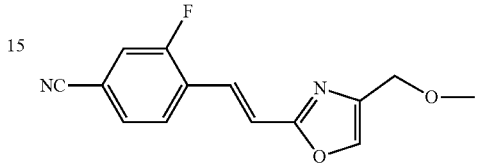

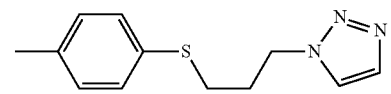

or a pharmaceutically acceptable salt thereof.

2. The compound of claim 1, selected from

Compound 130

Compound 141

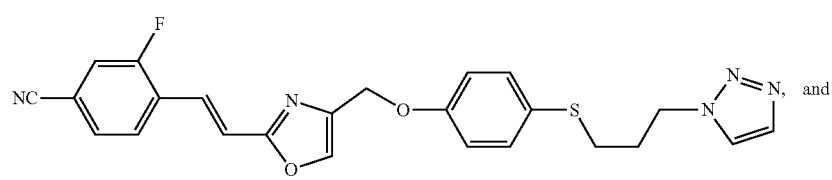 and

Compound 147 or a pharmaceutically acceptable salt thereof.

3. A method for treating acute myeloid leukemia (AML), said method comprising administering to a subject in need thereof an effective amount of a compound of claim 1 or a pharmaceutically acceptable salt thereof.

4. A pharmaceutical composition comprising the compound, or pharmaceutically acceptable salt thereof, of claim 1.

5. A method for treating acute myeloid leukemia (AML), said method comprising administering to a subject in need thereof an effective amount of a compound of claim 2 or a pharmaceutically acceptable salt thereof.

6. A pharmaceutical composition comprising the compound, or pharmaceutically acceptable salt thereof, of claim 2.

\* \* \* \* \*